US011963982B2

(12) United States Patent
Aupepin De Lamothe-Dreuzy et al.

(10) Patent No.: US 11,963,982 B2
(45) Date of Patent: Apr. 23, 2024

(54) CRISPR/RNA-GUIDED NUCLEASE SYSTEMS AND METHODS

(71) Applicant: Editas Medicine, Inc., Cambridge, MA (US)

(72) Inventors: Edouard Aupepin De Lamothe-Dreuzy, Boston, MA (US); Jack Heath, Winchester, MA (US); Jennifer Leah Gori, Jamaica Plain, MA (US); Luis Barrera, Somerville, MA (US)

(73) Assignee: EDITAS MEDICINE, INC., Cambridge, MA (US)

( * ) Notice: Subject to any disclaimer, the term of this patent is extended or adjusted under 35 U.S.C. 154(b) by 904 days.

(21) Appl. No.: 16/678,912

(22) Filed: Nov. 8, 2019

(65) Prior Publication Data

US 2020/0155606 A1 May 21, 2020

Related U.S. Application Data

(63) Continuation of application No. PCT/US2018/032172, filed on May 10, 2018.

(60) Provisional application No. 62/504,527, filed on May 10, 2017, provisional application No. 62/504,522, filed on May 10, 2017.

(51) Int. Cl.

| | |
|---|---|
| ***C12N 15/11*** | (2006.01) |
| ***A61K 35/18*** | (2015.01) |
| ***C12N 5/078*** | (2010.01) |
| ***C12N 5/0789*** | (2010.01) |
| ***C12N 9/22*** | (2006.01) |
| ***C12N 15/90*** | (2006.01) |

(52) U.S. Cl.

CPC ............ *A61K 35/18* (2013.01); *C12N 5/0641* (2013.01); *C12N 5/0647* (2013.01); *C12N 9/22* (2013.01); *C12N 15/111* (2013.01); *C12N 15/907* (2013.01); *C12N 2310/20* (2017.05); *C12N 2320/10* (2013.01); *C12N 2320/30* (2013.01)

(58) Field of Classification Search

None

See application file for complete search history.

(56) References Cited

U.S. PATENT DOCUMENTS

| | | | |
|---|---|---|---|
| 6,413,540 | B1 | 7/2002 | Yaacobi |
| 6,586,240 | B1 | 7/2003 | Singer et al. |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,394 | B2 | 11/2014 | Chalasani et al. |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 9,322,037 | B2 | 4/2016 | Liu et al. |
| 9,499,847 | B2 | 11/2016 | Porter et al. |
| 2003/0186238 | A1 | 10/2003 | Allawi et al. |
| 2007/0020627 | A1 | 1/2007 | Barbas |
| 2010/0055793 | A1 | 3/2010 | Chandrasegaran et al. |
| 2010/0055798 | A1 | 3/2010 | Battersby |
| 2010/0076057 | A1 | 3/2010 | Sontheimer et al. |
| 2011/0059502 | A1 | 3/2011 | Chalasani |
| 2011/0189776 | A1 | 8/2011 | Terns et al. |
| 2011/0223638 | A1 | 9/2011 | Wiedenheft et al. |
| 2011/0236894 | A1 | 9/2011 | Rao et al. |
| 2011/0301073 | A1 | 12/2011 | Gregory et al. |
| 2012/0270273 | A1 | 10/2012 | Zhang et al. |
| 2013/0130248 | A1 | 5/2013 | Haurwitz et al. |
| 2013/0253040 | A1 | 9/2013 | Miller et al. |
| 2014/0068797 | A1 | 3/2014 | Doudna et al. |
| 2014/0179770 | A1 | 6/2014 | Zhang et al. |
| 2014/0242699 | A1 | 8/2014 | Zhang |
| 2014/0309177 | A1 | 10/2014 | Perez-Pinera et al. |
| 2014/0315985 | A1 | 10/2014 | May et al. |
| 2014/0335620 | A1 | 11/2014 | Zhang et al. |
| 2014/0342456 | A1 | 11/2014 | Mali et al. |
| 2014/0342457 | A1 | 11/2014 | Mali et al. |
| 2014/0342458 | A1 | 11/2014 | Mali et al. |
| 2014/0356958 | A1 | 12/2014 | Mali et al. |
| 2015/0056705 | A1 | 2/2015 | Conway et al. |

(Continued)

FOREIGN PATENT DOCUMENTS

| | | | |
|---|---|---|---|
| WO | 2002/089767 | A1 | 11/2002 |
| WO | 2003/072788 | A1 | 9/2003 |

(Continued)

OTHER PUBLICATIONS

De Dreuzy, E., et al., "EDIT-301: An Experimental Autologous Cell Therapy Comprising Cas12a-RNP Modified mPB-CD34+ Cells for the Potential Treatment of SCD," Blood 134(Suppl. 1):4636 (2019).

De Dreuzy, E., et al., "Robust Pre-Clinical Results and Large-Scale Manufacturing Process for Edit-301: An Autologous Cell Therapy for the Potential Treatment of SCD," Blood 136(Suppl. 1):45-46 (2020).

Heath, J., et al., "EDIT-301: An Autologous Cell Therapy to Promote Fetal Hemoglobin Expression for the Potential Treatment of Sickle Cell Disease," Hemasphere 4(S1):S292 (2020).

European Patent Office, International Search Report and Written Opinion dated Apr. 13, 2021 for PCT/US2020/063854, 18 pages.

Kim, D., et al., "Genome-wide analysis reveals specificities of Cpf1 endonucleases in human cells," Nat. Biotechnol. 34(8):863-868 (2016).

(Continued)

*Primary Examiner* — Brian Whiteman

(74) *Attorney, Agent, or Firm* — Perkins Coie LLP; Courtney Prochnow

(57) ABSTRACT

Genome editing systems, guide RNAs, dead guide RNAs, and CRISPR-mediated methods are provided for altering portions of a target nucleic acid.

18 Claims, 53 Drawing Sheets

Specification includes a Sequence Listing.

(56) References Cited

U.S. PATENT DOCUMENTS

| | | | | |
|---|---|---|---|---|
| 2015/0132269 | A1* | 5/2015 | Orkin | C12N 9/22 435/325 |
| 2015/0232833 | A1 | 8/2015 | Mali et al. | |
| 2015/0259704 | A1 | 9/2015 | Church et al. | |
| 2016/0153005 | A1 | 6/2016 | Zhang et al. | |
| 2016/0281111 | A1 | 9/2016 | Cotta-Ramusino et al. | |
| 2016/0289675 | A1 | 10/2016 | Ryan et al. | |
| 2016/0324987 | A1 | 11/2016 | Wang et al. | |
| 2016/0340661 | A1 | 11/2016 | Cong et al. | |
| 2017/0058298 | A1 | 3/2017 | Kennedy et al. | |
| 2018/0273609 | A1 | 9/2018 | Porteus et al. | |
| 2018/0291370 | A1 | 10/2018 | Gersbach et al. | |
| 2019/0010495 | A1* | 1/2019 | Boitano | A61K 35/15 |
| 2019/0241911 | A1 | 8/2019 | Dong et al. | |
| 2020/0299661 | A1 | 9/2020 | Gori et al. | |
| 2020/0299689 | A1 | 9/2020 | Lee | |

FOREIGN PATENT DOCUMENTS

| | | | | |
|---|---|---|---|---|
| WO | 2008/108989 | A2 | 9/2008 | |
| WO | 2010/054108 | A9 | 5/2010 | |
| WO | 2011/143124 | A2 | 11/2011 | |
| WO | 2011/146121 | A1 | 11/2011 | |
| WO | 2012/145601 | A2 | 10/2012 | |
| WO | 2012/164565 | A8 | 12/2012 | |
| WO | 2013/012674 | A1 | 1/2013 | |
| WO | 2013/066438 | A2 | 5/2013 | |
| WO | 2013/082519 | A2 | 6/2013 | |
| WO | 2013/098244 | A1 | 7/2013 | |
| WO | 2013/126794 | A1 | 8/2013 | |
| WO | 2013/141680 | A1 | 9/2013 | |
| WO | 2013/142578 | A1 | 9/2013 | |
| WO | 2013/163628 | A2 | 10/2013 | |
| WO | 2013/176772 | A1 | 11/2013 | |
| WO | 2013/181228 | A1 | 12/2013 | |
| WO | 2014/018423 | A8 | 1/2014 | |
| WO | 2014/022702 | A2 | 2/2014 | |
| WO | 2014/036219 | A2 | 3/2014 | |
| WO | 2014/059255 | A1 | 4/2014 | |
| WO | 2014/065596 | A1 | 5/2014 | |
| WO | 2014/085593 | A1 | 6/2014 | |
| WO | 2014/089290 | A1 | 6/2014 | |
| WO | 2014/093479 | A1 | 6/2014 | |
| WO | 2014/093595 | A1 | 6/2014 | |
| WO | 2014/093622 | A8 | 6/2014 | |
| WO | 2014/093635 | A9 | 6/2014 | |
| WO | 2014/093655 | A2 | 6/2014 | |
| WO | 2014/093661 | A2 | 6/2014 | |
| WO | 2014/093694 | A1 | 6/2014 | |
| WO | 2014/093709 | A1 | 6/2014 | |
| WO | 2014/093712 | A1 | 6/2014 | |
| WO | 2014/093718 | A1 | 6/2014 | |
| WO | 2014/099744 | A1 | 6/2014 | |
| WO | 2014/099750 | A2 | 6/2014 | |
| WO | WO-2014085593 | A1 * | 6/2014 | A61K 35/12 |
| WO | 2014/124284 | A1 | 8/2014 | |
| WO | 2014/144288 | A1 | 9/2014 | |
| WO | 2014/144592 | A2 | 9/2014 | |
| WO | 2014/144761 | A2 | 9/2014 | |
| WO | 2014/152432 | A2 | 9/2014 | |
| WO | 2014/186585 | A2 | 11/2014 | |
| WO | 2014/197568 | A2 | 12/2014 | |
| WO | 2014/197748 | A1 | 12/2014 | |
| WO | 2014/204578 | A1 | 12/2014 | |
| WO | 2014/204725 | A8 | 12/2014 | |
| WO | 2015/006290 | A1 | 1/2015 | |
| WO | 2015/006294 | A | 1/2015 | |
| WO | 2015/006498 | A2 | 1/2015 | |
| WO | 2015/013583 | A8 | 1/2015 | |
| WO | 2015/021353 | A1 | 2/2015 | |
| WO | 2015/027134 | A1 | 2/2015 | |
| WO | 2015/035136 | A8 | 3/2015 | |
| WO | 2015/035139 | A2 | 3/2015 | |
| WO | 2015/035162 | A2 | 3/2015 | |
| WO | 2015/048577 | A2 | 4/2015 | |
| WO | 2015/048690 | A1 | 4/2015 | |
| WO | 2015/070083 | A1 | 5/2015 | |
| WO | 2015/071474 | A9 | 5/2015 | |
| WO | 2015/077290 | A2 | 5/2015 | |
| WO | 2015/077318 | A1 | 5/2015 | |
| WO | 2015/089406 | A1 | 6/2015 | |
| WO | 2015/089462 | A1 | 6/2015 | |
| WO | 2015/099850 | A1 | 7/2015 | |
| WO | 2015/138510 | A8 | 9/2015 | |
| WO | 2015/148860 | | 10/2015 | |
| WO | 2015/148863 | A2 | 10/2015 | |
| WO | 2015/188056 | A1 | 12/2015 | |
| WO | 2015/195621 | A1 | 12/2015 | |
| WO | 2016/011080 | A2 | 1/2016 | |
| WO | 2016/022363 | A9 | 2/2016 | |
| WO | 2016/073990 | A2 | 5/2016 | |
| WO | 2016/094872 | A1 | 6/2016 | |
| WO | 2016/135557 | A2 | 9/2016 | |
| WO | 2016/135558 | A2 | 9/2016 | |
| WO | 2016/182959 | A1 | 11/2016 | |
| WO | 2016/186772 | A2 | 11/2016 | |
| WO | 2016/205613 | A1 | 12/2016 | |
| WO | 2016/205749 | A1 | 12/2016 | |
| WO | 2017/035416 | A2 | 3/2017 | |
| WO | 2017/077394 | A2 | 5/2017 | |
| WO | 2017/106657 | A1 | 6/2017 | |
| WO | 2017/160890 | A1 | 9/2017 | |
| WO | 2017/184768 | | 10/2017 | |
| WO | 2017/191503 | A1 | 11/2017 | |
| WO | 2018/017754 | A1 | 1/2018 | |
| WO | 2018/126176 | A1 | 7/2018 | |
| WO | 2018/142364 | A1 | 8/2018 | |
| WO | 2018/170184 | A1 | 9/2018 | |
| WO | 2018/209158 | A2 | 11/2018 | |
| WO | 2019/118516 | A1 | 6/2019 | |
| WO | 2019/178416 | A1 | 9/2019 | |
| WO | 2019/178426 | A1 | 9/2019 | |
| WO | 2021/119040 | A1 | 6/2021 | |

OTHER PUBLICATIONS

Kleinstiver, B.P., et al., "Genome-Wide Specificities of CRISPR-Cas Cpf1 Nucleases in Human Cells," Nat. Biotechnol. 34(8):869-874 (2016).

Sakuma, T., et al., "Multiplex Genome Engineering in Human Cells Using All-in-One CRISPR/Cas9 Vector System," Sci. Rep. 4(5400):1-6 (2014).

Ding, Q., et al., "Enhanced Efficiency of Human Pluripotent Stem Cell Genme Editing through Replacing TALENs with CRIPSRs," Cell Stem Cell 12:393-394 (2013).

Heintze, J., et al., "A CRISPR CASe for High-Throughput Silencing," Front. Genet. 4(193):1-6 (2013).

Mukherjee-Clavin, B., et al., "Current Approaches for Efficient Genetic Editing in Human Pluripotent Stem Cells," Front. Biol. 8(5):461-467 (2013).

Cramer, M. L., et al., "Induction of T-Cell Infiltration and Programmed Death Ligand 2 Expression by Adeno-Associated Virus in Rhesus Macaque Skeletal Muscle and Modulation by Prednisone," Hum. Gene Ther. 28(6):493-509 (2017).

Kumar, S. R.P., et al., "Clinical development of gene therapy: results and lessons from recent successes," Mol. Ther. Methods Clin. Dev. 3:16034 (2016).

Sobrevals, L., et al., "AAV Vectors Transduce Hepatocytes In Vivo as Efficiently in Cirrhotic as in Healthy Rat Livers," Gene Ther. 19:411-417 (2012).

Zetsche, B., et al., "Multiplex Gene Editing by CRISPR-Cpf1 Through Autonomous Processing of a Single crRNA Array," Nat. Biotechnol. 35(1):31-34 (2017).

Ahern, E.J., et al., "The Prevalence of the Rarer Inherited Haemoglobin Defects in Adult Jamaicans," Br. J. Haematol. 25(4):437-444 (1973).

Akinbami, A.O., et al., "Hereditary Persistence of Fetal Hemoglobin Caused by Single Nucleotide Promoter Mutations in Sickle Cell Trait and Hb SC Disease," Hemoglobin 40(1):64-65 (2016).

(56) References Cited

OTHER PUBLICATIONS

Al-Attar, S., et al., "Clustered Regularly Interspaced Short Palindromic Repeats (CRISPRs): The Hallmark of an Ingenious Antiviral Defense Mechanism in Prokaryotes," Biol. Chem. 392:277-289 (2011).
Aliyu, Z.Y., et al., "Sickle Cell Disease and Pulmonary Hypertension in Africa: A Global Perspective and Review of Epidemiology, Pathophysiology, and Management," Am. J. Hematol. 83(1):63-70 (2008).
Altschul, S. F., et al., "Gapped BLAST and PSI-BLAST: A New Generation of Protein Database Search Programs," Nucleic Acids Res. 25(17):3389-3402 (1997).
Altschul, S. F., et al., "Basic Local Alignment Search Tool," J. Mol. Biol. 215(3):403-410 (1990).
Amrani, N., et al., "NmeCas9 is an Intrinsically High-Fidelity Genome-Editing Platform," Genome Biol. 19:214 (2018).
Anders, C., et al., "Structural Basis of PAM-Dependent Target DNA Recognition by the Cas9 Endonuclease," Nature 513(7519):569-573 (2014).
Andreas, S., et al., "Enhanced Efficiency Through Nuclear Localization Signal Fusion on Phage PhiC31-Integrase: Activity Comparison with Cre and FLPe Recombinase in Mammalian Cells," Nucleic Acids Res. 30(11):2299-2306 (2002).
Angastiniotis, M., et al., "Global Epidemiology of Hemoglobin Disorders," Ann. N.Y. Acad. Sci. 850:251-269 (1998).
Anonymous, Third Party Observation for EP13818570.7, Oct. 1, 2014, 15 pages.
Anonymous, Third Party Observation for EP13824232.6, Sep. 8, 2014, 48 pages.
Anonymous, Third Party Observation for EP13824232.6, Sep. 22, 2014, 19 pages.
Anonymous, Third Party Observation for EP13824232.6, Oct. 22, 2014, 7 pages.
Bae, S., et al., "Cas-OFFinder: A Fast and Versatile Algorithm that Searches for Potential Off-Target Sites of Cas9 RNA-Guided Endonucleases," Bioinformatics 30(10):1473-1475 (2014).
Baker, M., "Gene Editing at CRISPR Speed," Nat. Biotechnol. 32(4):309-312 (2014).
Barbosa, C.G., et al., "Promoter Region Sequence Differences in the A and G Gamma Globin Genes of Brazilian Sickle Cell Anemia Patients," Braz. J. Med. Biol. Res. 43(8):705-711 (2010).
Barker, C. S., et al., "Increased DNA Microarray Hybridization Specificity Using sscDNA Targets," BMC Genomics 6:57 (2005).
Baron-Benhamou, J., et al., "Using the LambdaN Peptide to Tether Proteins to RNAs," Methods Mol. Biol. 257:135-153 (2004).
Barrangou, R., "RNA-Mediated Programmable DNA Cleavage," Nat. Biotechnol. 30(9):836-838 (2012).
Barretina, J., et al., "The Cancer Cell Line Encyclopedia Enables Predictive Modeling of Anticancer Drug Sensitivity," Nature 483(7391):603-607 (2012).
Bassett, A. R., et al., "CRISPR/Cas9 and Genome Editing in *Drosophila*," J. Genet. Genom. 41:7-19 (2014).
Bauer, D. E., et al., "An Erythroid Enhancer of BCL11A Subject to Genetic Variation Determines Fetal Hemoglobin Level," Science 342(6155):253-257 (2013).
Beerli, R. R., et al., "Toward Controlling Gene Expresion at Will: Specific Regulation of the erbB-2/HER-2 Promoter by Using Polydactyl Zinc Finger Proteins Constructed from Modular Building Blocks," Proc. Natl. Acad. Sci. 95:14628-14633 (1998).
Bhaya, D., et al., "CRISPR-Cas Systems in Bacteria and Archaea: Versatile Small RNAs for Adaptive Defense and Regulation," Annu. Rev. Genet. 45:273-297 (2011).
Bikard, D., et al., "Programmable Repression and Activation of Bacterial Gene Expression Using an Engineered CRISPR-Cas System," Nucl. Acids Res. 41(15):7429-7437 (2013).
Bitinaite, J., et al., "FokI Dimerization is Required for DNA Cleavage," Proc. Natl. Acad. Sci. 95:10570-10575 (1998).
Boch, J., et al., "Breaking the Code of DNA Binding Specificity of TAL-Type III Effectors," Science 326(5959):1509-1512 (2009).
Boch, J., et al., "Xanthomonas AvrBs3 Family-Type III Effectors: Discovery and Function," Annu. Rev. Phytopathol. 48:419-436 (2010).
Bothmer, A., et al., "Characterization of the Interplay Between DNA Repair and CRISPR/Cas9-Induced DNA Lesions at an Endogenous Locus," Nat. Commun. 8:13905 (2017).
Bouva, M. J., et al., "Known and New Delta Globin Gene Mutations and Their Diagnostic Significance," Haematologica 91(1):129-132 (2006).
Briner, A.E., et al., "Guide RNA Functional Modules Direct Cas9 Activity and Orthogonality," Mol. Cell 56(2):333-339 (2014).
Broad Institute, Communication Forwarding Declaration of Feng Zhang for U.S. Appl. No. 14/256,912, dated Nov. 24, 2014, 5 pages.
Broad Institute, Information Disclosure Statement submitted for U.S. Appl. No. 14/256,912, citing Electronic Mail from T. Kowalski to which references Briner et al., Nov. 3, 2014, 8 pages.
Broad Institute, Request for Oral Examination for EP13818570.7, dated Oct. 27, 2014, 3 pages.
Broad Institute, Response to EP Examination Report for EP13824232.6, dated Dec. 31, 2014, 44 pages.
Broad Institute, Response to Third Party Observations and Request for Oral Hearing for EP13824232.6, Oct. 27, 2014, 9 pages.
Broad Institute, Response to Third Party Observations, with redlined and clean amended claims, for EP13818570.7, Oct. 16, 2014, 30 pages.
Broad Institute, Response to Third Party Observations, with redlined and clean amended claims, for EP13824232.6, Oct. 2, 2014, 16 pages.
Brousseau, D.C., et al., "The Number of People with Sickle-Cell Disease in the United States: National and State Estimates," Am. J. Hematol. 85(1):77-78 (2010).
Brummelkamp, T. R., et al., "A System for Stable Expression of Short Interfering RNAs in Mammalian Cells," Science 296(5567):550-553 (2002).
Burstein, D., et al., "New CRISPR-Cas Systems from Uncultivated Microbes," Nature 542(7640):237-241 (2017).
Caldecott, K.W., "Single-Strand Break Repair and Genetic Disease," Nat. Rev. Genet. 9(8):619-631 (2008).
Canver, M. C., "Evaluation of the Clinical Success of Ex Vivo and In Vivo Gene Therapy," Journal of Young Investitgators, http://www.hyi.org/issue/evaluation-of-the-clinical-success-of-ex-vivo-and-in-vivo-gene-therapy/, 9 pages (2009).
Canver, M. C., et al., "BCL11A Enancer Dissection by Cas9-Mediated In Situ Saturating Mutagenesis," Nature 527(7577):192-197 (2015).
Carroll, D., "A CRISPR Approach to Gene Targeting," Mol. Ther. 20(9):1658-1660 (2012).
Cassini, A., et al., "A Highly Specific SpCas9 Variant is Identified by In Vivo Screening in Yeast," Nat. Biotechnol. 36(3):265-271 (2018).
Cathomen, T., et al., "Zinc-Finger Nucleases: The Next Generation Emerges," Mol. Ther. 16:1200-1207 (2008).
Cermak, T., et al., "Efficient Design and Assembly of Custom TALEN and Other TAL Effector-Based Constructs for DNA Targeting," Nucl. Acids Res. 39(12):e82 (2011).
Chandrakasan, S., et al., "Gene Therapy for Hemoglobinopathies: The State of the Field and the Future," Hematol. Oncol. Clin. North Am. 28(2):199-216 (2014).
Chang, K.H., et al., "Long-Term Engraftment and Fetal Globin Induction upon BCL11A Gene Editing in Bone-Marrow-Derived CD34+ Hematopoietic Stem and Progenitor Cells," Mol. Ther. Methods Clin. Dev. 4:137-148 (2017).
Chassanidis, C., et al., "The Hellenic Type of Nondeletional Hereditary Persistence of Fetal Hemoglobin Results from a Novel Mutation (g.-109G>T) in the HBG2 Gene Promoter," Ann. Hematol. 88(6):549-555 (2009).
Chen, X., et al., "Fusion Protein Linkers: Property, Design and Functionality," Adv. Drug Deliv. Rev. 65(10):1357-1369 (2013).
Chen, F., et al., "Targeted Activation of Diverse CRISPR-Cas Systems for Mammalian Genome Editing Via Proximal CRISPR Targeting," Nat. Commun. 8:14958 (2017).
Chen, J. S., et al., "Enhanced Proofreading Governs CRISPR-Cas9 Targeting Accuracy," Nature 550(7676):407-410 (2017).

(56) References Cited

OTHER PUBLICATIONS

Cho, S. W., et al., Supplementary Information: Targeted Genome Engineering in Human Cells With the Cas9 RNA-Guided Endonuclease, Nature Biotechnology (Mar. 2013) vol. 31, No. 3, 11 pages.
Cho, S. W., et al., "Targeted Genome Engineering in Human Cells with the Cas9 RNA-Guided Endonuclease," Nat. Biotechnol. 31(3):230-232 (2013).
Christian, M., et al., "Targeting DNA Double-Strand Breaks With TAL Effector Nucleases," Genetics 186:757-761 (2010).
Christian, M., et al., "Targeting DNA Double-Strand Breaks With TAL Effector Nucleases," Genetics Supporting Information, 1SI-8SI (2010).
Chylinski, K., et al., "The TrackRNA and Cas9 Families of Type II CRISPR-Cas Immunity Systems," RNA Biol. 10(5):726-737 (2013).
Cong, L., et al., "Multiplex Genome Engineering Using CRISPR/Cas Systems," Science 339(6121):819-823 (2013).
Cong, L. et al., "Supplementary Material: Multiplex Genome Engineering Using CRISPR-Cas Systems," Science Express (Jul. 5, 2012).
Cong, L. et al., "Supplementary Material: Multiplex Genome Engineering Using CRISPR-Cas Systems," Science Express (Jan. 3, 2013).
Cornish-Bowden, A., "Nomenclature for Incompletely Specified Bases in Nucleic Acid Sequences: Recommendations 1984," Nucleic Acids Res. 13(9):3021-3030 (1985).
Cradick, T. J., et al., "CRISPR/Cas9 Systems Targeting Beta-Globin and CCR5 Genes Have Substantial Off-Target Activity," Nucleic Acids Res. 41(20):9584-9592 (2013).
Datsenko, K. A., et al., "Molecular Memory of Prior Infections Activates the CRISPR/Cas Adaptive Bacterial Immunity System," Nat. Commun. 3:945 (2012).
Davis, L., et al., "Homology-Directed Repair of DNA Nicks Via Pathways Distinct from Canonical Double-Strand Break Repair," PNAS 111(10):E924-932 (2014).
Deltcheva, E., et al., CRISPR RNA Maturation by Trans-Encoded Small RNA and Host Factor RNase III, Nature 471:602-607 (2011).
Deltcheva, E., et al., Supplementary Figures: CRISPR RNA Maturation by Trans-Encoded Small RNA and Host Factor RNase III. Downloaded from www.nature.com/nature, p. 1-35, 2011.
Deveau, H., et al., "Phage Response to CRISPR-Encoded Resistance in *Streptococcus thermophilus*," J. Bacteriol. 190(4):1390-1400 (2008).
Dever, D. P., et al., "CRISPR/Cas9 Beta-Globin Gene Targeting in Human Haematopoietic Stem Cells," Nature 539:384-389 (2016).
Dicarlo, J. E., et al., "Genome Engineering in *Saccharomyces cerevisiae* Using CRISPR-Cas Systems," Nucl. Acids Res. 41(7):4336-43 (2013).
Dingwall, C., et al., "A Polypeptide Domain That Specifies Migration of Nucleoplasmin Into the Nucleus," Cell 30:449-458 (1982).
Dreszer, T. R., et al., "The UCSC Genome Browser Database: Extensions and Updates 2011," Nucl. Acids Res. 40:D918-D923 (2012).
Esvelt, K.M., et al., "A System for the Continuous Directed Evolution of Biomolecules," Nature 472(7344):499-503 (2011).
Esvelt, K. M., et al., "Orthogonal Cas9 Proteins for RNA-Guided Gene Regulation and Editing," Nat. Methods 10(11):1116-1121 (2013).
Fine, E.J., et al., "Trans-Spliced Cas9 Allows Cleavage of HBB and CCR5 Genes in Human Cells Using Compact Expression Cassettes," Sci. Rep. 5:10777 (2015).
Fonfara, I., et al., "Phylogeny of Cas9 Determines Functional Exchangeability of Dual-RNA and Cas9 Among Orthologous Type II CRISPR- Cas Systems," Nucl. Acids Res.42(4):2577-2590 (2014).
Friedland, A.E., et al., "Characterization of *Staphylococcus aureus* Cas9: A Smaller Cas9 for All-in-One Adeno-Associated Virus Delivery and Paired Nickase Applications," Genome Biol. 16:257 (2015).
Frit, P., et al., "Alternative End-Joining Pathway(s): Bricolage at DNA Breaks," DNA Repair (Amst) 17:81-97 (2014).
Fu, Y., et al., "High-Frequency Off-Target Mutagenesis Induced by CRISPR-Cas Nucleases in Human Cells," Nat. Biotechnol. 31:822-826 (2013).
Fu, Y., et al., "Targeted Genome Editing in Human Cells Using CRISPR/Cas Nucleases and Truncated Guide RNAs," Methods Enzymol. 546:21-45 (2014).
Fu, Y., et al., "Improving CRISPR-Cas Nuclease Specificity Using Truncated Guide RNAs," Nat. Biotechnol. 32(3):279-284 (2014).
Gabriel, R., et al., "An Unbiased Genome-Wide Analysis of Zinc-Finger Nuclease Specificity," Nat. Biotechnol. 29:816-823 (2011).
Garneau, J. E., et al., "The CRISPR-Cas Bacterial Immune Systems Cleaves Bacteriophage and Plasmid DNA," Nature 468:67-71 (2010).
Gasiunas, G., et al., "Cas9-crRNA Ribonucleoprotein Complex Mediates Specific DNA Cleavage for Adaptive Immunity in Bacteria," Proc. Natl. Acad. Sci. 109(39):E2579-E2586 (2012).
Giarratana, M. C., et al., "Proof of Principle for Transfusion of In Vitro- Generated Red Blood Cells," Blood 118(19):5071-5079 (2011).
Gilbert, L. A., et al., "CRISPR-Mediated Modular RNA-Guided Regulation of Transcription in Eukaryotes," Cell 154(2):442-451 (2013).
Goldfarb, D. S., et al., "Synthetic Peptides as Nuclear Localization Signals," Nature 322:641-644 (1986).
Gratz, S. J., et al., "Genome Engineering of *Drosophila* with the CRISPR RNA-Guided Cas9 Nuclease," Genetics 194(4):1029-1035 (2013).
Grieger, J. C., et al., "Production and Characterization of Adeno-Associated Viral Vectors," Nat. Protoc. 1(3):1412-1428 (2006).
Guilinger, J. P., et al., "Fusion of Catalytically Inactive Cas9 to Fokl Nuclease Improves the Specificity of Genome Modification," Nat Biotechnol. 32(6):577-583 (2014).
Guo, X., et al., "RNA-Dependent Folding and Stabilization of C5 Protein During Assembly of the *E. coli* Rnase P Holoenzyme," J. Mol. Biol. 360:190-203 (2006).
Guo, Q., et al., "Cold shock' increases the frequency of homology directed repair gene editing in induced pluripotent stem cells," Sci. Rep. 8(1):2080 (2018).
Gustafsson, C., et al., "Codon Bias and Heterologous Protein Expression," Trends Biotechnol. 22(7):346-353 (2004).
Haft, D. H., et al., "A Guild of 45 CRISPR-Associated (Cas) Protein Families and Multiple CRISPR/Cas Subtypes Exist in Prokaryotic Genomes," PLOS Comput. Biol. 1(6):e60 (2005).
Hale, C. R., et al., "Essential Features and Rational Design of CRISPR RNAs That Function With the Cas RAMP Module Complex to Cleave RNAs," Mol. Cell 45(3):292-302 (2012).
Hatoum-Aslan, A., et al. "Mature Clustered Regularly Interspaced, Short Palindromic Repeats RNA 5,9,14 (crRNA) Length is Measured by a Ruler Mechanism Anchored at the Precursor Processing Site," Proc. Natl. Acad. Sci. 108(52):21218-21222 (2011).
Heigwer, F., et al., "E-CRISP: Fast CRISPR Target Site Identification," Nat. Methods 11(2):122-123 (2014).
Hinz, J. M., et al., "Nucleosomes Selectively Inhibit Cas9 Off-Target Activity at a Site Located at the Nucleosome Edge," J. Biol. Chem. 291(48):24851-24856 (2016).
Hoban, M. D., et al., "A genome editing primer for the hematologist," Blood 127(21):2525-2535 (2016).
Hockemeyer, D., et al., "Efficient Targeting of Expressed and Silent Genes in Human ESCs and iPSCs Using Zinc-Finger Nucleases," Nat. Biotechnol. 27(9):851-857 (2009).
Hockemeyer, D., et al., "Genetic Engineering of Human luripotent Cells Using TALE Nucleases," Nat. Biotechnol. 29:731-734 (2011).
Holt, N, et al., "Zinc Finger Nuclease-Mediated CCR5 Konockout Hematopoietic Stem Cell Transplantation Controls HIV-1 In Vivo," Nat. Biotechnol. 28(8):839-847 (2010).
Horvath, P., et al., "CRISPR/Cas, The Immune System of Bacteria and Archaea," Science 327(5962):167-170 (2010).
Horvath, P., et al., "RNA-Guided Genome Editing A La Carte," Cell Res. 23:733-734 (2013).
Hou, Z., et al., "Efficient Genome Engineering in Human Pluripotent Stem Cells Using Cas9 from Neisseria Meningitidis," Proc. Natl. Acad. Sci. U.S.A. 110(39):15644-15649 (2013).
Hsu, P.D., et al., "DNA Targeting Specificity of RNA-Guided Cas9 Nucleases," Nat. Biotechnol. 31(9):827-832 (2013).

(56) References Cited

OTHER PUBLICATIONS

Huang, X., et al., "Production of Gene-Corrected Adult Beta Globin Protein in Human Erythrocytes Differentiated from Patient iPSCs After Genome Editing of the Sickle Point Mutation," Stem Cells 33:1470-1479 (2015).
Hwang, W. Y., et al., "Heritable and Precise Zebrafish Genome Editing Using a CRISPR-Cas System," PLoS One 8(7):e68708 (2013).
Hwang, W. Y., et al., "Efficient Genome Editing in Zebrafish Using a CRISPR-Cas System," Nat. Biotechnol. 31(3):227-229 (2013).
Hyun, P. S., et al., "Therapeutic CRISPR/Cas9 Genome Editing for Treating Sickle Cell Disease," Blood 128(22):4703 (2016).
Iyama, T., et al., "DNA Repair Mechanisms in Dividing and Non-Dividing Cells," DNA Repair (Amst.) 12(8):620-636 (2013).
Iyer, L. M., et al., "Prediction of Novel Families of Enzymes Involved in Oxidative and Other Complex Modifications of Bases in Nucleic Acids," Cell Cycle 8(11):1698-1710 (2009).
Jiang, W., et al., "RNA-Guided Editing of Bacterial Genomes Using CRISPR-Cas Systems," Nat. Biotechnol. 31(3):233-239 (2013).
Jinek, M., et al., "A Programmable Dual-RNA-Guided DNA Endonuclease in Adaptive Bacterial Immunity," Science 337(6096):816-821 (2012).
Jinek, M., et al., "Structures of Cas9 Endonucleases Reveal RNA-Mediated Conformational Activation," Science 343(6176):1247997 (2014).
Jinek, M., et al., "RNA-Programmed Genome Editing in Human Cells," eLife 2:e00471 (2013).
Joung, J., et al., "Genome-Scale CRISPR-Cas9 Knockout and Transcriptional Activation Screening," Nat. Protoc. 12(4):828-863 (2017).
Kaiser, J., "The Gene Editor CRISPR Won't Fully Fix Sick People Anytime Soon. Here's Why," (May 3, 2016), Biol., Technol, CRISPR, DOI: 10.1126/science.aaf5689, 5 pages.
Karolchik, D., et al., "The UCSC Table Browser Data Retrieval Tool," Nucleic Acids Research 32:D493-496 (2004).
Karvelis, T., et al., "crRNA and tracrRNA Guide Cas9-Mediated DNA Interference in *Streptococcus thermophilus*," RNA Biol. 10(5):841-851 (2013).
Kent, W. J., et al., "The Human Genome Browser at UCSC," Genome Research 12:996-1006 (2002).
Keryer-Bibens, C., et al., "Tethering of Proteins to RNAs by Bacteriophage Proteins," Biol. Cell, 100:125-138 (2008).
Khalil, A. S., et al., "Synthetic Biology: Applications Come of Age," Nat. Rev. Genet. 11(5):367-379 (2010).
Kim, H.S., et al., "Problems Encountered in Detecting a Targeted Gene by the Polymerase Chain Reaction," Gene 103:227-233 (1991).
Kim, Y.G., et al., "Hybrid Restriction Enzymes: Zinc Finger Fusions to Fok I Cleavage Domain," Proc. Natl. Acad. Sci. USA 93:1156-1160 (1996).
Kim, E., et al., "In Vivo Genome Editing with a Small Cas9 Orthologue Derived from Campylobacter Jejuni," Nat. Commun. 8:14500 (2017).
King, N. M.P., et al., "En Route to Ethical Recommendations for Gene Transfer Clinical Trials," Mol. Ther. 16(3):432-438 (2008).
Kleinstiver, B.P., et al., "Broadening the Targeting Range of *Staphylococcus aureus* CRISPR-Cas9 by Modifying PAM Recognition," Nat. Biotechnol. 33(12):1293-1298 (2015).
Kleinstiver, B.P., et al., "Engineered CRISPR-Cas9 Nucleases with Altered PAM Specificities," Nature 523(7561):481-485 (2015).
Kleinstiver, B.P., et al., "High-Fidelity CRISPR-Cas9 Nucleases with No. Detectable Genome-Wide Off-Target Effects," Nature 529(7587):490-495 (2016).
Koike-Yusa, H., et al., "Genome-Wide Recessive Genetic Screening in Mammalian Cells with a Lentiviral CRISPR-Guide RNA Library," Nat. Biotechnol. 32(3):267-273 (2014).
Komor, A.C., et al., "Programmable Editing of a Target Base in Genomic DNA Without Double-Stranded DNA Cleavage," Nature 533(7603):420-424 (2016).
Kosuri, S., et al., "A Scalable Gene Synthesis Platform Using High-Fidelity DNA Microchips," Nat. Biotechnol. 28(12):1295-1299 (2010).
Kurita, R., et al., "Establishment of Immortalized Human Erythroid Progenitor Cell Lines Able to Produce Enucleated Red Blood Cells," PLoS One 8(3):e59890 (2013).
Lambowitz, A. M., et al., "Group II Introns: Mobile Ribozymes that Invade DNA," Cold Spring Harb. Perspect. Biol. 3:a003616 (2011).
Langmead, B., et al., "Ultrafast and Memory-Efficient Alignment of Short DNA Sequences to the Human Genome," Genome Biology 10(3):R25 (2009).
Lederer, C. W., et al., "Beta Testing: Preclinical Genome Editing in Beta-Globin Disorders," Cell Gene Therapeutic Insights 1(2):231-242 (2015).
Lee, J.H., et al., "A Robust Approach to Identifying Tissue-Specific Gene Expression Regulatory Variants Using Personalized Human Induced Pluripotent Stem Cells," PLoS Genetics 5(11):e1000718 (2009).
Lee, J., et al., "Non-Endocytic Delivery of Functional Engineered Nanoparticles into the Cytoplasm of Live Cells Using a Novel, High-Throughput Microfluidic Device," Nano Lett. 12(12):6322-6327 (2012).
Lee, J. K., et al., "Directed evolution of CRISPR-Cas9 to Increase Its Specificity," Nat. Commun. 9:3048 (2018).
Li, G.M., "Mechanisms and Functions of DNA Mismatch Repair," Cell Res. 18(1):85-98 (2008).
Li, T., et al., "TAL Nucleases (TALNs): Hybrid Proteins Composed of TAL Effectors and FokI DNA-Cleavage Domain," Nucl. Acids Res.39(1): 359-372 (2011).
Li, H., et al., "In Vivo Genome Editing Restores Hemostasis in a Mouse Model of Hemophilia," Nature 475(7355):217-221 (2011).
Li, T., et al., "Modularly Assembled Designer TAL Effector Nucleases for Targeted Gene Knockout and Gene Replacement in Eukaryotes," Nucl. Acids Res. 39(14):6315-6325 (2011).
Liang, P., et al., "CRISPR/Cas9-Mediated Gene Editing in Human Tripronuclear Zygotes," Protein Cell 6(5):363-372 (2015).
Lidonnici, M. R., et al., "Gene Therapy and Gene Editing Strategies for Hemoglobinopathies," Blood Cells, Molecules & Diseases 70:87-101 (2018).
Lombardo, A., et al., "Gene Editing in Human Stem Cells Using Xinc Finger Nucleases and Integrase-Defective Lentiviral Vector Delivery," Nat. Biotechnol. 25(11):1298-1306 (2007).
Lorenz, R., et al., "ViennaRNA Package 2.0," Algorithms for Molecular Biology 6:26 (2011).
Maeder, M. L., et al., "CRISPR RNA-Guided Activation of Endogenous Human Genes," Nat. Methods 10:977-979 (2013).
Maeder, M. L., et al., "Rapid "Open-Source" Engineering of Customized Zinc-Finger Nucleases for Highly Efficient Gene Modification," Mol. Cell 31(2):294-301 (2008).
Makarova, K. S., et al., "A Putative RNA-Interference-Based Immune System in Prokaryotes: Computational Analysis of the Predicted Enzymatic Machinery, Functional Analogies with Eukaryotic RNAi, and Hypothetical Mechanisms of Action," Biol. Direct. 1:7 (2006).
Makarova, K. S., et al., "Unification of Cas Protein Families and a Simple Scenario for the Origin and Evolution of CRISPR-Cas Systems," Biol. Direct 6:38 (2011).
Makarova, K.S., et al., "Evolution and Classification of the CRISPR-Cas Systems," Nat. Rev. Microbiol. 9(6):467-477 (2011).
Mali, P., et al., "CAS9 Transcriptional Activators for Target Specificity Screening and Paired Nickases for Cooperative Genome Engineering," Nat. Biotechnol. 31:833-838 (2013).
Mali, P., et al., "Cas9 as a Versatile Tool for Engineering Biology," Nat. Methods 10(10):957-963 (2013).
Mali, P., et al., "RNA-Guided Human Genome Engineering Via Cas9," Science 339(6121):823-826 (2013).
Mantovani, R., et al., "The Effects of HPFH Mutations in the Human Gamma-Globin Promoter on Binding of Ubiquitous and Erythroid Specific Nuclear Factors," Nucleic Acids Res. 16(16):7783-7797 (1988).
Marteijn, J.A., et al., "Understanding Nucleotide Excision Repair and Its Role in Cancer and Ageing," Nat. Rev. Mol. Cell Biol. 15(7):465-481 (2014).

(56) References Cited

OTHER PUBLICATIONS

Martyn, G.E., et al., "The Regulation of Human Globin Promoters by CCAAT Box Elements and the Recruitment of NF-Y," Biochim. Biophys. Acta 1860(5):525-536 (2017).
Mathews, D. H., et al., "Expanded Sequence Dependence of Thermodynamic Parameters Improves Prediction of RNA Secondary Structure," J. Mol. Biol. 288:911-940 (1999).
Miller, J. C., et al., "An Improved Zinc-Finger Nuclease Architecture for Highly Specific Genome Editing," Nat. Biotechnol. 25:778-785 (2007).
Miller, J. C., et al., "A TALE Nuclease Architecture for Efficient Genome Editing," Nat. Biotechnol. 29(2):143-150 (2011).
Miyagishim M., et al., "U6 Promoter-Driven siRNAs with Four Uridine 3' Overhangs Efficiently Suppress Targeted Gene Expression in Mammalian Cells," Nat. Biotechnol. 20(5):497-500 (2002).
Moscou, M. J., et al., "A Simple Cipher Governs DNA Recognition by TAL Effectors," Science 326(5959):1501 (2009).
Myers, E. W., et al., "Optimal Alignments in Linear Space," Comput. Appl. Biosci. 4(1):11-17 (1988).
Nakamura, Y., et al., "Codon Usage Tabulated From International DNA Sequence Databases: Status for the Year 2000," Nucl. Acids Res. 28(1):292 (2000).
Needleman, S. B., et al., "A General Method Applicable to the Search for Similarities in the Amino Acid Sequence of Two Proteins," J. Mol. Biol. 48(3):443-453 (1970).
Nishimasu, H., et al., "Crystal Structure of Cas9 in Complex with Guide RNA and Target DNA," Cell 156(5):935-949 (2014).
Nishimasu, H., et al., "Crystal Structure of *Staphylococcus aureus* Cas9," Cell 162:1113-1126 (2015).
Nishimasu, H., et al., "Engineered CRISPR-Cas9 Nuclease with Expanded Targeting Space," Science 361(6408):1259-1262 (2018).
Notta, F., et al., "Isolation of Single Human Hematopoietic Stem Cells Capable of Long-Term Multilineage Engraftment," Science 333(6039):218-221 (2011).
Ou, Z., et al., "The Combination of CRISPR/Cas9 and iPSC Technologies in the Gene Therapy of Human Beta-Thalassemia in Mice," Scientific Reports 6(1):32463 (2016).
Paix, A., et al., "Precision Genome Editing Using CRISPR-Cas9 and Linear Repair Templates in C. Elegans," Methods 121-121:86-93 (2017).
Pattanayak, V., et al., "High-Throughput Profiling of Off-Target DNA Cleavage Reveals RNA-Programmed Cas9 Nuclease Specificity," Nat. Biotechnol. 31:839-843 (2013).
Pattanayak, V., et al., "Revealing Off-Target Cleavage Specificities of Zinc-Finger Nucleases by In Vitro Selection," Nat. Methods 8:765-770 (2011).
Patterson, S. S., et al., "Codon Optimization of Bacterial Luciferase (lux) for Expression in Mammalian Cells," J. Ind. Microbio. Biotechnology 32:115-123 (2005).
Pearson, W. R., et al., "Improved Tools for Biological Sequence Comparison," Proc. Natl. Acad. Sci. U.S.A. 85(8):2444-2448 (1988).
Pellissier, L. P., et al., "Specific Tools for Targeting and Expression in Muller Glial Cells," Mol. Ther. Methods Clin. Dev. 1:14009 (2014).
Peng, R., et al., "Potential Pitfalls of CRISPR/Cas9-Mediated Genome Editing," FEBS J. 283:1218-1231 (2016).
Perez, E. E., et al., "Establishment of HIV-1 Resistance in CD4+ T Cells by Genome Editing Using Zinc-Finger Nucleases," Nat. Biotechnol. 26:808-816 (2008).
Porteus, M. H., et al., "Gene Targeting Using Zinc Finger Nucleases," Nat. Biotechnol. 23(8):967-973 (2005).
Pougach, K., et al., "Transcription, Processing and Function of CRISPR Cassettes in *Escherichia coli*," Mol. Microbiol. 77(6):1367-1379 (2010).
Pride, D. T., et al., "Analysis of Streptococcal CRISPRs from Human Saliva Reveals Substantial Sequence Diversity Within and Between Subjects Over Time," Genome Res. 21:126-136 (2011).
Purnick, P. E. M., et al., "The Second Wave of Synthetic Biology: From Modules to Systems," Nat. Rev. Mol. Cell Biol. 10(6):410-422 (2009).
Qi, L. S., et al., "Repurposing CRISPR as an RNA-Guided Platform for Sequence-Specific Control of Gene Expression," Cell 152:1173-1183 (2013).
Qi, L., et al., "RNA Processing Enables Predictable Programming of Gene Expression," Nat. Biotechnol. 30(10):1002-1007 (2012).
Quinlan, A. R., et al., "BEDTools: A Flexible Suite of Utilities for Comparing Genomic Features," Bioinformatics 26(6):841-842 (2010).
Ran, F.A., et al., "Double Nicking by RNA-Guided CRISPR Cas9 for Enhanced Genome Editing Specificity," Cell 154(6):1380-1389 (2013).
Ran, F. A., et al., "In Vivo Genome Editing Using *Staphylococcus aureus* Cas9," Nature 520(7546):186-191 (2015).
Rand, T. A., et al., "Argonaute2 Cleaves the Anti-Guide Strand of siRNA During RISC Activation," Cell 123:621-629 (2005).
Raymond, C. S., et al., "High-Efficiency FLP and PhiC31 Site-Specific Recombination in Mammalian Cells," PLoS One 2(1):e162 (2007).
Rebar, E. J., et al., "Zinc Finger Phage: Affinity Selection of Fingers with New DNA-Binding Specificities," Science 263(5147):671-673 (1994).
Rebar, E. J., et al., "Induction of Angiogenesis in a Mouse Model Using Engineered Transcription Factors," Nat. Med. 8(12):1427-1432 (2008).
Recht, M. I., et al., "Monitoring Assembly of Ribonucleoprotein Complexes by Isothermal Titration Calorimetry," Methods in Mol. Biol. 488:117-127 (2008).
Regalado, A., "Who Owns the Biggest Biotech Discovery of the Century?," MIT Technology Review, Dec. 4, 2014, http://www.technologyreview.com/featuredstory/532796/who-owns-the-biggest- -biotech-discovery-of-the-century/.
Reyon, D., et al., "FLASH Assembly of TALENs for High-Throughput Genome Editing," Nat. Biotech. 30:460-465 (2012).
Rho, M., et al. "Diverse CRISPRs Evolving in Human Microbiomes." PLoS Genetics 8(6):e1002441 (2012).
Richardson, C. D., et al., "Enhancing Homology-Directed Genome Editing by Catalytically Active and Inactive CRISPR-Cas9 Using Asymmetric Donor DNA," Nat. Biotechnol. 34(3):339-344 (2016).
Sander, J. D., et al., "Zinc Finger Targeter (ZiFiT): An Engineered Zinc Finger/Target Site Design Tool," Nucleic Acids Res. 35:W599-W605 (2007).
Sander, J. D., et al., "ZiFIT (Zinc Finger Targeter): An Updated Zinc Finger Engineering Tool," Nucleic Acids Res. 38:W462-468 (2010).
Sander, J. D., et al., "CRISPR-Cas Systems for Editing, Regulating and Targeting Genomes," Nat. Biotechnol. 32(4):347-355 (2014).
Sanders, R., "Cheap and Easy Technique to Snip DNA Could Revolutionize Gene Therapy", Berkeley News Online, pp. 1-3 (Jan. 7, 2013).
Sanjana, N. E., et al., "A Transcription Activator-Like Effector (TALE) Toolbox for Genome Engineering," Nat. Protoc. 7(1):171-192 (2012).
Sankaran, V. G., et al., "Human Fetal Hemoglobin Expression is Regulated by the Developmental Stage-Specific Repressor BCL11A," Science 322(5909):1839-1842 (2008).
Sapranauskas, R., et al., "The *Streptococcus thermophilus* CRISPR-Cas System Provides Immunity in *Escherichia coli*," Nucl. Acids Res.39:9275-9282 (2011).
Sather, B. D., et al., "Efficient Modification of CCR5 in Primary Human Hematopoietic Cells Using a Mega TAL Nuclease and AAV Donor Template," Sci. Trans. Med. 7(307):307ra156 (2015).
Schramm, L., et al., "Recruitment of RNA Polymerase III to Its Target Promoters," Genes Devel. 16:2593-2620 (2002).
Selleck, W., et al., "Biophysical Characterization and Direct Delivery of S. Pyogenes Cas9 Ribonucleoprotein Complexes," Editas Medicine, Apr. 27, 2015, retrieved from URL http://www.editasmedicine.com/documents/ASGCT_poster_2015_Will.pdf.
Shalem, O., et al., "Genome-Scale CRISPR-Cas9 Knockout Screening in Human Cells," Science 343:84 (2014).
Shanks, P., "CRISPR Opportunities . . . For What? And for Whom?," Biopolitical Times, Dec. 4, 2014, http://www.biopoliticaltimes.org/article.php?id=8235.
Sharma, R., et al., "In Vivo Genome Editing of the Albumin Locus as a Platform for Protein Replacement Therapy," Blood 126(15):1777-1784 (2015).

(56) References Cited

OTHER PUBLICATIONS

Shayakhmetov, D. M., et al., "Analysis of Adenovirus Sequestration in the Liver, Transduction of Hepatic Cells, and Innate Toxicity after Injection of Fiber-Modified Vectors," J. Virol. 78(10):5368-5381 (2004).
Shen, B., et al., "Generation of Gene-Modified Mice via Cas9/RNA-Mediated Gene Targeting," Cell Res. 23:720-723 (2013).
Shmakov, S., et al., "Discovery and Functional Characterization of Diverse Class 2 CRISPR-Cas Systems," Mol. Cell 60(3):385-397 (2015).
Smith, C., et al., "Efficient and Allele-Specific Genome Editing of Disease Loci in Human iPSCs," Mol. Ther. 23(3):570-577 (2015).
Smith, T. F., et al., "Comparison of Biosequences," Adv. Appl. Math. 2(4):482-489 (1981).
Song, B., et al., "Improved Hematopoietic Differentiation Efficiency of Gene-Corrected Beta-Thalassemia Induced Pluripotent Stem Cells by CRISPR/Cas9 System," Stem Cells Devel. 24(9):1053-1065 (2015).
Sontheimer, E., "Project 7: Establishing RNA-Directed DNA Targeting in Eukaryotic Cells; Project dates: Nov. 16, 2011 to Dec. 31, 2012," Physical Sciences—Oncology Center (Feb. 4, 2012).
Sternberg, S.H., et al., "DNA Interrogation by the CRISPR RNA-Guided Endonuclease Cas9," Nature 507(7490):62-67 (2014).
Strecker, J., et al., "Engineering of CRISPR-Cas12b for Human Genome Editing," Nat. Commun. 10:212 (2019).
Sugimoto, N., et al., "Thermodynamic Parameters to Predict Stability of RNA/DNA Hybrid Duplexes," Biochem. 34:11211-11216 (1995).
Sugimoto, N., et al., "Thermodynamics-Structure Relationship of Single Mismatches in RNA/DNA Duplexes," Biochem. 39(37):11270-11281 (2000).
Superti-Furga, G., et al., "The -117 Mutation in Greek HPFH Affects the Binding of Three Nuclear Factors to the CCAAT Region of the Gamma-Globin Gene," EMBO J. 7(10):3099-3107 (1988).
Szczepek, M., et al., "Structure-Based Redesign of the Dimerization Interface Reduces the Toxicity of Zinc-Finger Nucleases," Nat. Biotechnol. 25:786-793 (2007).
Tang, L., et al., "CRISPR/Cas9-Mediated Gene Editing in Human Zygotes Using Cas9 Protein," Mol. Genet. Genom. 292(3):525-533 (2017).
Teng, F., et al., "Repurposing CRISPR-Cas12b for Mammalian Genome Engineering," Cell Discov. 4:63 (2018).
Terns, M. P., et al., "CRISPR-based Adaptive Immune Systems," Curr. Opin. Microbiol. 14:321-327 (2011).
Thein, S.L., et al., "Control of Fetal Hemoglobin: New Insights Emerging from Genomics and Clinical Implications," Hum. Mol. Genet. 18(R2):R216-R223 (2009).
Thorpe, S. J., et al., "Immunochemical Estimation of Haemoglobin Types in Red Blood Cells by FACS Analysis," Br. J. Haematol. 87:125-132 (1994).
Thurman, R. E., et al., "The Accessible Chromatin Landscape of the Human Genome," Nature 489(7414):75-82 (2012).
Tolia, N. H., et al., "Slicer and the Argonautes," Nat. Chem. Biol. 3(1):36-43 (2007).
Tolpin, Thomas W., Third Party Observation for EP13793997.1, Jan. 6, 2015, 50 pages.
Traxler, E., et al., "Genome Editing Recreates Hereditary Persistence of Fetal Hemoglobin in Primary Human Erythroblasts," Blood J. 126(23):640 (2015).
Traxler, E. A., et al., "A Genome-Editing Strategy to Treat Beta-Hemoglobinopathies that Recapitulates a Muation Associated with a Benign Genetic Condition," Nat. Med. 22(9):987-990 (2016).
Truong, L. N., et al., "Microhomology-Mediated End Joining and Homologous Recombination Share the Initial End Resection Step to Repair DNA Double-Strand Breaks in Mammalian Cells," PNAS 110(19):7720-7725 (2013).
Tsai, S. Q., et al., "Dimeric CRISPR RNA-Guided FokI Nucleases for Highly Specific Genome Editing," Nat. Biotechnol. 32(6):569-576 (2014).
Tsai, S.Q., et al., "Open-Source GuideSeq Software for Analysis of GUIDE-Seq Data," Nat. Biotechnol. 34(5):483 (2016).
Urnov, F. D., et al., "Highly Efficient Endogenous Human Gene Correction Using Designed Zinc-Finger Nucleases," Nature 435:646-651 (2005).
Van Der Oost, J., "New Tool for Genome Surgery," Science 336:768-768 (2013).
Van Der Ploeg, J. R., "Analysis of CRISPR in *Streptococcus* Mutans Suggests Frequent Occurrence of Acquired Immunity Against Infection by M102-Like Bacteriophages," Microbiology 155:1966-1976 (2009).
Van Overbeek, M., et al., "DNA Repair Profiling Reveals Nonrandom Outcomes at Cas9-Mediated Breaks," Mol. Cell 63:633-646 (2016).
Waber, P.G., et al., "Concordance of a Point Mutation 5' to the A Gamma-Globin Gene with A Gamma Beta + Hereditary Persistence of Fetal Hemoglobin in Greeks," Blood 67(2):551-554 (1986).
Wang, H., et al., "One-Step Generation of Mice Carrying Mutations in Multiple Genes By CRISPR/Cas-Mediated Genome Engineering," Cell 153(4):910-918 (2013).
Wang, J., et al., "Homology-Driven Genome Editing in Hematopoietic Stem and Progenitor Cells Using ZFN mRNA and AAV6 Donors," Nat. Biotechnol. 33(12):1256-1263 (2015).
Wang, J., et al., "Highly Efficient Homology-Driven Genome Editing in Human T Cells by Combining Zinc-Finger Nuclease mRNA and AAV6 Donor Delivery," Nucleic Acids Res. 44(3):e30 (2016).
Wang, T., et al., "Genetic Screens in Human Cells Using the CRISPR-Cas9 System," Science 343(6166):80-84 (2013).
Wang, J., et al., "xCas9 Expands the Scope of Genome Editing with Reduced Efficiency in Rice," Plant Biotechnol. J. 17:709-711 (2019).
Wiedenheft, B., et al., "RNA-Guided Genetic Silencing Systems in Bacteria and Archaea," Nature 482:331-338 (2012).
Wu, X., et al., "Genome-Wide Binding of the CRISPR Endonuclease Cas9 in Mammalian Cells," Nat. Biotechnol. 32(7):670-676 (2014).
Wu, Y., et al., "Correction of a Genetic Disease in Mouse via Use of CRISPR-Cas9," Cell Stem Cell 13(6):659-662 (2013).
Wu, Y., et al., "Highly Efficient Therapeutic Gene Editing of Human Hematopoietic Stem Cells," Nat. Med. 25(5):776-783 (2019).
Xiao, A., et al., "CasOT: A Genome-Wide Cas9/gRNA Off-Target Searching Tool," Bioinformatics 30(8):1180-1182 (2014).
Xu, Q., et al., "Design of 240,000 Orthogonal 25mer DNA Barcode Probes," Proc. Natl. Acad. Sci. 106(7):2289-2294 (2009).
Xu, J., et al., "Transcriptional Silencing of {Gamma}-Globin by BCL11A Involves Long-Range Interactions and Cooperation with SOX6," Genes Dev. 24(8):783-798 (2010).
Yamano, T., et al., "Crystal Structure of Cpf1 in Complex with Guide RNA and Target DNA," Cell 165(4):949-962 (2016).
Yan, W. X., et al., "Functionally Diversse Type V CRISPR-Cas Systems," Science 363:88-91 (2019).
Yang, H., et al., "One-Step Generation of Mice Carrying Reporter and Conditional Alleles by CRISPR/Cas-Mediated Genome Engineering," Cell 154(6):1370-1390 (2013).
Zetsche, B., et al., "A Split-Cas9 Architecture for Inducible Genome Editing and Transcription Modulation," Nat. Biotechnol. 33(2):139-142 (2015).
Zetsche, B., et al., "Cpf1 Is a Single RNA-Guided Endonuclease of a Class 2 CRISPR-Cas System," Cell 163(3):759-771 (2015).
Zou, J., et al., "Gene Targeting of a Disease-Related Gene in Human Induced Pluripotent Stem and Embryonic Stem Cells," Cell Stem Cell 5(1):97-110 (2009).
Zou, J., et al., "Site-Specific Gene Correction of a Point Mutation in Human iPS Cells Derived from an Adult Patient with Sickle Cell Disease," Blood 118(17):4599-4608 (2011).
European Patent Office, International Search Report and Written Opinion dated Jun. 24, 2015 for PCT/US2015/019064.
European Patent Office, International Search Report and Written Opinion dated Jul. 1, 2015 for PCT/US2015/019790.
European Patent Office, International Search Report and Written Opinion dated Sep. 28, 2015 for PCT/US2015/022856.
European Patent Office, International Search Report and Written Opinion dated Jul. 31, 2015 for PCT/US2015/022851.
European Patent Office, International Search Report and Written Opinion dated Aug. 10, 2015 for PCT/US2015/023906.

(56) References Cited

OTHER PUBLICATIONS

European Patent Office, International Search Report and Written Opinion dated Jun. 12, 2017 for PCT/US2017/024163.
European Patent Office, International Search Report and Written Opinion dated Jul. 28, 2016 for PCT/US2016/029252.
European Patent Office, International Search Report and Written Opinion dated May 29, 2017 for PCT/US2017/022377.
European Patent Office, International Search Report and Written Opinion dated Aug. 20, 2018 for PCT/US2018/022516.
European Patent Office, International Search Report and Written Opinion dated Dec. 3, 2018 for PCT/US2018/032172.
European Patent Office, International Search Report and Written Opinion dated Mar. 13, 2019 for PCT/US2018/059700.
European Patent Office, International Search Report and Written Opinion dated Jul. 1, 2019 for PCT/US2019/022360.
United States Patent and Trademark Office, International Search Report and Written Opinion for PCT/US2013/075317, dated Apr. 15, 2014, 12 pages.
United States Patent and Trademark Office, International Search Report and Written Opinion for PCT/US2013/075326, dated Aug. 22, 2014, 13 pages.
United States Patent and Trademark Office, International Search Report and Written Opinion for PCT/US2014/027335, dated Jul. 16, 2014, 13 pages.
United States Patent and Trademark Office, International Search Report and Written Opinion for PCT/US2014/028630, dated Jul. 24, 2014, 9 pages.
Bothmer, A., et al., "Detection and Modulation of DNA Translocations During Multi-Gene Genome Editing in T Cells," The CRISPR Journal 3(3):177-187 (2020).
Cost, G. J., et al., Geneseq Accession No. BBD49192 (2014), 2 pages.
Fu, B. X. H., et al., "Landscape of Target: Guide Homology Effects on Cas9-Mediated Cleavage," Nucl. Acids Res. 42(22):13778-13787 (2014).
Giannoukos, G., et al., "UDiTaS™, a genome editing detection method for indels and genome rearrangements," BMC Genomics 19:212 (2018).
Giarratana, M. C., et al., "Ex vivo generation of fully mature human red blood cells from hematopoietic stem cells," Nat. Biotechnol. 23(1):69-74 (2005).
Hu, X., "CRISPR/Cas9 System and Its Applications in Human Hematopoietic Cells," Blood Cells, Molecules & Diseases 62:6-12 (2016).
Kleinstiver, B. P., et al., "Engineered CRISPR-Cas12a variants with increased activities and improved targeting ranges for gene, epigenetic and base editing," Nat. Biotechnol. 37(3):276-282 (2019).
Kosicki, M., et al., "Repair of Double-Strand Breaks Induced by CRISPR-Cas9 Leads to Large Deletions and Complex Rearrangements," Nat. Biotechnol. 36(8):765-771 (2018).
Krieg, A. M., et al., GeneSeq Accession No. BAY71542 (2013).
Metais, J.Y., et al., "Genome Editing of HBG1 and HBG2 to Induce Fetal Hemoglobin," Blood Adv. 3(21):3379-92 (2019).
Pausch, P., et al., "CRISPR-Caso from Huge Phages is a Hypercompact Genome Editor," Science ;369(6501):333-337 (2020).
Reeks, J., et al., "Structure of a Dimeric Crenarchaeal Cas6 Enzyme with an Atypical Active Site for CRISPR RNA Processing," Biochem. J. 452:223-230 (2013).
Strohkendl, I., et al., "Kinetic Basis for DNA Target Specificity of CRISPR-Cas12a," Mol Cell. 71(5):816-824 (2018).
Swarts, D. C., et al., "Cas9 Versus Cas 12a/Cpf1: Structure-Function Comparisons and Implications for Genome Editing," WIREs RNA 9:e1481 (2018).
Vidigal, J. A., et al.,"Rapid and Efficient One-Step Generation of Paired gRNA CRISPR-Cas9 Libraries," Nat. Commun. 6:8083 (2015).
European Patent Office, International Search Report and Written Opinion dated Mar. 6, 2020 for PCT/US2019/063766, 12 pages.
Bernaudin, F., et al., "Long-Term Results of Related Myeloablative Stem-Cell Transplantation to Cure Sickle Cell Disease," Blood 110(7):2749-2756 (2007).
Steinberg, M. H., et al., "Fetal Hemoglobin in Sickle Cell Anemia: A Glass Half Full?" Blood 123(4):481-485 (2014).
Van Diemen, F. R., et al., "CRISPR/Cas9, A Powerful Tool to Target Human Herpesviruses," Cell. Microbiol. 19:e12694 (2017).
Walters, M. C., et al., "Bone Marrow Transplantation for Sickle Cell Disease," New Engl. J. Med. 335(6):369-376 (1996).
European Patent Office, International Search Report and Written Opinion dated Nov. 22, 2022 for PCT/US2022/039192, 13 pages.

* cited by examiner

Enriched in high-HbF fraction (Enrichment >=2 [log2])

○ Not disrupting the distal CCAAT-box
△ Disrupting 1-2nt of the distal CCAAT-box
□ Disrupting 3-5nt of the distal CCAAT-box No/Low enrichment in high-HbF fraction
(Enrichment <2 [log2])

○ Not disrupting the distal CCAAT-box
△ Disrupting 1-2nt of the distal CCAAT-box
□ Disrupting 3-5nt of the distal CCAAT-box

SEQUENCE LISTING

<160> NUMBER OF SEQ ID NOS: 987

<210> SEQ ID NO 1
<211> LENGTH: 1345
<212> TYPE: PRT
<213> ORGANISM: Streptococcus mutans
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (759)..(766)
<223> OTHER INFORMATION: RuvC-like domain
<220> FEATURE:
<221> NAME/KEY: misc_feature
<222> LOCATION: (837)..(863)
<223> OTHER INFORMATION: HNH-like domain
<220> FEATURE:
<221> NAME/KEY: misc_feature
<222> LOCATION: (982)..(989)
<223> OTHER INFORMATION: RuvC-like domain

<400> SEQUENCE: 1

```
Met Lys Lys Pro Tyr Ser Ile Gly Leu Asp Ile Gly Thr Asn Ser Val
1               5                   10                  15

Gly Trp Ala Val Val Thr Asp Asp Tyr Lys Val Pro Ala Lys Lys Met
            20                  25                  30

Lys Val Leu Gly Asn Thr Asp Lys Ser His Ile Glu Lys Asn Leu Leu
        35                  40                  45

Gly Ala Leu Leu Phe Asp Ser Gly Asn Thr Ala Glu Asp Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Glu Glu Met Gly Lys Val Asp Asp Ser
                85                  90                  95

Phe Phe His Arg Leu Glu Asp Ser Phe Leu Val Thr Glu Asp Lys Arg
            100                 105                 110

Gly Glu Arg His Pro Ile Phe Gly Asn Leu Glu Glu Glu Val Lys Tyr
        115                 120                 125

His Glu Asn Phe Pro Thr Ile Tyr His Leu Arg Gln Tyr Leu Ala Asp
    130                 135                 140

Asn Pro Glu Lys Val Asp Leu Arg Leu Val Tyr Leu Ala Leu Ala His
145                 150                 155                 160

Ile Ile Lys Phe Arg Gly His Phe Leu Ile Glu Gly Lys Phe Asp Thr
                165                 170                 175

Arg Asn Asn Asp Val Gln Arg Leu Phe Gln Glu Phe Leu Ala Val Tyr
            180                 185                 190

Asp Asn Thr Phe Glu Asn Ser Ser Leu Gln Glu Gln Asn Val Gln Val
        195                 200                 205

Glu Glu Ile Leu Thr Asp Lys Ile Ser Lys Ser Ala Lys Lys Asp Arg
    210                 215                 220

Val Leu Lys Leu Phe Pro Asn Glu Lys Ser Asn Gly Arg Phe Ala Glu
225                 230                 235                 240

Phe Leu Lys Leu Ile Val Gly Asn Gln Ala Asp Phe Lys Lys His Phe
                245                 250                 255

Glu Leu Glu Glu Lys Ala Pro Leu Gln Phe Ser Lys Asp Thr Tyr Glu
            260                 265                 270

Glu Glu Leu Glu Val Leu Leu Ala Gln Ile Gly Asp Asn Tyr Ala Glu
        275                 280                 285
```

-continued

```
Leu Phe Leu Ser Ala Lys Lys Leu Tyr Asp Ser Ile Leu Leu Ser Gly
    290                 295                 300

Ile Leu Thr Val Thr Asp Val Gly Thr Lys Ala Pro Leu Ser Ala Ser
305                 310                 315                 320

Met Ile Gln Arg Tyr Asn Glu His Gln Met Asp Leu Ala Gln Leu Lys
                325                 330                 335

Gln Phe Ile Arg Gln Lys Leu Ser Asp Lys Tyr Asn Glu Val Phe Ser
            340                 345                 350

Asp Val Ser Lys Asp Gly Tyr Ala Gly Tyr Ile Asp Gly Lys Thr Asn
        355                 360                 365

Gln Glu Ala Phe Tyr Lys Tyr Leu Lys Gly Leu Leu Asn Lys Ile Glu
    370                 375                 380

Gly Ser Gly Tyr Phe Leu Asp Lys Ile Glu Arg Glu Asp Phe Leu Arg
385                 390                 395                 400

Lys Gln Arg Thr Phe Asp Asn Gly Ser Ile Pro His Gln Ile His Leu
                405                 410                 415

Gln Glu Met Arg Ala Ile Ile Arg Arg Gln Ala Glu Phe Tyr Pro Phe
            420                 425                 430

Leu Ala Asp Asn Gln Asp Arg Ile Glu Lys Leu Leu Thr Phe Arg Ile
        435                 440                 445

Pro Tyr Tyr Val Gly Pro Leu Ala Arg Gly Lys Ser Asp Phe Ala Trp
    450                 455                 460

Leu Ser Arg Lys Ser Ala Asp Lys Ile Thr Pro Trp Asn Phe Asp Glu
465                 470                 475                 480

Ile Val Asp Lys Glu Ser Ser Ala Glu Ala Phe Ile Asn Arg Met Thr
                485                 490                 495

Asn Tyr Asp Leu Tyr Leu Pro Asn Gln Lys Val Leu Pro Lys His Ser
            500                 505                 510

Leu Leu Tyr Glu Lys Phe Thr Val Tyr Asn Glu Leu Thr Lys Val Lys
        515                 520                 525

Tyr Lys Thr Glu Gln Gly Lys Thr Ala Phe Phe Asp Ala Asn Met Lys
    530                 535                 540

Gln Glu Ile Phe Asp Gly Val Phe Lys Val Tyr Arg Lys Val Thr Lys
545                 550                 555                 560

Asp Lys Leu Met Asp Phe Leu Glu Lys Glu Phe Asp Glu Phe Arg Ile
                565                 570                 575

Val Asp Leu Thr Gly Leu Asp Lys Glu Asn Lys Val Phe Asn Ala Ser
            580                 585                 590

Tyr Gly Thr Tyr His Asp Leu Cys Lys Ile Leu Asp Lys Asp Phe Leu
        595                 600                 605

Asp Asn Ser Lys Asn Glu Lys Ile Leu Glu Asp Ile Val Leu Thr Leu
    610                 615                 620

Thr Leu Phe Glu Asp Arg Glu Met Ile Arg Lys Arg Leu Glu Asn Tyr
625                 630                 635                 640

Ser Asp Leu Leu Thr Lys Glu Gln Val Lys Lys Leu Glu Arg Arg His
                645                 650                 655

Tyr Thr Gly Trp Gly Arg Leu Ser Ala Glu Leu Ile His Gly Ile Arg
            660                 665                 670

Asn Lys Glu Ser Arg Lys Thr Ile Leu Asp Tyr Leu Ile Asp Asp Gly
        675                 680                 685

Asn Ser Asn Arg Asn Phe Met Gln Leu Ile Asn Asp Asp Ala Leu Ser
    690                 695                 700
```

-continued

```
Phe Lys Glu Glu Ile Ala Lys Ala Gln Val Ile Gly Glu Thr Asp Asn
705                 710                 715                 720

Leu Asn Gln Val Val Ser Asp Ile Ala Gly Ser Pro Ala Ile Lys Lys
                725                 730                 735

Gly Ile Leu Gln Ser Leu Lys Ile Val Asp Glu Leu Val Lys Ile Met
            740                 745                 750

Gly His Gln Pro Glu Asn Ile Val Val Glu Met Ala Arg Glu Asn Gln
        755                 760                 765

Phe Thr Asn Gln Gly Arg Arg Asn Ser Gln Gln Arg Leu Lys Gly Leu
    770                 775                 780

Thr Asp Ser Ile Lys Glu Phe Gly Ser Gln Ile Leu Lys Glu His Pro
785                 790                 795                 800

Val Glu Asn Ser Gln Leu Gln Asn Asp Arg Leu Phe Leu Tyr Tyr Leu
                805                 810                 815

Gln Asn Gly Arg Asp Met Tyr Thr Gly Glu Glu Leu Asp Ile Asp Tyr
            820                 825                 830

Leu Ser Gln Tyr Asp Ile Asp His Ile Ile Pro Gln Ala Phe Ile Lys
        835                 840                 845

Asp Asn Ser Ile Asp Asn Arg Val Leu Thr Ser Ser Lys Glu Asn Arg
    850                 855                 860

Gly Lys Ser Asp Asp Val Pro Ser Lys Asp Val Val Arg Lys Met Lys
865                 870                 875                 880

Ser Tyr Trp Ser Lys Leu Leu Ser Ala Lys Leu Ile Thr Gln Arg Lys
                885                 890                 895

Phe Asp Asn Leu Thr Lys Ala Glu Arg Gly Gly Leu Thr Asp Asp Asp
            900                 905                 910

Lys Ala Gly Phe Ile Lys Arg Gln Leu Val Glu Thr Arg Gln Ile Thr
        915                 920                 925

Lys His Val Ala Arg Ile Leu Asp Glu Arg Phe Asn Thr Glu Thr Asp
    930                 935                 940

Glu Asn Asn Lys Lys Ile Arg Gln Val Lys Ile Val Thr Leu Lys Ser
945                 950                 955                 960

Asn Leu Val Ser Asn Phe Arg Lys Glu Phe Glu Leu Tyr Lys Val Arg
                965                 970                 975

Glu Ile Asn Asp Tyr His His Ala His Asp Ala Tyr Leu Asn Ala Val
            980                 985                 990

Ile Gly Lys Ala Leu Leu Gly Val  Tyr Pro Gln Leu Glu  Pro Glu Phe
        995                 1000                 1005

Val Tyr  Gly Asp Tyr Pro His  Phe His Gly His Lys  Glu Asn Lys
    1010                 1015                 1020

Ala Thr  Ala Lys Lys Phe Phe  Tyr Ser Asn Ile Met  Asn Phe Phe
    1025                 1030                 1035

Lys Lys  Asp Asp Val Arg Thr  Asp Lys Asn Gly Glu  Ile Ile Trp
    1040                 1045                 1050

Lys Lys  Asp Glu His Ile Ser  Asn Ile Lys Lys Val  Leu Ser Tyr
    1055                 1060                 1065

Pro Gln  Val Asn Ile Val Lys  Lys Val Glu Glu Gln  Thr Gly Gly
    1070                 1075                 1080

Phe Ser  Lys Glu Ser Ile Leu  Pro Lys Gly Asn Ser  Asp Lys Leu
    1085                 1090                 1095

Ile Pro  Arg Lys Thr Lys Lys  Phe Tyr Trp Asp Thr  Lys Lys Tyr
    1100                 1105                 1110

Gly Gly  Phe Asp Ser Pro Ile  Val Ala Tyr Ser Ile  Leu Val Ile
```

```
    1115                1120                1125

Ala Asp  Ile Glu Lys Gly Lys  Ser Lys Lys Leu Lys  Thr Val Lys
    1130                1135                1140

Ala Leu  Val Gly Val Thr Ile  Met Glu Lys Met Thr  Phe Glu Arg
    1145                1150                1155

Asp Pro  Val Ala Phe Leu Glu  Arg Lys Gly Tyr Arg  Asn Val Gln
    1160                1165                1170

Glu Glu  Asn Ile Ile Lys Leu  Pro Lys Tyr Ser Leu  Phe Lys Leu
    1175                1180                1185

Glu Asn  Gly Arg Lys Arg Leu  Leu Ala Ser Ala Arg  Glu Leu Gln
    1190                1195                1200

Lys Gly  Asn Glu Ile Val Leu  Pro Asn His Leu Gly  Thr Leu Leu
    1205                1210                1215

Tyr His  Ala Lys Asn Ile His  Lys Val Asp Glu Pro  Lys His Leu
    1220                1225                1230

Asp Tyr  Val Asp Lys His Lys  Asp Glu Phe Lys Glu  Leu Leu Asp
    1235                1240                1245

Val Val  Ser Asn Phe Ser Lys  Lys Tyr Thr Leu Ala  Glu Gly Asn
    1250                1255                1260

Leu Glu  Lys Ile Lys Glu Leu  Tyr Ala Gln Asn Asn  Gly Glu Asp
    1265                1270                1275

Leu Lys  Glu Leu Ala Ser Ser  Phe Ile Asn Leu Leu  Thr Phe Thr
    1280                1285                1290

Ala Ile  Gly Ala Pro Ala Thr  Phe Lys Phe Phe Asp  Lys Asn Ile
    1295                1300                1305

Asp Arg  Lys Arg Tyr Thr Ser  Thr Thr Glu Ile Leu  Asn Ala Thr
    1310                1315                1320

Leu Ile  His Gln Ser Ile Thr  Gly Leu Tyr Glu Thr  Arg Ile Asp
    1325                1330                1335

Leu Asn  Lys Leu Gly Gly Asp
    1340                1345


<210> SEQ ID NO 2
<211> LENGTH: 1368
<212> TYPE: PRT
<213> ORGANISM: Streptococcus pyogenes
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (759)..(766)
<223> OTHER INFORMATION: RuvC-like domain
<220> FEATURE:
<221> NAME/KEY: misc_feature
<222> LOCATION: (837)..(863)
<223> OTHER INFORMATION: HNH-like domain
<220> FEATURE:
<221> NAME/KEY: misc_feature
<222> LOCATION: (982)..(989)
<223> OTHER INFORMATION: RuvC-like domain

<400> SEQUENCE: 2

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45
```

-continued

```
Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460
```

-continued

```
Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
```

```
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290
```

```
Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365


<210> SEQ ID NO 3
<211> LENGTH: 4107
<212> TYPE: DNA
<213> ORGANISM: Streptococcus pyogenes

<400> SEQUENCE: 3

atggataaaa agtacagcat cgggctggac atcggtacaa actcagtggg gtgggccgtg     60

attacggacg agtacaaggt accctccaaa aaatttaaag tgctgggtaa cacggacaga    120

cactctataa agaaaaatct tattggagcc ttgctgttcg actcaggcga gacagccgaa    180

gccacaaggt tgaagcggac cgccaggagg cggtatacca ggagaaagaa ccgcatatgc    240

tacctgcaag aaatcttcag taacgagatg gcaaaggttg acgatagctt tttccatcgc    300

ctggaagaat cctttcttgt tgaggaagac aagaagcacg aacggcaccc catctttggc    360

aatattgtcg acgaagtggc atatcacgaa aagtacccga ctatctacca cctcaggaag    420

aagctggtgg actctaccga taaggcggac ctcagactta tttatttggc actcgcccac    480

atgattaaat ttagaggaca tttcttgatc gagggcgacc tgaacccgga caacagtgac    540

gtcgataagc tgttcatcca acttgtgcag acctacaatc aactgttcga agaaaaccct    600

ataaatgctt caggagtcga cgctaaagca atcctgtccg cgcgcctctc aaaatctaga    660

agacttgaga atctgattgc tcagttgccc ggggaaaaga aaaatggatt gtttggcaac    720

ctgatcgccc tcagtctcgg actgacccca aatttcaaaa gtaacttcga cctggccgaa    780

gacgctaagc tccagctgtc caaggacaca tacgatgacg acctcgacaa tctgctggcc    840

cagattgggg atcagtacgc cgatctcttt ttggcagcaa agaacctgtc cgacgccatc    900

ctgttgagcg atatcttgag agtgaacacc gaaattacta aagcacccct tagcgcatct    960

atgatcaagc ggtacgacga gcatcatcag gatctgaccc tgctgaaggc tcttgtgagg   1020

caacagctcc ccgaaaaata caaggaaatc ttctttgacc agagcaaaaa cggctacgct   1080

ggctatatag atggtggggc cagtcaggag gaattctata aattcatcaa gcccattctc   1140

gagaaaatgg acggcacaga ggagttgctg gtcaaactta acagggagga cctgctgcgg   1200

aagcagcgga cctttgacaa cgggtctatc ccccaccaga ttcatctggg cgaactgcac   1260

gcaatcctga ggaggcagga ggatttttat cctttttctta aagataaccg cgagaaaata   1320

gaaaagattc ttacattcag gatcccgtac tacgtgggac ctctcgcccg gggcaattca   1380

cggtttgcct ggatgacaag gaagtcagag gagactatta caccttggaa cttcgaagaa   1440

gtggtggaca agggtgcatc tgcccagtct ttcatcgagc ggatgacaaa ttttgacaag   1500

aacctcccta atgagaaggt gctgcccaaa cattctctgc tctacgagta ctttaccgtc   1560

tacaatgaac tgactaaagt caagtacgtc accgagggaa tgaggaagcc ggcattcctt   1620

agtggagaac agaagaaggc gattgtagac ctgttgttca agaccaacag gaaggtgact   1680
```

-continued gtgaagcaac ttaaagaaga ctactttaag aagatcgaat gttttgacag tgtggaaatt 1740
tcaggggttg aagaccgctt caatgcgtca ttggggactt accatgatct tctcaagatc 1800
ataaaggaca aagacttcct ggacaacgaa gaaaatgagg atattctcga agacatcgtc 1860
ctcaccctga ccctgttcga agacagggaa atgatagaag agcgcttgaa aacctatgcc 1920
cacctcttcg acgataaagt tatgaagcag ctgaagcgca ggagatacac aggatgggga 1980
agattgtcaa ggaagctgat caatggaatt agggataaac agagtggcaa gaccatactg 2040
gatttcctca aatctgatgg cttcgccaat aggaacttca tgcaactgat tcacgatgac 2100
tctcttacct tcaaggagga cattcaaaag gctcaggtga gcgggcaggg agactccctt 2160
catgaacaca tcgcgaattt ggcaggttcc cccgctatta aaaagggcat ccttcaaact 2220
gtcaaggtgg tggatgaatt ggtcaaggta atgggcagac ataagccaga aaatattgtg 2280
atcgagatgg cccgcgaaaa ccagaccaca cagaagggcc agaaaaatag tagagagcgg 2340
atgaagagga tcgaggaggg catcaaagag ctgggatctc agattctcaa agaacacccc 2400
gtagaaaaca cacagctgca gaacgaaaaa ttgtacttgt actatctgca gaacggcaga 2460
gacatgtacg tcgaccaaga acttgatatt aatagactgt ccgactatga cgtagaccat 2520
atcgtgcccc agtccttcct gaaggacgac tccattgata acaaagtctt gacaagaagc 2580
gacaagaaca ggggtaaaag tgataatgtg cctagcgagg aggtggtgaa aaaaatgaag 2640
aactactggc gacagctgct taatgcaaag ctcattacac aacggaagtt cgataatctg 2700
acgaaagcag agagaggtgg cttgtctgag ttggacaagg cagggtttat taagcggcag 2760
ctggtggaaa ctaggcagat cacaaagcac gtggcgcaga ttttggacag ccggatgaac 2820
acaaaatacg acgaaaatga taaactgata cgagaggtca aagttatcac gctgaaaagc 2880
aagctggtgt ccgattttcg gaaagacttc cagttctaca aagttcgcga gattaataac 2940
taccatcatg ctcacgatgc gtacctgaac gctgttgtcg ggaccgcctt gataaagaag 3000
tacccaaagc tggaatccga gttcgtatac ggggattaca aagtgtacga tgtgaggaaa 3060
atgatagcca agtccgagca ggagattgga aaggccacag ctaagtactt cttttattct 3120
aacatcatga attttttaa gacggaaatt accctggcca acggagagat cagaaagcgg 3180
ccccttatag agacaaatgg tgaaacaggt gaaatcgtct gggataaggg cagggatttc 3240
gctactgtga ggaaggtgct gagtatgcca caggtaaata tcgtgaaaaa aaccgaagta 3300
cagaccggag gattttccaa ggaaagcatt ttgcctaaaa gaaactcaga caagctcatc 3360
gcccgcaaga aagattggga ccctaagaaa tacgggggat ttgactcacc caccgtagcc 3420
tattctgtgc tggtggtagc taaggtggaa aaaggaaagt ctaagaagct gaagtccgtg 3480
aaggaactct tgggaatcac tatcatggaa agatcatcct ttgaaaagaa ccctatcgat 3540
ttcctggagg ctaagggtta caaggaggtc aagaaagacc tcatcattaa actgccaaaa 3600
tactctctct tcgagctgga aaatggcagg aagagaatgt tggccagcgc cggagagctg 3660
caaaagggaa acgagcttgc tctgccctcc aaatatgtta attttctcta tctcgcttcc 3720
cactatgaaa agctgaaagg gtctcccgaa gataacgagc agaagcagct gttcgtcgaa 3780
cagcacaagc actatctgga tgaaataatc gaacaaataa gcgagttcag caaaagggtt 3840
atcctggcgg atgctaattt ggacaaagta ctgtctgctt ataacaagca ccgggataag 3900
cctattaggg aacaagccga gaatataatt cacctcttta cactcacgaa tctcggagcc 3960
cccgccgcct tcaaatactt tgatacgact atcgaccgga aacggtatac cagtaccaaa 4020

-continued gaggtcctcg atgccaccct catccaccag tcaattactg gcctgtacga aacacggatc 4080
gacctctctc aactgggcgg cgactag 4107

<210> SEQ ID NO 4
<211> LENGTH: 1388
<212> TYPE: PRT
<213> ORGANISM: Streptococcus thermophilus
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (760)..(767)
<223> OTHER INFORMATION: RuvC-like domain
<220> FEATURE:
<221> NAME/KEY: misc_feature
<222> LOCATION: (844)..(870)
<223> OTHER INFORMATION: HNH-like domain
<220> FEATURE:
<221> NAME/KEY: misc_feature
<222> LOCATION: (989)..(996)
<223> OTHER INFORMATION: RuvC-like domain

<400> SEQUENCE: 4

Met Thr Lys Pro Tyr Ser Ile Gly Leu Asp Ile Gly Thr Asn Ser Val
1 5 10 15

Gly Trp Ala Val Thr Thr Asp Asn Tyr Lys Val Pro Ser Lys Lys Met
20 25 30

Lys Val Leu Gly Asn Thr Ser Lys Lys Tyr Ile Lys Lys Asn Leu Leu
35 40 45

Gly Val Leu Leu Phe Asp Ser Gly Ile Thr Ala Glu Gly Arg Arg Leu
50 55 60

Lys Arg Thr Ala Arg Arg Arg Tyr Thr Arg Arg Arg Asn Arg Ile Leu
65 70 75 80

Tyr Leu Gln Glu Ile Phe Ser Thr Glu Met Ala Thr Leu Asp Asp Ala
85 90 95

Phe Phe Gln Arg Leu Asp Asp Ser Phe Leu Val Pro Asp Asp Lys Arg
100 105 110

Asp Ser Lys Tyr Pro Ile Phe Gly Asn Leu Val Glu Glu Lys Ala Tyr
115 120 125

His Asp Glu Phe Pro Thr Ile Tyr His Leu Arg Lys Tyr Leu Ala Asp
130 135 140

Ser Thr Lys Lys Ala Asp Leu Arg Leu Val Tyr Leu Ala Leu Ala His
145 150 155 160

Met Ile Lys Tyr Arg Gly His Phe Leu Ile Glu Gly Glu Phe Asn Ser
165 170 175

Lys Asn Asn Asp Ile Gln Lys Asn Phe Gln Asp Phe Leu Asp Thr Tyr
180 185 190

Asn Ala Ile Phe Glu Ser Asp Leu Ser Leu Glu Asn Ser Lys Gln Leu
195 200 205

Glu Glu Ile Val Lys Asp Lys Ile Ser Lys Leu Glu Lys Lys Asp Arg
210 215 220

Ile Leu Lys Leu Phe Pro Gly Glu Lys Asn Ser Gly Ile Phe Ser Glu
225 230 235 240

Phe Leu Lys Leu Ile Val Gly Asn Gln Ala Asp Phe Arg Lys Cys Phe
245 250 255

Asn Leu Asp Glu Lys Ala Ser Leu His Phe Ser Lys Glu Ser Tyr Asp
260 265 270

```
Glu Asp Leu Glu Thr Leu Leu Gly Tyr Ile Gly Asp Asp Tyr Ser Asp
        275                 280                 285

Val Phe Leu Lys Ala Lys Lys Leu Tyr Asp Ala Ile Leu Leu Ser Gly
    290                 295                 300

Phe Leu Thr Val Thr Asp Asn Glu Thr Glu Ala Pro Leu Ser Ser Ala
305                 310                 315                 320

Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
            340                 345                 350

Asp Asp Thr Lys Asn Gly Tyr Ala Gly Tyr Ile Asp Gly Lys Thr Asn
        355                 360                 365

Gln Glu Asp Phe Tyr Val Tyr Leu Lys Lys Leu Leu Ala Glu Phe Glu
    370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
            420                 425                 430

Leu Ala Lys Asn Lys Glu Arg Ile Glu Lys Ile Leu Thr Phe Arg Ile
        435                 440                 445

Pro Tyr Tyr Val Gly Pro Leu Ala Arg Gly Asn Ser Asp Phe Ala Trp
    450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510

Leu Leu Tyr Glu Thr Phe Asn Val Tyr Asn Glu Leu Thr Lys Val Arg
        515                 520                 525

Phe Ile Ala Glu Ser Met Arg Asp Tyr Gln Phe Leu Asp Ser Lys Gln
    530                 535                 540

Lys Lys Asp Ile Val Arg Leu Tyr Phe Lys Asp Lys Arg Lys Val Thr
545                 550                 555                 560

Asp Lys Asp Ile Ile Glu Tyr Leu His Ala Ile Tyr Gly Tyr Asp Gly
                565                 570                 575

Ile Glu Leu Lys Gly Ile Glu Lys Gln Phe Asn Ser Ser Leu Ser Thr
            580                 585                 590

Tyr His Asp Leu Leu Asn Ile Ile Asn Asp Lys Glu Phe Leu Asp Asp
        595                 600                 605

Ser Ser Asn Glu Ala Ile Ile Glu Glu Ile Ile His Thr Leu Thr Ile
    610                 615                 620

Phe Glu Asp Arg Glu Met Ile Lys Gln Arg Leu Ser Lys Phe Glu Asn
625                 630                 635                 640

Ile Phe Asp Lys Ser Val Leu Lys Lys Leu Ser Arg Arg His Tyr Thr
                645                 650                 655

Gly Trp Gly Lys Leu Ser Ala Lys Leu Ile Asn Gly Ile Arg Asp Glu
            660                 665                 670

Lys Ser Gly Asn Thr Ile Leu Asp Tyr Leu Ile Asp Asp Gly Ile Ser
        675                 680                 685

Asn Arg Asn Phe Met Gln Leu Ile His Asp Asp Ala Leu Ser Phe Lys
```

-continued

```
    690                 695                 700

Lys Lys Ile Gln Lys Ala Gln Ile Ile Gly Asp Glu Asp Lys Gly Asn
705                 710                 715                 720

Ile Lys Glu Val Val Lys Ser Leu Pro Gly Ser Pro Ala Ile Lys Lys
                725                 730                 735

Gly Ile Leu Gln Ser Ile Lys Ile Val Asp Glu Leu Val Lys Val Met
            740                 745                 750

Gly Gly Arg Lys Pro Glu Ser Ile Val Val Glu Met Ala Arg Glu Asn
        755                 760                 765

Gln Tyr Thr Asn Gln Gly Lys Ser Asn Ser Gln Gln Arg Leu Lys Arg
    770                 775                 780

Leu Glu Lys Ser Leu Lys Glu Leu Gly Ser Lys Ile Leu Lys Glu Asn
785                 790                 795                 800

Ile Pro Ala Lys Leu Ser Lys Ile Asp Asn Asn Ala Leu Gln Asn Asp
                805                 810                 815

Arg Leu Tyr Leu Tyr Tyr Leu Gln Asn Gly Lys Asp Met Tyr Thr Gly
            820                 825                 830

Asp Asp Leu Asp Ile Asp Arg Leu Ser Asn Tyr Asp Ile Asp His Ile
        835                 840                 845

Ile Pro Gln Ala Phe Leu Lys Asp Asn Ser Ile Asp Asn Lys Val Leu
    850                 855                 860

Val Ser Ser Ala Ser Asn Arg Gly Lys Ser Asp Asp Val Pro Ser Leu
865                 870                 875                 880

Glu Val Val Lys Lys Arg Lys Thr Phe Trp Tyr Gln Leu Leu Lys Ser
                885                 890                 895

Lys Leu Ile Ser Gln Arg Lys Phe Asp Asn Leu Thr Lys Ala Glu Arg
            900                 905                 910

Gly Gly Leu Ser Pro Glu Asp Lys Ala Gly Phe Ile Gln Arg Gln Leu
        915                 920                 925

Val Glu Thr Arg Gln Ile Thr Lys His Val Ala Arg Leu Leu Asp Glu
    930                 935                 940

Lys Phe Asn Asn Lys Lys Asp Glu Asn Asn Arg Ala Val Arg Thr Val
945                 950                 955                 960

Lys Ile Ile Thr Leu Lys Ser Thr Leu Val Ser Gln Phe Arg Lys Asp
                965                 970                 975

Phe Glu Leu Tyr Lys Val Arg Glu Ile Asn Asp Phe His His Ala His
            980                 985                 990

Asp Ala Tyr Leu Asn Ala Val Val  Ala Ser Ala Leu Leu  Lys Lys Tyr
        995                 1000                1005

Pro Lys  Leu Glu Pro Glu Phe  Val Tyr Gly Asp Tyr  Pro Lys Tyr
    1010                1015                1020

Asn Ser  Phe Arg Glu Arg Lys  Ser Ala Thr Glu Lys  Val Tyr Phe
    1025                1030                1035

Tyr Ser  Asn Ile Met Asn Ile  Phe Lys Lys Ser Ile  Ser Leu Ala
    1040                1045                1050

Asp Gly  Arg Val Ile Glu Arg  Pro Leu Ile Glu Val  Asn Glu Glu
    1055                1060                1065

Thr Gly  Glu Ser Val Trp Asn  Lys Glu Ser Asp Leu  Ala Thr Val
    1070                1075                1080

Arg Arg  Val Leu Ser Tyr Pro  Gln Val Asn Val Val  Lys Lys Val
    1085                1090                1095

Glu Glu  Gln Asn His Gly Leu  Asp Arg Gly Lys Pro  Lys Gly Leu
    1100                1105                1110
```

```
Phe Asn  Ala Asn Leu Ser Ser  Lys Pro Lys Pro Asn  Ser Asn Glu
    1115                 1120                 1125

Asn Leu  Val Gly Ala Lys Glu  Tyr Leu Asp Pro Lys  Lys Tyr Gly
    1130                 1135                 1140

Gly Tyr  Ala Gly Ile Ser Asn  Ser Phe Thr Val Leu  Val Lys Gly
    1145                 1150                 1155

Thr Ile  Glu Lys Gly Ala Lys  Lys Lys Ile Thr Asn  Val Leu Glu
    1160                 1165                 1170

Phe Gln  Gly Ile Ser Ile Leu  Asp Arg Ile Asn Tyr  Arg Lys Asp
    1175                 1180                 1185

Lys Leu  Asn Phe Leu Leu Glu  Lys Gly Tyr Lys Asp  Ile Glu Leu
    1190                 1195                 1200

Ile Ile  Glu Leu Pro Lys Tyr  Ser Leu Phe Glu Leu  Ser Asp Gly
    1205                 1210                 1215

Ser Arg  Arg Met Leu Ala Ser  Ile Leu Ser Thr Asn  Asn Lys Arg
    1220                 1225                 1230

Gly Glu  Ile His Lys Gly Asn  Gln Ile Phe Leu Ser  Gln Lys Phe
    1235                 1240                 1245

Val Lys  Leu Leu Tyr His Ala  Lys Arg Ile Ser Asn  Thr Ile Asn
    1250                 1255                 1260

Glu Asn  His Arg Lys Tyr Val  Glu Asn His Lys Lys  Glu Phe Glu
    1265                 1270                 1275

Glu Leu  Phe Tyr Tyr Ile Leu  Glu Phe Asn Glu Asn  Tyr Val Gly
    1280                 1285                 1290

Ala Lys  Lys Asn Gly Lys Leu  Leu Asn Ser Ala Phe  Gln Ser Trp
    1295                 1300                 1305

Gln Asn  His Ser Ile Asp Glu  Leu Cys Ser Ser Phe  Ile Gly Pro
    1310                 1315                 1320

Thr Gly  Ser Glu Arg Lys Gly  Leu Phe Glu Leu Thr  Ser Arg Gly
    1325                 1330                 1335

Ser Ala  Ala Asp Phe Glu Phe  Leu Gly Val Lys Ile  Pro Arg Tyr
    1340                 1345                 1350

Arg Asp  Tyr Thr Pro Ser Ser  Leu Leu Lys Asp Ala  Thr Leu Ile
    1355                 1360                 1365

His Gln  Ser Val Thr Gly Leu  Tyr Glu Thr Arg Ile  Asp Leu Ala
    1370                 1375                 1380

Lys Leu  Gly Glu Gly
    1385
```

```
<210> SEQ ID NO 5
<211> LENGTH: 1334
<212> TYPE: PRT
<213> ORGANISM: Listeria innocua
<220> FEATURE:
<221> NAME/KEY: misc_feature
<222> LOCATION: (10)..(21)
<223> OTHER INFORMATION: N-terminal RuvC-like domain
<220> FEATURE:
<221> NAME/KEY: misc_feature
<222> LOCATION: (762)..(769)
<223> OTHER INFORMATION: RuvC-like domain
<220> FEATURE:
<221> NAME/KEY: misc_feature
<222> LOCATION: (840)..(866)
<223> OTHER INFORMATION: HNH-like domain
<220> FEATURE:
<221> NAME/KEY: misc_feature
<222> LOCATION: (985)..(992)
<223> OTHER INFORMATION: RuvC-like domain
```

-continued

<400> SEQUENCE: 5

Met Lys Lys Pro Tyr Thr Ile Gly Leu Asp Ile Gly Thr Asn Ser Val
1               5                   10                  15

Gly Trp Ala Val Leu Thr Asp Gln Tyr Asp Leu Val Lys Arg Lys Met
            20                  25                  30

Lys Ile Ala Gly Asp Ser Glu Lys Lys Gln Ile Lys Lys Asn Phe Trp
        35                  40                  45

Gly Val Arg Leu Phe Asp Glu Gly Gln Thr Ala Ala Asp Arg Arg Met
    50                  55                  60

Ala Arg Thr Ala Arg Arg Arg Ile Glu Arg Arg Arg Asn Arg Ile Ser
65                  70                  75                  80

Tyr Leu Gln Gly Ile Phe Ala Glu Glu Met Ser Lys Thr Asp Ala Asn
                85                  90                  95

Phe Phe Cys Arg Leu Ser Asp Ser Phe Tyr Val Asp Asn Glu Lys Arg
            100                 105                 110

Asn Ser Arg His Pro Phe Phe Ala Thr Ile Glu Glu Glu Val Glu Tyr
        115                 120                 125

His Lys Asn Tyr Pro Thr Ile Tyr His Leu Arg Glu Glu Leu Val Asn
    130                 135                 140

Ser Ser Glu Lys Ala Asp Leu Arg Leu Val Tyr Leu Ala Leu Ala His
145                 150                 155                 160

Ile Ile Lys Tyr Arg Gly Asn Phe Leu Ile Glu Gly Ala Leu Asp Thr
                165                 170                 175

Gln Asn Thr Ser Val Asp Gly Ile Tyr Lys Gln Phe Ile Gln Thr Tyr
            180                 185                 190

Asn Gln Val Phe Ala Ser Gly Ile Glu Asp Gly Ser Leu Lys Lys Leu
        195                 200                 205

Glu Asp Asn Lys Asp Val Ala Lys Ile Leu Val Glu Lys Val Thr Arg
    210                 215                 220

Lys Glu Lys Leu Glu Arg Ile Leu Lys Leu Tyr Pro Gly Glu Lys Ser
225                 230                 235                 240

Ala Gly Met Phe Ala Gln Phe Ile Ser Leu Ile Val Gly Ser Lys Gly
                245                 250                 255

Asn Phe Gln Lys Pro Phe Asp Leu Ile Glu Lys Ser Asp Ile Glu Cys
            260                 265                 270

Ala Lys Asp Ser Tyr Glu Glu Asp Leu Glu Ser Leu Leu Ala Leu Ile
        275                 280                 285

Gly Asp Glu Tyr Ala Glu Leu Phe Val Ala Ala Lys Asn Ala Tyr Ser
    290                 295                 300

Ala Val Val Leu Ser Ser Ile Ile Thr Val Ala Glu Thr Glu Thr Asn
305                 310                 315                 320

Ala Lys Leu Ser Ala Ser Met Ile Glu Arg Phe Asp Thr His Glu Glu
                325                 330                 335

Asp Leu Gly Glu Leu Lys Ala Phe Ile Lys Leu His Leu Pro Lys His
            340                 345                 350

Tyr Glu Glu Ile Phe Ser Asn Thr Glu Lys His Gly Tyr Ala Gly Tyr
        355                 360                 365

Ile Asp Gly Lys Thr Lys Gln Ala Asp Phe Tyr Lys Tyr Met Lys Met
    370                 375                 380

Thr Leu Glu Asn Ile Glu Gly Ala Asp Tyr Phe Ile Ala Lys Ile Glu
385                 390                 395                 400

Lys Glu Asn Phe Leu Arg Lys Gln Arg Thr Phe Asp Asn Gly Ala Ile

-continued

```
                405                 410                 415

Pro His Gln Leu His Leu Glu Glu Leu Glu Ala Ile Leu His Gln Gln
            420                 425                 430

Ala Lys Tyr Tyr Pro Phe Leu Lys Glu Asn Tyr Asp Lys Ile Lys Ser
        435                 440                 445

Leu Val Thr Phe Arg Ile Pro Tyr Phe Val Gly Pro Leu Ala Asn Gly
    450                 455                 460

Gln Ser Glu Phe Ala Trp Leu Thr Arg Lys Ala Asp Gly Glu Ile Arg
465                 470                 475                 480

Pro Trp Asn Ile Glu Glu Lys Val Asp Phe Gly Lys Ser Ala Val Asp
                485                 490                 495

Phe Ile Glu Lys Met Thr Asn Lys Asp Thr Tyr Leu Pro Lys Glu Asn
            500                 505                 510

Val Leu Pro Lys His Ser Leu Cys Tyr Gln Lys Tyr Leu Val Tyr Asn
        515                 520                 525

Glu Leu Thr Lys Val Arg Tyr Ile Asn Asp Gln Gly Lys Thr Ser Tyr
    530                 535                 540

Phe Ser Gly Gln Glu Lys Glu Gln Ile Phe Asn Asp Leu Phe Lys Gln
545                 550                 555                 560

Lys Arg Lys Val Lys Lys Lys Asp Leu Glu Leu Phe Leu Arg Asn Met
                565                 570                 575

Ser His Val Glu Ser Pro Thr Ile Glu Gly Leu Glu Asp Ser Phe Asn
            580                 585                 590

Ser Ser Tyr Ser Thr Tyr His Asp Leu Leu Lys Val Gly Ile Lys Gln
        595                 600                 605

Glu Ile Leu Asp Asn Pro Val Asn Thr Glu Met Leu Glu Asn Ile Val
    610                 615                 620

Lys Ile Leu Thr Val Phe Glu Asp Lys Arg Met Ile Lys Glu Gln Leu
625                 630                 635                 640

Gln Gln Phe Ser Asp Val Leu Asp Gly Val Val Leu Lys Lys Leu Glu
                645                 650                 655

Arg Arg His Tyr Thr Gly Trp Gly Arg Leu Ser Ala Lys Leu Leu Met
            660                 665                 670

Gly Ile Arg Asp Lys Gln Ser His Leu Thr Ile Leu Asp Tyr Leu Met
        675                 680                 685

Asn Asp Asp Gly Leu Asn Arg Asn Leu Met Gln Leu Ile Asn Asp Ser
    690                 695                 700

Asn Leu Ser Phe Lys Ser Ile Ile Glu Lys Glu Gln Val Thr Thr Ala
705                 710                 715                 720

Asp Lys Asp Ile Gln Ser Ile Val Ala Asp Leu Ala Gly Ser Pro Ala
                725                 730                 735

Ile Lys Lys Gly Ile Leu Gln Ser Leu Lys Ile Val Asp Glu Leu Val
            740                 745                 750

Ser Val Met Gly Tyr Pro Pro Gln Thr Ile Val Val Glu Met Ala Arg
        755                 760                 765

Glu Asn Gln Thr Thr Gly Lys Gly Lys Asn Asn Ser Arg Pro Arg Tyr
    770                 775                 780

Lys Ser Leu Glu Lys Ala Ile Lys Glu Phe Gly Ser Gln Ile Leu Lys
785                 790                 795                 800

Glu His Pro Thr Asp Asn Gln Glu Leu Arg Asn Asn Arg Leu Tyr Leu
                805                 810                 815

Tyr Tyr Leu Gln Asn Gly Lys Asp Met Tyr Thr Gly Gln Asp Leu Asp
            820                 825                 830
```

-continued

```
Ile His Asn Leu Ser Asn Tyr Asp Ile Asp His Ile Val Pro Gln Ser
      835                 840                 845

Phe Ile Thr Asp Asn Ser Ile Asp Asn Leu Val Leu Thr Ser Ser Ala
    850                 855                 860

Gly Asn Arg Glu Lys Gly Asp Asp Val Pro Pro Leu Glu Ile Val Arg
865                 870                 875                 880

Lys Arg Lys Val Phe Trp Glu Lys Leu Tyr Gln Gly Asn Leu Met Ser
                885                 890                 895

Lys Arg Lys Phe Asp Tyr Leu Thr Lys Ala Glu Arg Gly Gly Leu Thr
            900                 905                 910

Glu Ala Asp Lys Ala Arg Phe Ile His Arg Gln Leu Val Glu Thr Arg
      915                 920                 925

Gln Ile Thr Lys Asn Val Ala Asn Ile Leu His Gln Arg Phe Asn Tyr
    930                 935                 940

Glu Lys Asp Asp His Gly Asn Thr Met Lys Gln Val Arg Ile Val Thr
945                 950                 955                 960

Leu Lys Ser Ala Leu Val Ser Gln Phe Arg Lys Gln Phe Gln Leu Tyr
                965                 970                 975

Lys Val Arg Asp Val Asn Asp Tyr His His Ala His Asp Ala Tyr Leu
            980                 985                 990

Asn Gly Val Val Ala Asn Thr Leu  Leu Lys Val Tyr Pro  Gln Leu Glu
      995                 1000                1005

Pro Glu  Phe Val Tyr Gly Asp  Tyr His Gln Phe Asp  Trp Phe Lys
    1010                1015                1020

Ala Asn  Lys Ala Thr Ala Lys  Lys Gln Phe Tyr Thr  Asn Ile Met
    1025                1030                1035

Leu Phe  Phe Ala Gln Lys Asp  Arg Ile Ile Asp Glu  Asn Gly Glu
    1040                1045                1050

Ile Leu  Trp Asp Lys Lys Tyr  Leu Asp Thr Val Lys  Lys Val Met
    1055                1060                1065

Ser Tyr  Arg Gln Met Asn Ile  Val Lys Lys Thr Glu  Ile Gln Lys
    1070                1075                1080

Gly Glu  Phe Ser Lys Ala Thr  Ile Lys Pro Lys Gly  Asn Ser Ser
    1085                1090                1095

Lys Leu  Ile Pro Arg Lys Thr  Asn Trp Asp Pro Met  Lys Tyr Gly
    1100                1105                1110

Gly Leu  Asp Ser Pro Asn Met  Ala Tyr Ala Val Val  Ile Glu Tyr
    1115                1120                1125

Ala Lys  Gly Lys Asn Lys Leu  Val Phe Glu Lys Lys  Ile Ile Arg
    1130                1135                1140

Val Thr  Ile Met Glu Arg Lys  Ala Phe Glu Lys Asp  Glu Lys Ala
    1145                1150                1155

Phe Leu  Glu Glu Gln Gly Tyr  Arg Gln Pro Lys Val  Leu Ala Lys
    1160                1165                1170

Leu Pro  Lys Tyr Thr Leu Tyr  Glu Cys Glu Glu Gly  Arg Arg Arg
    1175                1180                1185

Met Leu  Ala Ser Ala Asn Glu  Ala Gln Lys Gly Asn  Gln Gln Val
    1190                1195                1200

Leu Pro  Asn His Leu Val Thr  Leu Leu His His Ala  Ala Asn Cys
    1205                1210                1215

Glu Val  Ser Asp Gly Lys Ser  Leu Asp Tyr Ile Glu  Ser Asn Arg
    1220                1225                1230
```

```
Glu Met  Phe Ala Glu Leu Leu  Ala His Val Ser Glu  Phe Ala Lys
    1235                 1240                 1245

Arg Tyr  Thr Leu Ala Glu Ala  Asn Leu Asn Lys Ile  Asn Gln Leu
    1250                 1255                 1260

Phe Glu  Gln Asn Lys Glu Gly  Asp Ile Lys Ala Ile  Ala Gln Ser
    1265                 1270                 1275

Phe Val  Asp Leu Met Ala Phe  Asn Ala Met Gly Ala  Pro Ala Ser
    1280                 1285                 1290

Phe Lys  Phe Phe Glu Thr Thr  Ile Glu Arg Lys Arg  Tyr Asn Asn
    1295                 1300                 1305

Leu Lys  Glu Leu Leu Asn Ser  Thr Ile Ile Tyr Gln  Ser Ile Thr
    1310                 1315                 1320

Gly Leu  Tyr Glu Ser Arg Lys  Arg Leu Asp Asp
    1325                 1330


<210> SEQ ID NO 6
<211> LENGTH: 1053
<212> TYPE: PRT
<213> ORGANISM: Staphylococcus aureus

<400> SEQUENCE: 6

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270
```

```
Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685
```

```
Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr  Tyr Arg Glu Tyr Leu  Glu Asn Met
        995                 1000                1005

Asn Asp  Lys Arg Pro Pro Arg  Ile Ile Lys Thr Ile  Ala Ser Lys
    1010                1015                1020

Thr Gln  Ser Ile Lys Lys Tyr  Ser Thr Asp Ile Leu  Gly Asn Leu
    1025                1030                1035

Tyr Glu  Val Lys Ser Lys Lys  His Pro Gln Ile Ile  Lys Lys Gly
    1040                1045                1050
```

<210> SEQ ID NO 7
<211> LENGTH: 3159
<212> TYPE: DNA
<213> ORGANISM: Staphylococcus aureus

<400> SEQUENCE: 7

```
atgaaaagga actacattct ggggctggac atcgggatta caagcgtggg gtatgggatt      60
```

-continued

```
attgactatg aaacaaggga cgtgatcgac gcaggcgtca gactgttcaa ggaggccaac    120
gtggaaaaca atgagggacg gagaagcaag aggggagcca ggcgcctgaa acgacggaga    180
aggcacagaa tccagagggt gaagaaactg ctgttcgatt acaacctgct gaccgaccat    240
tctgagctga gtggaattaa tccttatgaa gccagggtga aaggcctgag tcagaagctg    300
tcagaggaag agttttccgc agctctgctg cacctggcta agcgccgagg agtgcataac    360
gtcaatgagg tggaagagga caccggcaac gagctgtcta caaaggaaca gatctcacgc    420
aatagcaaag ctctggaaga gaagtatgtc gcagagctgc agctggaacg gctgaagaaa    480
gatggcgagg tgagagggtc aattaatagg ttcaagacaa gcgactacgt caaagaagcc    540
aagcagctgc tgaaagtgca gaaggcttac caccagctgg atcagagctt catcgatact    600
tatatcgacc tgctggagac tcggagaacc tactatgagg gaccaggaga agggagcccc    660
ttcggatgga aagacatcaa ggaatggtac gagatgctga tgggacattg cacctatttt    720
ccagaagagc tgagaagcgt caagtacgct tataacgcag atctgtacaa cgccctgaat    780
gacctgaaca acctggtcat caccagggat gaaaacgaga aactggaata ctatgagaag    840
ttccagatca tcgaaaacgt gtttaagcag aagaaaaagc ctacactgaa acagattgct    900
aaggagatcc tggtcaacga agaggacatc aagggctacc gggtgacaag cactggaaaa    960
ccagagttca ccaatctgaa agtgtatcac gatattaagg acatcacagc acggaaagaa   1020
atcattgaga acgccgaact gctggatcag attgctaaga tcctgactat ctaccagagc   1080
tccgaggaca tccaggaaga gctgactaac ctgaacagcg agctgaccca ggaagagatc   1140
gaacagatta gtaatctgaa ggggtacacc ggaacacaca acctgtccct gaaagctatc   1200
aatctgattc tggatgagct gtggcataca aacgacaatc agattgcaat ctttaaccgg   1260
ctgaagctgg tcccaaaaaa ggtggacctg agtcagcaga aagagatccc aaccacactg   1320
gtggacgatt tcattctgtc acccgtggtc aagcggagct tcatccagag catcaaagtg   1380
atcaacgcca tcatcaagaa gtacggcctg cccaatgata tcattatcga gctggctagg   1440
gagaagaaca gcaaggacgc acagaagatg atcaatgaga tgcagaaacg aaaccggcag   1500
accaatgaac gcattgaaga gattatccga actaccggga aagagaacgc aaagtacctg   1560
attgaaaaaa tcaagctgca cgatatgcag gagggaaagt gtctgtattc tctggaggcc   1620
atccccctgg aggacctgct gaacaatcca ttcaactacg aggtcgatca tattatcccc   1680
agaagcgtgt ccttcgacaa ttcctttaac aacaaggtgc tggtcaagca ggaagagaac   1740
tctaaaaagg gcaataggac tcctttccag tacctgtcta gttcagattc caagatctct   1800
tacgaaacct ttaaaaagca cattctgaat ctggccaaag gaaagggccg catcagcaag   1860
accaaaaagg agtacctgct ggaagagcgg gacatcaaca gattctccgt ccagaaggat   1920
tttattaacc ggaatctggt ggacacaaga tacgctactc gcggcctgat gaatctgctg   1980
cgatcctatt tccgggtgaa caatctggat gtgaaagtca agtccatcaa cggcgggttc   2040
acatcttttc tgaggcgcaa atggaagttt aaaaaggagc gcaacaaagg gtacaagcac   2100
catgccgaag atgctctgat tatcgcaaat gccgacttca tctttaagga gtggaaaaag   2160
ctggacaaag ccaagaaagt gatggagaac cagatgttcg aagagaagca ggccgaatct   2220
atgcccgaaa tcgagacaga acaggagtac aaggagattt tcatcactcc tcaccagatc   2280
aagcatatca aggatttcaa ggactacaag tactctcacc gggtggataa aaagcccaac   2340
agagagctga tcaatgacac cctgtatagt acaagaaaag acgataaggg gaataccctg   2400
attgtgaaca atctgaacgg actgtacgac aaagataatg acaagctgaa aaagctgatc   2460
```

```
aacaaaagtc ccgagaagct gctgatgtac caccatgatc ctcagacata tcagaaactg   2520

aagctgatta tggagcagta cggcgacgag aagaacccac tgtataagta ctatgaagag   2580

actgggaact acctgaccaa gtatagcaaa aaggataatg gccccgtgat caagaagatc   2640

aagtactatg ggaacaagct gaatgcccat ctggacatca cagacgatta ccctaacagt   2700

cgcaacaagg tggtcaagct gtcactgaag ccatacagat tcgatgtcta tctggacaac   2760

ggcgtgtata aatttgtgac tgtcaagaat ctggatgtca tcaaaaagga gaactactat   2820

gaagtgaata gcaagtgcta cgaagaggct aaaaagctga aaaagattag caaccaggca   2880

gagttcatcg cctcctttta caacaacgac ctgattaaga tcaatggcga actgtatagg   2940

gtcatcgggg tgaacaatga tctgctgaac cgcattgaag tgaatatgat tgacatcact   3000

taccgagagt atctggaaaa catgaatgat aagcgccccc ctcgaattat caaaacaatt   3060

gcctctaaga ctcagagtat caaaaagtac tcaaccgaca ttctgggaaa cctgtatgag   3120

gtgaagagca aaaagcaccc tcagattatc aaaaagggc                          3159
```

<210> SEQ ID NO 8
<211> LENGTH: 3159
<212> TYPE: DNA
<213> ORGANISM: Staphylococcus aureus

<400> SEQUENCE: 8

```
atgaagcgga actacatcct gggcctggac atcggcatca ccagcgtggg ctacggcatc     60

atcgactacg agacacggga cgtgatcgat gccggcgtgc ggctgttcaa agaggccaac    120

gtggaaaaca acgagggcag gcggagcaag agaggcgcca gaaggctgaa gcggcggagg    180

cggcatagaa tccagagagt gaagaagctg ctgttcgact acaacctgct gaccgaccac    240

agcgagctga gcggcatcaa cccctacgag gccagagtga agggcctgag ccagaagctg    300

agcgaggaag agttctctgc cgccctgctg cacctggcca agagaagagg cgtgcacaac    360

gtgaacgagg tggaagagga caccggcaac gagctgtcca ccaaagagca gatcagccgg    420

aacagcaagg ccctggaaga gaaatacgtg gccgaactgc agctggaacg gctgaagaaa    480

gacggcgaag tgcggggcag catcaacaga ttcaagacca gcgactacgt gaaagaagcc    540

aaacagctgc tgaaggtgca gaaggcctac caccagctgg accagagctt catcgacacc    600

tacatcgacc tgctggaaac ccggcggacc tactatgagg gacctggcga gggcagcccc    660

ttcggctgga aggacatcaa agaatggtac gagatgctga tgggccactg cacctacttc    720

cccgaggaac tgcggagcgt gaagtacgcc tacaacgccg acctgtacaa cgccctgaac    780

gacctgaaca atctcgtgat caccagggac gagaacgaga agctggaata ttacgagaag    840

ttccagatca tcgagaacgt gttcaagcag aagaagaagc ccaccctgaa gcagatcgcc    900

aaagaaatcc tcgtgaacga agaggatatt aagggctaca gagtgaccag caccggcaag    960

cccgagttca ccaacctgaa ggtgtaccac gacatcaagg acattaccgc ccggaaagag   1020

attattgaga acgccgagct gctggatcag attgccaaga tcctgaccat ctaccagagc   1080

agcgaggaca tccaggaaga actgaccaat ctgaactccg agctgaccca ggaagagatc   1140

gagcagatct ctaatctgaa gggctatacc ggcacccaca acctgagcct gaaggccatc   1200

aacctgatcc tggacgagct gtggcacacc aacgacaacc agatcgctat cttcaaccgg   1260

ctgaagctgg tgcccaagaa ggtggacctg tcccagcaga aagagatccc caccaccctg   1320

gtggacgact tcatcctgag ccccgtcgtg aagagaagct tcatccagag catcaaagtg   1380
```

atcaacgcca tcatcaagaa gtacggcctg cccaacgaca tcattatcga gctggcccgc 1440
gagaagaact ccaaggacgc ccagaaaatg atcaacgaga tgcagaagcg gaaccggcag 1500
accaacgagc ggatcgagga aatcatccgg accaccggca aagagaacgc caagtacctg 1560
atcgagaaga tcaagctgca cgacatgcag gaaggcaagt gcctgtacag cctggaagcc 1620
atccctctgg aagatctgct gaacaacccc ttcaactatg aggtggacca catcatcccc 1680
agaagcgtgt ccttcgacaa cagcttcaac aacaaggtgc tcgtgaagca ggaagaaaac 1740
agcaagaagg gcaaccggac cccattccag tacctgagca gcagcgacag caagatcagc 1800
tacgaaacct tcaagaagca catcctgaat ctggccaagg gcaagggcag aatcagcaag 1860
accaagaaag agtatctgct ggaagaacgg gacatcaaca ggttctccgt gcagaaagac 1920
ttcatcaacc ggaacctggt ggataccaga tacgccacca gaggcctgat gaacctgctg 1980
cggagctact tcagagtgaa caacctggac gtgaaagtga agtccatcaa tggcggcttc 2040
accagctttc tgcggcggaa gtggaagttt aagaaagagc ggaacaaggg gtacaagcac 2100
cacgccgagg acgccctgat cattgccaac gccgatttca tcttcaaaga gtggaagaaa 2160
ctggacaagg ccaaaaaagt gatggaaaac cagatgttcg aggaaaagca ggccgagagc 2220
atgcccgaga tcgaaaccga gcaggagtac aaagagatct tcatcacccc ccaccagatc 2280
aagcacatta aggacttcaa ggactacaag tacagccacc gggtggacaa gaagcctaat 2340
agagagctga ttaacgacac cctgtactcc acccggaagg acgacaaggg caacaccctg 2400
atcgtgaaca atctgaacgg cctgtacgac aaggacaatg acaagctgaa aaagctgatc 2460
aacaagagcc ccgaaaagct gctgatgtac caccacgacc cccagaccta ccagaaactg 2520
aagctgatta tggaacagta cggcgacgag aagaatcccc tgtacaagta ctacgaggaa 2580
accgggaact acctgaccaa gtactccaaa aaggacaacg gccccgtgat caagaagatt 2640
aagtattacg gcaacaaact gaacgcccat ctggacatca ccgacgacta ccccaacagc 2700
agaaacaagg tcgtgaagct gtccctgaag ccctacagat tcgacgtgta cctggacaat 2760
ggcgtgtaca agttcgtgac cgtgaagaat ctggatgtga tcaaaaaaga aaactactac 2820
gaagtgaata gcaagtgcta tgaggaagct aagaagctga agaagatcag caaccaggcc 2880
gagtttatcg cctccttcta caacaacgat ctgatcaaga tcaacggcga gctgtataga 2940
gtgatcggcg tgaacaacga cctgctgaac cggatcgaag tgaacatgat cgacatcacc 3000
taccgcgagt acctggaaaa catgaacgac aagaggcccc ccaggatcat taagacaatc 3060
gcctccaaga cccagagcat taagaagtac agcacagaca ttctgggcaa cctgtatgaa 3120
gtgaaatcta agaagcaccc tcagatcatc aaaaagggc 3159

<210> SEQ ID NO 9
<211> LENGTH: 3159
<212> TYPE: DNA
<213> ORGANISM: Staphylococcus aureus

<400> SEQUENCE: 9
atgaagcgca actacatcct cggactggac atcggcatta cctccgtggg atacggcatc 60
atcgattacg aaactaggga tgtgatcgac gctggagtca ggctgttcaa agaggcgaac 120
gtggagaaca acgagggggcg gcgctcaaag aggggggccc gccggctgaa gcgccgccgc 180
agacatagaa tccagcgcgt gaagaagctg ctgttcgact acaaccttct gaccgaccac 240
tccgaacttt ccggcatcaa cccatatgag gctagagtga agggattgtc ccaaaagctg 300
tccgaggaag agttctccgc cgcgttgctc cacctcgcca agcgcagggg agtgcacaat 360

-continued

```
gtgaacgaag tggaagaaga taccggaaac gagctgtcca ccaaggagca gatcagccgg    420
aactccaagg ccctggaaga gaaatacgtg gcggaactgc aactggagcg gctgaagaaa    480
gacggagaag tgcgcggctc gatcaaccgc ttcaagacct cggactacgt gaaggaggcc    540
aagcagctcc tgaaagtgca aaaggcctat caccaacttg accagtcctt tatcgatacc    600
tacatcgatc tgctcgagac tcggcggact tactacgagg gtccagggga gggctcccca    660
tttggttgga aggatattaa ggagtggtac gaaatgctga tgggacactg cacatacttc    720
cctgaggagc tgcggagcgt gaaatacgca tacaacgcag acctgtacaa cgcgctgaac    780
gacctgaaca atctcgtgat cacccgggac gagaacgaaa agctcgagta ttacgaaaag    840
ttccagatta ttgagaacgt gttcaaacag aagaagaagc cgacactgaa gcagattgcc    900
aaggaaatcc tcgtgaacga agaggacatc aagggctatc gagtgacctc aacgggaaag    960
ccggagttca ccaatctgaa ggtctaccac gacatcaaag acattaccgc ccggaaggag   1020
atcattgaga acgcggagct gttggaccag attgcgaaga ttctgaccat ctaccaatcc   1080
tccgaggata ttcaggaaga actcaccaac ctcaacagcg aactgaccca ggaggagata   1140
gagcaaatct ccaacctgaa gggctacacc ggaactcata acctgagcct gaaggccatc   1200
aacttgatcc tggacgagct gtggcacacc aacgataacc agatcgctat tttcaatcgg   1260
ctgaagctgg tccccaagaa agtggacctc tcacaacaaa aggagatccc tactaccctt   1320
gtggacgatt tcattctgtc ccccgtggtc aagagaagct tcatacagtc aatcaaagtg   1380
atcaatgcca ttatcaagaa atacggtctg cccaacgaca ttatcattga gctcgcccgc   1440
gagaagaact cgaaggacgc ccagaagatg attaacgaaa tgcagaagag gaaccgacag   1500
actaacgaac ggatcgaaga aatcatccgg accaccggga aggaaaacgc gaagtacctg   1560
atcgaaaaga tcaagctcca tgacatgcag gaaggaaagt gtctgtactc gctggaggcc   1620
attccgctgg aggacttgct gaacaaccct tttaactacg aagtggatca tatcattccg   1680
aggagcgtgt cattcgacaa ttccttcaac aacaaggtcc tcgtgaagca ggaggaaaac   1740
tcgaagaagg gaaaccgcac gccgttccag tacctgagca gcagcgactc caagatttcc   1800
tacgaaacct tcaagaagca catcctcaac ctggcaaagg ggaagggtcg catctccaag   1860
accaagaagg aatatctgct ggaagaaaga gacatcaaca gattctccgt gcaaaaggac   1920
ttcatcaacc gcaacctcgt ggatactaga tacgctactc ggggtctgat gaacctcctg   1980
agaagctact ttagagtgaa caatctggac gtgaaggtca agtcgattaa cggaggtttc   2040
acctccttcc tgcggcgcaa gtggaagttc aagaaggaac ggaacaaggg ctacaagcac   2100
cacgccgagg acgccctgat cattgccaac gccgacttca tcttcaaaga atggaagaaa   2160
cttgacaagg ctaagaaggt catggaaaac cagatgttcg aagaaaagca ggccgagtct   2220
atgcctgaaa tcgagactga acaggagtac aaggaaatct ttattacgcc acaccagatc   2280
aaacacatca aggatttcaa ggattacaag tactcacatc gcgtggacaa aaagccgaac   2340
agggaactga tcaacgacac cctctactcc acccggaagg atgacaaagg gaataccctc   2400
atcgtcaaca accttaacgg cctgtacgac aaggacaacg ataagctgaa gaagctcatt   2460
aacaagtcgc ccgaaaagtt gctgatgtac caccacgacc ctcagactta ccagaagctc   2520
aagctgatca tggagcagta tggggacgag aaaaacccgt tgtacaagta ctacgaagaa   2580
actgggaatt atctgactaa gtactccaag aaagataacg gccccgtgat taagaagatt   2640
aagtactacg gcaacaagct gaacgcccat ctggacatca ccgatgacta ccctaattcc   2700
```

-continued

```
cgcaacaagg tcgtcaagct gagcctcaag ccctaccggt ttgatgtgta ccttgacaat   2760

ggagtgtaca agttcgtgac tgtgaagaac cttgacgtga tcaagaagga gaactactac   2820

gaagtcaact ccaagtgcta cgaggaagca aagaagttga agaagatctc gaaccaggcc   2880

gagttcattg cctccttcta taacaacgac ctgattaaga tcaacggcga actgtaccgc   2940

gtcattggcg tgaacaacga tctcctgaac cgcatcgaag tgaacatgat cgacatcact   3000

taccgggaat acctggagaa tatgaacgac aagcgcccgc cccggatcat taagactatc   3060

gcctcaaaga cccagtcgat caagaagtac agcaccgaca tcctgggcaa cctgtacgag   3120

gtcaaatcga agaagcaccc ccagatcatc aagaaggga                          3159
```

<210> SEQ ID NO 10
<211> LENGTH: 3159
<212> TYPE: DNA
<213> ORGANISM: Staphylococcus aureus

<400> SEQUENCE: 10

```
atgaaaagga actacattct ggggctggcc atcgggatta caagcgtggg gtatgggatt     60

attgactatg aaacaaggga cgtgatcgac gcaggcgtca gactgttcaa ggaggccaac    120

gtggaaaaca atgagggacg gagaagcaag aggggagcca ggcgcctgaa acgacggaga    180

aggcacagaa tccagagggt gaagaaactg ctgttcgatt acaacctgct gaccgaccat    240

tctgagctga gtggaattaa tccttatgaa gccagggtga aaggcctgag tcagaagctg    300

tcagaggaag agttttccgc agctctgctg cacctggcta agcgccgagg agtgcataac    360

gtcaatgagg tggaagagga caccggcaac gagctgtcta caaaggaaca gatctcacgc    420

aatagcaaag ctctggaaga gaagtatgtc gcagagctgc agctggaacg gctgaagaaa    480

gatggcgagg tgagagggtc aattaatagg ttcaagacaa gcgactacgt caaagaagcc    540

aagcagctgc tgaaagtgca gaaggcttac caccagctgg atcagagctt catcgatact    600

tatatcgacc tgctggagac tcggagaacc tactatgagg gaccaggaga agggagcccc    660

ttcggatgga aagacatcaa ggaatggtac gagatgctga tgggacattg cacctatttt    720

ccagaagagc tgagaagcgt caagtacgct tataacgcag atctgtacaa cgccctgaat    780

gacctgaaca acctggtcat caccagggat gaaaacgaga aactggaata ctatgagaag    840

ttccagatca tcgaaaacgt gtttaagcag aagaaaaagc ctacactgaa acagattgct    900

aaggagatcc tggtcaacga agaggacatc aagggctacc gggtgacaag cactggaaaa    960

ccagagttca ccaatctgaa agtgtatcac gatattaagg acatcacagc acggaaagaa   1020

atcattgaga acgccgaact gctggatcag attgctaaga tcctgactat ctaccagagc   1080

tccgaggaca tccaggaaga gctgactaac ctgaacagcg agctgaccca ggaagagatc   1140

gaacagatta gtaatctgaa ggggtacacc ggaacacaca acctgtccct gaaagctatc   1200

aatctgattc tggatgagct gtggcataca aacgacaatc agattgcaat ctttaaccgg   1260

ctgaagctgg tcccaaaaaa ggtggacctg agtcagcaga aagagatccc aaccacactg   1320

gtggacgatt tcattctgtc acccgtggtc aagcggagct tcatccagag catcaaagtg   1380

atcaacgcca tcatcaagaa gtacggcctg cccaatgata tcattatcga gctggctagg   1440

gagaagaaca gcaaggacgc acagaagatg atcaatgaga tgcagaaacg aaaccggcag   1500

accaatgaac gcattgaaga gattatccga actaccggga aagagaacgc aaagtacctg   1560

attgaaaaaa tcaagctgca cgatatgcag gagggaaagt gtctgtattc tctggaggcc   1620

atcccccctgg aggacctgct gaacaatcca ttcaactacg aggtcgatca tattatcccc   1680
```

agaagcgtgt ccttcgacaa ttcctttaac aacaaggtgc tggtcaagca ggaagagaac 1740
tctaaaaagg gcaataggac tcctttccag tacctgtcta gttcagattc caagatctct 1800
tacgaaacct ttaaaaagca cattctgaat ctggccaaag gaaagggccg catcagcaag 1860
accaaaaagg agtacctgct ggaagagcgg gacatcaaca gattctccgt ccagaaggat 1920
tttattaacc ggaatctggt ggacacaaga tacgctactc gcggcctgat gaatctgctg 1980
cgatcctatt tccgggtgaa caatctggat gtgaaagtca agtccatcaa cggcgggttc 2040
acatcttttc tgaggcgcaa atggaagttt aaaaaggagc gcaacaaagg gtacaagcac 2100
catgccgaag atgctctgat tatcgcaaat gccgacttca tctttaagga gtggaaaaag 2160
ctggacaaag ccaagaaagt gatggagaac cagatgttcg aagagaagca ggccgaatct 2220
atgcccgaaa tcgagacaga acaggagtac aaggagattt tcatcactcc tcaccagatc 2280
aagcatatca aggatttcaa ggactacaag tactctcacc gggtggataa aaagcccaac 2340
agagagctga tcaatgacac cctgtatagt acaagaaaag acgataaggg gaataccctg 2400
attgtgaaca atctgaacgg actgtacgac aaagataatg acaagctgaa aaagctgatc 2460
aacaaaagtc ccgagaagct gctgatgtac caccatgatc ctcagacata tcagaaactg 2520
aagctgatta tggagcagta cggcgacgag aagaacccac tgtataagta ctatgaagag 2580
actgggaact acctgaccaa gtatagcaaa aaggataatg gccccgtgat caagaagatc 2640
aagtactatg ggaacaagct gaatgcccat ctggacatca cagacgatta ccctaacagt 2700
cgcaacaagg tggtcaagct gtcactgaag ccatacagat tcgatgtcta tctggacaac 2760
ggcgtgtata aatttgtgac tgtcaagaat ctggatgtca tcaaaaagga gaactactat 2820
gaagtgaata gcaagtgcta cgaagaggct aaaaagctga aaaagattag caaccaggca 2880
gagttcatcg cctcctttta caacaacgac ctgattaaga tcaatggcga actgtatagg 2940
gtcatcgggg tgaacaatga tctgctgaac cgcattgaag tgaatatgat tgacatcact 3000
taccgagagt atctggaaaa catgaatgat aagcgccccc ctcgaattat caaaacaatt 3060
gcctctaaga ctcagagtat caaaaagtac tcaaccgaca ttctgggaaa cctgtatgag 3120
gtgaagagca aaaagcaccc tcagattatc aaaaagggc 3159

<210> SEQ ID NO 11
<211> LENGTH: 3159
<212> TYPE: DNA
<213> ORGANISM: Staphylococcus aureus

<400> SEQUENCE: 11
atgaaaagga actacattct ggggctggac atcgggatta caagcgtggg gtatgggatt 60
attgactatg aaacaaggga cgtgatcgac gcaggcgtca gactgttcaa ggaggccaac 120
gtggaaaaca atgagggacg gagaagcaag aggggagcca ggcgcctgaa acgacggaga 180
aggcacagaa tccagagggt gaagaaactg ctgttcgatt acaacctgct gaccgaccat 240
tctgagctga gtggaattaa tccttatgaa gccagggtga aaggcctgag tcagaagctg 300
tcagaggaag agttttccgc agctctgctg cacctggcta agcgccgagg agtgcataac 360
gtcaatgagg tggaagagga caccggcaac gagctgtcta caaaggaaca gatctcacgc 420
aatagcaaag ctctggaaga gaagtatgtc gcagagctgc agctggaacg gctgaagaaa 480
gatggcgagg tgagagggtc aattaatagg ttcaagacaa gcgactacgt caaagaagcc 540
aagcagctgc tgaaagtgca gaaggcttac caccagctgg atcagagctt catcgatact 600

-continued

```
tatatcgacc tgctggagac tcggagaacc tactatgagg gaccaggaga agggagcccc    660
ttcggatgga aagacatcaa ggaatggtac gagatgctga tgggacattg cacctatttt    720
ccagaagagc tgagaagcgt caagtacgct tataacgcag atctgtacaa cgccctgaat    780
gacctgaaca acctggtcat caccagggat gaaaacgaga aactggaata ctatgagaag    840
ttccagatca tcgaaaacgt gtttaagcag aagaaaaagc ctacactgaa acagattgct    900
aaggagatcc tggtcaacga agaggacatc aagggctacc gggtgacaag cactggaaaa    960
ccagagttca ccaatctgaa agtgtatcac gatattaagg acatcacagc acggaaagaa   1020
atcattgaga acgccgaact gctggatcag attgctaaga tcctgactat ctaccagagc   1080
tccgaggaca tccaggaaga gctgactaac ctgaacagcg agctgaccca ggaagagatc   1140
gaacagatta gtaatctgaa ggggtacacc ggaacacaca acctgtccct gaaagctatc   1200
aatctgattc tggatgagct gtggcataca aacgacaatc agattgcaat ctttaaccgg   1260
ctgaagctgg tcccaaaaaa ggtggacctg agtcagcaga aagagatccc aaccacactg   1320
gtggacgatt tcattctgtc acccgtggtc aagcggagct tcatccagag catcaaagtg   1380
atcaacgcca tcatcaagaa gtacggcctg cccaatgata tcattatcga gctggctagg   1440
gagaagaaca gcaaggacgc acagaagatg atcaatgaga tgcagaaacg aaaccggcag   1500
accaatgaac gcattgaaga gattatccga actaccggga aagagaacgc aaagtacctg   1560
attgaaaaaa tcaagctgca cgatatgcag gagggaaagt gtctgtattc tctggaggcc   1620
atcccctgg aggacctgct gaacaatcca ttcaactacg aggtcgatca tattatcccc   1680
agaagcgtgt ccttcgacaa ttcctttaac aacaaggtgc tggtcaagca ggaagaggcc   1740
tctaaaaagg gcaataggac tcctttccag tacctgtcta gttcagattc caagatctct   1800
tacgaaacct ttaaaaagca cattctgaat ctggccaaag gaaagggccg catcagcaag   1860
accaaaaagg agtacctgct ggaagagcgg gacatcaaca gattctccgt ccagaaggat   1920
tttattaacc ggaatctggt ggacacaaga tacgctactc gcggcctgat gaatctgctg   1980
cgatcctatt tccgggtgaa caatctggat gtgaaagtca agtccatcaa cggcgggttc   2040
acatcttttc tgaggcgcaa atggaagttt aaaaaggagc gcaacaaagg gtacaagcac   2100
catgccgaag atgctctgat tatcgcaaat gccgacttca tctttaagga gtggaaaaag   2160
ctggacaaag ccaagaaagt gatggagaac cagatgttcg aagagaagca ggccgaatct   2220
atgcccgaaa tcgagacaga acaggagtac aaggagattt tcatcactcc tcaccagatc   2280
aagcatatca aggatttcaa ggactacaag tactctcacc gggtggataa aaagcccaac   2340
agagagctga tcaatgacac cctgtatagt acaagaaaag acgataaggg gaataccctg   2400
attgtgaaca atctgaacgg actgtacgac aaagataatg acaagctgaa aaagctgatc   2460
aacaaaagtc ccgagaagct gctgatgtac caccatgatc ctcagacata tcagaaactg   2520
aagctgatta tggagcagta cggcgacgag aagaacccac tgtataagta ctatgaagag   2580
actgggaact acctgaccaa gtatagcaaa aaggataatg gccccgtgat caagaagatc   2640
aagtactatg ggaacaagct gaatgcccat ctggacatca cagacgatta ccctaacagt   2700
cgcaacaagg tggtcaagct gtcactgaag ccatacagat tcgatgtcta tctggacaac   2760
ggcgtgtata aatttgtgac tgtcaagaat ctggatgtca tcaaaaagga gaactactat   2820
gaagtgaata gcaagtgcta cgaagaggct aaaaagctga aaaagattag caaccaggca   2880
gagttcatcg cctcctttta caacaacgac ctgattaaga tcaatggcga actgtatagg   2940
gtcatcgggg tgaacaatga tctgctgaac cgcattgaag tgaatatgat tgacatcact   3000
```

```
taccgagagt atctggaaaa catgaatgat aagcgccccc ctcgaattat caaaacaatt   3060

gcctctaaga ctcagagtat caaaaagtac tcaaccgaca ttctgggaaa cctgtatgag   3120

gtgaagagca aaaagcaccc tcagattatc aaaaagggc                          3159


<210> SEQ ID NO 12
<211> LENGTH: 1082
<212> TYPE: PRT
<213> ORGANISM: Neisseria meningitidis

<400> SEQUENCE: 12

Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Asp
            20                  25                  30

Glu Asn Pro Ile Cys Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Arg Ala His Arg Leu Leu
65                  70                  75                  80

Arg Ala Arg Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
    210                 215                 220

Pro His Val Ser Gly Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
        275                 280                 285

Leu Glu Gln Gly Ser Glu Arg Pro Leu Thr Asp Thr Glu Arg Ala Thr
    290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
```

-continued

```
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
    370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Lys Arg Tyr Asp Glu Ala Cys Ala Glu Ile
        435                 440                 445

Tyr Gly Asp His Tyr Gly Lys Lys Asn Thr Glu Glu Lys Ile Tyr Leu
    450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
        515                 520                 525

Asp Arg Glu Lys Ala Ala Ala Lys Phe Arg Glu Tyr Phe Pro Asn Phe
    530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Asp His Ala Leu Pro Phe
            580                 585                 590

Ser Arg Thr Trp Asp Asp Ser Phe Asn Asn Lys Val Leu Val Leu Gly
        595                 600                 605

Ser Glu Asn Gln Asn Lys Gly Asn Gln Thr Pro Tyr Glu Tyr Phe Asn
    610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
                645                 650                 655

Phe Asp Glu Asp Gly Phe Lys Glu Arg Asn Leu Asn Asp Thr Arg Tyr
            660                 665                 670

Val Asn Arg Phe Leu Cys Gln Phe Val Ala Asp Arg Met Arg Leu Thr
        675                 680                 685

Gly Lys Gly Lys Lys Arg Val Phe Ala Ser Asn Gly Gln Ile Thr Asn
    690                 695                 700

Leu Leu Arg Gly Phe Trp Gly Leu Arg Lys Val Arg Ala Glu Asn Asp
705                 710                 715                 720

Arg His His Ala Leu Asp Ala Val Val Val Ala Cys Ser Thr Val Ala
                725                 730                 735

Met Gln Gln Lys Ile Thr Arg Phe Val Arg Tyr Lys Glu Met Asn Ala
            740                 745                 750

Phe Asp Gly Lys Thr Ile Asp Lys Glu Thr Gly Glu Val Leu His Gln
        755                 760                 765
```

```
Lys Thr His Phe Pro Gln Pro Trp Glu Phe Phe Ala Gln Glu Val Met
    770                 775                 780

Ile Arg Val Phe Gly Lys Pro Asp Gly Lys Pro Glu Phe Glu Glu Ala
785                 790                 795                 800

Asp Thr Pro Glu Lys Leu Arg Thr Leu Leu Ala Glu Lys Leu Ser Ser
                805                 810                 815

Arg Pro Glu Ala Val His Glu Tyr Val Thr Pro Leu Phe Val Ser Arg
            820                 825                 830

Ala Pro Asn Arg Lys Met Ser Gly Gln Gly His Met Glu Thr Val Lys
        835                 840                 845

Ser Ala Lys Arg Leu Asp Glu Gly Val Ser Val Leu Arg Val Pro Leu
    850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Ala Glu Pro Phe Tyr Lys Tyr Asp Lys
            900                 905                 910

Ala Gly Asn Arg Thr Gln Gln Val Lys Ala Val Arg Val Glu Gln Val
        915                 920                 925

Gln Lys Thr Gly Val Trp Val Arg Asn His Asn Gly Ile Ala Asp Asn
    930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Gln Gly Lys Asp Glu Glu Asp Trp Gln Leu Ile Asp
            980                 985                 990

Asp Ser Phe Asn Phe Lys Phe Ser  Leu His Pro Asn Asp  Leu Val Glu
        995                 1000                1005

Val Ile  Thr Lys Lys Ala Arg  Met Phe Gly Tyr Phe  Ala Ser Cys
    1010                1015                1020

His Arg  Gly Thr Gly Asn Ile  Asn Ile Arg Ile His  Asp Leu Asp
    1025                1030                1035

His Lys  Ile Gly Lys Asn Gly  Ile Leu Glu Gly Ile  Gly Val Lys
    1040                1045                1050

Thr Ala  Leu Ser Phe Gln Lys  Tyr Gln Ile Asp Glu  Leu Gly Lys
    1055                1060                1065

Glu Ile  Arg Pro Cys Arg Leu  Lys Lys Arg Pro Pro  Val Arg
    1070                1075                1080
```

<210> SEQ ID NO 13
<211> LENGTH: 3249
<212> TYPE: DNA
<213> ORGANISM: Neisseria meningitidis
<220> FEATURE:
<221> NAME/KEY: misc_feature
<222> LOCATION: (1)..(3249)
<223> OTHER INFORMATION: Exemplary codon optimized Cas9

<400> SEQUENCE: 13

```
atggccgcct tcaagcccaa ccccatcaac tacatcctgg gcctggacat cggcatcgcc      60

agcgtgggct gggccatggt ggagatcgac gaggacgaga accccatctg cctgatcgac     120

ctgggtgtgc gcgtgttcga gcgcgctgag gtgcccaaga ctggtgacag tctggctatg     180
```

-continued

```
gctcgccggc ttgctcgctc tgttcggcgc cttactcgcc ggcgcgctca ccgccttctg    240
cgcgctcgcc gcctgctgaa gcgcgagggt gtgctgcagg ctgccgactt cgacgagaac    300
ggcctgatca agagcctgcc caacactcct tggcagctgc gcgctgccgc tctggaccgc    360
aagctgactc ctctggagtg gagcgccgtg ctgctgcacc tgatcaagca ccgcggctac    420
ctgagccagc gcaagaacga gggcgagacc gccgacaagg agctgggtgc tctgctgaag    480
ggcgtggccg acaacgccca cgccctgcag actggtgact tccgcactcc tgctgagctg    540
gccctgaaca agttcgagaa ggagagcggc cacatccgca accagcgcgg cgactacagc    600
cacaccttca gccgcaagga cctgcaggcc gagctgatcc tgctgttcga gaagcagaag    660
gagttcggca acccccacgt gagcggcggc ctgaaggagg gcatcgagac cctgctgatg    720
acccagcgcc ccgccctgag cggcgacgcc gtgcagaaga tgctgggcca ctgcaccttc    780
gagccagccg agcccaaggc cgccaagaac acctacaccg ccgagcgctt catctggctg    840
accaagctga acaacctgcg catcctggag cagggcagcg agcgccccct gaccgacacc    900
gagcgcgcca ccctgatgga cgagccctac cgcaagagca agctgaccta cgcccaggcc    960
cgcaagctgc tgggtctgga ggacaccgcc ttcttcaagg gcctgcgcta cggcaaggac   1020
aacgccgagg ccagcaccct gatggagatg aaggcctacc acgccatcag ccgcgccctg   1080
gagaaggagg gcctgaagga caagaagagt cctctgaacc tgagccccga gctgcaggac   1140
gagatcggca ccgccttcag cctgttcaag accgacgagg acatcaccgg ccgcctgaag   1200
gaccgcatcc agcccgagat cctggaggcc ctgctgaagc acatcagctt cgacaagttc   1260
gtgcagatca gcctgaaggc cctgcgccgc atcgtgcccc tgatggagca gggcaagcgc   1320
tacgacgagg cctgcgccga gatctacggc gaccactacg gcaagaagaa caccgaggag   1380
aagatctacc tgcctcctat ccccgccgac gagatccgca accccgtggt gctgcgcgcc   1440
ctgagccagg cccgcaaggt gatcaacggc gtggtgcgcc gctacggcag ccccgcccgc   1500
atccacatcg agaccgcccg cgaggtgggc aagagcttca aggaccgcaa ggagatcgag   1560
aagcgccagg aggagaaccg caaggaccgc gagaaggccg ccgccaagtt ccgcgagtac   1620
ttccccaact tcgtgggcga gcccaagagc aaggacatcc tgaagctgcg cctgtacgag   1680
cagcagcacg gcaagtgcct gtacagcggc aaggagatca acctgggccg cctgaacgag   1740
aagggctacg tggagatcga ccacgccctg cccttcagcc gcacctggga cgacagcttc   1800
aacaacaagg tgctggtgct gggcagcgag aaccagaaca agggcaacca gacccccctac   1860
gagtacttca acggcaagga caacagccgc gagtggcagg agttcaaggc ccgcgtggag   1920
accagccgct tcccccgcag caagaagcag cgcatcctgc tgcagaagtt cgacgaggac   1980
ggcttcaagg agcgcaacct gaacgacacc cgctacgtga accgcttcct gtgccagttc   2040
gtggccgacc gcatgcgcct gaccggcaag ggcaagaagc gcgtgttcgc cagcaacggc   2100
cagatcacca acctgctgcg cggcttctgg ggcctgcgca aggtgcgcgc cgagaacgac   2160
cgccaccacg ccctggacgc cgtggtggtg gcctgcagca ccgtggccat gcagcagaag   2220
atcacccgct tcgtgcgcta caaggagatg aacgccttcg acggtaaaac catcgacaag   2280
gagaccggcg aggtgctgca ccagaagacc cacttccccc agccctggga gttcttcgcc   2340
caggaggtga tgatccgcgt gttcggcaag cccgacggca agcccgagtt cgaggaggcc   2400
gacacccccg agaagctgcg caccctgctg gccgagaagc tgagcagccg ccctgaggcc   2460
gtgcacgagt acgtgactcc tctgttcgtg agccgcgccc ccaaccgcaa gatgagcggt   2520
cagggtcaca tggagaccgt gaagagcgcc aagcgcctgg acgagggcgt gagcgtgctg   2580
```

```
cgcgtgcccc tgacccagct gaagctgaag gacctggaga agatggtgaa ccgcgagcgc   2640

gagcccaagc tgtacgaggc cctgaaggcc cgcctggagg cccacaagga cgaccccgcc   2700

aaggccttcg ccgagccctt ctacaagtac gacaaggccg gcaaccgcac ccagcaggtg   2760

aaggccgtgc gcgtggagca ggtgcagaag accggcgtgt gggtgcgcaa ccacaacggc   2820

atcgccgaca acgccaccat ggtgcgcgtg gacgtgttcg agaagggcga caagtactac   2880

ctggtgccca tctacagctg gcaggtggcc aagggcatcc tgcccgaccg cgccgtggtg   2940

cagggcaagg acgaggagga ctggcagctg atcgacgaca gcttcaactt caagttcagc   3000

ctgcacccca acgacctggt ggaggtgatc accaagaagg cccgcatgtt cggctacttc   3060

gccagctgcc accgcggcac cggcaacatc aacatccgca tccacgacct ggaccacaag   3120

atcggcaaga acggcatcct ggagggcatc ggcgtgaaga ccgccctgag cttccagaag   3180

taccagatcg acgagctggg caaggagatc cgcccctgcc gcctgaagaa gcgccctcct   3240

gtgcgctaa                                                           3249
```

```
<210> SEQ ID NO 14
<211> LENGTH: 859
<212> TYPE: PRT
<213> ORGANISM: Artificial Sequence
<220> FEATURE:
<223> OTHER INFORMATION: Synthetic Cas9 consensus sequence derived from
      Sm, Sp, St, and Li Cas9 sequences
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(18)
<223> OTHER INFORMATION: N-terminal RuvC-like domain
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(31)
<223> OTHER INFORMATION: Each Xaa can independently be any naturally
      occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
```

<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Each Xaa can independently be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
<222> LOCATION: (128)..(133)
<223> OTHER INFORMATION: Each Xaa can independently be any naturally occurring amino acid
<220> FEATURE:
<221> NAME/KEY: misc_feature
<222> LOCATION: (135)..(135)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (139)..(147)
<223> OTHER INFORMATION: Each Xaa can independently be any naturally
occurring amino acid
<220> FEATURE:
<221> NAME/KEY: misc_feature
<222> LOCATION: (153)..(155)
<223> OTHER INFORMATION: Each Xaa can independently be any naturally
occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (166)..(168)
<223> OTHER INFORMATION: Each Xaa can independently be any naturally
occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (171)..(171)
<223> OTHER INFORMATION: Xaa can be any naturally occurring amino acid
<220> FEATURE:
<221> NAME/KEY: misc_feature
<222> LOCATION: (173)..(175)
<223> OTHER INFORMATION: Each Xaa can independently be any naturally
occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (185)..(187)
<223> OTHER INFORMATION: Each Xaa can independently be any naturally
occurring amino acid
<220> FEATURE:
<221> NAME/KEY: misc_feature
<222> LOCATION: (189)..(189)
<223> OTHER INFORMATION: Xaa can be any naturally occurring amino acid
<220> FEATURE:
<221> NAME/KEY: misc_feature
<222> LOCATION: (192)..(195)
<223> OTHER INFORMATION: Each Xaa can independently be any naturally
occurring amino acid
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
<222> LOCATION: (202)..(202)

```
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (207)..(207)
<223> OTHER INFORMATION: Xaa can be any naturally occurring amino acid
<220> FEATURE:
<221> NAME/KEY: misc_feature
<222> LOCATION: (210)..(210)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (220)..(220)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (224)..(224)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (241)..(241)
<223> OTHER INFORMATION: Xaa can be any naturally occurring amino acid
<220> FEATURE:
<221> NAME/KEY: misc_feature
<222> LOCATION: (244)..(246)
<223> OTHER INFORMATION: Each Xaa can independently be any naturally
      occurring amino acid
<220> FEATURE:
<221> NAME/KEY: misc_feature
<222> LOCATION: (248)..(248)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (250)..(250)
<223> OTHER INFORMATION: Xaa can be any naturally occurring amino acid
<220> FEATURE:
<221> NAME/KEY: misc_feature
<222> LOCATION: (252)..(254)
<223> OTHER INFORMATION: Each Xaa can independently be any naturally
      occurring amino acid
<220> FEATURE:
<221> NAME/KEY: misc_feature
<222> LOCATION: (256)..(256)
<223> OTHER INFORMATION: Xaa can be any naturally occurring amino acid
```

<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (268)..(268)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (273)..(273)
<223> OTHER INFORMATION: Xaa can be any naturally occurring amino acid
<220> FEATURE:
<221> NAME/KEY: misc_feature
<222> LOCATION: (277)..(277)
<223> OTHER INFORMATION: Xaa can be any naturally occurring amino acid
<220> FEATURE:
<221> NAME/KEY: misc_feature
<222> LOCATION: (280)..(280)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (283)..(283)
<223> OTHER INFORMATION: Xaa can be any naturally occurring amino acid
<220> FEATURE:
<221> NAME/KEY: misc_feature
<222> LOCATION: (289)..(289)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (292)..(294)
<223> OTHER INFORMATION: Each Xaa can independently be any naturally
occurring amino acid
<220> FEATURE:
<221> NAME/KEY: misc_feature
<222> LOCATION: (301)..(301)
<223> OTHER INFORMATION: Xaa can be any naturally occurring amino acid
<220> FEATURE:
<221> NAME/KEY: misc_feature
<222> LOCATION: (308)..(308)
<223> OTHER INFORMATION: Xaa can be any naturally occurring amino acid
<220> FEATURE:
<221> NAME/KEY: misc_feature
<222> LOCATION: (319)..(322)
<223> OTHER INFORMATION: Each Xaa can independently be any naturally
occurring amino acid
<220> FEATURE:
<221> NAME/KEY: misc_feature
<222> LOCATION: (328)..(328)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (335)..(337)
<223> OTHER INFORMATION: Each Xaa can independently be any naturally
occurring amino acid
<220> FEATURE:
<221> NAME/KEY: misc_feature
<222> LOCATION: (346)..(346)
<223> OTHER INFORMATION: Xaa can be any naturally occurring amino acid
<220> FEATURE:
<221> NAME/KEY: misc_feature
<222> LOCATION: (347)..(347)
<223> OTHER INFORMATION: Xaa can be any naturally occurring amino acid

```
<220> FEATURE:
<221> NAME/KEY: misc_feature
<222> LOCATION: (356)..(361)
<223> OTHER INFORMATION: Each Xaa can independently be any naturally
      occurring amino acid
<220> FEATURE:
<221> NAME/KEY: misc_feature
<222> LOCATION: (363)..(363)
<223> OTHER INFORMATION: Xaa can be any naturally occurring amino acid
<220> FEATURE:
<221> NAME/KEY: misc_feature
<222> LOCATION: (370)..(373)
<223> OTHER INFORMATION: Each Xaa can independently be any naturally
      occurring amino acid
<220> FEATURE:
<221> NAME/KEY: misc_feature
<222> LOCATION: (375)..(375)
<223> OTHER INFORMATION: Xaa can be any naturally occurring amino acid
<220> FEATURE:
<221> NAME/KEY: misc_feature
<222> LOCATION: (376)..(376)
<223> OTHER INFORMATION: Xaa can be any naturally occurring amino acid
<220> FEATURE:
<221> NAME/KEY: misc_feature
<222> LOCATION: (379)..(379)
<223> OTHER INFORMATION: Xaa can be any naturally occurring amino acid
<220> FEATURE:
<221> NAME/KEY: misc_feature
<222> LOCATION: (386)..(390)
<223> OTHER INFORMATION: Each Xaa can independently be any naturally
      occurring amino acid
<220> FEATURE:
<221> NAME/KEY: misc_feature
<222> LOCATION: (393)..(393)
<223> OTHER INFORMATION: Xaa can be any naturally occurring amino acid
<220> FEATURE:
<221> NAME/KEY: misc_feature
<222> LOCATION: (395)..(395)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (398)..(398)
<223> OTHER INFORMATION: Xaa can be any naturally occurring amino acid
<220> FEATURE:
<221> NAME/KEY: misc_feature
<222> LOCATION: (400)..(400)
<223> OTHER INFORMATION: Xaa can be any naturally occurring amino acid
<220> FEATURE:
<221> NAME/KEY: misc_feature
<222> LOCATION: (403)..(403)
<223> OTHER INFORMATION: Xaa can be any naturally occurring amino acid
<220> FEATURE:
<221> NAME/KEY: misc_feature
<222> LOCATION: (407)..(407)
<223> OTHER INFORMATION: Xaa can be any naturally occurring amino acid
<220> FEATURE:
<221> NAME/KEY: misc_feature
<222> LOCATION: (410)..(410)
<223> OTHER INFORMATION: Xaa can be any naturally occurring amino acid
<220> FEATURE:
<221> NAME/KEY: misc_feature
<222> LOCATION: (411)..(411)
<223> OTHER INFORMATION: Xaa can be any naturally occurring amino acid
<220> FEATURE:
<221> NAME/KEY: misc_feature
<222> LOCATION: (413)..(416)
<223> OTHER INFORMATION: Each Xaa can independently be any naturally
      occurring amino acid
<220> FEATURE:
<221> NAME/KEY: misc_feature
<222> LOCATION: (418)..(418)
<223> OTHER INFORMATION: Xaa can be any naturally occurring amino acid
<220> FEATURE:
<221> NAME/KEY: misc_feature
<222> LOCATION: (422)..(422)
```

<223> OTHER INFORMATION: Xaa can be any naturally occurring amino acid
<220> FEATURE:
<221> NAME/KEY: misc_feature
<222> LOCATION: (428)..(428)
<223> OTHER INFORMATION: Xaa can be any naturally occurring amino acid
<220> FEATURE:
<221> NAME/KEY: misc_feature
<222> LOCATION: (431)..(431)
<223> OTHER INFORMATION: Xaa can be any naturally occurring amino acid
<220> FEATURE:
<221> NAME/KEY: misc_feature
<222> LOCATION: (433)..(433)
<223> OTHER INFORMATION: Xaa can be any naturally occurring amino acid
<220> FEATURE:
<221> NAME/KEY: misc_feature
<222> LOCATION: (437)..(439)
<223> OTHER INFORMATION: Each Xaa can independently be any naturally
occurring amino acid
<220> FEATURE:
<221> NAME/KEY: misc_feature
<222> LOCATION: (445)..(445)
<223> OTHER INFORMATION: Xaa can be any naturally occurring amino acid
<220> FEATURE:
<221> NAME/KEY: misc_feature
<222> LOCATION: (451)..(451)
<223> OTHER INFORMATION: Xaa can be any naturally occurring amino acid
<220> FEATURE:
<221> NAME/KEY: misc_feature
<222> LOCATION: (456)..(456)
<223> OTHER INFORMATION: Xaa can be any naturally occurring amino acid
<220> FEATURE:
<221> NAME/KEY: misc_feature
<222> LOCATION: (459)..(459)
<223> OTHER INFORMATION: Xaa can be any naturally occurring amino acid
<220> FEATURE:
<221> NAME/KEY: misc_feature
<222> LOCATION: (465)..(469)
<223> OTHER INFORMATION: Each Xaa can independently be any naturally
occurring amino acid
<220> FEATURE:
<221> NAME/KEY: misc_feature
<222> LOCATION: (481)..(481)
<223> OTHER INFORMATION: Xaa can be any naturally occurring amino acid
<220> FEATURE:
<221> NAME/KEY: misc_feature
<222> LOCATION: (482)..(482)
<223> OTHER INFORMATION: Xaa can be any naturally occurring amino acid
<220> FEATURE:
<221> NAME/KEY: misc_feature
<222> LOCATION: (484)..(484)
<223> OTHER INFORMATION: Xaa can be any naturally occurring amino acid
<220> FEATURE:
<221> NAME/KEY: misc_feature
<222> LOCATION: (490)..(490)
<223> OTHER INFORMATION: Xaa can be any naturally occurring amino acid
<220> FEATURE:
<221> NAME/KEY: misc_feature
<222> LOCATION: (494)..(494)
<223> OTHER INFORMATION: Xaa can be any naturally occurring amino acid
<220> FEATURE:
<221> NAME/KEY: misc_feature
<222> LOCATION: (495)..(502)
<223> OTHER INFORMATION: RuvC-like domain
<220> FEATURE:
<221> NAME/KEY: misc_feature
<222> LOCATION: (497)..(497)
<223> OTHER INFORMATION: Xaa can be any naturally occurring amino acid
<220> FEATURE:
<221> NAME/KEY: misc_feature
<222> LOCATION: (506)..(506)
<223> OTHER INFORMATION: Xaa can be any naturally occurring amino acid
<220> FEATURE:
<221> NAME/KEY: misc_feature
<222> LOCATION: (510)..(510)
<223> OTHER INFORMATION: Xaa can be any naturally occurring amino acid
<220> FEATURE:
<221> NAME/KEY: misc_feature
<222> LOCATION: (513)..(513)
<223> OTHER INFORMATION: Xaa can be any naturally occurring amino acid
<220> FEATURE:
<221> NAME/KEY: misc_feature
<222> LOCATION: (514)..(514)
<223> OTHER INFORMATION: Xaa can be any naturally occurring amino acid
<220> FEATURE:
<221> NAME/KEY: misc_feature
<222> LOCATION: (517)..(517)
<223> OTHER INFORMATION: Xaa can be any naturally occurring amino acid
<220> FEATURE:
<221> NAME/KEY: misc_feature
<222> LOCATION: (520)..(520)
<223> OTHER INFORMATION: Xaa can be any naturally occurring amino acid
<220> FEATURE:
<221> NAME/KEY: misc_feature
<222> LOCATION: (525)..(525)
<223> OTHER INFORMATION: Xaa can be any naturally occurring amino acid
<220> FEATURE:
<221> NAME/KEY: misc_feature
<222> LOCATION: (526)..(526)
<223> OTHER INFORMATION: Xaa can be any naturally occurring amino acid
<220> FEATURE:
<221> NAME/KEY: misc_feature
<222> LOCATION: (529)..(529)
<223> OTHER INFORMATION: Xaa can be any naturally occurring amino acid
<220> FEATURE:
<221> NAME/KEY: misc_feature
<222> LOCATION: (531)..(531)
<223> OTHER INFORMATION: Xaa can be any naturally occurring amino acid
<220> FEATURE:
<221> NAME/KEY: misc_feature
<222> LOCATION: (532)..(532)
<223> OTHER INFORMATION: Xaa can be any naturally occurring amino acid
<220> FEATURE:
<221> NAME/KEY: misc_feature
<222> LOCATION: (534)..(534)
<223> OTHER INFORMATION: Xaa can be any naturally occurring amino acid
<220> FEATURE:
<221> NAME/KEY: misc_feature
<222> LOCATION: (542)..(542)
<223> OTHER INFORMATION: Xaa can be any naturally occurring amino acid
<220> FEATURE:
<221> NAME/KEY: misc_feature
<222> LOCATION: (546)..(546)
<223> OTHER INFORMATION: Xaa can be any naturally occurring amino acid
<220> FEATURE:
<221> NAME/KEY: misc_feature
<222> LOCATION: (547)..(547)
<223> OTHER INFORMATION: Xaa can be any naturally occurring amino acid
<220> FEATURE:
<221> NAME/KEY: misc_feature
<222> LOCATION: (553)..(553)
<223> OTHER INFORMATION: Xaa can be any naturally occurring amino acid
<220> FEATURE:
<221> NAME/KEY: misc_feature
<222> LOCATION: (555)..(575)
<223> OTHER INFORMATION: HNH-like domain
<220> FEATURE:
<221> NAME/KEY: misc_feature
<222> LOCATION: (556)..(556)
<223> OTHER INFORMATION: Xaa can be any naturally occurring amino acid
<220> FEATURE:
<221> NAME/KEY: misc_feature
<222> LOCATION: (560)..(560)
<223> OTHER INFORMATION: Xaa can be any naturally occurring amino acid
<220> FEATURE:
<221> NAME/KEY: misc_feature
<222> LOCATION: (563)..(563)
<223> OTHER INFORMATION: Xaa can be any naturally occurring amino acid
<220> FEATURE:
<221> NAME/KEY: misc_feature
<222> LOCATION: (565)..(565)
<223> OTHER INFORMATION: Xaa can be any naturally occurring amino acid
<220> FEATURE:
<221> NAME/KEY: misc_feature
<222> LOCATION: (567)..(567)
<223> OTHER INFORMATION: Xaa can be any naturally occurring amino acid
<220> FEATURE:
<221> NAME/KEY: misc_feature
<222> LOCATION: (579)..(579)

<223> OTHER INFORMATION: Xaa can be any naturally occurring amino acid
<220> FEATURE:
<221> NAME/KEY: misc_feature
<222> LOCATION: (582)..(582)
<223> OTHER INFORMATION: Xaa can be any naturally occurring amino acid
<220> FEATURE:
<221> NAME/KEY: misc_feature
<222> LOCATION: (583)..(583)
<223> OTHER INFORMATION: Xaa can be any naturally occurring amino acid
<220> FEATURE:
<221> NAME/KEY: misc_feature
<222> LOCATION: (585)..(585)
<223> OTHER INFORMATION: Xaa can be any naturally occurring amino acid
<220> FEATURE:
<221> NAME/KEY: misc_feature
<222> LOCATION: (588)..(588)
<223> OTHER INFORMATION: Xaa can be any naturally occurring amino acid
<220> FEATURE:
<221> NAME/KEY: misc_feature
<222> LOCATION: (590)..(590)
<223> OTHER INFORMATION: Xaa can be any naturally occurring amino acid
<220> FEATURE:
<221> NAME/KEY: misc_feature
<222> LOCATION: (592)..(592)
<223> OTHER INFORMATION: Xaa can be any naturally occurring amino acid
<220> FEATURE:
<221> NAME/KEY: misc_feature
<222> LOCATION: (594)..(596)
<223> OTHER INFORMATION: Each Xaa can independently be any naturally occurring amino acid
<220> FEATURE:
<221> NAME/KEY: misc_feature
<222> LOCATION: (610)..(610)
<223> OTHER INFORMATION: Xaa can be any naturally occurring amino acid
<220> FEATURE:
<221> NAME/KEY: misc_feature
<222> LOCATION: (616)..(616)
<223> OTHER INFORMATION: Xaa can be any naturally occurring amino acid
<220> FEATURE:
<221> NAME/KEY: misc_feature
<222> LOCATION: (628)..(628)
<223> OTHER INFORMATION: Xaa can be any naturally occurring amino acid
<220> FEATURE:
<221> NAME/KEY: misc_feature
<222> LOCATION: (631)..(631)
<223> OTHER INFORMATION: Xaa can be any naturally occurring amino acid
<220> FEATURE:
<221> NAME/KEY: misc_feature
<222> LOCATION: (633)..(633)
<223> OTHER INFORMATION: Xaa can be any naturally occurring amino acid
<220> FEATURE:
<221> NAME/KEY: misc_feature
<222> LOCATION: (634)..(634)
<223> OTHER INFORMATION: Xaa can be any naturally occurring amino acid
<220> FEATURE:
<221> NAME/KEY: misc_feature
<222> LOCATION: (636)..(636)
<223> OTHER INFORMATION: Xaa can be any naturally occurring amino acid
<220> FEATURE:
<221> NAME/KEY: misc_feature
<222> LOCATION: (638)..(641)
<223> OTHER INFORMATION: Each Xaa can independently be any naturally occurring amino acid
<220> FEATURE:
<221> NAME/KEY: misc_feature
<222> LOCATION: (643)..(645)
<223> OTHER INFORMATION: Each Xaa can independently be any naturally occurring amino acid
<220> FEATURE:
<221> NAME/KEY: misc_feature
<222> LOCATION: (653)..(653)
<223> OTHER INFORMATION: Xaa can be any naturally occurring amino acid
<220> FEATURE:
<221> NAME/KEY: misc_feature
<222> LOCATION: (657)..(657)
<223> OTHER INFORMATION: Xaa can be any naturally occurring amino acid
<220> FEATURE:
<221> NAME/KEY: misc_feature
<222> LOCATION: (659)..(659)

<223> OTHER INFORMATION: Xaa can be any naturally occurring amino acid
<220> FEATURE:
<221> NAME/KEY: misc_feature
<222> LOCATION: (660)..(660)
<223> OTHER INFORMATION: Xaa can be any naturally occurring amino acid
<220> FEATURE:
<221> NAME/KEY: misc_feature
<222> LOCATION: (665)..(665)
<223> OTHER INFORMATION: Xaa can be any naturally occurring amino acid
<220> FEATURE:
<221> NAME/KEY: misc_feature
<222> LOCATION: (666)..(666)
<223> OTHER INFORMATION: Xaa can be any naturally occurring amino acid
<220> FEATURE:
<221> NAME/KEY: misc_feature
<222> LOCATION: (668)..(668)
<223> OTHER INFORMATION: Xaa can be any naturally occurring amino acid
<220> FEATURE:
<221> NAME/KEY: misc_feature
<222> LOCATION: (669)..(669)
<223> OTHER INFORMATION: Xaa can be any naturally occurring amino acid
<220> FEATURE:
<221> NAME/KEY: misc_feature
<222> LOCATION: (670)..(677)
<223> OTHER INFORMATION: RuvC-like domain
<220> FEATURE:
<221> NAME/KEY: misc_feature
<222> LOCATION: (680)..(680)
<223> OTHER INFORMATION: Xaa can be any naturally occurring amino acid
<220> FEATURE:
<221> NAME/KEY: misc_feature
<222> LOCATION: (681)..(681)
<223> OTHER INFORMATION: Xaa can be any naturally occurring amino acid
<220> FEATURE:
<221> NAME/KEY: misc_feature
<222> LOCATION: (683)..(683)
<223> OTHER INFORMATION: Xaa can be any naturally occurring amino acid
<220> FEATURE:
<221> NAME/KEY: misc_feature
<222> LOCATION: (686)..(686)
<223> OTHER INFORMATION: Xaa can be any naturally occurring amino acid
<220> FEATURE:
<221> NAME/KEY: misc_feature
<222> LOCATION: (696)..(696)
<223> OTHER INFORMATION: Xaa can be any naturally occurring amino acid
<220> FEATURE:
<221> NAME/KEY: misc_feature
<222> LOCATION: (697)..(697)
<223> OTHER INFORMATION: Xaa can be any naturally occurring amino acid
<220> FEATURE:
<221> NAME/KEY: misc_feature
<222> LOCATION: (704)..(704)
<223> OTHER INFORMATION: Xaa can be any naturally occurring amino acid
<220> FEATURE:
<221> NAME/KEY: misc_feature
<222> LOCATION: (708)..(708)
<223> OTHER INFORMATION: Xaa can be any naturally occurring amino acid
<220> FEATURE:
<221> NAME/KEY: misc_feature
<222> LOCATION: (710)..(710)
<223> OTHER INFORMATION: Xaa can be any naturally occurring amino acid
<220> FEATURE:
<221> NAME/KEY: misc_feature
<222> LOCATION: (711)..(711)
<223> OTHER INFORMATION: Xaa can be any naturally occurring amino acid
<220> FEATURE:
<221> NAME/KEY: misc_feature
<222> LOCATION: (714)..(714)
<223> OTHER INFORMATION: Xaa can be any naturally occurring amino acid
<220> FEATURE:
<221> NAME/KEY: misc_feature
<222> LOCATION: (717)..(720)
<223> OTHER INFORMATION: Each Xaa can independently be any naturally
occurring amino acid
<220> FEATURE:
<221> NAME/KEY: misc_feature
<222> LOCATION: (722)..(722)
<223> OTHER INFORMATION: Xaa can be any naturally occurring amino acid
<220> FEATURE:

<221> NAME/KEY: misc_feature
<222> LOCATION: (725)..(725)
<223> OTHER INFORMATION: Xaa can be any naturally occurring amino acid
<220> FEATURE:
<221> NAME/KEY: misc_feature
<222> LOCATION: (727)..(727)
<223> OTHER INFORMATION: Xaa can be any naturally occurring amino acid
<220> FEATURE:
<221> NAME/KEY: misc_feature
<222> LOCATION: (733)..(735)
<223> OTHER INFORMATION: Each Xaa can independently be any naturally occurring amino acid
<220> FEATURE:
<221> NAME/KEY: misc_feature
<222> LOCATION: (740)..(740)
<223> OTHER INFORMATION: Xaa can be any naturally occurring amino acid
<220> FEATURE:
<221> NAME/KEY: misc_feature
<222> LOCATION: (742)..(742)
<223> OTHER INFORMATION: Xaa can be any naturally occurring amino acid
<220> FEATURE:
<221> NAME/KEY: misc_feature
<222> LOCATION: (749)..(754)
<223> OTHER INFORMATION: Each Xaa can independently be any naturally occurring amino acid
<220> FEATURE:
<221> NAME/KEY: misc_feature
<222> LOCATION: (758)..(761)
<223> OTHER INFORMATION: Each Xaa can independently be any naturally occurring amino acid
<220> FEATURE:
<221> NAME/KEY: misc_feature
<222> LOCATION: (763)..(768)
<223> OTHER INFORMATION: Each Xaa can independently be any naturally occurring amino acid
<220> FEATURE:
<221> NAME/KEY: misc_feature
<222> LOCATION: (771)..(771)
<223> OTHER INFORMATION: Xaa can be any naturally occurring amino acid
<220> FEATURE:
<221> NAME/KEY: misc_feature
<222> LOCATION: (774)..(777)
<223> OTHER INFORMATION: Each Xaa can independently be any naturally occurring amino acid
<220> FEATURE:
<221> NAME/KEY: misc_feature
<222> LOCATION: (782)..(782)
<223> OTHER INFORMATION: Xaa can be any naturally occurring amino acid
<220> FEATURE:
<221> NAME/KEY: misc_feature
<222> LOCATION: (784)..(786)
<223> OTHER INFORMATION: Each Xaa can independently be any naturally occurring amino acid
<220> FEATURE:
<221> NAME/KEY: misc_feature
<222> LOCATION: (788)..(788)
<223> OTHER INFORMATION: Xaa can be any naturally occurring amino acid
<220> FEATURE:
<221> NAME/KEY: misc_feature
<222> LOCATION: (790)..(790)
<223> OTHER INFORMATION: Xaa can be any naturally occurring amino acid
<220> FEATURE:
<221> NAME/KEY: misc_feature
<222> LOCATION: (795)..(795)
<223> OTHER INFORMATION: Xaa can be any naturally occurring amino acid
<220> FEATURE:
<221> NAME/KEY: misc_feature
<222> LOCATION: (799)..(799)
<223> OTHER INFORMATION: Xaa can be any naturally occurring amino acid
<220> FEATURE:
<221> NAME/KEY: misc_feature
<222> LOCATION: (801)..(801)
<223> OTHER INFORMATION: Xaa can be any naturally occurring amino acid
<220> FEATURE:
<221> NAME/KEY: misc_feature
<222> LOCATION: (802)..(802)
<223> OTHER INFORMATION: Xaa can be any naturally occurring amino acid
<220> FEATURE:
<221> NAME/KEY: misc_feature
<222> LOCATION: (804)..(804)
<223> OTHER INFORMATION: Xaa can be any naturally occurring amino acid
<220> FEATURE:
<221> NAME/KEY: misc_feature
<222> LOCATION: (806)..(813)
<223> OTHER INFORMATION: Each Xaa can independently be any naturally occurring amino acid
<220> FEATURE:
<221> NAME/KEY: misc_feature
<222> LOCATION: (815)..(818)
<223> OTHER INFORMATION: Each Xaa can independently be any naturally occurring amino acid
<220> FEATURE:
<221> NAME/KEY: misc_feature
<222> LOCATION: (820)..(820)
<223> OTHER INFORMATION: Xaa can be any naturally occurring amino acid
<220> FEATURE:
<221> NAME/KEY: misc_feature
<222> LOCATION: (823)..(827)
<223> OTHER INFORMATION: Each Xaa can independently be any naturally occurring amino acid
<220> FEATURE:
<221> NAME/KEY: misc_feature
<222> LOCATION: (829)..(829)
<223> OTHER INFORMATION: Xaa can be any naturally occurring amino acid
<220> FEATURE:
<221> NAME/KEY: misc_feature
<222> LOCATION: (830)..(830)
<223> OTHER INFORMATION: Xaa can be any naturally occurring amino acid
<220> FEATURE:
<221> NAME/KEY: misc_feature
<222> LOCATION: (832)..(832)
<223> OTHER INFORMATION: Xaa can be any naturally occurring amino acid
<220> FEATURE:
<221> NAME/KEY: misc_feature
<222> LOCATION: (835)..(837)
<223> OTHER INFORMATION: Each Xaa can independently be any naturally occurring amino acid
<220> FEATURE:
<221> NAME/KEY: misc_feature
<222> LOCATION: (842)..(844)
<223> OTHER INFORMATION: Each Xaa can independently be any naturally occurring amino acid
<220> FEATURE:
<221> NAME/KEY: misc_feature
<222> LOCATION: (846)..(846)
<223> OTHER INFORMATION: Xaa can be any naturally occurring amino acid
<220> FEATURE:
<221> NAME/KEY: misc_feature
<222> LOCATION: (848)..(848)
<223> OTHER INFORMATION: Xaa can be any naturally occurring amino acid
<220> FEATURE:
<221> NAME/KEY: misc_feature
<222> LOCATION: (851)..(851)
<223> OTHER INFORMATION: Xaa can be any naturally occurring amino acid
<220> FEATURE:
<221> NAME/KEY: misc_feature
<222> LOCATION: (857)..(857)
<223> OTHER INFORMATION: Xaa can be any naturally occurring amino acid
<220> FEATURE:
<221> NAME/KEY: misc_feature
<222> LOCATION: (857)..(857)
<223> OTHER INFORMATION: Xaa can be any naturally occurring amino acid

<400> SEQUENCE: 14

```
Met Lys Tyr Xaa Ile Gly Leu Asp Ile Gly Thr Asn Ser Val Gly Trp
1               5                   10                  15

Ala Val Thr Asp Xaa Tyr Xaa Xaa Lys Xaa Lys Gly Xaa Xaa Xaa Ile
            20                  25                  30

Xaa Lys Asn Xaa Gly Leu Phe Asp Gly Thr Ala Arg Xaa Arg Thr Ala
        35                  40                  45

Arg Arg Arg Arg Arg Xaa Asn Arg Ile Tyr Leu Gln Ile Phe Xaa Glu
    50                  55                  60

Met Asp Phe Phe Arg Leu Xaa Ser Phe Val Xaa Xaa Lys Xaa Xaa Xaa
```

```
65                  70                  75                  80

Pro Xaa Phe Xaa Xaa Glu Tyr His Xaa Xaa Pro Thr Ile Tyr His Leu
                85                  90                  95

Arg Xaa Leu Xaa Lys Asp Leu Arg Leu Xaa Tyr Leu Ala Leu Ala His
            100                 105                 110

Xaa Ile Lys Xaa Arg Gly Asn Phe Leu Ile Glu Gly Xaa Xaa Asn Xaa
        115                 120                 125

Xaa Xaa Xaa Xaa Xaa Tyr Xaa Phe Xaa Ile Xaa Xaa Xaa Xaa Xaa
    130                 135                 140

Xaa Xaa Xaa Pro Glu Lys Gly Phe Xaa Xaa Xaa Leu Xaa Gly Xaa Phe
145                 150                 155                 160

Xaa Phe Xaa Leu Glu Xaa Xaa Xaa Lys Xaa Xaa Tyr Xaa Xaa Xaa Leu
                165                 170                 175

Xaa Leu Leu Ile Gly Asp Xaa Tyr Xaa Xaa Xaa Phe Xaa Ala Lys Xaa
            180                 185                 190

Xaa Xaa Xaa Leu Ser Xaa Xaa Val Thr Xaa Ala Leu Ser Xaa Xaa Met
        195                 200                 205

Ile Xaa Arg Xaa Xaa His Asp Leu Leu Lys Xaa Xaa Tyr Xaa Glu Xaa
    210                 215                 220

Phe Xaa Lys Gly Tyr Ala Gly Tyr Ile Asp Gly Xaa Gln Phe Tyr Xaa
225                 230                 235                 240

Xaa Lys Leu Xaa Xaa Xaa Gly Xaa Xaa Xaa Lys Xaa Xaa Xaa Glu Xaa
                245                 250                 255

Xaa Leu Arg Lys Gln Arg Thr Phe Asp Asn Gly Xaa Ile Pro Xaa Gln
            260                 265                 270

Xaa His Leu Glu Xaa Ala Ile Xaa Xaa Gln Xaa Tyr Pro Phe Leu Asn
        275                 280                 285

Xaa Xaa Ile Xaa Xaa Xaa Thr Phe Arg Ile Pro Tyr Xaa Val Gly Pro
    290                 295                 300

Leu Ala Gly Xaa Ser Phe Ala Trp Arg Lys Ile Pro Trp Asn Xaa Xaa
305                 310                 315                 320

Xaa Xaa Asp Ser Ala Phe Ile Xaa Xaa Met Thr Asp Leu Pro Xaa Xaa
                325                 330                 335

Xaa Val Leu Pro Lys His Ser Leu Tyr Xaa Xaa Val Tyr Asn Glu Leu
            340                 345                 350

Thr Lys Val Xaa Xaa Xaa Xaa Xaa Xaa Lys Xaa Ile Phe Lys Arg Lys
        355                 360                 365

Val Xaa Xaa Xaa Xaa Gly Xaa Xaa Phe Asn Xaa Ser Thr Tyr His Asp
    370                 375                 380

Leu Xaa Xaa Xaa Xaa Xaa Leu Asp Xaa Asn Xaa Xaa Glu Xaa Ile Xaa
385                 390                 395                 400

Leu Thr Xaa Phe Glu Asp Xaa Met Ile Xaa Xaa Leu Xaa Xaa Xaa Xaa
                405                 410                 415

Lys Xaa Leu Arg Arg Xaa Tyr Thr Gly Trp Gly Xaa Leu Ser Xaa Leu
            420                 425                 430

Xaa Gly Ile Arg Xaa Xaa Xaa Ser Thr Ile Leu Asp Xaa Leu Asp Asn
        435                 440                 445

Arg Asn Xaa Met Gln Leu Ile Xaa Asp Leu Xaa Phe Lys Ile Lys Gln
    450                 455                 460

Xaa Xaa Xaa Xaa Xaa Gly Ser Pro Ala Ile Lys Lys Gly Ile Leu Gln
465                 470                 475                 480

Xaa Xaa Lys Xaa Val Asp Glu Leu Val Xaa Met Gly Pro Xaa Ile Val
                485                 490                 495
```

```
Xaa Glu Met Ala Arg Glu Asn Gln Thr Xaa Gly Asn Ser Xaa Arg Lys
            500                 505                 510

Xaa Xaa Lys Glu Xaa Gly Ser Xaa Ile Leu Lys Glu Xaa Xaa Asn Leu
        515                 520                 525

Xaa Asn Xaa Xaa Leu Xaa Leu Tyr Tyr Leu Gln Asn Gly Xaa Asp Met
    530                 535                 540

Tyr Xaa Xaa Leu Asp Ile Leu Ser Xaa Tyr Asp Xaa Asp His Ile Xaa
545                 550                 555                 560

Pro Gln Xaa Phe Xaa Asp Xaa Ser Ile Asp Asn Val Leu Ser Asn Arg
                565                 570                 575

Lys Asp Xaa Val Pro Xaa Xaa Val Xaa Lys Lys Xaa Trp Xaa Leu Xaa
            580                 585                 590

Leu Xaa Xaa Xaa Arg Lys Phe Asp Leu Thr Lys Ala Glu Arg Gly Gly
        595                 600                 605

Leu Xaa Asp Lys Ala Phe Ile Xaa Arg Gln Leu Val Glu Thr Arg Gln
    610                 615                 620

Ile Thr Lys Xaa Val Ala Xaa Leu Xaa Xaa Asn Xaa Asp Xaa Xaa Xaa
625                 630                 635                 640

Xaa Val Xaa Xaa Xaa Thr Leu Lys Ser Leu Val Ser Xaa Phe Arg Lys
                645                 650                 655

Xaa Phe Xaa Xaa Leu Tyr Lys Val Xaa Xaa Asn Xaa Xaa His His Ala
            660                 665                 670

His Asp Ala Tyr Leu Asn Val Xaa Xaa Leu Xaa Tyr Pro Xaa Leu Glu
        675                 680                 685

Glu Phe Val Tyr Gly Asp Tyr Xaa Xaa Lys Ala Thr Lys Phe Tyr Xaa
    690                 695                 700

Asn Ile Met Xaa Phe Xaa Xaa Gly Glu Xaa Trp Lys Xaa Xaa Xaa Xaa
705                 710                 715                 720

Val Xaa Met Gln Xaa Asn Xaa Val Lys Lys Glu Gln Xaa Xaa Xaa Pro
                725                 730                 735

Lys Asn Ser Xaa Leu Xaa Lys Asp Lys Tyr Gly Gly Xaa Xaa Xaa Xaa
            740                 745                 750

Xaa Xaa Lys Gly Lys Xaa Xaa Xaa Xaa Ile Xaa Xaa Xaa Xaa Xaa Xaa
        755                 760                 765

Phe Leu Xaa Gly Tyr Xaa Xaa Xaa Xaa Leu Pro Lys Tyr Xaa Leu Xaa
    770                 775                 780

Xaa Xaa Gly Xaa Arg Xaa Leu Ala Ser Glu Xaa Lys Gly Asn Xaa Leu
785                 790                 795                 800

Xaa Xaa Leu Xaa Ala Xaa Xaa Xaa Xaa Xaa Xaa Xaa Xaa Glu Xaa Xaa
                805                 810                 815

Xaa Xaa Phe Xaa Ala Asn Xaa Xaa Xaa Xaa Xaa Leu Xaa Xaa Gly Xaa
            820                 825                 830

Ala Phe Xaa Xaa Xaa Ile Arg Arg Tyr Xaa Xaa Xaa Thr Xaa Ile Xaa
        835                 840                 845

Gln Ser Xaa Thr Gly Leu Tyr Glu Xaa Arg Leu
    850                 855
```

<210> SEQ ID NO 15
<211> LENGTH: 8
<212> TYPE: PRT
<213> ORGANISM: Artificial Sequence
<220> FEATURE:
<223> OTHER INFORMATION: RuvC-like domain
<220> FEATURE:
<221> NAME/KEY: VARIANT
<222> LOCATION: (2)..(2)
<223> OTHER INFORMATION: Xaa is Val or His
<220> FEATURE:
<221> NAME/KEY: VARIANT
<222> LOCATION: (3)..(3)
<223> OTHER INFORMATION: Xaa is Ile, Leu, or Val
<220> FEATURE:
<221> NAME/KEY: VARIANT
<222> LOCATION: (5)..(5)
<223> OTHER INFORMATION: Xaa is Met or Thr

<400> SEQUENCE: 15

Ile Xaa Xaa Glu Xaa Ala Arg Glu
1 5

<210> SEQ ID NO 16
<211> LENGTH: 8
<212> TYPE: PRT
<213> ORGANISM: Artificial Sequence
<220> FEATURE:
<223> OTHER INFORMATION: RuvC-like domain
<220> FEATURE:
<221> NAME/KEY: VARIANT
<222> LOCATION: (3)..(3)
<223> OTHER INFORMATION: Xaa is Ile, Leu, or Val

<400> SEQUENCE: 16

Ile Val Xaa Glu Met Ala Arg Glu
1 5

<210> SEQ ID NO 17
<211> LENGTH: 8
<212> TYPE: PRT
<213> ORGANISM: Artificial Sequence
<220> FEATURE:
<223> OTHER INFORMATION: RuvC-like domain
<220> FEATURE:
<221> NAME/KEY: VARIANT
<222> LOCATION: (4)..(4)
<223> OTHER INFORMATION: Xaa is His or Leu
<220> FEATURE:
<221> NAME/KEY: VARIANT
<222> LOCATION: (7)..(7)
<223> OTHER INFORMATION: Xaa is Arg or Val
<220> FEATURE:
<221> NAME/KEY: VARIANT
<222> LOCATION: (8)..(8)
<223> OTHER INFORMATION: Xaa is Glu or Val

<400> SEQUENCE: 17

His His Ala Xaa Asp Ala Xaa Xaa
1 5

<210> SEQ ID NO 18
<211> LENGTH: 8
<212> TYPE: PRT
<213> ORGANISM: Artificial Sequence
<220> FEATURE:
<223> OTHER INFORMATION: RuvC-like domain

<400> SEQUENCE: 18

His His Ala His Asp Ala Tyr Leu
1 5

<210> SEQ ID NO 19
<211> LENGTH: 30
<212> TYPE: PRT
<213> ORGANISM: Artificial Sequence
<220> FEATURE:
<223> OTHER INFORMATION: N-terminal RuvC-like domain
<220> FEATURE:

```
<221> NAME/KEY: VARIANT
<222> LOCATION: (2)..(2)
<223> OTHER INFORMATION: Xaa is Lys or Pro
<220> FEATURE:
<221> NAME/KEY: VARIANT
<222> LOCATION: (4)..(4)
<223> OTHER INFORMATION: Xaa is Val, Leu, Ile, or Phe
<220> FEATURE:
<221> NAME/KEY: VARIANT
<222> LOCATION: (5)..(5)
<223> OTHER INFORMATION: Xaa is Gly, Ala, or Ser
<220> FEATURE:
<221> NAME/KEY: VARIANT
<222> LOCATION: (6)..(6)
<223> OTHER INFORMATION: Xaa is Leu, Ile, Val, or Phe
<220> FEATURE:
<221> NAME/KEY: MOD_RES
<222> LOCATION: (7)..(26)
<223> OTHER INFORMATION: N-terminal RuvC-like domain, each Xaa can be
      any amino acid or absent, region may encompass 5-20 residues
<220> FEATURE:
<221> NAME/KEY: VARIANT
<222> LOCATION: (29)..(29)
<223> OTHER INFORMATION: Xaa is Asp, Glu, Asn, or Gln

<400> SEQUENCE: 19

Lys Xaa Tyr Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Thr Asp Xaa Tyr
            20                  25                  30


<210> SEQ ID NO 20
<211> LENGTH: 12
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: VARIANT
<222> LOCATION: (2)..(2)
<223> OTHER INFORMATION: Xaa is Ile, Val, Met, Leu, or Thr
<220> FEATURE:
<221> NAME/KEY: VARIANT
<222> LOCATION: (4)..(4)
<223> OTHER INFORMATION: Xaa is Thr, Ile, Val, Ser, Asn, Tyr, Glu, or
      Leu
<220> FEATURE:
<221> NAME/KEY: VARIANT
<222> LOCATION: (5)..(5)
<223> OTHER INFORMATION: Xaa is Asn, Ser, Gly, Ala, Asp, Thr, Arg, Met,
      or Phe
<220> FEATURE:
<221> NAME/KEY: VARIANT
<222> LOCATION: (6)..(6)
<223> OTHER INFORMATION: Xaa is Ser, Tyr, Asn, or Phe
<220> FEATURE:
<221> NAME/KEY: VARIANT
<222> LOCATION: (7)..(7)
<223> OTHER INFORMATION: Xaa is Val, Ile, Leu, Cys, Thr, or Phe
<220> FEATURE:
<221> NAME/KEY: VARIANT
<222> LOCATION: (9)..(9)
<223> OTHER INFORMATION: Xaa is Trp, Phe, Val, Tyr, Ser, or Leu
<220> FEATURE:
<221> NAME/KEY: VARIANT
<222> LOCATION: (10)..(10)
<223> OTHER INFORMATION: Xaa is Ala, Ser, Cys, Val, or Gly
<220> FEATURE:
<221> NAME/KEY: VARIANT
<222> LOCATION: (11)..(11)
<223> OTHER INFORMATION: Xaa is Val, Ile, Leu, Ala, Met, or His
<220> FEATURE:
<221> NAME/KEY: VARIANT
<222> LOCATION: (12)..(12)
<223> OTHER INFORMATION: Any amino acid or absent
```

<400> SEQUENCE: 20

Asp Xaa Gly Xaa Xaa Xaa Xaa Gly Xaa Xaa Xaa Xaa
1 5 10

<210> SEQ ID NO 21
<211> LENGTH: 12
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: VARIANT
<222> LOCATION: (2)..(2)
<223> OTHER INFORMATION: Xaa is Ile, Val, Met, Leu, or Thr
<220> FEATURE:
<221> NAME/KEY: VARIANT
<222> LOCATION: (4)..(4)
<223> OTHER INFORMATION: Xaa is Thr, Ile, Val, Ser, Asn, Tyr, Glu, or Leu
<220> FEATURE:
<221> NAME/KEY: VARIANT
<222> LOCATION: (5)..(5)
<223> OTHER INFORMATION: Xaa is Asn, Ser, Gly, Ala, Asp, Thr, Arg, Met, or Phe
<220> FEATURE:
<221> NAME/KEY: VARIANT
<222> LOCATION: (7)..(7)
<223> OTHER INFORMATION: Xaa is Val, Ile, Leu, Cys, Thr, or Phe
<220> FEATURE:
<221> NAME/KEY: VARIANT
<222> LOCATION: (9)..(9)
<223> OTHER INFORMATION: Xaa is Trp, Phe, Val, Tyr, Ser, or Leu
<220> FEATURE:
<221> NAME/KEY: VARIANT
<222> LOCATION: (10)..(10)
<223> OTHER INFORMATION: Xaa is Ala, Ser, Cys, Val, or Gly
<220> FEATURE:
<221> NAME/KEY: VARIANT
<222> LOCATION: (11)..(11)
<223> OTHER INFORMATION: Xaa is Val, Ile, Leu, Ala, Met, or His
<220> FEATURE:
<221> NAME/KEY: VARIANT
<222> LOCATION: (12)..(12)
<223> OTHER INFORMATION: Any amino acid or absent

<400> SEQUENCE: 21

Asp Xaa Gly Xaa Xaa Ser Xaa Gly Xaa Xaa Xaa Xaa
1 5 10

<210> SEQ ID NO 22
<211> LENGTH: 12
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: VARIANT
<222> LOCATION: (4)..(4)
<223> OTHER INFORMATION: Xaa is Thr, Ile, Val, Ser, Asn, Tyr, Glu, or Leu
<220> FEATURE:
<221> NAME/KEY: VARIANT
<222> LOCATION: (5)..(5)
<223> OTHER INFORMATION: Xaa is Asn, Ser, Gly, Ala, Asp, Thr, Arg, Met, or Phe
<220> FEATURE:
<221> NAME/KEY: VARIANT
<222> LOCATION: (11)..(11)
<223> OTHER INFORMATION: Xaa is Val, Ile, Leu, Ala, Met, or His
<220> FEATURE:
<221> NAME/KEY: VARIANT
<222> LOCATION: (12)..(12)
<223> OTHER INFORMATION: Any amino acid or absent

<400> SEQUENCE: 22

```
Asp Ile Gly Xaa Xaa Ser Val Gly Trp Ala Xaa Xaa
1               5                   10


<210> SEQ ID NO 23
<211> LENGTH: 12
<212> TYPE: PRT
<213> ORGANISM: Artificial Sequence
<220> FEATURE:
<223> OTHER INFORMATION: N-terminal RuvC-like domain
<220> FEATURE:
<221> NAME/KEY: MOD_RES
<222> LOCATION: (12)..(12)
<223> OTHER INFORMATION: Any non-polar alkyl amino acid or a hydroxyl
      amino acid

<400> SEQUENCE: 23

Asp Ile Gly Thr Asn Ser Val Gly Trp Ala Val Xaa
1               5                   10


<210> SEQ ID NO 24
<211> LENGTH: 73
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (8)..(8)
<223> OTHER INFORMATION: Xaa is Lys or Arg
<220> FEATURE:
<221> NAME/KEY: VARIANT
<222> LOCATION: (12)..(12)
<223> OTHER INFORMATION: Xaa is Val or Thr
<220> FEATURE:
<221> NAME/KEY: VARIANT
<222> LOCATION: (13)..(13)
<223> OTHER INFORMATION: Xaa is Gly or Asp
<220> FEATURE:
<221> NAME/KEY: VARIANT
<222> LOCATION: (14)..(14)
<223> OTHER INFORMATION: Xaa is Glu, Gln, or Asp
<220> FEATURE:
<221> NAME/KEY: VARIANT
<222> LOCATION: (15)..(15)
<223> OTHER INFORMATION: Xaa is Glu or Asp
<220> FEATURE:
<221> NAME/KEY: VARIANT
<222> LOCATION: (19)..(19)
<223> OTHER INFORMATION: Xaa is Asp, Asn, or His
<220> FEATURE:
<221> NAME/KEY: VARIANT
<222> LOCATION: (20)..(20)
<223> OTHER INFORMATION: Xaa is Tyr, Arg, or Asn
<220> FEATURE:
<221> NAME/KEY: VARIANT
<222> LOCATION: (23)..(23)
<223> OTHER INFORMATION: Xaa is Gln, Asp, or Asn
<220> FEATURE:
<221> NAME/KEY: MOD_RES
<222> LOCATION: (25)..(64)
<223> OTHER INFORMATION: HNH-like domain, each Xaa can be any amino acid
      or absent, region may encompass 15-40 residues
<220> FEATURE:
<221> NAME/KEY: VARIANT
<222> LOCATION: (67)..(67)
<223> OTHER INFORMATION: Xaa is Gly or Glu
<220> FEATURE:
<221> NAME/KEY: VARIANT
<222> LOCATION: (69)..(69)
<223> OTHER INFORMATION: Xaa is Ser or Gly
<220> FEATURE:
<221> NAME/KEY: VARIANT
<222> LOCATION: (71)..(71)
<223> OTHER INFORMATION: Xaa is Asp or Asn
```

<400> SEQUENCE: 24

```
Leu Tyr Tyr Leu Gln Asn Gly Xaa Asp Met Tyr Xaa Xaa Xaa Xaa Leu
1               5                   10                  15

Asp Ile Xaa Xaa Leu Ser Xaa Tyr Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Asn Arg Xaa Lys Xaa Asp Xaa Val Pro
65                  70
```

<210> SEQ ID NO 25
<211> LENGTH: 27
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (1)..(1)
<223> OTHER INFORMATION: Xaa is Asp, Glu, Gln, or Asn
<220> FEATURE:
<221> NAME/KEY: VARIANT
<222> LOCATION: (2)..(2)
<223> OTHER INFORMATION: Xaa is Leu, Ile, Arg, Gln, Val, Met, or Lys
<220> FEATURE:
<221> NAME/KEY: VARIANT
<222> LOCATION: (3)..(3)
<223> OTHER INFORMATION: Xaa is Asp or Glu
<220> FEATURE:
<221> NAME/KEY: VARIANT
<222> LOCATION: (5)..(5)
<223> OTHER INFORMATION: Xaa is Ile, Val, Thr, Ala, or Leu
<220> FEATURE:
<221> NAME/KEY: VARIANT
<222> LOCATION: (6)..(6)
<223> OTHER INFORMATION: Xaa is Val, Tyr, Ile, Leu, Phe, or Trp
<220> FEATURE:
<221> NAME/KEY: VARIANT
<222> LOCATION: (8)..(8)
<223> OTHER INFORMATION: Xaa is Gln, His, Arg, Lys, Tyr, Ile, Leu, Phe, or Trp
<220> FEATURE:
<221> NAME/KEY: VARIANT
<222> LOCATION: (9)..(9)
<223> OTHER INFORMATION: Xaa is Ser, Ala, Asp, Thr, or Lys
<220> FEATURE:
<221> NAME/KEY: VARIANT
<222> LOCATION: (10)..(10)
<223> OTHER INFORMATION: Xaa is Phe, Leu, Val, Lys, Tyr, Met, Ile, Arg, Ala, Glu, Asp, or Gln
<220> FEATURE:
<221> NAME/KEY: VARIANT
<222> LOCATION: (11)..(11)
<223> OTHER INFORMATION: Xaa is Leu, Arg, Thr, Ile, Val, Ser, Cys, Tyr, Lys, Phe, or Gly
<220> FEATURE:
<221> NAME/KEY: VARIANT
<222> LOCATION: (12)..(12)
<223> OTHER INFORMATION: Xaa is Lys, Gln, Tyr, Thr, Phe, Leu, Trp, Met, Ala, Glu, Gly, or Ser
<220> FEATURE:
<221> NAME/KEY: VARIANT
<222> LOCATION: (13)..(13)
<223> OTHER INFORMATION: Xaa is Asp, Ser, Asn, Arg, Leu, or Thr
<220> FEATURE:
<221> NAME/KEY: VARIANT
<222> LOCATION: (14)..(14)
<223> OTHER INFORMATION: Xaa is Asp, Asn, or Ser
<220> FEATURE:
<221> NAME/KEY: VARIANT
<222> LOCATION: (15)..(15)

```
<223> OTHER INFORMATION: Xaa is Ser, Ala, Thr, Gly, or Arg
<220> FEATURE:
<221> NAME/KEY: VARIANT
<222> LOCATION: (16)..(16)
<223> OTHER INFORMATION: Xaa is Ile, Leu, Phe, Ser, Arg, Tyr, Gln, Trp,
      Asp, Lys, or His
<220> FEATURE:
<221> NAME/KEY: VARIANT
<222> LOCATION: (17)..(17)
<223> OTHER INFORMATION: Xaa is Asp, Ser, Ile, Asn, Glu, Ala, His, Phe,
      Leu, Gln, Met, Gly, Tyr, or Val
<220> FEATURE:
<221> NAME/KEY: VARIANT
<222> LOCATION: (19)..(19)
<223> OTHER INFORMATION: Xaa is Lys, Leu, Arg, Met, Thr, or Phe
<220> FEATURE:
<221> NAME/KEY: VARIANT
<222> LOCATION: (20)..(20)
<223> OTHER INFORMATION: Xaa is Val, Leu, Ile, Ala, or Thr
<220> FEATURE:
<221> NAME/KEY: VARIANT
<222> LOCATION: (21)..(21)
<223> OTHER INFORMATION: Xaa is Leu, Ile, Val, or Ala
<220> FEATURE:
<221> NAME/KEY: VARIANT
<222> LOCATION: (22)..(22)
<223> OTHER INFORMATION: Xaa is Thr, Val, Cys, Glu, Ser, or Ala
<220> FEATURE:
<221> NAME/KEY: VARIANT
<222> LOCATION: (23)..(23)
<223> OTHER INFORMATION: Xaa is Arg, Phe, Thr, Trp, Glu, Leu, Asn, Cys,
      Lys, Val, Ser, Gln, Ile, Tyr, His, or Ala
<220> FEATURE:
<221> NAME/KEY: VARIANT
<222> LOCATION: (24)..(24)
<223> OTHER INFORMATION: Xaa is Ser, Pro, Arg, Lys, Asn, Ala, His, Gln,
      Gly, or Leu
<220> FEATURE:
<221> NAME/KEY: VARIANT
<222> LOCATION: (25)..(25)
<223> OTHER INFORMATION: Xaa is Asp, Gly, Thr, Asn, Ser, Lys, Ala, Ile,
      Glu, Leu, Gln, Arg, or Tyr
<220> FEATURE:
<221> NAME/KEY: VARIANT
<222> LOCATION: (26)..(26)
<223> OTHER INFORMATION: Xaa is Lys, Val, Ala, Glu, Tyr, Ile, Cys, Leu,
      Ser, Thr, Gly, Lys, Met, Asp, or Phe

<400> SEQUENCE: 25

Xaa Xaa Xaa His Xaa Xaa Pro Xaa Xaa Xaa Xaa Xaa Xaa Xaa Xaa Xaa
1               5                   10                  15

Xaa Asn Xaa Xaa Xaa Xaa Xaa Xaa Xaa Xaa Asn
            20                  25


<210> SEQ ID NO 26
<211> LENGTH: 27
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (1)..(1)
<223> OTHER INFORMATION: Xaa is Asp or Glu
<220> FEATURE:
<221> NAME/KEY: VARIANT
<222> LOCATION: (2)..(2)
<223> OTHER INFORMATION: Xaa is Leu, Ile, Arg, Gln, Val, Met, or Lys
<220> FEATURE:
<221> NAME/KEY: VARIANT
<222> LOCATION: (3)..(3)
<223> OTHER INFORMATION: Xaa is Asp or Glu
<220> FEATURE:
<221> NAME/KEY: VARIANT
<222> LOCATION: (5)..(5)
<223> OTHER INFORMATION: Xaa is Ile, Val, Thr, Ala, or Leu
```

<220> FEATURE:
<221> NAME/KEY: VARIANT
<222> LOCATION: (6)..(6)
<223> OTHER INFORMATION: Xaa is Val, Tyr, Ile, Leu, Phe, or Trp
<220> FEATURE:
<221> NAME/KEY: VARIANT
<222> LOCATION: (8)..(8)
<223> OTHER INFORMATION: Xaa is Gln, His, Arg, Lys, Tyr, Ile, Leu, Phe, or Trp
<220> FEATURE:
<221> NAME/KEY: VARIANT
<222> LOCATION: (10)..(10)
<223> OTHER INFORMATION: Xaa is Phe, Leu, Val, Lys, Tyr, Met, Ile, Arg, Ala, Glu, Asp, or Gln
<220> FEATURE:
<221> NAME/KEY: VARIANT
<222> LOCATION: (11)..(11)
<223> OTHER INFORMATION: Xaa is Leu, Arg, Thr, Ile, Val, Ser, Cys, Tyr, Lys, Phe, or Gly
<220> FEATURE:
<221> NAME/KEY: VARIANT
<222> LOCATION: (12)..(12)
<223> OTHER INFORMATION: Xaa is Lys, Gln, Tyr, Thr, Phe, Leu, Trp, Met, Ala, Glu, Gly, or Ser
<220> FEATURE:
<221> NAME/KEY: VARIANT
<222> LOCATION: (16)..(16)
<223> OTHER INFORMATION: Xaa is Ile, Leu, Phe, Ser, Arg, Tyr, Gln, Trp, Asp, Lys, or His
<220> FEATURE:
<221> NAME/KEY: VARIANT
<222> LOCATION: (17)..(17)
<223> OTHER INFORMATION: Xaa is Asp, Ser, Ile, Asn, Glu, Ala, His, Phe, Leu, Gln, Met, Gly, Tyr, or Val
<220> FEATURE:
<221> NAME/KEY: VARIANT
<222> LOCATION: (22)..(22)
<223> OTHER INFORMATION: Xaa is Thr, Val, Cys, Glu, Ser, or Ala
<220> FEATURE:
<221> NAME/KEY: VARIANT
<222> LOCATION: (23)..(23)
<223> OTHER INFORMATION: Xaa is Arg, Phe, Thr, Trp, Glu, Leu, Asn, Cys, Lys, Val, Ser, Gln, Ile, Tyr, His, or Ala
<220> FEATURE:
<221> NAME/KEY: VARIANT
<222> LOCATION: (24)..(24)
<223> OTHER INFORMATION: Xaa is Ser, Pro, Arg, Lys, Asn, Ala, His, Gln, Gly, or Leu
<220> FEATURE:
<221> NAME/KEY: VARIANT
<222> LOCATION: (25)..(25)
<223> OTHER INFORMATION: Xaa is Asp, Gly, Thr, Asn, Ser, Lys, Ala, Ile, Glu, Leu, Gln, Arg, or Tyr
<220> FEATURE:
<221> NAME/KEY: VARIANT
<222> LOCATION: (26)..(26)
<223> OTHER INFORMATION: Xaa is Lys, Val, Ala, Glu, Tyr, Ile, Cys, Leu, Ser, Thr, Gly, Lys, Met, Asp, or Phe

<400> SEQUENCE: 26

```
Xaa Xaa Xaa His Xaa Xaa Pro Xaa Ser Xaa Xaa Xaa Asp Asp Ser Xaa
1               5                   10                  15

Xaa Asn Lys Val Leu Xaa Xaa Xaa Xaa Xaa Asn
            20                  25
```

<210> SEQ ID NO 27
<211> LENGTH: 27
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (1)..(1)
<223> OTHER INFORMATION: Xaa is Asp or Glu
<220> FEATURE:

<221> NAME/KEY: VARIANT
<222> LOCATION: (3)..(3)
<223> OTHER INFORMATION: Xaa is Asp or Glu
<220> FEATURE:
<221> NAME/KEY: VARIANT
<222> LOCATION: (8)..(8)
<223> OTHER INFORMATION: Xaa is Gln, His, Arg, Lys, Tyr, Ile, Leu, or Trp
<220> FEATURE:
<221> NAME/KEY: VARIANT
<222> LOCATION: (10)..(10)
<223> OTHER INFORMATION: Xaa is Phe, Leu, Val, Lys, Tyr, Met, Ile, Arg, Ala, Glu, Asp, or Gln
<220> FEATURE:
<221> NAME/KEY: VARIANT
<222> LOCATION: (11)..(11)
<223> OTHER INFORMATION: Xaa is Leu, Arg, Thr, Ile, Val, Ser, Cys, Tyr, Lys, Phe, or Gly
<220> FEATURE:
<221> NAME/KEY: VARIANT
<222> LOCATION: (12)..(12)
<223> OTHER INFORMATION: Xaa is Lys, Gln, Tyr, Thr, Phe, Leu, Trp, Met, Ala, Glu, Gly, or Ser
<220> FEATURE:
<221> NAME/KEY: VARIANT
<222> LOCATION: (16)..(16)
<223> OTHER INFORMATION: Xaa is Ile, Leu, Phe, Ser, Arg, Tyr, Gln, Trp, Asp, Lys, or His
<220> FEATURE:
<221> NAME/KEY: VARIANT
<222> LOCATION: (17)..(17)
<223> OTHER INFORMATION: Xaa is Asp, Ser, Ile, Asn, Glu, Ala, His, Phe, Leu, Gln, Met, Gly, Tyr, or Val
<220> FEATURE:
<221> NAME/KEY: VARIANT
<222> LOCATION: (23)..(23)
<223> OTHER INFORMATION: Xaa is Arg, Phe, Thr, Trp, Glu, Leu, Asn, Cys, Lys, Val, Ser, Gln, Ile, Tyr, His, or Ala
<220> FEATURE:
<221> NAME/KEY: VARIANT
<222> LOCATION: (24)..(24)
<223> OTHER INFORMATION: Xaa is Ser, Pro, Arg, Lys, Asn, Ala, His, Gln, Gly, or Leu
<220> FEATURE:
<221> NAME/KEY: VARIANT
<222> LOCATION: (25)..(25)
<223> OTHER INFORMATION: Xaa is Asp, Gly, Thr, Asn, Ser, Lys, Ala, Ile, Glu, Leu, Gln, Arg, or Tyr
<220> FEATURE:
<221> NAME/KEY: VARIANT
<222> LOCATION: (26)..(26)
<223> OTHER INFORMATION: Xaa is Lys, Val, Ala, Glu, Tyr, Ile, Cys, Leu, Ser, Thr, Gly, Lys, Met, Asp, or Phe

<400> SEQUENCE: 27

```
Xaa Val Xaa His Ile Val Pro Xaa Ser Xaa Xaa Xaa Asp Asp Ser Xaa
1               5                   10                  15

Xaa Asn Lys Val Leu Thr Xaa Xaa Xaa Xaa Asn
            20                  25
```

<210> SEQ ID NO 28
<211> LENGTH: 27
<212> TYPE: PRT
<213> ORGANISM: Artificial Sequence
<220> FEATURE:
<223> OTHER INFORMATION: HNH-like domain
<220> FEATURE:
<221> NAME/KEY: VARIANT
<222> LOCATION: (2)..(2)
<223> OTHER INFORMATION: Xaa is Ile or Val
<220> FEATURE:
<221> NAME/KEY: VARIANT
<222> LOCATION: (6)..(6)
<223> OTHER INFORMATION: Xaa is Ile or Val
<220> FEATURE:
<221> NAME/KEY: VARIANT
<222> LOCATION: (9)..(9)
<223> OTHER INFORMATION: Xaa is Ala or Ser
<220> FEATURE:
<221> NAME/KEY: VARIANT
<222> LOCATION: (11)..(11)
<223> OTHER INFORMATION: Xaa is Ile or Leu
<220> FEATURE:
<221> NAME/KEY: VARIANT
<222> LOCATION: (12)..(12)
<223> OTHER INFORMATION: Xaa is Lys or Thr
<220> FEATURE:
<221> NAME/KEY: VARIANT
<222> LOCATION: (14)..(14)
<223> OTHER INFORMATION: Xaa is Asp or Asn
<220> FEATURE:
<221> NAME/KEY: VARIANT
<222> LOCATION: (19)..(19)
<223> OTHER INFORMATION: Xaa is Arg, Lys, or Leu
<220> FEATURE:
<221> NAME/KEY: VARIANT
<222> LOCATION: (22)..(22)
<223> OTHER INFORMATION: Xaa is Thr or Val
<220> FEATURE:
<221> NAME/KEY: VARIANT
<222> LOCATION: (23)..(23)
<223> OTHER INFORMATION: Xaa is Ser or Arg
<220> FEATURE:
<221> NAME/KEY: VARIANT
<222> LOCATION: (25)..(25)
<223> OTHER INFORMATION: Xaa is Lys, Asp, or Ala
<220> FEATURE:
<221> NAME/KEY: VARIANT
<222> LOCATION: (26)..(26)
<223> OTHER INFORMATION: Xaa is Glu, Lys, Gly, or Asn

<400> SEQUENCE: 28

Asp Xaa Asp His Ile Xaa Pro Gln Xaa Phe Xaa Xaa Asp Xaa Ser Ile
1               5                   10                  15

Asp Asn Xaa Val Leu Xaa Xaa Ser Xaa Xaa Asn
            20                  25

<210> SEQ ID NO 29
<211> LENGTH: 116
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: targeting region
<220> FEATURE:
<221> NAME/KEY: misc_feature
<222> LOCATION: (21)..(42)
<223> OTHER INFORMATION: first complementarity domain
<220> FEATURE:
<221> NAME/KEY: misc_feature
<222> LOCATION: (43)..(46)
<223> OTHER INFORMATION: linking domain
<220> FEATURE:
<221> NAME/KEY: misc_feature
<222> LOCATION: (47)..(70)
<223> OTHER INFORMATION: second complementarity domain

<400> SEQUENCE: 29
nnnnnnnnnn nnnnnnnnnn guuuuagagc uaugcuguuu uggaaacaaa acagcauagc 60
aaguuaaaau aaggcuaguc cguuaucaac uugaaaaagu ggcaccgagu cggugc 116

<210> SEQ ID NO 30

<211> LENGTH: 116
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: targeting region
<220> FEATURE:
<221> NAME/KEY: misc_feature
<222> LOCATION: (21)..(42)
<223> OTHER INFORMATION: first complementarity domain
<220> FEATURE:
<221> NAME/KEY: misc_feature
<222> LOCATION: (43)..(46)
<223> OTHER INFORMATION: linking domain
<220> FEATURE:
<221> NAME/KEY: misc_feature
<222> LOCATION: (47)..(70)
<223> OTHER INFORMATION: second complementarity domain

<400> SEQUENCE: 30
nnnnnnnnnn nnnnnnnnnn guauuagagc uaugcuguau uggaaacaau acagcauagc 60
aaguuaauau aaggcuaguc cguuaucaac uugaaaaagu ggcaccgagu cggugc 116

<210> SEQ ID NO 31
<211> LENGTH: 96
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: targeting domain
<220> FEATURE:
<221> NAME/KEY: misc_feature
<222> LOCATION: (21)..(32)
<223> OTHER INFORMATION: first complementarity domain
<220> FEATURE:
<221> NAME/KEY: misc_feature
<222> LOCATION: (33)..(36)
<223> OTHER INFORMATION: linking domain
<220> FEATURE:
<221> NAME/KEY: misc_feature
<222> LOCATION: (37)..(50)
<223> OTHER INFORMATION: second complementarity domain
<220> FEATURE:
<221> NAME/KEY: misc_feature
<222> LOCATION: (51)..(62)
<223> OTHER INFORMATION: proximal domain

<400> SEQUENCE: 31
nnnnnnnnnn nnnnnnnnnn guuuaagagc uagaaauagc aaguuuaaau aaggcuaguc 60
cguuaucaac uugaaaaagu ggcaccgagu cggugc 96

<210> SEQ ID NO 32
<211> LENGTH: 47
<212> TYPE: RNA
<213> ORGANISM: Artificial Sequence
<220> FEATURE:
<223> OTHER INFORMATION: gRNA proximal and tail domains derived from S. pyogenes

<400> SEQUENCE: 32
aaggcuaguc cguuaucaac uugaaaaagu ggcaccgagu cggugcu 47

<210> SEQ ID NO 33
<211> LENGTH: 49
<212> TYPE: RNA
<213> ORGANISM: Artificial Sequence
<220> FEATURE:
<223> OTHER INFORMATION: gRNA proximal and tail domains

<400> SEQUENCE: 33
aaggcuaguc cguuaucaac uugaaaaagu ggcaccgagu cgguggugc 49

<210> SEQ ID NO 34
<211> LENGTH: 51
<212> TYPE: RNA
<213> ORGANISM: Artificial Sequence
<220> FEATURE:
<223> OTHER INFORMATION: gRNA proximal and tail domains

<400> SEQUENCE: 34
aaggcuaguc cguuaucaac uugaaaaagu ggcaccgagu cggugcggau c 51

<210> SEQ ID NO 35
<211> LENGTH: 31
<212> TYPE: RNA
<213> ORGANISM: Artificial Sequence
<220> FEATURE:
<223> OTHER INFORMATION: gRNA proximal and tail domains

<400> SEQUENCE: 35
aaggcuaguc cguuaucaac uugaaaaagu g 31

<210> SEQ ID NO 36
<211> LENGTH: 18
<212> TYPE: RNA
<213> ORGANISM: Artificial Sequence
<220> FEATURE:
<223> OTHER INFORMATION: gRNA proximal and tail domains

<400> SEQUENCE: 36
aaggcuaguc cguuauca 18

<210> SEQ ID NO 37
<211> LENGTH: 12
<212> TYPE: RNA
<213> ORGANISM: Artificial Sequence
<220> FEATURE:
<223> OTHER INFORMATION: gRNA proximal and tail domains

<400> SEQUENCE: 37
aaggcuaguc cg 12

<210> SEQ ID NO 38
<211> LENGTH: 102
<212> TYPE: RNA
<213> ORGANISM: Artificial Sequence
<220> FEATURE:
<223> OTHER INFORMATION: Unimolecular gRNA derived from S. aureus
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain

<400> SEQUENCE: 38
nnnnnnnnnn nnnnnnnnnn guuuuaguac ucuggaaaca gaaucuacua aaacaaggca 60
aaaugccgug uuuaucucgu caacuuguug gcgagauuuu uu 102

<210> SEQ ID NO 39
<211> LENGTH: 42
<212> TYPE: RNA
<213> ORGANISM: Artificial
<220> FEATURE:
<223> OTHER INFORMATION: Modular gRNA derived from S. pyogenes
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(42)
<223> OTHER INFORMATION: First complementarity domain

<400> SEQUENCE: 39
nnnnnnnnnn nnnnnnnnnn guuuuagagc uaugcuguuu ug 42

<210> SEQ ID NO 40
<211> LENGTH: 85
<212> TYPE: RNA
<213> ORGANISM: Artificial Sequence
<220> FEATURE:
<223> OTHER INFORMATION: Modular gRNA derived from S. pyogenes
<220> FEATURE:
<221> NAME/KEY: misc_feature
<222> LOCATION: (1)..(9)
<223> OTHER INFORMATION: 5' extension domain
<220> FEATURE:
<221> NAME/KEY: misc_feature
<222> LOCATION: (10)..(33)
<223> OTHER INFORMATION: Second complementarity domain
<220> FEATURE:
<221> NAME/KEY: misc_feature
<222> LOCATION: (34)..(45)
<223> OTHER INFORMATION: Proximal domain
<220> FEATURE:
<221> NAME/KEY: misc_feature
<222> LOCATION: (46)..(85)
<223> OTHER INFORMATION: Tail domain

<400> SEQUENCE: 40
ggaaccauuc aaaacagcau agcaaguuaa aauaaggcua guccguuauc aacuugaaaa 60
aguggcaccg agucggugcu uuuuu 85

<210> SEQ ID NO 41
<211> LENGTH: 62
<212> TYPE: RNA
<213> ORGANISM: Artificial Sequence
<220> FEATURE:
<223> OTHER INFORMATION: Unimolecular gRNA derived from S. pyogenes
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(32)

<223> OTHER INFORMATION: First complementarity domain
<220> FEATURE:
<221> NAME/KEY: misc_feature
<222> LOCATION: (33)..(36)
<223> OTHER INFORMATION: Linking domain
<220> FEATURE:
<221> NAME/KEY: misc_feature
<222> LOCATION: (37)..(50)
<223> OTHER INFORMATION: Second complementarity domain
<220> FEATURE:
<221> NAME/KEY: misc_feature
<222> LOCATION: (51)..(62)
<223> OTHER INFORMATION: Proximal domain

<400> SEQUENCE: 41
nnnnnnnnnn nnnnnnnnnn guuuuagagc uagaaauagc aaguuaaaau aaggcuaguc 60
cg 62

<210> SEQ ID NO 42
<211> LENGTH: 102
<212> TYPE: RNA
<213> ORGANISM: Artificial Sequence
<220> FEATURE:
<223> OTHER INFORMATION: Unimolecular gRNA derived from S. pyogenes
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(32)
<223> OTHER INFORMATION: First complementarity domain
<220> FEATURE:
<221> NAME/KEY: misc_feature
<222> LOCATION: (33)..(36)
<223> OTHER INFORMATION: Linking domain
<220> FEATURE:
<221> NAME/KEY: misc_feature
<222> LOCATION: (37)..(50)
<223> OTHER INFORMATION: Second complementarity domain
<220> FEATURE:
<221> NAME/KEY: misc_feature
<222> LOCATION: (51)..(62)
<223> OTHER INFORMATION: Proximal domain
<220> FEATURE:
<221> NAME/KEY: misc_feature
<222> LOCATION: (63)..(102)
<223> OTHER INFORMATION: Tail domain

<400> SEQUENCE: 42
nnnnnnnnnn nnnnnnnnnn guuuuagagc uagaaauagc aaguuaaaau aaggcuaguc 60
cguuaucaac uugaaaaagu ggcaccgagu cggugcuuuu uu 102

<210> SEQ ID NO 43
<211> LENGTH: 75
<212> TYPE: RNA
<213> ORGANISM: Artificial Sequence
<220> FEATURE:
<223> OTHER INFORMATION: Unimolecular gRNA derived from S. pyogenes
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (21)..(36)
<223> OTHER INFORMATION: First complementarity domain
<220> FEATURE:
<221> NAME/KEY: misc_feature
<222> LOCATION: (37)..(40)
<223> OTHER INFORMATION: Linking domain
<220> FEATURE:
<221> NAME/KEY: misc_feature
<222> LOCATION: (41)..(58)
<223> OTHER INFORMATION: Second complementarity domain
<220> FEATURE:
<221> NAME/KEY: misc_feature
<222> LOCATION: (59)..(70)
<223> OTHER INFORMATION: Proximal domain
<220> FEATURE:
<221> NAME/KEY: misc_feature
<222> LOCATION: (71)..(75)
<223> OTHER INFORMATION: Tail domain

<400> SEQUENCE: 43
nnnnnnnnnn nnnnnnnnnn guuuuagagc uaugcugaaa agcauagcaa guuaaaauaa 60
ggcuaguccg uuauc 75

<210> SEQ ID NO 44
<211> LENGTH: 87
<212> TYPE: RNA
<213> ORGANISM: Artificial Sequence
<220> FEATURE:
<223> OTHER INFORMATION: Unimolecular gRNA derived from S. pyogenes
<220> FEATURE:
<221> NAME/KEY: misc_feature
<222> LOCATION: (1)..(20)
<223> OTHER INFORMATION: a, c, u, g, unknown or other
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(32)
<223> OTHER INFORMATION: First complementarity domain
<220> FEATURE:
<221> NAME/KEY: misc_feature
<222> LOCATION: (43)..(46)
<223> OTHER INFORMATION: Linking domain
<220> FEATURE:
<221> NAME/KEY: misc_feature
<222> LOCATION: (57)..(70)
<223> OTHER INFORMATION: Second complementarity domain
<220> FEATURE:
<221> NAME/KEY: misc_feature
<222> LOCATION: (71)..(82)
<223> OTHER INFORMATION: Proximal domain
<220> FEATURE:
<221> NAME/KEY: misc_feature
<222> LOCATION: (83)..(87)
<223> OTHER INFORMATION: Tail domain

<400> SEQUENCE: 44
nnnnnnnnnn nnnnnnnnnn guuuuagagc uaugcuguuu uggaaacaaa acagcauagc 60
aaguuaaaau aaggcuaguc cguuauc 87

<210> SEQ ID NO 45
<211> LENGTH: 42
<212> TYPE: RNA
<213> ORGANISM: Artificial Sequence
<220> FEATURE:
<223> OTHER INFORMATION: Modular gRNA derived from S. thermophilus
<220> FEATURE:
<221> NAME/KEY: misc_feature
<222> LOCATION: (1)..(20)
<223> OTHER INFORMATION: a, c, u, g, unknown or other
<220> FEATURE:

<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(42)
<223> OTHER INFORMATION: First complementarity domain

<400> SEQUENCE: 45
nnnnnnnnnn nnnnnnnnnn guuuuagagc uguguuguuu cg 42

<210> SEQ ID NO 46
<211> LENGTH: 78
<212> TYPE: RNA
<213> ORGANISM: Artificial Sequence
<220> FEATURE:
<223> OTHER INFORMATION: Modular gRNA derived from S. thermophilus
<220> FEATURE:
<221> NAME/KEY: misc_feature
<222> LOCATION: (1)..(3)
<223> OTHER INFORMATION: 5' extension domain
<220> FEATURE:
<221> NAME/KEY: misc_feature
<222> LOCATION: (4)..(27)
<223> OTHER INFORMATION: Second complementarity domain
<220> FEATURE:
<221> NAME/KEY: misc_feature
<222> LOCATION: (28)..(40)
<223> OTHER INFORMATION: Proximal domain
<220> FEATURE:
<221> NAME/KEY: misc_feature
<222> LOCATION: (41)..(78)
<223> OTHER INFORMATION: Tail domain

<400> SEQUENCE: 46
gggcgaaaca acacagcgag uuaaaauaag gcuuaguccg uacucaacuu gaaaaggugg 60
caccgauucg guguuuuu 78

<210> SEQ ID NO 47
<211> LENGTH: 85
<212> TYPE: RNA
<213> ORGANISM: Artificial Sequence
<220> FEATURE:
<223> OTHER INFORMATION: Modular gRNA derived from S. pyogenes

<400> SEQUENCE: 47
gaaccauuca aaacagcaua gcaaguuaaa auaaggcuag uccguuauca acuugaaaaa 60
guggcaccga gucggugcuu uuuuu 85

<210> SEQ ID NO 48
<211> LENGTH: 96
<212> TYPE: RNA
<213> ORGANISM: Artificial Sequence
<220> FEATURE:
<223> OTHER INFORMATION: gRNA from S. pyogenes
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain

<400> SEQUENCE: 48
nnnnnnnnnn nnnnnnnnnn guuuuagagc uagaaauagc aaguuaaaau aaggcuaguc 60
cguuaucaac uugaaaaagu ggcaccgagu cggugc 96

<210> SEQ ID NO 49
<211> LENGTH: 96
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(32)
<223> OTHER INFORMATION: First complementarity domain
<220> FEATURE:
<221> NAME/KEY: misc_feature
<222> LOCATION: (33)..(36)
<223> OTHER INFORMATION: Linking domain
<220> FEATURE:
<221> NAME/KEY: misc_feature
<222> LOCATION: (37)..(50)
<223> OTHER INFORMATION: Second complementarity domain
<220> FEATURE:
<221> NAME/KEY: misc_feature
<222> LOCATION: (51)..(62)
<223> OTHER INFORMATION: Proximal domain

<400> SEQUENCE: 49
nnnnnnnnnn nnnnnnnnnn guauuagagc uagaaauagc aaguuaauau aaggcuaguc 60
cguuaucaac uugaaaaagu ggcaccgagu cggugc 96

<210> SEQ ID NO 50
<211> LENGTH: 104
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(36)
<223> OTHER INFORMATION: First complementarity domain
<220> FEATURE:
<221> NAME/KEY: misc_feature
<222> LOCATION: (37)..(40)
<223> OTHER INFORMATION: Linking domain
<220> FEATURE:
<221> NAME/KEY: misc_feature
<222> LOCATION: (41)..(58)
<223> OTHER INFORMATION: Second complementarity domain

<400> SEQUENCE: 50
nnnnnnnnnn nnnnnnnnnn guuuuagagc uaugcugaaa agcauagcaa guuaaaauaa 60
ggcuaguccg uuaucaacuu gaaaaagugg caccgagucg gugc 104

<210> SEQ ID NO 51
<211> LENGTH: 106
<212> TYPE: RNA
<213> ORGANISM: Artificial Sequence
<220> FEATURE:
<223> OTHER INFORMATION: gRNA
<220> FEATURE:

<221> NAME/KEY: misc_feature
<222> LOCATION: (1)..(20)
<223> OTHER INFORMATION: n is a, c, g, or u
<220> FEATURE:
<221> NAME/KEY: misc_feature
<222> LOCATION: (1)..(20)
<223> OTHER INFORMATION: Targeting domain
<220> FEATURE:
<221> NAME/KEY: misc_feature
<222> LOCATION: (21)..(37)
<223> OTHER INFORMATION: First complementarity domain
<220> FEATURE:
<221> NAME/KEY: misc_feature
<222> LOCATION: (38)..(41)
<223> OTHER INFORMATION: Linking domain
<220> FEATURE:
<221> NAME/KEY: misc_feature
<222> LOCATION: (42)..(60)
<223> OTHER INFORMATION: Second complementarity domain

<400> SEQUENCE: 51
nnnnnnnnnn nnnnnnnnnn guuuuagagc uaugcuggaa acagcauagc aaguuaaaau 60
aaggcuaguc cguuaucaac uugaaaaagu ggcaccgagu cggugc 106

<210> SEQ ID NO 52
<211> LENGTH: 12
<212> TYPE: PRT
<213> ORGANISM: Peptoniphilus duerdenii

<400> SEQUENCE: 52

Asp Ile Gly Thr Ala Ser Val Gly Trp Ala Val Thr
1 5 10

<210> SEQ ID NO 53
<211> LENGTH: 12
<212> TYPE: PRT
<213> ORGANISM: Treponema denticola

<400> SEQUENCE: 53

Asp Val Gly Thr Gly Ser Val Gly Trp Ala Val Thr
1 5 10

<210> SEQ ID NO 54
<211> LENGTH: 12
<212> TYPE: PRT
<213> ORGANISM: S. mutans

<400> SEQUENCE: 54

Asp Ile Gly Thr Asn Ser Val Gly Trp Ala Val Val
1 5 10

<210> SEQ ID NO 55
<211> LENGTH: 12
<212> TYPE: PRT
<213> ORGANISM: S. pyogenes

<400> SEQUENCE: 55

Asp Ile Gly Thr Asn Ser Val Gly Trp Ala Val Ile
1 5 10

<210> SEQ ID NO 56
<211> LENGTH: 12
<212> TYPE: PRT
<213> ORGANISM: L. innocua

<400> SEQUENCE: 56

Asp Ile Gly Thr Asn Ser Val Gly Trp Ala Val Leu 1 5 10

<210> SEQ ID NO 57
<211> LENGTH: 12
<212> TYPE: PRT
<213> ORGANISM: Flavobacterium branchiophilum FL-15

<400> SEQUENCE: 57

Asp Leu Gly Thr Asn Ser Ile Gly Trp Ala Val Val
1 5 10

<210> SEQ ID NO 58
<211> LENGTH: 11
<212> TYPE: PRT
<213> ORGANISM: Pedobacter glucosidilyticus

<400> SEQUENCE: 58

Asp Leu Gly Thr Asn Ser Ile Gly Trp Ala Ile
1 5 10

<210> SEQ ID NO 59
<211> LENGTH: 12
<212> TYPE: PRT
<213> ORGANISM: Bacteroides fragilis, NCTC 9343

<400> SEQUENCE: 59

Asp Leu Gly Thr Asn Ser Ile Gly Trp Ala Leu Val
1 5 10

<210> SEQ ID NO 60
<211> LENGTH: 12
<212> TYPE: PRT
<213> ORGANISM: Fusobacterium nucleatum

<400> SEQUENCE: 60

Asp Ile Gly Thr Asn Ser Val Gly Trp Cys Val Thr
1 5 10

<210> SEQ ID NO 61
<211> LENGTH: 12
<212> TYPE: PRT
<213> ORGANISM: Acidaminococcus sp. D21

<400> SEQUENCE: 61

Asp Ile Gly Thr Asn Ser Val Gly Tyr Ala Val Thr
1 5 10

<210> SEQ ID NO 62
<211> LENGTH: 12
<212> TYPE: PRT
<213> ORGANISM: Coprococcus catus GD-7

<400> SEQUENCE: 62

Asp Met Gly Thr Gly Ser Leu Gly Trp Ala Val Thr
1 5 10

<210> SEQ ID NO 63
<211> LENGTH: 12
<212> TYPE: PRT
<213> ORGANISM: Oenococcus kitaharae DSM 17330

<400> SEQUENCE: 63

Asp Ile Gly Thr Ser Ser Val Gly Trp Ala Ala Ile
1 5 10

<210> SEQ ID NO 64
<211> LENGTH: 12
<212> TYPE: PRT
<213> ORGANISM: Catenibacterium mitsuokai DSM 15897

<400> SEQUENCE: 64

Asp Leu Gly Thr Gly Ser Val Gly Trp Ala Val Val
1               5                   10

<210> SEQ ID NO 65
<211> LENGTH: 12
<212> TYPE: PRT
<213> ORGANISM: Mycoplasma gallisepticum str. F

<400> SEQUENCE: 65

Asp Leu Gly Val Gly Ser Val Gly Trp Ala Ile Val
1               5                   10

<210> SEQ ID NO 66
<211> LENGTH: 12
<212> TYPE: PRT
<213> ORGANISM: Mycoplasma ovipneumoniae SC01

<400> SEQUENCE: 66

Asp Leu Gly Ile Ala Ser Ile Gly Trp Ala Ile Ile
1               5                   10

<210> SEQ ID NO 67
<211> LENGTH: 12
<212> TYPE: PRT
<213> ORGANISM: Mycoplasma canis PG 14

<400> SEQUENCE: 67

Asp Leu Gly Ile Ala Ser Val Gly Trp Ala Ile Val
1               5                   10

<210> SEQ ID NO 68
<211> LENGTH: 12
<212> TYPE: PRT
<213> ORGANISM: Mycoplasma synoviae 53

<400> SEQUENCE: 68

Asp Leu Gly Val Ala Ser Val Gly Trp Ser Ile Val
1               5                   10

<210> SEQ ID NO 69
<211> LENGTH: 12
<212> TYPE: PRT
<213> ORGANISM: Eubacterium rectale

<400> SEQUENCE: 69

Asp Ile Gly Ile Ala Ser Val Gly Trp Ala Ile Leu
1               5                   10

<210> SEQ ID NO 70
<211> LENGTH: 12
<212> TYPE: PRT
<213> ORGANISM: Enterococcus faecalis TX0012

<400> SEQUENCE: 70

Asp Leu Gly Ile Ser Ser Val Gly Trp Ser Val Ile
1               5                   10

<210> SEQ ID NO 71

<211> LENGTH: 12
<212> TYPE: PRT
<213> ORGANISM: Ilyobacter polytropus DSM 2926

<400> SEQUENCE: 71

Asp Ile Gly Ile Ala Ser Val Gly Trp Ser Val Ile
1 5 10

<210> SEQ ID NO 72
<211> LENGTH: 12
<212> TYPE: PRT
<213> ORGANISM: Ruminococcus albus 8

<400> SEQUENCE: 72

Asp Val Gly Ile Gly Ser Ile Gly Trp Ala Val Ile
1 5 10

<210> SEQ ID NO 73
<211> LENGTH: 12
<212> TYPE: PRT
<213> ORGANISM: Elusimicrobium minutum Pei191

<400> SEQUENCE: 73

Asp Leu Gly Val Gly Ser Ile Gly Phe Ala Ile Val
1 5 10

<210> SEQ ID NO 74
<211> LENGTH: 12
<212> TYPE: PRT
<213> ORGANISM: Akkermansia muciniphila

<400> SEQUENCE: 74

Asp Ile Gly Tyr Ala Ser Ile Gly Trp Ala Val Ile
1 5 10

<210> SEQ ID NO 75
<211> LENGTH: 12
<212> TYPE: PRT
<213> ORGANISM: Prevotella ruminicola

<400> SEQUENCE: 75

Asp Thr Gly Thr Asn Ser Leu Gly Trp Ala Ile Val
1 5 10

<210> SEQ ID NO 76
<211> LENGTH: 12
<212> TYPE: PRT
<213> ORGANISM: Cand. Puniceispirillum marinum

<400> SEQUENCE: 76

Asp Leu Gly Thr Asn Ser Ile Gly Trp Cys Leu Leu
1 5 10

<210> SEQ ID NO 77
<211> LENGTH: 12
<212> TYPE: PRT
<213> ORGANISM: Rhodospirillum rubrum

<400> SEQUENCE: 77

Asp Ile Gly Thr Asp Ser Leu Gly Trp Ala Val Phe
1 5 10

<210> SEQ ID NO 78
<211> LENGTH: 12
<212> TYPE: PRT

<213> ORGANISM: Lactobacillus rhamnosus GG

<400> SEQUENCE: 78

Asp Ile Gly Ser Asn Ser Ile Gly Phe Ala Val Val
1 5 10

<210> SEQ ID NO 79
<211> LENGTH: 12
<212> TYPE: PRT
<213> ORGANISM: Sphaerochaeta globus str. Buddy

<400> SEQUENCE: 79

Asp Leu Gly Val Gly Ser Ile Gly Val Ala Val Ala
1 5 10

<210> SEQ ID NO 80
<211> LENGTH: 12
<212> TYPE: PRT
<213> ORGANISM: Rhodopseudomonas palustris

<400> SEQUENCE: 80

Asp Leu Gly Ile Ala Ser Cys Gly Trp Gly Val Val
1 5 10

<210> SEQ ID NO 81
<211> LENGTH: 12
<212> TYPE: PRT
<213> ORGANISM: Mycoplasma mobile 163K

<400> SEQUENCE: 81

Asp Leu Gly Ile Ala Ser Val Gly Trp Cys Leu Thr
1 5 10

<210> SEQ ID NO 82
<211> LENGTH: 12
<212> TYPE: PRT
<213> ORGANISM: Streptococcus thermophilus LMD-9

<400> SEQUENCE: 82

Asp Ile Gly Ile Gly Ser Val Gly Val Gly Ile Leu
1 5 10

<210> SEQ ID NO 83
<211> LENGTH: 12
<212> TYPE: PRT
<213> ORGANISM: Staphylococcus lugdunensis M23590

<400> SEQUENCE: 83

Asp Ile Gly Ile Thr Ser Val Gly Tyr Gly Leu Ile
1 5 10

<210> SEQ ID NO 84
<211> LENGTH: 12
<212> TYPE: PRT
<213> ORGANISM: Eubacterium dolichum DSM 3991

<400> SEQUENCE: 84

Asp Ile Gly Ile Thr Ser Val Gly Phe Gly Ile Ile
1 5 10

<210> SEQ ID NO 85
<211> LENGTH: 12
<212> TYPE: PRT
<213> ORGANISM: Lactobacillus coryniformis KCTC 3535

<400> SEQUENCE: 85

Asp Val Gly Ile Thr Ser Thr Gly Tyr Ala Val Leu
1 5 10

<210> SEQ ID NO 86
<211> LENGTH: 12
<212> TYPE: PRT
<213> ORGANISM: Nitratifractor salsuginis DSM 16511

<400> SEQUENCE: 86

Asp Leu Gly Ile Thr Ser Phe Gly Tyr Ala Ile Leu
1 5 10

<210> SEQ ID NO 87
<211> LENGTH: 12
<212> TYPE: PRT
<213> ORGANISM: Bifidobacterium bifidum S17

<400> SEQUENCE: 87

Asp Ile Gly Asn Ala Ser Val Gly Trp Ser Ala Phe
1 5 10

<210> SEQ ID NO 88
<211> LENGTH: 12
<212> TYPE: PRT
<213> ORGANISM: Lactobacillus gasseri

<400> SEQUENCE: 88

Asp Val Gly Thr Asn Ser Cys Gly Trp Val Ala Met
1 5 10

<210> SEQ ID NO 89
<211> LENGTH: 12
<212> TYPE: PRT
<213> ORGANISM: Acidothermus cellulolyticus 11B

<400> SEQUENCE: 89

Asp Val Gly Glu Arg Ser Ile Gly Leu Ala Ala Val
1 5 10

<210> SEQ ID NO 90
<211> LENGTH: 12
<212> TYPE: PRT
<213> ORGANISM: Bifidobacterium longum DJO10A

<400> SEQUENCE: 90

Asp Val Gly Leu Asn Ser Val Gly Leu Ala Ala Val
1 5 10

<210> SEQ ID NO 91
<211> LENGTH: 12
<212> TYPE: PRT
<213> ORGANISM: Bifidobacterium dentium

<400> SEQUENCE: 91

Asp Val Gly Leu Met Ser Val Gly Leu Ala Ala Ile
1 5 10

<210> SEQ ID NO 92
<211> LENGTH: 12
<212> TYPE: PRT
<213> ORGANISM: Corynebacterium diphtheriae

<400> SEQUENCE: 92

Asp Val Gly Thr Phe Ser Val Gly Leu Ala Ala Ile
1 5 10

<210> SEQ ID NO 93
<211> LENGTH: 12
<212> TYPE: PRT
<213> ORGANISM: Staphylococcus pseudintermedius ED99

<400> SEQUENCE: 93

Asp Ile Gly Thr Gly Ser Val Gly Tyr Ala Cys Met
1 5 10

<210> SEQ ID NO 94
<211> LENGTH: 12
<212> TYPE: PRT
<213> ORGANISM: Capnocytophaga ochracea

<400> SEQUENCE: 94

Asp Leu Gly Thr Thr Ser Ile Gly Phe Ala His Ile
1 5 10

<210> SEQ ID NO 95
<211> LENGTH: 12
<212> TYPE: PRT
<213> ORGANISM: Prevotella denticola

<400> SEQUENCE: 95

Asp Leu Gly Thr Asn Ser Ile Gly Ser Ser Val Arg
1 5 10

<210> SEQ ID NO 96
<211> LENGTH: 12
<212> TYPE: PRT
<213> ORGANISM: Ralstonia solanacearum

<400> SEQUENCE: 96

Asp Ile Gly Thr Asn Ser Ile Gly Trp Ala Val Ile
1 5 10

<210> SEQ ID NO 97
<211> LENGTH: 12
<212> TYPE: PRT
<213> ORGANISM: Pasteurella multocida str. Pm70

<400> SEQUENCE: 97

Asp Leu Gly Ile Ala Ser Val Gly Trp Ala Val Val
1 5 10

<210> SEQ ID NO 98
<211> LENGTH: 12
<212> TYPE: PRT
<213> ORGANISM: Comamonas granuli

<400> SEQUENCE: 98

Asp Ile Gly Ile Ala Ser Val Gly Trp Ala Val Leu
1 5 10

<210> SEQ ID NO 99
<211> LENGTH: 12
<212> TYPE: PRT
<213> ORGANISM: Helicobacter mustelae 12198

<400> SEQUENCE: 99

Asp Ile Gly Ile Ala Ser Ile Gly Trp Ala Val Ile
1 5 10

<210> SEQ ID NO 100
<211> LENGTH: 12
<212> TYPE: PRT
<213> ORGANISM: Agathobacter rectalis

<400> SEQUENCE: 100

Asp Ile Gly Ile Ala Ser Val Gly Trp Ala Ile Ile
1 5 10

<210> SEQ ID NO 101
<211> LENGTH: 12
<212> TYPE: PRT
<213> ORGANISM: Clostridium cellulolyticum H10

<400> SEQUENCE: 101

Asp Val Gly Ile Ala Ser Val Gly Trp Ala Val Ile
1 5 10

<210> SEQ ID NO 102
<211> LENGTH: 11
<212> TYPE: PRT
<213> ORGANISM: Methylophilus sp. OH31

<400> SEQUENCE: 102

Asp Ile Gly Ile Ala Ser Val Gly Trp Ala Leu
1 5 10

<210> SEQ ID NO 103
<211> LENGTH: 12
<212> TYPE: PRT
<213> ORGANISM: Neisseria meningitidis

<400> SEQUENCE: 103

Asp Ile Gly Ile Ala Ser Val Gly Trp Ala Met Val
1 5 10

<210> SEQ ID NO 104
<211> LENGTH: 12
<212> TYPE: PRT
<213> ORGANISM: Clostridium perfringens

<400> SEQUENCE: 104

Asp Ile Gly Ile Thr Ser Val Gly Trp Ala Val Ile
1 5 10

<210> SEQ ID NO 105
<211> LENGTH: 12
<212> TYPE: PRT
<213> ORGANISM: Wolinella succinogenes DSM 1740

<400> SEQUENCE: 105

Asp Leu Gly Ile Ser Ser Leu Gly Trp Ala Ile Val
1 5 10

<210> SEQ ID NO 106
<211> LENGTH: 12
<212> TYPE: PRT
<213> ORGANISM: Azospirillum sp. B510

<400> SEQUENCE: 106

Asp Leu Gly Thr Asn Ser Ile Gly Trp Gly Leu Leu
1 5 10

<210> SEQ ID NO 107
<211> LENGTH: 12
<212> TYPE: PRT
<213> ORGANISM: Verminephrobacter eiseniae

<400> SEQUENCE: 107

Asp Leu Gly Ser Thr Ser Leu Gly Trp Ala Ile Phe
1 5 10

<210> SEQ ID NO 108
<211> LENGTH: 12
<212> TYPE: PRT
<213> ORGANISM: Campylobacter jejuni, NCTC 11168

<400> SEQUENCE: 108

Asp Ile Gly Ile Ser Ser Ile Gly Trp Ala Phe Ser
1 5 10

<210> SEQ ID NO 109
<211> LENGTH: 12
<212> TYPE: PRT
<213> ORGANISM: Parvibaculum lavamentivorans DS-1

<400> SEQUENCE: 109

Asp Ile Gly Thr Thr Ser Ile Gly Phe Ser Val Ile
1 5 10

<210> SEQ ID NO 110
<211> LENGTH: 12
<212> TYPE: PRT
<213> ORGANISM: Dinoroseobacter shibae DFL 12

<400> SEQUENCE: 110

Asp Ile Gly Thr Ser Ser Ile Gly Trp Trp Leu Tyr
1 5 10

<210> SEQ ID NO 111
<211> LENGTH: 12
<212> TYPE: PRT
<213> ORGANISM: Nitrobacter hamburgensis X14

<400> SEQUENCE: 111

Asp Leu Gly Ser Asn Ser Leu Gly Trp Phe Val Thr
1 5 10

<210> SEQ ID NO 112
<211> LENGTH: 12
<212> TYPE: PRT
<213> ORGANISM: Bradyrhizobium sp. BTAi1

<400> SEQUENCE: 112

Asp Leu Gly Ala Asn Ser Leu Gly Trp Phe Val Val
1 5 10

<210> SEQ ID NO 113
<211> LENGTH: 15
<212> TYPE: PRT
<213> ORGANISM: Bacillus cereus

<400> SEQUENCE: 113

Asp Ile Gly Leu Arg Ile Gly Ile Thr Ser Cys Gly Trp Ser Ile
1 5 10 15

<210> SEQ ID NO 114
<211> LENGTH: 12

<212> TYPE: PRT
<213> ORGANISM: Sutterella wadsworthensis

<400> SEQUENCE: 114

Asp Met Gly Ala Lys Tyr Thr Gly Val Phe Tyr Ala
1 5 10

<210> SEQ ID NO 115
<211> LENGTH: 12
<212> TYPE: PRT
<213> ORGANISM: Wolinella succinogenes DSM 1740

<400> SEQUENCE: 115

Asp Leu Gly Gly Lys Asn Thr Gly Phe Phe Ser Phe
1 5 10

<210> SEQ ID NO 116
<211> LENGTH: 12
<212> TYPE: PRT
<213> ORGANISM: Francisella tularensis

<400> SEQUENCE: 116

Asp Leu Gly Val Lys Asn Thr Gly Val Phe Ser Ala
1 5 10

<210> SEQ ID NO 117
<211> LENGTH: 12
<212> TYPE: PRT
<213> ORGANISM: Gamma proteobacterium HTCC5015

<400> SEQUENCE: 117

Asp Leu Gly Ala Lys Phe Thr Gly Val Ala Leu Tyr
1 5 10

<210> SEQ ID NO 118
<211> LENGTH: 12
<212> TYPE: PRT
<213> ORGANISM: Legionella pneumophila str. Paris

<400> SEQUENCE: 118

Asp Leu Gly Gly Lys Phe Thr Gly Val Cys Leu Ser
1 5 10

<210> SEQ ID NO 119
<211> LENGTH: 12
<212> TYPE: PRT
<213> ORGANISM: Parasutterella excrementihominis

<400> SEQUENCE: 119

Asp Leu Gly Gly Thr Tyr Thr Gly Thr Phe Ile Thr
1 5 10

<210> SEQ ID NO 120
<211> LENGTH: 12
<212> TYPE: PRT
<213> ORGANISM: S. thermophilus

<400> SEQUENCE: 120

Asp Ile Gly Thr Asn Ser Val Gly Trp Ala Val Thr
1 5 10

<210> SEQ ID NO 121
<211> LENGTH: 12
<212> TYPE: PRT
<213> ORGANISM: Eubacterium yurii

<400> SEQUENCE: 121

Asp Val Gly Thr Asn Ser Val Gly Trp Ala Val Thr
1               5                   10

<210> SEQ ID NO 122
<211> LENGTH: 12
<212> TYPE: PRT
<213> ORGANISM: Butyrivibrio hungatei

<400> SEQUENCE: 122

Asp Met Gly Thr Asn Ser Val Gly Trp Ala Val Thr
1               5                   10

<210> SEQ ID NO 123
<211> LENGTH: 12
<212> TYPE: PRT
<213> ORGANISM: Solobacterium moorei F0204

<400> SEQUENCE: 123

Asp Val Gly Thr Ser Ser Val Gly Trp Ala Val Thr
1               5                   10

<210> SEQ ID NO 124
<211> LENGTH: 27
<212> TYPE: PRT
<213> ORGANISM: Treponema denticola

<400> SEQUENCE: 124

Asp Ile Asp His Ile Tyr Pro Gln Ser Lys Ile Lys Asp Asp Ser Ile
1               5                   10                  15

Ser Asn Arg Val Leu Val Cys Ser Ser Cys Asn
            20                  25

<210> SEQ ID NO 125
<211> LENGTH: 27
<212> TYPE: PRT
<213> ORGANISM: Coprococcus catus GD-7

<400> SEQUENCE: 125

Asp Ile Asp His Ile Tyr Pro Gln Ser Lys Thr Met Asp Asp Ser Leu
1               5                   10                  15

Asn Asn Arg Val Leu Val Lys Lys Asn Tyr Asn
            20                  25

<210> SEQ ID NO 126
<211> LENGTH: 27
<212> TYPE: PRT
<213> ORGANISM: Peptoniphilus duerdenii

<400> SEQUENCE: 126

Asp Gln Asp His Ile Tyr Pro Lys Ser Lys Ile Tyr Asp Asp Ser Leu
1               5                   10                  15

Glu Asn Arg Val Leu Val Lys Lys Asn Leu Asn
            20                  25

<210> SEQ ID NO 127
<211> LENGTH: 27
<212> TYPE: PRT
<213> ORGANISM: Catenibacterium mitsuokai DSM 15897

<400> SEQUENCE: 127

Gln Ile Asp His Ile Val Pro Gln Ser Leu Val Lys Asp Asp Ser Phe

```
1               5                   10                  15

Asp Asn Arg Val Leu Val Val Pro Ser Glu Asn
            20                  25


<210> SEQ ID NO 128
<211> LENGTH: 27
<212> TYPE: PRT
<213> ORGANISM: S. mutans

<400> SEQUENCE: 128

Asp Ile Asp His Ile Ile Pro Gln Ala Phe Ile Lys Asp Asn Ser Ile
1               5                   10                  15

Asp Asn Arg Val Leu Thr Ser Ser Lys Glu Asn
            20                  25


<210> SEQ ID NO 129
<211> LENGTH: 27
<212> TYPE: PRT
<213> ORGANISM: S. thermophilus

<400> SEQUENCE: 129

Asp Ile Asp His Ile Ile Pro Gln Ala Phe Leu Lys Asp Asn Ser Ile
1               5                   10                  15

Asp Asn Lys Val Leu Val Ser Ser Ala Ser Asn
            20                  25


<210> SEQ ID NO 130
<211> LENGTH: 27
<212> TYPE: PRT
<213> ORGANISM: Oenococcus kitaharae DSM 17330

<400> SEQUENCE: 130

Asp Ile Asp His Ile Ile Pro Gln Ala Tyr Thr Lys Asp Asn Ser Leu
1               5                   10                  15

Asp Asn Arg Val Leu Val Ser Asn Ile Thr Asn
            20                  25


<210> SEQ ID NO 131
<211> LENGTH: 27
<212> TYPE: PRT
<213> ORGANISM: L. inocua

<400> SEQUENCE: 131

Asp Ile Asp His Ile Val Pro Gln Ser Phe Ile Thr Asp Asn Ser Ile
1               5                   10                  15

Asp Asn Leu Val Leu Thr Ser Ser Ala Gly Asn
            20                  25


<210> SEQ ID NO 132
<211> LENGTH: 27
<212> TYPE: PRT
<213> ORGANISM: S. pyogenes

<400> SEQUENCE: 132

Asp Val Asp His Ile Val Pro Gln Ser Phe Leu Lys Asp Asp Ser Ile
1               5                   10                  15

Asp Asn Lys Val Leu Thr Arg Ser Asp Lys Asn
            20                  25


<210> SEQ ID NO 133
<211> LENGTH: 27
<212> TYPE: PRT
```

<213> ORGANISM: Acidaminococcus sp. D21

<400> SEQUENCE: 133

Asn Ile Asp His Ile Tyr Pro Gln Ser Met Val Lys Asp Asp Ser Leu
1               5                   10                  15

Asp Asn Lys Val Leu Val Gln Ser Glu Ile Asn
            20                  25

<210> SEQ ID NO 134
<211> LENGTH: 27
<212> TYPE: PRT
<213> ORGANISM: Lactobacillus rhamnosus GG

<400> SEQUENCE: 134

Asp Ile Asp His Ile Leu Pro Gln Ser Leu Ile Lys Asp Asp Ser Leu
1               5                   10                  15

Asp Asn Arg Val Leu Val Asn Ala Thr Ile Asn
            20                  25

<210> SEQ ID NO 135
<211> LENGTH: 27
<212> TYPE: PRT
<213> ORGANISM: Lactobacillus gasseri

<400> SEQUENCE: 135

Asp Ile Asp His Ile Leu Pro Gln Ser Phe Ile Lys Asp Asp Ser Leu
1               5                   10                  15

Glu Asn Arg Val Leu Val Lys Lys Ala Val Asn
            20                  25

<210> SEQ ID NO 136
<211> LENGTH: 27
<212> TYPE: PRT
<213> ORGANISM: Staphylococcus pseudintermedius ED99

<400> SEQUENCE: 136

Glu Val Asp His Ile Phe Pro Arg Ser Phe Ile Lys Asp Asp Ser Ile
1               5                   10                  15

Asp Asn Lys Val Leu Val Ile Lys Lys Met Asn
            20                  25

<210> SEQ ID NO 137
<211> LENGTH: 27
<212> TYPE: PRT
<213> ORGANISM: Olsenella uli

<400> SEQUENCE: 137

Glu Val Asp His Ile Ile Pro Arg Ser Tyr Ile Lys Asp Asp Ser Phe
1               5                   10                  15

Glu Asn Lys Val Leu Val Tyr Arg Glu Glu Asn
            20                  25

<210> SEQ ID NO 138
<211> LENGTH: 27
<212> TYPE: PRT
<213> ORGANISM: Bifidobacterium bifidum S17

<400> SEQUENCE: 138

Asp Ile Asp His Ile Ile Pro Gln Ala Val Thr Gln Asn Asp Ser Ile
1               5                   10                  15

Asp Asn Arg Val Leu Val Ala Arg Ala Glu Asn
            20                  25

<210> SEQ ID NO 139
<211> LENGTH: 27
<212> TYPE: PRT
<213> ORGANISM: Mycoplasma gallisepticum str. F

<400> SEQUENCE: 139

```
Glu Ile Asp His Ile Ile Pro Tyr Ser Ile Ser Phe Asp Asp Ser Ser
1               5                   10                  15

Ser Asn Lys Leu Leu Val Leu Ala Glu Ser Asn
            20                  25
```

<210> SEQ ID NO 140
<211> LENGTH: 27
<212> TYPE: PRT
<213> ORGANISM: Mycoplasma canis PG 14

<400> SEQUENCE: 140

```
Glu Ile Asp His Ile Ile Pro Tyr Ser Leu Cys Phe Asp Asp Ser Ser
1               5                   10                  15

Ala Asn Lys Val Leu Val His Lys Gln Ser Asn
            20                  25
```

<210> SEQ ID NO 141
<211> LENGTH: 27
<212> TYPE: PRT
<213> ORGANISM: Ilyobacter polytropus DSM 2926

<400> SEQUENCE: 141

```
Asp Ile Asp His Ile Ile Pro Tyr Ser Arg Ser Met Asp Asp Ser Tyr
1               5                   10                  15

Ser Asn Lys Val Leu Val Leu Ser Gly Glu Asn
            20                  25
```

<210> SEQ ID NO 142
<211> LENGTH: 27
<212> TYPE: PRT
<213> ORGANISM: Uncultured Termite group 1 bacterium

<400> SEQUENCE: 142

```
Asp Ile Asp His Ile Ile Pro Tyr Ser Lys Ser Met Asp Asp Ser Phe
1               5                   10                  15

Asn Asn Lys Val Leu Cys Leu Ala Glu Glu Asn
            20                  25
```

<210> SEQ ID NO 143
<211> LENGTH: 27
<212> TYPE: PRT
<213> ORGANISM: Campylobacter jejuni

<400> SEQUENCE: 143

```
Glu Ile Asp His Ile Tyr Pro Tyr Ser Arg Ser Phe Asp Asp Ser Tyr
1               5                   10                  15

Met Asn Lys Val Leu Val Phe Thr Lys Gln Asn
            20                  25
```

<210> SEQ ID NO 144
<211> LENGTH: 27
<212> TYPE: PRT
<213> ORGANISM: Clostridium cellulolyticum H10

<400> SEQUENCE: 144

```
Gln Ile Asp His Ile Tyr Pro Tyr Ser Arg Ser Met Asp Asp Ser Tyr
1               5                   10                  15

Met Asn Lys Val Leu Val Leu Thr Asp Glu Asn
            20                  25


<210> SEQ ID NO 145
<211> LENGTH: 27
<212> TYPE: PRT
<213> ORGANISM: Clostridium perfringens

<400> SEQUENCE: 145

Glu Ile Asp His Ile Ile Pro Phe Ser Arg Ser Phe Asp Asp Ser Leu
1               5                   10                  15

Ser Asn Lys Ile Leu Val Leu Gly Ser Glu Asn
            20                  25


<210> SEQ ID NO 146
<211> LENGTH: 27
<212> TYPE: PRT
<213> ORGANISM: N. meningitides

<400> SEQUENCE: 146

Glu Ile Asp His Ala Leu Pro Phe Ser Arg Thr Trp Asp Asp Ser Phe
1               5                   10                  15

Asn Asn Lys Val Leu Val Leu Gly Ser Glu Asn
            20                  25


<210> SEQ ID NO 147
<211> LENGTH: 27
<212> TYPE: PRT
<213> ORGANISM: Pasteurella multocida str. Pm70

<400> SEQUENCE: 147

Glu Ile Asp His Ala Leu Pro Phe Ser Arg Thr Trp Asp Asp Ser Phe
1               5                   10                  15

Asn Asn Lys Val Leu Val Leu Ala Ser Glu Asn
            20                  25


<210> SEQ ID NO 148
<211> LENGTH: 27
<212> TYPE: PRT
<213> ORGANISM: Enterococcus faecalis TX0012

<400> SEQUENCE: 148

Glu Ile Asp His Ile Ile Pro Ile Ser Ile Ser Leu Asp Asp Ser Ile
1               5                   10                  15

Asn Asn Lys Val Leu Val Leu Ser Lys Ala Asn
            20                  25


<210> SEQ ID NO 149
<211> LENGTH: 27
<212> TYPE: PRT
<213> ORGANISM: Eubacterium dolichum DSM 3991

<400> SEQUENCE: 149

Glu Val Asp His Ile Ile Pro Ile Ser Ile Ser Leu Asp Asp Ser Ile
1               5                   10                  15

Thr Asn Lys Val Leu Val Thr His Arg Glu Asn
            20                  25


<210> SEQ ID NO 150
<211> LENGTH: 27
```

<212> TYPE: PRT
<213> ORGANISM: Acidovorax ebreus

<400> SEQUENCE: 150

```
Gln Val Asp His Ala Leu Pro Tyr Ser Arg Ser Tyr Asp Asp Ser Lys
1               5                   10                  15

Asn Asn Lys Val Leu Val Leu Thr His Glu Asn
            20                  25
```

<210> SEQ ID NO 151
<211> LENGTH: 27
<212> TYPE: PRT
<213> ORGANISM: Streptococcus thermophilus LMD-9

<400> SEQUENCE: 151

```
Glu Val Asp His Ile Leu Pro Leu Ser Ile Thr Phe Asp Asp Ser Leu
1               5                   10                  15

Ala Asn Lys Val Leu Val Tyr Ala Thr Ala Asn
            20                  25
```

<210> SEQ ID NO 152
<211> LENGTH: 27
<212> TYPE: PRT
<213> ORGANISM: Eubacterium rectale

<400> SEQUENCE: 152

```
Glu Ile Asp His Ile Ile Pro Arg Ser Ile Ser Phe Asp Asp Ala Arg
1               5                   10                  15

Ser Asn Lys Val Leu Val Tyr Arg Ser Glu Asn
            20                  25
```

<210> SEQ ID NO 153
<211> LENGTH: 27
<212> TYPE: PRT
<213> ORGANISM: Staphylococcus lugdunensis M23590

<400> SEQUENCE: 153

```
Glu Val Asp His Ile Ile Pro Arg Ser Val Ser Phe Asp Asn Ser Tyr
1               5                   10                  15

His Asn Lys Val Leu Val Lys Gln Ser Glu Asn
            20                  25
```

<210> SEQ ID NO 154
<211> LENGTH: 27
<212> TYPE: PRT
<213> ORGANISM: Roseburia intestinalis

<400> SEQUENCE: 154

```
Asp Ile Asp His Ile Leu Pro Tyr Ser Ile Thr Phe Asp Asp Ser Phe
1               5                   10                  15

Arg Asn Lys Val Leu Val Thr Ser Gln Glu Asn
            20                  25
```

<210> SEQ ID NO 155
<211> LENGTH: 27
<212> TYPE: PRT
<213> ORGANISM: Wolinella succinogenes DSM 1740

<400> SEQUENCE: 155

```
Glu Ile Asp His Ile Leu Pro Arg Ser Arg Ser Ala Asp Asp Ser Phe
1               5                   10                  15

Ala Asn Lys Val Leu Cys Leu Ala Arg Ala Asn
```

```
            20                  25


<210> SEQ ID NO 156
<211> LENGTH: 27
<212> TYPE: PRT
<213> ORGANISM: Cand. Puniceispirillum marinum

<400> SEQUENCE: 156

Glu Ile Glu His Leu Leu Pro Phe Ser Leu Thr Leu Asp Asp Ser Met
1               5                   10                  15

Ala Asn Lys Thr Val Cys Phe Arg Gln Ala Asn
            20                  25


<210> SEQ ID NO 157
<211> LENGTH: 27
<212> TYPE: PRT
<213> ORGANISM: Azospirillum sp. B510

<400> SEQUENCE: 157

Asp Ile Asp His Ile Leu Pro Phe Ser Val Ser Leu Asp Asp Ser Ala
1               5                   10                  15

Ala Asn Lys Val Val Cys Leu Arg Glu Ala Asn
            20                  25


<210> SEQ ID NO 158
<211> LENGTH: 27
<212> TYPE: PRT
<213> ORGANISM: Bradyrhizobium sp. BTAi1

<400> SEQUENCE: 158

Asp Ile Asp His Leu Ile Pro Phe Ser Ile Ser Trp Asp Asp Ser Ala
1               5                   10                  15

Ala Asn Lys Val Val Cys Met Arg Tyr Ala Asn
            20                  25


<210> SEQ ID NO 159
<211> LENGTH: 27
<212> TYPE: PRT
<213> ORGANISM: Nitrobacter hamburgensis X14

<400> SEQUENCE: 159

Asp Ile Asp His Ile Leu Pro Val Ala Met Thr Leu Asp Asp Ser Pro
1               5                   10                  15

Ala Asn Lys Ile Ile Cys Met Arg Tyr Ala Asn
            20                  25


<210> SEQ ID NO 160
<211> LENGTH: 27
<212> TYPE: PRT
<213> ORGANISM: Dinoroseobacter shibae

<400> SEQUENCE: 160

Asp Val Asp His Ile Leu Pro Tyr Ser Arg Thr Leu Asp Asp Ser Phe
1               5                   10                  15

Pro Asn Arg Thr Leu Cys Leu Arg Glu Ala Asn
            20                  25


<210> SEQ ID NO 161
<211> LENGTH: 27
<212> TYPE: PRT
<213> ORGANISM: Verminephrobacter eiseniae

<400> SEQUENCE: 161
```

```
Glu Ile Glu His Ile Leu Pro Phe Ser Arg Thr Leu Asp Asp Ser Leu
1               5                   10                  15

Asn Asn Arg Thr Val Ala Met Arg Arg Ala Asn
            20                  25


<210> SEQ ID NO 162
<211> LENGTH: 27
<212> TYPE: PRT
<213> ORGANISM: Lactobacillus coryniformis KCTC 3535

<400> SEQUENCE: 162

Glu Val Asp His Ile Ile Pro Tyr Ser Ile Ser Trp Asp Asp Ser Tyr
1               5                   10                  15

Thr Asn Lys Val Leu Thr Ser Ala Lys Cys Asn
            20                  25


<210> SEQ ID NO 163
<211> LENGTH: 27
<212> TYPE: PRT
<213> ORGANISM: Rhodopseudomonas palustris

<400> SEQUENCE: 163

Gln Val Asp His Ile Leu Pro Trp Ser Arg Phe Gly Asp Asp Ser Tyr
1               5                   10                  15

Leu Asn Lys Thr Leu Cys Thr Ala Arg Ser Asn
            20                  25


<210> SEQ ID NO 164
<211> LENGTH: 27
<212> TYPE: PRT
<213> ORGANISM: Ralstonia syzygii R24

<400> SEQUENCE: 164

Gln Val Asp His Ile Leu Pro Phe Ser Lys Thr Leu Asp Asp Ser Phe
1               5                   10                  15

Ala Asn Lys Val Leu Ala Gln His Asp Ala Asn
            20                  25


<210> SEQ ID NO 165
<211> LENGTH: 27
<212> TYPE: PRT
<213> ORGANISM: Helicobacter mustelae 12198

<400> SEQUENCE: 165

Gln Ile Asp His Ala Phe Pro Leu Ser Arg Ser Leu Asp Asp Ser Gln
1               5                   10                  15

Ser Asn Lys Val Leu Cys Leu Thr Ser Ser Asn
            20                  25


<210> SEQ ID NO 166
<211> LENGTH: 27
<212> TYPE: PRT
<213> ORGANISM: Mycoplasma mobile 163K

<400> SEQUENCE: 166

Asp Ile Asp His Ile Val Pro Arg Ser Ile Ser Phe Asp Asp Ser Phe
1               5                   10                  15

Ser Asn Leu Val Ile Val Asn Lys Leu Asp Asn
            20                  25


<210> SEQ ID NO 167
```

<211> LENGTH: 27
<212> TYPE: PRT
<213> ORGANISM: Mycoplasma ovipneumoniae SC01

<400> SEQUENCE: 167

Glu Ile Glu His Ile Ile Pro Tyr Ser Met Ser Tyr Asp Asn Ser Gln
1 5 10 15

Ala Asn Lys Ile Leu Thr Glu Lys Ala Glu Asn
20 25

<210> SEQ ID NO 168
<211> LENGTH: 27
<212> TYPE: PRT
<213> ORGANISM: Mycoplasma synoviae 53

<400> SEQUENCE: 168

Glu Ile Asp His Val Ile Pro Tyr Ser Lys Ser Ala Asp Asp Ser Trp
1 5 10 15

Phe Asn Lys Leu Leu Val Lys Lys Ser Thr Asn
20 25

<210> SEQ ID NO 169
<211> LENGTH: 27
<212> TYPE: PRT
<213> ORGANISM: Aminomonas paucivorans DSM 12260

<400> SEQUENCE: 169

Glu Met Asp His Ile Leu Pro Tyr Ser Arg Ser Leu Asp Asn Gly Trp
1 5 10 15

His Asn Arg Val Leu Val His Gly Lys Asp Asn
20 25

<210> SEQ ID NO 170
<211> LENGTH: 27
<212> TYPE: PRT
<213> ORGANISM: Ruminococcus albus 8

<400> SEQUENCE: 170

Glu Val Asp His Ile Val Pro Tyr Ser Leu Ile Leu Asp Asn Thr Ile
1 5 10 15

Asn Asn Lys Ala Leu Val Tyr Ala Glu Glu Asn
20 25

<210> SEQ ID NO 171
<211> LENGTH: 27
<212> TYPE: PRT
<213> ORGANISM: Fibrobacter succinogenes

<400> SEQUENCE: 171

Glu Ile Glu His Val Ile Pro Gln Ser Leu Tyr Phe Asp Asp Ser Phe
1 5 10 15

Ser Asn Lys Val Ile Cys Glu Ala Glu Val Asn
20 25

<210> SEQ ID NO 172
<211> LENGTH: 27
<212> TYPE: PRT
<213> ORGANISM: Bacteroides fragilis, NCTC 9343

<400> SEQUENCE: 172

Asp Ile Glu His Ile Ile Pro Gln Ala Arg Leu Phe Asp Asp Ser Phe
1 5 10 15

-continued

```
Ser Asn Lys Thr Leu Glu Ala Arg Ser Val Asn
            20                  25


<210> SEQ ID NO 173
<211> LENGTH: 27
<212> TYPE: PRT
<213> ORGANISM: Capnocytophaga sputigena

<400> SEQUENCE: 173

Glu Ile Glu His Ile Val Pro Lys Ala Arg Val Phe Asp Asp Ser Phe
1               5                   10                  15

Ser Asn Lys Thr Leu Thr Phe His Arg Ile Asn
            20                  25


<210> SEQ ID NO 174
<211> LENGTH: 28
<212> TYPE: PRT
<213> ORGANISM: Finegoldia magna

<400> SEQUENCE: 174

Asp Lys Asp His Ile Ile Pro Gln Ser Met Lys Lys Asp Asp Ser Ile
1               5                   10                  15

Ile Asn Asn Leu Val Leu Val Asn Lys Asn Ala Asn
            20                  25


<210> SEQ ID NO 175
<211> LENGTH: 27
<212> TYPE: PRT
<213> ORGANISM: Parvibaculum lavamentivorans DS-1

<400> SEQUENCE: 175

Glu Val Glu His Ile Trp Pro Arg Ser Arg Ser Phe Asp Asn Ser Pro
1               5                   10                  15

Arg Asn Lys Thr Leu Cys Arg Lys Asp Val Asn
            20                  25


<210> SEQ ID NO 176
<211> LENGTH: 27
<212> TYPE: PRT
<213> ORGANISM: Bacillus cereus

<400> SEQUENCE: 176

Ile Val Asn His Ile Ile Pro Tyr Asn Arg Ser Phe Asp Asp Thr Tyr
1               5                   10                  15

His Asn Arg Val Leu Thr Leu Thr Glu Thr Lys
            20                  25


<210> SEQ ID NO 177
<211> LENGTH: 27
<212> TYPE: PRT
<213> ORGANISM: Prevotella micans

<400> SEQUENCE: 177

Asp Met Glu His Thr Ile Pro Lys Ser Ile Ser Phe Asp Asn Ser Asp
1               5                   10                  15

Gln Asn Leu Thr Leu Cys Glu Ser Tyr Tyr Asn
            20                  25


<210> SEQ ID NO 178
<211> LENGTH: 27
<212> TYPE: PRT
<213> ORGANISM: Prevotella ruminicola
```

<400> SEQUENCE: 178

Asp Ile Glu His Thr Ile Pro Arg Ser Ala Gly Gly Asp Ser Thr Lys
1               5                   10                  15

Met Asn Leu Thr Leu Cys Ser Ser Arg Phe Asn
            20                  25

<210> SEQ ID NO 179
<211> LENGTH: 27
<212> TYPE: PRT
<213> ORGANISM: Flavobacterium columnare

<400> SEQUENCE: 179

Asp Ile Glu His Thr Ile Pro Arg Ser Ile Ser Gln Asp Asn Ser Gln
1               5                   10                  15

Met Asn Lys Thr Leu Cys Ser Leu Lys Phe Asn
            20                  25

<210> SEQ ID NO 180
<211> LENGTH: 27
<212> TYPE: PRT
<213> ORGANISM: Rhodospirillum rubrum

<400> SEQUENCE: 180

Asp Ile Asp His Val Ile Pro Leu Ala Arg Gly Gly Arg Asp Ser Leu
1               5                   10                  15

Asp Asn Met Val Leu Cys Gln Ser Asp Ala Asn
            20                  25

<210> SEQ ID NO 181
<211> LENGTH: 27
<212> TYPE: PRT
<213> ORGANISM: Elusimicrobium minutum Pei191

<400> SEQUENCE: 181

Asp Ile Glu His Leu Phe Pro Ile Ala Glu Ser Glu Asp Asn Gly Arg
1               5                   10                  15

Asn Asn Leu Val Ile Ser His Ser Ala Cys Asn
            20                  25

<210> SEQ ID NO 182
<211> LENGTH: 27
<212> TYPE: PRT
<213> ORGANISM: Sphaerochaeta globus str. Buddy

<400> SEQUENCE: 182

Asp Val Asp His Ile Phe Pro Arg Asp Asp Thr Ala Asp Asn Ser Tyr
1               5                   10                  15

Gly Asn Lys Val Val Ala His Arg Gln Cys Asn
            20                  25

<210> SEQ ID NO 183
<211> LENGTH: 27
<212> TYPE: PRT
<213> ORGANISM: Nitratifractor salsuginis DSM 16511

<400> SEQUENCE: 183

Asp Ile Glu His Ile Val Pro Gln Ser Leu Gly Gly Leu Ser Thr Asp
1               5                   10                  15

Tyr Asn Thr Ile Val Thr Leu Lys Ser Val Asn
            20                  25

<210> SEQ ID NO 184
<211> LENGTH: 27
<212> TYPE: PRT
<213> ORGANISM: Acidothermus cellulolyticus 11B

<400> SEQUENCE: 184

Glu Leu Asp His Ile Val Pro Arg Thr Asp Gly Gly Ser Asn Arg His
1               5                   10                  15

Glu Asn Leu Ala Ile Thr Cys Gly Ala Cys Asn
            20                  25

<210> SEQ ID NO 185
<211> LENGTH: 28
<212> TYPE: PRT
<213> ORGANISM: Bifidobacterium longum DJO10A

<400> SEQUENCE: 185

Glu Met Asp His Ile Val Pro Arg Lys Gly Val Gly Ser Thr Asn Thr
1               5                   10                  15

Arg Thr Asn Phe Ala Ala Val Cys Ala Glu Cys Asn
            20                  25

<210> SEQ ID NO 186
<211> LENGTH: 28
<212> TYPE: PRT
<213> ORGANISM: Bifidobacterium dentium

<400> SEQUENCE: 186

Glu Met Asp His Ile Val Pro Arg Lys Gly Val Gly Ser Thr Asn Thr
1               5                   10                  15

Arg Val Asn Leu Ala Ala Ala Cys Ala Ala Cys Asn
            20                  25

<210> SEQ ID NO 187
<211> LENGTH: 28
<212> TYPE: PRT
<213> ORGANISM: Corynebacterium diphtheriae

<400> SEQUENCE: 187

Glu Met Asp His Ile Val Pro Arg Ala Gly Gln Gly Ser Thr Asn Thr
1               5                   10                  15

Arg Glu Asn Leu Val Ala Val Cys His Arg Cys Asn
            20                  25

<210> SEQ ID NO 188
<211> LENGTH: 33
<212> TYPE: PRT
<213> ORGANISM: Sutterella wadsworthensis

<400> SEQUENCE: 188

Glu Ile Asp His Ile Leu Pro Arg Ser Leu Ile Lys Asp Ala Arg Gly
1               5                   10                  15

Ile Val Phe Asn Ala Glu Pro Asn Leu Ile Tyr Ala Ser Ser Arg Gly
            20                  25                  30

Asn

<210> SEQ ID NO 189
<211> LENGTH: 33
<212> TYPE: PRT
<213> ORGANISM: Gamma proteobacterium HTCC5015

<400> SEQUENCE: 189

Glu Ile Asp His Ile Ile Pro Arg Ser Leu Thr Gly Arg Thr Lys Lys
1 5 10 15

Thr Val Phe Asn Ser Glu Ala Asn Leu Ile Tyr Cys Ser Ser Lys Gly
20 25 30

Asn

<210> SEQ ID NO 190
<211> LENGTH: 33
<212> TYPE: PRT
<213> ORGANISM: Parasutterella excrementihominis

<400> SEQUENCE: 190

Glu Ile Asp His Ile Ile Pro Arg Ser Leu Thr Leu Lys Lys Ser Glu
1 5 10 15

Ser Ile Tyr Asn Ser Glu Val Asn Leu Ile Phe Val Ser Ala Gln Gly
20 25 30

Asn

<210> SEQ ID NO 191
<211> LENGTH: 33
<212> TYPE: PRT
<213> ORGANISM: Legionella pneumophila str. Paris

<400> SEQUENCE: 191

Glu Ile Asp His Ile Tyr Pro Arg Ser Leu Ser Lys Lys His Phe Gly
1 5 10 15

Val Ile Phe Asn Ser Glu Val Asn Leu Ile Tyr Cys Ser Ser Gln Gly
20 25 30

Asn

<210> SEQ ID NO 192
<211> LENGTH: 33
<212> TYPE: PRT
<213> ORGANISM: Wolinella succinogenes DSM 1740

<400> SEQUENCE: 192

Glu Ile Asp His Ile Leu Pro Arg Ser His Thr Leu Lys Ile Tyr Gly
1 5 10 15

Thr Val Phe Asn Pro Glu Gly Asn Leu Ile Tyr Val His Gln Lys Cys
20 25 30

Asn

<210> SEQ ID NO 193
<211> LENGTH: 30
<212> TYPE: PRT
<213> ORGANISM: Francisella tularensis

<400> SEQUENCE: 193

Glu Leu Asp His Ile Ile Pro Arg Ser His Lys Lys Tyr Gly Thr Leu
1 5 10 15

Asn Asp Glu Ala Asn Leu Ile Cys Val Thr Arg Gly Asp Asn
20 25 30

<210> SEQ ID NO 194
<211> LENGTH: 27
<212> TYPE: PRT
<213> ORGANISM: Akkermansia muciniphila

<400> SEQUENCE: 194

Glu Leu Glu His Ile Val Pro His Ser Phe Arg Gln Ser Asn Ala Leu

```
1               5                   10                  15

Ser Ser Leu Val Leu Thr Trp Pro Gly Val Asn
            20                  25


<210> SEQ ID NO 195
<211> LENGTH: 27
<212> TYPE: PRT
<213> ORGANISM: Solobacterium moorei F0204

<400> SEQUENCE: 195

Asp Ile Asp His Ile Tyr Pro Arg Ser Lys Ile Lys Asp Asp Ser Ile
1               5                   10                  15

Thr Asn Arg Val Leu Val Glu Lys Asp Ile Asn
            20                  25


<210> SEQ ID NO 196
<211> LENGTH: 28
<212> TYPE: PRT
<213> ORGANISM: Veillonella atypica ACS-134-V-Col7a

<400> SEQUENCE: 196

Tyr Asp Ile Asp His Ile Tyr Pro Arg Ser Leu Thr Lys Asp Asp Ser
1               5                   10                  15

Phe Asp Asn Leu Val Leu Cys Glu Arg Thr Ala Asn
            20                  25


<210> SEQ ID NO 197
<211> LENGTH: 28
<212> TYPE: PRT
<213> ORGANISM: Fusobacterium nucleatum

<400> SEQUENCE: 197

Asp Ile Asp His Ile Tyr Pro Arg Ser Lys Val Ile Lys Asp Asp Ser
1               5                   10                  15

Phe Asp Asn Leu Val Leu Val Leu Lys Asn Glu Asn
            20                  25


<210> SEQ ID NO 198
<211> LENGTH: 27
<212> TYPE: PRT
<213> ORGANISM: Filifactor alocis

<400> SEQUENCE: 198

Asp Arg Asp His Ile Tyr Pro Gln Ser Lys Ile Lys Asp Asp Ser Ile
1               5                   10                  15

Asp Asn Leu Val Leu Val Asn Lys Thr Tyr Asn
            20                  25


<210> SEQ ID NO 199
<211> LENGTH: 5
<212> TYPE: DNA
<213> ORGANISM: Streptococcus thermophilus
<220> FEATURE:
<221> NAME/KEY: misc_feature
<222> LOCATION: (1)..(1)
<223> OTHER INFORMATION: Any nucleotide (e.g., A, G, C, or T)
<220> FEATURE:
<221> NAME/KEY: misc_feature
<222> LOCATION: (4)..(4)
<223> OTHER INFORMATION: Any nucleotide (e.g., A, G, C, or T)

<400> SEQUENCE: 199

nggng                                                                   5
```

<210> SEQ ID NO 200
<211> LENGTH: 7
<212> TYPE: DNA
<213> ORGANISM: Streptococcus thermophilus
<220> FEATURE:
<221> NAME/KEY: misc_feature
<222> LOCATION: (1)..(1)
<223> OTHER INFORMATION: Any nucleotide (e.g., A, G, C, or T)
<220> FEATURE:
<221> NAME/KEY: misc_feature
<222> LOCATION: (2)..(2)
<223> OTHER INFORMATION: Any nucleotide (e.g., A, G, C, or T)
<220> FEATURE:
<221> NAME/KEY: misc_feature
<222> LOCATION: (7)..(7)
<223> OTHER INFORMATION: A or T

<400> SEQUENCE: 200 nnagaaw 7

<210> SEQ ID NO 201
<211> LENGTH: 4
<212> TYPE: DNA
<213> ORGANISM: Streptococcus mutans
<220> FEATURE:
<221> NAME/KEY: misc_feature
<222> LOCATION: (1)..(1)
<223> OTHER INFORMATION: Any nucleotide (e.g., A, G, C, or T)
<220> FEATURE:
<221> NAME/KEY: misc_feature
<222> LOCATION: (4)..(4)
<223> OTHER INFORMATION: A or G

<400> SEQUENCE: 201 naar 4

<210> SEQ ID NO 202
<211> LENGTH: 5
<212> TYPE: DNA
<213> ORGANISM: Staphylococcus aureus
<220> FEATURE:
<221> NAME/KEY: misc_feature
<222> LOCATION: (1)..(1)
<223> OTHER INFORMATION: Any nucleotide (e.g., A, G, C, or T)
<220> FEATURE:
<221> NAME/KEY: misc_feature
<222> LOCATION: (2)..(2)
<223> OTHER INFORMATION: Any nucleotide (e.g., A, G, C, or T)
<220> FEATURE:
<221> NAME/KEY: misc_feature
<222> LOCATION: (4)..(4)
<223> OTHER INFORMATION: A or G
<220> FEATURE:
<221> NAME/KEY: misc_feature
<222> LOCATION: (5)..(5)
<223> OTHER INFORMATION: A or G

<400> SEQUENCE: 202 nngrr 5

<210> SEQ ID NO 203
<211> LENGTH: 6
<212> TYPE: DNA
<213> ORGANISM: Staphylococcus aureus
<220> FEATURE:
<221> NAME/KEY: misc_feature
<222> LOCATION: (1)..(1)
<223> OTHER INFORMATION: Any nucleotide (e.g., A, G, C, or T)
<220> FEATURE:
<221> NAME/KEY: misc_feature
<222> LOCATION: (2)..(2)
<223> OTHER INFORMATION: Any nucleotide (e.g., A, G, C, or T)

<220> FEATURE:
<221> NAME/KEY: misc_feature
<222> LOCATION: (4)..(4)
<223> OTHER INFORMATION: A or G
<220> FEATURE:
<221> NAME/KEY: misc_feature
<222> LOCATION: (5)..(5)
<223> OTHER INFORMATION: A or G
<220> FEATURE:
<221> NAME/KEY: misc_feature
<222> LOCATION: (6)..(6)
<223> OTHER INFORMATION: Any nucleotide (e.g., A, G, C, or T)

<400> SEQUENCE: 203 nngrrn 6

<210> SEQ ID NO 204
<211> LENGTH: 6
<212> TYPE: DNA
<213> ORGANISM: Staphylococcus aureus
<220> FEATURE:
<221> NAME/KEY: misc_feature
<222> LOCATION: (1)..(1)
<223> OTHER INFORMATION: Any nucleotide (e.g., A, G, C, or T)
<220> FEATURE:
<221> NAME/KEY: misc_feature
<222> LOCATION: (2)..(2)
<223> OTHER INFORMATION: Any nucleotide (e.g., A, G, C, or T)
<220> FEATURE:
<221> NAME/KEY: misc_feature
<222> LOCATION: (4)..(4)
<223> OTHER INFORMATION: A or G
<220> FEATURE:
<221> NAME/KEY: misc_feature
<222> LOCATION: (5)..(5)
<223> OTHER INFORMATION: A or G

<400> SEQUENCE: 204 nngrrt 6

<210> SEQ ID NO 205
<211> LENGTH: 6
<212> TYPE: DNA
<213> ORGANISM: Staphylococcus aureus
<220> FEATURE:
<221> NAME/KEY: misc_feature
<222> LOCATION: (1)..(1)
<223> OTHER INFORMATION: Any nucleotide (e.g., A, G, C, or T)
<220> FEATURE:
<221> NAME/KEY: misc_feature
<222> LOCATION: (2)..(2)
<223> OTHER INFORMATION: Any nucleotide (e.g., A, G, C, or T)
<220> FEATURE:
<221> NAME/KEY: misc_feature
<222> LOCATION: (4)..(4)
<223> OTHER INFORMATION: A or G
<220> FEATURE:
<221> NAME/KEY: misc_feature
<222> LOCATION: (5)..(5)
<223> OTHER INFORMATION: A or G
<220> FEATURE:
<221> NAME/KEY: misc_feature
<222> LOCATION: (6)..(6)
<223> OTHER INFORMATION: A, G, or C

<400> SEQUENCE: 205 nngrrv 6

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251
<211> LENGTH: 17
<212> TYPE: RNA
<213> ORGANISM: Artificial Sequence
<220> FEATURE:
<223> OTHER INFORMATION: Targeting domain

<400> SEQUENCE: 251
gaaggaaacu agcuaaa 17

<210> SEQ ID NO 252
<211> LENGTH: 20
<212> TYPE: RNA
<213> ORGANISM: Artificial Sequence
<220> FEATURE:
<223> OTHER INFORMATION: Targeting domain

<400> SEQUENCE: 252
ggagaaggaa acuagcuaaa 20

<210> SEQ ID NO 253
<211> LENGTH: 20
<212> TYPE: RNA
<213> ORGANISM: Artificial Sequence
<220> FEATURE:
<223> OTHER INFORMATION: Targeting domain

<400> SEQUENCE: 253
gggagaagga aacuagcuaa 20

<210> SEQ ID NO 254
<211> LENGTH: 20
<212> TYPE: RNA
<213> ORGANISM: Artificial Sequence
<220> FEATURE:
<223> OTHER INFORMATION: Targeting domain

<400> SEQUENCE: 254
guauccucua ugaugggaga 20

<210> SEQ ID NO 255
<211> LENGTH: 20
<212> TYPE: RNA
<213> ORGANISM: Artificial Sequence
<220> FEATURE:
<223> OTHER INFORMATION: Targeting domain

<400> SEQUENCE: 255
guuuccuucu cccaucauag 20

<210> SEQ ID NO 256
<211> LENGTH: 20
<212> TYPE: RNA
<213> ORGANISM: Artificial Sequence
<220> FEATURE:
<223> OTHER INFORMATION: Targeting domain

<400> SEQUENCE: 256
guccugguau ccucuaugau 20

<210> SEQ ID NO 257
<211> LENGTH: 17
<212> TYPE: RNA
<213> ORGANISM: Artificial Sequence
<220> FEATURE:
<223> OTHER INFORMATION: Targeting domain

<400> SEQUENCE: 257
agaaggaaac uagcuaa 17

<210> SEQ ID NO 258

<211> LENGTH: 17
<212> TYPE: RNA
<213> ORGANISM: Artificial Sequence
<220> FEATURE:
<223> OTHER INFORMATION: Targeting domain

<400> SEQUENCE: 258
uccucuauga ugggaga 17

<210> SEQ ID NO 259
<211> LENGTH: 17
<212> TYPE: RNA
<213> ORGANISM: Artificial Sequence
<220> FEATURE:
<223> OTHER INFORMATION: Targeting domain

<400> SEQUENCE: 259
ccugguaucc ucuauga 17

<210> SEQ ID NO 260
<211> LENGTH: 17
<212> TYPE: RNA
<213> ORGANISM: Artificial Sequence
<220> FEATURE:
<223> OTHER INFORMATION: Targeting domain

<400> SEQUENCE: 260
ccaucauaga ggauacc 17

<210> SEQ ID NO 261
<211> LENGTH: 17
<212> TYPE: RNA
<213> ORGANISM: Artificial Sequence
<220> FEATURE:
<223> OTHER INFORMATION: Targeting domain

<400> SEQUENCE: 261
uccuucuccc aucauag 17

<210> SEQ ID NO 262
<211> LENGTH: 17
<212> TYPE: RNA
<213> ORGANISM: Artificial Sequence
<220> FEATURE:
<223> OTHER INFORMATION: Targeting domain

<400> SEQUENCE: 262
uagcaguauc cucuugg 17

<210> SEQ ID NO 263
<211> LENGTH: 17
<212> TYPE: RNA
<213> ORGANISM: Artificial Sequence
<220> FEATURE:
<223> OTHER INFORMATION: Targeting domain

<400> SEQUENCE: 263
uuagcaguau ccucuug 17

<210> SEQ ID NO 264
<211> LENGTH: 17
<212> TYPE: RNA
<213> ORGANISM: Artificial Sequence
<220> FEATURE:
<223> OTHER INFORMATION: Targeting domain

<400> SEQUENCE: 264
aacuggaaug acugaau 17

<210> SEQ ID NO 265
<211> LENGTH: 17
<212> TYPE: RNA
<213> ORGANISM: Artificial Sequence
<220> FEATURE:
<223> OTHER INFORMATION: Targeting domain

<400> SEQUENCE: 265
cugguauccu cuaugau 17

<210> SEQ ID NO 266
<211> LENGTH: 17
<212> TYPE: RNA
<213> ORGANISM: Artificial Sequence
<220> FEATURE:
<223> OTHER INFORMATION: Targeting domain

<400> SEQUENCE: 266
aauuagcagu auccucu 17

<210> SEQ ID NO 267
<211> LENGTH: 17
<212> TYPE: RNA
<213> ORGANISM: Artificial Sequence
<220> FEATURE:
<223> OTHER INFORMATION: Targeting domain

<400> SEQUENCE: 267
auuagcagua uccucuu 17

<210> SEQ ID NO 268
<211> LENGTH: 20
<212> TYPE: RNA
<213> ORGANISM: Artificial Sequence
<220> FEATURE:
<223> OTHER INFORMATION: Targeting domain

<400> SEQUENCE: 268
aguccuggua uccucuauga 20

<210> SEQ ID NO 269
<211> LENGTH: 20
<212> TYPE: RNA
<213> ORGANISM: Artificial Sequence
<220> FEATURE:
<223> OTHER INFORMATION: Targeting domain

<400> SEQUENCE: 269
cucccaucau agaggauacc 20

<210> SEQ ID NO 270
<211> LENGTH: 20
<212> TYPE: RNA
<213> ORGANISM: Artificial Sequence
<220> FEATURE:
<223> OTHER INFORMATION: Targeting domain

<400> SEQUENCE: 270
aauuagcagu auccucuugg 20

<210> SEQ ID NO 271
<211> LENGTH: 20
<212> TYPE: RNA

<213> ORGANISM: Artificial Sequence
<220> FEATURE:
<223> OTHER INFORMATION: Targeting domain

<400> SEQUENCE: 271
aaauuagcag uauccucuug 20

<210> SEQ ID NO 272
<211> LENGTH: 20
<212> TYPE: RNA
<213> ORGANISM: Artificial Sequence
<220> FEATURE:
<223> OTHER INFORMATION: Targeting domain

<400> SEQUENCE: 272
aaaaacugga augacugaau 20

<210> SEQ ID NO 273
<211> LENGTH: 20
<212> TYPE: RNA
<213> ORGANISM: Artificial Sequence
<220> FEATURE:
<223> OTHER INFORMATION: Targeting domain

<400> SEQUENCE: 273
aaaaauuagc aguauccucu 20

<210> SEQ ID NO 274
<211> LENGTH: 20
<212> TYPE: RNA
<213> ORGANISM: Artificial Sequence
<220> FEATURE:
<223> OTHER INFORMATION: Targeting domain

<400> SEQUENCE: 274
aaaauuagca guauccucuu 20

<210> SEQ ID NO 275
<211> LENGTH: 17
<212> TYPE: RNA
<213> ORGANISM: Artificial Sequence
<220> FEATURE:
<223> OTHER INFORMATION: Targeting domain

<400> SEQUENCE: 275
gaaucggaac aaggcaa 17

<210> SEQ ID NO 276
<211> LENGTH: 17
<212> TYPE: RNA
<213> ORGANISM: Artificial Sequence
<220> FEATURE:
<223> OTHER INFORMATION: Targeting domain

<400> SEQUENCE: 276
gaccaauagc cuugaca 17

<210> SEQ ID NO 277
<211> LENGTH: 17
<212> TYPE: RNA
<213> ORGANISM: Artificial Sequence
<220> FEATURE:
<223> OTHER INFORMATION: Targeting domain

<400> SEQUENCE: 277
ggcuauuggu caaggca 17

<210> SEQ ID NO 278
<211> LENGTH: 17
<212> TYPE: RNA
<213> ORGANISM: Artificial Sequence
<220> FEATURE:
<223> OTHER INFORMATION: Targeting domain

<400> SEQUENCE: 278
gucaaggcua uugguca 17

<210> SEQ ID NO 279
<211> LENGTH: 17
<212> TYPE: RNA
<213> ORGANISM: Artificial Sequence
<220> FEATURE:
<223> OTHER INFORMATION: Targeting domain

<400> SEQUENCE: 279
guguguggaa cugcuga 17

<210> SEQ ID NO 280
<211> LENGTH: 17
<212> TYPE: RNA
<213> ORGANISM: Artificial Sequence
<220> FEATURE:
<223> OTHER INFORMATION: Targeting domain

<400> SEQUENCE: 280
gggccggcgg cuggcua 17

<210> SEQ ID NO 281
<211> LENGTH: 17
<212> TYPE: RNA
<213> ORGANISM: Artificial Sequence
<220> FEATURE:
<223> OTHER INFORMATION: Targeting domain

<400> SEQUENCE: 281
gaguauccag ugaggcc 17

<210> SEQ ID NO 282
<211> LENGTH: 17
<212> TYPE: RNA
<213> ORGANISM: Artificial Sequence
<220> FEATURE:
<223> OTHER INFORMATION: Targeting domain

<400> SEQUENCE: 282
gcugacaaaa gaagucc 17

<210> SEQ ID NO 283
<211> LENGTH: 17
<212> TYPE: RNA
<213> ORGANISM: Artificial Sequence
<220> FEATURE:
<223> OTHER INFORMATION: Targeting domain

<400> SEQUENCE: 283
ggccaggggc cggcggc 17

<210> SEQ ID NO 284
<211> LENGTH: 17
<212> TYPE: RNA
<213> ORGANISM: Artificial Sequence
<220> FEATURE:

<223> OTHER INFORMATION: Targeting domain

<400> SEQUENCE: 284
gggaaggggc ccccaag 17

<210> SEQ ID NO 285
<211> LENGTH: 17
<212> TYPE: RNA
<213> ORGANISM: Artificial Sequence
<220> FEATURE:
<223> OTHER INFORMATION: Targeting domain

<400> SEQUENCE: 285
gagauagugu ggggaag 17

<210> SEQ ID NO 286
<211> LENGTH: 17
<212> TYPE: RNA
<213> ORGANISM: Artificial Sequence
<220> FEATURE:
<223> OTHER INFORMATION: Targeting domain

<400> SEQUENCE: 286
guauccagug aggccag 17

<210> SEQ ID NO 287
<211> LENGTH: 17
<212> TYPE: RNA
<213> ORGANISM: Artificial Sequence
<220> FEATURE:
<223> OTHER INFORMATION: Targeting domain

<400> SEQUENCE: 287
gugaggccag gggccgg 17

<210> SEQ ID NO 288
<211> LENGTH: 17
<212> TYPE: RNA
<213> ORGANISM: Artificial Sequence
<220> FEATURE:
<223> OTHER INFORMATION: Targeting domain

<400> SEQUENCE: 288
gcuggccaac ccauggg 17

<210> SEQ ID NO 289
<211> LENGTH: 17
<212> TYPE: RNA
<213> ORGANISM: Artificial Sequence
<220> FEATURE:
<223> OTHER INFORMATION: Targeting domain

<400> SEQUENCE: 289
ggcuaaacuc cacccau 17

<210> SEQ ID NO 290
<211> LENGTH: 17
<212> TYPE: RNA
<213> ORGANISM: Artificial Sequence
<220> FEATURE:
<223> OTHER INFORMATION: Targeting domain

<400> SEQUENCE: 290
ggauacucua agacuau 17

<210> SEQ ID NO 291
<211> LENGTH: 17
<212> TYPE: RNA
<213> ORGANISM: Artificial Sequence
<220> FEATURE:
<223> OTHER INFORMATION: Targeting domain

<400> SEQUENCE: 291
ggggccggcg gcuggcu 17

<210> SEQ ID NO 292
<211> LENGTH: 20
<212> TYPE: RNA
<213> ORGANISM: Artificial Sequence
<220> FEATURE:
<223> OTHER INFORMATION: Targeting domain

<400> SEQUENCE: 292
ggcuagggau gaagaauaaa 20

<210> SEQ ID NO 293
<211> LENGTH: 20
<212> TYPE: RNA
<213> ORGANISM: Artificial Sequence
<220> FEATURE:
<223> OTHER INFORMATION: Targeting domain

<400> SEQUENCE: 293
gagugugugg aacugcugaa 20

<210> SEQ ID NO 294
<211> LENGTH: 20
<212> TYPE: RNA
<213> ORGANISM: Artificial Sequence
<220> FEATURE:
<223> OTHER INFORMATION: Targeting domain

<400> SEQUENCE: 294
ggaaugacug aaucggaaca 20

<210> SEQ ID NO 295
<211> LENGTH: 20
<212> TYPE: RNA
<213> ORGANISM: Artificial Sequence
<220> FEATURE:
<223> OTHER INFORMATION: Targeting domain

<400> SEQUENCE: 295
gcauugagau agugugggga 20

<210> SEQ ID NO 296
<211> LENGTH: 20
<212> TYPE: RNA
<213> ORGANISM: Artificial Sequence
<220> FEATURE:
<223> OTHER INFORMATION: Targeting domain

<400> SEQUENCE: 296
gcuauugguc aaggcaaggc 20

<210> SEQ ID NO 297
<211> LENGTH: 20
<212> TYPE: RNA
<213> ORGANISM: Artificial Sequence
<220> FEATURE:
<223> OTHER INFORMATION: Targeting domain

<400> SEQUENCE: 297
guggggaagg ggcccccaag 20

<210> SEQ ID NO 298
<211> LENGTH: 20
<212> TYPE: RNA
<213> ORGANISM: Artificial Sequence
<220> FEATURE:
<223> OTHER INFORMATION: Targeting domain

<400> SEQUENCE: 298
ggcaaggcug gccaacccau 20

<210> SEQ ID NO 299
<211> LENGTH: 20
<212> TYPE: RNA
<213> ORGANISM: Artificial Sequence
<220> FEATURE:
<223> OTHER INFORMATION: Targeting domain

<400> SEQUENCE: 299
guuugccuug ucaaggcuau 20

<210> SEQ ID NO 300
<211> LENGTH: 20
<212> TYPE: RNA
<213> ORGANISM: Artificial Sequence
<220> FEATURE:
<223> OTHER INFORMATION: Targeting domain

<400> SEQUENCE: 300
gcuaaacucc acccaugggu 20

<210> SEQ ID NO 301
<211> LENGTH: 17
<212> TYPE: RNA
<213> ORGANISM: Artificial Sequence
<220> FEATURE:
<223> OTHER INFORMATION: Targeting domain

<400> SEQUENCE: 301
caaauaucug ucugaaa 17

<210> SEQ ID NO 302
<211> LENGTH: 17
<212> TYPE: RNA
<213> ORGANISM: Artificial Sequence
<220> FEATURE:
<223> OTHER INFORMATION: Targeting domain

<400> SEQUENCE: 302
uagggaugaa gaauaaa 17

<210> SEQ ID NO 303
<211> LENGTH: 17
<212> TYPE: RNA
<213> ORGANISM: Artificial Sequence
<220> FEATURE:
<223> OTHER INFORMATION: Targeting domain

<400> SEQUENCE: 303
ugagauagug uggggaa 17

<210> SEQ ID NO 304
<211> LENGTH: 17

```
<212> TYPE: RNA
<213> ORGANISM: Artificial Sequence
<220> FEATURE:
<223> OTHER INFORMATION: Targeting domain

<400> SEQUENCE: 304

uguguggaac ugcugaa                                                    17

<210> SEQ ID NO 305
<211> LENGTH: 17
<212> TYPE: RNA
<213> ORGANISM: Artificial Sequence
<220> FEATURE:
<223> OTHER INFORMATION: Targeting domain

<400> SEQUENCE: 305

augacugaau cggaaca                                                    17

<210> SEQ ID NO 306
<211> LENGTH: 17
<212> TYPE: RNA
<213> ORGANISM: Artificial Sequence
<220> FEATURE:
<223> OTHER INFORMATION: Targeting domain

<400> SEQUENCE: 306

caaggcuggc caaccca                                                    17

<210> SEQ ID NO 307
<211> LENGTH: 17
<212> TYPE: RNA
<213> ORGANISM: Artificial Sequence
<220> FEATURE:
<223> OTHER INFORMATION: Targeting domain

<400> SEQUENCE: 307

uggcuaaacu ccaccca                                                    17

<210> SEQ ID NO 308
<211> LENGTH: 17
<212> TYPE: RNA
<213> ORGANISM: Artificial Sequence
<220> FEATURE:
<223> OTHER INFORMATION: Targeting domain

<400> SEQUENCE: 308

uggguggagu uuagcca                                                    17

<210> SEQ ID NO 309
<211> LENGTH: 17
<212> TYPE: RNA
<213> ORGANISM: Artificial Sequence
<220> FEATURE:
<223> OTHER INFORMATION: Targeting domain

<400> SEQUENCE: 309

aguauccagu gaggcca                                                    17

<210> SEQ ID NO 310
<211> LENGTH: 17
<212> TYPE: RNA
<213> ORGANISM: Artificial Sequence
<220> FEATURE:
<223> OTHER INFORMATION: Targeting domain

<400> SEQUENCE: 310
```

```
ucaaguuugc cuuguca                                              17

<210> SEQ ID NO 311
<211> LENGTH: 17
<212> TYPE: RNA
<213> ORGANISM: Artificial Sequence
<220> FEATURE:
<223> OTHER INFORMATION: Targeting domain

<400> SEQUENCE: 311

uugagauagu gugggga                                              17

<210> SEQ ID NO 312
<211> LENGTH: 17
<212> TYPE: RNA
<213> ORGANISM: Artificial Sequence
<220> FEATURE:
<223> OTHER INFORMATION: Targeting domain

<400> SEQUENCE: 312

auaaauuaga gaaaaac                                              17

<210> SEQ ID NO 313
<211> LENGTH: 17
<212> TYPE: RNA
<213> ORGANISM: Artificial Sequence
<220> FEATURE:
<223> OTHER INFORMATION: Targeting domain

<400> SEQUENCE: 313

ccggccccug gccucac                                              17

<210> SEQ ID NO 314
<211> LENGTH: 17
<212> TYPE: RNA
<213> ORGANISM: Artificial Sequence
<220> FEATURE:
<223> OTHER INFORMATION: Targeting domain

<400> SEQUENCE: 314

agccagccgc cggcccc                                              17

<210> SEQ ID NO 315
<211> LENGTH: 17
<212> TYPE: RNA
<213> ORGANISM: Artificial Sequence
<220> FEATURE:
<223> OTHER INFORMATION: Targeting domain

<400> SEQUENCE: 315

cugucugaaa cgguccc                                              17

<210> SEQ ID NO 316
<211> LENGTH: 17
<212> TYPE: RNA
<213> ORGANISM: Artificial Sequence
<220> FEATURE:
<223> OTHER INFORMATION: Targeting domain

<400> SEQUENCE: 316

auggguggag uuuagcc                                              17

<210> SEQ ID NO 317
<211> LENGTH: 17
<212> TYPE: RNA
<213> ORGANISM: Artificial Sequence
```

<220> FEATURE:
<223> OTHER INFORMATION: Targeting domain

<400> SEQUENCE: 317
caucccuagc cagccgc 17

<210> SEQ ID NO 318
<211> LENGTH: 17
<212> TYPE: RNA
<213> ORGANISM: Artificial Sequence
<220> FEATURE:
<223> OTHER INFORMATION: Targeting domain

<400> SEQUENCE: 318
auuggucaag gcaaggc 17

<210> SEQ ID NO 319
<211> LENGTH: 17
<212> TYPE: RNA
<213> ORGANISM: Artificial Sequence
<220> FEATURE:
<223> OTHER INFORMATION: Targeting domain

<400> SEQUENCE: 319
ccagugaggc caggggc 17

<210> SEQ ID NO 320
<211> LENGTH: 17
<212> TYPE: RNA
<213> ORGANISM: Artificial Sequence
<220> FEATURE:
<223> OTHER INFORMATION: Targeting domain

<400> SEQUENCE: 320
uuccacacac ucgcuuc 17

<210> SEQ ID NO 321
<211> LENGTH: 17
<212> TYPE: RNA
<213> ORGANISM: Artificial Sequence
<220> FEATURE:
<223> OTHER INFORMATION: Targeting domain

<400> SEQUENCE: 321
cgcuucugga acgucug 17

<210> SEQ ID NO 322
<211> LENGTH: 17
<212> TYPE: RNA
<213> ORGANISM: Artificial Sequence
<220> FEATURE:
<223> OTHER INFORMATION: Targeting domain

<400> SEQUENCE: 322
ucuuagagua uccagug 17

<210> SEQ ID NO 323
<211> LENGTH: 17
<212> TYPE: RNA
<213> ORGANISM: Artificial Sequence
<220> FEATURE:
<223> OTHER INFORMATION: Targeting domain

<400> SEQUENCE: 323
uuugcauuga gauagug 17

<210> SEQ ID NO 324
<211> LENGTH: 17
<212> TYPE: RNA
<213> ORGANISM: Artificial Sequence
<220> FEATURE:
<223> OTHER INFORMATION: Targeting domain

<400> SEQUENCE: 324
uuccagaagc gagugug 17

<210> SEQ ID NO 325
<211> LENGTH: 17
<212> TYPE: RNA
<213> ORGANISM: Artificial Sequence
<220> FEATURE:
<223> OTHER INFORMATION: Targeting domain

<400> SEQUENCE: 325
ugcauugaga uagugug 17

<210> SEQ ID NO 326
<211> LENGTH: 17
<212> TYPE: RNA
<213> ORGANISM: Artificial Sequence
<220> FEATURE:
<223> OTHER INFORMATION: Targeting domain

<400> SEQUENCE: 326
aaggcuggcc aacccau 17

<210> SEQ ID NO 327
<211> LENGTH: 17
<212> TYPE: RNA
<213> ORGANISM: Artificial Sequence
<220> FEATURE:
<223> OTHER INFORMATION: Targeting domain

<400> SEQUENCE: 327
ugccuuguca aggcuau 17

<210> SEQ ID NO 328
<211> LENGTH: 17
<212> TYPE: RNA
<213> ORGANISM: Artificial Sequence
<220> FEATURE:
<223> OTHER INFORMATION: Targeting domain

<400> SEQUENCE: 328
aaacuccacc caugggu 17

<210> SEQ ID NO 329
<211> LENGTH: 17
<212> TYPE: RNA
<213> ORGANISM: Artificial Sequence
<220> FEATURE:
<223> OTHER INFORMATION: Targeting domain

<400> SEQUENCE: 329
uugcauugag auagugu 17

<210> SEQ ID NO 330
<211> LENGTH: 20
<212> TYPE: RNA
<213> ORGANISM: Artificial Sequence
<220> FEATURE:
<223> OTHER INFORMATION: Targeting domain

<400> SEQUENCE: 330
augcaaauau cugucugaaa 20

<210> SEQ ID NO 331
<211> LENGTH: 20
<212> TYPE: RNA
<213> ORGANISM: Artificial Sequence
<220> FEATURE:
<223> OTHER INFORMATION: Targeting domain

<400> SEQUENCE: 331
acugaaucgg aacaaggcaa 20

<210> SEQ ID NO 332
<211> LENGTH: 20
<212> TYPE: RNA
<213> ORGANISM: Artificial Sequence
<220> FEATURE:
<223> OTHER INFORMATION: Targeting domain

<400> SEQUENCE: 332
cauugagaua gugugggaa 20

<210> SEQ ID NO 333
<211> LENGTH: 20
<212> TYPE: RNA
<213> ORGANISM: Artificial Sequence
<220> FEATURE:
<223> OTHER INFORMATION: Targeting domain

<400> SEQUENCE: 333
cuugaccaau agccuugaca 20

<210> SEQ ID NO 334
<211> LENGTH: 20
<212> TYPE: RNA
<213> ORGANISM: Artificial Sequence
<220> FEATURE:
<223> OTHER INFORMATION: Targeting domain

<400> SEQUENCE: 334
aggcaaggcu ggccaaccca 20

<210> SEQ ID NO 335
<211> LENGTH: 20
<212> TYPE: RNA
<213> ORGANISM: Artificial Sequence
<220> FEATURE:
<223> OTHER INFORMATION: Targeting domain

<400> SEQUENCE: 335
cccuggcuaa acuccaccca 20

<210> SEQ ID NO 336
<211> LENGTH: 20
<212> TYPE: RNA
<213> ORGANISM: Artificial Sequence
<220> FEATURE:
<223> OTHER INFORMATION: Targeting domain

<400> SEQUENCE: 336
ccaugggugg aguuuagcca 20

<210> SEQ ID NO 337

<211> LENGTH: 20
<212> TYPE: RNA
<213> ORGANISM: Artificial Sequence
<220> FEATURE:
<223> OTHER INFORMATION: Targeting domain

<400> SEQUENCE: 337
uagaguaucc agugaggcca 20

<210> SEQ ID NO 338
<211> LENGTH: 20
<212> TYPE: RNA
<213> ORGANISM: Artificial Sequence
<220> FEATURE:
<223> OTHER INFORMATION: Targeting domain

<400> SEQUENCE: 338
caaggcuauu ggucaaggca 20

<210> SEQ ID NO 339
<211> LENGTH: 20
<212> TYPE: RNA
<213> ORGANISM: Artificial Sequence
<220> FEATURE:
<223> OTHER INFORMATION: Targeting domain

<400> SEQUENCE: 339
cuugucaagg cuauugguca 20

<210> SEQ ID NO 340
<211> LENGTH: 20
<212> TYPE: RNA
<213> ORGANISM: Artificial Sequence
<220> FEATURE:
<223> OTHER INFORMATION: Targeting domain

<400> SEQUENCE: 340
uggucaaguu ugccuuguca 20

<210> SEQ ID NO 341
<211> LENGTH: 20
<212> TYPE: RNA
<213> ORGANISM: Artificial Sequence
<220> FEATURE:
<223> OTHER INFORMATION: Targeting domain

<400> SEQUENCE: 341
cgagugugug gaacugcuga 20

<210> SEQ ID NO 342
<211> LENGTH: 20
<212> TYPE: RNA
<213> ORGANISM: Artificial Sequence
<220> FEATURE:
<223> OTHER INFORMATION: Targeting domain

<400> SEQUENCE: 342
caggggccgg cggcuggcua 20

<210> SEQ ID NO 343
<211> LENGTH: 20
<212> TYPE: RNA
<213> ORGANISM: Artificial Sequence
<220> FEATURE:
<223> OTHER INFORMATION: Targeting domain

<400> SEQUENCE: 343
agaauaaauu agagaaaaac 20

<210> SEQ ID NO 344
<211> LENGTH: 20
<212> TYPE: RNA
<213> ORGANISM: Artificial Sequence
<220> FEATURE:
<223> OTHER INFORMATION: Targeting domain

<400> SEQUENCE: 344
ccgccggccc cuggccucac 20

<210> SEQ ID NO 345
<211> LENGTH: 20
<212> TYPE: RNA
<213> ORGANISM: Artificial Sequence
<220> FEATURE:
<223> OTHER INFORMATION: Targeting domain

<400> SEQUENCE: 345
ccuagccagc cgccggcccc 20

<210> SEQ ID NO 346
<211> LENGTH: 20
<212> TYPE: RNA
<213> ORGANISM: Artificial Sequence
<220> FEATURE:
<223> OTHER INFORMATION: Targeting domain

<400> SEQUENCE: 346
uaucugucug aaacgguccc 20

<210> SEQ ID NO 347
<211> LENGTH: 20
<212> TYPE: RNA
<213> ORGANISM: Artificial Sequence
<220> FEATURE:
<223> OTHER INFORMATION: Targeting domain

<400> SEQUENCE: 347
cccaugggug gaguuuagcc 20

<210> SEQ ID NO 348
<211> LENGTH: 20
<212> TYPE: RNA
<213> ORGANISM: Artificial Sequence
<220> FEATURE:
<223> OTHER INFORMATION: Targeting domain

<400> SEQUENCE: 348
uuagaguauc cagugaggcc 20

<210> SEQ ID NO 349
<211> LENGTH: 20
<212> TYPE: RNA
<213> ORGANISM: Artificial Sequence
<220> FEATURE:
<223> OTHER INFORMATION: Targeting domain

<400> SEQUENCE: 349
acggcugaca aaagaagucc 20

<210> SEQ ID NO 350
<211> LENGTH: 20
<212> TYPE: RNA

<213> ORGANISM: Artificial Sequence
<220> FEATURE:
<223> OTHER INFORMATION: Targeting domain

<400> SEQUENCE: 350
cuucaucccu agccagccgc 20

<210> SEQ ID NO 351
<211> LENGTH: 20
<212> TYPE: RNA
<213> ORGANISM: Artificial Sequence
<220> FEATURE:
<223> OTHER INFORMATION: Targeting domain

<400> SEQUENCE: 351
ugaggccagg ggccggcggc 20

<210> SEQ ID NO 352
<211> LENGTH: 20
<212> TYPE: RNA
<213> ORGANISM: Artificial Sequence
<220> FEATURE:
<223> OTHER INFORMATION: Targeting domain

<400> SEQUENCE: 352
uauccaguga ggccaggggc 20

<210> SEQ ID NO 353
<211> LENGTH: 20
<212> TYPE: RNA
<213> ORGANISM: Artificial Sequence
<220> FEATURE:
<223> OTHER INFORMATION: Targeting domain

<400> SEQUENCE: 353
caguuccaca cacucgcuuc 20

<210> SEQ ID NO 354
<211> LENGTH: 20
<212> TYPE: RNA
<213> ORGANISM: Artificial Sequence
<220> FEATURE:
<223> OTHER INFORMATION: Targeting domain

<400> SEQUENCE: 354
auugagauag uguggggaag 20

<210> SEQ ID NO 355
<211> LENGTH: 20
<212> TYPE: RNA
<213> ORGANISM: Artificial Sequence
<220> FEATURE:
<223> OTHER INFORMATION: Targeting domain

<400> SEQUENCE: 355
agaguaucca gugaggccag 20

<210> SEQ ID NO 356
<211> LENGTH: 20
<212> TYPE: RNA
<213> ORGANISM: Artificial Sequence
<220> FEATURE:
<223> OTHER INFORMATION: Targeting domain

<400> SEQUENCE: 356
ccagugaggc caggggccgg 20

<210> SEQ ID NO 357
<211> LENGTH: 20
<212> TYPE: RNA
<213> ORGANISM: Artificial Sequence
<220> FEATURE:
<223> OTHER INFORMATION: Targeting domain

<400> SEQUENCE: 357
aaggcuggcc aacccauggg 20

<210> SEQ ID NO 358
<211> LENGTH: 20
<212> TYPE: RNA
<213> ORGANISM: Artificial Sequence
<220> FEATURE:
<223> OTHER INFORMATION: Targeting domain

<400> SEQUENCE: 358
acucgcuucu ggaacgucug 20

<210> SEQ ID NO 359
<211> LENGTH: 20
<212> TYPE: RNA
<213> ORGANISM: Artificial Sequence
<220> FEATURE:
<223> OTHER INFORMATION: Targeting domain

<400> SEQUENCE: 359
uagucuuaga guauccagug 20

<210> SEQ ID NO 360
<211> LENGTH: 20
<212> TYPE: RNA
<213> ORGANISM: Artificial Sequence
<220> FEATURE:
<223> OTHER INFORMATION: Targeting domain

<400> SEQUENCE: 360
auauuugcau ugagauagug 20

<210> SEQ ID NO 361
<211> LENGTH: 20
<212> TYPE: RNA
<213> ORGANISM: Artificial Sequence
<220> FEATURE:
<223> OTHER INFORMATION: Targeting domain

<400> SEQUENCE: 361
acguuccaga agcgagugug 20

<210> SEQ ID NO 362
<211> LENGTH: 20
<212> TYPE: RNA
<213> ORGANISM: Artificial Sequence
<220> FEATURE:
<223> OTHER INFORMATION: Targeting domain

<400> SEQUENCE: 362
auuugcauug agauagugug 20

<210> SEQ ID NO 363
<211> LENGTH: 20
<212> TYPE: RNA
<213> ORGANISM: Artificial Sequence
<220> FEATURE:

<223> OTHER INFORMATION: Targeting domain

<400> SEQUENCE: 363
ccuggcuaaa cuccacccau 20

<210> SEQ ID NO 364
<211> LENGTH: 20
<212> TYPE: RNA
<213> ORGANISM: Artificial Sequence
<220> FEATURE:
<223> OTHER INFORMATION: Targeting domain

<400> SEQUENCE: 364
acuggauacu cuaagacuau 20

<210> SEQ ID NO 365
<211> LENGTH: 20
<212> TYPE: RNA
<213> ORGANISM: Artificial Sequence
<220> FEATURE:
<223> OTHER INFORMATION: Targeting domain

<400> SEQUENCE: 365
ccaggggccg gcggcuggcu 20

<210> SEQ ID NO 366
<211> LENGTH: 20
<212> TYPE: RNA
<213> ORGANISM: Artificial Sequence
<220> FEATURE:
<223> OTHER INFORMATION: Targeting domain

<400> SEQUENCE: 366
uauuugcauu gagauagugu 20

<210> SEQ ID NO 367
<211> LENGTH: 19
<212> TYPE: RNA
<213> ORGANISM: Artificial Sequence
<220> FEATURE:
<223> OTHER INFORMATION: Targeting domain

<400> SEQUENCE: 367
guuuccuucu cccaucaua 19

<210> SEQ ID NO 368
<211> LENGTH: 23
<212> TYPE: RNA
<213> ORGANISM: Artificial Sequence
<220> FEATURE:
<223> OTHER INFORMATION: Targeting domain

<400> SEQUENCE: 368
gcuaguuucc uucucccauc aua 23

<210> SEQ ID NO 369
<211> LENGTH: 19
<212> TYPE: RNA
<213> ORGANISM: Artificial Sequence
<220> FEATURE:
<223> OTHER INFORMATION: Targeting domain

<400> SEQUENCE: 369
gaauaaauua gagaaaaac 19

<210> SEQ ID NO 370
<211> LENGTH: 22
<212> TYPE: RNA
<213> ORGANISM: Artificial Sequence
<220> FEATURE:
<223> OTHER INFORMATION: Targeting domain

<400> SEQUENCE: 370
gaagaauaaa uuagagaaaa ac 22

<210> SEQ ID NO 371
<211> LENGTH: 23
<212> TYPE: RNA
<213> ORGANISM: Artificial Sequence
<220> FEATURE:
<223> OTHER INFORMATION: Targeting domain

<400> SEQUENCE: 371
ggaagaauaa auuagagaaa aac 23

<210> SEQ ID NO 372
<211> LENGTH: 24
<212> TYPE: RNA
<213> ORGANISM: Artificial Sequence
<220> FEATURE:
<223> OTHER INFORMATION: Targeting domain

<400> SEQUENCE: 372
gggaagaaua aauuagagaa aaac 24

<210> SEQ ID NO 373
<211> LENGTH: 20
<212> TYPE: RNA
<213> ORGANISM: Artificial Sequence
<220> FEATURE:
<223> OTHER INFORMATION: Targeting domain

<400> SEQUENCE: 373
gaaggaaacu agcuaaaggg 20

<210> SEQ ID NO 374
<211> LENGTH: 22
<212> TYPE: RNA
<213> ORGANISM: Artificial Sequence
<220> FEATURE:
<223> OTHER INFORMATION: Targeting domain

<400> SEQUENCE: 374
gagaaggaaa cuagcuaaag gg 22

<210> SEQ ID NO 375
<211> LENGTH: 23
<212> TYPE: RNA
<213> ORGANISM: Artificial Sequence
<220> FEATURE:
<223> OTHER INFORMATION: Targeting domain

<400> SEQUENCE: 375
ggagaaggaa acuagcuaaa ggg 23

<210> SEQ ID NO 376
<211> LENGTH: 24
<212> TYPE: RNA
<213> ORGANISM: Artificial Sequence
<220> FEATURE:
<223> OTHER INFORMATION: Targeting domain

<400> SEQUENCE: 376
gggagaagga aacuagcuaa aggg 24

<210> SEQ ID NO 377
<211> LENGTH: 18
<212> TYPE: RNA
<213> ORGANISM: Artificial Sequence
<220> FEATURE:
<223> OTHER INFORMATION: Targeting domain

<400> SEQUENCE: 377
uuuccuucuc ccaucaua 18

<210> SEQ ID NO 378
<211> LENGTH: 20
<212> TYPE: RNA
<213> ORGANISM: Artificial Sequence
<220> FEATURE:
<223> OTHER INFORMATION: Targeting domain

<400> SEQUENCE: 378
aguuuccuuc ucccaucaua 20

<210> SEQ ID NO 379
<211> LENGTH: 21
<212> TYPE: RNA
<213> ORGANISM: Artificial Sequence
<220> FEATURE:
<223> OTHER INFORMATION: Targeting domain

<400> SEQUENCE: 379
uaguuuccuu cucccaucau a 21

<210> SEQ ID NO 380
<211> LENGTH: 22
<212> TYPE: RNA
<213> ORGANISM: Artificial Sequence
<220> FEATURE:
<223> OTHER INFORMATION: Targeting domain

<400> SEQUENCE: 380
cuaguuuccu ucucccauca ua 22

<210> SEQ ID NO 381
<211> LENGTH: 24
<212> TYPE: RNA
<213> ORGANISM: Artificial Sequence
<220> FEATURE:
<223> OTHER INFORMATION: Targeting domain

<400> SEQUENCE: 381
agcuaguuuc cuucucccau caua 24

<210> SEQ ID NO 382
<211> LENGTH: 18
<212> TYPE: RNA
<213> ORGANISM: Artificial Sequence
<220> FEATURE:
<223> OTHER INFORMATION: Targeting domain

<400> SEQUENCE: 382
agagaaaaac uggaauga 18

<210> SEQ ID NO 383
<211> LENGTH: 19

<212> TYPE: RNA
<213> ORGANISM: Artificial Sequence
<220> FEATURE:
<223> OTHER INFORMATION: Targeting domain

<400> SEQUENCE: 383
uagagaaaaa cuggaauga 19

<210> SEQ ID NO 384
<211> LENGTH: 20
<212> TYPE: RNA
<213> ORGANISM: Artificial Sequence
<220> FEATURE:
<223> OTHER INFORMATION: Targeting domain

<400> SEQUENCE: 384
uuagagaaaa acuggaauga 20

<210> SEQ ID NO 385
<211> LENGTH: 21
<212> TYPE: RNA
<213> ORGANISM: Artificial Sequence
<220> FEATURE:
<223> OTHER INFORMATION: Targeting domain

<400> SEQUENCE: 385
auuagagaaa aacuggaaug a 21

<210> SEQ ID NO 386
<211> LENGTH: 22
<212> TYPE: RNA
<213> ORGANISM: Artificial Sequence
<220> FEATURE:
<223> OTHER INFORMATION: Targeting domain

<400> SEQUENCE: 386
aauuagagaa aaacuggaau ga 22

<210> SEQ ID NO 387
<211> LENGTH: 23
<212> TYPE: RNA
<213> ORGANISM: Artificial Sequence
<220> FEATURE:
<223> OTHER INFORMATION: Targeting domain

<400> SEQUENCE: 387
aaauuagaga aaaacuggaa uga 23

<210> SEQ ID NO 388
<211> LENGTH: 24
<212> TYPE: RNA
<213> ORGANISM: Artificial Sequence
<220> FEATURE:
<223> OTHER INFORMATION: Targeting domain

<400> SEQUENCE: 388
uaaauuagag aaaaacugga auga 24

<210> SEQ ID NO 389
<211> LENGTH: 18
<212> TYPE: RNA
<213> ORGANISM: Artificial Sequence
<220> FEATURE:
<223> OTHER INFORMATION: Targeting domain

<400> SEQUENCE: 389

-continued aauaaauuag agaaaaac 18

<210> SEQ ID NO 390
<211> LENGTH: 21
<212> TYPE: RNA
<213> ORGANISM: Artificial Sequence
<220> FEATURE:
<223> OTHER INFORMATION: Targeting domain

<400> SEQUENCE: 390
aagaauaaau uagagaaaaa c 21

<210> SEQ ID NO 391
<211> LENGTH: 18
<212> TYPE: RNA
<213> ORGANISM: Artificial Sequence
<220> FEATURE:
<223> OTHER INFORMATION: Targeting domain

<400> SEQUENCE: 391
aggaaacuag cuaaaggg 18

<210> SEQ ID NO 392
<211> LENGTH: 19
<212> TYPE: RNA
<213> ORGANISM: Artificial Sequence
<220> FEATURE:
<223> OTHER INFORMATION: Targeting domain

<400> SEQUENCE: 392
aaggaaacua gcuaaaggg 19

<210> SEQ ID NO 393
<211> LENGTH: 21
<212> TYPE: RNA
<213> ORGANISM: Artificial Sequence
<220> FEATURE:
<223> OTHER INFORMATION: Targeting domain

<400> SEQUENCE: 393
agaaggaaac uagcuaaagg g 21

<210> SEQ ID NO 394
<211> LENGTH: 18
<212> TYPE: RNA
<213> ORGANISM: Artificial Sequence
<220> FEATURE:
<223> OTHER INFORMATION: Targeting domain

<400> SEQUENCE: 394
uggggaaggg gcccccaa 18

<210> SEQ ID NO 395
<211> LENGTH: 19
<212> TYPE: RNA
<213> ORGANISM: Artificial Sequence
<220> FEATURE:
<223> OTHER INFORMATION: Targeting domain

<400> SEQUENCE: 395
guggggaagg ggcccccaa 19

<210> SEQ ID NO 396
<211> LENGTH: 20
<212> TYPE: RNA
<213> ORGANISM: Artificial Sequence
<220> FEATURE:
<223> OTHER INFORMATION: Targeting domain

<400> SEQUENCE: 396 ugugggggaag gggccccccaa 20

<210> SEQ ID NO 397
<211> LENGTH: 21
<212> TYPE: RNA
<213> ORGANISM: Artificial Sequence
<220> FEATURE:
<223> OTHER INFORMATION: Targeting domain

<400> SEQUENCE: 397
guguggggaa ggggccccca a 21

<210> SEQ ID NO 398
<211> LENGTH: 22
<212> TYPE: RNA
<213> ORGANISM: Artificial Sequence
<220> FEATURE:
<223> OTHER INFORMATION: Targeting domain

<400> SEQUENCE: 398
agugugggga aggggccccc aa 22

<210> SEQ ID NO 399
<211> LENGTH: 23
<212> TYPE: RNA
<213> ORGANISM: Artificial Sequence
<220> FEATURE:
<223> OTHER INFORMATION: Targeting domain

<400> SEQUENCE: 399
uagugugggg aaggggcccc caa 23

<210> SEQ ID NO 400
<211> LENGTH: 24
<212> TYPE: RNA
<213> ORGANISM: Artificial Sequence
<220> FEATURE:
<223> OTHER INFORMATION: Targeting domain

<400> SEQUENCE: 400 auagugugggg gaaggggccc ccaa 24

<210> SEQ ID NO 401
<211> LENGTH: 18
<212> TYPE: RNA
<213> ORGANISM: Artificial Sequence
<220> FEATURE:
<223> OTHER INFORMATION: Targeting domain

<400> SEQUENCE: 401
accucagacg uuccagaa 18

<210> SEQ ID NO 402
<211> LENGTH: 19
<212> TYPE: RNA
<213> ORGANISM: Artificial Sequence
<220> FEATURE:
<223> OTHER INFORMATION: Targeting domain

<400> SEQUENCE: 402
aaccucagac guuccagaa 19

<210> SEQ ID NO 403
<211> LENGTH: 20
<212> TYPE: RNA
<213> ORGANISM: Artificial Sequence
<220> FEATURE:
<223> OTHER INFORMATION: Targeting domain

<400> SEQUENCE: 403
uaaccucaga cguuccagaa 20

<210> SEQ ID NO 404
<211> LENGTH: 21
<212> TYPE: RNA
<213> ORGANISM: Artificial Sequence
<220> FEATURE:
<223> OTHER INFORMATION: Targeting domain

<400> SEQUENCE: 404
auaaccucag acguuccaga a 21

<210> SEQ ID NO 405
<211> LENGTH: 22
<212> TYPE: RNA
<213> ORGANISM: Artificial Sequence
<220> FEATURE:
<223> OTHER INFORMATION: Targeting domain

<400> SEQUENCE: 405
gauaaccuca gacguuccag aa 22

<210> SEQ ID NO 406
<211> LENGTH: 23
<212> TYPE: RNA
<213> ORGANISM: Artificial Sequence
<220> FEATURE:
<223> OTHER INFORMATION: Targeting domain

<400> SEQUENCE: 406
ugauaaccuc agacguucca gaa 23

<210> SEQ ID NO 407
<211> LENGTH: 24
<212> TYPE: RNA
<213> ORGANISM: Artificial Sequence
<220> FEATURE:
<223> OTHER INFORMATION: Targeting domain

<400> SEQUENCE: 407
uugauaaccu cagacguucc agaa 24

<210> SEQ ID NO 408
<211> LENGTH: 18
<212> TYPE: RNA
<213> ORGANISM: Artificial Sequence
<220> FEATURE:
<223> OTHER INFORMATION: Targeting domain

<400> SEQUENCE: 408
cgccggcccc uggccuca 18

<210> SEQ ID NO 409
<211> LENGTH: 19
<212> TYPE: RNA
<213> ORGANISM: Artificial Sequence
<220> FEATURE:
<223> OTHER INFORMATION: Targeting domain

<400> SEQUENCE: 409
ccgccggccc cuggccuca 19

<210> SEQ ID NO 410
<211> LENGTH: 20
<212> TYPE: RNA
<213> ORGANISM: Artificial Sequence
<220> FEATURE:
<223> OTHER INFORMATION: Targeting domain

<400> SEQUENCE: 410
gccgccggcc ccuggccuca 20

<210> SEQ ID NO 411
<211> LENGTH: 21
<212> TYPE: RNA
<213> ORGANISM: Artificial Sequence
<220> FEATURE:
<223> OTHER INFORMATION: Targeting domain

<400> SEQUENCE: 411
agccgccggc cccuggccuc a 21

<210> SEQ ID NO 412
<211> LENGTH: 22
<212> TYPE: RNA
<213> ORGANISM: Artificial Sequence
<220> FEATURE:
<223> OTHER INFORMATION: Targeting domain

<400> SEQUENCE: 412
cagccgccgg ccccuggccu ca 22

<210> SEQ ID NO 413
<211> LENGTH: 23
<212> TYPE: RNA
<213> ORGANISM: Artificial Sequence
<220> FEATURE:
<223> OTHER INFORMATION: Targeting domain

<400> SEQUENCE: 413
ccagccgccg gccccuggcc uca 23

<210> SEQ ID NO 414
<211> LENGTH: 24
<212> TYPE: RNA
<213> ORGANISM: Artificial Sequence
<220> FEATURE:
<223> OTHER INFORMATION: Targeting domain

<400> SEQUENCE: 414
gccagccgcc ggccccuggc cuca 24

<210> SEQ ID NO 415
<211> LENGTH: 18
<212> TYPE: RNA
<213> ORGANISM: Artificial Sequence
<220> FEATURE:
<223> OTHER INFORMATION: Targeting domain

<400> SEQUENCE: 415
ggcaaggcug gccaaccc 18

<210> SEQ ID NO 416

<211> LENGTH: 19
<212> TYPE: RNA
<213> ORGANISM: Artificial Sequence
<220> FEATURE:
<223> OTHER INFORMATION: Targeting domain

<400> SEQUENCE: 416
aggcaaggcu ggccaaccc 19

<210> SEQ ID NO 417
<211> LENGTH: 20
<212> TYPE: RNA
<213> ORGANISM: Artificial Sequence
<220> FEATURE:
<223> OTHER INFORMATION: Targeting domain

<400> SEQUENCE: 417
aaggcaaggc uggccaaccc 20

<210> SEQ ID NO 418
<211> LENGTH: 21
<212> TYPE: RNA
<213> ORGANISM: Artificial Sequence
<220> FEATURE:
<223> OTHER INFORMATION: Targeting domain

<400> SEQUENCE: 418
caaggcaagg cuggccaacc c 21

<210> SEQ ID NO 419
<211> LENGTH: 22
<212> TYPE: RNA
<213> ORGANISM: Artificial Sequence
<220> FEATURE:
<223> OTHER INFORMATION: Targeting domain

<400> SEQUENCE: 419
ucaaggcaag gcuggccaac cc 22

<210> SEQ ID NO 420
<211> LENGTH: 23
<212> TYPE: RNA
<213> ORGANISM: Artificial Sequence
<220> FEATURE:
<223> OTHER INFORMATION: Targeting domain

<400> SEQUENCE: 420
gucaaggcaa ggcuggccaa ccc 23

<210> SEQ ID NO 421
<211> LENGTH: 24
<212> TYPE: RNA
<213> ORGANISM: Artificial Sequence
<220> FEATURE:
<223> OTHER INFORMATION: Targeting domain

<400> SEQUENCE: 421
ggucaaggca aggcuggcca accc 24

<210> SEQ ID NO 422
<211> LENGTH: 18
<212> TYPE: RNA
<213> ORGANISM: Artificial Sequence
<220> FEATURE:
<223> OTHER INFORMATION: Targeting domain

<400> SEQUENCE: 422
ggcuggccaa cccauggg 18

<210> SEQ ID NO 423
<211> LENGTH: 19
<212> TYPE: RNA
<213> ORGANISM: Artificial Sequence
<220> FEATURE:
<223> OTHER INFORMATION: Targeting domain

<400> SEQUENCE: 423
aggcuggcca acccauggg 19

<210> SEQ ID NO 424
<211> LENGTH: 21
<212> TYPE: RNA
<213> ORGANISM: Artificial Sequence
<220> FEATURE:
<223> OTHER INFORMATION: Targeting domain

<400> SEQUENCE: 424
caaggcuggc caacccaugg g 21

<210> SEQ ID NO 425
<211> LENGTH: 22
<212> TYPE: RNA
<213> ORGANISM: Artificial Sequence
<220> FEATURE:
<223> OTHER INFORMATION: Targeting domain

<400> SEQUENCE: 425
gcaaggcugg ccaacccaug gg 22

<210> SEQ ID NO 426
<211> LENGTH: 23
<212> TYPE: RNA
<213> ORGANISM: Artificial Sequence
<220> FEATURE:
<223> OTHER INFORMATION: Targeting domain

<400> SEQUENCE: 426
ggcaaggcug gccaacccau ggg 23

<210> SEQ ID NO 427
<211> LENGTH: 24
<212> TYPE: RNA
<213> ORGANISM: Artificial Sequence
<220> FEATURE:
<223> OTHER INFORMATION: Targeting domain

<400> SEQUENCE: 427
aggcaaggcu ggccaaccca uggg 24

<210> SEQ ID NO 428
<211> LENGTH: 18
<212> TYPE: RNA
<213> ORGANISM: Artificial Sequence
<220> FEATURE:
<223> OTHER INFORMATION: Targeting domain

<400> SEQUENCE: 428
gagugugugg aacugcug 18

<210> SEQ ID NO 429
<211> LENGTH: 19
<212> TYPE: RNA

<213> ORGANISM: Artificial Sequence
<220> FEATURE:
<223> OTHER INFORMATION: Targeting domain

<400> SEQUENCE: 429
cgagugugug gaacugcug 19

<210> SEQ ID NO 430
<211> LENGTH: 20
<212> TYPE: RNA
<213> ORGANISM: Artificial Sequence
<220> FEATURE:
<223> OTHER INFORMATION: Targeting domain

<400> SEQUENCE: 430
gcgagugugu ggaacugcug 20

<210> SEQ ID NO 431
<211> LENGTH: 21
<212> TYPE: RNA
<213> ORGANISM: Artificial Sequence
<220> FEATURE:
<223> OTHER INFORMATION: Targeting domain

<400> SEQUENCE: 431
agcgagugug uggaacugcu g 21

<210> SEQ ID NO 432
<211> LENGTH: 22
<212> TYPE: RNA
<213> ORGANISM: Artificial Sequence
<220> FEATURE:
<223> OTHER INFORMATION: Targeting domain

<400> SEQUENCE: 432
aagcgagugu guggaacugc ug 22

<210> SEQ ID NO 433
<211> LENGTH: 23
<212> TYPE: RNA
<213> ORGANISM: Artificial Sequence
<220> FEATURE:
<223> OTHER INFORMATION: Targeting domain

<400> SEQUENCE: 433
gaagcgagug uguggaacug cug 23

<210> SEQ ID NO 434
<211> LENGTH: 24
<212> TYPE: RNA
<213> ORGANISM: Artificial Sequence
<220> FEATURE:
<223> OTHER INFORMATION: Targeting domain

<400> SEQUENCE: 434
agaagcgagu guguggaacu gcug 24

<210> SEQ ID NO 435
<211> LENGTH: 18
<212> TYPE: RNA
<213> ORGANISM: Artificial Sequence
<220> FEATURE:
<223> OTHER INFORMATION: Targeting domain

<400> SEQUENCE: 435
ccuggcuaaa cuccaccc 18

<210> SEQ ID NO 436
<211> LENGTH: 19
<212> TYPE: RNA
<213> ORGANISM: Artificial Sequence
<220> FEATURE:
<223> OTHER INFORMATION: Targeting domain

<400> SEQUENCE: 436
cccuggcuaa acuccaccc 19

<210> SEQ ID NO 437
<211> LENGTH: 20
<212> TYPE: RNA
<213> ORGANISM: Artificial Sequence
<220> FEATURE:
<223> OTHER INFORMATION: Targeting domain

<400> SEQUENCE: 437
ucccuggcua aacuccaccc 20

<210> SEQ ID NO 438
<211> LENGTH: 21
<212> TYPE: RNA
<213> ORGANISM: Artificial Sequence
<220> FEATURE:
<223> OTHER INFORMATION: Targeting domain

<400> SEQUENCE: 438
gucccuggcu aaacuccacc c 21

<210> SEQ ID NO 439
<211> LENGTH: 22
<212> TYPE: RNA
<213> ORGANISM: Artificial Sequence
<220> FEATURE:
<223> OTHER INFORMATION: Targeting domain

<400> SEQUENCE: 439
ggucccuggc uaaacuccac cc 22

<210> SEQ ID NO 440
<211> LENGTH: 23
<212> TYPE: RNA
<213> ORGANISM: Artificial Sequence
<220> FEATURE:
<223> OTHER INFORMATION: Targeting domain

<400> SEQUENCE: 440
cggucccugg cuaaacucca ccc 23

<210> SEQ ID NO 441
<211> LENGTH: 24
<212> TYPE: RNA
<213> ORGANISM: Artificial Sequence
<220> FEATURE:
<223> OTHER INFORMATION: Targeting domain

<400> SEQUENCE: 441
acggucccug gcuaaacucc accc 24

<210> SEQ ID NO 442
<211> LENGTH: 18
<212> TYPE: RNA
<213> ORGANISM: Artificial Sequence
<220> FEATURE:

<223> OTHER INFORMATION: Targeting domain

<400> SEQUENCE: 442
ggcggcuggc uagggaug 18

<210> SEQ ID NO 443
<211> LENGTH: 19
<212> TYPE: RNA
<213> ORGANISM: Artificial Sequence
<220> FEATURE:
<223> OTHER INFORMATION: Targeting domain

<400> SEQUENCE: 443
cggcggcugg cuagggaug 19

<210> SEQ ID NO 444
<211> LENGTH: 20
<212> TYPE: RNA
<213> ORGANISM: Artificial Sequence
<220> FEATURE:
<223> OTHER INFORMATION: Targeting domain

<400> SEQUENCE: 444
ccggcggcug gcuagggaug 20

<210> SEQ ID NO 445
<211> LENGTH: 21
<212> TYPE: RNA
<213> ORGANISM: Artificial Sequence
<220> FEATURE:
<223> OTHER INFORMATION: Targeting domain

<400> SEQUENCE: 445
gccggcggcu ggcuagggau g 21

<210> SEQ ID NO 446
<211> LENGTH: 22
<212> TYPE: RNA
<213> ORGANISM: Artificial Sequence
<220> FEATURE:
<223> OTHER INFORMATION: Targeting domain

<400> SEQUENCE: 446
ggccggcggc uggcuaggga ug 22

<210> SEQ ID NO 447
<211> LENGTH: 23
<212> TYPE: RNA
<213> ORGANISM: Artificial Sequence
<220> FEATURE:
<223> OTHER INFORMATION: Targeting domain

<400> SEQUENCE: 447
gggccggcgg cuggcuaggg aug 23

<210> SEQ ID NO 448
<211> LENGTH: 24
<212> TYPE: RNA
<213> ORGANISM: Artificial Sequence
<220> FEATURE:
<223> OTHER INFORMATION: Targeting domain

<400> SEQUENCE: 448
ggggccggcg gcuggcuagg gaug 24

<210> SEQ ID NO 449
<211> LENGTH: 18
<212> TYPE: RNA
<213> ORGANISM: Artificial Sequence
<220> FEATURE:
<223> OTHER INFORMATION: Targeting domain

<400> SEQUENCE: 449
aggggccggc ggcuggcu 18

<210> SEQ ID NO 450
<211> LENGTH: 19
<212> TYPE: RNA
<213> ORGANISM: Artificial Sequence
<220> FEATURE:
<223> OTHER INFORMATION: Targeting domain

<400> SEQUENCE: 450
caggggccgg cggcuggcu 19

<210> SEQ ID NO 451
<211> LENGTH: 21
<212> TYPE: RNA
<213> ORGANISM: Artificial Sequence
<220> FEATURE:
<223> OTHER INFORMATION: Targeting domain

<400> SEQUENCE: 451
gccaggggcc ggcggcuggc u 21

<210> SEQ ID NO 452
<211> LENGTH: 22
<212> TYPE: RNA
<213> ORGANISM: Artificial Sequence
<220> FEATURE:
<223> OTHER INFORMATION: Targeting domain

<400> SEQUENCE: 452
ggccaggggc cggcggcugg cu 22

<210> SEQ ID NO 453
<211> LENGTH: 23
<212> TYPE: RNA
<213> ORGANISM: Artificial Sequence
<220> FEATURE:
<223> OTHER INFORMATION: Targeting domain

<400> SEQUENCE: 453
aggccagggg ccggcggcug gcu 23

<210> SEQ ID NO 454
<211> LENGTH: 24
<212> TYPE: RNA
<213> ORGANISM: Artificial Sequence
<220> FEATURE:
<223> OTHER INFORMATION: Targeting domain

<400> SEQUENCE: 454
gaggccaggg gccggcggcu ggcu 24

<210> SEQ ID NO 455
<211> LENGTH: 18
<212> TYPE: RNA
<213> ORGANISM: Artificial Sequence
<220> FEATURE:
<223> OTHER INFORMATION: Targeting domain

<400> SEQUENCE: 455
aaacuugacc aauagucu 18

<210> SEQ ID NO 456
<211> LENGTH: 19
<212> TYPE: RNA
<213> ORGANISM: Artificial Sequence
<220> FEATURE:
<223> OTHER INFORMATION: Targeting domain

<400> SEQUENCE: 456
caaacuugac caauagucu 19

<210> SEQ ID NO 457
<211> LENGTH: 20
<212> TYPE: RNA
<213> ORGANISM: Artificial Sequence
<220> FEATURE:
<223> OTHER INFORMATION: Targeting domain

<400> SEQUENCE: 457
gcaaacuuga ccaauagucu 20

<210> SEQ ID NO 458
<211> LENGTH: 21
<212> TYPE: RNA
<213> ORGANISM: Artificial Sequence
<220> FEATURE:
<223> OTHER INFORMATION: Targeting domain

<400> SEQUENCE: 458
ggcaaacuug accaauaguc u 21

<210> SEQ ID NO 459
<211> LENGTH: 22
<212> TYPE: RNA
<213> ORGANISM: Artificial Sequence
<220> FEATURE:
<223> OTHER INFORMATION: Targeting domain

<400> SEQUENCE: 459
aggcaaacuu gaccaauagu cu 22

<210> SEQ ID NO 460
<211> LENGTH: 23
<212> TYPE: RNA
<213> ORGANISM: Artificial Sequence
<220> FEATURE:
<223> OTHER INFORMATION: Targeting domain

<400> SEQUENCE: 460
aaggcaaacu ugaccaauag ucu 23

<210> SEQ ID NO 461
<211> LENGTH: 24
<212> TYPE: RNA
<213> ORGANISM: Artificial Sequence
<220> FEATURE:
<223> OTHER INFORMATION: Targeting domain

<400> SEQUENCE: 461
caaggcaaac uugaccaaua gucu 24

<210> SEQ ID NO 462
<211> LENGTH: 18

<212> TYPE: RNA
<213> ORGANISM: Artificial Sequence
<220> FEATURE:
<223> OTHER INFORMATION: Targeting domain

<400> SEQUENCE: 462
uucagacaga uauuugca 18

<210> SEQ ID NO 463
<211> LENGTH: 19
<212> TYPE: RNA
<213> ORGANISM: Artificial Sequence
<220> FEATURE:
<223> OTHER INFORMATION: Targeting domain

<400> SEQUENCE: 463
uuucagacag auauuugca 19

<210> SEQ ID NO 464
<211> LENGTH: 20
<212> TYPE: RNA
<213> ORGANISM: Artificial Sequence
<220> FEATURE:
<223> OTHER INFORMATION: Targeting domain

<400> SEQUENCE: 464
guuucagaca gauauuugca 20

<210> SEQ ID NO 465
<211> LENGTH: 21
<212> TYPE: RNA
<213> ORGANISM: Artificial Sequence
<220> FEATURE:
<223> OTHER INFORMATION: Targeting domain

<400> SEQUENCE: 465
cguuucagac agauauuugc a 21

<210> SEQ ID NO 466
<211> LENGTH: 22
<212> TYPE: RNA
<213> ORGANISM: Artificial Sequence
<220> FEATURE:
<223> OTHER INFORMATION: Targeting domain

<400> SEQUENCE: 466
ccguuucaga cagauauuug ca 22

<210> SEQ ID NO 467
<211> LENGTH: 23
<212> TYPE: RNA
<213> ORGANISM: Artificial Sequence
<220> FEATURE:
<223> OTHER INFORMATION: Targeting domain

<400> SEQUENCE: 467
accguuucag acagauauuu gca 23

<210> SEQ ID NO 468
<211> LENGTH: 24
<212> TYPE: RNA
<213> ORGANISM: Artificial Sequence
<220> FEATURE:
<223> OTHER INFORMATION: Targeting domain

<400> SEQUENCE: 468
gaccguuuca gacagauauu ugca 24

<210> SEQ ID NO 469
<211> LENGTH: 18
<212> TYPE: RNA
<213> ORGANISM: Artificial Sequence
<220> FEATURE:
<223> OTHER INFORMATION: Targeting domain

<400> SEQUENCE: 469
aguuuccuuc ucccauca 18

<210> SEQ ID NO 470
<211> LENGTH: 19
<212> TYPE: RNA
<213> ORGANISM: Artificial Sequence
<220> FEATURE:
<223> OTHER INFORMATION: Targeting domain

<400> SEQUENCE: 470
uaguuuccuu cucccauca 19

<210> SEQ ID NO 471
<211> LENGTH: 20
<212> TYPE: RNA
<213> ORGANISM: Artificial Sequence
<220> FEATURE:
<223> OTHER INFORMATION: Targeting domain

<400> SEQUENCE: 471
cuaguuuccu ucucccauca 20

<210> SEQ ID NO 472
<211> LENGTH: 21
<212> TYPE: RNA
<213> ORGANISM: Artificial Sequence
<220> FEATURE:
<223> OTHER INFORMATION: Targeting domain

<400> SEQUENCE: 472
gcuaguuucc uucucccauc a 21

<210> SEQ ID NO 473
<211> LENGTH: 22
<212> TYPE: RNA
<213> ORGANISM: Artificial Sequence
<220> FEATURE:
<223> OTHER INFORMATION: Targeting domain

<400> SEQUENCE: 473
agcuaguuuc cuucucccau ca 22

<210> SEQ ID NO 474
<211> LENGTH: 23
<212> TYPE: RNA
<213> ORGANISM: Artificial Sequence
<220> FEATURE:
<223> OTHER INFORMATION: Targeting domain

<400> SEQUENCE: 474
uagcuaguuu ccuucuccca uca 23

<210> SEQ ID NO 475
<211> LENGTH: 24
<212> TYPE: RNA
<213> ORGANISM: Artificial Sequence
<220> FEATURE:
<223> OTHER INFORMATION: Targeting domain

<400> SEQUENCE: 475
uuagcuaguu uccuucuccc auca 24

<210> SEQ ID NO 476
<211> LENGTH: 18
<212> TYPE: RNA
<213> ORGANISM: Artificial Sequence
<220> FEATURE:
<223> OTHER INFORMATION: Targeting domain

<400> SEQUENCE: 476
auugagauag ugugggga 18

<210> SEQ ID NO 477
<211> LENGTH: 19
<212> TYPE: RNA
<213> ORGANISM: Artificial Sequence
<220> FEATURE:
<223> OTHER INFORMATION: Targeting domain

<400> SEQUENCE: 477
cauugagaua gugugggga 19

<210> SEQ ID NO 478
<211> LENGTH: 21
<212> TYPE: RNA
<213> ORGANISM: Artificial Sequence
<220> FEATURE:
<223> OTHER INFORMATION: Targeting domain

<400> SEQUENCE: 478
ugcauugaga uagugugggg a 21

<210> SEQ ID NO 479
<211> LENGTH: 22
<212> TYPE: RNA
<213> ORGANISM: Artificial Sequence
<220> FEATURE:
<223> OTHER INFORMATION: Targeting domain

<400> SEQUENCE: 479
uugcauugag auagugugggg ga 22

<210> SEQ ID NO 480
<211> LENGTH: 23
<212> TYPE: RNA
<213> ORGANISM: Artificial Sequence
<220> FEATURE:
<223> OTHER INFORMATION: Targeting domain

<400> SEQUENCE: 480
uuugcauuga gauagugugg gga 23

<210> SEQ ID NO 481
<211> LENGTH: 24
<212> TYPE: RNA
<213> ORGANISM: Artificial Sequence
<220> FEATURE:
<223> OTHER INFORMATION: Targeting domain

<400> SEQUENCE: 481
auuugcauug agauagugug ggga 24

<210> SEQ ID NO 482
<211> LENGTH: 18
<212> TYPE: RNA
<213> ORGANISM: Artificial Sequence
<220> FEATURE:
<223> OTHER INFORMATION: Targeting domain

<400> SEQUENCE: 482
ucccaucaua gaggauac 18

<210> SEQ ID NO 483
<211> LENGTH: 19
<212> TYPE: RNA
<213> ORGANISM: Artificial Sequence
<220> FEATURE:
<223> OTHER INFORMATION: Targeting domain

<400> SEQUENCE: 483
cucccaucau agaggauac 19

<210> SEQ ID NO 484
<211> LENGTH: 20
<212> TYPE: RNA
<213> ORGANISM: Artificial Sequence
<220> FEATURE:
<223> OTHER INFORMATION: Targeting domain

<400> SEQUENCE: 484
ucucccauca uagaggauac 20

<210> SEQ ID NO 485
<211> LENGTH: 21
<212> TYPE: RNA
<213> ORGANISM: Artificial Sequence
<220> FEATURE:
<223> OTHER INFORMATION: Targeting domain

<400> SEQUENCE: 485
uucucccauc auagaggaua c 21

<210> SEQ ID NO 486
<211> LENGTH: 22
<212> TYPE: RNA
<213> ORGANISM: Artificial Sequence
<220> FEATURE:
<223> OTHER INFORMATION: Targeting domain

<400> SEQUENCE: 486
cuucucccau cauagaggau ac 22

<210> SEQ ID NO 487
<211> LENGTH: 23
<212> TYPE: RNA
<213> ORGANISM: Artificial Sequence
<220> FEATURE:
<223> OTHER INFORMATION: Targeting domain

<400> SEQUENCE: 487
ccuucuccca ucauagagga uac 23

<210> SEQ ID NO 488
<211> LENGTH: 24
<212> TYPE: RNA
<213> ORGANISM: Artificial Sequence
<220> FEATURE:
<223> OTHER INFORMATION: Targeting domain

```
<400> SEQUENCE: 488

uccuucuccc aucauagagg auac                                          24

<210> SEQ ID NO 489
<211> LENGTH: 18
<212> TYPE: RNA
<213> ORGANISM: Artificial Sequence
<220> FEATURE:
<223> OTHER INFORMATION: Targeting domain

<400> SEQUENCE: 489

ugugggaag gggccccc                                                  18

<210> SEQ ID NO 490
<211> LENGTH: 19
<212> TYPE: RNA
<213> ORGANISM: Artificial Sequence
<220> FEATURE:
<223> OTHER INFORMATION: Targeting domain

<400> SEQUENCE: 490

gugugggaa ggggccccc                                                 19

<210> SEQ ID NO 491
<211> LENGTH: 20
<212> TYPE: RNA
<213> ORGANISM: Artificial Sequence
<220> FEATURE:
<223> OTHER INFORMATION: Targeting domain

<400> SEQUENCE: 491

agugugggga aggggccccc                                               20

<210> SEQ ID NO 492
<211> LENGTH: 21
<212> TYPE: RNA
<213> ORGANISM: Artificial Sequence
<220> FEATURE:
<223> OTHER INFORMATION: Targeting domain

<400> SEQUENCE: 492

uagugugggg aaggggcccc c                                             21

<210> SEQ ID NO 493
<211> LENGTH: 22
<212> TYPE: RNA
<213> ORGANISM: Artificial Sequence
<220> FEATURE:
<223> OTHER INFORMATION: Targeting domain

<400> SEQUENCE: 493

auaguguggg gaaggggccc cc                                            22

<210> SEQ ID NO 494
<211> LENGTH: 23
<212> TYPE: RNA
<213> ORGANISM: Artificial Sequence
<220> FEATURE:
<223> OTHER INFORMATION: Targeting domain

<400> SEQUENCE: 494

gauagugugg ggaaggggcc ccc                                           23

<210> SEQ ID NO 495
```

```
<211> LENGTH: 24
<212> TYPE: RNA
<213> ORGANISM: Artificial Sequence
<220> FEATURE:
<223> OTHER INFORMATION: Targeting domain

<400> SEQUENCE: 495

agauagugug gggaaggggc cccc                                              24

<210> SEQ ID NO 496
<211> LENGTH: 18
<212> TYPE: RNA
<213> ORGANISM: Artificial Sequence
<220> FEATURE:
<223> OTHER INFORMATION: Targeting domain

<400> SEQUENCE: 496

caugggugga guuuagcc                                                     18

<210> SEQ ID NO 497
<211> LENGTH: 19
<212> TYPE: RNA
<213> ORGANISM: Artificial Sequence
<220> FEATURE:
<223> OTHER INFORMATION: Targeting domain

<400> SEQUENCE: 497

ccaugggugg aguuuagcc                                                    19

<210> SEQ ID NO 498
<211> LENGTH: 21
<212> TYPE: RNA
<213> ORGANISM: Artificial Sequence
<220> FEATURE:
<223> OTHER INFORMATION: Targeting domain

<400> SEQUENCE: 498

acccaugggu ggaguuuagc c                                                 21

<210> SEQ ID NO 499
<211> LENGTH: 22
<212> TYPE: RNA
<213> ORGANISM: Artificial Sequence
<220> FEATURE:
<223> OTHER INFORMATION: Targeting domain

<400> SEQUENCE: 499

aacccauggg uggaguuuag cc                                                22

<210> SEQ ID NO 500
<211> LENGTH: 23
<212> TYPE: RNA
<213> ORGANISM: Artificial Sequence
<220> FEATURE:
<223> OTHER INFORMATION: Targeting domain

<400> SEQUENCE: 500

caacccaugg guggaguuua gcc                                               23

<210> SEQ ID NO 501
<211> LENGTH: 24
<212> TYPE: RNA
<213> ORGANISM: Artificial Sequence
<220> FEATURE:
<223> OTHER INFORMATION: Targeting domain

<400> SEQUENCE: 501
```

ccaacccaug gguggaguuu agcc 24

<210> SEQ ID NO 502
<211> LENGTH: 18
<212> TYPE: RNA
<213> ORGANISM: Artificial Sequence
<220> FEATURE:
<223> OTHER INFORMATION: Targeting domain

<400> SEQUENCE: 502
ccaugggugg aguuuagc 18

<210> SEQ ID NO 503
<211> LENGTH: 19
<212> TYPE: RNA
<213> ORGANISM: Artificial Sequence
<220> FEATURE:
<223> OTHER INFORMATION: Targeting domain

<400> SEQUENCE: 503
cccaugggug gaguuuagc 19

<210> SEQ ID NO 504
<211> LENGTH: 20
<212> TYPE: RNA
<213> ORGANISM: Artificial Sequence
<220> FEATURE:
<223> OTHER INFORMATION: Targeting domain

<400> SEQUENCE: 504
acccaugggu ggaguuuagc 20

<210> SEQ ID NO 505
<211> LENGTH: 21
<212> TYPE: RNA
<213> ORGANISM: Artificial Sequence
<220> FEATURE:
<223> OTHER INFORMATION: Targeting domain

<400> SEQUENCE: 505
aacccauggg uggaguuuag c 21

<210> SEQ ID NO 506
<211> LENGTH: 22
<212> TYPE: RNA
<213> ORGANISM: Artificial Sequence
<220> FEATURE:
<223> OTHER INFORMATION: Targeting domain

<400> SEQUENCE: 506
caacccaugg guggaguuua gc 22

<210> SEQ ID NO 507
<211> LENGTH: 23
<212> TYPE: RNA
<213> ORGANISM: Artificial Sequence
<220> FEATURE:
<223> OTHER INFORMATION: Targeting domain

<400> SEQUENCE: 507
ccaacccaug gguggaguuu agc 23

<210> SEQ ID NO 508
<211> LENGTH: 24
<212> TYPE: RNA

<213> ORGANISM: Artificial Sequence
<220> FEATURE:
<223> OTHER INFORMATION: Targeting domain

<400> SEQUENCE: 508
gccaacccau ggguggaguu uagc 24

<210> SEQ ID NO 509
<211> LENGTH: 18
<212> TYPE: RNA
<213> ORGANISM: Artificial Sequence
<220> FEATURE:
<223> OTHER INFORMATION: Targeting domain

<400> SEQUENCE: 509
ugauaaccuc agacguuc 18

<210> SEQ ID NO 510
<211> LENGTH: 19
<212> TYPE: RNA
<213> ORGANISM: Artificial Sequence
<220> FEATURE:
<223> OTHER INFORMATION: Targeting domain

<400> SEQUENCE: 510
uugauaaccu cagacguuc 19

<210> SEQ ID NO 511
<211> LENGTH: 20
<212> TYPE: RNA
<213> ORGANISM: Artificial Sequence
<220> FEATURE:
<223> OTHER INFORMATION: Targeting domain

<400> SEQUENCE: 511
auugauaacc ucagacguuc 20

<210> SEQ ID NO 512
<211> LENGTH: 21
<212> TYPE: RNA
<213> ORGANISM: Artificial Sequence
<220> FEATURE:
<223> OTHER INFORMATION: Targeting domain

<400> SEQUENCE: 512
uauugauaac cucagacguu c 21

<210> SEQ ID NO 513
<211> LENGTH: 22
<212> TYPE: RNA
<213> ORGANISM: Artificial Sequence
<220> FEATURE:
<223> OTHER INFORMATION: Targeting domain

<400> SEQUENCE: 513
uuauugauaa ccucagacgu uc 22

<210> SEQ ID NO 514
<211> LENGTH: 23
<212> TYPE: RNA
<213> ORGANISM: Artificial Sequence
<220> FEATURE:
<223> OTHER INFORMATION: Targeting domain

<400> SEQUENCE: 514
cuuauugaua accucagacg uuc 23

<210> SEQ ID NO 515
<211> LENGTH: 24
<212> TYPE: RNA
<213> ORGANISM: Artificial Sequence
<220> FEATURE:
<223> OTHER INFORMATION: Targeting domain

<400> SEQUENCE: 515
gcuuauugau aaccucagac guuc 24

<210> SEQ ID NO 516
<211> LENGTH: 18
<212> TYPE: RNA
<213> ORGANISM: Artificial Sequence
<220> FEATURE:
<223> OTHER INFORMATION: Targeting domain

<400> SEQUENCE: 516
cauugagaua gugugggg 18

<210> SEQ ID NO 517
<211> LENGTH: 19
<212> TYPE: RNA
<213> ORGANISM: Artificial Sequence
<220> FEATURE:
<223> OTHER INFORMATION: Targeting domain

<400> SEQUENCE: 517
gcauugagau agugugggg 19

<210> SEQ ID NO 518
<211> LENGTH: 20
<212> TYPE: RNA
<213> ORGANISM: Artificial Sequence
<220> FEATURE:
<223> OTHER INFORMATION: Targeting domain

<400> SEQUENCE: 518
ugcauugaga uagugugggg 20

<210> SEQ ID NO 519
<211> LENGTH: 21
<212> TYPE: RNA
<213> ORGANISM: Artificial Sequence
<220> FEATURE:
<223> OTHER INFORMATION: Targeting domain

<400> SEQUENCE: 519
uugcauugag auaguguggg g 21

<210> SEQ ID NO 520
<211> LENGTH: 22
<212> TYPE: RNA
<213> ORGANISM: Artificial Sequence
<220> FEATURE:
<223> OTHER INFORMATION: Targeting domain

<400> SEQUENCE: 520
uuugcauuga gauagugugg gg 22

<210> SEQ ID NO 521
<211> LENGTH: 23
<212> TYPE: RNA
<213> ORGANISM: Artificial Sequence
<220> FEATURE:

<223> OTHER INFORMATION: Targeting domain

<400> SEQUENCE: 521
auuugcauug agauagugug ggg 23

<210> SEQ ID NO 522
<211> LENGTH: 24
<212> TYPE: RNA
<213> ORGANISM: Artificial Sequence
<220> FEATURE:
<223> OTHER INFORMATION: Targeting domain

<400> SEQUENCE: 522
uauuugcauu gagauagugu gggg 24

<210> SEQ ID NO 523
<211> LENGTH: 18
<212> TYPE: RNA
<213> ORGANISM: Artificial Sequence
<220> FEATURE:
<223> OTHER INFORMATION: Targeting domain

<400> SEQUENCE: 523
aggcuggcca acccaugg 18

<210> SEQ ID NO 524
<211> LENGTH: 19
<212> TYPE: RNA
<213> ORGANISM: Artificial Sequence
<220> FEATURE:
<223> OTHER INFORMATION: Targeting domain

<400> SEQUENCE: 524
aaggcuggcc aacccaugg 19

<210> SEQ ID NO 525
<211> LENGTH: 20
<212> TYPE: RNA
<213> ORGANISM: Artificial Sequence
<220> FEATURE:
<223> OTHER INFORMATION: Targeting domain

<400> SEQUENCE: 525
caaggcuggc caacccaugg 20

<210> SEQ ID NO 526
<211> LENGTH: 21
<212> TYPE: RNA
<213> ORGANISM: Artificial Sequence
<220> FEATURE:
<223> OTHER INFORMATION: Targeting domain

<400> SEQUENCE: 526
gcaaggcugg ccaacccaug g 21

<210> SEQ ID NO 527
<211> LENGTH: 22
<212> TYPE: RNA
<213> ORGANISM: Artificial Sequence
<220> FEATURE:
<223> OTHER INFORMATION: Targeting domain

<400> SEQUENCE: 527
ggcaaggcug gccaacccau gg 22

<210> SEQ ID NO 528
<211> LENGTH: 23
<212> TYPE: RNA
<213> ORGANISM: Artificial Sequence
<220> FEATURE:
<223> OTHER INFORMATION: Targeting domain

<400> SEQUENCE: 528
aggcaaggcu ggccaaccca ugg 23

<210> SEQ ID NO 529
<211> LENGTH: 24
<212> TYPE: RNA
<213> ORGANISM: Artificial Sequence
<220> FEATURE:
<223> OTHER INFORMATION: Targeting domain

<400> SEQUENCE: 529
aaggcaaggc uggccaaccc augg 24

<210> SEQ ID NO 530
<211> LENGTH: 18
<212> TYPE: RNA
<213> ORGANISM: Artificial Sequence
<220> FEATURE:
<223> OTHER INFORMATION: Targeting domain

<400> SEQUENCE: 530
agcgagugug uggaacug 18

<210> SEQ ID NO 531
<211> LENGTH: 19
<212> TYPE: RNA
<213> ORGANISM: Artificial Sequence
<220> FEATURE:
<223> OTHER INFORMATION: Targeting domain

<400> SEQUENCE: 531
aagcgagugu guggaacug 19

<210> SEQ ID NO 532
<211> LENGTH: 20
<212> TYPE: RNA
<213> ORGANISM: Artificial Sequence
<220> FEATURE:
<223> OTHER INFORMATION: Targeting domain

<400> SEQUENCE: 532
gaagcgagug uguggaacug 20

<210> SEQ ID NO 533
<211> LENGTH: 21
<212> TYPE: RNA
<213> ORGANISM: Artificial Sequence
<220> FEATURE:
<223> OTHER INFORMATION: Targeting domain

<400> SEQUENCE: 533
agaagcgagu guguggaacu g 21

<210> SEQ ID NO 534
<211> LENGTH: 22
<212> TYPE: RNA
<213> ORGANISM: Artificial Sequence
<220> FEATURE:
<223> OTHER INFORMATION: Targeting domain

```
<400> SEQUENCE: 534

cagaagcgag uguguggaac ug                                              22

<210> SEQ ID NO 535
<211> LENGTH: 23
<212> TYPE: RNA
<213> ORGANISM: Artificial Sequence
<220> FEATURE:
<223> OTHER INFORMATION: Targeting domain

<400> SEQUENCE: 535

ccagaagcga guguguggaa cug                                             23

<210> SEQ ID NO 536
<211> LENGTH: 24
<212> TYPE: RNA
<213> ORGANISM: Artificial Sequence
<220> FEATURE:
<223> OTHER INFORMATION: Targeting domain

<400> SEQUENCE: 536

uccagaagcg agugugugga acug                                            24

<210> SEQ ID NO 537
<211> LENGTH: 18
<212> TYPE: RNA
<213> ORGANISM: Artificial Sequence
<220> FEATURE:
<223> OTHER INFORMATION: Targeting domain

<400> SEQUENCE: 537

auuugcauug agauagug                                                   18

<210> SEQ ID NO 538
<211> LENGTH: 19
<212> TYPE: RNA
<213> ORGANISM: Artificial Sequence
<220> FEATURE:
<223> OTHER INFORMATION: Targeting domain

<400> SEQUENCE: 538

uauuugcauu gagauagug                                                  19

<210> SEQ ID NO 539
<211> LENGTH: 21
<212> TYPE: RNA
<213> ORGANISM: Artificial Sequence
<220> FEATURE:
<223> OTHER INFORMATION: Targeting domain

<400> SEQUENCE: 539

gauauuugca uugagauagu g                                               21

<210> SEQ ID NO 540
<211> LENGTH: 22
<212> TYPE: RNA
<213> ORGANISM: Artificial Sequence
<220> FEATURE:
<223> OTHER INFORMATION: Targeting domain

<400> SEQUENCE: 540

agauauuugc auugagauag ug                                              22

<210> SEQ ID NO 541
<211> LENGTH: 23
```

<212> TYPE: RNA
<213> ORGANISM: Artificial Sequence
<220> FEATURE:
<223> OTHER INFORMATION: Targeting domain

<400> SEQUENCE: 541
cagauauuug cauugagaua gug 23

<210> SEQ ID NO 542
<211> LENGTH: 24
<212> TYPE: RNA
<213> ORGANISM: Artificial Sequence
<220> FEATURE:
<223> OTHER INFORMATION: Targeting domain

<400> SEQUENCE: 542
acagauauuu gcauugagau agug 24

<210> SEQ ID NO 543
<211> LENGTH: 18
<212> TYPE: RNA
<213> ORGANISM: Artificial Sequence
<220> FEATURE:
<223> OTHER INFORMATION: Targeting domain

<400> SEQUENCE: 543
guuccagaag cgagugug 18

<210> SEQ ID NO 544
<211> LENGTH: 19
<212> TYPE: RNA
<213> ORGANISM: Artificial Sequence
<220> FEATURE:
<223> OTHER INFORMATION: Targeting domain

<400> SEQUENCE: 544
cguuccagaa gcgagugug 19

<210> SEQ ID NO 545
<211> LENGTH: 21
<212> TYPE: RNA
<213> ORGANISM: Artificial Sequence
<220> FEATURE:
<223> OTHER INFORMATION: Targeting domain

<400> SEQUENCE: 545
gacguuccag aagcgagugu g 21

<210> SEQ ID NO 546
<211> LENGTH: 22
<212> TYPE: RNA
<213> ORGANISM: Artificial Sequence
<220> FEATURE:
<223> OTHER INFORMATION: Targeting domain

<400> SEQUENCE: 546
agacguucca gaagcgagug ug 22

<210> SEQ ID NO 547
<211> LENGTH: 23
<212> TYPE: RNA
<213> ORGANISM: Artificial Sequence
<220> FEATURE:
<223> OTHER INFORMATION: Targeting domain

<400> SEQUENCE: 547
cagacguucc agaagcgagu gug 23

<210> SEQ ID NO 548
<211> LENGTH: 24
<212> TYPE: RNA
<213> ORGANISM: Artificial Sequence
<220> FEATURE:
<223> OTHER INFORMATION: Targeting domain

<400> SEQUENCE: 548
ucagacguuc cagaagcgag ugug 24

<210> SEQ ID NO 549
<211> LENGTH: 18
<212> TYPE: RNA
<213> ORGANISM: Artificial Sequence
<220> FEATURE:
<223> OTHER INFORMATION: Targeting domain

<400> SEQUENCE: 549
uugcauugag auagugug 18

<210> SEQ ID NO 550
<211> LENGTH: 19
<212> TYPE: RNA
<213> ORGANISM: Artificial Sequence
<220> FEATURE:
<223> OTHER INFORMATION: Targeting domain

<400> SEQUENCE: 550
uuugcauuga gauagugug 19

<210> SEQ ID NO 551
<211> LENGTH: 21
<212> TYPE: RNA
<213> ORGANISM: Artificial Sequence
<220> FEATURE:
<223> OTHER INFORMATION: Targeting domain

<400> SEQUENCE: 551
uauuugcauu gagauagugu g 21

<210> SEQ ID NO 552
<211> LENGTH: 22
<212> TYPE: RNA
<213> ORGANISM: Artificial Sequence
<220> FEATURE:
<223> OTHER INFORMATION: Targeting domain

<400> SEQUENCE: 552
auauuugcau ugagauagug ug 22

<210> SEQ ID NO 553
<211> LENGTH: 23
<212> TYPE: RNA
<213> ORGANISM: Artificial Sequence
<220> FEATURE:
<223> OTHER INFORMATION: Targeting domain

<400> SEQUENCE: 553
gauauuugca uugagauagu gug 23

<210> SEQ ID NO 554
<211> LENGTH: 24
<212> TYPE: RNA
<213> ORGANISM: Artificial Sequence
<220> FEATURE:
<223> OTHER INFORMATION: Targeting domain

<400> SEQUENCE: 554
agauauuugc auugagauag ugug 24

<210> SEQ ID NO 555
<211> LENGTH: 18
<212> TYPE: RNA
<213> ORGANISM: Artificial Sequence
<220> FEATURE:
<223> OTHER INFORMATION: Targeting domain

<400> SEQUENCE: 555
uauuugcauu gagauagu 18

<210> SEQ ID NO 556
<211> LENGTH: 19
<212> TYPE: RNA
<213> ORGANISM: Artificial Sequence
<220> FEATURE:
<223> OTHER INFORMATION: Targeting domain

<400> SEQUENCE: 556
auauuugcau ugagauagu 19

<210> SEQ ID NO 557
<211> LENGTH: 20
<212> TYPE: RNA
<213> ORGANISM: Artificial Sequence
<220> FEATURE:
<223> OTHER INFORMATION: Targeting domain

<400> SEQUENCE: 557
gauauuugca uugagauagu 20

<210> SEQ ID NO 558
<211> LENGTH: 21
<212> TYPE: RNA
<213> ORGANISM: Artificial Sequence
<220> FEATURE:
<223> OTHER INFORMATION: Targeting domain

<400> SEQUENCE: 558
agauauuugc auugagauag u 21

<210> SEQ ID NO 559
<211> LENGTH: 22
<212> TYPE: RNA
<213> ORGANISM: Artificial Sequence
<220> FEATURE:
<223> OTHER INFORMATION: Targeting domain

<400> SEQUENCE: 559
cagauauuug cauugagaua gu 22

<210> SEQ ID NO 560
<211> LENGTH: 23
<212> TYPE: RNA
<213> ORGANISM: Artificial Sequence
<220> FEATURE:
<223> OTHER INFORMATION: Targeting domain

<400> SEQUENCE: 560
acagauauuu gcauugagau agu 23

<210> SEQ ID NO 561
<211> LENGTH: 24
<212> TYPE: RNA
<213> ORGANISM: Artificial Sequence
<220> FEATURE:
<223> OTHER INFORMATION: Targeting domain

<400> SEQUENCE: 561
gacagauauu ugcauugaga uagu 24

<210> SEQ ID NO 562
<211> LENGTH: 18
<212> TYPE: RNA
<213> ORGANISM: Artificial Sequence
<220> FEATURE:
<223> OTHER INFORMATION: Targeting domain

<400> SEQUENCE: 562
cguuccagaa gcgagugu 18

<210> SEQ ID NO 563
<211> LENGTH: 19
<212> TYPE: RNA
<213> ORGANISM: Artificial Sequence
<220> FEATURE:
<223> OTHER INFORMATION: Targeting domain

<400> SEQUENCE: 563
acguuccaga agcgagugu 19

<210> SEQ ID NO 564
<211> LENGTH: 20
<212> TYPE: RNA
<213> ORGANISM: Artificial Sequence
<220> FEATURE:
<223> OTHER INFORMATION: Targeting domain

<400> SEQUENCE: 564
gacguuccag aagcgagugu 20

<210> SEQ ID NO 565
<211> LENGTH: 21
<212> TYPE: RNA
<213> ORGANISM: Artificial Sequence
<220> FEATURE:
<223> OTHER INFORMATION: Targeting domain

<400> SEQUENCE: 565
agacguucca gaagcgagug u 21

<210> SEQ ID NO 566
<211> LENGTH: 22
<212> TYPE: RNA
<213> ORGANISM: Artificial Sequence
<220> FEATURE:
<223> OTHER INFORMATION: Targeting domain

<400> SEQUENCE: 566
cagacguucc agaagcgagu gu 22

<210> SEQ ID NO 567
<211> LENGTH: 23
<212> TYPE: RNA
<213> ORGANISM: Artificial Sequence
<220> FEATURE:
<223> OTHER INFORMATION: Targeting domain

<400> SEQUENCE: 567
ucagacguuc cagaagcgag ugu 23

<210> SEQ ID NO 568
<211> LENGTH: 24
<212> TYPE: RNA
<213> ORGANISM: Artificial Sequence
<220> FEATURE:
<223> OTHER INFORMATION: Targeting domain

<400> SEQUENCE: 568
cucagacguu ccagaagcga gugu 24

<210> SEQ ID NO 569
<211> LENGTH: 18
<212> TYPE: RNA
<213> ORGANISM: Artificial Sequence
<220> FEATURE:
<223> OTHER INFORMATION: Targeting domain

<400> SEQUENCE: 569
uuugcauuga gauagugu 18

<210> SEQ ID NO 570
<211> LENGTH: 19
<212> TYPE: RNA
<213> ORGANISM: Artificial Sequence
<220> FEATURE:
<223> OTHER INFORMATION: Targeting domain

<400> SEQUENCE: 570
auuugcauug agauagugu 19

<210> SEQ ID NO 571
<211> LENGTH: 21
<212> TYPE: RNA
<213> ORGANISM: Artificial Sequence
<220> FEATURE:
<223> OTHER INFORMATION: Targeting domain

<400> SEQUENCE: 571
auauuugcau ugagauagug u 21

<210> SEQ ID NO 572
<211> LENGTH: 22
<212> TYPE: RNA
<213> ORGANISM: Artificial Sequence
<220> FEATURE:
<223> OTHER INFORMATION: Targeting domain

<400> SEQUENCE: 572
gauauuugca uugagauagu gu 22

<210> SEQ ID NO 573
<211> LENGTH: 23
<212> TYPE: RNA
<213> ORGANISM: Artificial Sequence
<220> FEATURE:
<223> OTHER INFORMATION: Targeting domain

<400> SEQUENCE: 573
agauauuugc auugagauag ugu 23

<210> SEQ ID NO 574

<211> LENGTH: 24
<212> TYPE: RNA
<213> ORGANISM: Artificial Sequence
<220> FEATURE:
<223> OTHER INFORMATION: Targeting domain

<400> SEQUENCE: 574
cagauauuug cauugagaua gugu 24

<210> SEQ ID NO 575
<211> LENGTH: 18
<212> TYPE: RNA
<213> ORGANISM: Artificial Sequence
<220> FEATURE:
<223> OTHER INFORMATION: Targeting domain

<400> SEQUENCE: 575
gaauaaauua gagaaaaa 18

<210> SEQ ID NO 576
<211> LENGTH: 19
<212> TYPE: RNA
<213> ORGANISM: Artificial Sequence
<220> FEATURE:
<223> OTHER INFORMATION: Targeting domain

<400> SEQUENCE: 576
agaauaaauu agagaaaaa 19

<210> SEQ ID NO 577
<211> LENGTH: 20
<212> TYPE: RNA
<213> ORGANISM: Artificial Sequence
<220> FEATURE:
<223> OTHER INFORMATION: Targeting domain

<400> SEQUENCE: 577
aagaauaaau uagagaaaaa 20

<210> SEQ ID NO 578
<211> LENGTH: 21
<212> TYPE: RNA
<213> ORGANISM: Artificial Sequence
<220> FEATURE:
<223> OTHER INFORMATION: Targeting domain

<400> SEQUENCE: 578
gaagaauaaa uuagagaaaa a 21

<210> SEQ ID NO 579
<211> LENGTH: 22
<212> TYPE: RNA
<213> ORGANISM: Artificial Sequence
<220> FEATURE:
<223> OTHER INFORMATION: Targeting domain

<400> SEQUENCE: 579
ggaagaauaa auuagagaaa aa 22

<210> SEQ ID NO 580
<211> LENGTH: 23
<212> TYPE: RNA
<213> ORGANISM: Artificial Sequence
<220> FEATURE:
<223> OTHER INFORMATION: Targeting domain

<400> SEQUENCE: 580
gggaagaaua aauuagagaa aaa 23

<210> SEQ ID NO 581
<211> LENGTH: 24
<212> TYPE: RNA
<213> ORGANISM: Artificial Sequence
<220> FEATURE:
<223> OTHER INFORMATION: Targeting domain

<400> SEQUENCE: 581
agggaagaau aaauuagaga aaaa 24

<210> SEQ ID NO 582
<211> LENGTH: 18
<212> TYPE: RNA
<213> ORGANISM: Artificial Sequence
<220> FEATURE:
<223> OTHER INFORMATION: Targeting domain

<400> SEQUENCE: 582
cuagggauga agaauaaa 18

<210> SEQ ID NO 583
<211> LENGTH: 19
<212> TYPE: RNA
<213> ORGANISM: Artificial Sequence
<220> FEATURE:
<223> OTHER INFORMATION: Targeting domain

<400> SEQUENCE: 583
gcuagggaug aagaauaaa 19

<210> SEQ ID NO 584
<211> LENGTH: 21
<212> TYPE: RNA
<213> ORGANISM: Artificial Sequence
<220> FEATURE:
<223> OTHER INFORMATION: Targeting domain

<400> SEQUENCE: 584
uggcuaggga ugaagaauaa a 21

<210> SEQ ID NO 585
<211> LENGTH: 22
<212> TYPE: RNA
<213> ORGANISM: Artificial Sequence
<220> FEATURE:
<223> OTHER INFORMATION: Targeting domain

<400> SEQUENCE: 585
cuggcuaggg augaagaaua aa 22

<210> SEQ ID NO 586
<211> LENGTH: 23
<212> TYPE: RNA
<213> ORGANISM: Artificial Sequence
<220> FEATURE:
<223> OTHER INFORMATION: Targeting domain

<400> SEQUENCE: 586
gcuggcuagg gaugaagaau aaa 23

<210> SEQ ID NO 587
<211> LENGTH: 24
<212> TYPE: RNA

<213> ORGANISM: Artificial Sequence
<220> FEATURE:
<223> OTHER INFORMATION: Targeting domain

<400> SEQUENCE: 587
ggcuggcuag ggaugaagaa uaaa 24

<210> SEQ ID NO 588
<211> LENGTH: 18
<212> TYPE: RNA
<213> ORGANISM: Artificial Sequence
<220> FEATURE:
<223> OTHER INFORMATION: Targeting domain

<400> SEQUENCE: 588
agaaggaaac uagcuaaa 18

<210> SEQ ID NO 589
<211> LENGTH: 19
<212> TYPE: RNA
<213> ORGANISM: Artificial Sequence
<220> FEATURE:
<223> OTHER INFORMATION: Targeting domain

<400> SEQUENCE: 589
gagaaggaaa cuagcuaaa 19

<210> SEQ ID NO 590
<211> LENGTH: 21
<212> TYPE: RNA
<213> ORGANISM: Artificial Sequence
<220> FEATURE:
<223> OTHER INFORMATION: Targeting domain

<400> SEQUENCE: 590
gggagaagga aacuagcuaa a 21

<210> SEQ ID NO 591
<211> LENGTH: 22
<212> TYPE: RNA
<213> ORGANISM: Artificial Sequence
<220> FEATURE:
<223> OTHER INFORMATION: Targeting domain

<400> SEQUENCE: 591
ugggagaagg aaacuagcua aa 22

<210> SEQ ID NO 592
<211> LENGTH: 23
<212> TYPE: RNA
<213> ORGANISM: Artificial Sequence
<220> FEATURE:
<223> OTHER INFORMATION: Targeting domain

<400> SEQUENCE: 592
augggagaag gaaacuagcu aaa 23

<210> SEQ ID NO 593
<211> LENGTH: 24
<212> TYPE: RNA
<213> ORGANISM: Artificial Sequence
<220> FEATURE:
<223> OTHER INFORMATION: Targeting domain

<400> SEQUENCE: 593
gaugggagaa ggaaacuagc uaaa 24

<210> SEQ ID NO 594
<211> LENGTH: 18
<212> TYPE: RNA
<213> ORGANISM: Artificial Sequence
<220> FEATURE:
<223> OTHER INFORMATION: Targeting domain

<400> SEQUENCE: 594
aaaacuggaa ugacugaa 18

<210> SEQ ID NO 595
<211> LENGTH: 19
<212> TYPE: RNA
<213> ORGANISM: Artificial Sequence
<220> FEATURE:
<223> OTHER INFORMATION: Targeting domain

<400> SEQUENCE: 595
aaaaacugga augacugaa 19

<210> SEQ ID NO 596
<211> LENGTH: 20
<212> TYPE: RNA
<213> ORGANISM: Artificial Sequence
<220> FEATURE:
<223> OTHER INFORMATION: Targeting domain

<400> SEQUENCE: 596
gaaaaacugg aaugacugaa 20

<210> SEQ ID NO 597
<211> LENGTH: 21
<212> TYPE: RNA
<213> ORGANISM: Artificial Sequence
<220> FEATURE:
<223> OTHER INFORMATION: Targeting domain

<400> SEQUENCE: 597
agaaaaacug gaaugacuga a 21

<210> SEQ ID NO 598
<211> LENGTH: 22
<212> TYPE: RNA
<213> ORGANISM: Artificial Sequence
<220> FEATURE:
<223> OTHER INFORMATION: Targeting domain

<400> SEQUENCE: 598
gagaaaaacu ggaaugacug aa 22

<210> SEQ ID NO 599
<211> LENGTH: 23
<212> TYPE: RNA
<213> ORGANISM: Artificial Sequence
<220> FEATURE:
<223> OTHER INFORMATION: Targeting domain

<400> SEQUENCE: 599
agagaaaaac uggaaugacu gaa 23

<210> SEQ ID NO 600
<211> LENGTH: 24
<212> TYPE: RNA
<213> ORGANISM: Artificial Sequence
<220> FEATURE:

<223> OTHER INFORMATION: Targeting domain

<400> SEQUENCE: 600
uagagaaaaa cuggaaugac ugaa 24

<210> SEQ ID NO 601
<211> LENGTH: 18
<212> TYPE: RNA
<213> ORGANISM: Artificial Sequence
<220> FEATURE:
<223> OTHER INFORMATION: Targeting domain

<400> SEQUENCE: 601
gcuagggaug aagaauaa 18

<210> SEQ ID NO 602
<211> LENGTH: 19
<212> TYPE: RNA
<213> ORGANISM: Artificial Sequence
<220> FEATURE:
<223> OTHER INFORMATION: Targeting domain

<400> SEQUENCE: 602
ggcuagggau gaagaauaa 19

<210> SEQ ID NO 603
<211> LENGTH: 20
<212> TYPE: RNA
<213> ORGANISM: Artificial Sequence
<220> FEATURE:
<223> OTHER INFORMATION: Targeting domain

<400> SEQUENCE: 603
uggcuaggga ugaagaauaa 20

<210> SEQ ID NO 604
<211> LENGTH: 21
<212> TYPE: RNA
<213> ORGANISM: Artificial Sequence
<220> FEATURE:
<223> OTHER INFORMATION: Targeting domain

<400> SEQUENCE: 604
cuggcuaggg augaagaaua a 21

<210> SEQ ID NO 605
<211> LENGTH: 22
<212> TYPE: RNA
<213> ORGANISM: Artificial Sequence
<220> FEATURE:
<223> OTHER INFORMATION: Targeting domain

<400> SEQUENCE: 605
gcuggcuagg gaugaagaau aa 22

<210> SEQ ID NO 606
<211> LENGTH: 23
<212> TYPE: RNA
<213> ORGANISM: Artificial Sequence
<220> FEATURE:
<223> OTHER INFORMATION: Targeting domain

<400> SEQUENCE: 606
ggcuggcuag ggaugaagaa uaa 23

<210> SEQ ID NO 607
<211> LENGTH: 24
<212> TYPE: RNA
<213> ORGANISM: Artificial Sequence
<220> FEATURE:
<223> OTHER INFORMATION: Targeting domain

<400> SEQUENCE: 607
cggcuggcua gggaugaaga auaa 24

<210> SEQ ID NO 608
<211> LENGTH: 18
<212> TYPE: RNA
<213> ORGANISM: Artificial Sequence
<220> FEATURE:
<223> OTHER INFORMATION: Targeting domain

<400> SEQUENCE: 608
gagaaggaaa cuagcuaa 18

<210> SEQ ID NO 609
<211> LENGTH: 19
<212> TYPE: RNA
<213> ORGANISM: Artificial Sequence
<220> FEATURE:
<223> OTHER INFORMATION: Targeting domain

<400> SEQUENCE: 609
ggagaaggaa acuagcuaa 19

<210> SEQ ID NO 610
<211> LENGTH: 21
<212> TYPE: RNA
<213> ORGANISM: Artificial Sequence
<220> FEATURE:
<223> OTHER INFORMATION: Targeting domain

<400> SEQUENCE: 610
ugggagaagg aaacuagcua a 21

<210> SEQ ID NO 611
<211> LENGTH: 22
<212> TYPE: RNA
<213> ORGANISM: Artificial Sequence
<220> FEATURE:
<223> OTHER INFORMATION: Targeting domain

<400> SEQUENCE: 611
augggagaag gaaacuagcu aa 22

<210> SEQ ID NO 612
<211> LENGTH: 23
<212> TYPE: RNA
<213> ORGANISM: Artificial Sequence
<220> FEATURE:
<223> OTHER INFORMATION: Targeting domain

<400> SEQUENCE: 612
gaugggagaa ggaaacuagc uaa 23

<210> SEQ ID NO 613
<211> LENGTH: 24
<212> TYPE: RNA
<213> ORGANISM: Artificial Sequence
<220> FEATURE:
<223> OTHER INFORMATION: Targeting domain

<400> SEQUENCE: 613
ugaugggaga aggaaacuag cuaa 24

<210> SEQ ID NO 614
<211> LENGTH: 18
<212> TYPE: RNA
<213> ORGANISM: Artificial Sequence
<220> FEATURE:
<223> OTHER INFORMATION: Targeting domain

<400> SEQUENCE: 614
auagucuuag aguaucca 18

<210> SEQ ID NO 615
<211> LENGTH: 19
<212> TYPE: RNA
<213> ORGANISM: Artificial Sequence
<220> FEATURE:
<223> OTHER INFORMATION: Targeting domain

<400> SEQUENCE: 615
aauagucuua gaguaucca 19

<210> SEQ ID NO 616
<211> LENGTH: 20
<212> TYPE: RNA
<213> ORGANISM: Artificial Sequence
<220> FEATURE:
<223> OTHER INFORMATION: Targeting domain

<400> SEQUENCE: 616
caauagucuu agaguaucca 20

<210> SEQ ID NO 617
<211> LENGTH: 21
<212> TYPE: RNA
<213> ORGANISM: Artificial Sequence
<220> FEATURE:
<223> OTHER INFORMATION: Targeting domain

<400> SEQUENCE: 617
ccaauagucu uagaguaucc a 21

<210> SEQ ID NO 618
<211> LENGTH: 22
<212> TYPE: RNA
<213> ORGANISM: Artificial Sequence
<220> FEATURE:
<223> OTHER INFORMATION: Targeting domain

<400> SEQUENCE: 618
accaauaguc uuagaguauc ca 22

<210> SEQ ID NO 619
<211> LENGTH: 23
<212> TYPE: RNA
<213> ORGANISM: Artificial Sequence
<220> FEATURE:
<223> OTHER INFORMATION: Targeting domain

<400> SEQUENCE: 619
gaccaauagu cuuagaguau cca 23

<210> SEQ ID NO 620
<211> LENGTH: 24

<212> TYPE: RNA
<213> ORGANISM: Artificial Sequence
<220> FEATURE:
<223> OTHER INFORMATION: Targeting domain

<400> SEQUENCE: 620
ugaccaauag ucuuagagua ucca 24

<210> SEQ ID NO 621
<211> LENGTH: 18
<212> TYPE: RNA
<213> ORGANISM: Artificial Sequence
<220> FEATURE:
<223> OTHER INFORMATION: Targeting domain

<400> SEQUENCE: 621
auccucuaug augggaga 18

<210> SEQ ID NO 622
<211> LENGTH: 19
<212> TYPE: RNA
<213> ORGANISM: Artificial Sequence
<220> FEATURE:
<223> OTHER INFORMATION: Targeting domain

<400> SEQUENCE: 622
uauccucuau gaugggaga 19

<210> SEQ ID NO 623
<211> LENGTH: 21
<212> TYPE: RNA
<213> ORGANISM: Artificial Sequence
<220> FEATURE:
<223> OTHER INFORMATION: Targeting domain

<400> SEQUENCE: 623
gguauccucu augaugggag a 21

<210> SEQ ID NO 624
<211> LENGTH: 22
<212> TYPE: RNA
<213> ORGANISM: Artificial Sequence
<220> FEATURE:
<223> OTHER INFORMATION: Targeting domain

<400> SEQUENCE: 624
ugguauccuc uaugauggga ga 22

<210> SEQ ID NO 625
<211> LENGTH: 23
<212> TYPE: RNA
<213> ORGANISM: Artificial Sequence
<220> FEATURE:
<223> OTHER INFORMATION: Targeting domain

<400> SEQUENCE: 625
cugguauccu cuaugauggg aga 23

<210> SEQ ID NO 626
<211> LENGTH: 24
<212> TYPE: RNA
<213> ORGANISM: Artificial Sequence
<220> FEATURE:
<223> OTHER INFORMATION: Targeting domain

<400> SEQUENCE: 626
ccugguaucc ucuaugaugg gaga 24

<210> SEQ ID NO 627
<211> LENGTH: 18
<212> TYPE: RNA
<213> ORGANISM: Artificial Sequence
<220> FEATURE:
<223> OTHER INFORMATION: Targeting domain

<400> SEQUENCE: 627
uccugguauc cucuauga 18

<210> SEQ ID NO 628
<211> LENGTH: 19
<212> TYPE: RNA
<213> ORGANISM: Artificial Sequence
<220> FEATURE:
<223> OTHER INFORMATION: Targeting domain

<400> SEQUENCE: 628
guccugguau ccucuauga 19

<210> SEQ ID NO 629
<211> LENGTH: 21
<212> TYPE: RNA
<213> ORGANISM: Artificial Sequence
<220> FEATURE:
<223> OTHER INFORMATION: Targeting domain

<400> SEQUENCE: 629
aaguccuggu auccucuaug a 21

<210> SEQ ID NO 630
<211> LENGTH: 22
<212> TYPE: RNA
<213> ORGANISM: Artificial Sequence
<220> FEATURE:
<223> OTHER INFORMATION: Targeting domain

<400> SEQUENCE: 630
gaaguccugg uauccucuau ga 22

<210> SEQ ID NO 631
<211> LENGTH: 23
<212> TYPE: RNA
<213> ORGANISM: Artificial Sequence
<220> FEATURE:
<223> OTHER INFORMATION: Targeting domain

<400> SEQUENCE: 631
agaaguccug guauccucua uga 23

<210> SEQ ID NO 632
<211> LENGTH: 24
<212> TYPE: RNA
<213> ORGANISM: Artificial Sequence
<220> FEATURE:
<223> OTHER INFORMATION: Targeting domain

<400> SEQUENCE: 632
aagaaguccu gguauccucu auga 24

<210> SEQ ID NO 633
<211> LENGTH: 18
<212> TYPE: RNA
<213> ORGANISM: Artificial Sequence
<220> FEATURE:
<223> OTHER INFORMATION: Targeting domain

<400> SEQUENCE: 633
ggagaaggaa acuagcua 18

<210> SEQ ID NO 634
<211> LENGTH: 19
<212> TYPE: RNA
<213> ORGANISM: Artificial Sequence
<220> FEATURE:
<223> OTHER INFORMATION: Targeting domain

<400> SEQUENCE: 634
gggagaagga aacuagcua 19

<210> SEQ ID NO 635
<211> LENGTH: 20
<212> TYPE: RNA
<213> ORGANISM: Artificial Sequence
<220> FEATURE:
<223> OTHER INFORMATION: Targeting domain

<400> SEQUENCE: 635
ugggagaagg aaacuagcua 20

<210> SEQ ID NO 636
<211> LENGTH: 21
<212> TYPE: RNA
<213> ORGANISM: Artificial Sequence
<220> FEATURE:
<223> OTHER INFORMATION: Targeting domain

<400> SEQUENCE: 636
augggagaag gaaacuagcu a 21

<210> SEQ ID NO 637
<211> LENGTH: 22
<212> TYPE: RNA
<213> ORGANISM: Artificial Sequence
<220> FEATURE:
<223> OTHER INFORMATION: Targeting domain

<400> SEQUENCE: 637
gaugggagaa ggaaacuagc ua 22

<210> SEQ ID NO 638
<211> LENGTH: 23
<212> TYPE: RNA
<213> ORGANISM: Artificial Sequence
<220> FEATURE:
<223> OTHER INFORMATION: Targeting domain

<400> SEQUENCE: 638
ugaugggaga aggaaacuag cua 23

<210> SEQ ID NO 639
<211> LENGTH: 24
<212> TYPE: RNA
<213> ORGANISM: Artificial Sequence
<220> FEATURE:
<223> OTHER INFORMATION: Targeting domain

<400> SEQUENCE: 639
augaugggag aaggaaacua gcua 24

<210> SEQ ID NO 640
<211> LENGTH: 18
<212> TYPE: RNA
<213> ORGANISM: Artificial Sequence
<220> FEATURE:
<223> OTHER INFORMATION: Targeting domain

<400> SEQUENCE: 640
aaagggaaga auaaauua 18

<210> SEQ ID NO 641
<211> LENGTH: 19
<212> TYPE: RNA
<213> ORGANISM: Artificial Sequence
<220> FEATURE:
<223> OTHER INFORMATION: Targeting domain

<400> SEQUENCE: 641
uaaagggaag aauaaauua 19

<210> SEQ ID NO 642
<211> LENGTH: 20
<212> TYPE: RNA
<213> ORGANISM: Artificial Sequence
<220> FEATURE:
<223> OTHER INFORMATION: Targeting domain

<400> SEQUENCE: 642
cuaaagggaa gaauaaauua 20

<210> SEQ ID NO 643
<211> LENGTH: 21
<212> TYPE: RNA
<213> ORGANISM: Artificial Sequence
<220> FEATURE:
<223> OTHER INFORMATION: Targeting domain

<400> SEQUENCE: 643
gcuaaaggga agaauaaauu a 21

<210> SEQ ID NO 644
<211> LENGTH: 22
<212> TYPE: RNA
<213> ORGANISM: Artificial Sequence
<220> FEATURE:
<223> OTHER INFORMATION: Targeting domain

<400> SEQUENCE: 644
agcuaaaggg aagaauaaau ua 22

<210> SEQ ID NO 645
<211> LENGTH: 23
<212> TYPE: RNA
<213> ORGANISM: Artificial Sequence
<220> FEATURE:
<223> OTHER INFORMATION: Targeting domain

<400> SEQUENCE: 645
uagcuaaagg gaagaauaaa uua 23

<210> SEQ ID NO 646
<211> LENGTH: 24
<212> TYPE: RNA
<213> ORGANISM: Artificial Sequence
<220> FEATURE:
<223> OTHER INFORMATION: Targeting domain

<400> SEQUENCE: 646
cuagcuaaag ggaagaauaa auua 24

<210> SEQ ID NO 647
<211> LENGTH: 18
<212> TYPE: RNA
<213> ORGANISM: Artificial Sequence
<220> FEATURE:
<223> OTHER INFORMATION: Targeting domain

<400> SEQUENCE: 647
agaguaucca gugaggcc 18

<210> SEQ ID NO 648
<211> LENGTH: 19
<212> TYPE: RNA
<213> ORGANISM: Artificial Sequence
<220> FEATURE:
<223> OTHER INFORMATION: Targeting domain

<400> SEQUENCE: 648
uagaguaucc agugaggcc 19

<210> SEQ ID NO 649
<211> LENGTH: 21
<212> TYPE: RNA
<213> ORGANISM: Artificial Sequence
<220> FEATURE:
<223> OTHER INFORMATION: Targeting domain

<400> SEQUENCE: 649
cuuagaguau ccagugaggc c 21

<210> SEQ ID NO 650
<211> LENGTH: 22
<212> TYPE: RNA
<213> ORGANISM: Artificial Sequence
<220> FEATURE:
<223> OTHER INFORMATION: Targeting domain

<400> SEQUENCE: 650
ucuuagagua uccagugagg cc 22

<210> SEQ ID NO 651
<211> LENGTH: 23
<212> TYPE: RNA
<213> ORGANISM: Artificial Sequence
<220> FEATURE:
<223> OTHER INFORMATION: Targeting domain

<400> SEQUENCE: 651
gucuuagagu auccagugag gcc 23

<210> SEQ ID NO 652
<211> LENGTH: 24
<212> TYPE: RNA
<213> ORGANISM: Artificial Sequence
<220> FEATURE:
<223> OTHER INFORMATION: Targeting domain

<400> SEQUENCE: 652
agucuuagag uauccaguga ggcc 24

<210> SEQ ID NO 653

-continued

<211> LENGTH: 18
<212> TYPE: RNA
<213> ORGANISM: Artificial Sequence
<220> FEATURE:
<223> OTHER INFORMATION: Targeting domain

<400> SEQUENCE: 653
uagaguaucc agugaggc 18

<210> SEQ ID NO 654
<211> LENGTH: 19
<212> TYPE: RNA
<213> ORGANISM: Artificial Sequence
<220> FEATURE:
<223> OTHER INFORMATION: Targeting domain

<400> SEQUENCE: 654
uuagaguauc cagugaggc 19

<210> SEQ ID NO 655
<211> LENGTH: 20
<212> TYPE: RNA
<213> ORGANISM: Artificial Sequence
<220> FEATURE:
<223> OTHER INFORMATION: Targeting domain

<400> SEQUENCE: 655
cuuagaguau ccagugaggc 20

<210> SEQ ID NO 656
<211> LENGTH: 21
<212> TYPE: RNA
<213> ORGANISM: Artificial Sequence
<220> FEATURE:
<223> OTHER INFORMATION: Targeting domain

<400> SEQUENCE: 656
ucuuagagua uccagugagg c 21

<210> SEQ ID NO 657
<211> LENGTH: 22
<212> TYPE: RNA
<213> ORGANISM: Artificial Sequence
<220> FEATURE:
<223> OTHER INFORMATION: Targeting domain

<400> SEQUENCE: 657
gucuuagagu auccagugag gc 22

<210> SEQ ID NO 658
<211> LENGTH: 23
<212> TYPE: RNA
<213> ORGANISM: Artificial Sequence
<220> FEATURE:
<223> OTHER INFORMATION: Targeting domain

<400> SEQUENCE: 658
agucuuagag uauccaguga ggc 23

<210> SEQ ID NO 659
<211> LENGTH: 24
<212> TYPE: RNA
<213> ORGANISM: Artificial Sequence
<220> FEATURE:
<223> OTHER INFORMATION: Targeting domain

<400> SEQUENCE: 659
uagucuuaga guauccagug aggc 24

<210> SEQ ID NO 660
<211> LENGTH: 18
<212> TYPE: RNA
<213> ORGANISM: Artificial Sequence
<220> FEATURE:
<223> OTHER INFORMATION: Targeting domain

<400> SEQUENCE: 660
caggggccgg cggcuggc 18

<210> SEQ ID NO 661
<211> LENGTH: 19
<212> TYPE: RNA
<213> ORGANISM: Artificial Sequence
<220> FEATURE:
<223> OTHER INFORMATION: Targeting domain

<400> SEQUENCE: 661
ccaggggccg gcggcuggc 19

<210> SEQ ID NO 662
<211> LENGTH: 20
<212> TYPE: RNA
<213> ORGANISM: Artificial Sequence
<220> FEATURE:
<223> OTHER INFORMATION: Targeting domain

<400> SEQUENCE: 662
gccaggggcc ggcggcuggc 20

<210> SEQ ID NO 663
<211> LENGTH: 21
<212> TYPE: RNA
<213> ORGANISM: Artificial Sequence
<220> FEATURE:
<223> OTHER INFORMATION: Targeting domain

<400> SEQUENCE: 663
ggccaggggc cggcggcugg c 21

<210> SEQ ID NO 664
<211> LENGTH: 22
<212> TYPE: RNA
<213> ORGANISM: Artificial Sequence
<220> FEATURE:
<223> OTHER INFORMATION: Targeting domain

<400> SEQUENCE: 664
aggccagggg ccggcggcug gc 22

<210> SEQ ID NO 665
<211> LENGTH: 23
<212> TYPE: RNA
<213> ORGANISM: Artificial Sequence
<220> FEATURE:
<223> OTHER INFORMATION: Targeting domain

<400> SEQUENCE: 665
gaggccaggg gccggcggcu ggc 23

<210> SEQ ID NO 666
<211> LENGTH: 24
<212> TYPE: RNA

<213> ORGANISM: Artificial Sequence
<220> FEATURE:
<223> OTHER INFORMATION: Targeting domain

<400> SEQUENCE: 666
ugaggccagg ggccggcggc uggc 24

<210> SEQ ID NO 667
<211> LENGTH: 18
<212> TYPE: RNA
<213> ORGANISM: Artificial Sequence
<220> FEATURE:
<223> OTHER INFORMATION: Targeting domain

<400> SEQUENCE: 667
aaaauuagca guauccuc 18

<210> SEQ ID NO 668
<211> LENGTH: 19
<212> TYPE: RNA
<213> ORGANISM: Artificial Sequence
<220> FEATURE:
<223> OTHER INFORMATION: Targeting domain

<400> SEQUENCE: 668
aaaaauuagc aguauccuc 19

<210> SEQ ID NO 669
<211> LENGTH: 20
<212> TYPE: RNA
<213> ORGANISM: Artificial Sequence
<220> FEATURE:
<223> OTHER INFORMATION: Targeting domain

<400> SEQUENCE: 669
aaaaaauuag caguauccuc 20

<210> SEQ ID NO 670
<211> LENGTH: 21
<212> TYPE: RNA
<213> ORGANISM: Artificial Sequence
<220> FEATURE:
<223> OTHER INFORMATION: Targeting domain

<400> SEQUENCE: 670
aaaaaaauua gcaguauccu c 21

<210> SEQ ID NO 671
<211> LENGTH: 22
<212> TYPE: RNA
<213> ORGANISM: Artificial Sequence
<220> FEATURE:
<223> OTHER INFORMATION: Targeting domain

<400> SEQUENCE: 671
aaaaaaaauu agcaguaucc uc 22

<210> SEQ ID NO 672
<211> LENGTH: 23
<212> TYPE: RNA
<213> ORGANISM: Artificial Sequence
<220> FEATURE:
<223> OTHER INFORMATION: Targeting domain

<400> SEQUENCE: 672
uaaaaaaaau uagcaguauc cuc 23

<210> SEQ ID NO 673
<211> LENGTH: 24
<212> TYPE: RNA
<213> ORGANISM: Artificial Sequence
<220> FEATURE:
<223> OTHER INFORMATION: Targeting domain

<400> SEQUENCE: 673
auaaaaaaaa uuagcaguau ccuc 24

<210> SEQ ID NO 674
<211> LENGTH: 18
<212> TYPE: RNA
<213> ORGANISM: Artificial Sequence
<220> FEATURE:
<223> OTHER INFORMATION: Targeting domain

<400> SEQUENCE: 674
guuccacaca cucgcuuc 18

<210> SEQ ID NO 675
<211> LENGTH: 19
<212> TYPE: RNA
<213> ORGANISM: Artificial Sequence
<220> FEATURE:
<223> OTHER INFORMATION: Targeting domain

<400> SEQUENCE: 675
aguuccacac acucgcuuc 19

<210> SEQ ID NO 676
<211> LENGTH: 21
<212> TYPE: RNA
<213> ORGANISM: Artificial Sequence
<220> FEATURE:
<223> OTHER INFORMATION: Targeting domain

<400> SEQUENCE: 676
gcaguuccac acacucgcuu c 21

<210> SEQ ID NO 677
<211> LENGTH: 22
<212> TYPE: RNA
<213> ORGANISM: Artificial Sequence
<220> FEATURE:
<223> OTHER INFORMATION: Targeting domain

<400> SEQUENCE: 677
agcaguucca cacacucgcu uc 22

<210> SEQ ID NO 678
<211> LENGTH: 23
<212> TYPE: RNA
<213> ORGANISM: Artificial Sequence
<220> FEATURE:
<223> OTHER INFORMATION: Targeting domain

<400> SEQUENCE: 678
cagcaguucc acacacucgc uuc 23

<210> SEQ ID NO 679
<211> LENGTH: 24
<212> TYPE: RNA
<213> ORGANISM: Artificial Sequence
<220> FEATURE:

<223> OTHER INFORMATION: Targeting domain

<400> SEQUENCE: 679
ucagcaguuc cacacacucg cuuc 24

<210> SEQ ID NO 680
<211> LENGTH: 18
<212> TYPE: RNA
<213> ORGANISM: Artificial Sequence
<220> FEATURE:
<223> OTHER INFORMATION: Targeting domain

<400> SEQUENCE: 680
uauccucuau gaugggag 18

<210> SEQ ID NO 681
<211> LENGTH: 19
<212> TYPE: RNA
<213> ORGANISM: Artificial Sequence
<220> FEATURE:
<223> OTHER INFORMATION: Targeting domain

<400> SEQUENCE: 681
guauccucua ugaugggag 19

<210> SEQ ID NO 682
<211> LENGTH: 20
<212> TYPE: RNA
<213> ORGANISM: Artificial Sequence
<220> FEATURE:
<223> OTHER INFORMATION: Targeting domain

<400> SEQUENCE: 682
gguauccucu augaugggag 20

<210> SEQ ID NO 683
<211> LENGTH: 21
<212> TYPE: RNA
<213> ORGANISM: Artificial Sequence
<220> FEATURE:
<223> OTHER INFORMATION: Targeting domain

<400> SEQUENCE: 683
ugguauccuc uaugauggga g 21

<210> SEQ ID NO 684
<211> LENGTH: 22
<212> TYPE: RNA
<213> ORGANISM: Artificial Sequence
<220> FEATURE:
<223> OTHER INFORMATION: Targeting domain

<400> SEQUENCE: 684
cugguauccu cuaugauggg ag 22

<210> SEQ ID NO 685
<211> LENGTH: 23
<212> TYPE: RNA
<213> ORGANISM: Artificial Sequence
<220> FEATURE:
<223> OTHER INFORMATION: Targeting domain

<400> SEQUENCE: 685
ccugguaucc ucuaugaugg gag 23

<210> SEQ ID NO 686
<211> LENGTH: 24
<212> TYPE: RNA
<213> ORGANISM: Artificial Sequence
<220> FEATURE:
<223> OTHER INFORMATION: Targeting domain

<400> SEQUENCE: 686
uccugguauc cucuaugaug ggag 24

<210> SEQ ID NO 687
<211> LENGTH: 18
<212> TYPE: RNA
<213> ORGANISM: Artificial Sequence
<220> FEATURE:
<223> OTHER INFORMATION: Targeting domain

<400> SEQUENCE: 687
gccggcggcu ggcuaggg 18

<210> SEQ ID NO 688
<211> LENGTH: 19
<212> TYPE: RNA
<213> ORGANISM: Artificial Sequence
<220> FEATURE:
<223> OTHER INFORMATION: Targeting domain

<400> SEQUENCE: 688
ggccggcggc uggcuaggg 19

<210> SEQ ID NO 689
<211> LENGTH: 20
<212> TYPE: RNA
<213> ORGANISM: Artificial Sequence
<220> FEATURE:
<223> OTHER INFORMATION: Targeting domain

<400> SEQUENCE: 689
gggccggcgg cuggcuaggg 20

<210> SEQ ID NO 690
<211> LENGTH: 21
<212> TYPE: RNA
<213> ORGANISM: Artificial Sequence
<220> FEATURE:
<223> OTHER INFORMATION: Targeting domain

<400> SEQUENCE: 690
ggggccggcg gcuggcuagg g 21

<210> SEQ ID NO 691
<211> LENGTH: 22
<212> TYPE: RNA
<213> ORGANISM: Artificial Sequence
<220> FEATURE:
<223> OTHER INFORMATION: Targeting domain

<400> SEQUENCE: 691
aggggccggc ggcuggcuag gg 22

<210> SEQ ID NO 692
<211> LENGTH: 23
<212> TYPE: RNA
<213> ORGANISM: Artificial Sequence
<220> FEATURE:
<223> OTHER INFORMATION: Targeting domain

<400> SEQUENCE: 692
caggggccgg cggcuggcua ggg 23

<210> SEQ ID NO 693
<211> LENGTH: 24
<212> TYPE: RNA
<213> ORGANISM: Artificial Sequence
<220> FEATURE:
<223> OTHER INFORMATION: Targeting domain

<400> SEQUENCE: 693
ccaggggccg gcggcuggcu aggg 24

<210> SEQ ID NO 694
<211> LENGTH: 18
<212> TYPE: RNA
<213> ORGANISM: Artificial Sequence
<220> FEATURE:
<223> OTHER INFORMATION: Targeting domain

<400> SEQUENCE: 694
ugguauccuc uaugaugg 18

<210> SEQ ID NO 695
<211> LENGTH: 19
<212> TYPE: RNA
<213> ORGANISM: Artificial Sequence
<220> FEATURE:
<223> OTHER INFORMATION: Targeting domain

<400> SEQUENCE: 695
cugguauccu cuaugaugg 19

<210> SEQ ID NO 696
<211> LENGTH: 20
<212> TYPE: RNA
<213> ORGANISM: Artificial Sequence
<220> FEATURE:
<223> OTHER INFORMATION: Targeting domain

<400> SEQUENCE: 696
ccugguaucc ucuaugaugg 20

<210> SEQ ID NO 697
<211> LENGTH: 21
<212> TYPE: RNA
<213> ORGANISM: Artificial Sequence
<220> FEATURE:
<223> OTHER INFORMATION: Targeting domain

<400> SEQUENCE: 697
uccugguauc cucuaugaug g 21

<210> SEQ ID NO 698
<211> LENGTH: 22
<212> TYPE: RNA
<213> ORGANISM: Artificial Sequence
<220> FEATURE:
<223> OTHER INFORMATION: Targeting domain

<400> SEQUENCE: 698
guccugguau ccucuaugau gg 22

<210> SEQ ID NO 699
<211> LENGTH: 23

<212> TYPE: RNA
<213> ORGANISM: Artificial Sequence
<220> FEATURE:
<223> OTHER INFORMATION: Targeting domain

<400> SEQUENCE: 699
aguccuggua uccucuauga ugg 23

<210> SEQ ID NO 700
<211> LENGTH: 24
<212> TYPE: RNA
<213> ORGANISM: Artificial Sequence
<220> FEATURE:
<223> OTHER INFORMATION: Targeting domain

<400> SEQUENCE: 700
aaguccuggu auccucuaug augg 24

<210> SEQ ID NO 701
<211> LENGTH: 18
<212> TYPE: RNA
<213> ORGANISM: Artificial Sequence
<220> FEATURE:
<223> OTHER INFORMATION: Targeting domain

<400> SEQUENCE: 701
guccugguau ccucuaug 18

<210> SEQ ID NO 702
<211> LENGTH: 19
<212> TYPE: RNA
<213> ORGANISM: Artificial Sequence
<220> FEATURE:
<223> OTHER INFORMATION: Targeting domain

<400> SEQUENCE: 702
aguccuggua uccucuaug 19

<210> SEQ ID NO 703
<211> LENGTH: 20
<212> TYPE: RNA
<213> ORGANISM: Artificial Sequence
<220> FEATURE:
<223> OTHER INFORMATION: Targeting domain

<400> SEQUENCE: 703
aaguccuggu auccucuaug 20

<210> SEQ ID NO 704
<211> LENGTH: 21
<212> TYPE: RNA
<213> ORGANISM: Artificial Sequence
<220> FEATURE:
<223> OTHER INFORMATION: Targeting domain

<400> SEQUENCE: 704
gaaguccugg uauccucuau g 21

<210> SEQ ID NO 705
<211> LENGTH: 22
<212> TYPE: RNA
<213> ORGANISM: Artificial Sequence
<220> FEATURE:
<223> OTHER INFORMATION: Targeting domain

<400> SEQUENCE: 705
agaaguccug guauccucua ug 22

<210> SEQ ID NO 706
<211> LENGTH: 23
<212> TYPE: RNA
<213> ORGANISM: Artificial Sequence
<220> FEATURE:
<223> OTHER INFORMATION: Targeting domain

<400> SEQUENCE: 706
aagaaguccu gguauccucu aug 23

<210> SEQ ID NO 707
<211> LENGTH: 24
<212> TYPE: RNA
<213> ORGANISM: Artificial Sequence
<220> FEATURE:
<223> OTHER INFORMATION: Targeting domain

<400> SEQUENCE: 707
aaagaagucc ugguauccuc uaug 24

<210> SEQ ID NO 708
<211> LENGTH: 18
<212> TYPE: RNA
<213> ORGANISM: Artificial Sequence
<220> FEATURE:
<223> OTHER INFORMATION: Targeting domain

<400> SEQUENCE: 708
cuaaagggaa gaauaaau 18

<210> SEQ ID NO 709
<211> LENGTH: 19
<212> TYPE: RNA
<213> ORGANISM: Artificial Sequence
<220> FEATURE:
<223> OTHER INFORMATION: Targeting domain

<400> SEQUENCE: 709
gcuaaaggga agaauaaau 19

<210> SEQ ID NO 710
<211> LENGTH: 20
<212> TYPE: RNA
<213> ORGANISM: Artificial Sequence
<220> FEATURE:
<223> OTHER INFORMATION: Targeting domain

<400> SEQUENCE: 710
agcuaaaggg aagaauaaau 20

<210> SEQ ID NO 711
<211> LENGTH: 21
<212> TYPE: RNA
<213> ORGANISM: Artificial Sequence
<220> FEATURE:
<223> OTHER INFORMATION: Targeting domain

<400> SEQUENCE: 711
uagcuaaagg gaagaauaaa u 21

<210> SEQ ID NO 712
<211> LENGTH: 22
<212> TYPE: RNA
<213> ORGANISM: Artificial Sequence
<220> FEATURE:
<223> OTHER INFORMATION: Targeting domain

<400> SEQUENCE: 712
cuagcuaaag ggaagaauaa au 22

<210> SEQ ID NO 713
<211> LENGTH: 23
<212> TYPE: RNA
<213> ORGANISM: Artificial Sequence
<220> FEATURE:
<223> OTHER INFORMATION: Targeting domain

<400> SEQUENCE: 713
acuagcuaaa gggaagaaua aau 23

<210> SEQ ID NO 714
<211> LENGTH: 24
<212> TYPE: RNA
<213> ORGANISM: Artificial Sequence
<220> FEATURE:
<223> OTHER INFORMATION: Targeting domain

<400> SEQUENCE: 714
aacuagcuaa agggaagaau aaau 24

<210> SEQ ID NO 715
<211> LENGTH: 18
<212> TYPE: RNA
<213> ORGANISM: Artificial Sequence
<220> FEATURE:
<223> OTHER INFORMATION: Targeting domain

<400> SEQUENCE: 715
aaacuggaau gacugaau 18

<210> SEQ ID NO 716
<211> LENGTH: 19
<212> TYPE: RNA
<213> ORGANISM: Artificial Sequence
<220> FEATURE:
<223> OTHER INFORMATION: Targeting domain

<400> SEQUENCE: 716
aaaacuggaa ugacugaau 19

<210> SEQ ID NO 717
<211> LENGTH: 21
<212> TYPE: RNA
<213> ORGANISM: Artificial Sequence
<220> FEATURE:
<223> OTHER INFORMATION: Targeting domain

<400> SEQUENCE: 717
gaaaaacugg aaugacugaa u 21

<210> SEQ ID NO 718
<211> LENGTH: 22
<212> TYPE: RNA
<213> ORGANISM: Artificial Sequence
<220> FEATURE:
<223> OTHER INFORMATION: Targeting domain

<400> SEQUENCE: 718
agaaaaacug gaaugacuga au 22

<210> SEQ ID NO 719
<211> LENGTH: 23
<212> TYPE: RNA
<213> ORGANISM: Artificial Sequence
<220> FEATURE:
<223> OTHER INFORMATION: Targeting domain

<400> SEQUENCE: 719
gagaaaaacu ggaaugacug aau 23

<210> SEQ ID NO 720
<211> LENGTH: 24
<212> TYPE: RNA
<213> ORGANISM: Artificial Sequence
<220> FEATURE:
<223> OTHER INFORMATION: Targeting domain

<400> SEQUENCE: 720
agagaaaaac uggaaugacu gaau 24

<210> SEQ ID NO 721
<211> LENGTH: 18
<212> TYPE: RNA
<213> ORGANISM: Artificial Sequence
<220> FEATURE:
<223> OTHER INFORMATION: Targeting domain

<400> SEQUENCE: 721
ccugguaucc ucuaugau 18

<210> SEQ ID NO 722
<211> LENGTH: 19
<212> TYPE: RNA
<213> ORGANISM: Artificial Sequence
<220> FEATURE:
<223> OTHER INFORMATION: Targeting domain

<400> SEQUENCE: 722
uccugguauc cucuaugau 19

<210> SEQ ID NO 723
<211> LENGTH: 21
<212> TYPE: RNA
<213> ORGANISM: Artificial Sequence
<220> FEATURE:
<223> OTHER INFORMATION: Targeting domain

<400> SEQUENCE: 723
aguccuggua uccucuauga u 21

<210> SEQ ID NO 724
<211> LENGTH: 22
<212> TYPE: RNA
<213> ORGANISM: Artificial Sequence
<220> FEATURE:
<223> OTHER INFORMATION: Targeting domain

<400> SEQUENCE: 724
aaguccuggu auccucuaug au 22

<210> SEQ ID NO 725
<211> LENGTH: 23
<212> TYPE: RNA
<213> ORGANISM: Artificial Sequence
<220> FEATURE:
<223> OTHER INFORMATION: Targeting domain

<400> SEQUENCE: 725
gaaguccugg uauccucuau gau 23

<210> SEQ ID NO 726
<211> LENGTH: 24
<212> TYPE: RNA
<213> ORGANISM: Artificial Sequence
<220> FEATURE:
<223> OTHER INFORMATION: Targeting domain

<400> SEQUENCE: 726
agaaguccug guauccucua ugau 24

<210> SEQ ID NO 727
<211> LENGTH: 18
<212> TYPE: RNA
<213> ORGANISM: Artificial Sequence
<220> FEATURE:
<223> OTHER INFORMATION: Targeting domain

<400> SEQUENCE: 727
aaauuagcag uauccucu 18

<210> SEQ ID NO 728
<211> LENGTH: 19
<212> TYPE: RNA
<213> ORGANISM: Artificial Sequence
<220> FEATURE:
<223> OTHER INFORMATION: Targeting domain

<400> SEQUENCE: 728
aaaauuagca guauccucu 19

<210> SEQ ID NO 729
<211> LENGTH: 21
<212> TYPE: RNA
<213> ORGANISM: Artificial Sequence
<220> FEATURE:
<223> OTHER INFORMATION: Targeting domain

<400> SEQUENCE: 729
aaaaaauuag caguauccuc u 21

<210> SEQ ID NO 730
<211> LENGTH: 22
<212> TYPE: RNA
<213> ORGANISM: Artificial Sequence
<220> FEATURE:
<223> OTHER INFORMATION: Targeting domain

<400> SEQUENCE: 730
aaaaaaauua gcaguauccu cu 22

<210> SEQ ID NO 731
<211> LENGTH: 23
<212> TYPE: RNA
<213> ORGANISM: Artificial Sequence
<220> FEATURE:
<223> OTHER INFORMATION: Targeting domain

<400> SEQUENCE: 731
aaaaaaaauu agcaguaucc ucu 23

<210> SEQ ID NO 732

```
<211> LENGTH: 24
<212> TYPE: RNA
<213> ORGANISM: Artificial Sequence
<220> FEATURE:
<223> OTHER INFORMATION: Targeting domain

<400> SEQUENCE: 732

uaaaaaaaau uagcaguauc cucu                                              24


<210> SEQ ID NO 733
<211> LENGTH: 18
<212> TYPE: RNA
<213> ORGANISM: Artificial Sequence
<220> FEATURE:
<223> OTHER INFORMATION: Targeting domain

<400> SEQUENCE: 733

cacucgcuuc uggaacgu                                                     18


<210> SEQ ID NO 734
<211> LENGTH: 19
<212> TYPE: RNA
<213> ORGANISM: Artificial Sequence
<220> FEATURE:
<223> OTHER INFORMATION: Targeting domain

<400> SEQUENCE: 734

acacucgcuu cuggaacgu                                                    19


<210> SEQ ID NO 735
<211> LENGTH: 20
<212> TYPE: RNA
<213> ORGANISM: Artificial Sequence
<220> FEATURE:
<223> OTHER INFORMATION: Targeting domain

<400> SEQUENCE: 735

cacacucgcu ucuggaacgu                                                   20


<210> SEQ ID NO 736
<211> LENGTH: 21
<212> TYPE: RNA
<213> ORGANISM: Artificial Sequence
<220> FEATURE:
<223> OTHER INFORMATION: Targeting domain

<400> SEQUENCE: 736

acacacucgc uucuggaacg u                                                 21


<210> SEQ ID NO 737
<211> LENGTH: 22
<212> TYPE: RNA
<213> ORGANISM: Artificial Sequence
<220> FEATURE:
<223> OTHER INFORMATION: Targeting domain

<400> SEQUENCE: 737

cacacacucg cuucuggaac gu                                                22


<210> SEQ ID NO 738
<211> LENGTH: 23
<212> TYPE: RNA
<213> ORGANISM: Artificial Sequence
<220> FEATURE:
<223> OTHER INFORMATION: Targeting domain

<400> SEQUENCE: 738
```

ccacacacuc gcuucuggaa cgu 23

<210> SEQ ID NO 739
<211> LENGTH: 24
<212> TYPE: RNA
<213> ORGANISM: Artificial Sequence
<220> FEATURE:
<223> OTHER INFORMATION: Targeting domain

<400> SEQUENCE: 739
uccacacacu cgcuucugga acgu 24

<210> SEQ ID NO 740
<211> LENGTH: 18
<212> TYPE: RNA
<213> ORGANISM: Artificial Sequence
<220> FEATURE:
<223> OTHER INFORMATION: Targeting domain

<400> SEQUENCE: 740
cucaaugcaa auaucugu 18

<210> SEQ ID NO 741
<211> LENGTH: 19
<212> TYPE: RNA
<213> ORGANISM: Artificial Sequence
<220> FEATURE:
<223> OTHER INFORMATION: Targeting domain

<400> SEQUENCE: 741
ucucaaugca aauaucugu 19

<210> SEQ ID NO 742
<211> LENGTH: 20
<212> TYPE: RNA
<213> ORGANISM: Artificial Sequence
<220> FEATURE:
<223> OTHER INFORMATION: Targeting domain

<400> SEQUENCE: 742
aucucaaugc aaauaucugu 20

<210> SEQ ID NO 743
<211> LENGTH: 21
<212> TYPE: RNA
<213> ORGANISM: Artificial Sequence
<220> FEATURE:
<223> OTHER INFORMATION: Targeting domain

<400> SEQUENCE: 743
uaucucaaug caaauaucug u 21

<210> SEQ ID NO 744
<211> LENGTH: 22
<212> TYPE: RNA
<213> ORGANISM: Artificial Sequence
<220> FEATURE:
<223> OTHER INFORMATION: Targeting domain

<400> SEQUENCE: 744
cuaucucaau gcaaauaucu gu 22

<210> SEQ ID NO 745
<211> LENGTH: 23
<212> TYPE: RNA

<213> ORGANISM: Artificial Sequence
<220> FEATURE:
<223> OTHER INFORMATION: Targeting domain

<400> SEQUENCE: 745
acuaucucaa ugcaaauauc ugu 23

<210> SEQ ID NO 746
<211> LENGTH: 24
<212> TYPE: RNA
<213> ORGANISM: Artificial Sequence
<220> FEATURE:
<223> OTHER INFORMATION: Targeting domain

<400> SEQUENCE: 746
cacuaucuca augcaaauau cugu 24

<210> SEQ ID NO 747
<211> LENGTH: 18
<212> TYPE: RNA
<213> ORGANISM: Artificial Sequence
<220> FEATURE:
<223> OTHER INFORMATION: Targeting domain

<400> SEQUENCE: 747
aguuccacac acucgcuu 18

<210> SEQ ID NO 748
<211> LENGTH: 19
<212> TYPE: RNA
<213> ORGANISM: Artificial Sequence
<220> FEATURE:
<223> OTHER INFORMATION: Targeting domain

<400> SEQUENCE: 748
caguuccaca cacucgcuu 19

<210> SEQ ID NO 749
<211> LENGTH: 20
<212> TYPE: RNA
<213> ORGANISM: Artificial Sequence
<220> FEATURE:
<223> OTHER INFORMATION: Targeting domain

<400> SEQUENCE: 749
gcaguuccac acacucgcuu 20

<210> SEQ ID NO 750
<211> LENGTH: 21
<212> TYPE: RNA
<213> ORGANISM: Artificial Sequence
<220> FEATURE:
<223> OTHER INFORMATION: Targeting domain

<400> SEQUENCE: 750
agcaguucca cacacucgcu u 21

<210> SEQ ID NO 751
<211> LENGTH: 22
<212> TYPE: RNA
<213> ORGANISM: Artificial Sequence
<220> FEATURE:
<223> OTHER INFORMATION: Targeting domain

<400> SEQUENCE: 751
cagcaguucc acacacucgc uu 22

<210> SEQ ID NO 752
<211> LENGTH: 23
<212> TYPE: RNA
<213> ORGANISM: Artificial Sequence
<220> FEATURE:
<223> OTHER INFORMATION: Targeting domain

<400> SEQUENCE: 752
ucagcaguuc cacacacucg cuu 23

<210> SEQ ID NO 753
<211> LENGTH: 24
<212> TYPE: RNA
<213> ORGANISM: Artificial Sequence
<220> FEATURE:
<223> OTHER INFORMATION: Targeting domain

<400> SEQUENCE: 753
uucagcaguu ccacacacuc gcuu 24

<210> SEQ ID NO 754
<211> LENGTH: 18
<212> TYPE: RNA
<213> ORGANISM: Artificial Sequence
<220> FEATURE:
<223> OTHER INFORMATION: Targeting domain

<400> SEQUENCE: 754
aauuagcagu auccucuu 18

<210> SEQ ID NO 755
<211> LENGTH: 19
<212> TYPE: RNA
<213> ORGANISM: Artificial Sequence
<220> FEATURE:
<223> OTHER INFORMATION: Targeting domain

<400> SEQUENCE: 755
aaauuagcag uauccucuu 19

<210> SEQ ID NO 756
<211> LENGTH: 21
<212> TYPE: RNA
<213> ORGANISM: Artificial Sequence
<220> FEATURE:
<223> OTHER INFORMATION: Targeting domain

<400> SEQUENCE: 756
aaaaauuagc aguauccucu u 21

<210> SEQ ID NO 757
<211> LENGTH: 22
<212> TYPE: RNA
<213> ORGANISM: Artificial Sequence
<220> FEATURE:
<223> OTHER INFORMATION: Targeting domain

<400> SEQUENCE: 757
aaaaaauuag caguauccuc uu 22

<210> SEQ ID NO 758
<211> LENGTH: 23
<212> TYPE: RNA
<213> ORGANISM: Artificial Sequence
<220> FEATURE:

<223> OTHER INFORMATION: Targeting domain

<400> SEQUENCE: 758
aaaaaaauua gcaguauccu cuu 23

<210> SEQ ID NO 759
<211> LENGTH: 24
<212> TYPE: RNA
<213> ORGANISM: Artificial Sequence
<220> FEATURE:
<223> OTHER INFORMATION: Targeting domain

<400> SEQUENCE: 759
aaaaaaaauu agcaguaucc ucuu 24

<210> SEQ ID NO 760
<211> LENGTH: 17
<212> TYPE: RNA
<213> ORGANISM: Artificial Sequence
<220> FEATURE:
<223> OTHER INFORMATION: Targeting domain

<400> SEQUENCE: 760
gaagaaaacu agcuaaa 17

<210> SEQ ID NO 761
<211> LENGTH: 17
<212> TYPE: RNA
<213> ORGANISM: Artificial Sequence
<220> FEATURE:
<223> OTHER INFORMATION: Targeting domain

<400> SEQUENCE: 761
gcagcaguau ccucuug 17

<210> SEQ ID NO 762
<211> LENGTH: 20
<212> TYPE: RNA
<213> ORGANISM: Artificial Sequence
<220> FEATURE:
<223> OTHER INFORMATION: Targeting domain

<400> SEQUENCE: 762
ggagaagaaa acuagcuaaa 20

<210> SEQ ID NO 763
<211> LENGTH: 20
<212> TYPE: RNA
<213> ORGANISM: Artificial Sequence
<220> FEATURE:
<223> OTHER INFORMATION: Targeting domain

<400> SEQUENCE: 763
gggagaagaa aacuagcuaa 20

<210> SEQ ID NO 764
<211> LENGTH: 20
<212> TYPE: RNA
<213> ORGANISM: Artificial Sequence
<220> FEATURE:
<223> OTHER INFORMATION: Targeting domain

<400> SEQUENCE: 764
guccugguau cuucuauggu 20

<210> SEQ ID NO 765
<211> LENGTH: 17
<212> TYPE: RNA
<213> ORGANISM: Artificial Sequence
<220> FEATURE:
<223> OTHER INFORMATION: Targeting domain

<400> SEQUENCE: 765
agaagaaaac uagcuaa 17

<210> SEQ ID NO 766
<211> LENGTH: 17
<212> TYPE: RNA
<213> ORGANISM: Artificial Sequence
<220> FEATURE:
<223> OTHER INFORMATION: Targeting domain

<400> SEQUENCE: 766
aguccuggua ucuucua 17

<210> SEQ ID NO 767
<211> LENGTH: 17
<212> TYPE: RNA
<213> ORGANISM: Artificial Sequence
<220> FEATURE:
<223> OTHER INFORMATION: Targeting domain

<400> SEQUENCE: 767
ccaccauaga agauacc 17

<210> SEQ ID NO 768
<211> LENGTH: 17
<212> TYPE: RNA
<213> ORGANISM: Artificial Sequence
<220> FEATURE:
<223> OTHER INFORMATION: Targeting domain

<400> SEQUENCE: 768
ccugguaucu ucuaugg 17

<210> SEQ ID NO 769
<211> LENGTH: 17
<212> TYPE: RNA
<213> ORGANISM: Artificial Sequence
<220> FEATURE:
<223> OTHER INFORMATION: Targeting domain

<400> SEQUENCE: 769
cagcaguauc cucuugg 17

<210> SEQ ID NO 770
<211> LENGTH: 17
<212> TYPE: RNA
<213> ORGANISM: Artificial Sequence
<220> FEATURE:
<223> OTHER INFORMATION: Targeting domain

<400> SEQUENCE: 770
aauuggaaug acugaau 17

<210> SEQ ID NO 771
<211> LENGTH: 17
<212> TYPE: RNA
<213> ORGANISM: Artificial Sequence
<220> FEATURE:
<223> OTHER INFORMATION: Targeting domain

<400> SEQUENCE: 771
cugguaucuu cuauggu 17

<210> SEQ ID NO 772
<211> LENGTH: 17
<212> TYPE: RNA
<213> ORGANISM: Artificial Sequence
<220> FEATURE:
<223> OTHER INFORMATION: Targeting domain

<400> SEQUENCE: 772
agcagcagua uccucuu 17

<210> SEQ ID NO 773
<211> LENGTH: 20
<212> TYPE: RNA
<213> ORGANISM: Artificial Sequence
<220> FEATURE:
<223> OTHER INFORMATION: Targeting domain

<400> SEQUENCE: 773
agaaguccug guaucuucua 20

<210> SEQ ID NO 774
<211> LENGTH: 20
<212> TYPE: RNA
<213> ORGANISM: Artificial Sequence
<220> FEATURE:
<223> OTHER INFORMATION: Targeting domain

<400> SEQUENCE: 774
cucccaccau agaagauacc 20

<210> SEQ ID NO 775
<211> LENGTH: 20
<212> TYPE: RNA
<213> ORGANISM: Artificial Sequence
<220> FEATURE:
<223> OTHER INFORMATION: Targeting domain

<400> SEQUENCE: 775
aguccuggua ucuucuaugg 20

<210> SEQ ID NO 776
<211> LENGTH: 20
<212> TYPE: RNA
<213> ORGANISM: Artificial Sequence
<220> FEATURE:
<223> OTHER INFORMATION: Targeting domain

<400> SEQUENCE: 776
aagcagcagu auccucuugg 20

<210> SEQ ID NO 777
<211> LENGTH: 20
<212> TYPE: RNA
<213> ORGANISM: Artificial Sequence
<220> FEATURE:
<223> OTHER INFORMATION: Targeting domain

<400> SEQUENCE: 777
uaagcagcag uauccucuug 20

<210> SEQ ID NO 778
<211> LENGTH: 20

```
<212> TYPE: RNA
<213> ORGANISM: Artificial Sequence
<220> FEATURE:
<223> OTHER INFORMATION: Targeting domain

<400> SEQUENCE: 778

agaauaaauu agagaaaaau                                               20

<210> SEQ ID NO 779
<211> LENGTH: 20
<212> TYPE: RNA
<213> ORGANISM: Artificial Sequence
<220> FEATURE:
<223> OTHER INFORMATION: Targeting domain

<400> SEQUENCE: 779

aaaaauugga augacugaau                                               20

<210> SEQ ID NO 780
<211> LENGTH: 20
<212> TYPE: RNA
<213> ORGANISM: Artificial Sequence
<220> FEATURE:
<223> OTHER INFORMATION: Targeting domain

<400> SEQUENCE: 780

auuaagcagc aguauccucu                                               20

<210> SEQ ID NO 781
<211> LENGTH: 20
<212> TYPE: RNA
<213> ORGANISM: Artificial Sequence
<220> FEATURE:
<223> OTHER INFORMATION: Targeting domain

<400> SEQUENCE: 781

uuaagcagca guauccucuu                                               20

<210> SEQ ID NO 782
<211> LENGTH: 17
<212> TYPE: RNA
<213> ORGANISM: Artificial Sequence
<220> FEATURE:
<223> OTHER INFORMATION: Targeting domain

<400> SEQUENCE: 782

auaaauuaga gaaaaau                                                  17

<210> SEQ ID NO 783
<211> LENGTH: 17
<212> TYPE: RNA
<213> ORGANISM: Artificial Sequence
<220> FEATURE:
<223> OTHER INFORMATION: Targeting domain

<400> SEQUENCE: 783

aagcagcagu auccucu                                                  17

<210> SEQ ID NO 784
<211> LENGTH: 20
<212> TYPE: RNA
<213> ORGANISM: Artificial Sequence
<220> FEATURE:
<223> OTHER INFORMATION: Targeting domain

<400> SEQUENCE: 784
```

gaagaaaacu agcuaaaggg 20

<210> SEQ ID NO 785
<211> LENGTH: 22
<212> TYPE: RNA
<213> ORGANISM: Artificial Sequence
<220> FEATURE:
<223> OTHER INFORMATION: Targeting domain

<400> SEQUENCE: 785
gagaagaaaa cuagcuaaag gg 22

<210> SEQ ID NO 786
<211> LENGTH: 23
<212> TYPE: RNA
<213> ORGANISM: Artificial Sequence
<220> FEATURE:
<223> OTHER INFORMATION: Targeting domain

<400> SEQUENCE: 786
ggagaagaaa acuagcuaaa ggg 23

<210> SEQ ID NO 787
<211> LENGTH: 24
<212> TYPE: RNA
<213> ORGANISM: Artificial Sequence
<220> FEATURE:
<223> OTHER INFORMATION: Targeting domain

<400> SEQUENCE: 787
gggagaagaa aacuagcuaa aggg 24

<210> SEQ ID NO 788
<211> LENGTH: 19
<212> TYPE: RNA
<213> ORGANISM: Artificial Sequence
<220> FEATURE:
<223> OTHER INFORMATION: Targeting domain

<400> SEQUENCE: 788
gaauaaauua gagaaaaau 19

<210> SEQ ID NO 789
<211> LENGTH: 22
<212> TYPE: RNA
<213> ORGANISM: Artificial Sequence
<220> FEATURE:
<223> OTHER INFORMATION: Targeting domain

<400> SEQUENCE: 789
gaagaauaaa uuagagaaaa au 22

<210> SEQ ID NO 790
<211> LENGTH: 23
<212> TYPE: RNA
<213> ORGANISM: Artificial Sequence
<220> FEATURE:
<223> OTHER INFORMATION: Targeting domain

<400> SEQUENCE: 790
ggaagaauaa auuagagaaa aau 23

<210> SEQ ID NO 791
<211> LENGTH: 24
<212> TYPE: RNA
<213> ORGANISM: Artificial Sequence
<220> FEATURE:
<223> OTHER INFORMATION: Targeting domain

<400> SEQUENCE: 791
gggaagaaua aauuagagaa aaau 24

<210> SEQ ID NO 792
<211> LENGTH: 18
<212> TYPE: RNA
<213> ORGANISM: Artificial Sequence
<220> FEATURE:
<223> OTHER INFORMATION: Targeting domain

<400> SEQUENCE: 792
agagaaaaau uggaauga 18

<210> SEQ ID NO 793
<211> LENGTH: 19
<212> TYPE: RNA
<213> ORGANISM: Artificial Sequence
<220> FEATURE:
<223> OTHER INFORMATION: Targeting domain

<400> SEQUENCE: 793
uagagaaaaa uuggaauga 19

<210> SEQ ID NO 794
<211> LENGTH: 20
<212> TYPE: RNA
<213> ORGANISM: Artificial Sequence
<220> FEATURE:
<223> OTHER INFORMATION: Targeting domain

<400> SEQUENCE: 794
uuagagaaaa auuggaauga 20

<210> SEQ ID NO 795
<211> LENGTH: 21
<212> TYPE: RNA
<213> ORGANISM: Artificial Sequence
<220> FEATURE:
<223> OTHER INFORMATION: Targeting domain

<400> SEQUENCE: 795
auuagagaaa aauuggaaug a 21

<210> SEQ ID NO 796
<211> LENGTH: 22
<212> TYPE: RNA
<213> ORGANISM: Artificial Sequence
<220> FEATURE:
<223> OTHER INFORMATION: Targeting domain

<400> SEQUENCE: 796
aauuagagaa aaauuggaau ga 22

<210> SEQ ID NO 797
<211> LENGTH: 23
<212> TYPE: RNA
<213> ORGANISM: Artificial Sequence
<220> FEATURE:
<223> OTHER INFORMATION: Targeting domain

<400> SEQUENCE: 797
aaauuagaga aaaauuggaa uga 23

<210> SEQ ID NO 798
<211> LENGTH: 24
<212> TYPE: RNA
<213> ORGANISM: Artificial Sequence
<220> FEATURE:
<223> OTHER INFORMATION: Targeting domain

<400> SEQUENCE: 798
uaaauuagag aaaaauugga auga 24

<210> SEQ ID NO 799
<211> LENGTH: 18
<212> TYPE: RNA
<213> ORGANISM: Artificial Sequence
<220> FEATURE:
<223> OTHER INFORMATION: Targeting domain

<400> SEQUENCE: 799
agaaaacuag cuaaaggg 18

<210> SEQ ID NO 800
<211> LENGTH: 19
<212> TYPE: RNA
<213> ORGANISM: Artificial Sequence
<220> FEATURE:
<223> OTHER INFORMATION: Targeting domain

<400> SEQUENCE: 800
aagaaaacua gcuaaaggg 19

<210> SEQ ID NO 801
<211> LENGTH: 21
<212> TYPE: RNA
<213> ORGANISM: Artificial Sequence
<220> FEATURE:
<223> OTHER INFORMATION: Targeting domain

<400> SEQUENCE: 801
agaagaaaac uagcuaaagg g 21

<210> SEQ ID NO 802
<211> LENGTH: 18
<212> TYPE: RNA
<213> ORGANISM: Artificial Sequence
<220> FEATURE:
<223> OTHER INFORMATION: Targeting domain

<400> SEQUENCE: 802
aauaaauuag agaaaaau 18

<210> SEQ ID NO 803
<211> LENGTH: 21
<212> TYPE: RNA
<213> ORGANISM: Artificial Sequence
<220> FEATURE:
<223> OTHER INFORMATION: Targeting domain

<400> SEQUENCE: 803
aagaauaaau uagagaaaaa u 21

<210> SEQ ID NO 804
<211> LENGTH: 18
<212> TYPE: RNA
<213> ORGANISM: Artificial Sequence
<220> FEATURE:
<223> OTHER INFORMATION: Targeting domain

<400> SEQUENCE: 804
aguuuucuuc ucccacca 18

<210> SEQ ID NO 805
<211> LENGTH: 19
<212> TYPE: RNA
<213> ORGANISM: Artificial Sequence
<220> FEATURE:
<223> OTHER INFORMATION: Targeting domain

<400> SEQUENCE: 805
uaguuuucuu cucccacca 19

<210> SEQ ID NO 806
<211> LENGTH: 20
<212> TYPE: RNA
<213> ORGANISM: Artificial Sequence
<220> FEATURE:
<223> OTHER INFORMATION: Targeting domain

<400> SEQUENCE: 806
cuaguuuucu ucucccacca 20

<210> SEQ ID NO 807
<211> LENGTH: 21
<212> TYPE: RNA
<213> ORGANISM: Artificial Sequence
<220> FEATURE:
<223> OTHER INFORMATION: Targeting domain

<400> SEQUENCE: 807
gcuaguuuuc uucucccacc a 21

<210> SEQ ID NO 808
<211> LENGTH: 22
<212> TYPE: RNA
<213> ORGANISM: Artificial Sequence
<220> FEATURE:
<223> OTHER INFORMATION: Targeting domain

<400> SEQUENCE: 808
agcuaguuuu cuucucccac ca 22

<210> SEQ ID NO 809
<211> LENGTH: 23
<212> TYPE: RNA
<213> ORGANISM: Artificial Sequence
<220> FEATURE:
<223> OTHER INFORMATION: Targeting domain

<400> SEQUENCE: 809
uagcuaguuu ucuucuccca cca 23

<210> SEQ ID NO 810
<211> LENGTH: 24
<212> TYPE: RNA
<213> ORGANISM: Artificial Sequence
<220> FEATURE:
<223> OTHER INFORMATION: Targeting domain

<400> SEQUENCE: 810
uuagcuaguu uucuucuccc acca 24

<210> SEQ ID NO 811

<211> LENGTH: 18
<212> TYPE: RNA
<213> ORGANISM: Artificial Sequence
<220> FEATURE:
<223> OTHER INFORMATION: Targeting domain

<400> SEQUENCE: 811
ucccaccaua gaagauac 18

<210> SEQ ID NO 812
<211> LENGTH: 19
<212> TYPE: RNA
<213> ORGANISM: Artificial Sequence
<220> FEATURE:
<223> OTHER INFORMATION: Targeting domain

<400> SEQUENCE: 812
cucccaccau agaagauac 19

<210> SEQ ID NO 813
<211> LENGTH: 20
<212> TYPE: RNA
<213> ORGANISM: Artificial Sequence
<220> FEATURE:
<223> OTHER INFORMATION: Targeting domain

<400> SEQUENCE: 813
ucucccacca uagaagauac 20

<210> SEQ ID NO 814
<211> LENGTH: 21
<212> TYPE: RNA
<213> ORGANISM: Artificial Sequence
<220> FEATURE:
<223> OTHER INFORMATION: Targeting domain

<400> SEQUENCE: 814
uucucccacc auagaagaua c 21

<210> SEQ ID NO 815
<211> LENGTH: 22
<212> TYPE: RNA
<213> ORGANISM: Artificial Sequence
<220> FEATURE:
<223> OTHER INFORMATION: Targeting domain

<400> SEQUENCE: 815
cuucucccac cauagaagau ac 22

<210> SEQ ID NO 816
<211> LENGTH: 23
<212> TYPE: RNA
<213> ORGANISM: Artificial Sequence
<220> FEATURE:
<223> OTHER INFORMATION: Targeting domain

<400> SEQUENCE: 816
ucuucuccca ccauagaaga uac 23

<210> SEQ ID NO 817
<211> LENGTH: 24
<212> TYPE: RNA
<213> ORGANISM: Artificial Sequence
<220> FEATURE:
<223> OTHER INFORMATION: Targeting domain

<400> SEQUENCE: 817
uucuucuccc accauagaag auac 24

<210> SEQ ID NO 818
<211> LENGTH: 18
<212> TYPE: RNA
<213> ORGANISM: Artificial Sequence
<220> FEATURE:
<223> OTHER INFORMATION: Targeting domain

<400> SEQUENCE: 818
agaagaaaac uagcuaaa 18

<210> SEQ ID NO 819
<211> LENGTH: 19
<212> TYPE: RNA
<213> ORGANISM: Artificial Sequence
<220> FEATURE:
<223> OTHER INFORMATION: Targeting domain

<400> SEQUENCE: 819
gagaagaaaa cuagcuaaa 19

<210> SEQ ID NO 820
<211> LENGTH: 21
<212> TYPE: RNA
<213> ORGANISM: Artificial Sequence
<220> FEATURE:
<223> OTHER INFORMATION: Targeting domain

<400> SEQUENCE: 820
gggagaagaa aacuagcuaa a 21

<210> SEQ ID NO 821
<211> LENGTH: 22
<212> TYPE: RNA
<213> ORGANISM: Artificial Sequence
<220> FEATURE:
<223> OTHER INFORMATION: Targeting domain

<400> SEQUENCE: 821
ugggagaaga aaacuagcua aa 22

<210> SEQ ID NO 822
<211> LENGTH: 23
<212> TYPE: RNA
<213> ORGANISM: Artificial Sequence
<220> FEATURE:
<223> OTHER INFORMATION: Targeting domain

<400> SEQUENCE: 822
gugggagaag aaaacuagcu aaa 23

<210> SEQ ID NO 823
<211> LENGTH: 24
<212> TYPE: RNA
<213> ORGANISM: Artificial Sequence
<220> FEATURE:
<223> OTHER INFORMATION: Targeting domain

<400> SEQUENCE: 823
ggugggagaa gaaaacuagc uaaa 24

<210> SEQ ID NO 824
<211> LENGTH: 18
<212> TYPE: RNA

<213> ORGANISM: Artificial Sequence
<220> FEATURE:
<223> OTHER INFORMATION: Targeting domain

<400> SEQUENCE: 824
aaaauuggaa ugacugaa 18

<210> SEQ ID NO 825
<211> LENGTH: 19
<212> TYPE: RNA
<213> ORGANISM: Artificial Sequence
<220> FEATURE:
<223> OTHER INFORMATION: Targeting domain

<400> SEQUENCE: 825
aaaaauugga augacugaa 19

<210> SEQ ID NO 826
<211> LENGTH: 20
<212> TYPE: RNA
<213> ORGANISM: Artificial Sequence
<220> FEATURE:
<223> OTHER INFORMATION: Targeting domain

<400> SEQUENCE: 826
gaaaaauugg aaugacugaa 20

<210> SEQ ID NO 827
<211> LENGTH: 21
<212> TYPE: RNA
<213> ORGANISM: Artificial Sequence
<220> FEATURE:
<223> OTHER INFORMATION: Targeting domain

<400> SEQUENCE: 827
agaaaaauug gaaugacuga a 21

<210> SEQ ID NO 828
<211> LENGTH: 22
<212> TYPE: RNA
<213> ORGANISM: Artificial Sequence
<220> FEATURE:
<223> OTHER INFORMATION: Targeting domain

<400> SEQUENCE: 828
gagaaaaauu ggaaugacug aa 22

<210> SEQ ID NO 829
<211> LENGTH: 23
<212> TYPE: RNA
<213> ORGANISM: Artificial Sequence
<220> FEATURE:
<223> OTHER INFORMATION: Targeting domain

<400> SEQUENCE: 829
agagaaaaau uggaaugacu gaa 23

<210> SEQ ID NO 830
<211> LENGTH: 24
<212> TYPE: RNA
<213> ORGANISM: Artificial Sequence
<220> FEATURE:
<223> OTHER INFORMATION: Targeting domain

<400> SEQUENCE: 830
uagagaaaaa uuggaaugac ugaa 24

<210> SEQ ID NO 831
<211> LENGTH: 18
<212> TYPE: RNA
<213> ORGANISM: Artificial Sequence
<220> FEATURE:
<223> OTHER INFORMATION: Targeting domain

<400> SEQUENCE: 831
gagaagaaaa cuagcuaa 18

<210> SEQ ID NO 832
<211> LENGTH: 19
<212> TYPE: RNA
<213> ORGANISM: Artificial Sequence
<220> FEATURE:
<223> OTHER INFORMATION: Targeting domain

<400> SEQUENCE: 832
ggagaagaaa acuagcuaa 19

<210> SEQ ID NO 833
<211> LENGTH: 21
<212> TYPE: RNA
<213> ORGANISM: Artificial Sequence
<220> FEATURE:
<223> OTHER INFORMATION: Targeting domain

<400> SEQUENCE: 833
ugggagaaga aaacuagcua a 21

<210> SEQ ID NO 834
<211> LENGTH: 22
<212> TYPE: RNA
<213> ORGANISM: Artificial Sequence
<220> FEATURE:
<223> OTHER INFORMATION: Targeting domain

<400> SEQUENCE: 834
gugggagaag aaaacuagcu aa 22

<210> SEQ ID NO 835
<211> LENGTH: 23
<212> TYPE: RNA
<213> ORGANISM: Artificial Sequence
<220> FEATURE:
<223> OTHER INFORMATION: Targeting domain

<400> SEQUENCE: 835
ggugggagaa gaaaacuagc uaa 23

<210> SEQ ID NO 836
<211> LENGTH: 24
<212> TYPE: RNA
<213> ORGANISM: Artificial Sequence
<220> FEATURE:
<223> OTHER INFORMATION: Targeting domain

<400> SEQUENCE: 836
uggugggaga agaaaacuag cuaa 24

<210> SEQ ID NO 837
<211> LENGTH: 18
<212> TYPE: RNA
<213> ORGANISM: Artificial Sequence
<220> FEATURE:

<223> OTHER INFORMATION: Targeting domain

<400> SEQUENCE: 837
ggagaagaaa acuagcua 18

<210> SEQ ID NO 838
<211> LENGTH: 19
<212> TYPE: RNA
<213> ORGANISM: Artificial Sequence
<220> FEATURE:
<223> OTHER INFORMATION: Targeting domain

<400> SEQUENCE: 838
gggagaagaa aacuagcua 19

<210> SEQ ID NO 839
<211> LENGTH: 20
<212> TYPE: RNA
<213> ORGANISM: Artificial Sequence
<220> FEATURE:
<223> OTHER INFORMATION: Targeting domain

<400> SEQUENCE: 839
ugggagaaga aaacuagcua 20

<210> SEQ ID NO 840
<211> LENGTH: 21
<212> TYPE: RNA
<213> ORGANISM: Artificial Sequence
<220> FEATURE:
<223> OTHER INFORMATION: Targeting domain

<400> SEQUENCE: 840
gugggagaag aaaacuagcu a 21

<210> SEQ ID NO 841
<211> LENGTH: 22
<212> TYPE: RNA
<213> ORGANISM: Artificial Sequence
<220> FEATURE:
<223> OTHER INFORMATION: Targeting domain

<400> SEQUENCE: 841
ggugggagaa gaaaacuagc ua 22

<210> SEQ ID NO 842
<211> LENGTH: 23
<212> TYPE: RNA
<213> ORGANISM: Artificial Sequence
<220> FEATURE:
<223> OTHER INFORMATION: Targeting domain

<400> SEQUENCE: 842
uggugggaga agaaaacuag cua 23

<210> SEQ ID NO 843
<211> LENGTH: 24
<212> TYPE: RNA
<213> ORGANISM: Artificial Sequence
<220> FEATURE:
<223> OTHER INFORMATION: Targeting domain

<400> SEQUENCE: 843
auggugggag aagaaaacua gcua 24

<210> SEQ ID NO 844
<211> LENGTH: 18
<212> TYPE: RNA
<213> ORGANISM: Artificial Sequence
<220> FEATURE:
<223> OTHER INFORMATION: Targeting domain

<400> SEQUENCE: 844
uuaagcagca guauccuc 18

<210> SEQ ID NO 845
<211> LENGTH: 19
<212> TYPE: RNA
<213> ORGANISM: Artificial Sequence
<220> FEATURE:
<223> OTHER INFORMATION: Targeting domain

<400> SEQUENCE: 845
auuaagcagc aguauccuc 19

<210> SEQ ID NO 846
<211> LENGTH: 20
<212> TYPE: RNA
<213> ORGANISM: Artificial Sequence
<220> FEATURE:
<223> OTHER INFORMATION: Targeting domain

<400> SEQUENCE: 846
aauuaagcag caguauccuc 20

<210> SEQ ID NO 847
<211> LENGTH: 21
<212> TYPE: RNA
<213> ORGANISM: Artificial Sequence
<220> FEATURE:
<223> OTHER INFORMATION: Targeting domain

<400> SEQUENCE: 847
aaauuaagca gcaguauccu c 21

<210> SEQ ID NO 848
<211> LENGTH: 22
<212> TYPE: RNA
<213> ORGANISM: Artificial Sequence
<220> FEATURE:
<223> OTHER INFORMATION: Targeting domain

<400> SEQUENCE: 848
aaaauuaagc agcaguaucc uc 22

<210> SEQ ID NO 849
<211> LENGTH: 23
<212> TYPE: RNA
<213> ORGANISM: Artificial Sequence
<220> FEATURE:
<223> OTHER INFORMATION: Targeting domain

<400> SEQUENCE: 849
aaaaauuaag cagcaguauc cuc 23

<210> SEQ ID NO 850
<211> LENGTH: 24
<212> TYPE: RNA
<213> ORGANISM: Artificial Sequence
<220> FEATURE:
<223> OTHER INFORMATION: Targeting domain

<400> SEQUENCE: 850
aaaaaauuaa gcagcaguau ccuc 24

<210> SEQ ID NO 851
<211> LENGTH: 18
<212> TYPE: RNA
<213> ORGANISM: Artificial Sequence
<220> FEATURE:
<223> OTHER INFORMATION: Targeting domain

<400> SEQUENCE: 851
uaucuucuau ggugggag 18

<210> SEQ ID NO 852
<211> LENGTH: 19
<212> TYPE: RNA
<213> ORGANISM: Artificial Sequence
<220> FEATURE:
<223> OTHER INFORMATION: Targeting domain

<400> SEQUENCE: 852
guaucuucua uggugggag 19

<210> SEQ ID NO 853
<211> LENGTH: 20
<212> TYPE: RNA
<213> ORGANISM: Artificial Sequence
<220> FEATURE:
<223> OTHER INFORMATION: Targeting domain

<400> SEQUENCE: 853
gguaucuucu auggugggag 20

<210> SEQ ID NO 854
<211> LENGTH: 21
<212> TYPE: RNA
<213> ORGANISM: Artificial Sequence
<220> FEATURE:
<223> OTHER INFORMATION: Targeting domain

<400> SEQUENCE: 854
ugguaucuuc uaugguggga g 21

<210> SEQ ID NO 855
<211> LENGTH: 22
<212> TYPE: RNA
<213> ORGANISM: Artificial Sequence
<220> FEATURE:
<223> OTHER INFORMATION: Targeting domain

<400> SEQUENCE: 855
cugguaucuu cuauggugg ag 22

<210> SEQ ID NO 856
<211> LENGTH: 23
<212> TYPE: RNA
<213> ORGANISM: Artificial Sequence
<220> FEATURE:
<223> OTHER INFORMATION: Targeting domain

<400> SEQUENCE: 856
ccugguaucu ucuauggugg gag 23

<210> SEQ ID NO 857
<211> LENGTH: 24

<212> TYPE: RNA
<213> ORGANISM: Artificial Sequence
<220> FEATURE:
<223> OTHER INFORMATION: Targeting domain

<400> SEQUENCE: 857
uccugguauc uucuauggug ggag 24

<210> SEQ ID NO 858
<211> LENGTH: 18
<212> TYPE: RNA
<213> ORGANISM: Artificial Sequence
<220> FEATURE:
<223> OTHER INFORMATION: Targeting domain

<400> SEQUENCE: 858
uccugguauc uucuaugg 18

<210> SEQ ID NO 859
<211> LENGTH: 19
<212> TYPE: RNA
<213> ORGANISM: Artificial Sequence
<220> FEATURE:
<223> OTHER INFORMATION: Targeting domain

<400> SEQUENCE: 859
guccugguau cuucuaugg 19

<210> SEQ ID NO 860
<211> LENGTH: 21
<212> TYPE: RNA
<213> ORGANISM: Artificial Sequence
<220> FEATURE:
<223> OTHER INFORMATION: Targeting domain

<400> SEQUENCE: 860
aaguccuggu aucuucuaug g 21

<210> SEQ ID NO 861
<211> LENGTH: 22
<212> TYPE: RNA
<213> ORGANISM: Artificial Sequence
<220> FEATURE:
<223> OTHER INFORMATION: Targeting domain

<400> SEQUENCE: 861
gaaguccugg uaucuucuau gg 22

<210> SEQ ID NO 862
<211> LENGTH: 23
<212> TYPE: RNA
<213> ORGANISM: Artificial Sequence
<220> FEATURE:
<223> OTHER INFORMATION: Targeting domain

<400> SEQUENCE: 862
agaaguccug guaucuucua ugg 23

<210> SEQ ID NO 863
<211> LENGTH: 24
<212> TYPE: RNA
<213> ORGANISM: Artificial Sequence
<220> FEATURE:
<223> OTHER INFORMATION: Targeting domain

<400> SEQUENCE: 863
aagaaguccu gguaucuucu augg 24

<210> SEQ ID NO 864
<211> LENGTH: 18
<212> TYPE: RNA
<213> ORGANISM: Artificial Sequence
<220> FEATURE:
<223> OTHER INFORMATION: Targeting domain

<400> SEQUENCE: 864
ugguaucuuc uauggugg 18

<210> SEQ ID NO 865
<211> LENGTH: 19
<212> TYPE: RNA
<213> ORGANISM: Artificial Sequence
<220> FEATURE:
<223> OTHER INFORMATION: Targeting domain

<400> SEQUENCE: 865
cugguaucuu cuauggugg 19

<210> SEQ ID NO 866
<211> LENGTH: 20
<212> TYPE: RNA
<213> ORGANISM: Artificial Sequence
<220> FEATURE:
<223> OTHER INFORMATION: Targeting domain

<400> SEQUENCE: 866
ccugguaucu ucuauggugg 20

<210> SEQ ID NO 867
<211> LENGTH: 21
<212> TYPE: RNA
<213> ORGANISM: Artificial Sequence
<220> FEATURE:
<223> OTHER INFORMATION: Targeting domain

<400> SEQUENCE: 867
uccugguauc uucuauggug g 21

<210> SEQ ID NO 868
<211> LENGTH: 22
<212> TYPE: RNA
<213> ORGANISM: Artificial Sequence
<220> FEATURE:
<223> OTHER INFORMATION: Targeting domain

<400> SEQUENCE: 868
guccugguau cuucuauggu gg 22

<210> SEQ ID NO 869
<211> LENGTH: 23
<212> TYPE: RNA
<213> ORGANISM: Artificial Sequence
<220> FEATURE:
<223> OTHER INFORMATION: Targeting domain

<400> SEQUENCE: 869
aguccuggua ucuucuaugg ugg 23

<210> SEQ ID NO 870
<211> LENGTH: 24
<212> TYPE: RNA
<213> ORGANISM: Artificial Sequence
<220> FEATURE:
<223> OTHER INFORMATION: Targeting domain

<400> SEQUENCE: 870
aaguccuggu aucuucuaug gugg 24

<210> SEQ ID NO 871
<211> LENGTH: 18
<212> TYPE: RNA
<213> ORGANISM: Artificial Sequence
<220> FEATURE:
<223> OTHER INFORMATION: Targeting domain

<400> SEQUENCE: 871
guccugguau cuucuaug 18

<210> SEQ ID NO 872
<211> LENGTH: 19
<212> TYPE: RNA
<213> ORGANISM: Artificial Sequence
<220> FEATURE:
<223> OTHER INFORMATION: Targeting domain

<400> SEQUENCE: 872
aguccuggua ucuucuaug 19

<210> SEQ ID NO 873
<211> LENGTH: 20
<212> TYPE: RNA
<213> ORGANISM: Artificial Sequence
<220> FEATURE:
<223> OTHER INFORMATION: Targeting domain

<400> SEQUENCE: 873
aaguccuggu aucuucuaug 20

<210> SEQ ID NO 874
<211> LENGTH: 21
<212> TYPE: RNA
<213> ORGANISM: Artificial Sequence
<220> FEATURE:
<223> OTHER INFORMATION: Targeting domain

<400> SEQUENCE: 874
gaaguccugg uaucuucuau g 21

<210> SEQ ID NO 875
<211> LENGTH: 22
<212> TYPE: RNA
<213> ORGANISM: Artificial Sequence
<220> FEATURE:
<223> OTHER INFORMATION: Targeting domain

<400> SEQUENCE: 875
agaaguccug guaucuucua ug 22

<210> SEQ ID NO 876
<211> LENGTH: 23
<212> TYPE: RNA
<213> ORGANISM: Artificial Sequence
<220> FEATURE:
<223> OTHER INFORMATION: Targeting domain

<400> SEQUENCE: 876
aagaaguccu gguaucuucu aug 23

<210> SEQ ID NO 877
<211> LENGTH: 24
<212> TYPE: RNA
<213> ORGANISM: Artificial Sequence
<220> FEATURE:
<223> OTHER INFORMATION: Targeting domain

<400> SEQUENCE: 877
aaagaagucc ugguaucuuc uaug 24

<210> SEQ ID NO 878
<211> LENGTH: 18
<212> TYPE: RNA
<213> ORGANISM: Artificial Sequence
<220> FEATURE:
<223> OTHER INFORMATION: Targeting domain

<400> SEQUENCE: 878
aaauuggaau gacugaau 18

<210> SEQ ID NO 879
<211> LENGTH: 19
<212> TYPE: RNA
<213> ORGANISM: Artificial Sequence
<220> FEATURE:
<223> OTHER INFORMATION: Targeting domain

<400> SEQUENCE: 879
aaaauuggaa ugacugaau 19

<210> SEQ ID NO 880
<211> LENGTH: 21
<212> TYPE: RNA
<213> ORGANISM: Artificial Sequence
<220> FEATURE:
<223> OTHER INFORMATION: Targeting domain

<400> SEQUENCE: 880
gaaaaauugg aaugacugaa u 21

<210> SEQ ID NO 881
<211> LENGTH: 22
<212> TYPE: RNA
<213> ORGANISM: Artificial Sequence
<220> FEATURE:
<223> OTHER INFORMATION: Targeting domain

<400> SEQUENCE: 881
agaaaaauug gaaugacuga au 22

<210> SEQ ID NO 882
<211> LENGTH: 23
<212> TYPE: RNA
<213> ORGANISM: Artificial Sequence
<220> FEATURE:
<223> OTHER INFORMATION: Targeting domain

<400> SEQUENCE: 882
gagaaaaauu ggaaugacug aau 23

<210> SEQ ID NO 883
<211> LENGTH: 24
<212> TYPE: RNA
<213> ORGANISM: Artificial Sequence
<220> FEATURE:
<223> OTHER INFORMATION: Targeting domain

<400> SEQUENCE: 883
agagaaaaau uggaaugacu gaau 24

<210> SEQ ID NO 884
<211> LENGTH: 18
<212> TYPE: RNA
<213> ORGANISM: Artificial Sequence
<220> FEATURE:
<223> OTHER INFORMATION: Targeting domain

<400> SEQUENCE: 884
uaagcagcag uauccucu 18

<210> SEQ ID NO 885
<211> LENGTH: 19
<212> TYPE: RNA
<213> ORGANISM: Artificial Sequence
<220> FEATURE:
<223> OTHER INFORMATION: Targeting domain

<400> SEQUENCE: 885
uuaagcagca guauccucu 19

<210> SEQ ID NO 886
<211> LENGTH: 21
<212> TYPE: RNA
<213> ORGANISM: Artificial Sequence
<220> FEATURE:
<223> OTHER INFORMATION: Targeting domain

<400> SEQUENCE: 886
aauuaagcag caguauccuc u 21

<210> SEQ ID NO 887
<211> LENGTH: 22
<212> TYPE: RNA
<213> ORGANISM: Artificial Sequence
<220> FEATURE:
<223> OTHER INFORMATION: Targeting domain

<400> SEQUENCE: 887
aaauuaagca gcaguauccu cu 22

<210> SEQ ID NO 888
<211> LENGTH: 23
<212> TYPE: RNA
<213> ORGANISM: Artificial Sequence
<220> FEATURE:
<223> OTHER INFORMATION: Targeting domain

<400> SEQUENCE: 888
aaaauuaagc agcaguaucc ucu 23

<210> SEQ ID NO 889
<211> LENGTH: 24
<212> TYPE: RNA
<213> ORGANISM: Artificial Sequence
<220> FEATURE:
<223> OTHER INFORMATION: Targeting domain

<400> SEQUENCE: 889
aaaaauuaag cagcaguauc cucu 24

<210> SEQ ID NO 890

<211> LENGTH: 18
<212> TYPE: RNA
<213> ORGANISM: Artificial Sequence
<220> FEATURE:
<223> OTHER INFORMATION: Targeting domain

<400> SEQUENCE: 890
ccugguaucu ucuauggu 18

<210> SEQ ID NO 891
<211> LENGTH: 19
<212> TYPE: RNA
<213> ORGANISM: Artificial Sequence
<220> FEATURE:
<223> OTHER INFORMATION: Targeting domain

<400> SEQUENCE: 891
uccugguauc uucuauggu 19

<210> SEQ ID NO 892
<211> LENGTH: 21
<212> TYPE: RNA
<213> ORGANISM: Artificial Sequence
<220> FEATURE:
<223> OTHER INFORMATION: Targeting domain

<400> SEQUENCE: 892
aguccuggua ucuucuaugg u 21

<210> SEQ ID NO 893
<211> LENGTH: 22
<212> TYPE: RNA
<213> ORGANISM: Artificial Sequence
<220> FEATURE:
<223> OTHER INFORMATION: Targeting domain

<400> SEQUENCE: 893
aaguccuggu aucuucuaug gu 22

<210> SEQ ID NO 894
<211> LENGTH: 23
<212> TYPE: RNA
<213> ORGANISM: Artificial Sequence
<220> FEATURE:
<223> OTHER INFORMATION: Targeting domain

<400> SEQUENCE: 894
gaaguccugg uaucuucuau ggu 23

<210> SEQ ID NO 895
<211> LENGTH: 24
<212> TYPE: RNA
<213> ORGANISM: Artificial Sequence
<220> FEATURE:
<223> OTHER INFORMATION: Targeting domain

<400> SEQUENCE: 895
agaaguccug guaucuucua uggu 24

<210> SEQ ID NO 896
<211> LENGTH: 18
<212> TYPE: RNA
<213> ORGANISM: Artificial Sequence
<220> FEATURE:
<223> OTHER INFORMATION: Targeting domain

<400> SEQUENCE: 896
aagcagcagu auccucuu 18

<210> SEQ ID NO 897
<211> LENGTH: 19
<212> TYPE: RNA
<213> ORGANISM: Artificial Sequence
<220> FEATURE:
<223> OTHER INFORMATION: Targeting domain

<400> SEQUENCE: 897
uaagcagcag uauccucuu 19

<210> SEQ ID NO 898
<211> LENGTH: 21
<212> TYPE: RNA
<213> ORGANISM: Artificial Sequence
<220> FEATURE:
<223> OTHER INFORMATION: Targeting domain

<400> SEQUENCE: 898
auuaagcagc aguauccucu u 21

<210> SEQ ID NO 899
<211> LENGTH: 22
<212> TYPE: RNA
<213> ORGANISM: Artificial Sequence
<220> FEATURE:
<223> OTHER INFORMATION: Targeting domain

<400> SEQUENCE: 899
aauuaagcag caguauccuc uu 22

<210> SEQ ID NO 900
<211> LENGTH: 23
<212> TYPE: RNA
<213> ORGANISM: Artificial Sequence
<220> FEATURE:
<223> OTHER INFORMATION: Targeting domain

<400> SEQUENCE: 900
aaauuaagca gcaguauccu cuu 23

<210> SEQ ID NO 901
<211> LENGTH: 24
<212> TYPE: RNA
<213> ORGANISM: Artificial Sequence
<220> FEATURE:
<223> OTHER INFORMATION: Targeting domain

<400> SEQUENCE: 901
aaaauuaagc agcaguaucc ucuu 24

<210> SEQ ID NO 902
<211> LENGTH: 4758
<212> TYPE: DNA
<213> ORGANISM: Homo sapiens
<220> FEATURE:
<221> NAME/KEY: misc_feature
<222> LOCATION: (2716)..(2719)
<223> OTHER INFORMATION: HPFH deletion site (4 bp del -225 to -222)
<220> FEATURE:
<221> NAME/KEY: misc_feature
<222> LOCATION: (2748)..(2753)
<223> OTHER INFORMATION: GATA1 binding motif
<220> FEATURE:
<221> NAME/KEY: misc_feature
<222> LOCATION: (2762)..(2767)

-continued

```
<223> OTHER INFORMATION: GATA1 binding motif
<220> FEATURE:
<221> NAME/KEY: misc_feature
<222> LOCATION: (2791)..(2799)
<223> OTHER INFORMATION: FKLF transcription factor binding motif
<220> FEATURE:
<221> NAME/KEY: misc_feature
<222> LOCATION: (2823)..(2830)
<223> OTHER INFORMATION: CP1/Coup TFII binding motif
<220> FEATURE:
<221> NAME/KEY: misc_feature
<222> LOCATION: (2824)..(2836)
<223> OTHER INFORMATION: HPFH deletion site (13 bp del -114 to -102)
<220> FEATURE:
<221> NAME/KEY: misc_feature
<222> LOCATION: (2991)..(2993)
<223> OTHER INFORMATION: Start codon

<400> SEQUENCE: 902

tttaggaagt caaggtttag gcagggatag ccattctatt ttattagggg caatactatt     60

tccaacggca tctggctttt ctcagccctt gtgaggctct acagggaggt tgaggtgtta    120

gagatcagag caggaaacag gtttttcttt ccacggtaac tacaatgaag tgatccttac    180

tttactaagg aacttttcat tttaagtgtt gacgcatgcc taaagaggtg aaattaatcc    240

cataccctta agtctacaga ctggtcacag catttcaagg aggagacctc attgtaagct    300

tctagggagg tggggactta ggtgaaggaa atgagccagc agaagctcac aagtcagcat    360

cagcgtgtca tgtctcagca gcagaacagc acggtcagat gaaaatatag tgtgaagaat    420

ttgtataaca ttaattgaga aggcagattc actggagttc ttatataatt gaaagttaat    480

gcacgttaat aagcaagagt ttagtttaat gtgatggtgt tatgaactta acgcttgtgt    540

ctccagaaaa ttcacatgct gaatccccaa ctcccaattg gctccatttg tgggggaggc    600

tttggaaaag taatcaggtt tagaggagct catgagagca gatccccatc atagaattat    660

tttcctcatc agaagcagag agattagcca tttctcttcc ttctggtgag gacacagtgg    720

gaagtcagcc acctgcaacc caggaagaga gccctgacca ggaaccagca gaaaagtgag    780

aaaaaatcct gttgttgaag tcacccagtc tatgctattt tgttatagca ccttgcacta    840

agtaaggcag atgaagaaag agaaaaaaat aagcttcggt gttcagtgga ttagaaacca    900

tgtttatctc aggtttacaa atctccactt gtcctctgtg tttcagaata aaataccaac    960

tctactactc tcatctgtaa gatgcaaata gtaagcctga gcccttctgt ctaactttga   1020

attctatttt ttcttcaacg tactttaggc ttgtaatgtg tttatataca gtgaaatgtc   1080

aagttctttc tttatatttc tttctttctt ttttttcctc agcctcagag ttttccacat   1140

gcccttccta ctttcaggaa cttctttctc caaacgtctt ctgcctggct ccatcaaatc   1200

ataaaggacc cacttcaaat gccatcactc actaccattt cacaattcgc actttctttc   1260

tttgtccttt tttttttag taaaacaagt ttataaaaaa ttgaaggaat aaatgaatgg   1320

ctacttcata ggcagagtag acgcaagggc tactggttgc cgatttttat tgttattttt   1380

caatagtatg ctaaacaagg ggtagattat ttatgctgcc catttttaga ccataaaaga   1440

taacttcctg atgttgccat ggcatttttt tccttttaat tttatttcat ttcattttaa   1500

tttcgaaggt acatgtgcag gatgtgcagg cttgttacat gggtaaatgt gtgtctttct   1560

ggccttttag ccatctgtat caatgagcag atataagctt tacacaggat catgaaggat   1620

gaaagaattt caccaatatt ataataattt caatcaacct gatagcttag gggataaact   1680

aatttgaaga tacagcttgc ctccgataag ccagaattcc agagcttctg gcattataat   1740

ctagcaaggt tagagatcat ggatcacttt cagagaaaaa caaaaacaaa ctaaccaaaa   1800
```

-continued

```
gcaaaacaga accaaaaaac caccataaat acttcctacc ctgttaatgg tccaatatgt   1860
cagaaacagc actgtgttag aaataaagct gtctaaagta cactaatatt cgagttataa   1920
tagtgtgtgg actattagtc aataaaaaca acccttgcct ctttagagtt gttttccatg   1980
tacacgcaca tcttatgtct tagagtaaga ttccctgaga agtgaaccta gcatttatac   2040
aagataatta attctaatcc acagtacctg ccaaagaaca ttctaccatc atctttactg   2100
agcatagaag agctacgcca aaaccctggg tcatcagcca gcacacacac ttatccagtg   2160
gtaaatacac atcatctggt gtatacatac atacctgaat atggaatcaa atatttttct   2220
aagatgaaac agtcatgatt tatttcaaat aggtacggat aagtagatat tgaggtaagc   2280
attaggtctt atattatgta acactaatct attactgcgc tgaaactgtg gctttataga   2340
aattgttttc actgcactat tgagaaatta agagataatg gcaaaagtca caaagagtat   2400
attcaaaaag aagtatagca ctttttcctt agaaaccact gctaactgaa agagactaag   2460
atttgtcccg tcaaaaatcc tggacctatg cctaaaacac atttcacaat ccctgaactt   2520
ttcaaaaatt ggtacatgct ttagctttaa actacaggcc tcactggagc tagagacaag   2580
aaggtaaaaa acggctgaca aaagaagtcc tggtatcctc tatgatggga gaaggaaact   2640
agctaaaggg aagaataaat tagagaaaaa ctggaatgac tgaatcggaa caaggcaaag   2700
gctataaaaa aaattagcag tatcctcttg gggccccctt ccccacacta tctcaatgca   2760
aatatctgtc tgaaacggtc cctggctaaa ctccacccat gggttggcca gccttgcctt   2820
gaccaatagc cttgacaagg caaacttgac caatagtctt agagtatcca gtgaggccag   2880
gggccggcgg ctggctaggg atgaagaata aaaggaagca cccttcagca gttccacaca   2940
ctcgcttctg gaacgtctga ggttatcaat aagctcctag tccagacgcc atgggtcatt   3000
tcacagagga ggacaaggct actatcacaa gcctgtgggg caaggtgaat gtggaagatg   3060
ctggaggaga aaccctggga aggtaggctc tggtgaccag gacaagggag ggaaggaagg   3120
accctgtgcc tggcaaaagt ccaggtcgct tctcaggatt tgtggcacct tctgactgtc   3180
aaactgttct tgtcaatctc acaggctcct ggttgtctac ccatggaccc agaggttctt   3240
tgacagcttt ggcaacctgt cctctgcctc tgccatcatg ggcaacccca aagtcaaggc   3300
acatggcaag aaggtgctga cttccttggg agatgccaca aagcacctgg atgatctcaa   3360
gggcaccttt gcccagctga gtgaactgca ctgtgacaag ctgcatgtgg atcctgagaa   3420
cttcaaggtg agtccaggag atgtttcagc cctgttgcct ttagtctcga ggcaacttag   3480
acaacggagt attgatctga gcacagcagg gtgtgagctg tttgaagata ctggggttgg   3540
gggtgaagaa actgcagagg actaactggg ctgagaccca gtggtaatgt tttagggcct   3600
aaggagtgcc tctaaaaatc tagatggaca attttgactt tgagaaaaga gaggtggaaa   3660
tgaggaaaat gacttttctt tattagattc cagtagaaag aactttcatc tttccctcat   3720
ttttgttgtt ttaaaacatc tatctggagg caggacaagt atggtcgtta aaaagatgca   3780
ggcagaaggc atatattggc tcagtcaaag tggggaactt tggtggccaa acatacattg   3840
ctaaggctat tcctatatca gctggacaca tataaaatgc tgctaatgct tcattacaaa   3900
cttatatcct ttaattccag atgggggcaa agtatgtcca ggggtgagga acaattgaaa   3960
catttgggct ggagtagatt ttgaaagtca gctctgtgtg tgtgtgtgtg tgtgcgcgcg   4020
cgcgtgtgtg tgtgtgtgtc agcgtgtgtt tcttttaacg tcttcagcct acaacataca   4080
gggttcatgg tggcaagaag atagcaagat ttaaattatg gccagtgact agtgcttgaa   4140
```

ggggaacaac tacctgcatt taatgggaag gcaaaatctc aggctttgag ggaagttaac 4200
ataggcttga ttctgggtgg aagcttggtg tgtagttatc tggaggccag gctggagctc 4260
tcagctcact atgggttcat ctttattgtc tcctttcatc tcaacagctc ctgggaaatg 4320
tgctggtgac cgttttggca atccatttcg gcaaagaatt cacccctgag gtgcaggctt 4380
cctggcagaa gatggtgact gcagtggcca gtgccctgtc ctccagatac cactgagctc 4440
actgcccatg attcagagct ttcaaggata ggctttattc tgcaagcaat acaaataata 4500
aatctattct gctgagagat cacacatgat tttcttcagc tctttttttt acatcttttt 4560
aaatatatga gccacaaagg gtttatattg agggaagtgt gtatgtgtat ttctgcatgc 4620
ctgtttgtgt ttgtggtgtg tgcatgctcc tcatttattt ttatatgaga tgtgcatttt 4680
gatgagcaaa taaaagcagt aaagacactt gtacacggga gttctgcaag tgggagtaaa 4740
tggtgtagga gaaatccg 4758

<210> SEQ ID NO 903
<211> LENGTH: 4773
<212> TYPE: DNA
<213> ORGANISM: Homo sapiens
<220> FEATURE:
<221> NAME/KEY: misc_feature
<222> LOCATION: (1233)..(1238)
<223> OTHER INFORMATION: GATA1 binding site
<220> FEATURE:
<221> NAME/KEY: misc_feature
<222> LOCATION: (2672)..(2677)
<223> OTHER INFORMATION: GATA1 binding site
<220> FEATURE:
<221> NAME/KEY: misc_feature
<222> LOCATION: (2686)..(2691)
<223> OTHER INFORMATION: GATA1 binding site
<220> FEATURE:
<221> NAME/KEY: misc_feature
<222> LOCATION: (2715)..(2723)
<223> OTHER INFORMATION: FKLF transcription factor binding motif
<220> FEATURE:
<221> NAME/KEY: misc_feature
<222> LOCATION: (2747)..(2754)
<223> OTHER INFORMATION: CP1/Coup TFII binding motif
<220> FEATURE:
<221> NAME/KEY: misc_feature
<222> LOCATION: (2748)..(2760)
<223> OTHER INFORMATION: HPFH deletion site (13 bp del -114 to -102)
<220> FEATURE:
<221> NAME/KEY: misc_feature
<222> LOCATION: (2915)..(2917)
<223> OTHER INFORMATION: Start codon

<400> SEQUENCE: 903
ttatgtcatt accagagtta aaattctata atggcttctc actccctacc actgaggaca 60
agtttatgtc cttaggttta tgcttccctg aaacaatacc acctgctatt ctccacttta 120
catatcaacg gcactggttc tttatctaac tctctggcac agcaggagtt tgttttcttc 180
tgcttcagag ctttgaattt actatttcag cttctaaact ttatttggca atgccttccc 240
atggcagatt ccttctgtca ttttgcctct gttcgaatac tttctcctta atttcattct 300
tagttaataa tatctgaaat tattttgttg tttaacttaa ttattaattt tatgtatgtt 360
ctacctagat tataatcttc agaggaaagt tttattctct gacttattta acttaaatgc 420
ccactacttt aaaaattatg acatttattt aacagatatt tgctgaacaa atgtttgaaa 480
atacatggga aagaatgctt gaaaacactt gaaattgctt gtgtaaagaa acagttttat 540
cagttaggat ttaatcaatg tcagaagcaa tgatatagga aaaatcgagg aataagacag 600
ttatggataa ggagaaatca acaaactctt aaaagatatt gcctcaaaag cataagagga 660
aataagggtt tatacatgac ttttagaaca ctgccttggt ttttggataa atggggaagt 720
tgtttgaaaa caggagggat cctagatatt ccttagtctg aggaggagca attaagattc 780
acttgtttag aggctgggag tggtggctca cgcctgtaat cccagaattt tgggaggcca 840
aggcaggcag atcacctgag gtcaagagtt caagaccaac ctggccaaca tggtgaaatc 900
ccatctctac aaaaatacaa aaattagaca ggcatgatgg caagtgcctg taatcccagc 960
tacttgggag gctgaggaag gagaattgct tgaacctgga aggcaggagt tgcagtgagc 1020
cgagatcata ccactgcact ccagcctggg tgacagaaca agactctgtc tcaaaaaaaa 1080
aaaagagaga ttcaaaagat tcacttgttt aggccttagc gggcttagac accagtctct 1140
gacacattct taaaggtcag gctctacaaa tggaacccaa ccagactctc agatatggcc 1200
aaagatctat acacacccat ctcacagatc ccctatctta aagagaccct aatttgggtt 1260
cacctcagtc tctataatct gtaccagcat accaataaaa atctttctca cccatcctta 1320
gattgagaga agtcacttat tattatgtga gtaactggaa gatactgata agttgacaaa 1380
tctttttctt tcctttctta ttcaactttt attttaactt ccaaagaaca agtgcaatat 1440
gtgcagcttt gttgcgcagg tcaacatgta tctttctggt cttttagccg cctaacactt 1500
tgagcagata taagccttac acaggattat gaagtctgaa aggattccac caatattatt 1560
ataattccta tcaacctgat aggttagggg aaggtagagc tctcctccaa taagccagat 1620
ttccagagtt tctgacgtca taatctacca aggtcatgga tcgagttcag agaaaaaaca 1680
aaagcaaaac caaacctacc aaaaaataaa aatcccaaag aaaaaataaa gaaaaaaaca 1740
gcatgaatac ttcctgccat gttaagtggc caatatgtca gaaacagcac tgagttacag 1800
ataaagatgt ctaaactaca gtgacatccc agctgtcaca gtgtgtggac tattagtcaa 1860
taaaacagtc cctgcctctt aagagttgtt ttccatgcaa atacatgtct tatgtcttag 1920
aataagattc cctaagaagt gaacctagca tttatacaag ataattaatt ctaatccata 1980
gtatctggta aagagcattc taccatcatc tttaccgagc atagaagagc tacaccaaaa 2040
ccctgggtca tcagccagca catacactta tccagtgata aatacacatc atcgggtgcc 2100
tacatacata cctgaatata aaaaaaatac ttttgctgag atgaaacagg cgtgatttat 2160
ttcaaatagg tacggataag tagatattga agtaaggatt cagtcttata ttatattaca 2220
taacattaat ctattcctgc actgaaactg ttgctttata ggatttttca ctacactaat 2280
gagaacttaa gagataatgg cctaaaacca cagagagtat attcaaagat aagtatagca 2340
cttcttattt ggaaaccaat gcttactaaa tgagactaag acgtgtccca tcaaaaatcc 2400
tggacctatg cctaaaacac atttcacaat ccctgaactt ttcaaaaatt ggtacatgct 2460
ttaactttaa actacaggcc tcactggagc tacagacaag aaggtgaaaa acggctgaca 2520
aaagaagtcc tggtatcttc tatggtggga gaagaaaact agctaaaggg aagaataaat 2580
tagagaaaaa ttggaatgac tgaatcggaa caaggcaaag gctataaaaa aaattaagca 2640
gcagtatcct cttgggggcc ccttccccac actatctcaa tgcaaatatc tgtctgaaac 2700
ggtccctggc taaactccac ccatgggttg gccagccttg ccttgaccaa tagccttgac 2760
aaggcaaact tgaccaatag tcttagagta tccagtgagg ccaggggccg gcggctggct 2820
agggatgaag aataaaagga agcacccttc agcagttcca cacactcgct tctggaacgt 2880
ctgaggttat caataagctc ctagtccaga cgccatgggt catttcacag aggaggacaa 2940
ggctactatc acaagcctgt ggggcaaggt gaatgtggaa gatgctggag gagaaaccct 3000
gggaaggtag gctctggtga ccaggacaag ggagggaagg aaggaccctg tgcctggcaa 3060
aagtccaggt cgcttctcag gatttgtggc accttctgac tgtcaaactg ttcttgtcaa 3120
tctcacaggc tcctggttgt ctacccatgg acccagaggt tctttgacag ctttggcaac 3180
ctgtcctctg cctctgccat catgggcaac cccaaagtca aggcacatgg caagaaggtg 3240
ctgacttcct tgggagatgc cataaagcac ctggatgatc tcaagggcac ctttgcccag 3300
ctgagtgaac tgcactgtga caagctgcat gtggatcctg agaacttcaa ggtgagtcca 3360
ggagatgttt cagcactgtt gcctttagtc tcgaggcaac ttagacaact gagtattgat 3420
ctgagcacag cagggtgtga gctgtttgaa gatactgggg ttgggagtga agaaactgca 3480
gaggactaac tgggctgaga cccagtggca atgttttagg gcctaaggag tgcctctgaa 3540
aatctagatg gacaactttg actttgagaa aagagaggtg gaaatgagga aaatgacttt 3600
tctttattag atttcggtag aaagaacttt cacctttccc ctatttttgt tattcgtttt 3660
aaaacatcta tctggaggca ggacaagtat ggtcattaaa aagatgcagg cagaaggcat 3720
atattggctc agtcaaagtg ggaactttg gtggccaaac atacattgct aaggctattc 3780
ctatatcagc tggacacata taaaatgctg ctaatgcttc attacaaact tatatccttt 3840
aattccagat gggggcaaag tatgtccagg ggtgaggaac aattgaaaca tttgggctgg 3900
agtagatttt gaaagtcagc tctgtgtgtg tgtgtgtgtg tgtgcgcgcg tgtgtttgtg 3960
tgtgtgtgag agcgtgtgtt tcttttaacg ttttcagcct acagcataca gggttcatgg 4020
tggcaagaag ataacaagat ttaaattatg gccagtgact agtgctgcaa gaagaacaac 4080
tacctgcatt taatgggaaa gcaaaatctc aggctttgag ggaagttaac ataggcttga 4140
ttctgggtgg aagcttggtg tgtagttatc tggaggccag gctggagctc tcagctcact 4200
atgggttcat ctttattgtc tcctttcatc tcaacagctc ctgggaaatg tgctggtgac 4260
cgttttggca atccatttcg gcaaagaatt cacccctgag gtgcaggctt cctggcagaa 4320
gatggtgact ggagtggcca gtgccctgtc ctccagatac cactgagctc actgcccatg 4380
atgcagagct ttcaaggata ggctttattc tgcaagcaat caaataataa atctattctg 4440
ctaagagatc acacatggtt gtcttcagtt ctttttttat gtctttttaa atatatgagc 4500
cacaaagggt tttatgttga gggatgtgtt tatgtgtatt tatacatggc tatgtgtgtt 4560
tgtgtcatgt gcacactcca cactttttg tttacgttag atgtgggttt tgatgagcaa 4620
ataaaagaac taggcaataa agaaacttgt acatgggagt tctgcaagtg ggagtaaaag 4680
gtgcaggaga aatctggttg gaagaaagac ctctatagga caggactcct cagaaacaga 4740
tgttttggaa gagatgggga aaggttcagt gaa 4773

<210> SEQ ID NO 904
<211> LENGTH: 87
<212> TYPE: DNA
<213> ORGANISM: Artificial Sequence
<220> FEATURE:
<223> OTHER INFORMATION: ssODN1 5' homology arm

<400> SEQUENCE: 904
gggtgcttcc ttttattctt catccctagc cagccgccgg cccctggcct cactggatac 60
tctaagacta ttggtcaagt ttgcctt 87

<210> SEQ ID NO 905
<211> LENGTH: 89
<212> TYPE: DNA
<213> ORGANISM: Artificial Sequence
<220> FEATURE:
<223> OTHER INFORMATION: ssODN1 3' homology arm

<400> SEQUENCE: 905
gtcaaggcaa ggctggccaa cccatgggtg gagtttagcc agggaccgtt tcagacagat 60
atttgcattg agatagtgtg gggaagggg 89

<210> SEQ ID NO 906
<211> LENGTH: 176
<212> TYPE: DNA
<213> ORGANISM: Artificial Sequence
<220> FEATURE:
<223> OTHER INFORMATION: ssODN1

<400> SEQUENCE: 906
gggtgcttcc ttttattctt catccctagc cagccgccgg cccctggcct cactggatac 60
tctaagacta ttggtcaagt ttgccttgtc aaggcaaggc tggccaaccc atgggtggag 120
tttagccagg gaccgtttca gacagatatt tgcattgaga tagtgtgggg aagggg 176

<210> SEQ ID NO 907
<211> LENGTH: 87
<212> TYPE: DNA
<213> ORGANISM: Artificial Sequence
<220> FEATURE:
<223> OTHER INFORMATION: PhTx ssODN1 5' homology arm
<220> FEATURE:
<221> NAME/KEY: misc_feature
<222> LOCATION: (1)..(1)
<223> OTHER INFORMATION: Modified to contain phosphorothioate

<400> SEQUENCE: 907
gggtgcttcc ttttattctt catccctagc cagccgccgg cccctggcct cactggatac 60
tctaagacta ttggtcaagt ttgcctt 87

<210> SEQ ID NO 908
<211> LENGTH: 89
<212> TYPE: DNA
<213> ORGANISM: Artificial Sequence
<220> FEATURE:
<223> OTHER INFORMATION: PhTx ssODN1 3' homology arm
<220> FEATURE:
<221> NAME/KEY: misc_feature
<222> LOCATION: (89)..(89)
<223> OTHER INFORMATION: Modified to contain phosphorothioate

<400> SEQUENCE: 908
gtcaaggcaa ggctggccaa cccatgggtg gagtttagcc agggaccgtt tcagacagat 60
atttgcattg agatagtgtg gggaagggg 89

<210> SEQ ID NO 909
<211> LENGTH: 176
<212> TYPE: DNA
<213> ORGANISM: Artificial Sequence
<220> FEATURE:
<223> OTHER INFORMATION: PhTx ssODN1
<220> FEATURE:
<221> NAME/KEY: misc_feature
<222> LOCATION: (1)..(1)
<223> OTHER INFORMATION: Modified to contain phosphorothioate
<220> FEATURE:
<221> NAME/KEY: misc_feature
<222> LOCATION: (176)..(176)
<223> OTHER INFORMATION: Modified to contain phosphorothioate

<400> SEQUENCE: 909
gggtgcttcc ttttattctt catccctagc cagccgccgg cccctggcct cactggatac 60
tctaagacta ttggtcaagt ttgccttgtc aaggcaaggc tggccaaccc atgggtggag 120
tttagccagg gaccgtttca gacagatatt tgcattgaga tagtgtgggg aagggg 176

<210> SEQ ID NO 910
<211> LENGTH: 17
<212> TYPE: DNA
<213> ORGANISM: Artificial Sequence
<220> FEATURE:
<223> OTHER INFORMATION: targeting domain

<400> SEQUENCE: 910
ggctattggt caaggca 17

<210> SEQ ID NO 911
<211> LENGTH: 20
<212> TYPE: DNA
<213> ORGANISM: Artificial Sequence
<220> FEATURE:
<223> OTHER INFORMATION: targeting domain

<400> SEQUENCE: 911
caaggctatt ggtcaaggca 20

<210> SEQ ID NO 912
<211> LENGTH: 17
<212> TYPE: DNA
<213> ORGANISM: Artificial Sequence
<220> FEATURE:
<223> OTHER INFORMATION: targeting domain

<400> SEQUENCE: 912
tgccttgtca aggctat 17

<210> SEQ ID NO 913
<211> LENGTH: 20
<212> TYPE: DNA
<213> ORGANISM: Artificial Sequence
<220> FEATURE:
<223> OTHER INFORMATION: targeting domain

<400> SEQUENCE: 913
gtttgccttg tcaaggctat 20

<210> SEQ ID NO 914
<211> LENGTH: 17
<212> TYPE: DNA
<213> ORGANISM: Artificial Sequence
<220> FEATURE:
<223> OTHER INFORMATION: targeting domain

<400> SEQUENCE: 914
gaccaatagc cttgaca 17

<210> SEQ ID NO 915
<211> LENGTH: 20
<212> TYPE: DNA
<213> ORGANISM: Artificial Sequence
<220> FEATURE:
<223> OTHER INFORMATION: targeting domain

<400> SEQUENCE: 915
cttgaccaat agccttgaca 20

<210> SEQ ID NO 916
<211> LENGTH: 17
<212> TYPE: DNA
<213> ORGANISM: Artificial Sequence
<220> FEATURE:
<223> OTHER INFORMATION: targeting domain

<400> SEQUENCE: 916
gtcaaggcta ttggtca 17

<210> SEQ ID NO 917
<211> LENGTH: 20
<212> TYPE: DNA
<213> ORGANISM: Artificial Sequence
<220> FEATURE:
<223> OTHER INFORMATION: targeting domain

<400> SEQUENCE: 917
cttgtcaagg ctattggtca 20

<210> SEQ ID NO 918
<211> LENGTH: 17
<212> TYPE: DNA
<213> ORGANISM: Artificial Sequence
<220> FEATURE:
<223> OTHER INFORMATION: targeting domain

<400> SEQUENCE: 918
tcaagtttgc cttgtca 17

<210> SEQ ID NO 919
<211> LENGTH: 20
<212> TYPE: DNA
<213> ORGANISM: Artificial Sequence
<220> FEATURE:
<223> OTHER INFORMATION: targeting domain

<400> SEQUENCE: 919
tggtcaagtt tgccttgtca 20

<210> SEQ ID NO 920
<211> LENGTH: 20
<212> TYPE: RNA
<213> ORGANISM: Artificial Sequence
<220> FEATURE:
<223> OTHER INFORMATION: targeting domain plus PAM (NGG)

<400> SEQUENCE: 920
ggcuauuggu caaggcaagg 20

<210> SEQ ID NO 921
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 921
caaggcuauu ggucaaggca agg 23

<210> SEQ ID NO 922
<211> LENGTH: 20
<212> TYPE: RNA
<213> ORGANISM: Artificial Sequence
<220> FEATURE:
<223> OTHER INFORMATION: targeting domain plus PAM (NGG)

<400> SEQUENCE: 922
ugccuuguca aggcuauugg 20

<210> SEQ ID NO 923
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 923
guuugccuug ucaaggcuau ugg 23

<210> SEQ ID NO 924
<211> LENGTH: 20
<212> TYPE: RNA
<213> ORGANISM: Artificial Sequence
<220> FEATURE:
<223> OTHER INFORMATION: targeting domain plus PAM (NGG)

<400> SEQUENCE: 924
gaccaauagc cuugacaagg 20

<210> SEQ ID NO 925
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 925
cuugaccaau agccuugaca agg 23

<210> SEQ ID NO 926
<211> LENGTH: 20
<212> TYPE: RNA
<213> ORGANISM: Artificial Sequence
<220> FEATURE:
<223> OTHER INFORMATION: targeting domain plus PAM (NGG)

<400> SEQUENCE: 926
gucaaggcua uuggucaagg 20

<210> SEQ ID NO 927
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 927
cuugucaagg cuauugguca agg 23

<210> SEQ ID NO 928
<211> LENGTH: 20
<212> TYPE: RNA
<213> ORGANISM: Artificial Sequence
<220> FEATURE:
<223> OTHER INFORMATION: targeting domain plus PAM (NGG)

<400> SEQUENCE: 928
ucaaguuugc cuugucaagg 20

<210> SEQ ID NO 929
<211> LENGTH: 23

<212> TYPE: RNA
<213> ORGANISM: Artificial Sequence
<220> FEATURE:
<223> OTHER INFORMATION: targeting domain plus PAM (NGG)

<400> SEQUENCE: 929
uggucaaguu ugccuuguca agg 23

<210> SEQ ID NO 930
<211> LENGTH: 20
<212> TYPE: DNA
<213> ORGANISM: Artificial Sequence
<220> FEATURE:
<223> OTHER INFORMATION: targeting domain plus PAM (NGG)

<400> SEQUENCE: 930
ggctattggt caaggcaagg 20

<210> SEQ ID NO 931
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 931
caaggctatt ggtcaaggca agg 23

<210> SEQ ID NO 932
<211> LENGTH: 20
<212> TYPE: DNA
<213> ORGANISM: Artificial Sequence
<220> FEATURE:
<223> OTHER INFORMATION: targeting domain plus PAM (NGG)

<400> SEQUENCE: 932
tgccttgtca aggctattgg 20

<210> SEQ ID NO 933
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 933
gtttgccttg tcaaggctat tgg 23

<210> SEQ ID NO 934
<211> LENGTH: 20
<212> TYPE: DNA
<213> ORGANISM: Artificial Sequence
<220> FEATURE:
<223> OTHER INFORMATION: targeting domain plus PAM (NGG)

<400> SEQUENCE: 934
gaccaatagc cttgacaagg 20

<210> SEQ ID NO 935
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 935
cttgaccaat agccttgaca agg 23

<210> SEQ ID NO 936
<211> LENGTH: 20
<212> TYPE: DNA
<213> ORGANISM: Artificial Sequence
<220> FEATURE:
<223> OTHER INFORMATION: targeting domain plus PAM (NGG)

<400> SEQUENCE: 936
gtcaaggcta ttggtcaagg 20

<210> SEQ ID NO 937
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 937
cttgtcaagg ctattggtca agg 23

<210> SEQ ID NO 938
<211> LENGTH: 20
<212> TYPE: DNA
<213> ORGANISM: Artificial Sequence
<220> FEATURE:
<223> OTHER INFORMATION: targeting domain plus PAM (NGG)

<400> SEQUENCE: 938
tcaagtttgc cttgtcaagg 20

<210> SEQ ID NO 939
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 939
tggtcaagtt tgccttgtca agg 23

<210> SEQ ID NO 940
<211> LENGTH: 17
<212> TYPE: RNA
<213> ORGANISM: Artificial Sequence
<220> FEATURE:
<223> OTHER INFORMATION: targeting domain

<400> SEQUENCE: 940
aguauccagu gaggcca 17

<210> SEQ ID NO 941
<211> LENGTH: 20
<212> TYPE: RNA
<213> ORGANISM: Artificial Sequence
<220> FEATURE:
<223> OTHER INFORMATION: targeting domain

<400> SEQUENCE: 941
ggcaaggcug gccaacccau 20

<210> SEQ ID NO 942
<211> LENGTH: 20
<212> TYPE: RNA
<213> ORGANISM: Artificial Sequence
<220> FEATURE:
<223> OTHER INFORMATION: targeting domain

<400> SEQUENCE: 942
uauuugcauu gagauagugu 20

<210> SEQ ID NO 943
<211> LENGTH: 17
<212> TYPE: DNA
<213> ORGANISM: Artificial Sequence
<220> FEATURE:
<223> OTHER INFORMATION: targeting domain

<400> SEQUENCE: 943
agtatccagt gaggcca 17

<210> SEQ ID NO 944
<211> LENGTH: 20
<212> TYPE: DNA
<213> ORGANISM: Artificial Sequence
<220> FEATURE:
<223> OTHER INFORMATION: targeting domain

<400> SEQUENCE: 944
ggcaaggctg gccaacccat 20

<210> SEQ ID NO 945
<211> LENGTH: 20
<212> TYPE: DNA
<213> ORGANISM: Artificial Sequence
<220> FEATURE:
<223> OTHER INFORMATION: targeting domain

<400> SEQUENCE: 945
tatttgcatt gagatagtgt 20

<210> SEQ ID NO 946
<211> LENGTH: 20
<212> TYPE: RNA
<213> ORGANISM: Artificial Sequence
<220> FEATURE:
<223> OTHER INFORMATION: targeting domain plus PAM (NGG)

<400> SEQUENCE: 946
aguauccagu gaggccaggg 20

<210> SEQ ID NO 947
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 947
ggcaaggcug gccaacccau ggg 23

<210> SEQ ID NO 948
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 948
uauuugcauu gagauagugu ggg 23

<210> SEQ ID NO 949
<211> LENGTH: 20
<212> TYPE: DNA
<213> ORGANISM: Artificial Sequence
<220> FEATURE:
<223> OTHER INFORMATION: targeting domain plus PAM (NGG)

<400> SEQUENCE: 949
agtatccagt gaggccaggg 20

<210> SEQ ID NO 950
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 950
ggcaaggctg gccaacccat ggg 23

<210> SEQ ID NO 951
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 951
tatttgcatt gagatagtgt ggg 23

<210> SEQ ID NO 952
<211> LENGTH: 20
<212> TYPE: RNA
<213> ORGANISM: Artificial Sequence
<220> FEATURE:
<223> OTHER INFORMATION: targeting domain

<400> SEQUENCE: 952
cuaacaguug cuuuuaucac 20

<210> SEQ ID NO 953
<211> LENGTH: 20
<212> TYPE: RNA
<213> ORGANISM: Artificial Sequence
<220> FEATURE:
<223> OTHER INFORMATION: targeting domain

<400> SEQUENCE: 953
gggcgugggu gggguagaag 20

<210> SEQ ID NO 954
<211> LENGTH: 20
<212> TYPE: RNA
<213> ORGANISM: Artificial Sequence
<220> FEATURE:
<223> OTHER INFORMATION: targeting domain

<400> SEQUENCE: 954
cucuuagaca uaacacacca 20

<210> SEQ ID NO 955
<211> LENGTH: 20
<212> TYPE: RNA
<213> ORGANISM: Artificial Sequence
<220> FEATURE:
<223> OTHER INFORMATION: targeting domain

<400> SEQUENCE: 955
aucagaggcc aaacccuucc 20

<210> SEQ ID NO 956
<211> LENGTH: 20
<212> TYPE: DNA
<213> ORGANISM: Artificial Sequence
<220> FEATURE:
<223> OTHER INFORMATION: targeting domain

<400> SEQUENCE: 956
ctaacagttg cttttatcac 20

<210> SEQ ID NO 957
<211> LENGTH: 20
<212> TYPE: DNA
<213> ORGANISM: Artificial Sequence
<220> FEATURE:
<223> OTHER INFORMATION: targeting domain

<400> SEQUENCE: 957
gggcgtgggt ggggtagaag 20

<210> SEQ ID NO 958
<211> LENGTH: 20
<212> TYPE: DNA
<213> ORGANISM: Artificial Sequence
<220> FEATURE:
<223> OTHER INFORMATION: targeting domain

<400> SEQUENCE: 958
ctcttagaca taacacacca 20

<210> SEQ ID NO 959
<211> LENGTH: 20
<212> TYPE: DNA
<213> ORGANISM: Artificial Sequence
<220> FEATURE:
<223> OTHER INFORMATION: targeting domain

<400> SEQUENCE: 959
atcagaggcc aaacccttcc 20

<210> SEQ ID NO 960
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 960
cuaacaguug cuuuuaucac agg 23

<210> SEQ ID NO 961
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 961
gggcgugggu gggguagaag agg 23

<210> SEQ ID NO 962

<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 962
cucuuagaca uaacacacca ggg 23

<210> SEQ ID NO 963
<211> LENGTH: 23
<212> TYPE: RNA
<213> ORGANISM: Artificial Sequence
<220> FEATURE:
<223> OTHER INFORMATION: targeting domain plus PAM (NGG)

<400> SEQUENCE: 963
aucagaggcc aaacccuucc ugg 23

<210> SEQ ID NO 964
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 964
ctaacagttg cttttatcac agg 23

<210> SEQ ID NO 965
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 965
gggcgtgggt ggggtagaag agg 23

<210> SEQ ID NO 966
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 966
ctcttagaca taacacacca ggg 23

<210> SEQ ID NO 967
<211> LENGTH: 23
<212> TYPE: DNA
<213> ORGANISM: Artificial Sequence
<220> FEATURE:
<223> OTHER INFORMATION: targeting domain plus PAM (NGG)

<400> SEQUENCE: 967
atcagaggcc aaacccttcc tgg 23

<210> SEQ ID NO 968
<211> LENGTH: 115
<212> TYPE: DNA
<213> ORGANISM: Artificial Sequence
<220> FEATURE:
<223> OTHER INFORMATION: +58 DHS enhancer

<400> SEQUENCE: 968
caactttgaa gctagtctag tgcaagctaa cagttgcttt tatcacaggc tccaggaagg 60
gtttggcctc tgattagggt gggggcgtgg gtggggtaga agaggactgg cagac 115

<210> SEQ ID NO 969
<211> LENGTH: 801
<212> TYPE: DNA
<213> ORGANISM: Artificial Sequence
<220> FEATURE:
<223> OTHER INFORMATION: +58 DHS enhancer region including ~500 bp upstream and ~200 bp downstream

<400> SEQUENCE: 969
aggtaccttt tgtgtgtatg tgctgattga gggcccattg agaatatttt gacttttagg 60
gaagctccaa actctcaaac cacagggatc acaacacata cgtgtgtctg ttatgacgtt 120
atatgtaagc atcacaacag gcagagaatg tctgcacccc accctggaaa acagcctgac 180
tgtgccccat gggcaaacca gactagttta tagggggttc tactctgagg tactgatgga 240
ccttgggtgc tattcctgtg ataaggaagg cagctagaca ggacttggga gttatctgta 300
gtgagatggc tgaaaagcga tacagggctg gctctatgcc ccaggtgtgc ataagtaaga 360
gcagatagct gattccagtg caaagtccat acaggtaata acataggcca gaaaagagat 420
atggcatcta ctcttagaca taacacacca gggtcaatac aactttgaag ctagtctagt 480
gcaagctaac agttgctttt atcacaggct ccaggaaggg tttggcctct gattagggtg 540
ggggcgtggg tggggtagaa gaggactggc agacctctcc atcggtggcc gtttgcccag 600
gggggcctct ttcggaaggc tctcttggtg atggagaatt ggattttatt tctcaatggg 660
aatgaaataa tttgtatgcc atgccgtgtg gactcccaaa attgtaaagg aggtgaagct 720
tcccctgtct gcactctccc ctcctcataa ttgtccattt ttcatctgtc gggctgtcca 780
cccatccatc acatataggc a 801

<210> SEQ ID NO 970
<211> LENGTH: 15
<212> TYPE: RNA
<213> ORGANISM: Artificial Sequence
<220> FEATURE:
<223> OTHER INFORMATION: tSpA dgRNA

<400> SEQUENCE: 970
ggcuggccaa cccau 15

<210> SEQ ID NO 971
<211> LENGTH: 15
<212> TYPE: DNA
<213> ORGANISM: Artificial Sequence
<220> FEATURE:
<223> OTHER INFORMATION: tSpA dgRNA

<400> SEQUENCE: 971
ggctggccaa cccat 15

<210> SEQ ID NO 972
<211> LENGTH: 15
<212> TYPE: RNA
<213> ORGANISM: Artificial Sequence
<220> FEATURE:
<223> OTHER INFORMATION: Sp180 dgRNA

<400> SEQUENCE: 972
gccggcggcu ggcua 15

<210> SEQ ID NO 973
<211> LENGTH: 15
<212> TYPE: DNA
<213> ORGANISM: Artificial Sequence
<220> FEATURE:
<223> OTHER INFORMATION: Sp180 dgRNA

<400> SEQUENCE: 973
gccggcggct ggcta 15

<210> SEQ ID NO 974
<211> LENGTH: 15
<212> TYPE: RNA
<213> ORGANISM: Artificial Sequence
<220> FEATURE:
<223> OTHER INFORMATION: Sp181 dgRNA

<400> SEQUENCE: 974
agugaggcca ggggc 15

<210> SEQ ID NO 975
<211> LENGTH: 15
<212> TYPE: DNA
<213> ORGANISM: Artificial Sequence
<220> FEATURE:
<223> OTHER INFORMATION: Sp181 dgRNA

<400> SEQUENCE: 975
agtgaggcca ggggc 15

<210> SEQ ID NO 976
<211> LENGTH: 15
<212> TYPE: RNA
<213> ORGANISM: Artificial Sequence
<220> FEATURE:
<223> OTHER INFORMATION: Sp182 dgRNA

<400> SEQUENCE: 976
uuagaguauc cagug 15

<210> SEQ ID NO 977
<211> LENGTH: 15
<212> TYPE: DNA
<213> ORGANISM: Artificial Sequence
<220> FEATURE:
<223> OTHER INFORMATION: Sp182 dgRNA

<400> SEQUENCE: 977
ttagagtatc cagtg 15

<210> SEQ ID NO 978
<211> LENGTH: 16
<212> TYPE: RNA
<213> ORGANISM: Artificial Sequence
<220> FEATURE:
<223> OTHER INFORMATION: tSpD

<400> SEQUENCE: 978
gauacucuaa gacuau 16

<210> SEQ ID NO 979
<211> LENGTH: 16
<212> TYPE: DNA
<213> ORGANISM: Artificial Sequence
<220> FEATURE:

<223> OTHER INFORMATION: tSpD

<400> SEQUENCE: 979
gatactctaa gactat 16

<210> SEQ ID NO 980
<211> LENGTH: 125
<212> TYPE: DNA
<213> ORGANISM: Artificial Sequence
<220> FEATURE:
<223> OTHER INFORMATION: BCL11A

<400> SEQUENCE: 980
gaggtctgcc agtcctcttc taccccaccc acgcccccac cctaatcaga ggccaaaccc 60
ttcctggagc ctgtgataaa agcaactgtt agcttgcact agactagctt caaagttgta 120
ttgac 125

<210> SEQ ID NO 981
<211> LENGTH: 76
<212> TYPE: DNA
<213> ORGANISM: Artificial Sequence
<220> FEATURE:
<223> OTHER INFORMATION: synthetic

<400> SEQUENCE: 981
ggcctcactg gatactctaa gactattggt caagtttgcc ttgtcaaggc tattggtcaa 60
ggcaaggctg gccaac 76

<210> SEQ ID NO 982
<211> LENGTH: 49
<212> TYPE: DNA
<213> ORGANISM: Artificial Sequence
<220> FEATURE:
<223> OTHER INFORMATION: synthetic

<400> SEQUENCE: 982
ggcctcactg gatactctaa gactattggt caaggcaagg ctggccaac 49

<210> SEQ ID NO 983
<211> LENGTH: 52
<212> TYPE: DNA
<213> ORGANISM: Artificial Sequence
<220> FEATURE:
<223> OTHER INFORMATION: HBG promoter
<220> FEATURE:
<221> NAME/KEY: misc_feature
<222> LOCATION: (8)..(10)
<223> OTHER INFORMATION: PAM sequence
<220> FEATURE:
<221> NAME/KEY: misc_feature
<222> LOCATION: (12)..(24)
<223> OTHER INFORMATION: -13 nt target region
<220> FEATURE:
<221> NAME/KEY: misc_feature
<222> LOCATION: (21)..(25)
<223> OTHER INFORMATION: Distal CCAAT box
<220> FEATURE:
<221> NAME/KEY: misc_feature
<222> LOCATION: (50)..(52)
<223> OTHER INFORMATION: PAM sequence

<400> SEQUENCE: 983
aagtttgcct tgtcaaggct attggtcaag gcaaggctgg ccaacccatg gg 52

<210> SEQ ID NO 984
<211> LENGTH: 13

-continued

```
<212> TYPE: DNA
<213> ORGANISM: Artificial Sequence
<220> FEATURE:
<223> OTHER INFORMATION: -13 nt target region

<400> SEQUENCE: 984

gtcaaggcta ttg                                                    13


<210> SEQ ID NO 985
<211> LENGTH: 12
<212> TYPE: DNA
<213> ORGANISM: Artificial Sequence
<220> FEATURE:
<223> OTHER INFORMATION: synthetic

<400> SEQUENCE: 985

ctattggtca ag                                                     12


<210> SEQ ID NO 986
<211> LENGTH: 6
<212> TYPE: PRT
<213> ORGANISM: Artificial Sequence
<220> FEATURE:
<223> OTHER INFORMATION: PAM sequence

<400> SEQUENCE: 986

Asn Asn Gly Arg Arg Thr
1               5


<210> SEQ ID NO 987
<211> LENGTH: 6
<212> TYPE: PRT
<213> ORGANISM: Artificial Sequence
<220> FEATURE:
<223> OTHER INFORMATION: PAM sequence

<400> SEQUENCE: 987

Asn Asn Gly Arg Arg Val
1               5
```

CRISPR/RNA-GUIDED NUCLEASE SYSTEMS AND METHODS

CROSS REFERENCE TO RELATED APPLICATIONS

The present application is a continuation of International Patent Application No. PCT/US2018/032172, filed May 10, 2018, which claims the benefit of U.S. Provisional Application No. 62/504,527, filed May 10, 2017 and U.S. Provisional Application No. 62/504,522, filed May 10, 2017; the contents of each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jul. 17, 2023, is named SecondSubstituteSequenceListing.txt and is 352,876 bytes in size.

FIELD

This disclosure relates to genome editing systems and methods for altering a target nucleic acid sequence, or modulating expression of a target nucleic acid sequence, and applications thereof in connection with enhancing editing of a target nucleic acid and applications thereof.

BACKGROUND

CRISPRs (Clustered Regularly Interspaced Short Palindromic Repeats) evolved in bacteria and archea as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complementary to the viral genome, mediates targeting of an RNA-guided nuclease to a target sequence in the viral genome. The RNA-guided nuclease, in turn, cleaves and thereby silences the viral target.

Recently, CRISPR-based genome editing systems have been adapted for genome editing in eukaryotic cells. The introduction of site-specific double strand breaks (DSBs) allows for target sequence alteration through endogenous DNA repair mechanisms, for example non-homologous end-joining (NHEJ) or homology-directed repair (HDR). Genome editing approaches made possible by CRISPR-based genome editing systems may revolutionize biology, and hold immense promise as tools for the treatment and prevention of disease. However, the activity of RNA-guided nucleases may be reduced or eliminated at certain genomic sites and/or in certain cell types, limiting the circumstances in which genome editing strategies may be successfully implemented.

The differences in RNA-guided nuclease activity across loci and cell types may be explained, in part, by differences in chromatin structure between them. Without wishing to be bound by any theory, it is thought that genome editing system activity may be decreased at loci where chromatin structure limits the access of RNA-guided nucleases to target regions in the DNA relative to other loci having less restrictive chromatin structure. Genome editing systems and methods that permit the modification of restrictive chromatin structure may facilitate the editing of sites that have previously been difficult to edit, but such systems and methods have not previously been described in the art.

Additionally, hemoglobin (Hb) carries oxygen in erythrocytes or red blood cells (RBCs) from the lungs to tissues. During prenatal development and until shortly after birth, hemoglobin is present in the form of fetal hemoglobin (HbF), a tetrameric protein composed of two alpha (α)-globin chains and two gamma (γ)-globin chains. HbF is largely replaced by adult hemoglobin (HbA), a tetrameric protein in which the γ-globin chains of HbF are replaced with beta (β)-globin chains, through a process known as globin switching. The average adult makes less than 1% HbF out of total hemoglobin (Thein 2009). The α-hemoglobin gene is located on chromosome 16, while the β-hemoglobin gene (HBB), A gamma (γA)-globin chain (HBG1, also known as gamma globin A), and G gamma (γG)-globin chain (HBG2, also known as gamma globin G) are located on chromosome 11 within the globin gene cluster (also referred to as the globin locus).

Mutations in HBB can cause hemoglobin disorders (i.e., hemoglobinopathies) including sickle cell disease (SCD) and beta-thalassemia (β-Thal). Approximately 93,000 people in the United States are diagnosed with a hemoglobinopathy. Worldwide, 300,000 children are born with hemoglobinopathies every year (Angastiniotis 1998). Because these conditions are associated with HBB mutations, their symptoms typically do not manifest until after globin switching from HbF to HbA.

SCD is the most common inherited hematologic disease in the United States, affecting approximately 80,000 people (Brousseau 2010). SCD is most common in people of African ancestry, for whom the prevalence of SCD is 1 in 500. In Africa, the prevalence of SCD is 15 million (Aliyu 2008). SCD is also more common in people of Indian, Saudi Arabian and Mediterranean descent. In those of Hispanic-American descent, the prevalence of sickle cell disease is 1 in 1,000 (Lewis 2014).

SCD is caused by a single homozygous mutation in the HBB gene, c.17A>T (HbS mutation). The sickle mutation is a point mutation (GAG>GTG) on HBB that results in substitution of valine for glutamic acid at amino acid position 6 in exon 1. The valine at position 6 of the β-hemoglobin chain is hydrophobic and causes a change in conformation of the β-globin protein when it is not bound to oxygen. This change of conformation causes HbS proteins to polymerize in the absence of oxygen, leading to deformation (i.e., sickling) of RBCs. SCD is inherited in an autosomal recessive manner, so that only patients with two HbS alleles have the disease. Heterozygous subjects have sickle cell trait, and may suffer from anemia and/or painful crises if they are severely dehydrated or oxygen deprived.

Sickle shaped RBCs cause multiple symptoms, including anemia, sickle cell crises, vaso-occlusive crises, aplastic crises, and acute chest syndrome. Sickle shaped RBCs are less elastic than wild-type RBCs and therefore cannot pass as easily through capillary beds and cause occlusion and ischemia (i.e., vaso-occlusion). Vaso-occlusive crisis occurs when sickle cells obstruct blood flow in the capillary bed of an organ leading to pain, ischemia, and necrosis. These episodes typically last 5-7 days. The spleen plays a role in clearing dysfunctional RBCs, and is therefore typically enlarged during early childhood and subject to frequent vaso-occlusive crises. By the end of childhood, the spleen in SCD patients is often infarcted, which leads to autosplenectomy. Hemolysis is a constant feature of SCD and causes anemia. Sickle cells survive for 10-20 days in circulation, while healthy RBCs survive for 90-120 days. SCD subjects are transfused as necessary to maintain adequate hemoglobin levels. Frequent transfusions place subjects at risk for infection with HIV, Hepatitis B, and Hepatitis C. Subjects may also suffer from acute chest crises and infarcts of extremities, end organs, and the central nervous system.

Subjects with SCD have decreased life expectancies. The prognosis for patients with SCD is steadily improving with careful, life-long management of crises and anemia. As of 2001, the average life expectancy of subjects with sickle cell disease was the mid-to-late 50's. Current treatments for SCD involve hydration and pain management during crises, and transfusions as needed to correct anemia.

Thalassemias (e.g., β-Thal, δ-Thal, and β/δ-Thal) cause chronic anemia. β-Thal is estimated to affect approximately 1 in 100,000 people worldwide. Its prevalence is higher in certain populations, including those of European descent, where its prevalence is approximately 1 in 10,000. β-Thal major, the more severe form of the disease, is life-threatening unless treated with lifelong blood transfusions and chelation therapy. In the United States, there are approximately 3,000 subjects with β-Thal major. β-Thal intermedia does not require blood transfusions, but it may cause growth delay and significant systemic abnormalities, and it frequently requires lifelong chelation therapy. Although HbA makes up the majority of hemoglobin in adult RBCs, approximately 3% of adult hemoglobin is in the form of HbA2, an HbA variant in which the two γ-globin chains are replaced with two delta (Δ)-globin chains. δ-Thal is associated with mutations in the A hemoglobin gene (HBD) that cause a loss of HBD expression. Co-inheritance of the HBD mutation can mask a diagnosis of β-Thal (i.e., β/δ-Thal) by decreasing the level of HbA2 to the normal range (Bouva 2006). β/δ-Thal is usually caused by deletion of the HBB and HBD sequences in both alleles. In homozygous (δo/δo βo/βo) patients, HBG is expressed, leading to production of HbF alone.

Like SCD, β-Thal is caused by mutations in the HBB gene. The most common HBB mutations leading to β-Thal are: c.-136C>G, c.92+1G>A, c.92+6T>C, c.93-21G>A, c.118C>T, c.316-106C>G, c.25_26delAA, c.27_28insG, c.92+5G>C, c.118C>T, c.135delC, c.315+1G>A, c.-78A>G, c.52A>T, c.59A>G, c.92+5G>C, c.124_127delTTCT, c.316-197C>T, c.-78A>G, c.52A>T, c.124_127delTTCT, c.316-197C>T, c.-138C>T, c.-79A>G, c.92+5G>C, c.75T>A, c.316-2A>G, and c.316-2A>C. These and other mutations associated with β-Thal cause mutated or absent β-globin chains, which causes a disruption of the normal Hb α-hemoglobin to β-hemoglobin ratio. Excess α-globin chains precipitate in erythroid precursors in the bone marrow.

In β-Thal major, both alleles of HBB contain nonsense, frameshift, or splicing mutations that leads to complete absence of β-globin production (denoted $\beta^0/\beta^0$). β-Thal major results in severe reduction in β-globin chains, leading to significant precipitation of α-globin chains in RBCs and more severe anemia.

β-Thal intermedia results from mutations in the 5' or 3' untranslated region of HBB, mutations in the promoter region or polyadenylation signal of HBB, or splicing mutations within the HBB gene. Patient genotypes are denoted βo/β+ or β+/β+. βo represents absent expression of a β-globin chain; β+ represents a dysfunctional but present β-globin chain. Phenotypic expression varies among patients. Since there is some production of β-globin, β-Thal intermedia results in less precipitation of α-globin chains in the erythroid precursors and less severe anemia than β-Thal major. However, there are more significant consequences of erythroid lineage expansion secondary to chronic anemia.

Subjects with β-Thal major present between the ages of 6 months and 2 years, and suffer from failure to thrive, fevers, hepatosplenomegaly, and diarrhea. Adequate treatment includes regular transfusions. Therapy for β-Thal major also includes splenectomy and treatment with hydroxyurea. If patients are regularly transfused, they will develop normally until the beginning of the second decade. At that time, they require chelation therapy (in addition to continued transfusions) to prevent complications of iron overload. Iron overload may manifest as growth delay or delay of sexual maturation. In adulthood, inadequate chelation therapy may lead to cardiomyopathy, cardiac arrhythmias, hepatic fibrosis and/or cirrhosis, diabetes, thyroid and parathyroid abnormalities, thrombosis, and osteoporosis. Frequent transfusions also put subjects at risk for infection with HIV, hepatitis B and hepatitis C.

β-Thal intermedia subjects generally present between the ages of 2-6 years. They do not generally require blood transfusions. However, bone abnormalities occur due to chronic hypertrophy of the erythroid lineage to compensate for chronic anemia. Subjects may have fractures of the long bones due to osteoporosis. Extramedullary erythropoiesis is common and leads to enlargement of the spleen, liver, and lymph nodes. It may also cause spinal cord compression and neurologic problems. Subjects also suffer from lower extremity ulcers and are at increased risk for thrombotic events, including stroke, pulmonary embolism, and deep vein thrombosis. Treatment of β-Thal intermedia includes splenectomy, folic acid supplementation, hydroxyurea therapy, and radiotherapy for extramedullary masses. Chelation therapy is used in subjects who develop iron overload.

Life expectancy is often diminished in β-Thal patients. Subjects with β-Thal major who do not receive transfusion therapy generally die in their second or third decade. Subjects with β-Thal major who receive regular transfusions and adequate chelation therapy can live into their fifth decade and beyond. Cardiac failure secondary to iron toxicity is the leading cause of death in β-Thal major subjects due to iron toxicity.

A variety of new treatments are currently in development for SCD and β-Thal. Delivery of an anti-sickling HBB gene via gene therapy is currently being investigated in clinical trials. However, the long-term efficacy and safety of this approach is unknown. Transplantation with hematopoietic stem cells (HSCs) from an HLA-matched allogeneic stem cell donor has been demonstrated to cure SCD and β-Thal, but this procedure involves risks including those associated with ablation therapy, which is required to prepare the subject for transplant, increases risk of life-threatening opportunistic infections, and risk of graft vs. host disease after transplantation. In addition, matched allogeneic donors often cannot be identified. Thus, there is a need for improved methods of managing these and other hemoglobinopathies.

SUMMARY

The present disclosure provides genome editing systems and related methods which allow for the modulation of indel signatures and frequency of certain indels mediated by genome editing systems, and guide RNAs (gRNAs), and CRISPR-mediated methods. Strategies which allow for increasing the frequency of productive indels are also provided. Provided herein are genome editing systems, gRNAs, and CRISPR-mediated methods for altering one or more genes.

Provided herein are genome editing systems, gRNAs, and CRISPR-mediated methods for altering one or more γ-globin genes (e.g., HBG1, HBG2, or HBG1 and HBG2), the erythroid specific enhancer of the BCL11A gene (BCL11Ae), or a combination thereof, and increasing expression of fetal hemoglobin (HbF). In certain embodiments, genome editing systems, gRNAs, and CRISPR-mediated methods may alter a 13 nucleotide (nt) target region that is 5' of the transcription site of the HBG1, HBG2, or HBG1 and HBG2 gene ("13 nt target region"). In certain embodiments, one or more gRNAs comprising a targeting domain set forth in SEQ ID NOs:251-901 or 940-942 may be used to introduce alterations in the 13 nt target region. In certain embodiments, genome editing systems, gRNAs, and CRISPR-mediated methods may alter a GATA1 binding motif in BCL11Ae that is in the +58 DNase I hypersensitive site (DHS) region of intron 2 of the BCL11A gene ("GATA1 binding motif in BCL11Ae"). In certain embodiments, one or more gRNAs comprising a targeting domain set forth in SEQ ID NOs:952-955 may be used to introduce alterations in the GATA1 binding motif in BCL11Ae. In certain embodiments, one or more gRNAs may be used to introduce alterations in the GATA1 binding motif in BCL11Ae and one or more gRNAs may be used to introduce alterations in the 13 nt target region of HBG1 and/or HBG2. In certain embodiments, genome editing systems, gRNAs, and CRISPR-mediated methods may alter a region within 50, 100, 200, 300, 400, or 500 bp of a proximal HBG1/2 promoter sequence including the 13 nt target region ("proximal HBG1/2 promoter target sequence").

The inventors have also addressed a key unmet need in the field by identifying a strategy for increasing accessibility to the chromatin using an RNA-guided helicase and dead guide RNA to unwind the DNA within or proximal to the target region to be edited (e.g., the 13 nt target region, proximal HBG1/2 promoter target sequence, and/or the GATA1 binding motif in BCL11Ae). This disclosure provides new and effective means of unwinding chromatin and thereby increasing accessibility of target regions to RNA-guided nucleases. Also provided herein are genome editing systems, guide RNAs, and CRISPR-mediated methods for unwinding and altering portions of a genome. Unwinding of the genome may be achieved using an RNA-guided helicase and/or a dead guide RNA configured to target an RNA-guided enzyme to a target region in DNA but not to support a cleavage event.

In one aspect, the disclosure relates to genome editing systems that may include an RNA-guided nuclease, a first guide RNA and a second guide RNA. In certain embodiments, the first and second guide RNAs may include first and second targeting domains complimentary to first and second sequences on opposite sides of positions of a 13 nt target region of a human HBG1 or HBG2 gene. One or both of the first and second sequences may overlap the 13 nt target region of the human HBG1 or HBG2 gene. The genome editing system may also include a nucleic acid template encoding a deletion of the 13 nt region of the human HBG1 or HBG2 gene. In certain embodiments, the RNA-guided nuclease may be an *S. pyogenes* Cas9 or a nickase, which optionally lacks RuvC activity. The first and second targeting domains may be complimentary to sequences immediately adjacent to a protospacer adjacent motif recognized by *S. pyogenes* Cas9. In certain embodiments, the first targeting domain may be complimentary to a sequence within positions c.-1,114 to -114 of a human HBG1 or HBG2 gene. In certain embodiments, at least one of the first and second targeting domains differ by no more than 3 nucleotides from a targeting domain listed in Table 7. The genome editing system may include first and second RNA-guided nucleases that, in some embodiments, are complexed with the first and second guide RNAs, respectively, forming first and second ribonucleoprotein complexes.

Continuing with this aspect of the disclosure, a genome editing system including any or all of the features described above may also include a third guide RNA, and optionally a fourth guide RNA. In certain embodiments, the third and fourth guide RNAs may include third and fourth targeting domains complimentary to third and fourth sequences on opposite sides of positions of a GATA1 binding motif in BCL11A erythroid enhancer (BCL11Ae) of a human BCL11A gene. One or both of the third and fourth sequences may optionally overlap the GATA1 binding motif in BCL11Ae of the human BCL11A gene. The genome editing systems may also include a nucleic acid template encoding a deletion of the GATA1 binding motif in BCL11Ae. In certain embodiments, the RNA-guided nuclease may be an *S. pyogenes* Cas9. In certain embodiments, the third and fourth targeting domains may be complimentary to sequences immediately adjacent to a protospacer adjacent motif recognized by *S. pyogenes* Cas9. In certain embodiments, the RNA-guided nuclease may be a nickase, which optionally lacks RuvC activity. In certain embodiments, the third targeting domain may be complimentary to a sequence within 1000 nucleotides upstream of the GATA1 binding motif in BCL11Ae. In certain embodiments, the third targeting domain may be complimentary to a sequence within 100 nucleotides upstream of the GATA1 binding motif in BCL11Ae. In certain embodiments, one of the third and fourth targeting domains may be complimentary to a sequence within 100 nucleotides downstream of the GATA1 binding motif in BCL11Ae. In certain embodiments, the fourth targeting domain may be complimentary to a sequence within 50 nucleotides downstream of the GATA1 binding motif in BCL11Ae. In certain embodiments, at least one of the third and fourth targeting domains differ by no more than 3 nucleotides from a targeting domain listed in Table 9. In certain embodiments, the genome editing systems may further include first and second RNA-guided nucleases. In certain embodiments, the first and second RNA-guided nucleases may be complexed with the third and fourth guide RNAs, respectively, forming third and fourth ribonucleoprotein complexes.

Continuing with this aspect of the disclosure, a genome editing system including any or all of the features described above may also include an RNA-guided helicase. In certain embodiments, the RNA-guided helicase may unwind nucleic acid within or proximate to the 13 nt target region or GATA1 binding motif in BCL11Ae of the human BCL11A gene. In certain embodiments, the RNA-guided helicase may be a fifth RNA-guided nuclease configured to lack nuclease activity. In certain embodiments, the RNA-guided nuclease may be complexed to a dead guide RNA including a fifth targeting domain of 15 or fewer nucleotides in length. In certain embodiments, the RNA-guided nuclease and dead guide RNA are not configured to recruit an exogenous trans-acting factor to the target region. In certain embodiments, the fifth targeting domain may be complimentary to a fifth sequence within or proximate to the 13 nt target region or GATA1 binding motif in BCL11Ae of the human BCL11A gene. In certain embodiments, the fifth targeting domain may include a nucleotide sequence that is identical to, or differs by no more than 1, 2, 3, 4, or 5 nucleotides from a nucleotide sequence set forth in Table 10. In certain embodiments, the fifth targeting domain may include a nucleotide sequence identical to the nucleotide sequence set forth in Table 10.

Another aspect of the disclosure relates to a method of altering a cell including contacting a cell with the genome editing systems described above and disclosed herein. In certain embodiments, the step of contacting the cell with the genome editing system may include contacting the cell with a solution including first and second ribonucleoprotein complexes. In certain embodiments, the step of contacting the cell with the solution may further include electroporating the cells, thereby introducing the first and second ribonucleoprotein complexes into the cell. In certain embodiments, the genome editing systems may further include contacting the cell with the genome editing system described above, in which the step of contacting the cell with the genome editing system may include contacting the cell with a solution including first, second, third, and optionally, fourth ribonucleoprotein complexes. In certain embodiments, the step of contacting the cell with the solution may further include electroporating the cells, thereby introducing the first, second, third, and optionally, fourth ribonucleoprotein complexes into the cell. In certain embodiments, the cell may be capable of differentiating into an erythroblast or a precursor of an erythroblast. In certain embodiments, the cell may be a CD34+ cell.

In one aspect, the disclosure relates to a CRISPR-mediated method of altering a cell including introducing a first DNA single strand break (SSB) or double strand break (DSB) within a genome of the cell between positions c.-614 to -102 of a human HBG1 or HBG2 gene and introducing a second SSB or DSB within the genome of the cell between positions c.-114 to -1 of the human HBG1 or HBG2 gene. In certain embodiments, the first and second SSBs or DSBs may be repaired by the cell in a manner that alters a 13 nt target region of the human HBG1 or HBG2 gene. In certain embodiments, the first and second SSBs or DSBs may be repaired by the cell in a manner that results in the deletion of all or part of a 13 nt target region of the human HBG1 or HBG2 gene. In certain embodiments, the first and second SSBs or DSBs may be repaired by the cell in a manner that results in the formation of at least one of an indel, a deletion, or an insertion in the 13 nt target region of the human HBG1 or HBG2 gene. In certain embodiments, the first and second SSBs or DSBs may be repaired by the cell in an error prone manner. In certain embodiments, the CRISPR-mediated method may further include introducing a third DNA single strand break (SSB) or double strand break (DSB) within 500 nucleotides upstream of a GATA1 binding motif in BCL11Ae of a human BCL11A gene and introducing a fourth SSB or DSB within the genome of the cell within 100 nucleotides downstream of the GATA1 binding motif in BCL11Ae of the human BCL11A gene. In certain embodiments, the third and fourth SSBs or DSBs may be repaired by the cell in a manner that alters the GATA1 binding motif in BCL11Ae of the human BCL11A gene. In certain embodiments, the third and fourth SSBs or DSBs may be repaired by the cell in a manner that results in the deletion of all or part of the GATA1 binding motif in BCL11Ae. In certain embodiments, the third and fourth SSBs or DSBs may be repaired by the cell in a manner that results in the formation of at least one of an indel, a deletion, or an insertion in the GATA1 binding motif in BCL11Ae. In certain embodiments, the third and fourth SSBs or DSBs may be repaired by the cell in an error prone manner.

In one aspect, the disclosure relates to compositions including a plurality of cells generated by the method disclosed above, in which at least 20%, 30%, 40%, 50%, 60%, 70%, 80% or 90% of the cells include an alteration of a sequence of a 13 nt target region of the human HBG1 or HBG2 gene or a plurality of cells generated by the method disclosed above, wherein at least 20%, 30%, 40%, 50%, 60%, 70%, 80% or 90% of the cells include an alteration of a sequence of a 13 nt target region of the human HBG1 or HBG2 gene and at least 20%, 30%, 40%, 50%, 60%, 70%, 80% or 90% of the cells include an alteration of a sequence of the GATA1 binding motif in BCL11Ae. In certain embodiments, at least a portion of the plurality of cells may be within an erythroid lineage. In certain embodiments, the plurality of cells may be characterized by an increased level of fetal hemoglobin expression relative to an unmodified plurality of cells. In certain embodiments, the level of fetal hemoglobin may be increased by at least 20%, 30%, 40%, 50%, 60%, 70%, 80% or 90%. In certain embodiments, the compositions may further include a pharmaceutically acceptable carrier.

In one aspect, the disclosure relates to a method of altering a cell, that includes unwinding a chromatin segment within or proximal to a target region of a nucleic acid in a cell and generating a double stranded break (DSB) within the target region of the nucleic acid whereby to alter the target region. In certain embodiments, the step of unwinding the chromatin segment may include contacting the chromatin segment with an RNA-guided helicase. In certain embodiments, the step of unwinding the chromatin does not include recruiting an exogenous trans-acting factor to the chromatin segment. The RNA-guided helicase may be an RNA-guided nuclease, and the RNA-guided nuclease may be complexed to a dead guide RNA (dgRNA) including a first targeting domain sequence of 15 or fewer nucleotides in length. In certain embodiments, the dgRNA may include modifications at the 5' or 3' end, including, but not limited to, an anti-reverse cap analog (ARCA) at the 5' end of the RNA, a polyA tail at the 3' end of the RNA, or both. In certain embodiments, the RNA-guided nuclease may be an enzymatically active RNA-guided nuclease or may be configured to lack nuclease activity. In certain embodiments, the targeting domain sequence of the dgRNA may be complementary to a sequence proximal to the target region. "Proximal to," in some embodiments herein, may mean within 10, 25, 50, 100, or 200 nucleotides of the target region. In certain embodiments, the step of unwinding the chromatin segment may not include forming a single or double-stranded break in the nucleic acid within the chromatin segment. In certain embodiments, the step of generating the DSB within the target region may include contacting the chromatin segment with an RNA-guided nuclease having nuclease activity. In certain embodiments, the RNA-guided nuclease having nuclease activity may be complexed to a gRNA including a targeting domain configured to overlap the target region.

Another aspect of the disclosure includes a method of inducing accessibility to a target region of a nucleic acid for editing in a cell including contacting the cell with an RNA-guided helicase and a dgRNA and unwinding DNA within or proximal to the target region with the RNA-guided helicase thereby inducing accessibility to the target region for editing. In various cases, the RNA-guided helicase and the dgRNA may be configured to associate within or proximal to the target region. In certain embodiments, the dgRNA may be configured such that it does not provide an RNA-guided nuclease cleavage event. In certain embodiments, the RNA-guided helicase and dgRNA may complex to form a dead ribonucleoprotein (RNP) that lacks cleavage activity. In certain embodiments, the dgRNA may include a targeting domain sequence of 15 or fewer nucleotides in length. In certain embodiments, the RNA-guided helicase may be an RNA-guided nuclease. In certain embodiments, the RNA-guided nuclease and dgRNA are not configured to recruit an exogenous trans-acting factor to the target region. In certain embodiments, the RNA-guided nuclease may be a Cas9 or a Cas9-fusion protein. In certain embodiments, the Cas9 may be an enzymatically active Cas9 or an enzymatically dead Cas9. In certain embodiments, the step of unwinding the DNA does not comprise forming a single or double-stranded break in the DNA. In certain embodiments, the RNA-guided nuclease having nuclease activity may be complexed to a gRNA including a targeting domain configured to overlap the target region.

In another aspect, the disclosure relates to a method of increasing a rate of indel formation in a nucleic acid that includes unwinding double stranded DNA within or proximal to a target region of the nucleic acid using an RNA-guided helicase configured to associate within or proximal to the target region and generating a DSB within the target region. In certain embodiments, generating a DSB within the target region results in forming an indel at the target region. In certain embodiments, the DSB may be repaired in a manner forming an indel at the target region. In certain embodiments, the rate of indel formation in the gene achieved using the RNA-guided helicase is increased compared to a rate of indel formation in the gene achieved without using the RNA-guided helicase. In certain embodiments, the RNA-guided helicase may form an RNP complex with a dgRNA configured to associate within or proximal to the target region. In certain embodiments, the dgRNA may include a targeting domain sequence of 15 nucleotides or less in length. In certain embodiments, the RNA-guided helicase may be an RNA-guided nuclease. In certain embodiments, the RNA-guided nuclease may be a Cas9 or a Cas9-fusion protein. In certain embodiments, the Cas9 may be an enzymatically active Cas9 or an enzymatically dead Cas9. In certain embodiments, the RNA-guided nuclease and the dgRNA are not configured to recruit an exogenous trans-acting factor to the target region. In certain embodiments, the step of unwinding the double stranded DNA does not include forming a single or double-stranded break in the DNA.

In yet another aspect, this disclosure relates to a method of deleting a segment of a target nucleic acid in a cell that includes contacting the cell with an RNA-guided helicase and generating a DSB within the target region, whereby a segment of the target nucleic acid is deleted. In certain embodiments, the DSB may be repaired in a manner that deletes a segment of the target nucleic acid. In certain embodiments, the RNA-guided helicase may be configured to associate within or proximal to a target region of the target nucleic acid and unwind double stranded DNA (dsDNA) within or proximal to the target region. In certain embodiments, the RNA-guided helicase may form an ribonucleoprotein complex with a dgRNA configured to associate within or proximal to the target region. In certain embodiments, the dgRNA may include a targeting domain sequence of 15 nucleotides or less in length. In certain embodiments, the RNA-guided helicase may be an RNA-guided nuclease. In certain embodiments, the RNA-guided nuclease may be a Cas9 or a Cas9-fusion protein. In certain embodiments, the Cas9 may be an enzymatically active Cas9 or an enzymatically dead Cas9. In certain embodiments, the RNA-guided nuclease and the dgRNA are not configured to recruit an exogenous trans-acting factor to the target region. In certain embodiments, the target nucleic acid may be a promoter region of a gene, a coding region of a gene, a non-coding region of a gene, an intron of a gene, or an exon of a gene. In certain embodiments, the segment of the target nucleic acid may be at least about 15, 20, 25, 30, 35, 40, 45, 50, 55, 60, 65, 70, 75, or 100 base pairs in length.

The disclosure also relates to a dead gRNA (dgRNA) molecule including a targeting domain comprising a truncation of a gRNA targeting domain. In certain embodiments, the gRNA targeting domain to be truncated may be a gRNA targeting domain set forth in Table 2 or Table 10. In certain embodiments, the gRNA targeting domain may be truncated from a 5' end of the gRNA targeting domain. In certain embodiments, the dgRNA may include a targeting domain sequence of 15 nucleotides or less in length. In certain embodiments, the first targeting domain may be the same as or may differ by no more than 3 nucleotides from a dgRNA targeting domain set forth in Table 10.

Another aspect of the disclosure relates to compositions including at least one polynucleotide encoding a plurality of gRNAs and an RNA-guided helicase, in which at least one gRNA may be a dgRNA configured such that it does not provide an RNA-guided nuclease cleavage event. In certain embodiments, the dgRNA may include a targeting domain sequence of 15 nucleotides or less in length. In certain embodiments, the RNA-guided helicase may be an RNA-guided nuclease. In certain embodiments, the RNA-guided nuclease may be a Cas9 or a Cas9-fusion protein. In certain embodiments, the Cas9 may be an enzymatically active Cas9 or an enzymatically dead Cas9. In certain embodiments, the RNA-guided nuclease and the dgRNA are not configured to recruit an exogenous trans-acting factor to the target region. In certain embodiments, the compositions further include a second RNA-guided nuclease configured to provide a cleavage event. In certain embodiments, the compositions further include a second gRNA configured to provide a cleavage event.

In another aspect, the disclosure relates to genome editing systems that include an RNA-guided nuclease and an RNA-guided helicase configured to associate with a target nucleic acid proximal to a target region of the target nucleic acid and induce a conformational change in the target region thereby promoting accessibility to the target region for the RNA-guided nuclease to form a break in the target region. The disclosure also relates to genome editing systems that include a dgRNA including a targeting domain sequence of 15 nucleotides or less in length, a first RNA-guided nuclease, and an RNA-guided helicase. In certain embodiments, the genome editing system further includes a gRNA. In certain embodiments, the gRNA and the first RNA-guided nuclease may associate with a target region in a target nucleic acid. In certain embodiments, the gRNA and the first RNA-guided nuclease may associate with a first PAM sequence in a target nucleic acid, wherein the first PAM sequence is facing outward. In certain embodiments, the RNA-guided helicase may be a second RNA-guided nuclease. In certain embodiments, the second RNA-guided nuclease and the dgRNA are not configured to recruit an exogenous trans-acting factor to the target region. In certain embodiments, the dgRNA and the second RNA-guided nuclease associate within or proximal to a target region in the target nucleic acid. In certain embodiments, the first RNA-guided nuclease and second RNA-guided nuclease may be complexed with the gRNA and dgRNAs, respectively, forming first and second ribonucleoprotein complexes.

In another aspect, the disclosure relates to a genome editing system that includes a dgRNA comprising a targeting domain sequence of 15 nucleotides or less in length, a first RNA-guided nuclease, and an RNA-guided helicase. In certain embodiments, the gRNA and the first RNA-guided nuclease may associate with a target region in a target nucleic acid. In certain embodiments, the gRNA and the first RNA-guided nuclease may associate with a first protospacer adjacent motif (PAM) sequence in a target nucleic acid. In certain embodiments, the first PAM sequence may be facing outward. In certain embodiments, the RNA-guided helicase may be a second RNA-guided nuclease. In certain embodiments, the second RNA-guided nuclease and the dgRNA are not configured to recruit an exogenous trans-acting factor to the target region. In certain embodiments, the dgRNA and the second RNA-guided nuclease may associate within or proximal to a target region in the target nucleic acid. In certain embodiments, the first RNA-guided nuclease and second RNA-guided nuclease may be complexed with the gRNA and dgRNAs, respectively, forming first and second ribonucleoprotein complexes. In certain embodiments, the dgRNA and the second RNA-guided nuclease may associate with a second PAM sequence in a target nucleic acid, wherein the second PAM sequence may be facing outward.

In another aspect, the disclosure relates to a genome editing system that includes a dgRNA, a first gRNA comprising a second targeting domain sequence greater than 17 nucleotides in length, and an RNA-guided nuclease. In certain embodiments, the RNA-guided nuclease and the dgRNA may be configured to associate within a first target region in a target nucleic acid. In certain embodiments, the RNA-guided nuclease and the first gRNA may be configured to associate within a second target region and generate a double stranded break (DSB) in the target nucleic acid whereby to create an indel between the first target region and the second target region. In certain embodiments, the dgRNA may comprise a first targeting domain sequence of 15 nucleotides or less in length. In certain embodiments, the dgRNA has reduced or no RNA-guided nuclease cleavage activity. In certain embodiments, the dgRNA may be configured such that it does not provide an RNA-guided nuclease cleavage event. In certain embodiments, the dgRNA and the RNA-guided nuclease may associate with a first protospacer adjacent motif (PAM) sequence in the target nucleic acid. In certain embodiments, the first PAM sequence may be facing outward. In certain embodiments, the first gRNA and the RNA-guided nuclease may associate with a second PAM sequence in the target nucleic acid. In certain embodiments, the second PAM sequence may be facing outward.

In another aspect, the disclosure relates to a method of altering a cell, including contacting the cell with a dgRNA, a first gRNA comprising a second targeting domain sequence greater than 17 nucleotides in length, and an RNA-guided nuclease. In certain embodiments, the RNA-guided nuclease and the dgRNA may be configured to associate within a first target region in a target nucleic acid. In certain embodiments, the RNA-guided nuclease and the first gRNA may associate within a second target region and generate a double stranded break (DSB) in the target nucleic acid whereby to create an indel between the first target region and the second target region. In certain embodiments, the dgRNA may comprise a first targeting domain sequence of 15 nucleotides or less in length. In certain embodiments, the dgRNA has reduced or no RNA-guided nuclease cleavage activity. In certain embodiments, the dgRNA may be configured such that it does not provide an RNA-guided nuclease cleavage event. In certain embodiments, the dgRNA and the RNA-guided nuclease may associate with a first protospacer adjacent motif (PAM) sequence in the target nucleic acid. In certain embodiments, the first PAM sequence may be facing outward. In certain embodiments, the first gRNA and the RNA-guided nuclease may associate with a second PAM sequence in the target nucleic acid. In certain embodiments, the second PAM sequence may be facing outward.

The disclosure herein also relates to methods of altering a cells, including contacting a cell with any of the genome editing systems disclosed herein. In certain embodiments, the step of contacting the cell may comprise contacting the cell with a solution comprising first and second ribonucleoprotein complexes. In certain embodiments, the step of contacting the cell with the solution further comprises electroporating the cells, thereby introducing the first and second ribonucleoprotein complexes into the cell.

In another aspect, the disclosure relates to cells that are altered using the methods disclosed herein. Cells that include a productive indel which results in HbF expression are also disclosed herein. In certain embodiments the indel may be produced by contacting the cell with a dgRNA, a first gRNA including a second targeting domain sequence greater than 17 nucleotides in length, and an RNA-guided nuclease. In certain embodiments, the RNA-guided nuclease and the dgRNA may be configured to associate within a first target region in a target nucleic acid. In certain embodiments, the RNA-guided nuclease and the first gRNA may associate with a second target region and generate a double stranded break (DSB) in the target nucleic acid whereby to create an indel between the first target region and the second target region. In certain embodiments, the cells disclosed herein, may be capable of differentiating into an erythroblast, erythrocyte, or a precursor of an erythrocyte or erythroblast. In certain embodiments, the cell may be a CD34+ cell.

A genome editing system or method including any of all of the features described above may include a target nucleic acid comprising a human HBG1, HBG2 gene, or a combination thereof. In certain embodiments, the target region may be a CCAAT box target region of the human HBG1, HBG2 gene, or a combination thereof. In certain embodiments, the first targeting domain sequence may be complementary to a first sequence on a side of a CCAAT box target region of the human HBG1, HBG2 gene, or a combination thereof, in which the first sequence optionally overlaps the CCAAT box target region of the human HBG1, HBG2 gene, or a combination thereof. In certain embodiments, the second targeting domain sequence may be complementary to a second sequence on a side of a CCAAT box target region of the human HBG1, HBG2 gene, or a combination thereof, in which the second sequence optionally overlaps the CCAAT box target region of the human HBG1, HBG2 gene, or a combination thereof. In certain embodiments, the first targeting domain may comprise a truncation of a gRNA targeting domain. In certain embodiments, the gRNA targeting domain may include the gRNAs set forth in Table 2 or Table 10, and the gRNA targeting domain has been truncated from a 5' end of the gRNA targeting domain. In certain embodiments, the first targeting domain may be the same as or differs by no more than 3 nucleotides from a dgRNA targeting domain set forth in Table 10. In certain embodiments, the second targeting domain differs by no more than 3 nucleotides from a gRNA targeting domain set forth in Table 2 or Table 10. In certain embodiments, the indel may alter the CCAAT box target region indel. In certain embodiments, the indel may be a productive indel resulting in an increased level of fetal hemoglobin expression. In certain embodiments, the gRNA, dgRNA, or both may be in vitro synthesized or chemically synthesized.

In certain embodiments, a cell may include at least one modified allele of the HBG locus generated by any of the methods for altering a cell disclosed herein, in which the modified allele of the HBG locus comprises an alteration of the human HBG1 gene, HBG2, gene, or a combination thereof.

In certain embodiments, an isolated population of cells may be modified by any of the methods for altering a cells disclosed herein, wherein the population of cells may include a distribution of indels that may be different from an isolated population of cells or their progenies of the same cell type that have not been modified by the method.

In certain embodiments, a plurality of cells may be generated by any of the methods for altering a cells disclosed herein, in which at least 20%, 30%, 40%, 50%, 60%, 70%, 80%, or 90% of the cells may include an alteration of a sequence in the CCAAT box target region of the human HBG1 gene, HBG2 gene or a combination thereof.

In certain embodiments, the cells disclosed herein may be used for a medicament. In certain embodiments, the cells may be for use in the treatment of β-hemoglobinopathy. In certain embodiments, β-hemoglobinopathy may be selected from the group consisting of sickle cell disease and beta-thalassemia.

In one aspect, the disclosure relates to compositions including a plurality of cells generated by a method including a dgRNA disclosed above, in which at least 20%, 30%, 40%, 50%, 60%, 70%, 80% or 90% of the cells include an alteration of a sequence of a CCAAT box target region of the human HBG1 or HBG2 gene or a plurality of cells generated by the method disclosed above, wherein at least 20%, 30%, 40%, 50%, 60%, 70%, 80% or 90% of the cells include an alteration of a sequence of a CCAAT box target region of the human HBG1 or HBG2. In certain embodiments, at least a portion of the plurality of cells may be within an erythroid lineage. In certain embodiments, the plurality of cells may be characterized by an increased level of fetal hemoglobin expression relative to an unmodified plurality of cells. In certain embodiments, the level of fetal hemoglobin may be increased by at least 20%, 30%, 40%, 50%, 60%, 70%, 80% or 90%. In certain embodiments, the compositions may further include a pharmaceutically acceptable carrier.

In one aspect, the disclosure relates to a population of cells modified by a genome editing system including a dgRNA described above, wherein the population of cells comprise a higher percentage of a productive indel relative to a population of cells not modified by the genome editing system. The disclosure also relates to a population of cells modified by the genome editing system including a dgRNA described above, wherein a higher percentage of the population of cells are capable of differentiating into a population of cells of an erythroid lineage that express HbF relative to a population of cells not modified by the genome editing system. In certain embodiments, the higher percentage may be at least about 15%, at least about 20%, at least about 25%, at least about 30%, or at least about 40% higher. In certain embodiments, the cells may be hematopoietic stem cells. In certain embodiments, the cells may be capable of differentiating into an erythroblast, erythrocyte, or a precursor of an erythrocyte or erythroblast. In certain embodiments, the indel may be created by a repair mechanism other than microhomology-mediated end joining (MMEJ) repair.

The disclosure also relates to the use of any of the cells disclosed herein in the manufacture of a medicament for treating β-hemoglobinopathy in a subject.

In one aspect, the disclosure relates to a method of treating a β-hemoglobinopathy in a subject in need thereof, comprising administering to the subject the cells disclosed herein. In certain embodiments, a method of treating a β-hemoglobinopathy in a subject in need thereof, may include administering a population of modified hematopoietic cells to the subject, wherein one or more cells have been altered according to the methods of altering a cell disclosed herein.

This listing is intended to be exemplary and illustrative rather than comprehensive and limiting. Additional aspects and embodiments may be set out in, or apparent from, the remainder of this disclosure and the claims.

BRIEF DESCRIPTION OF THE DRAWINGS

The accompanying drawings are intended to provide illustrative, and schematic rather than comprehensive, examples of certain aspects and embodiments of the present disclosure. The drawings are not intended to be limiting or binding to any particular theory or model, and are not necessarily to scale. Without limiting the foregoing, nucleic acids and polypeptides may be depicted as linear sequences, or as schematic two- or three-dimensional structures; these depictions are intended to be illustrative rather than limiting or binding to any particular model or theory regarding their structure.

FIG. 1. Each gene in the γ-globin gene cluster is transcriptionally regulated by a proximal promoter. While not wishing to be bound by any particular theory, it is generally thought that $A_\gamma$ and/or $G_\gamma$ expression is activated by engagement between the proximal promoter with the distal strong erythroid-specific enhancer, the locus control region (LCR). Long-range transactivation by the LCR is thought to be mediated by alteration of chromatin configuration/confirmation. The LCR is marked by 4 erythroid specific DNase I hypersensitive sites (HS1-4) and 2 distal enhancer elements (5' HS and 3' HS1). γ-like gene globin gene expression is regulated in a developmental stage-specific manner, and expression of globin genes changes coincide with changes in the main site of blood production.

FIG. 3A Gene editing as determined by T7E1 endonuclease assay analysis (referred to interchangeably as a "T7E1 analysis") of HBG1 and HBG2 locus-specific PCR products amplified from genomic DNA extracted from K562 cells after electroporation with DNA encoding *S. pyogenes*-specific gRNAs and plasmid DNA encoding *S. pyogenes* Cas9. FIG. 3B Gene editing as determined by DNA sequence analysis of PCR products amplified from the HBG1 locus in genomic DNA extracted from K562 cells after electroporation with DNA encoding the indicated gRNA and Cas9 plasmid. FIG. 3C Gene editing as determined by DNA sequence analysis of PCR products amplified from the HBG2 locus in genomic DNA extracted from K562 cells after electroporation with DNA encoding the indicated gRNA and Cas9 plasmid. For FIG. 3B-C, the types of editing events (insertions, deletions) and subtypes of deletions (13 nt target partially [12 nt HPFH] or fully [13-26 nt HPFH] deleted, other sequences deleted [other deletions]) are indicated by the differently shaded/patterned bars.

FIG. 4A depicts the percentage of indels detected by T7E1 analysis of HBG1 and HBG2 specific PCR products amplified from gDNA extracted from CB $CD34^+$ cells treated with the indicated RNPs or donor matched untreated control cells (n=3 CB $CD34^+$ cells, 3 separate experiments). Data shown represent the mean and error bars correspond to standard deviation across the 3 separate donors/experiments. FIG. 4B depicts the percentage of indels detected by T7E1 analysis of HBG2 specific PCR product amplified from gDNA extracted from CB $CD34^+$ cells or adult $CD34^+$ cells treated with the indicated RNPs or donor matched untreated control cells (n=3 CB $CD34^+$ cells, n=3 mobilized peripheral blood (mPB) $CD34^+$ cells, 3 separate experiments). Data shown represent the mean and error bars correspond to standard deviation across the 3 separate donors/experiments. FIG. 4C (Top panel) depicts indels as detected by T7E1 analysis of HBG2 PCR products amplified from gDNA extracted from human CB $CD34^+$ cells electroporated with HBG Sp35 RNP or HBG Sp37 RNP+/−ssODN (unmodified or with PhTx modified 5' and 3' ends). The lower left panel shows the level of gene editing as determined by Sanger DNA sequence analysis of gDNA from cells edited with HBF Sp37 RNP and ssODN. The lower right panel shows the specific types of deletions detected within total deletions.

FIG. 5A depicts the percentage of indels detected by T7E1 analysis of HBG2 PCR product amplified from gDNA extracted from mPB $CD34^+$ cells treated with the RNP or donor matched untreated control cells. FIG. 5B depicts the fold change in HBG mRNA expression in day 7 erythroblasts that were differentiated from RNP treated and untreated donor matched control mPB $CD34^+$ cells. mRNA levels are normalized to GAPDH and calibrated to the levels detected in untreated controls on the corresponding days of differentiation.

FIG. 6A shows hematopoietic myeloid/erythroid colony forming cell (CFC) potential, where the number and subtype of colonies are indicated (GEMM: granulocyte-erythroid-monocyte-macrophage colony, E: erythroid colony, GM: granulocyte-macrophage colony, M: macrophage colony, G: granulocyte colony). FIG. 6B depicts the percentage of Glycophorin A expressed over the time course of erythroid differentiation as determined by flow cytometry analysis at the indicated time points and for the indicated samples.

FIG. 10C depicts the % of HbF protein detected by HPLC analysis (% HbF=100%×HbF/(HbF+HbA). FIG. 10D depicts the hematopoietic activity of the RNP treated and donor matched untreated control $CD34^+$ cells in colony forming cell (CFC) assays. CFCs shown are per thousand $CD34^+$ cells plated. FIG. 10E depicts human blood $CD45^+$ cell reconstitution of the peripheral blood in immunodeficient mice (NSG) 1 month after transplantation with donor matched human mPB $CD34^+$ that were either untreated (0 μM), or treated with one of two doses (2.5 and 3.75 μM) of D10A RNP and paired gRNAs. FIG. 10F depicts human blood $CD45^+$ cell reconstitution of the peripheral blood in immunodeficient mice (NSG) 2 months after transplantation. FIGS. 10G and 10H depict the lineage distributions following human $CD45^+$ blood cell reconstitution of NSG mice at 1 month (FIG. 10G) and 2 months (FIG. 10H).

erythroid specific enhancer of BCL11A (BCL11Ae) (genomic coordinates: chr2: 60,495,265 to 60,495,270).

Figure 13A:
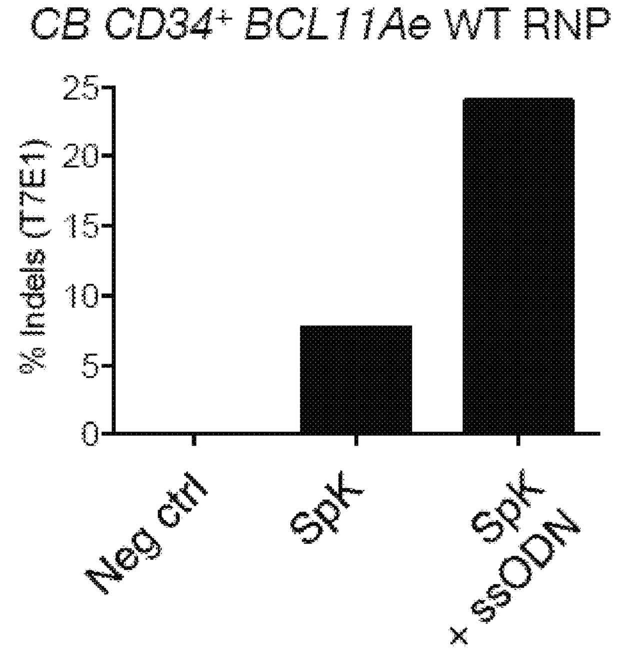
Figure 13B:
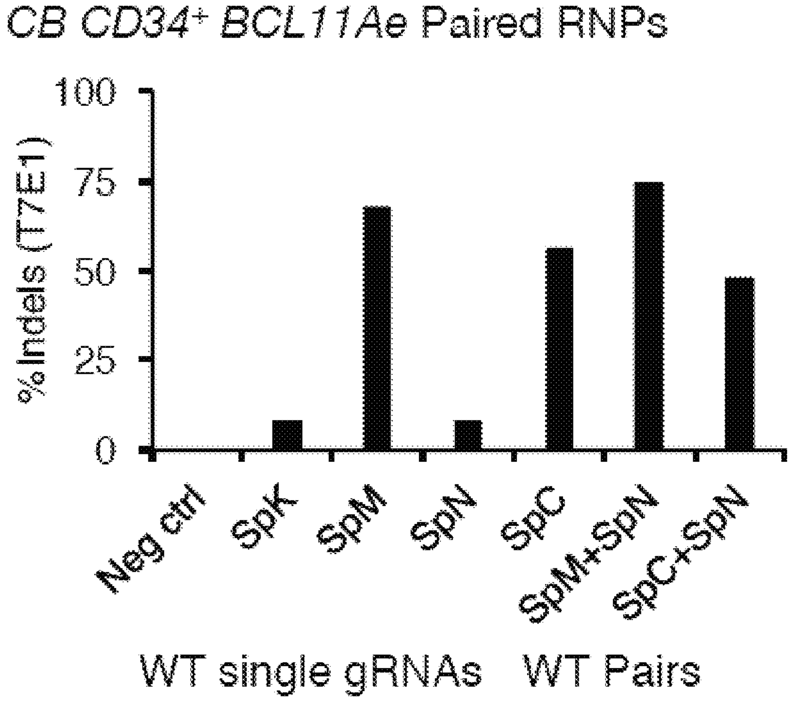

FIG. 13A depicts the percentage of indels detected by T7E1 endonuclease analysis of BCL11A PCR products amplified from gDNA extracted from CB $CD34^+$ cells treated with the indicated RNP+/−ssODN or donor matched untreated control cells. Data shown represent the mean of three 3 separate donors/experiments. FIG. 13B depicts indels detected by T7E1 endonuclease analysis of BCL11A PCR products amplified from gDNA extracted from CB $CD34^+$ cells treated with the indicated WT RNP (single gRNA targeting the BCL11A erythroid enhancer complexed to WT *S. pyogenes* Cas9 having both RuvC and HNH activity) or paired nickase RNP (paired gRNAs targeting the BCL11A erythroid enhancer (BCL11Ae) complexed to *S. pyogenes* Cas9 nickases sharing the same HNH single stranded cutting activity (e.g., D10A), as well as the hematopoietic activity of cells in each condition.

Figure 14A:
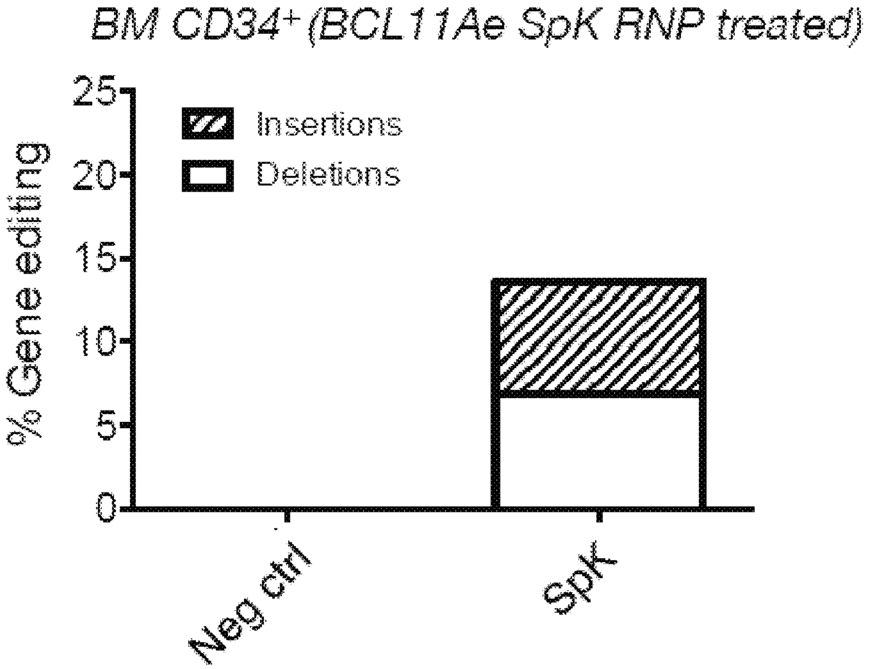
Figure 14B:
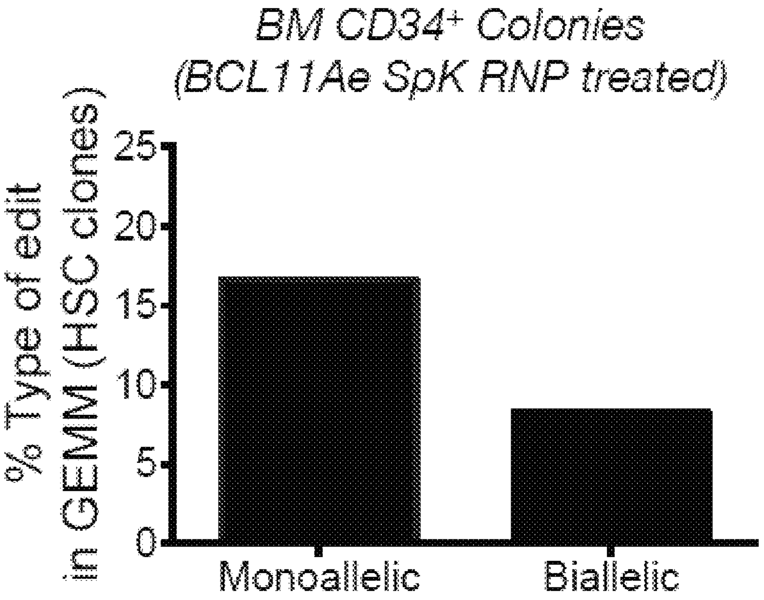
Figure 14C:
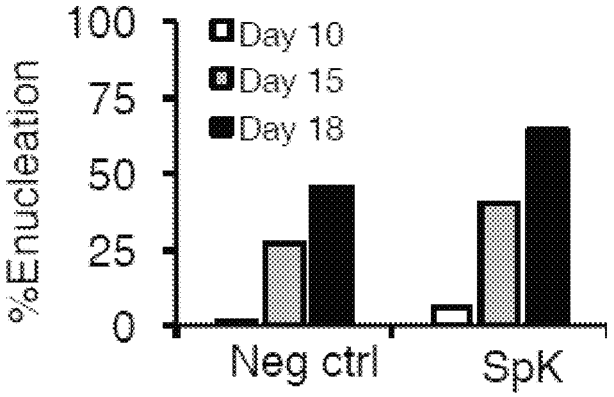
Figure 14D:
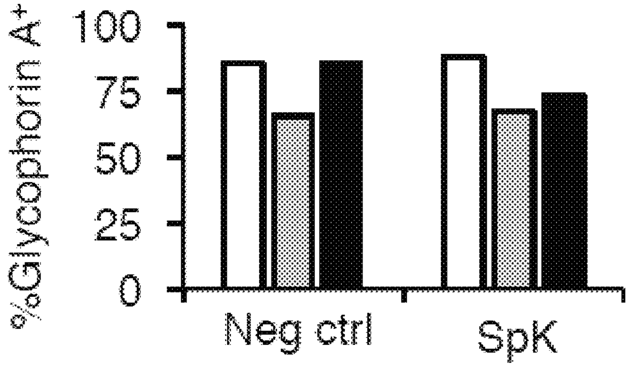
Figure 14E:
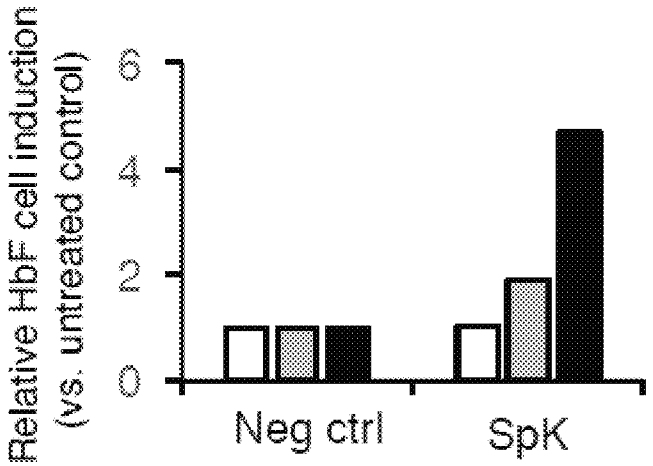

FIG. 14A depicts the editing frequency of BCL11Ae (using single gRNA approach targeting the GATA1 motif) in adult human BM $CD34^+$ cells. FIG. 14B depicts the monoallelic and biallelic editing detected in hematopoietic colonies (GEMMs, clonal progeny of BCL11Ae RNP treated $CD34^+$ cells) as determined by DNA sequencing analysis. FIG. 14C depicts the kinetics of erythroblast maturation (enucleation as determined by $DRAQ5^-$ cells detected by flow cytometry analysis). FIG. 14D depicts the acquisition of erythroid phenotype (Glycophorin $A^+$ cells) in differentiated control and RNP-treated BM $CD34^+$ cells, while FIG. 14E shows the fold increase in $HbF^+$ cells as determined by flow cytometry analysis relative to HbF+ cells in untreated donor matched control samples.

Figure 15A:
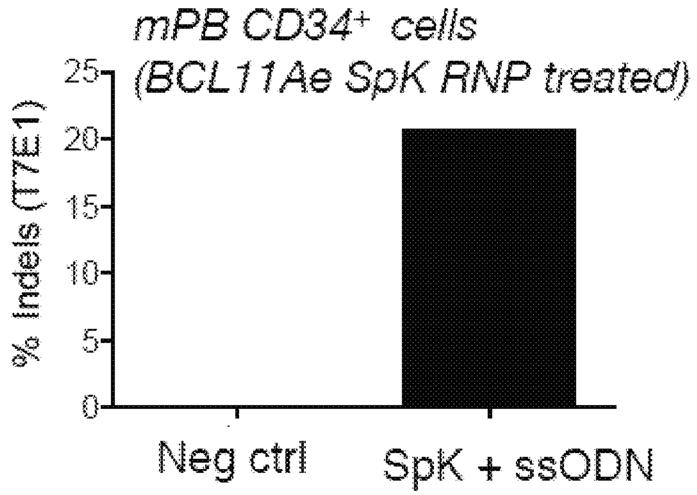
Figure 15B:
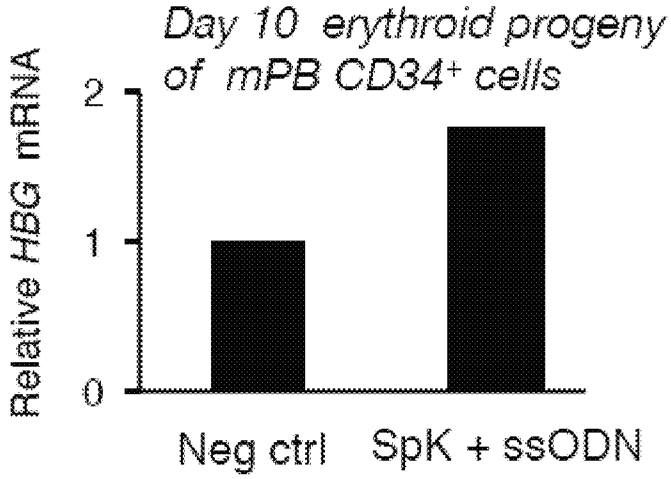
Figure 15C:
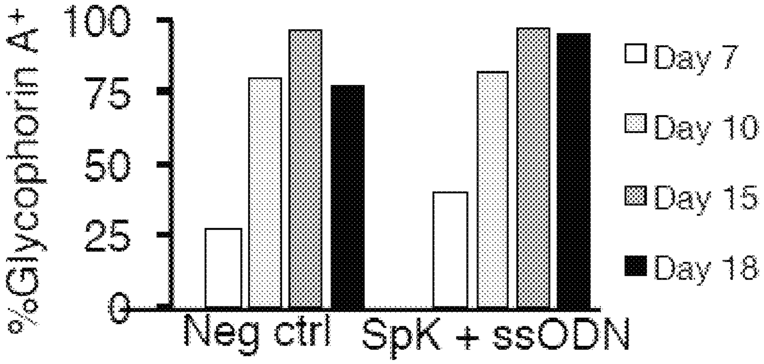

FIGS. 15A-C depicts gene editing of BCL11Ae in adult human mPB $CD34^+$ cells and induction of fetal hemoglobin in erythroid progeny of RNP and ssODN treated cells after electroporation of mPB $CD34^+$ cells with BCL11Ae RNP+ nonspecific ssODN (i.e., no homology to BCL11Ae target region). FIG. 15A depicts the percentage of indels detected by T7E1 analysis of HBG2 PCR product amplified from gDNA extracted from mPB $CD34^+$ cells treated with the BCL11Ae RNP and nonspecific ssODN or donor matched untreated control cells. FIG. 15B depicts the fold change in HBG mRNA expression in day 10 erythroblasts that were differentiated from BCL11Ae RNP treated and untreated donor matched control mPB $CD34^+$ cells (mRNA levels are normalized to GAPDH and calibrated to the levels detected in untreated controls on the corresponding days of differentiation). FIG. 15C depicts the percentage of Glycophorin A expressed over the time course of erythroid differentiation of mPB $CD34^+$ cells+/− treatment with BCL11Ae RNP and nonspecific ssODN, as determined by flow cytometry analysis at the indicated time points and for the indicated samples.

Figure 16:
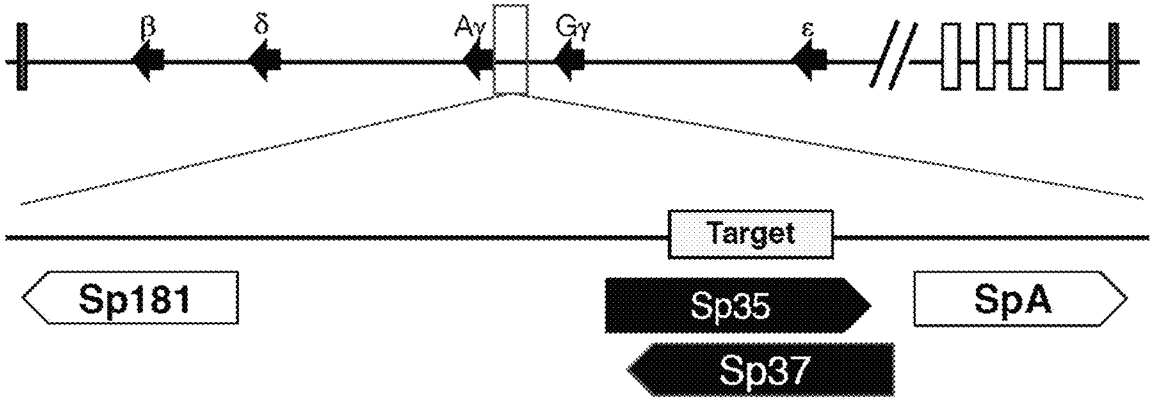

FIG. 16 depicts a schematic of the -110 nt target region in the gamma hemoglobin gene (HBG) promoter (grey box) and the relative locations of homologous sequences to dead gRNAs (dgRNAs) and wild-type gRNAs. dgRNAs that have a truncated targeting domain sequence and do not promote Cas9 cutting are depicted (i.e., Sp181 dgRNA and truncated (t)SpA dgRNA, Table 10) as white arrows. gRNAs that have a full-length targeting domain sequence, which promote Cas9 cutting are depicted as black arrows (i.e., Sp35 and Sp37 gRNAs, Table 10).

Figure 17:
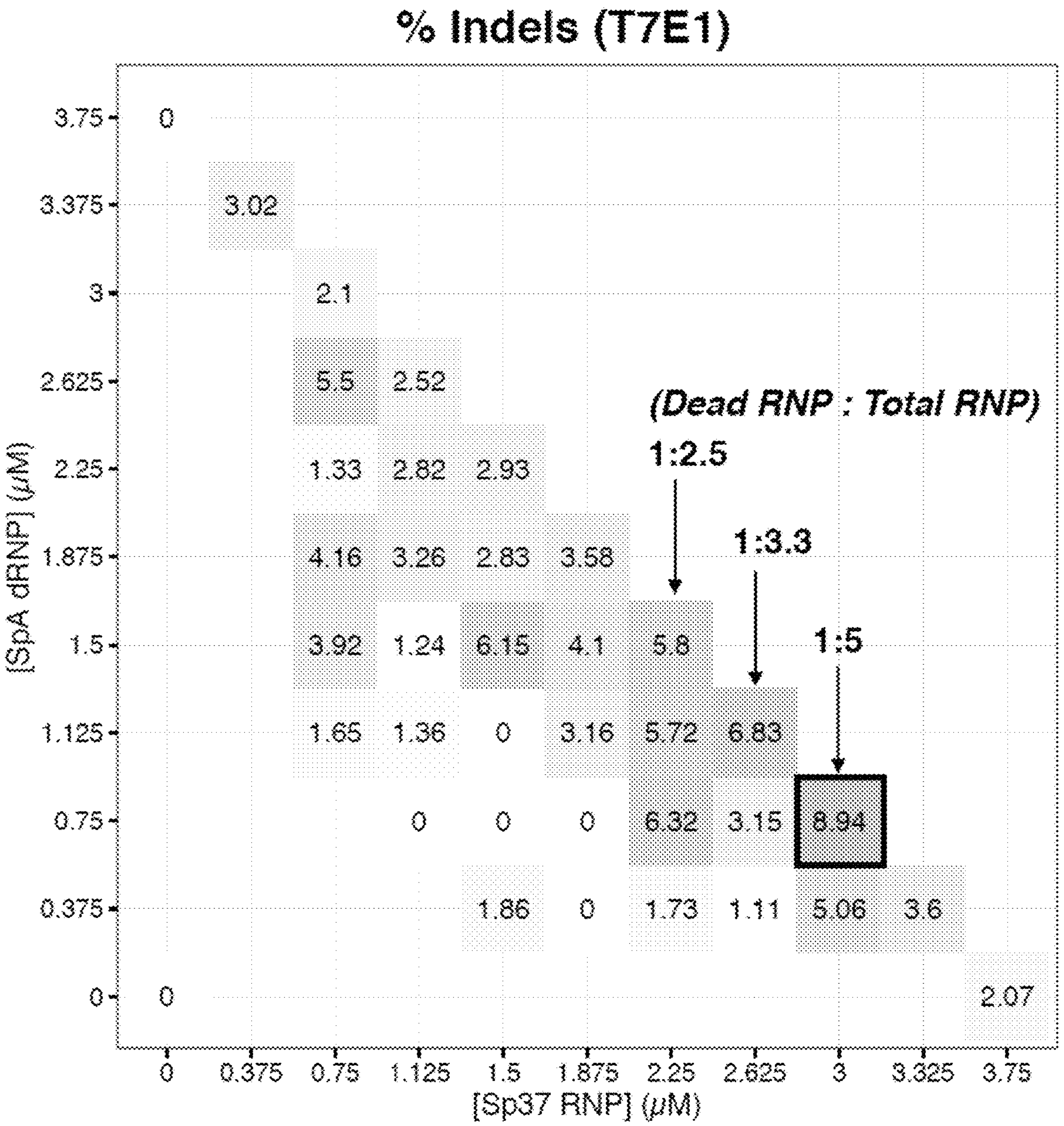

FIG. 17 shows the percentage of edits determined by T7E1 endonuclease analysis of HBG2 PCR product amplified from genomic DNA (gDNA) extracted from mobilized peripheral blood (mPB) $CD34^+$ cells after codelivery of a dead ribonucleoprotein (dRNP) (i.e., SpA dRNP) and a wild-type (WT) RNP (i.e., Sp37 RNP). tSpA dRNP comprises WT Cas9 protein complexed to a truncated gRNA (tSpA dgRNA, Table 10) (i.e., dead (d)RNA15-mer version of SpA) and Sp37 RNP comprises WT Cas9 protein complexed to gRNA Sp37 (Table 10).

Figure 18:
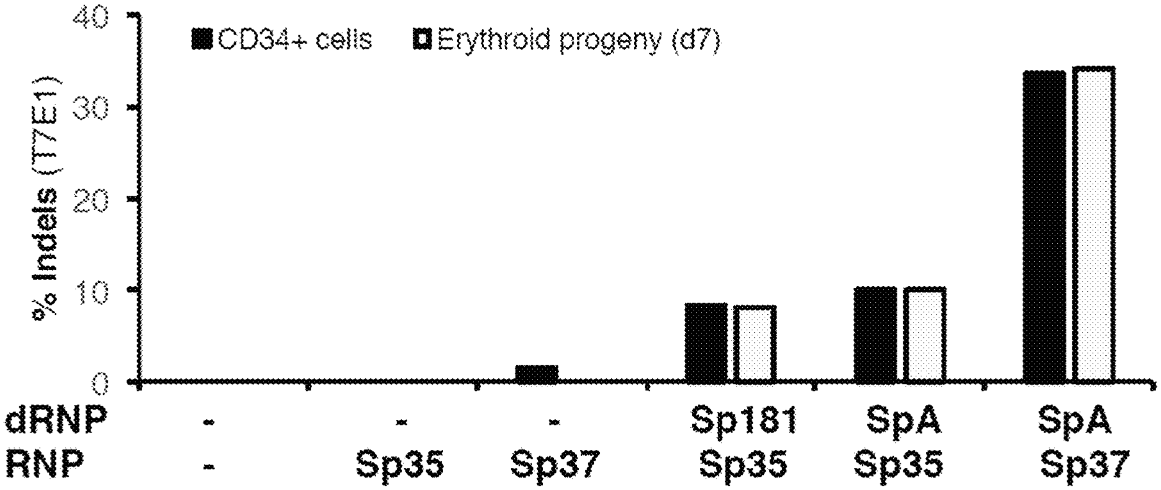

FIG. 18 depicts the percentage of edits detected by T7E1 analysis of HBG PCR product amplified from gDNA extracted from mPB $CD34^+$ cells after delivery of Sp35 RNP alone (i.e., Sp35 gRNA complexed with WT Cas 9 protein)) or codelivery of Sp35 RNP and dRNPs that target the same or opposite DNA strand as Sp35 RNP (i.e., Sp181 dRNP (Sp181 dgRNA complexed with WT Cas9 protein) and tSpA dRNP (tSpA dgRNA complexed with WT Cas9 protein)) (see also FIG. 16). Black bars indicate the level of indels detected in the mPB $CD34^+$ cells. White bars indicate the level of indels detected in the mPB $CD34^+$ cells maintained in the day 7 erythroid progeny of edited cells.

Figure 19:
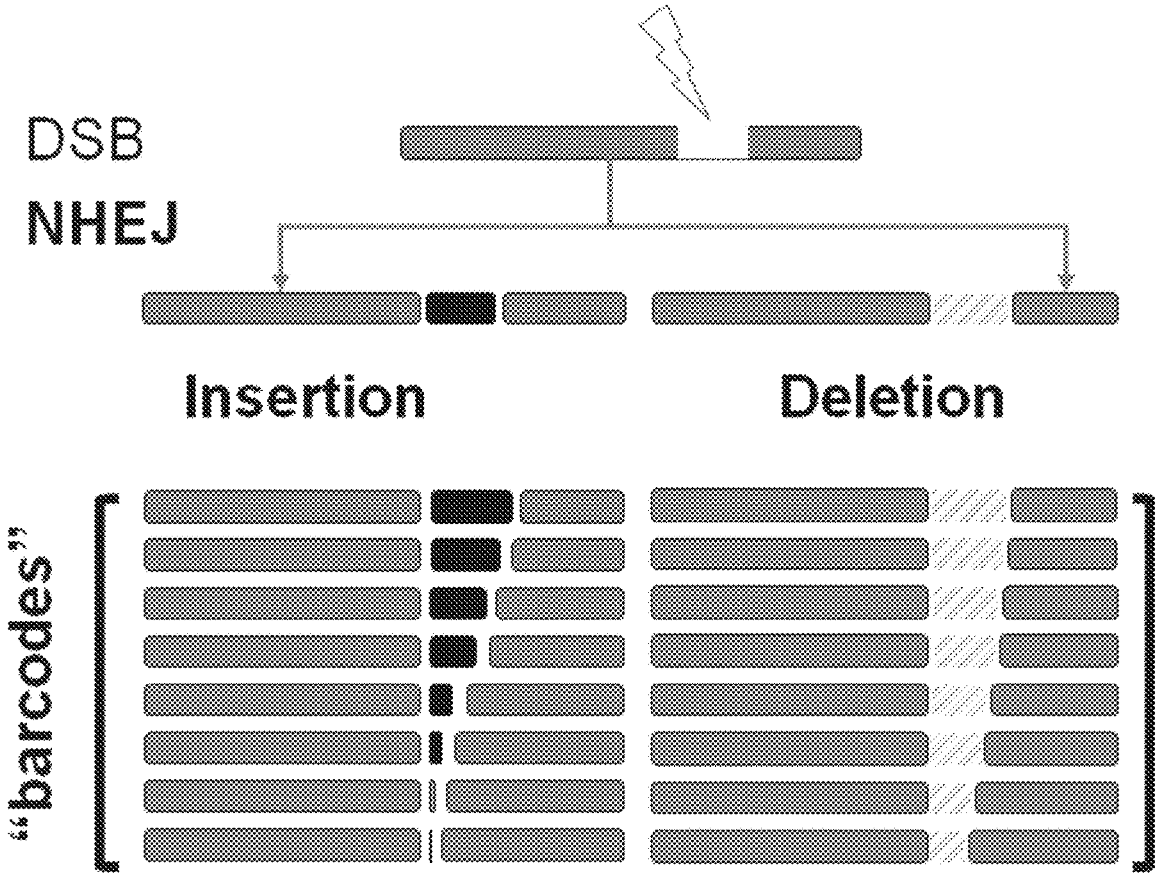

FIG. 19 shows a schematic of the variety of insertions and deletions resulting from double strand breaks repaired through NHEJ. Each unique edit (e.g., insertion or deletion) may serve as a unique identifier (or "barcode") for an individual cell or clone of cells descended therefrom.

Figure 20:
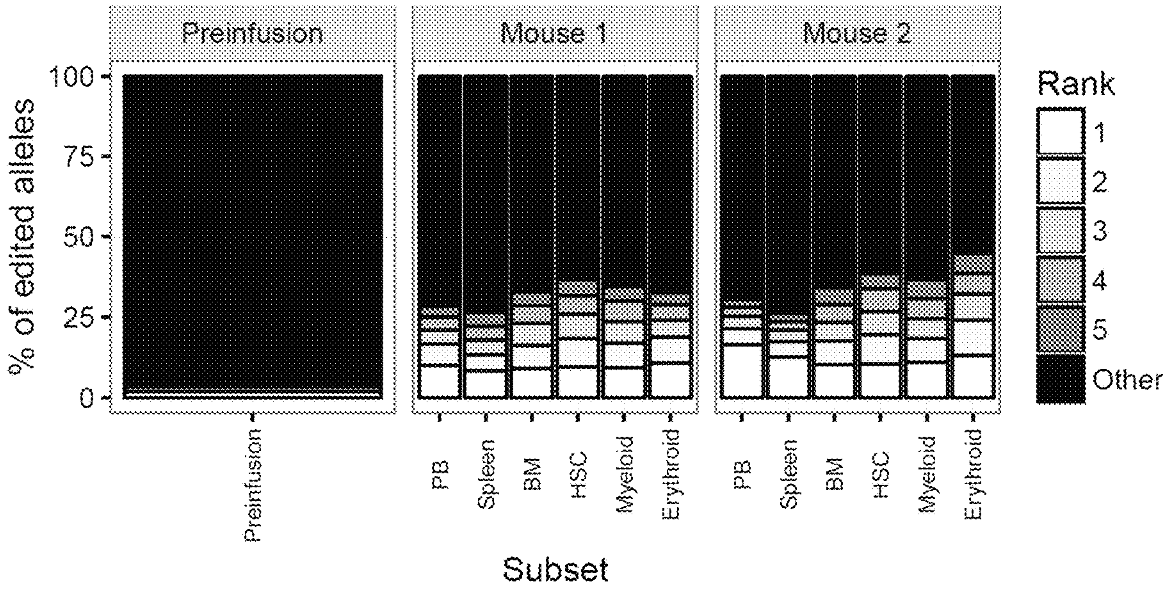

FIG. 20 depicts a graphical rank ordering of the most abundant edited alleles in pre-infusion human HSCs and in lineages or tissue populations derived from long-term engrafting cells from two experimental replicates at 16-weeks post-infusion. Genomic DNA from cells electroporated with a ribonucleoprotein complex targeting the HBB locus was harvested and sequencing reads were aligned to an unedited or WT reference sequence. The frequency of individual edited alleles among the total number of reads from each sample was quantified and ranked. White and grey bars represent to five most abundant unique alleles in each sample, with white bars representing the most abundant unique allele, and less frequent alleles being represented by progressively darker shades of grey. Black bars represent unique alleles outside of the top 5 in terms of frequency. These data indicate that the most frequent alleles in each sample represent a comparatively small fraction of the total reads, and that the distribution of reads varies across lineages or tissue populations derived from the same pre-infusion pool, indicating that diversity of edited alleles is preserved in long-term engrafting HSCs and their progeny.

Figure 21:
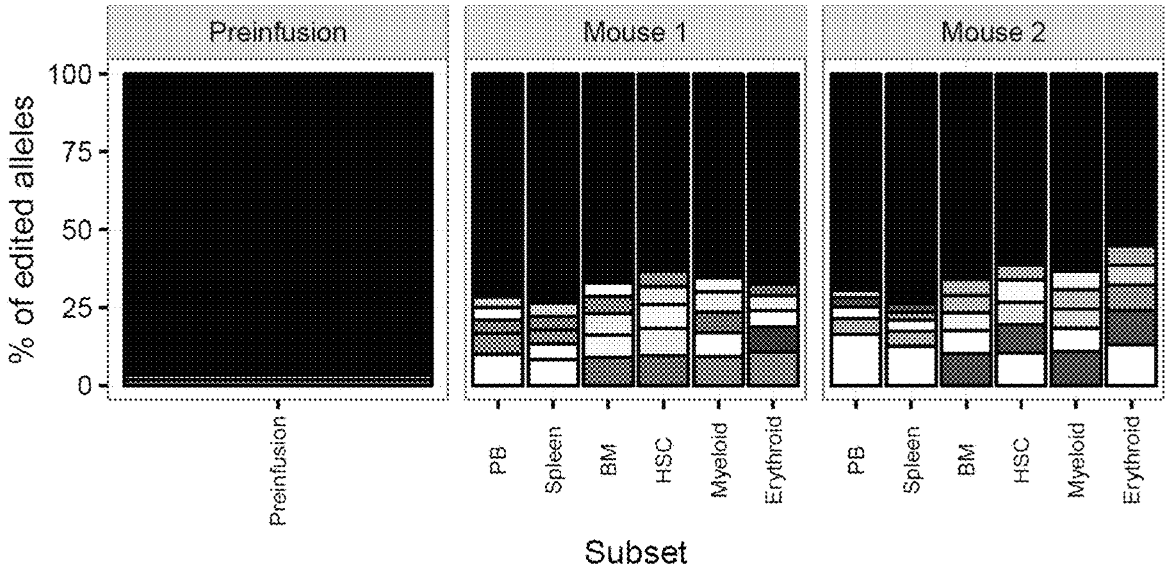

FIG. 21 depicts a graphical rank-ordering of the abundance of edited alleles in pre-infusion human HSCs and in lineages or tissue populations derived from long-term engrafting cells in two experimental replicates at 16-weeks post-infusion. Editing and analysis were performed as described for FIG. 20, but the white bars correspond to the edited allele observed at the highest frequency in the pre-infusion edited HSC sample, and progressively darker bars correspond to less frequently observed alleles in the pre-infusion sample. Bars of the same color represent the same edited allele in each sample. Black bars represent unique alleles outside of the top 5 in any of the samples shown. The figure indicates that the frequency of individual alleles in tissue populations or lineages derived from long-term engrafting HSCs varies from the frequency of the same alleles in pre-infusion samples, consistent with the relatively low level of representation of long-term engrafting HSCs in the bulk CD34+ cell population.

Figure 22:
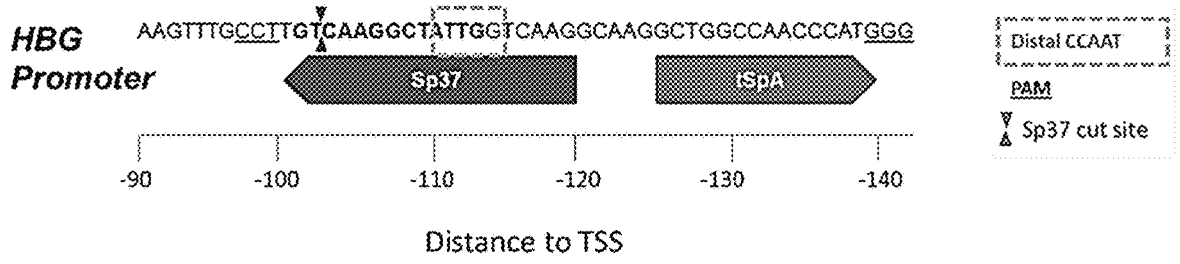

FIG. 22 (SEQ ID NO: 983) depicts, in schematic form, a portion of the HBG promoter sequence and the relative locations of homologous sequences to truncated SpA (tSpA) dgRNA (Table 10) and Sp37 gRNA (Table 10). The -13 nt target region ("-114 to -102 del" GTCAAGGCTATTG, SEQ ID NO: 984) is shown by bolded letters. The sequence of the distal CCAAT box ("ATTGG") is represented by dashed lines. PAM sequences are underlined.

Figure 23:
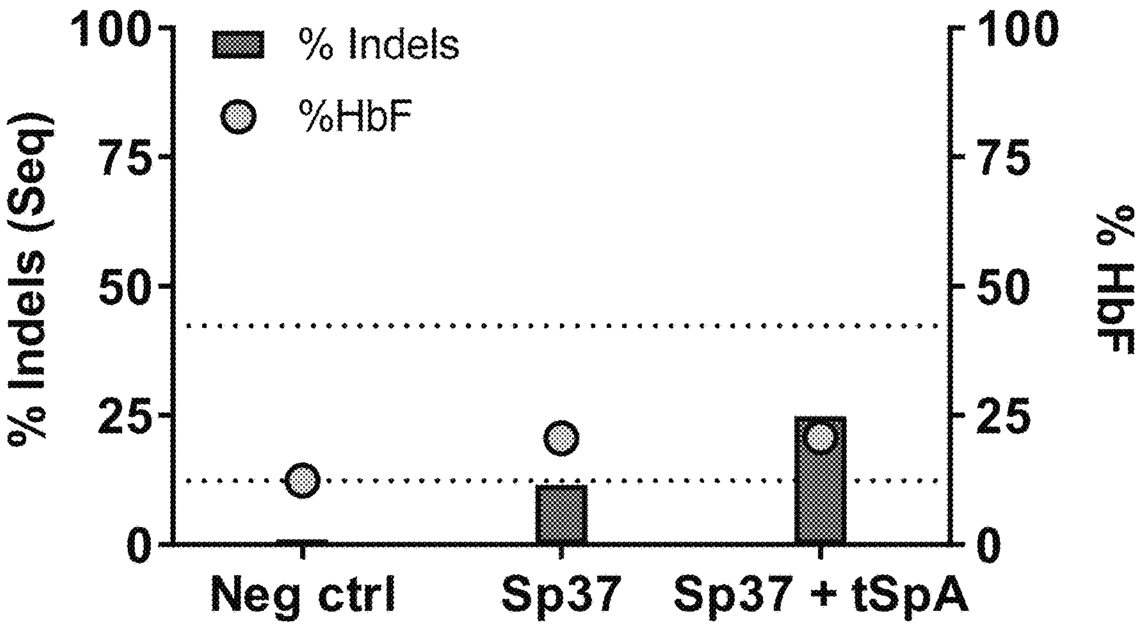

FIG. 23 depicts the percentage of indels detected by Next Generation Sequencing (NGS) analysis of HBG PCR product amplified from gDNA extracted from mPB $CD34^+$ cells after delivery of Sp37 RNP alone (in vitro transcribed (IVT) Sp37 gRNA complexed with WT S. *Pyogenes* Cas 9 protein) or codelivery of Sp37 RNP (IVT Sp37 gRNA complexed with WT S. *Pyogenes* Cas 9 protein) and tSpA dRNP (IVT tSpA dgRNA complexed with WT *S. pyogenes* Cas9 protein). Black bars indicate the level of indels detected in the mPB $CD34^+$ cells. Grey circles indicate the percentage of HbF protein expression as determined by UPLC tetramer analysis of hemoglobin expression in the erythroid progeny of the edited cells. The hemoglobin tetramers, $\alpha2\beta2$ or $\alpha2\gamma2$, were dissociated by using a gradually increasing acetonitrile gradient which periodically elutes them from the liquid chromatography column. The relative quantity of each subunit was then determined using the area under the curve (AUC), with HbF % representing AUC (Aγ+Gγ)/(Aγ+Gγ+(3) or HbF=Total Gamma/Total Beta-like.

Figure 24:
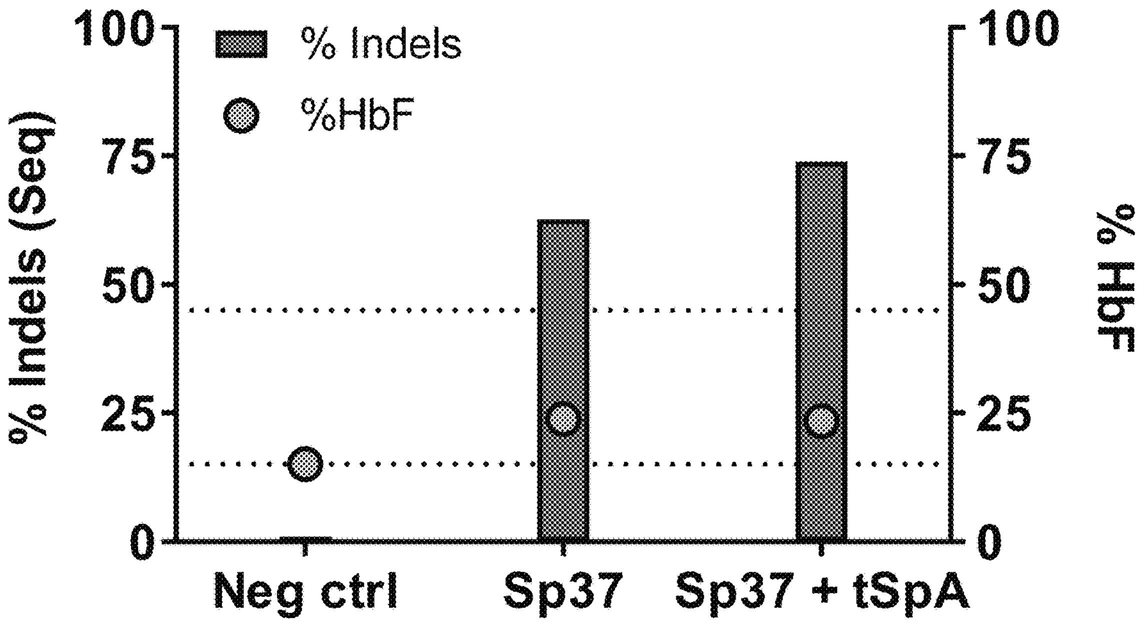

FIG. 24 depicts the percentage of indels detected by NGS analysis of HBG PCR product amplified from gDNA extracted from mPB $CD34^+$ cells after delivery of Sp37 RNP alone (chemically synthesized Sp37 gRNA complexed with WT *S. pyogenes* Cas 9 protein) or codelivery of Sp37 RNP (chemically synthesized Sp37 gRNA complexed with WT *S. pyogenes* Cas 9 protein) and tSpA dRNP (chemically synthesized tSpA dgRNA complexed with WT *S. pyogenes* Cas9 protein). Black bars indicate the level of indels detected in the mPB $CD34^+$ cells. Grey circles indicate the percentage of HbF protein expression as determined by UPLC tetramer analysis of hemoglobin expression in erythroid progeny of the edited cells. The hemoglobin tetramers, $\alpha2\beta2$ or $\alpha2\gamma2$, were dissociated by using a gradually increasing acetonitrile gradient which periodically elutes them from the liquid chromatography column. The relative quantity of each subunit was then determined using the area under the curve (AUC), with HbF % representing AUC (Aγ+Gγ)/(Aγ+Gγ+(3) or HbF=Total Gamma/Total Beta-like.

Figure 25:
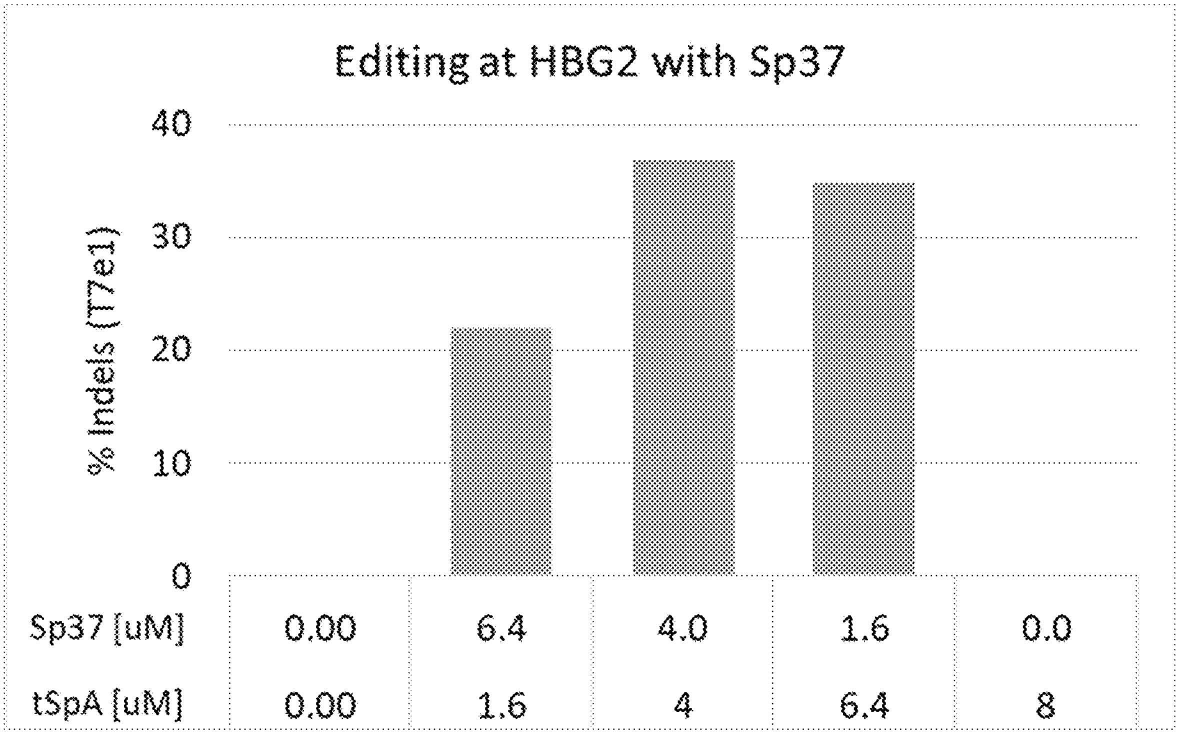

FIG. 25 depicts the percentage of indels detected by T7E1 analysis of HBG2 PCR product amplified from gDNA extracted from mPB CD34+ cells after codelivery of varying concentrations of Sp37 RNP (IVT Sp37 gRNA complexed with *S. pyogenes* WT Cas9 protein) and tSpA dRNP (IVT tSpA dgRNA complexed with *S. pyogenes* WT Cas9 protein).

Figure 26A:
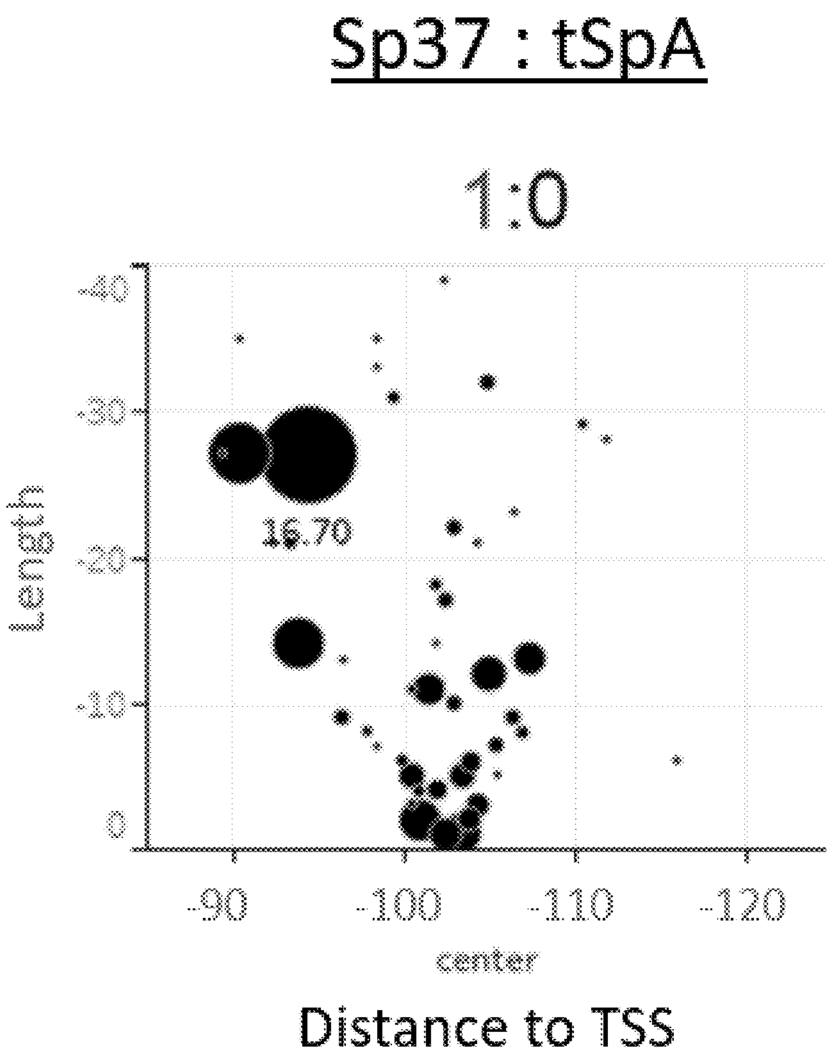
Figure 26B:
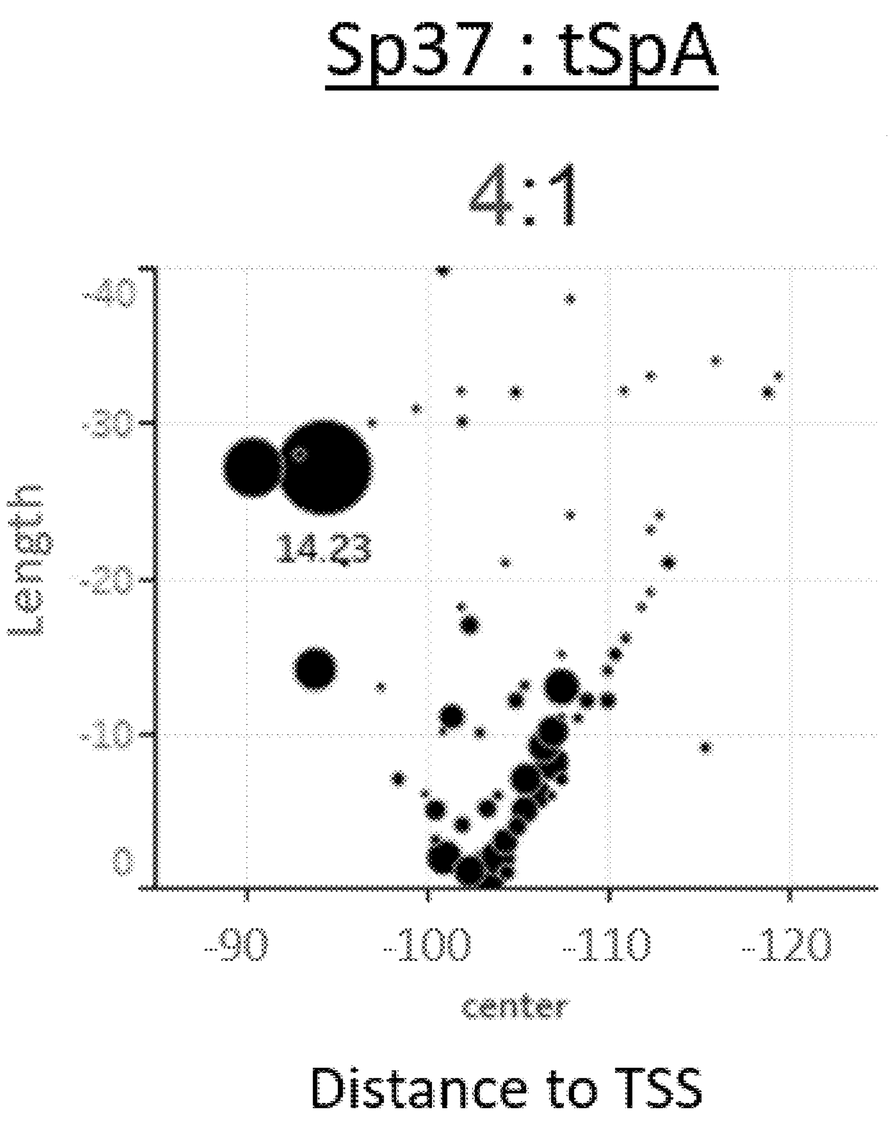
Figure 26C:
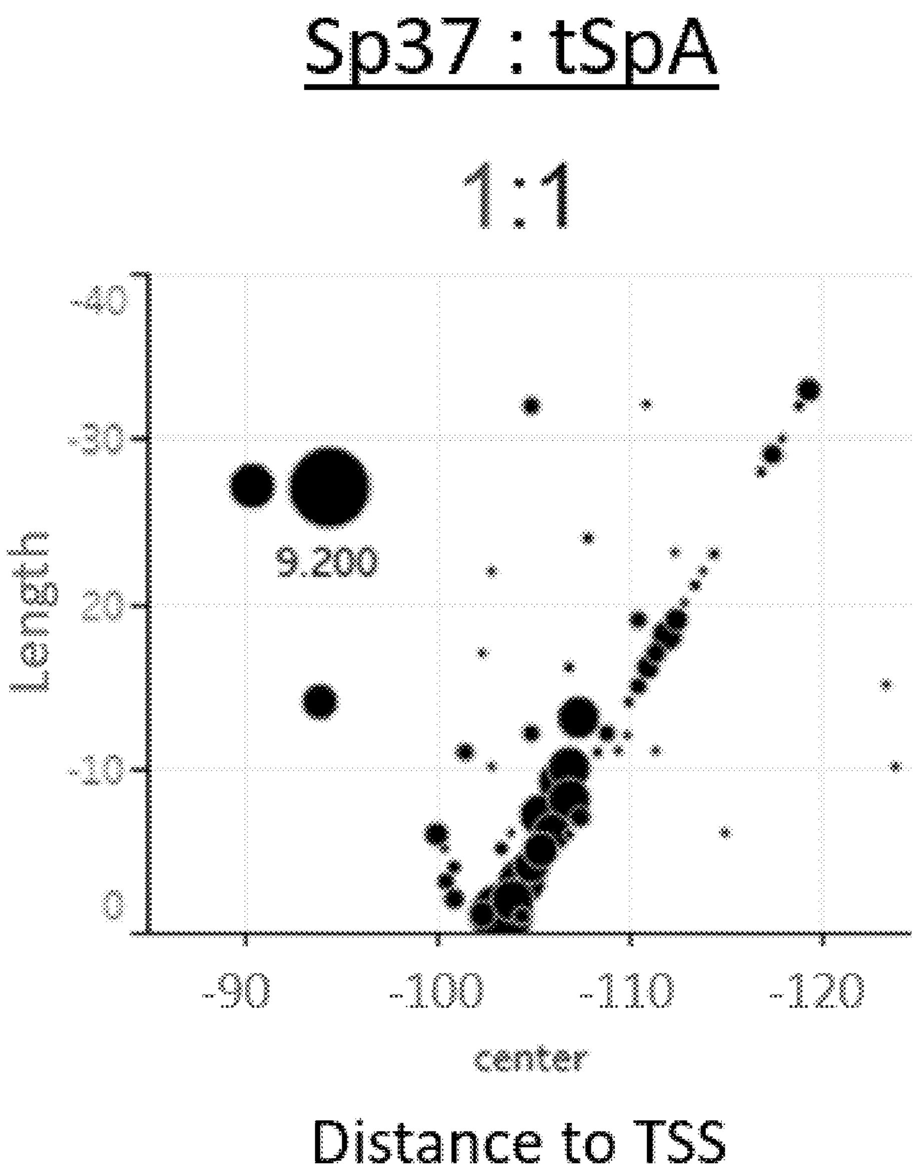
Figure 26D:
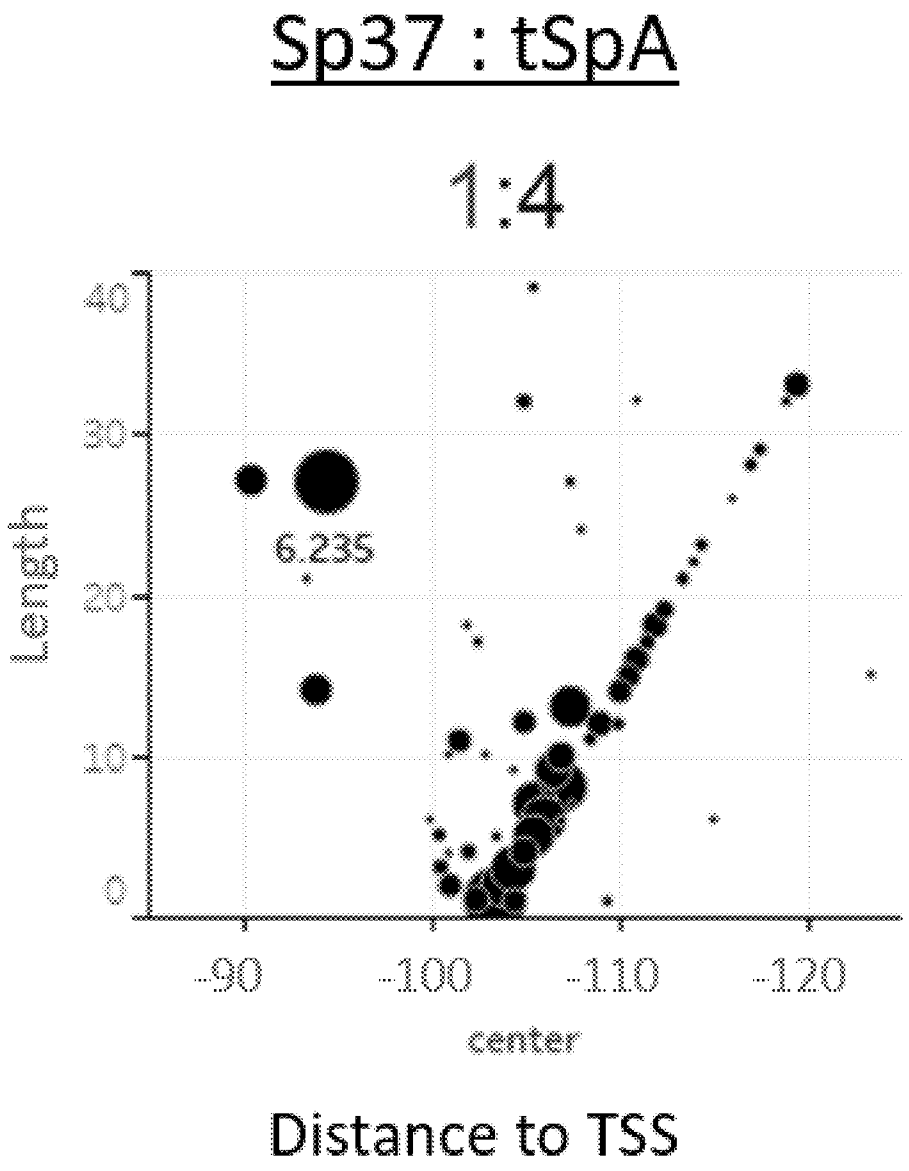

FIGS. 26A-D depicts the deletion profiles observed with varying concentrations of active Sp37 RNP (IVT Sp37 gRNA complexed with *S. pyogenes* WT Cas9 protein) codelivered with varying concentrations of inactive tSpA RNP (IVT tSpA gRNA complexed with *S. pyogenes* WT Cas9 protein). FIG. 26A depicts the deletion profile observed with a 1:0 ratio of Sp37 RNP (8 μM):tSpA RNP (0 μM). FIG. 26B depicts the deletion profile observed with a 4:1 ratio of Sp37 RNP (6.4 μM):tSpA RNP (1.6 μM). FIG. 26C depicts the deletion profile observed with a 1:1 ratio of Sp37 RNP (4 μM):tSpA RNP (4 μM). FIG. 26D depicts the deletion profile observed with a 1:4 ratio of Sp37 RNP (1.6 μM):tSpA RNP (6.4 μM). For FIGS. 26A-D, the X axis represents the position of the center of the deletions (0-based numbering) in relation to the transcription start site (TSS) of the HBG gene, and the Y axis represents the deletion length in nucleotides. Each dot represents a unique deletion. The size of the dot represents the frequency of each deletion as detected by NGS.

Figure 27A:
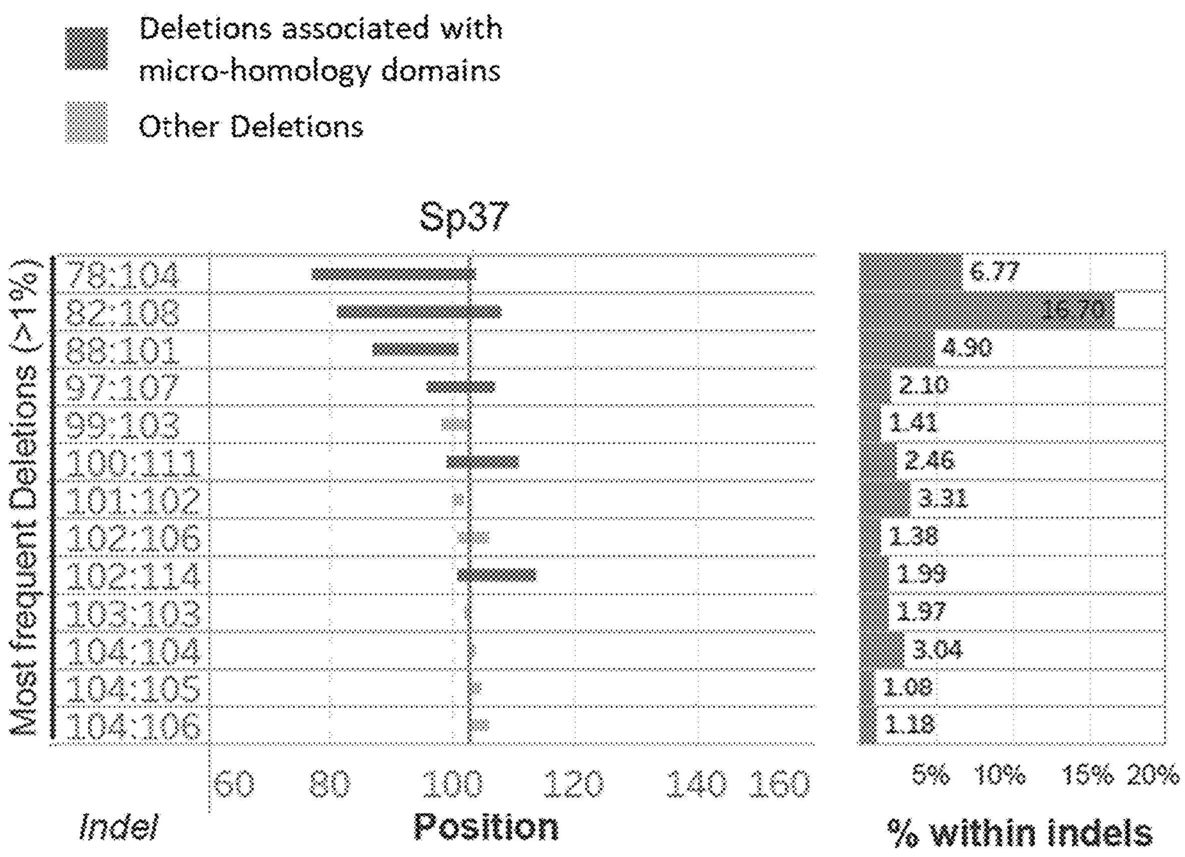
Figure 27B:
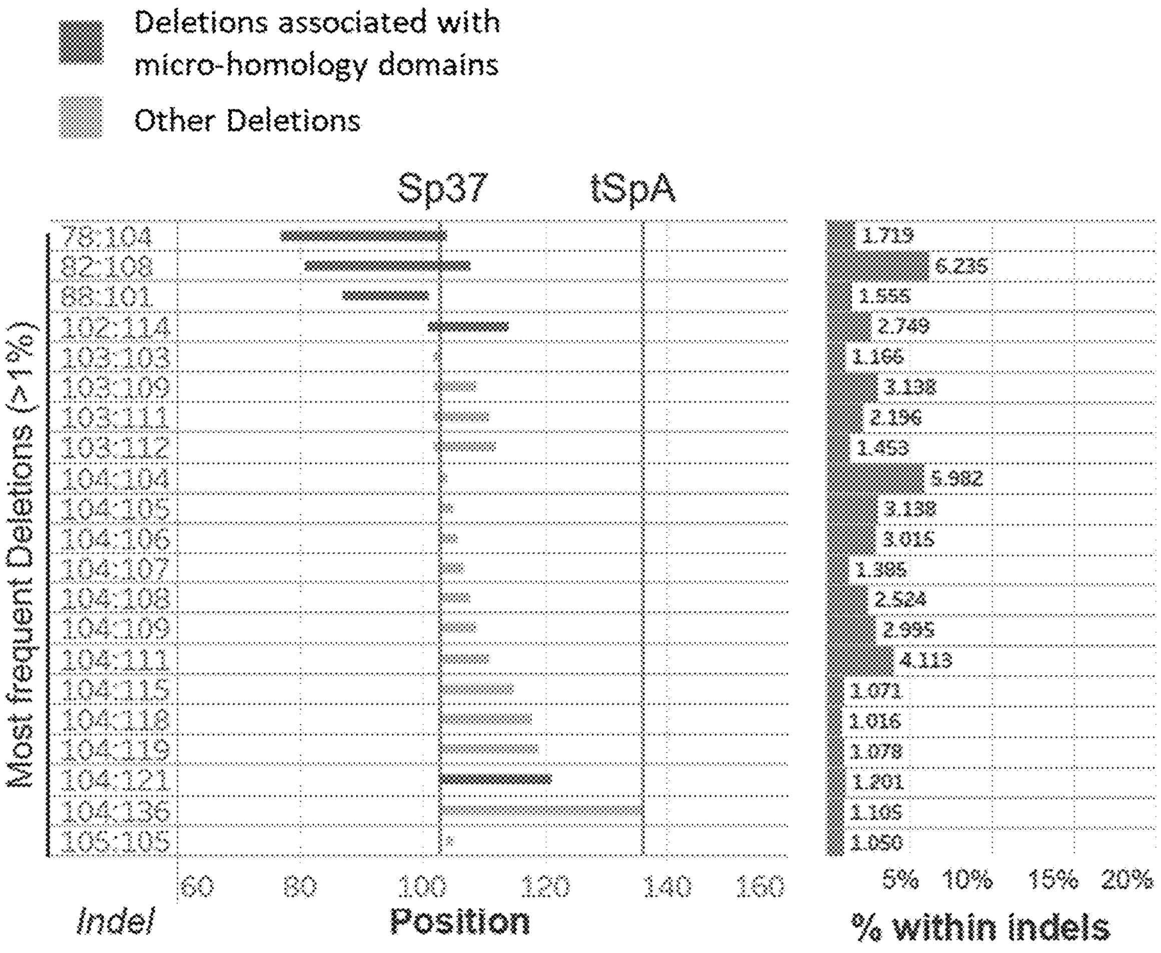

FIGS. 27A-B depict the most common deletions (representing >1% of all edited alleles) generated by Sp37 RNP (chemically synthesized Sp37 gRNA complexed with *S. pyogenes* WT Cas9 protein) alone or Sp37 RNP (chemically synthesized Sp37 gRNA complexed with *S. pyogenes* WT Cas9 protein) codelivered with tSpA RNP (chemically synthesized tSpA gRNA complexed with *S. pyogenes* WT Cas9 protein). FIG. 27A depicts the most common deletions observed after editing by Sp37 RNP alone. The left graph indicates the size and the location of the deletions. Dark grey indicates deletions associated with microhomology domains (as determined by deletions whose sequence starts or ends with 2 nt or more of homology with the sequence flanking the other extremity of the deletion). Light grey indicates all other deletions. The right graph shows the contribution of each deletion to the overall indel profile (frequency of the deletion among the edited alleles as detected by NGS). FIG. 27B depicts the most common deletions observed after editing by Sp37 RNP codelivered with tSpA RNP. The left graph indicates the size of the deletions and the location of the deletions. Dark grey indicates deletions associated with microhomology domains (as determined by deletions whose sequence starts or ends with 2 nt or more of homology with the sequence flanking the other extremity of the deletion). Light grey indicates all other deletions. The right graph shows the contribution of each deletion to the overall indel profile (frequency of the deletion among the edited alleles as detected by NGS).

Figure 28A:
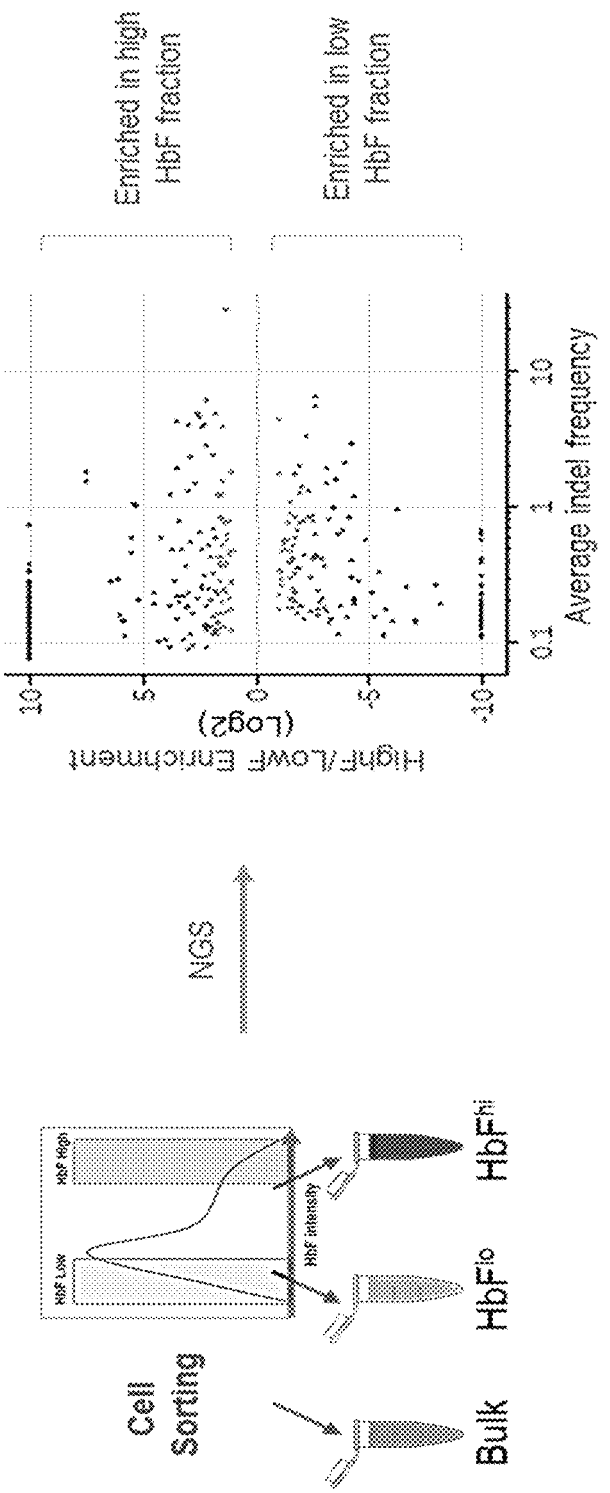
Figure 28B:
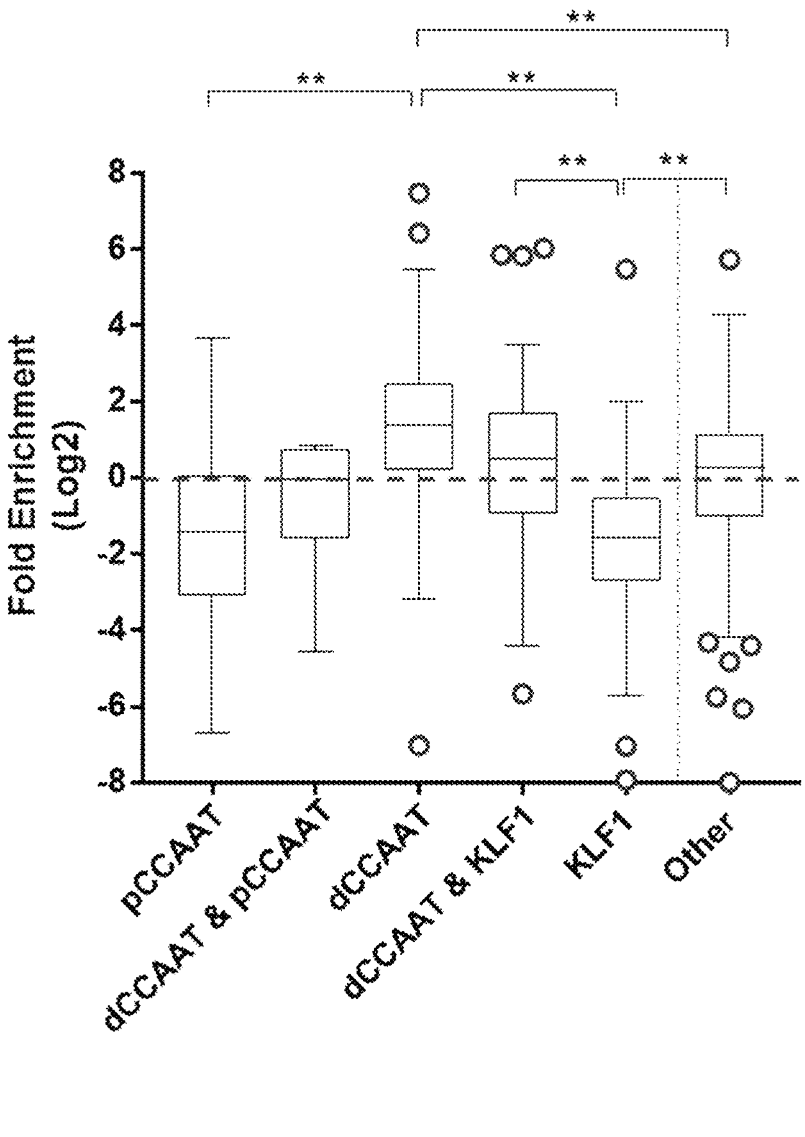
Figure 28C:
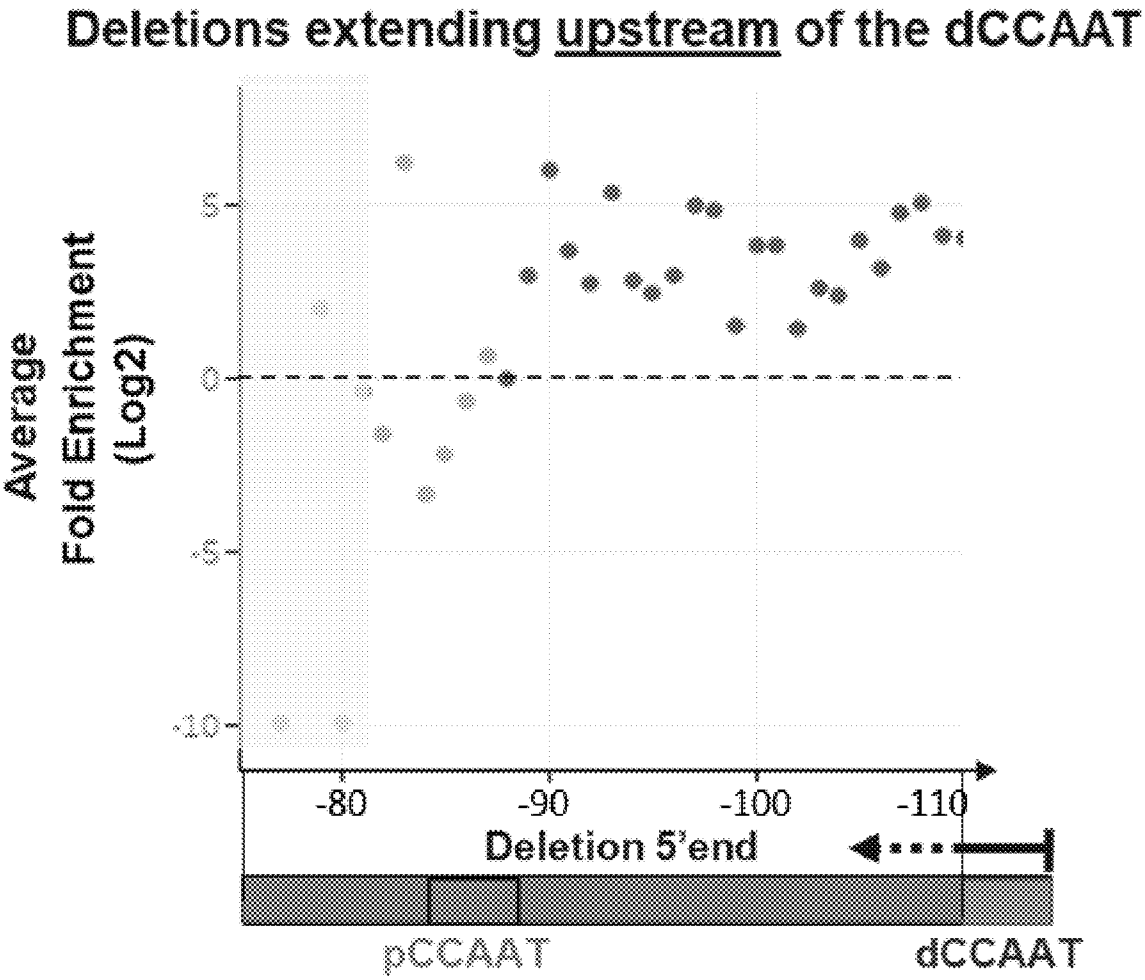
Figure 28D:
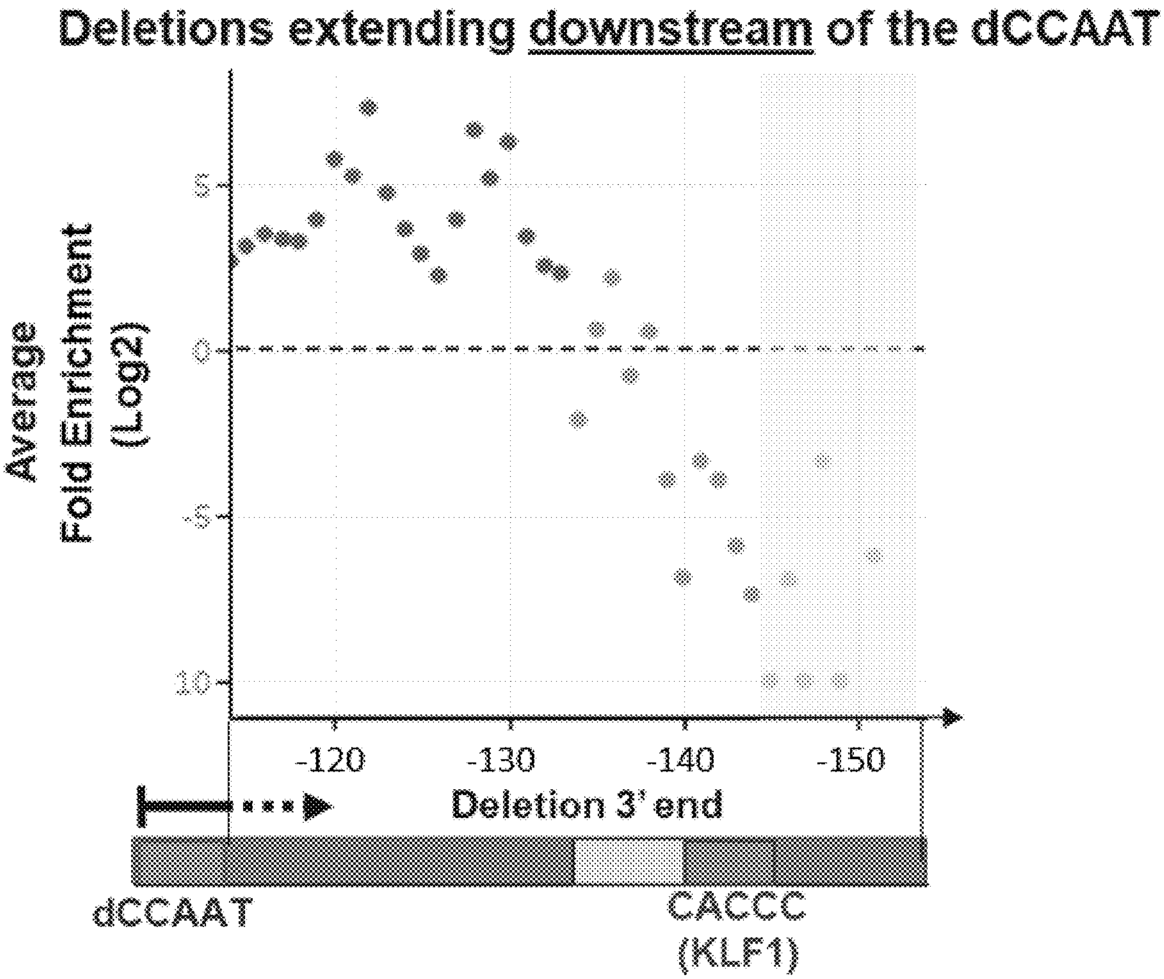
Figure 28E:
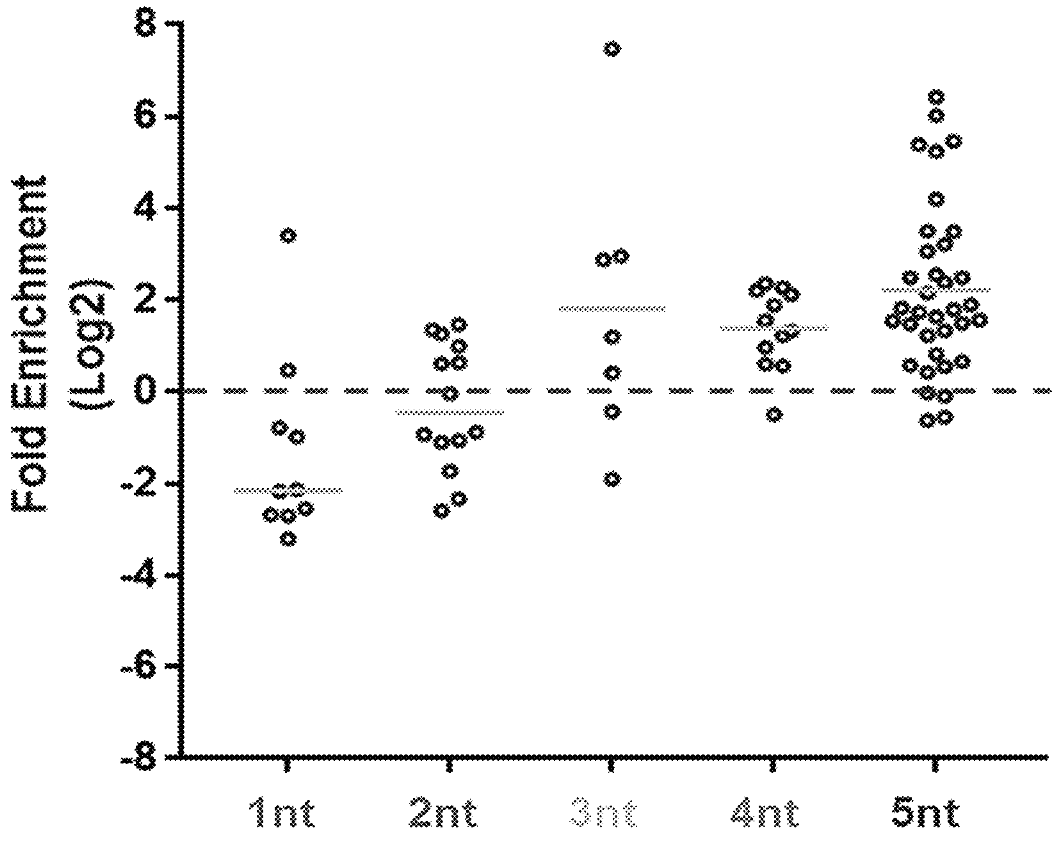
Figure 28F:
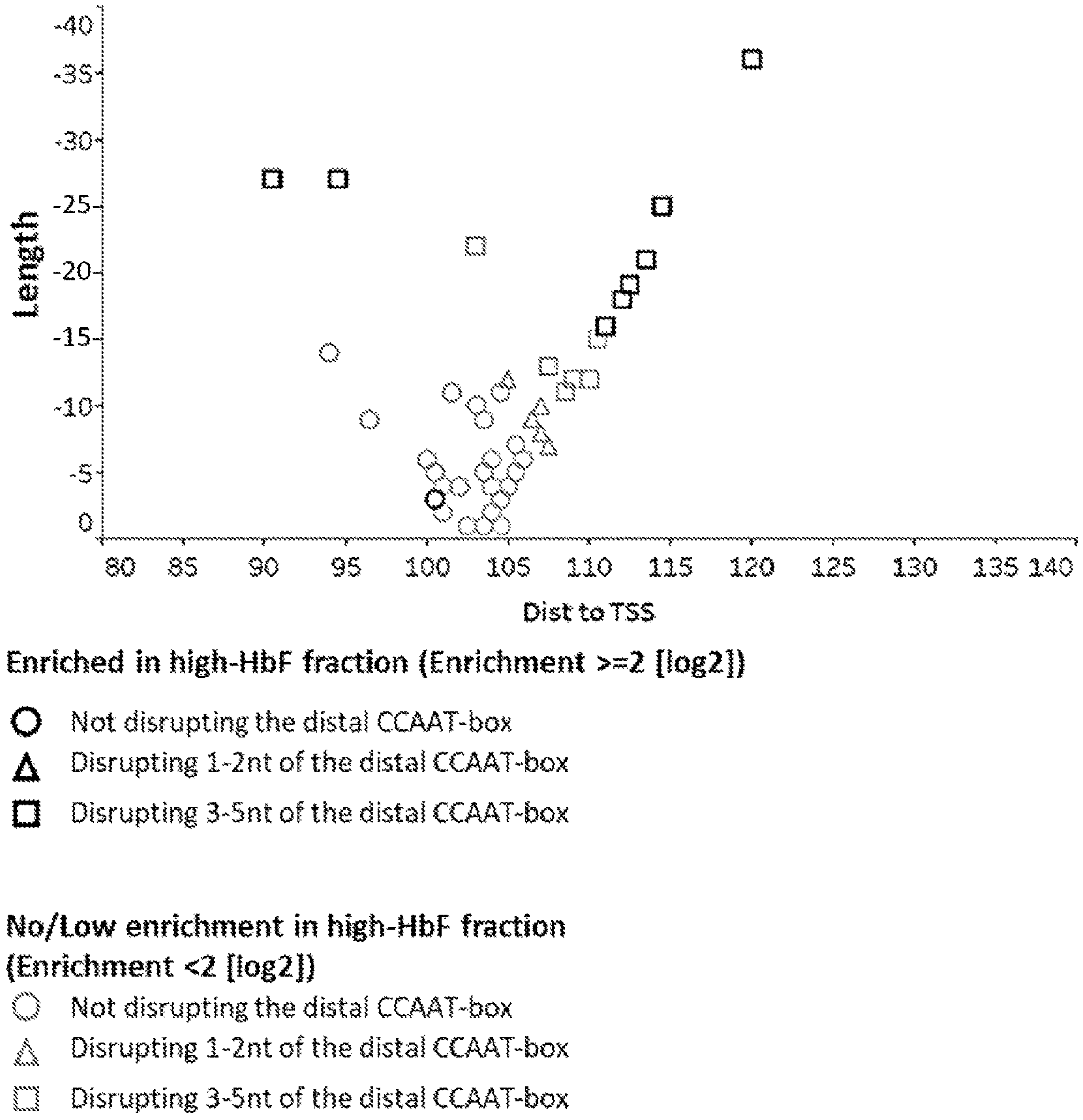

FIGS. 28A-F depicts the characterization of productive, HbF-inducing deletions, at or near the distal CCAAT box. FIG. 28A depicts a schematic of the cell sorting analysis and genotype:phenotype analysis performed to determine which groups of deletions provide HbF induction. Briefly, mPB CD34+ cells were independently electroporated with single or paired RNP targeting the distal CCAAT box. After erythroid differentiation, the cells were sorted based on high HbF and low HbF protein expression. The indel frequency was determined by NGS analysis of the HBG PCR product amplified from the gDNA extracted from the high-HbF and low HbF cell fractions (right panel). FIG. 28B depicts the average fold enrichment of deletions disrupting only the proximal CCAAT box ("pCCAAT", pos. HBG-111:-115), deletions disrupting both the proximal CCAAT box and the distal CCAAT box ("pCCAAT & dCCAAT" respectively pos. HBG-84:-88 and pos. HBG-111:-115), deletions disrupting only the distal CCAAT box ("dCCAAT" HBG-111:-115), deletions disrupting both the distal CCAAT box and the KLF binding area ("KLF & dCCAAT" respectively pos. HBG-111:-115 and pos. HBG-130:-144), deletions disrupting only the KLF1 binding area ("KLF", as defined by the CACCC box and an additional 10 nt at pos. HBG-130:-144), and deletions disrupting none of those genomic domains ("Others"). The values are depicted in a Tukey plot. Statistical analysis was performed by one ANOVA and post-hoc Tukey comparison test between all groups. Statistical significance is indicated when observed. : $p<0.01$. FIG. 28C depicts the average fold enrichment in the high HbF fraction of deletions disrupting the distal CCAAT box depending on the 5' boundary of the deletions (shown on the X axis). FIG. 28D depicts the average fold enrichment in the high HbF fraction of deletions disrupting the distal CCAAT box depending on the 3' boundary of the deletions (shown on the X axis). For FIGS. 28C and 28D, "dCCAAT" represents the distal CCAAT box (pos. HBG-111:-115), "pCCAAT" represents the proximal CCAAT box (pos. HBG-84:-88), and KLF1 represents KLF1 binding site at the CACCC box (pos. HBG-140:-144). FIG. 28E depicts the average fold enrichment in the high HbF fraction of deletions disrupting 1, 2, 3, 4, or 5 nucleotide at the distal CCAAT box, regardless of the overall deletion length. A list of exemplary productive deletions that were shown to induce HbF expression (as defined by average enrichment in the high HbF fraction >2[log 2]) can be found within Table 12. FIG. 28**F depicts the position and length of deletions frequently generated by Sp37 RNP or Sp37 RNP+tSpA dRNP (overlaid). Dark symbols indicate indels that were identified to be enriched in the high HbF fraction (as defined by average enrichment in the high HbF fraction >2[log 2]; regardless of the RNP used to generate the indels). The number of nucleotides of the distal CCAAT box disrupted by the deletions is indicated by the shape of the symbol (circles: disrupts 0 nt of the distal CCAAT box, triangles: disrupts 1 to 2 nucleotides of the distal CCAAT box, squares: disrupts 3 to 5 nucleotides of the distal CCAAT box).

Figure 29A:
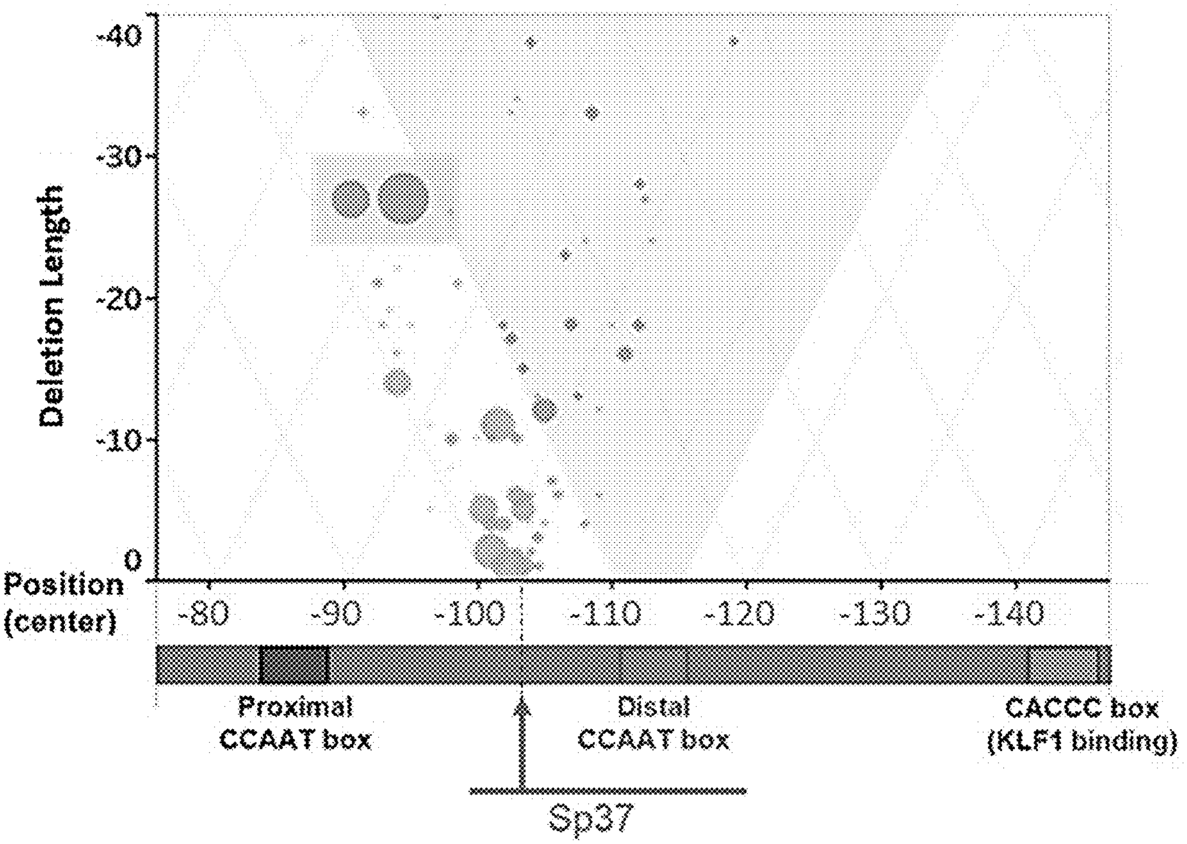
Figure 29B:
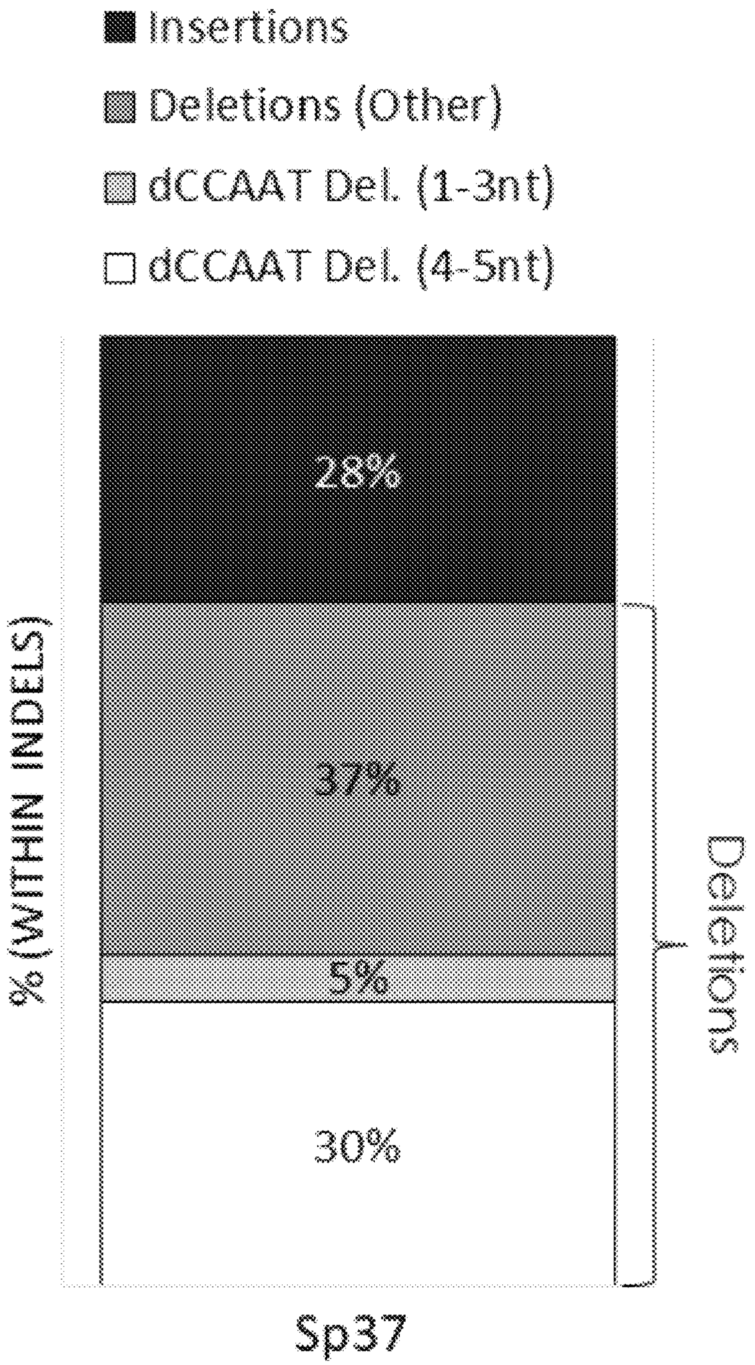

FIGS. 29A-B depict indels generated by Sp37 RNP (chemically synthesized Sp37 gRNA complexed with *S. pyogenes* WT Cas9 protein). FIG. 29A depicts the length and position of deletions generated in the region of the target distal CCAAT box (pos. HBG-111:-115) with the size of each dot representing the relative frequency of each deletion, i.e. larger dots represent a more common deletion. The X-axis represent the center of the deletions in the 0-based coordinate system relative to the HBG TSS (i.e., the deletion HBG:-112:-115 [1-based] is centered at -113 nt [0-based] from the HBG TSS. The Y axis represents the deletion length in nucleotides. Each dot represents a unique deletion. The Sp37 gRNA cut site is indicated by an arrow at position X=103 nt [0-based] from the HBG TSS. The shaded grey triangular region depicts the area in which indels disrupt the distal CCAAT box, predicted to represent productive indels leading to HbF expression, based on results from Example 12. For example, small deletions originating from the Sp37 gRNA cut site and extending less than 8 nt downstream (i.e., deletion HBG-104:-108, which is 5 nts in length and centered at -105.5 nt from the HBG TSS [0-based]), do not disrupt the dCCAAT box (at position HBG-111:-115) and is thus not covered by the shaded area. However, larger deletions, originating from the Sp37 gRNA cut site and extending further downstream of position HBG:-110 (i.e., HBG-104:-123, which is 20 nts in length and centered at -113 from the HBG TSS [0-based]), do disrupt the dCCAAT box and are thus predicted to promote HbF induction based on results from Example 12, as depicted by their location within the shaded region. Due to the repetitive nature of the sequence at this locus, some deletions may have ambiguous coordinates. For example, one 27 nt deletion removing one of the duplicated sequences, CTATTGGTCAAG (SEQ ID NO: 985), surrounding the proximal and distal CCAAT box (at position HBG-82:-93 and position HBG-109:121; depicted in FIG. 31), can be described as HBG:-82:-108, HBG:-94:-120, or any 27 nt long deletion in between. This deletion, as well as the deletion at position HBG:-78:-103, has the particularity to generate a single CCAAT box promoter that could be generated as the result of a distal CCAAT box deletion or proximal CCAAT box deletion. According to the observed HbF expression observed for both those deletions (as determined by enrichment of those indel in the high HbF fraction, as reported in Table 12) and the reported essential role of the proximal CCAAT box for HBG expression (Martyn 2017), those deletions were classified as distal CCAAT box deletions, and were thus included in the shaded area. FIG. 29B depicts the fraction of predicted productive deletions (based on results from Example 12) generated by Sp37 RNP among all indels. The fraction of other deletions and insertions is also detailed. Insertions=28%, Deletions (Other)=37%, dCCAAT Del. (1-3 nt)=5%, and dCCAAT Del. (4-5 nt)=30%.

Figure 30A:
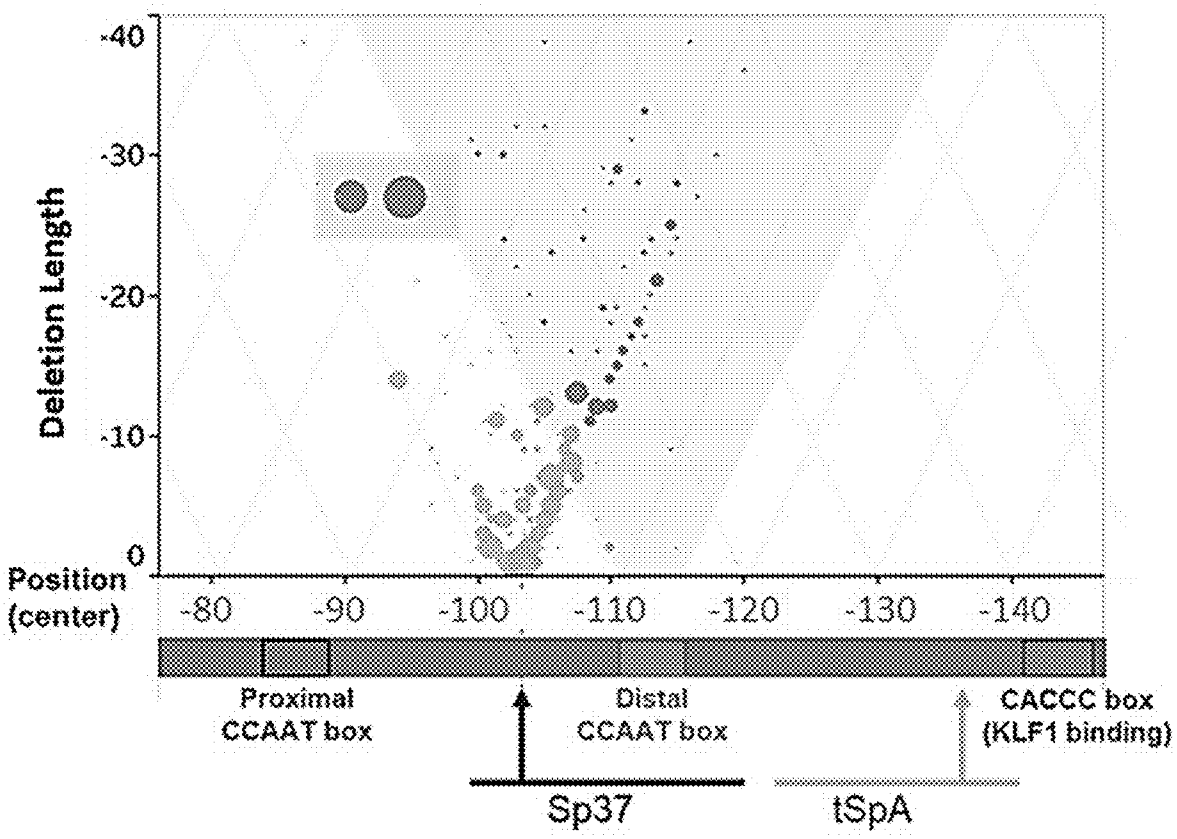
Figure 30B:
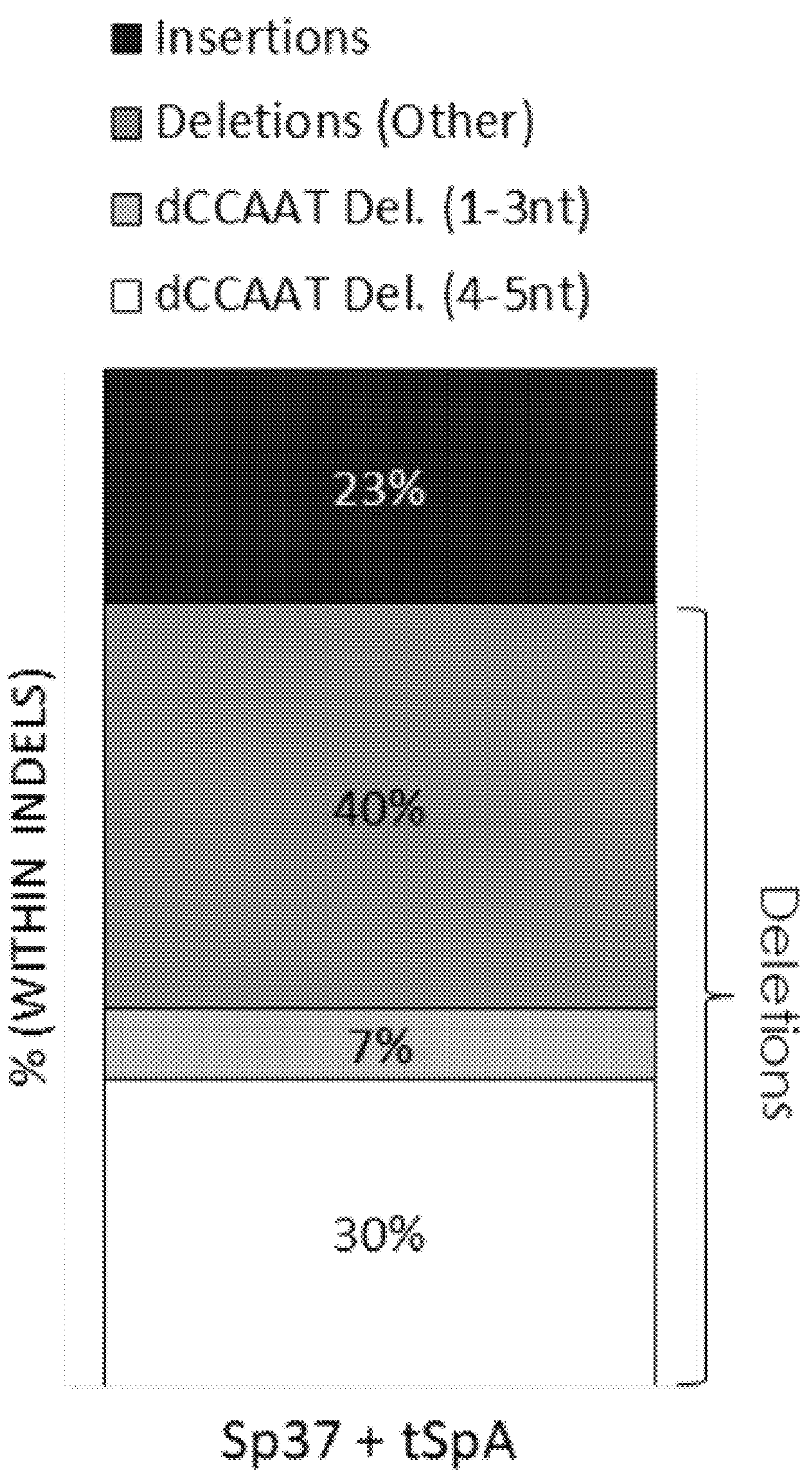

FIGS. 30A-B depict indels generated by Sp37 RNP (chemically synthesized Sp37 gRNA complexed with WT Cas9 protein) codelivered with tSpA RNP (chemically synthesized tSpA gRNA complexed with WT Cas9 protein), as determined by NGS analysis of the HBG PCR product from samples whose total editing and HbF results are described in FIG. 24. FIG. 30A depicts the length and position of deletions generated in the regions near and at the proximal CCAAT box (pos. HBG 84:-88), distal CCAAT box (pos. HBG-111:-115), and CACCC box (KLF1 binding site) (pos. HBG-140:-144), with the size of each dot representing the relative frequency of each deletion, i.e. larger dots represent a more common deletion. The X-axis represents the center of the deletions in the 0-based coordinate system relative to the HBG TSS (i.e., the deletion HBG:-112:-115 [1-based] is centered at -113 nt [0-based] from the HBG TSS). The Y axis represents the deletion length in nucleotides. Each dot represents a unique deletion. The Sp37 gRNA cut site is indicated by an arrow at position X=103 nt [0-based] from the HBG TSS. The shaded grey triangular region depicts the area in which indels are disrupting the distal CCAAT box, predicted to represent productive indels leading to HbF expression, based on results from Example 12. For example, small deletions originating from the Sp37 gRNA cut site and extending less than 8 nt downstream (i.e., deletion HBG-104:-108, of length 5 and centered at -105.5 nt from the HBG TSS [0-based]), do not disrupt the dCCAAT box (at position HBG-111:-115) and are thus not covered by the shaded area. However, larger deletions, originating from the Sp37 gRNA cut site and extending further downstream of position HBG:-110 (i.e., HBG-104:-123 of length 20 and centered at -113 from the HBG TSS [0-based]), do disrupt the dCCAAT box and are thus predicted to promote HbF induction based on results from Example 12, as depicted by their location within the shaded region. Due to the repetitive nature of the sequence at this locus, some deletions may have ambiguous coordinates. For example, one 27 nt deletion removing one of the duplicated sequence, CTATTGGTCAAG (SEQ ID NO: 985), surrounding the proximal and distal CCAAT box (at position HBG-82:-93 and position HBG-109:121; depicted in FIG. 31), can be described as HBG:-82:-108, HBG:-94:-120, or any 27 nt long deletion in between. This deletion, as well as the deletion at position HBG:-78:-103 have the particularity to generate a single CCAAT box promoter that could be described as the result of a distal CCAAT box deletion or proximal CCAAT box deletion. According to the observed HbF expression observed for both those deletions (as determined by enrichment of those indel in the high HbF fraction, as reported in Table 12) and the reported essential role of the proximal CCAAT box for HBG expression (Martyn 2017), those deletions were classified as productive distal CCAAT box deletions, and thus included in the shaded area. FIG. 30B depicts the fraction of predicted productive deletions (based on results from Example 12) generated by Sp37 RNP among all indels. The fraction of other deletions and insertions is also detailed. Insertions=23%, Deletions (Other)=40%, dCCAAT Del. (1-3 nt)=7%, and dCCAAT Del. (4-5 nt)=30%.

Figure 31:
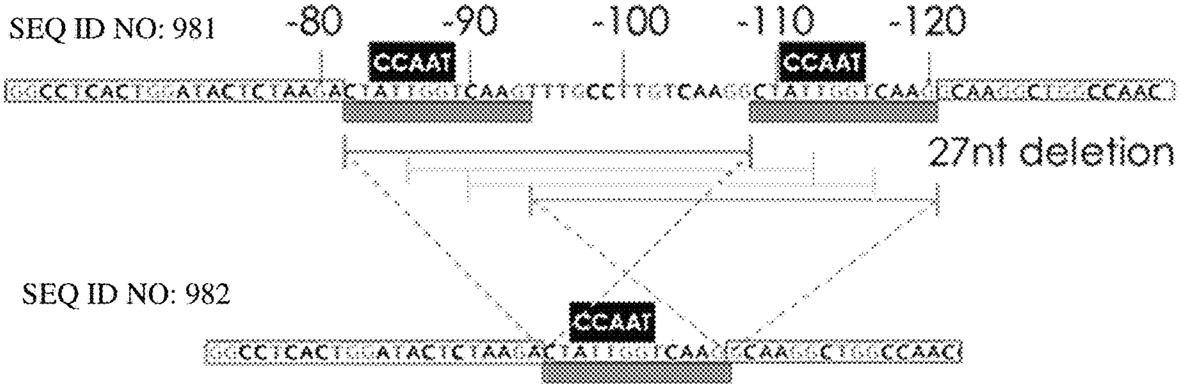

FIG. 31 depicts a 27 nt deletion commonly generated by Sp37 RNP alone or paired with tSpA RNP. This deletion has the particularity of removing one of the duplicated sequence, CTATTGGTCAAG, surrounding the proximal and distal CCAAT box (at position HBG-82:-93 and position HBG- 109:121). Due to the repetitive nature of the sequence at this locus, it can be described as HBG:-82:-108, HBG:-94:-120, or any 27 nt long deletion in between. As depicted in the figure showing four examples of coordinates describing the same 27 nt long deletion, any deletion matching the former criteria would lead to a unique resulting sequence after DNA repair. This deletion is also an example of deletion associated with micro-homologies. The 5' end of the deleted sequence (using coordinates HBG:-82:-108) contains a 12 nt long sequence perfectly homologous to the sequence immediately flanking the 3' end of the deletion. This deletion, whose high frequency after editing CD34+ cells with Sp37 RNP is unusual considering its length, is likely a favored repair outcome due to the presence of homologous domain facilitating DSB repair by micro-homology mediated end joining.

Figure 32A:
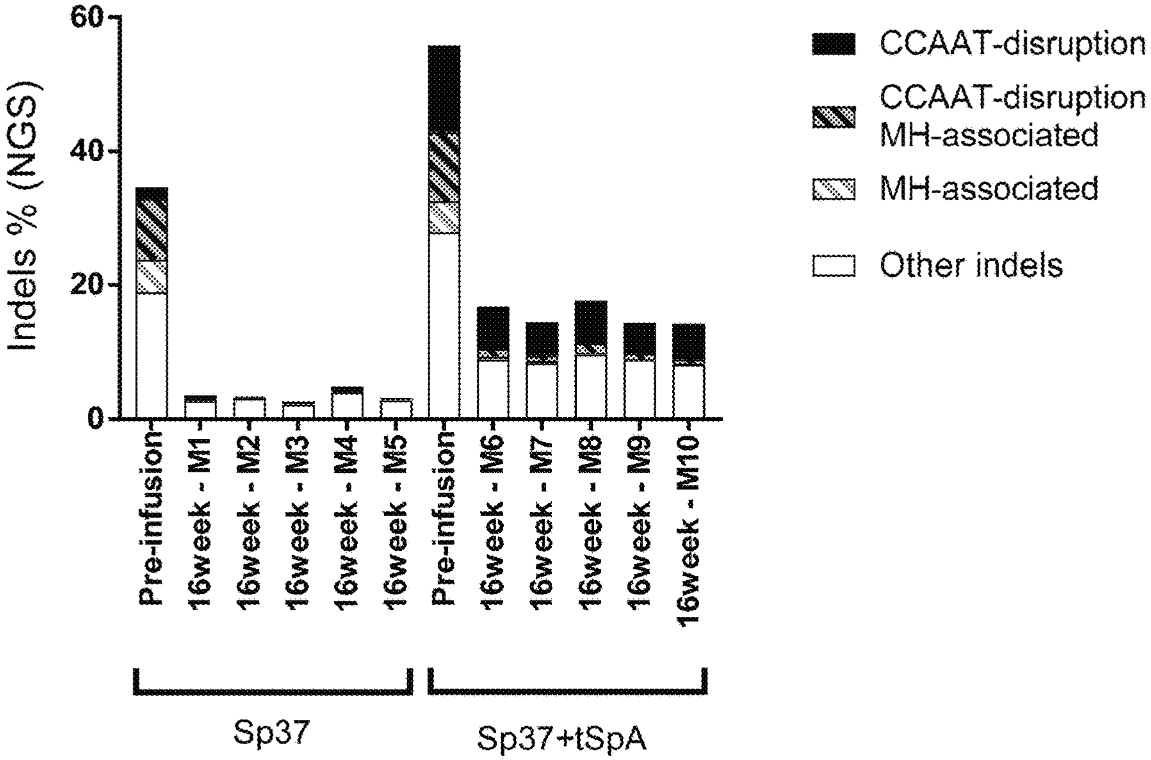
Figure 32B:
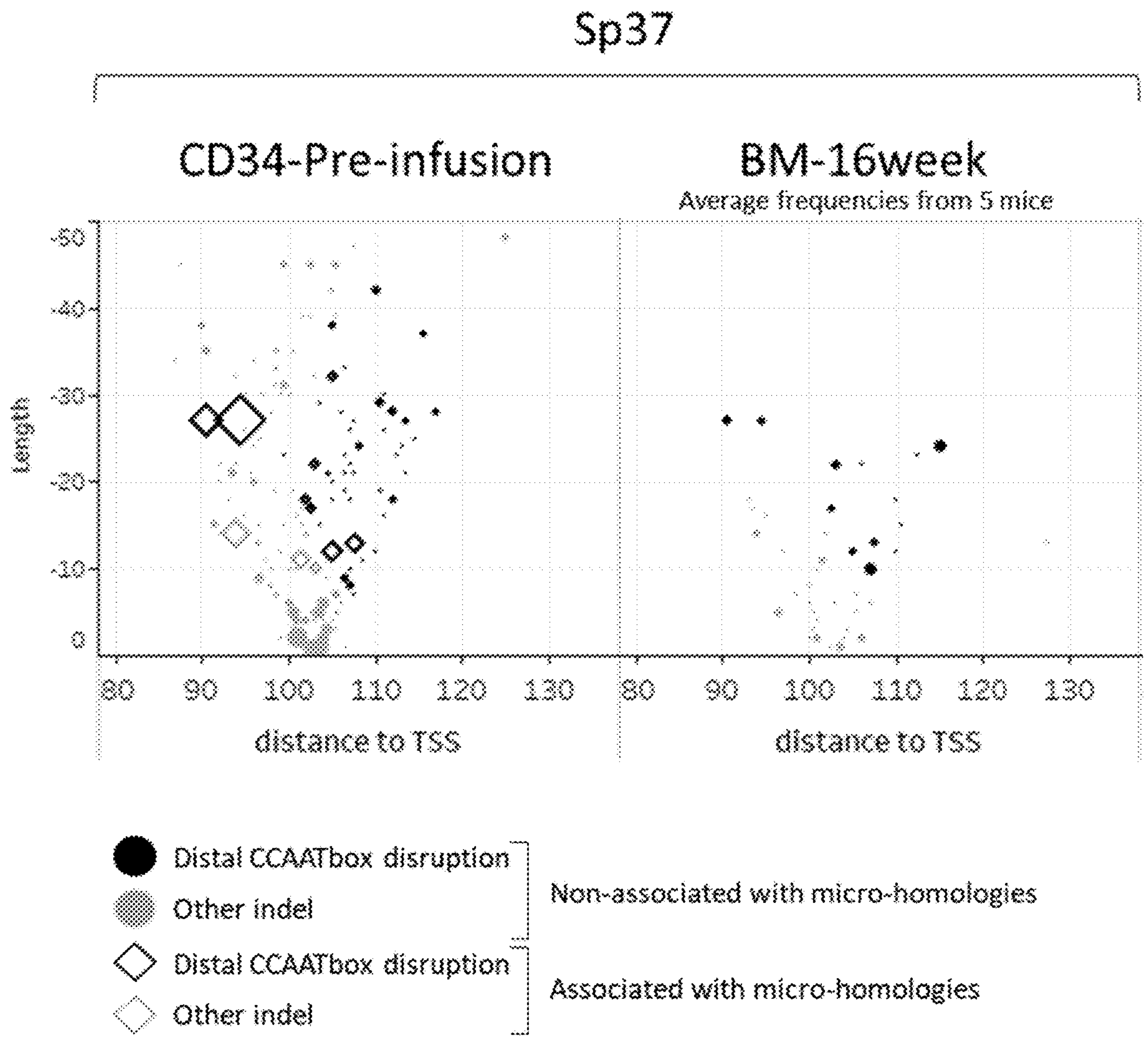
Figure 32C:
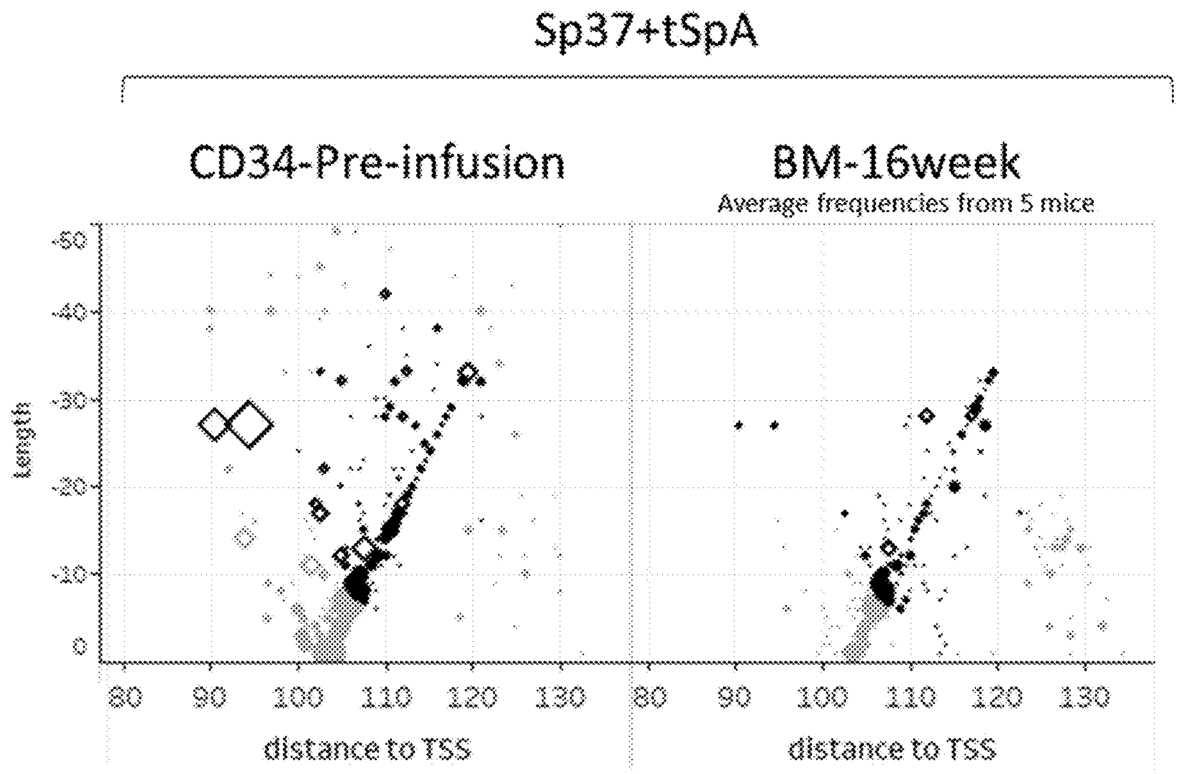

FIGS. 32A-C depict editing detected in mPB CD34+ cells infused in nonirradiated NOD,B6.SCID Il2rγ−/− Kit(W41/W41) (NBSGW) mice. mPB CD34+ cells were electroporated with Sp37 RNP (comprising IVT Sp37 gRNA (SEQ ID NO:333, Table 10) complexed with *S. pyogenes* wildtype Cas9) delivered alone (8 μM) or co-delivered with tSpA dRNP (6.4 μM+1.6 (Sp37+tSpA)) (comprising IVT tSpA dgRNA (SEQ ID NO:970, Table 10) complexed with *S. pyogenes* wildtype Cas9). FIG. 32A depicts the percentage of editing as determined by NGS for the pre-infusion modified mPB CD34+ cells ("Preinfusion") and for the human engrafted cells extracted from the bone marrow of the mice 16 weeks after infusion of the modified mPB CD34+ cells ("16 week—M[1-10]", representing long term NBSGW-repopulating hematopoietic stem cells). Indels that disrupt the CCAAT box and are not associated with micro-homology domains ("CCAAT-disruption"), indels that disrupt the CCAAT box and are associated with micro-homology domains ("CCAAT-disruption MH associated"), indels that do not disrupt the CCAAT box and are associated with micro-homology domains ("MH-associated") and all other indels ("Other indels") were identified for each of the 10 mice tested (M1-10). FIG. 32B. depicts the deletion profile observed after treatment with Sp37 RNP in the pre-infusion mPB CD34+ cells and from the human cells collected from the bone marrow of the NBSGW mice 16 weeks after infusion of the modified mPB CD34+ cells (long term NBSGW-repopulating hematopoietic stem cells) as detected by NGS analysis. FIG. 32C depicts the deletion profile observed after treatment with Sp37 RNP+tSpA dRNP in the pre-infusion mPB CD34+ cells and from the human cells collected from the bone marrow of the NBSGW mice 16 weeks after infusion of the modified mPB CD34+ cells (long term NBSGW-repopulating hematopoietic stem cells) as detected by NGS analysis. For FIGS. 32B and 32C, the center of the deletion relative to the transcription start site (TSS) of the HBG gene is shown on the X axis [0-based numbering] and the nucleotide length of the deletion is shown on the Y axis. Each symbol represents a unique deletion. The size of the symbol represents the frequency of each deletion or the average frequency of each deletion across all analyzed mice for 16-weeks in vivo samples) as detected by NGS, i.e., larger symbols represent a more common deletion. CCAAT box disrupting and non-CCAAT box disrupting deletions associated with micro-homology domains are shown, as well as those which are not associated with micro-homology domains.

DETAILED DESCRIPTION

Definitions and Abbreviations

Unless otherwise specified, each of the following terms has the meaning associated with it in this section.

The indefinite articles "a" and "an" refer to at least one of the associated noun, and are used interchangeably with the terms "at least one" and "one or more." For example, "a module" means at least one module, or one or more modules.

The conjunctions "or" and "and/or" are used interchangeably as non-exclusive disjunctions.

"Domain" is used to describe a segment of a protein or nucleic acid. Unless otherwise indicated, a domain is not required to have any specific functional property.

The term "exogenous trans-acting factor" refers to any peptide or nucleotide component of a genome editing system that both (a) interacts with an RNA-guided nuclease or gRNA by means of a modification, such as a peptide or nucleotide insertion or fusion, to the RNA-guided nuclease or gRNA, and (b) interacts with a target DNA to alter a helical structure thereof. Peptide or nucleotide insertions or fusions may include, without limitation, direct covalent linkages between the RNA-guided nuclease or gRNA and the exogenous trans-acting factor, and/or non-covalent linkages mediated by the insertion or fusion of RNA/protein interaction domains such as MS2 loops and protein/protein interaction domains such as a PDZ, Lim or SH1, 2 or 3 domains. Other specific RNA and amino acid interaction motifs will be familiar to those of skill in the art. Trans-acting factors may include, generally, transcriptional activators.

An "indel" is an insertion and/or deletion in a nucleic acid sequence. An indel may be the product of the repair of a DNA double strand break, such as a double strand break formed by a genome editing system of the present disclosure. An indel is most commonly formed when a break is repaired by an "error prone" repair pathway such as the NHEJ pathway described below.

"Gene conversion" refers to the alteration of a DNA sequence by incorporation of an endogenous homologous sequence (e.g., a homologous sequence within a gene array). "Gene correction" refers to the alteration of a DNA sequence by incorporation of an exogenous homologous sequence, such as an exogenous single- or double stranded donor template DNA. Gene conversion and gene correction are products of the repair of DNA double-strand breaks by HDR pathways such as those described below.

Indels, gene conversion, gene correction, and other genome editing outcomes are typically assessed by sequencing (most commonly by "next-gen" or "sequencing-by-synthesis" methods, though Sanger sequencing may still be used) and are quantified by the relative frequency of numerical changes (e.g., ±1, ±2 or more bases) at a site of interest among all sequencing reads. DNA samples for sequencing may be prepared by a variety of methods known in the art, and may involve the amplification of sites of interest by polymerase chain reaction (PCR), the capture of DNA ends generated by double strand breaks, as in the GUIDEseq process described in Tsai 2016 (incorporated by reference herein) or by other means well known in the art. Genome editing outcomes may also be assessed by in situ hybridization methods such as the FiberComb™ system commercialized by Genomic Vision (Bagneux, France), and by any other suitable methods known in the art.

"Target region" refers to a region of a nucleic acid that includes one or more nucleotides to be edited. In certain embodiments, the target region may be a target region of a genome.

"Productive indel" refers to an indel (deletion and/or insertion) that results in HbF expression. In certain embodiments, a productive indel may induce HbF expression. In certain embodiments, a productive indel may result in an increased level of HbF expression. Exemplary examples of productive indels are listed in Table 12.

"Alt-HDR," "alternative homology-directed repair," or "alternative HDR" are used interchangeably to refer to the process of repairing DNA damage using a homologous nucleic acid (e.g., an endogenous homologous sequence, e.g., a sister chromatid, or an exogenous nucleic acid, e.g., a template nucleic acid). Alt-HDR is distinct from canonical HDR in that the process utilizes different pathways from canonical HDR, and can be inhibited by the canonical HDR mediators, RAD51 and BRCA2. Alt-HDR is also distinguished by the involvement of a single-stranded or nicked homologous nucleic acid template, whereas canonical HDR generally involves a double-stranded homologous template.

"Canonical HDR," "canonical homology-directed repair" or "cHDR" refer to the process of repairing DNA damage using a homologous nucleic acid (e.g., an endogenous homologous sequence, e.g., a sister chromatid, or an exogenous nucleic acid, e.g., a template nucleic acid). Canonical HDR typically acts when there has been significant resection at the double strand break, forming at least one single stranded portion of DNA. In a normal cell, cHDR typically involves a series of steps such as recognition of the break, stabilization of the break, resection, stabilization of single stranded DNA, formation of a DNA crossover intermediate, resolution of the crossover intermediate, and ligation. The process requires RAD51 and BRCA2, and the homologous nucleic acid is typically double-stranded.

Unless indicated otherwise, the term "HDR" as used herein encompasses both canonical HDR and alt-HDR.

"Non-homologous end joining" or "NHEJ" refers to ligation mediated repair and/or non-template mediated repair including canonical NHEJ (cNHEJ) and alternative NHEJ (altNHEJ), which in turn includes microhomology-mediated end joining (MMEJ), single-strand annealing (SSA), and synthesis-dependent microhomology-mediated end joining (SD-MMEJ).

"Replacement" or "replaced," when used with reference to a modification of a molecule (e.g., a nucleic acid or protein), does not require a process limitation but merely indicates that the replacement entity is present.

"Subject" means a human, mouse, or non-human primate. A human subject can be any age (e.g., an infant, child, young adult, or adult), and may suffer from a disease, or may be in need of alteration of a gene.

"Treat," "treating," and "treatment" mean the treatment of a disease in a subject (e.g., a human subject), including one or more of inhibiting the disease, i.e., arresting or preventing its development or progression; relieving the disease, i.e., causing regression of the disease state; relieving one or more symptoms of the disease; and curing the disease.

"Prevent," "preventing," and "prevention" refer to the prevention of a disease in a subject, including (a) avoiding or precluding the disease; (b) affecting the predisposition toward the disease; or (c) preventing or delaying the onset of at least one symptom of the disease.

A "kit" refers to any collection of two or more components that together constitute a functional unit that can be employed for a specific purpose. By way of illustration (and not limitation), one kit according to this disclosure can include a gRNA complexed or able to complex with an RNA-guided nuclease, and accompanied by (e.g., suspended in, or suspendable in) a pharmaceutically acceptable carrier. In certain embodiments, the kit can include a dead guide RNA. The kit can be used to introduce the complex into, for example, a cell or a subject, for the purpose of causing a desired genomic alteration in such cell or subject. The components of a kit can be packaged together, or they may be separately packaged. Kits according to this disclosure also optionally include directions for use (DFU) that describe the use of the kit e.g., according to a method of this disclosure. The DFU can be physically packaged with the kit, or it can be made available to a user of the kit, for instance by electronic means.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides, nucleotide sequences, nucleic acids etc. can be chimeric mixtures or derivatives or modified versions thereof, single-stranded or double-stranded. They can be modified at the base moiety, sugar moiety, or phosphate backbone, for example, to improve stability of the molecule, its hybridization parameters, etc. A nucleotide sequence typically carries genetic information, including, but not limited to, the information used by cellular machinery to make proteins and enzymes. These terms include double- or single-stranded genomic DNA, RNA, any synthetic and genetically manipulated polynucleotide, and both sense and antisense polynucleotides. These terms also include nucleic acids containing modified bases.

Conventional IUPAC notation is used in nucleotide sequences presented herein, as shown in Table 1, below (see also Cornish-Bowden 1985, incorporated by reference herein). It should be noted, however, that "T" denotes "Thymine or Uracil" in those instances where a sequence may be encoded by either DNA or RNA, for example in gRNA targeting domains.

TABLE 1

IUPAC nucleic acid notation

| Character | Base |
|---|---|
| A | Adenine |
| T | Thymine |
| G | Guanine |
| C | Cytosine |
| U | Uracil |
| K | G or T/U |
| M | A or C |
| R | A or G |
| Y | C or T/U |
| S | C or G |
| W | A or T/U |
| B | C, G or T/U |
| V | A, C or G |
| H | A, C or T/U |
| D | A, G or T/U |
| N | A, C, G or T/U |

The terms "protein," "peptide" and "polypeptide" are used interchangeably to refer to a sequential chain of amino acids linked together via peptide bonds. The terms include individual proteins, groups or complexes of proteins that associate together, as well as fragments or portions, variants, derivatives and analogs of such proteins. Peptide sequences are presented herein using conventional notation, beginning with the amino or N-terminus on the left, and proceeding to the carboxyl or C-terminus on the right. Standard one-letter or three-letter abbreviations can be used.

The term "variant" refers to an entity such as a polypeptide, polynucleotide or small molecule that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity.

The notation "CCAAT box target region" and the like refer to a sequence that is 5' of the transcription start site (TSS) of the HBG1 and/or HBG2 gene. CCAAT boxes are highly conserved motifs within the promoter region of a-like and β-like globin genes. The regions within or near the CCAAT box play important roles in globin gene regulation. For example, the γ-globin distal CCAAT box is associated with hereditary persistence of fetal hemoglobin. A number of transcription factors have been reported to bind to the duplicated CCAAT box region of the γ-globin promoter, e.g., NF-Y, COUP-TFII (NF-E3), CDP, GATA1/NF-E1 and DRED (Martyn 2017). While not wishing to be bound by theory, it is believed that the binding sites of the transcriptional activator NF-Y overlaps with transcriptional repressors at the γ-globin promoter. HPFH mutations present within the distal γ-globin promoter region, e.g., within or near the CCAAT box, may alter the competitive binding of those factors and thus contribute to the increased γ-globin expression and elevated levels of HbF. Genomic locations provided herein for HBG1 and HBG2 are based on the coordinates provided in NCBI Reference Sequence NC_000011, "*Homo sapiens* chromosome 11, GRCh38.p12 Primary Assembly," (Version NC_000011.10). The distal CCAAT box of HBG1 and HBG2 is positioned at HBG1 and HBG2 c.-111 to -115 (Genomic location is Hg38 Chr11:5,249,968 to Chr11:5,249,972 and Hg38 Chr11:5,254,892 to Chr11:5254896, respectively). The HBG1 c.-111 to -115 region is exemplified in SEQ ID NO:902 (HBG1) at positions 2823-2827, and the HBG2 c.-111 to -115 region is exemplified in SEQ ID NO:903 (HBG2) at positions 2747-2751. In certain embodiments, the "CCAAT box target region" denotes the region that is at or near the distal CCAAT box and includes the nucleotides of the distal CCAAT box and 25 nucleotides upstream (5') and 25 nucleotides downstream (3') of the distal CCAAT box (i.e., HBG1/2 c.-86 to -140 (Genomic location is Hg38 Chr11:5249943 to Hg38 Chr11:5249997 and Hg38 Chr11:5254867 to Hg38 Chr11:5254921, respectively)). The HBG1 c.-86 to -140 region is exemplified in SEQ ID NO:902 (HBG1) at positions 2798-2852, and the HBG2 c.-86 to -140 region is exemplified in SEQ ID NO:903 (HBG2) at positions 2723-2776. In certain embodiments, the "CCAAT box target region" denotes the region that is at or near the distal CCAAT box and includes the nucleotides of the distal CCAAT box and 35 nucleotides upstream (5'), 30 nucleotides upstream (5'), 25 nucleotides upstream (5'), 20 nucleotides upstream (5'), 15 nucleotides upstream (5'), 10 nucleotides upstream (5'), or 5 nucleotides upstream (5') and 35 nucleotides downstream (3'), 30 nucleotides downstream (3'), 25 nucleotides downstream (3'), 20 nucleotides downstream (3'), 15 nucleotides downstream (3'), 10 nucleotides downstream (3'), or 5 nucleotides downstream (3') of the distal CCAAT box. In certain embodiments, the "CCAAT box target region" denotes the region that is at or near the distal CCAAT box and includes the nucleotides of the distal CCAAT box and 5 nucleotides upstream (5') and 5 nucleotides downstream (3') of the distal CCAAT box (i.e., HBG1/2 c.-106 to -120 (Genomic location is Hg38 Chr11:5249963 to Hg38 Chr11:5249977 (HGB1 and Hg38 Chr11:5254887 to Hg38 Chr11:5254901, respectively)). The HBG1 c.-106 to -120 region is exemplified in SEQ ID NO:902 (HBG1) at positions 2818-2832, and the HBG2 c.-106 to -120 region is exemplified in SEQ ID NO:903 (HBG2) at positions 2742-2756. The term "CCAAT box target site alteration" and the like refer to alterations (e.g., deletions, insertions, mutations) of one or more nucleotides of the CCAAT box target region. Examples of exemplary CCAAT box target region alterations include, without limitation, the 1 nt deletion, 4 nt deletion, lint deletion, 13 nt deletion, and 18 nt deletion, and -117 G>A alteration. Additional exemplary CCAAT box target region alterations include the productive indels set forth in Table 12. As used herein, the terms "CCAAT box" and "CAAT box" can be used interchangeably.

The notations "c.-114 to -102 region," "c.-102 to -114 region," "-102:-114," "13 nt target region" and the like refer to a sequence that is 5' of the transcription start site (TSS) of the HBG1 and/or HBG2 gene at the genomic location Hg38 Chr11:5,249,959 to Hg38 Chr11:5,249,971 and Hg38 Chr11:5,254,883 to Hg38 Chr11:5,254,895, respectively. The HBG1 c.-102 to -114 region is exemplified in SEQ ID NO:902 (HBG1) at positions 2824-2836 and the HBG2 c.-102 to -114 region is exemplified in SEQ ID NO:903 (HBG2) at positions 2748-2760. The term "13 nt deletion" and the like refer to deletions of the 13 nt target region.

The notations "c.-121 to -104 region," "c.-104 to -121 region," "-104:-121," "18 nt target region," and the like refer to a sequence that is 5' of the transcription start site (TSS) of the HBG1 and/or HBG2 gene at the genomic location Hg38 Chr11:5,249,961 to Hg38 Chr11:5,249,978 and Hg38 Chr11:5,254,885 to Hg38 Chr11: 5,254,902, respectively. The HBG1 c.-104 to -121 region is exemplified in SEQ ID NO:902 (HBG1) at positions 2817-2834, and the HBG2 c.-104 to -121 region is exemplified in SEQ ID NO:903 (HBG2) at positions 2741-2758. The term "18 nt deletion" and the like refer to deletions of the 18 nt target region.

The notations "c.-105 to -115 region," "c.-115 to -105 region," "-105:-115," "11 nt target region," and the like refer to a sequence that is 5' of the transcription start site (TSS) of the HBG1 and/or HBG2 gene at the genomic location Hg38 Chr11:5,249,962 to Hg38 Chr11:5,249,972 and Hg38 Chr11:5,254,886 to Hg38 Chr11:5,254,896, respectively. The HBG1 c.-105 to -115 region is exemplified in SEQ ID NO:902 (HBG1) at positions 2823-2833, and the HBG2 c.-105 to -115 region is exemplified in SEQ ID NO:903 (HBG2) at positions 2747-2757. The term "11 nt deletion" and the like refer to deletions of the 11 nt target region.

The notations "c.-115 to -112 region," "c.-112 to -115 region," "-112:-115," "4 nt target region," and the like refer to a sequence that is 5' of the transcription start site (TSS) of the HBG1 and/or HBG2 gene at the genomic location Hg38 Chr11:5,249,969 to Hg38 Chr11:5,249,972 and Hg38 Chr11:5,254,893 to Hg38 Chr11:5,254,896, respectively. The HBG1 c.-112 to -115 region is exemplified in SEQ ID NO:902 at positions 2823-2826, and the HBG2 c.-112 to -115 region is exemplified in SEQ ID NO:903 (HBG2) at positions 2747-2750. The term "4 nt deletion" and the like refer to deletions of the 4 nt target region.

The notations "c.-116 region," "HBG-116," "1 nt target region," and the like refer to a sequence that is 5' of the transcription start site (TSS) of the HBG1 and/or HBG2 gene at the genomic location Hg38 Chr11:5,249,973 and Hg38 Chr11:5,254,897, respectively. The HBG1 c.-116 region is exemplified in SEQ ID NO:902 at position 2822, and the HBG2 c.-116 region is exemplified in SEQ ID NO:903 (HBG2) at position 2746. The term "1 nt deletion" and the like refer to deletions of the 1 nt target region.

The notations "c.-117 G>A region," "HBG-117 G>A," "-117 G>A target region" and the like refer to a sequence that is 5' of the transcription start site (TSS) of the HBG1 and/or HBG2 gene at the genomic location Hg38 Chr11:5,249,974 to Hg38 Chr11:5,249,974 and Hg38 Chr11:5,254,898 to Hg38 Chr11:5,254,898, respectively. The HBG1 c.-117 G>A region is exemplified by a substitution from guanine (G) to adenine (A) in SEQ ID NO:902 at position 2821, and the HBG2 c.-117 G>A region is exemplified by a substitution from G to A in SEQ ID NO:903 (HBG2) at position 2745. The term "-117 G>A alteration" and the like refer to a substitution from G to A at the -117G>A target region.

The term "proximal HBG1/2 promoter target sequence" denotes the region within 50, 100, 200, 300, 400, or 500 bp of a proximal HBG1/2 promoter sequence including the 13 nt target region. Alterations by genome editing systems according to this disclosure facilitate (e.g., cause, promote or tend to increase the likelihood of) upregulation of HbF production in erythroid progeny.

The term "GATA1 binding motif in BCL11Ae" refers to the sequence that is the GATA1 binding motif in the erythroid specific enhancer of BCL11A (BCL11Ae) that is in the +58 DNase I hypersensitive site (DHS) region of intron 2 of the BCL11A gene. The genomic coordinates for the GATA1 binding motif in BCL11Ae are chr2: 60,495,265 to 60,495,270. The +58 DHS site comprises a 115 base pair (bp) sequence as set forth in SEQ ID NO:968. The +58 DHS site sequence, including ~500 bp upstream and ~200 bp downstream is set forth in SEQ ID NO:969.

Overview

The various embodiments of this disclosure generally relate to genome editing systems configured to introduce alterations (e.g., a deletion or insertion, or other mutation) into chromosomal DNA that enhance transcription of the HBG1 and/or HBG2 genes, which encode the γA and γG subunits of hemoglobin, respectively. Exemplary mutations are made in or around the CCAAT box target region, 13 nt target region and/or into the GATA1 binding motif in BCL11Ae of HBG1 and/or HBG2.

Targeted Genome Editing for Fetal Hemoglobin Induction

Fetal hemoglobin (HbF) expression can be induced using various genome strategies. For example, HbF expression can be induced through targeted disruption of the CCAAT box target region, 13 nt target region, proximal HBG1/2 promoter target sequence, and or the erythroid cell specific expression of a transcriptional repressor, BCL11A (BCL11Ae) (also discussed in commonly-assigned International Patent Publication No. WO 2015/148860 by Friedland et al. ("Friedland"), published Oct. 1, 2015, which is incorporated by reference in its entirety herein), which encodes a repressor that silences HBG1 and HBG2 (Canvers 2015). In certain embodiments, the region of BCL11Ae targeted for disruption may be the GATA1 binding motif in BCL11Ae. In certain embodiments, genome editing systems disclosed herein may be used to introduce alterations into the GATA1 binding motif in BCL11Ae, the CCAAT box target region, and/or the 13 nt target region of HBG1 and/or HBG2.

The genome editing systems of this disclosure can include an RNA-guided nuclease such as Cas9 or Cpf1 and one or more gRNAs having a targeting domain that is complementary to a sequence in or near the target region, and optionally one or more of a DNA donor template that encodes a specific mutation (such as a deletion or insertion) in or near the target region, and/or an agent that enhances the efficiency with which such mutations are generated including, without limitation, a random oligonucleotide, a small molecule agonist or antagonist of a gene product involved in DNA repair or a DNA damage response, or a peptide agent.

A variety of approaches to the introduction of mutations into the CCAAT box target region, 13 nt target region, proximal HBG1/2 promoter target sequence, and/or the GATA1 binding motif in BCL11Ae may be employed in the embodiments of the present disclosure. In one approach, a single alteration, such as a double-strand break, is made within the CCAAT box target region, 13 nt target region, proximal HBG1/2 promoter target sequence, and/or the GATA1 binding motif in BCL11Ae, and is repaired in a way that disrupts the function of the region, for example by the formation of an indel or by the incorporation of a donor template sequence that encodes the deletion of the region. In a second approach, two or more alterations are made on either side of the region, resulting in the deletion of the intervening sequence, including the CCAAT box target region, 13 nt target region and/or the GATA1 binding motif in BCL11Ae.

The treatment of hemoglobinopathies by gene therapy and/or genome editing is complicated by the fact that the cells that are phenotypically affected by the disease, erythrocytes or RBCs, are enucleated, and do not contain genetic material encoding either the aberrant hemoglobin protein (Hb) subunits nor the γA or γG subunits targeted in the exemplary genome editing approaches described above. This complication is addressed, in certain embodiments of this disclosure, by the alteration of cells that are competent to differentiate into, or otherwise give rise to, erythrocytes. Cells within the erythroid lineage that are altered according to various embodiments of this disclosure include, without limitation, hematopoietic stem and progenitor cells (HSCs), erythroblasts (including basophilic, polychromatic and/or orthochromatic erythroblasts), proerythroblasts, polychromatic erythrocytes or reticulocytes, embryonic stem (ES) cells, and/or induced pluripotent stem (iPSC) cells. These cells may be altered in situ (e.g., within a tissue of a subject) or ex vivo. Implementations of genome editing systems for in situ and ex vivo alteration of cells is described under the heading "Implementation of genome editing systems: delivery, formulations, and routes of administration" below.

In certain embodiments, alterations that result in induction of γA and/or γG expression are obtained through the use of a genome editing system comprising an RNA-guided nuclease and at least one gRNA having a targeting domain complementary to a sequence within the 13 nt target region of HBG1 and/or HBG2 or proximate thereto (e.g., within 10, 20, 30, 40, or 50, 100, 200, 300, 400 or 500 bases of the 13 nt target region). As is discussed in greater detail below, the RNA-guided nuclease and gRNA form a complex that is capable of associating with and altering the 13 nt target region or a region proximate thereto. Examples of suitable targeting domains directed to the 13 nt target region of HBG1 and/or HBG2 or proximate thereto for use in the embodiments disclosed herein include, without limitation, those set forth in SEQ ID NOs:251-901, 940-942.

In certain embodiments, alterations that result in induction of HbF expression are obtained through the use of a genome editing system comprising an RNA-guided nuclease and at least one gRNA having a targeting domain complementary to a sequence within the GATA1 binding motif in BCL11Ae or proximate thereto (e.g., within 10, 20, 30, 40, or 50, 100, 200, 300, 400 or 500 bases of the GATA1 binding motif in BCL11Ae). In certain embodiments, the RNA-guided nuclease and gRNA form a complex that is capable of associating with and altering the GATA1 binding motif in BCL11Ae. Examples of suitable targeting domains directed to the GATA1 binding motif in BCL11Ae for use in the embodiments disclosed herein include, without limitation, those set forth in SEQ ID NOs:952-955.

The genome editing system can be implemented in a variety of ways, as is discussed below in detail. As an example, a genome editing system of this disclosure can be implemented as a ribonucleoprotein complex or a plurality of complexes in which multiple gRNAs are used. This ribonucleoprotein complex can be introduced into a target cell using art-known methods, including electroporation, as described in commonly-assigned International Patent Publication No. WO 2016/182959 by Jennifer Gori ("Gori"), published Nov. 17, 2016, which is incorporated by reference in its entirety herein.

The ribonucleoprotein complexes within these compositions are introduced into target cells by art-known methods, including without limitation electroporation (e.g., using the Nucleofection™ technology commercialized by Lonza, Basel, Switzerland or similar technologies commercialized by, for example, Maxcyte Inc. Gaithersburg, Maryland) and lipofection (e.g., using Lipofectamine™ reagent commercialized by Thermo Fisher Scientific, Waltham Massachusetts). Alternatively, or additionally, ribonucleoprotein complexes are formed within the target cells themselves following introduction of nucleic acids encoding the RNA-guided nuclease and/or gRNA. These and other delivery modalities are described in general terms below and in Gori.

Cells that have been altered ex vivo according to this disclosure can be manipulated (e.g., expanded, passaged, frozen, differentiated, de-differentiated, transduced with a transgene, etc.) prior to their delivery to a subject. The cells are, variously, delivered to a subject from which they are obtained (in an "autologous" transplant), or to a recipient who is immunologically distinct from a donor of the cells (in an "allogeneic" transplant).

In some cases, an autologous transplant includes the steps of obtaining, from the subject, a plurality of cells, either circulating in peripheral blood, or within the marrow or other tissue (e.g., spleen, skin, etc.), and manipulating those cells to enrich for cells in the erythroid lineage (e.g., by induction to generate iPSCs, purification of cells expressing certain cell surface markers such as CD34, CD90, CD49f and/or not expressing surface markers characteristic of non-erythroid lineages such as CD10, CD14, CD38, etc.). The cells are, optionally or additionally, expanded, transduced with a transgene, exposed to a cytokine or other peptide or small molecule agent, and/or frozen/thawed prior to transduction with a genome editing system targeting the CCAAT box target region, 13 nt target region, proximal HBG1/2 promoter target sequence, and/or the GATA1 binding motif in BCL11Ae. The genome editing system can be implemented or delivered to the cells in any suitable format, including as a ribonucleoprotein complex, as separated protein and nucleic acid components, and/or as nucleic acids encoding the components of the genome editing system.

However it is implemented, a genome editing system may include, or may be co-delivered with, one or more factors that improve the viability of the cells during and after editing, including without limitation an aryl hydrocarbon receptor antagonist such as StemRegenin-1 (SR1), UM171, LGC0006, alpha-naphthoflavone, and CH-223191, and/or an innate immune response antagonist such as cyclosporin A, dexamethasone, resveratrol, a MyD88 inhibitory peptide, an RNAi agent targeting Myd88, a B18R recombinant protein, a glucocorticoid, OxPAPC, a TLR antagonist, rapamycin, BX795, and a RLR shRNA. These and other factors that improve the viability of the cells during and after editing are described in Gori, under the heading "I. Optimization of Stem Cells" from page 36 through page 61, which is incorporated by reference herein.

The cells, following delivery of the genome editing system, are optionally manipulated e.g., to enrich for HSCs and/or cells in the erythroid lineage and/or for edited cells, to expand them, freeze/thaw, or otherwise prepare the cells for return to the subject. The edited cells are then returned to the subject, for instance in the circulatory system by means of intravenous delivery or delivery or into a solid tissue such as bone marrow.

Functionally, alteration of the CCAAT box target region, 13 nt target region, proximal HBG1/2 promoter target sequence, and/or the GATA1 binding motif in BCL11Ae using the compositions, methods and genome editing systems of this disclosure results in significant induction, among hemoglobin-expressing cells, of γA and/or γG subunits (referred to interchangeably as HbF expression), e.g., at least 5%, 10%, 15%, 20%, 25%, 30%, 35%, 40%, 45%, 50% or greater induction of γA and/or γG subunit expression relative to unmodified controls. This induction of protein expression is generally the result of alteration of the CCAAT box target region, 13 nt target region, proximal HBG1/2 promoter target sequence, and/or the GATA1 binding motif in BCL11Ae (expressed, e.g., in terms of the percentage of total genomes comprising indel mutations within the plurality of cells) in some or all of the plurality of cells that are treated, e.g., at least 5%, 10%, 15%, 20%, 25%, 30%, 35%, 40%, 45%, 50% of the plurality of cells comprise at least one allele comprising a sequence alteration, including, without limitation, an indel, insertion, or deletion in or near the CCAAT box target region, 13 nt target region, proximal HBG1/2 promoter target sequence, and/or the GATA1 binding motif in BCL11Ae.

The functional effects of alterations caused or facilitated by the genome editing systems and methods of the present disclosure can be assessed in any number of suitable ways. For example, the effects of alterations on expression of fetal hemoglobin can be assessed at the protein or mRNA level. Expression of HBG1 and HBG2 mRNA can be assessed by digital droplet PCR (ddPCR), which is performed on cDNA samples obtained by reverse transcription of mRNA harvested from treated or untreated samples. Primers for HBG1, HBG2, HBB, and/or HBA may be used individually or multiplexed using methods known in the art. For example, ddPCR analysis of samples may be conducted using the QX200™ ddPCR system commercialized by Bio Rad (Hercules, CA), and associated protocols published by BioRad. Fetal hemoglobin protein may be assessed by high pressure liquid chromatography (HPLC), for example, according to the methods discussed on pp. 143-44 of Chang 2017, incorporated by reference herein, or fast protein liquid chromatography (FPLC) using ion-exchange and/or reverse phase columns to resolve HbF, HbB and HbA and/or γA and γG globin chains as is known in the art.

It should be noted that the rate at which the CCAAT box target region, 13 nt target region, proximal HBG1/2 promoter target sequence, and/or the GATA1 binding motif in BCL11Ae is altered in the target cells can be modified by the use of optional genome editing system components such as oligonucleotide donor templates. Donor template design is described in general terms below under the heading "Donor template design." Donor templates for use in targeting the 13 nt target region may include, without limitation, donor templates encoding alterations (e.g., deletions) of HBG1 c.-114 to -102 (corresponding to nucleotides 2824-2836 of SEQ ID NO: 902), HBG1 c.-225 to -222 (corresponding to nucleotides 2716-2719 of SEQ ID NO:902)), and/or HBG2 c.-114 to -102 (corresponding to nucleotides 2748-2760 of SEQ ID NO:903). Exemplary 5' and 3' homology arms, and exemplary full-length donor templates encoding deletions such as c.-114 to -102 are also presented below (SEQ ID NOS: 904-909). Donor templates used herein may be non-specific templates that are non-homologous to regions of DNA within or near the target sequence. In certain embodiments, donor templates for use in targeting the 13 nt target region may include, without limitation, non-target specific templates that are nonhomologous to regions of DNA within or near the 13 nt target region. For example, a non-specific donor template for use in targeting the 13 nt target region may be non-homologous to the regions of DNA within or near the 13 nt target region and may comprise a donor template encoding the deletion of HBG1 c.-225 to -222 (corresponding to nucleotides 2716-2719 of SEQ ID NO:902). In certain embodiments, donor templates for use in targeting the GATA1 binding motif in BCL11Ae may include, without limitation, non-target specific templates that are nonhomologous to regions of DNA within or near GATA1 binding motif in BCL11Ae target sequence. Other donor templates for use in targeting BCL11Ae may include, without limitation, donor templates including alternations (e.g., deletions) of BCL11Ae, including, without limitation, the GATA1 motif in BCL11Ae.

RNA-Guided Helicases and Dead Guide RNAs

Various embodiments of the present disclosure also generally relate to genome editing systems configured to alter the helical structure of a nucleic acid to enhance genome editing of a target region (e.g., the CCAAT box target region, 13 nt target region, proximal HBG1/2 promoter target sequence, and/or the GATA1 binding motif in BCL11Ae) in the nucleic acid, and methods and compositions thereof. Many embodiments relate to the observation that positioning an event that alters the helical structure of DNA within or adjacent to target regions in nucleic acid may improve the activity of genome editing systems directed to such target regions. Without wishing to be bound by any theory, it is thought that alterations of helical structure (e.g., by unwinding) within or proximal to DNA target regions may induce or increase accessibility of a genome editing system to the target region, resulting in increased editing of the target regions by the genome editing system.

CRISPR nucleases evolved primarily to defend bacteria against viral pathogens, whose genomes are not naturally organized into chromatin. By contrast, when eukaryotic genomes are organized into nucleosomal units comprising genomic DNA segments coiled around histones. CRISPR nucleases from several bacterial families have been found to be inactive for editing eukaryotic DNA, suggesting the ability to edit nucleosome-bound DNA might differ across enzymes (Ran 2015). Biochemical evidence shows that *S. pyogenes* Cas9 can cleave DNA efficiently at nucleosome edges, but has reduced activity when the target site is positioned near the center of nucleosome dyad (Hinz 2016).

In many cell types, target sites of interest may be strongly bound by nucleosomes, or may only possess adjacent PAMs for enzymes that do not edit efficiently in the presence of nucleosomes. In this case, the problematic nucleosomes could be displaced first by using adjacent target sites that are closer to the nucleosome edge or are bound by an enzyme that is more effective at binding nucleosomal DNA. However, cleavage at these adjacent sites could be detrimental to the therapeutic strategy. Therefore, having a programmable enzyme that binds these adjacent sites but does not cleave can enable more efficient functional editing.

It will be evident to the skilled artisan that the simplified systems and methods described herein offer several advantages over competing approaches. For example, a related strategy using catalytically inactive (dead) enzymes targeting sites adjacent to the site where editing is desired has been described in the literature (Chen 2017). However, this strategy entails a potential safety issue: if the full-length gRNAs complexed with a catalytically inactive nuclease molecule dissociates and later reassociates with a catalytically active nuclease enzyme, the gRNAs could introduce undesirable off-target edits. In contrast, the systems and methods of the present disclosure eliminates this risk because it relies on the observation that a dead gRNA (dgRNA) (gRNAs with a targeting domain of 15 nucleotides or less) allow an RNA-guided nuclease to bind, but not cleave, its target cite. Thus, the dgRNAs provided herein will not support nuclease activity irrespective of their association with any particular RNA-guided nuclease molecule. By using these dead gRNAs, adjacent target sites can be used to aid in nucleosome displacement without the risk of guide RNA swapping between active and inactive enzyme.

Another related strategy utilizes recruitment of exogenous trans-acting factors to facilitate nucleosome displacement. However, the systems and methods of this disclosure are advantageous over this strategy because they do not require gRNA modifications beyond truncation of the targeting domain, do not require the recruitment of exogenous trans-acting factors, and do not require transcriptional activation to achieve increased rates of editing.

Additionally, the use of dead gRNAs in the genome editing systems of the present disclosure are advantageous because they are not expected to result in any new delivery/solubility or folding/manufacturing considerations relative to genome editing systems utilizing full-length gRNAs. However, a skilled artisan might expect to encounter such problems in genome editing systems that utilize a exogenous trans-acting factors, which may entail large fusion proteins and/or RNA insertions or fusions. Further, dead gRNA strategies are likely to be capable of implementation using existing manufacturing, delivery, and other commercial processes that have been designed for wild-type nuclease products with relatively few substantial changes.

A variety of approaches to the unwinding and alteration of nucleic acid are employed in the various embodiments of this disclosure. One approach comprises unwinding (or opening of) a chromatin segment within or proximal to a target region (e.g., the CCAAT box target region, 13 nt target region, proximal HBG1/2 promoter target sequence, and/or the GATA1 binding motif in BCL11Ae) of a nucleic acid in a cell and generating a double stranded break (DSB) within the target region of the nucleic acid whereby the target region is altered. In certain embodiments, the DSB may be repaired in a manner that alters the target region. Unwinding the chromatin segment using the methods provided herein may facilitate increased access of catalytically active RNPs (e.g., catalytically active RNA-guided nucleases and gRNAs) to the chromatin to allow for more efficient editing of the DNA. For example, these methods may be used to edit target regions in chromatin that are difficult for a ribonucleoprotein (e.g., RNA-guided nuclease complexed to gRNA) to access because the chromatin is occupied by nucleosomes, such as closed chromatin. In certain embodiments, the unwinding of the chromatin segment occurs via RNA-guided helicase activity. In certain embodiments, the unwinding step does not require recruiting an exogenous trans-acting factor to the chromatin segment. In certain embodiments, the step of unwinding the chromatin segment does not comprise forming a single or double-stranded break in the nucleic acid within the chromatin segment.

In certain embodiments of the approaches and methods described above, the alteration of DNA helical structure is achieved through the action of an "RNA-guided helicase," which term is generally used to refer to a molecule, typically a peptide, that (a) interacts (e.g., complexes) with a gRNA, and (b) together with the gRNA, associates with and unwinds, but does not cleave, a target site. RNA-guided helicases may, in certain embodiments, comprise RNA-guided nucleases configured to lack nuclease activity. However, the inventors have observed that even a cleavage-competent RNA-guided nuclease may be adapted for use as an RNA-guided helicase by complexing it to a dead gRNA having a truncated targeting domain of 15 or fewer nucleotides in length. Complexes of wild-type RNA-guided nucleases with dead gRNAs exhibit reduced or eliminated RNA-cleavage activity, but appear to retain helicase activity. RNA-guided helicases and dead gRNAs are described in greater detail below.

Regarding RNA-guided helicases, according to the present disclosure an RNA-guided helicase may comprise any of the RNA-guided nucleases disclosed herein and infra under the heading entitled "RNA-guided nucleases," including, without limitation, a Cas9 or Cpf1 RNA-guided nuclease. The helicase activity of these RNA-guided nucleases allow for unwinding of DNA, providing increased access of genome editing system components (e.g., without limitation, catalytically active RNA-guided nuclease and gRNAs) to the desired target region to be edited (e.g., the CCAAT box target region, 13 nt target region, proximal HBG1/2 promoter target sequence, and/or the GATA1 binding motif in BCL11Ae). In certain embodiments, the RNA-guided nuclease may be a catalytically active RNA-guided nuclease with nuclease activity. In certain embodiments, the RNA-guided helicase may be configured to lack nuclease activity. For example, in certain embodiments, the RNA-guided helicase may be a catalytically inactive RNA-guided nuclease that lacks nuclease activity, such as a catalytically dead Cas9 molecule, which still provides helicase activity. In certain embodiments, an RNA-guided helicase may form a complex with a dead gRNA, forming a dead RNP that cannot cleave nucleic acid. In other embodiments, the RNA-guided helicase may be a catalytically active RNA-guided nuclease complexed to a dead gRNA, forming a dead RNP that cannot cleave nucleic acid. In certain embodiments, the RNA-guided nuclease is not configured to recruit an exogenous trans-acting factor to the desired target region to be edited (e.g., the CCAAT box target region, 13 nt target region, proximal HBG1/2 promoter target sequence, and/or the GATA1 binding motif in BCL11Ae).

Turning to dead gRNAs, these include any of the dead gRNAs discussed herein and infra under the heading entitled "Dead gRNA molecules." Dead gRNAs (also referred to herein as "dgRNAs") may be generated by truncating the 5' end of a gRNA targeting domain sequence, resulting in a targeting domain sequence of 15 nucleotides or fewer in length. In certain embodiments, a dgRNA may be generated by truncating the 5' end of any one of a gRNA targeting domain sequence disclosed herein in Table 2 or Table 10. Dead guide RNA molecules according to the present disclosure include dead guide RNA molecules that have reduced, low, or undetectable cleavage activity. The targeting domain sequences of dead guide RNAs may be shorter in length by 1, 2, 3, 4, 5, 6, 7, 8, 9, or 10 nucleotides compared to the targeting domain sequence of active guide RNAs. Dead gRNA molecules may comprise targeting domains complementary to regions proximal to or within a target region (e.g., the CCAAT box target region, 13 nt target region, proximal HBG1/2 promoter target sequence, and/or the GATA1 binding motif in BCL11Ae) in a target nucleic acid. In certain embodiments, "proximal to" may denote the region within 10, 25, 50, 100, or 200 nucleotides of a target region (e.g., the CCAAT box target region, 13 nt target region, proximal HBG1/2 promoter target sequence, and/or the GATA1 binding motif in BCL11Ae). In certain embodiments, dead gRNAs comprise targeting domains complementary to the transcription strand or non-transcription strand of DNA. In certain embodiments, the dead guide RNA is not configured to recruit an exogenous trans-acting factor to a target region (e.g., the CCAAT box target region, 13 nt target region, proximal HBG1/2 promoter target sequence, and/or the GATA1 binding motif in BCL11Ae).

Also provided herein are methods of increasing a rate of indel formation in a target nucleic acid by unwinding DNA within or proximal to the target region (e.g., the CCAAT box target region, 13 nt target region, proximal HBG1/2 promoter target sequence, and/or the GATA1 binding motif in BCL11Ae) using an RNA-guided helicase, generating a DSB within the target region, and forming an indel in the target region through repair of the DSB. The step of unwinding the DNA using an RNA-guided helicase provides for increased indel formation compared to a method of forming indels that does not use a helicase.

This disclosure further encompasses methods of deleting a segment of a target nucleic acid in a cell, comprising contacting the cell with an RNA-guided helicase and generating a double strand break (DSB) within the target region (e.g., the CCAAT box target region, 13 nt target region, proximal HBG1/2 promoter target sequence, and/or the GATA1 binding motif in BCL11Ae). In certain embodiments, the RNA-guided helicase is configured to associate within or proximal to a target region of the target nucleic acid and unwind double stranded DNA (dsDNA) within or proximal to the target region. In certain embodiments, the target nucleic acid is a promoter region of a gene, a coding region of a gene, a non-coding region of a gene, an intron of a gene, or an exon of a gene. In certain embodiments, the segment of the target nucleic acid to be deleted may is at least about 15, 20, 25, 30, 35, 40, 45, 50, 55, 60, 65, 70, 75, or 100 base pairs in length. In certain embodiments, the DSB is repaired in a manner that deletes the segment of the target nucleic acid.

Genome editing systems configured to introduce alterations of helical structure may be implemented in a variety of ways, as is discussed below in detail. As an example, a genome editing system of this disclosure can be implemented as a ribonucleoprotein complex or a plurality of complexes in which multiple gRNAs are used. In certain embodiments, a ribonucleoprotein complex of the genome editing system may be an RNA-guided helicase complexed to a dead guide RNA. Ribonucleoprotein complexes can be introduced into a target cell using art-known methods, including electroporation, as described in Gori. Genome editing systems incorporating RNA-guided helicases may also be modified in any suitable manner, including without limitation by the inclusion of one or more of a DNA donor template that encodes a specific mutation (such as a deletion or insertion) in or near the target region, and/or an agent that enhances the efficiency with which such mutations are generated including, without limitation, a random oligonucleotide, a small molecule agonist or antagonist of a gene product involved in DNA repair or a DNA damage response, or a peptide agent. These modifications are described in greater detail below, under the heading "Genome Editing Strategies." For clarity, this disclosure includes compositions comprising one or more gRNAs, dead gRNAs, RNA-guided helicases, RNA-guided nucleases, or a combination thereof.

While several of the exemplary embodiments above have focused on DNA unwinding, it should be noted that other helical alterations are within the scope of the present disclosure. These include, without limitation, overwinding, underwinding, increase or decrease of torsional strain on DNA strands within or proximate to a target region (e.g., through topoisomerase activity), denaturation or strand separation, and/or other suitable alterations resulting in modifications of chromatin structure. Each of these alterations may be catalyzed by an RNA-guided activity, or by the recruitment of an endogenous factor to a target region.

Also provided herein are genome editing systems and methods of altering one or more indels (e.g., indel signature) generated by an active guide. As the inventors have discovered herein, pairing of a dead RNP (dRNP) (i.e., a dead guide RNA complexed with an RNA-guided nuclease) and an active RNP (i.e., an active guide RNA complexed with an RNA-guided nuclease) can result in a change of the directionality of the indels (e.g., indel signature) generated by the active RNP alone (without a dRNP). As shown in the examples below, the use of the dead guide RNA may result in an increased frequency of larger deletions extending from the active guide RNA cut site toward the dead guide RNA binding site. Thus, the dead guide RNA may be used to effectively "orient" deletion editing toward a desired target site. In certain embodiments, the use of the dead guide RNA with an active guide RNA may increase the frequency of deletions that are not associated with micro-homologies.

Although the examples disclosed in the Examples section below are directed to alterations of the CCAAT box target region, skilled artisans would contemplate that the genome editing systems, methods, cells and compositions described herein may be used to alter any other target region, for example, without limitation, to increase the frequency of deletions at the target region, increase the frequency of deletions at the target region that are not associated with micro-homologies (e.g., not repaired via MMEJ).

This overview has focused on a handful of exemplary embodiments that illustrate the principles of genome editing systems and CRISPR-mediated methods of altering cells. For clarity, however, this disclosure encompasses modifications and variations that have not been expressly addressed above, but will be evident to those of skill in the art. With that in mind, the following disclosure is intended to illustrate the operating principles of genome editing systems more generally. What follows should not be understood as limiting, but rather illustrative of certain principles of genome editing systems and CRISPR-mediated methods utilizing these systems, which, in combination with the instant disclosure, will inform those of skill in the art about additional implementations and modifications that are within its scope.

Genome Editing Systems

The term "genome editing system" refers to any system having RNA-guided DNA editing activity. Genome editing systems of the present disclosure include at least two components adapted from naturally occurring CRISPR systems: a gRNA and an RNA-guided nuclease. These two components form a complex that is capable of associating with a specific nucleic acid sequence and editing the DNA in or around that nucleic acid sequence, for instance by making one or more of a single-strand break (an SSB or nick), a double-strand break (a DSB) and/or a point mutation.

In certain embodiments, the genome editing systems in this disclosure may include a helicase for unwinding DNA. In certain embodiments, the helicase may be an RNA-guided helicase. In certain embodiments, the RNA-guided helicase may be an RNA-guided nuclease as described herein, such as a Cas9 or Cpf1 molecule. In certain embodiments, the RNA-guided nuclease is not configured to recruit an exogenous trans-acting factor to a target region. In certain embodiments, the RNA-guided nuclease may be configured to lack nuclease activity. In certain embodiments, the RNA-guided helicase may be complexed with a dead guide RNA as disclosed herein. For example, the dead guide RNA (dgRNA) may comprise a targeting domain sequence less than 15 nucleotides in length. In certain embodiments, the dead guide RNA is not configured to recruit an exogenous trans-acting factor to a target region.

Naturally occurring CRISPR systems are organized evolutionarily into two classes and five types (Makarova 2011, incorporated by reference herein), and while genome editing systems of the present disclosure may adapt components of any type or class of naturally occurring CRISPR system, the embodiments presented herein are generally adapted from Class 2, and type II or V CRISPR systems. Class 2 systems, which encompass types II and V, are characterized by relatively large, multidomain RNA-guided nuclease proteins (e.g., Cas9 or Cpf1) and one or more guide RNAs (e.g., a crRNA and, optionally, a tracrRNA) that form ribonucleoprotein (RNP) complexes that associate with (i.e., target) and cleave specific loci complementary to a targeting (or spacer) sequence of the crRNA. Genome editing systems according to the present disclosure similarly target and edit cellular DNA sequences, but differ significantly from CRISPR systems occurring in nature. For example, the unimolecular guide RNAs described herein do not occur in nature, and both guide RNAs and RNA-guided nucleases according to this disclosure may incorporate any number of non-naturally occurring modifications.

Genome editing systems can be implemented (e.g., administered or delivered to a cell or a subject) in a variety of ways, and different implementations may be suitable for distinct applications. For instance, a genome editing system is implemented, in certain embodiments, as a protein/RNA complex (a ribonucleoprotein, or RNP), which can be included in a pharmaceutical composition that optionally includes a pharmaceutically acceptable carrier and/or an encapsulating agent, such as, without limitation, a lipid or polymer micro- or nano-particle, micelle, or liposome. In certain embodiments, a genome editing system is implemented as one or more nucleic acids encoding the RNA-guided nuclease and guide RNA components described above (optionally with one or more additional components); in certain embodiments, the genome editing system is implemented as one or more vectors comprising such nucleic acids, for instance a viral vector such as an adeno-associated virus (see section below under the heading "Implementation of genome editing systems: delivery, formulations, and routes of administration"); and in certain embodiments, the genome editing system is implemented as a combination of any of the foregoing. Additional or modified implementations that operate according to the principles set forth herein will be apparent to the skilled artisan and are within the scope of this disclosure.

It should be noted that the genome editing systems of the present disclosure can be targeted to a single specific nucleotide sequence, or may be targeted to—and capable of editing in parallel—two or more specific nucleotide sequences through the use of two or more guide RNAs. The use of multiple gRNAs is referred to as "multiplexing" throughout this disclosure, and can be employed to target multiple, unrelated target sequences of interest, or to form multiple SSBs or DSBs within a single target domain and, in some cases, to generate specific edits within such target domain. For example, International Patent Publication No. WO 2015/138510 by Maeder et al. ("Maeder"), which is incorporated by reference herein, describes a genome editing system for correcting a point mutation (C.2991+1655A to G) in the human CEP290 gene that results in the creation of a cryptic splice site, which in turn reduces or eliminates the function of the gene. The genome editing system of Maeder utilizes two guide RNAs targeted to sequences on either side of (i.e., flanking) the point mutation, and forms DSBs that flank the mutation. This, in turn, promotes deletion of the intervening sequence, including the mutation, thereby eliminating the cryptic splice site and restoring normal gene function.

As another example, WO 2016/073990 by Cotta-Ramusino et al. ("Cotta-Ramusino"), which is incorporated by reference herein, describes a genome editing system that utilizes two gRNAs in combination with a Cas9 nickase (a Cas9 that makes a single strand nick such as *S. pyogenes* D10A), an arrangement termed a "dual-nickase system." The dual-nickase system of Cotta-Ramusino is configured to make two nicks on opposite strands of a sequence of interest that are offset by one or more nucleotides, which nicks combine to create a double strand break having an overhang (5' in the case of Cotta-Ramusino, though 3' overhangs are also possible). The overhang, in turn, can facilitate homology directed repair events in some circumstances. And, as another example, International Patent Publication No. WO 2015/070083 by Palestrant et al. (incorporated by reference herein) describes a gRNA targeted to a nucleotide sequence encoding Cas9 (referred to as a "governing RNA"), which can be included in a genome editing system comprising one or more additional gRNAs to permit transient expression of a Cas9 that might otherwise be constitutively expressed, for example in some virally transduced cells. These multiplexing applications are intended to be exemplary, rather than limiting, and the skilled artisan will appreciate that other applications of multiplexing are generally compatible with the genome editing systems described here.

As disclosed herein, in certain embodiments, genome editing systems may comprise multiple gRNAs that may be used to introduce mutations into the GATA1 binding motif in BCL11Ae, the CCAAT box target region, or the 13 nt target region of HBG1 and/or HBG2. In certain embodiments, genome editing systems disclosed herein may comprise multiple gRNAs used to introduce mutations into the GATA1 binding motif in BCL11Ae and the 13 nt target region of HBG1 and/or HBG2.

Genome editing systems can, in some instances, form double strand breaks that are repaired by cellular DNA double-strand break mechanisms such as NHEJ or HDR. These mechanisms are described throughout the literature (see, e.g., Davis 2014 (describing Alt-HDR), Frit 2014 (describing Alt-NHEJ), and Iyama 2013 (describing canonical HDR and NHEJ pathways generally), all of which are incorporated by reference herein).

Where genome editing systems operate by forming DSBs, such systems optionally include one or more components that promote or facilitate a particular mode of double-strand break repair or a particular repair outcome. For instance, Cotta-Ramusino also describes genome editing systems in which a single stranded oligonucleotide "donor template" is added; the donor template is incorporated into a target region of cellular DNA that is cleaved by the genome editing system, and can result in a change in the target sequence.

In certain embodiments, genome editing systems modify a target sequence, or modify expression of a gene in or near the target sequence, without causing single- or double-strand breaks. For example, a genome editing system may include an RNA-guided nuclease fused to a functional domain that acts on DNA, thereby modifying the target sequence or its expression. As one example, an RNA-guided nuclease can be connected to (e.g., fused to) a cytidine deaminase functional domain, and may operate by generating targeted C-to-A substitutions. Exemplary nuclease/deaminase fusions are described in Komor 2016, which is incorporated by reference herein. Alternatively, a genome editing system may utilize a cleavage-inactivated (i.e., a "dead") nuclease, such as a dead Cas9 (dCas9), and may operate by forming stable complexes on one or more targeted regions of cellular DNA, thereby interfering with functions involving the targeted region(s) including, without limitation, mRNA transcription, chromatin remodeling, etc. In certain embodiments, a genome editing system may include an RNA-guided helicase that unwinds DNA within or proximal to the target sequence, without causing single- or double-stranded breaks. For example a genome editing system may include an RNA-guided helicase configured to associate within or near the target sequence to unwind DNA and induce accessibility to the target sequence. In certain embodiments, the RNA-guided helicase may be complexed to a dead guide RNA that is configured to lack cleavage activity allowing for unwinding of the DNA without causing breaks in the DNA.

Guide RNA (gRNA) Molecules

The terms "guide RNA" and "gRNA" refer to any nucleic acid that promotes the specific association (or "targeting") of an RNA-guided nuclease such as a Cas9 or a Cpf1 to a target sequence such as a genomic or episomal sequence in a cell. gRNAs can be unimolecular (comprising a single RNA molecule, and referred to alternatively as chimeric), or modular (comprising more than one, and typically two, separate RNA molecules, such as a crRNA and a tracrRNA, which are usually associated with one another, for instance by duplexing). gRNAs and their component parts are described throughout the literature, for instance in Briner 2014, which is incorporated by reference), and in Cotta-Ramusino. Examples of modular and unimolecular gRNAs that may be used according to the embodiments herein include, without limitation, the sequences set forth in SEQ ID NOs:29-31 and 38-51. Examples of gRNA proximal and tail domains that may be used according to the embodiments herein include, without limitation, the sequences set forth in SEQ ID NOs:32-37.

In bacteria and archea, type II CRISPR systems generally comprise an RNA-guided nuclease protein such as Cas9, a CRISPR RNA (crRNA) that includes a 5' region that is complementary to a foreign sequence, and a trans-activating crRNA (tracrRNA) that includes a 5' region that is complementary to, and forms a duplex with, a 3' region of the crRNA. While not intending to be bound by any theory, it is thought that this duplex facilitates the formation of—and is necessary for the activity of—the Cas9/gRNA complex. As type II CRISPR systems were adapted for use in gene editing, it was discovered that the crRNA and tracrRNA could be joined into a single unimolecular or chimeric guide RNA, in one non-limiting example, by means of a four nucleotide (e.g., GAAA) "tetraloop" or "linker" sequence bridging complementary regions of the crRNA (at its 3' end) and the tracrRNA (at its 5' end) (Mali 2013; Jiang 2013; Jinek 2012; all incorporated by reference herein).

Guide RNAs, whether unimolecular or modular, include a "targeting domain" that is fully or partially complementary to a target domain within a target sequence, such as a DNA sequence in the genome of a cell where editing is desired. Targeting domains are referred to by various names in the literature, including without limitation "guide sequences" (Hsu et al., Nat Biotechnol. 2013 September; 31(9): 827-832, ("Hsu"), incorporated by reference herein), "complementarity regions" (Cotta-Ramusino), "spacers" (Briner 2014) and generically as "crRNAs" (Jiang). Irrespective of the names they are given, targeting domains are typically 10-30 nucleotides in length, and in certain embodiments are 16-24 nucleotides in length (for instance, 16, 17, 18, 19, 20, 21, 22, 23 or 24 nucleotides in length), and are at or near the 5' terminus of in the case of a Cas9 gRNA, and at or near the 3' terminus in the case of a Cpf1 gRNA.

In addition to the targeting domains, gRNAs typically (but not necessarily, as discussed below) include a plurality of domains that may influence the formation or activity of gRNA/Cas9 complexes. For instance, as mentioned above, the duplexed structure formed by first and secondary complementarity domains of a gRNA (also referred to as a repeat:anti-repeat duplex) interacts with the recognition (REC) lobe of Cas9 and can mediate the formation of Cas9/gRNA complexes (Nishimasu et al., Cell 156, 935-949, Feb. 27, 2014 ("Nishimasu 2014") and Nishimasu et al., Cell 162, 1113-1126, Aug. 27, 2015 ("Nishimasu 2015"), both incorporated by reference herein. It should be noted that the first and/or second complementarity domains may contain one or more poly-A tracts, which can be recognized by RNA polymerases as a termination signal. The sequence of the first and second complementarity domains are, therefore, optionally modified to eliminate these tracts and promote the complete in vitro transcription of gRNAs, for instance through the use of A-G swaps as described in Briner 2014, or A-U swaps. These and other similar modifications to the first and second complementarity domains are within the scope of the present disclosure.

Along with the first and second complementarity domains, Cas9 gRNAs typically include two or more additional duplexed regions that are involved in nuclease activity in vivo but not necessarily in vitro. (Nishimasu 2015). A first stem-loop one near the 3' portion of the second complementarity domain is referred to variously as the "proximal domain," (Cotta-Ramusino) "stem loop 1" (Nishimasu 2014 and 2015) and the "nexus" (Briner 2014). One or more additional stem loop structures are generally present near the 3' end of the gRNA, with the number varying by species: *S. pyogenes* gRNAs typically include two 3' stem loops (for a total of four stem loop structures including the repeat:anti-repeat duplex), while *S. aureus* and other species have only one (for a total of three stem loop structures). A description of conserved stem loop structures (and gRNA structures more generally) organized by species is provided in Briner 2014.

While the foregoing description has focused on gRNAs for use with Cas9, it should be appreciated that other RNA-guided nucleases exist which utilize gRNAs that differ in some ways from those described to this point. For instance, Cpf1 ("CRISPR from Prevotella and Franciscella 1") is a recently discovered RNA-guided nuclease that does not require a tracrRNA to function (Zetsche 2015b, incorporated by reference herein). A gRNA for use in a Cpf1 genome editing system generally includes a targeting domain and a complementarity domain (alternately referred to as a "handle"). It should also be noted that, in gRNAs for use with Cpf1, the targeting domain is usually present at or near the 3' end, rather than the 5' end as described above in connection with Cas9 gRNAs (the handle is at or near the 5' end of a Cpf1 gRNA).

Those of skill in the art will appreciate, however, that although structural differences may exist between gRNAs from different prokaryotic species, or between Cpf1 and Cas9 gRNAs, the principles by which gRNAs operate are generally consistent. Because of this consistency of operation, gRNAs can be defined, in broad terms, by their targeting domain sequences, and skilled artisans will appreciate that a given targeting domain sequence can be incorporated in any suitable gRNA, including a unimolecular or chimeric gRNA, or a gRNA that includes one or more chemical modifications and/or sequential modifications (substitutions, additional nucleotides, truncations, etc.). Thus, for economy of presentation in this disclosure, gRNAs may be described solely in terms of their targeting domain sequences.

More generally, skilled artisans will appreciate that some aspects of the present disclosure relate to systems, methods and compositions that can be implemented using multiple RNA-guided nucleases. For this reason, unless otherwise specified, the term gRNA should be understood to encompass any suitable gRNA that can be used with any RNA-guided nuclease, and not only those gRNAs that are compatible with a particular species of Cas9 or Cpf1. By way of illustration, the term gRNA can, in certain embodiments, include a gRNA for use with any RNA-guided nuclease occurring in a Class 2 CRISPR system, such as a type II or type V or CRISPR system, or an RNA-guided nuclease derived or adapted therefrom.

In certain embodiments, the gRNAs and dgRNAs described herein may be prepared using art-known methods, including, without limitation, chemical synthesis and in vitro transcription (IVT). IVT typically involves the transcription of RNA from a DNA template by means of a bacterial RNA polymerase such as T7 polymerase. Chemical synthesis methods are described throughout the literature, for instance by Beaucage and Carruthers, Curr Protoc Nucleic Acid Chem. 2001 May; Chapter 3: Unit 3.3 (Beaucage & Carruthers), which is incorporated by reference in its entirety herein. Other methods of synthesis that may be used to prepare the gRNAs and dgRNAs described herein are set forth in International Patent Application No. PCT/US17/69019 filed Dec. 29, 2017, which is incorporated by reference in its entirety herein.

gRNA Design

Methods for selection and validation of target sequences as well as off-target analyses have been described previously (see, e.g., Mali 2013; Hsu 2013; Fu 2014; Heigwer 2014; Bae 2014; Xiao 2014; all incorporated by reference herein). As a non-limiting example, gRNA design may involve the use of a software tool to optimize the choice of potential target sequences corresponding to a user's target sequence, e.g., to minimize total off-target activity across the genome. While off-target activity is not limited to cleavage, the cleavage efficiency at each off-target sequence can be predicted, e.g., using an experimentally-derived weighting scheme. These and other guide selection methods are described in detail in Maeder and Cotta-Ramusino.

With respect to selection of gRNA targeting domain sequences directed to HBG1/2 target sites (e.g., the 13 nt target region), an in-silico gRNA target domain identification tool was utilized, and the hits were stratified into four tiers. For *S. pyogenes*, tier 1 targeting domains were selected based on (1) distance upstream or downstream from either end of the target site (i.e., HBG1/2 13 nt target region), specifically within 400 bp of either end of the target site, (2) a high level of orthogonality, and (3) the presence of 5' G. Tier 2 targeting domains were selected based on (1) distance upstream or downstream from either end of the target site (i.e., HBG1/2 13 nt target region), specifically within 400 bp of either end of the target site, and (2) a high level of orthogonality. Tier 3 targeting domains were selected based on (1) distance upstream or downstream from either end of the target site (i.e., HBG1/2 13 nt target region), specifically within 400 bp of either end of the target site and (2) the presence of 5' G. Tier 4 targeting domains were selected based on distance upstream or downstream from either end of the target site (i.e., HBG1/2 13 nt target region), specifically within 400 bp of either end of the target site.

For *S. aureus*, tier 1 targeting domains were selected based on (1) distance upstream or downstream from either end of the target site (i.e., HBG1/2 13 nt target region), specifically within 400 bp of either end of the target site, (2) a high level of orthogonality, (3) the presence of 5' G, and (4) PAM having the sequence NNGRRT (SEQ ID NO:204). Tier 2 targeting domains were selected based on (1) distance upstream or downstream from either end of the target site (i.e., HBG1/2 13 nt target), specifically within 400 bp of either end of the target site, (2) a high level of orthogonality, and (3) PAM having the sequence NNGRRT (SEQ ID NO:204). Tier 3 targeting domains were selected based on (1) distance upstream or downstream from either end of the target site (i.e., HBG1/2 13 nt target region), specifically within 400 bp of either end of the target site, and (2) PAM having the sequence NNGRRT (SEQ ID NO:204). Tier 4 targeting domains were selected based on (1) distance upstream or downstream from either end of the target site (i.e., HBG1/2 13 nt target), specifically within 400 bp of either end of the target site, and (2) PAM having the sequence NNGRRV (SEQ ID NO:205).

Table 2, below, presents targeting domains for *S. pyogenes* and *S. aureus* gRNAs, broken out by (a) tier (1, 2, 3 or 4) and (b) HBG1 or HBG2.

TABLE 2 gRNA targeting domain sequences for HBG1/2 target sites

| | | HBG1 | HBG2 |
|---|---|---|---|
| *S. pyogenes* | Tier 1 | 251-256 | 760-764 |
| | Tier 2 | 257-274 | 765-781 |
| | Tier 3 | 275-300 | 275-281, 283-300 |
| | Tier 4 | 301-366 | 301-311, 313-342, 344-348, 350-366, 782, 783 |
| *S. aureus* | Tier 1 | 367-376 | 784-791 |
| | Tier 2 | 343, 377-393 | 778, 792-803 |
| | Tier 3 | 357, 365, 394-461 | 357, 365, 394-461 |
| | Tier 4 | 252-254, 256, 268, 272-274, 292, 295, 347, 348, 353, 360-362, 366, 598-759 | 292, 295, 347, 348, 353, 360-362, 366, 462-468 476-481, 489-587, 601-607, 614-620, 640-666, 674-679, 687-693, 708-714, 733-753, 762-764, 775, 779-781, 804-901 |

gRNAs may be designed to target the erythroid specific enhancer of BCL11A (BCL11Ae) to disrupt expression of a transcriptional repressor, BCL11A (Friedland). gRNAs were designed to target the GATA1 binding motif that is in the erythroid specific enhancer of BCL11A that is in the +58 DHS region of intron 2 (i.e., the GATA1 binding motif in BCL11Ae), where the +58 DHS enhancer region comprises the sequence set forth in SEQ ID NO:968. Targeting domain sequences of gRNAs that were designed to target disruption of the GATA1 binding motif in BCL11Ae, include, but are not limited to, the sequences set forth in SEQ ID NOs:952-955. Targeting domain sequences plus PAM (NGG) of gRNAs that were designed to target disruption of the GATA1 binding motif in BCL11Ae, include, but are not limited to, the sequences set forth in SEQ ID NOs:960-963.

gRNA Modifications

The activity, stability, or other characteristics of gRNAs can be altered through the incorporation of certain modifications. As one example, transiently expressed or delivered nucleic acids can be prone to degradation by, e.g., cellular nucleases. Accordingly, the gRNAs described herein can contain one or more modified nucleosides or nucleotides which introduce stability toward nucleases. While not wishing to be bound by theory it is also believed that certain modified gRNAs described herein can exhibit a reduced innate immune response when introduced into cells. Those of skill in the art will be aware of certain cellular responses commonly observed in cells, e.g., mammalian cells, in response to exogenous nucleic acids, particularly those of viral or bacterial origin. Such responses, which can include induction of cytokine expression and release and cell death, may be reduced or eliminated altogether by the modifications presented herein.

Certain exemplary modifications discussed in this section can be included at any position within a gRNA sequence including, without limitation at or near the 5' end (e.g., within 1-10, 1-5, or 1-2 nucleotides of the 5' end) and/or at or near the 3' end (e.g., within 1-10, 1-5, or 1-2 nucleotides of the 3' end). In some cases, modifications are positioned within functional motifs, such as the repeat-anti-repeat duplex of a Cas9 gRNA, a stem loop structure of a Cas9 or Cpf1 gRNA, and/or a targeting domain of a gRNA.

As one example, the 5' end of a gRNA can include a eukaryotic mRNA cap structure or cap analog (e.g., a G(5)ppp(5)G cap analog, a m7G(5)ppp(5)G cap analog, or a 3'-O-Me-m7G(5)ppp(5)G anti reverse cap analog (ARCA)), as shown below:

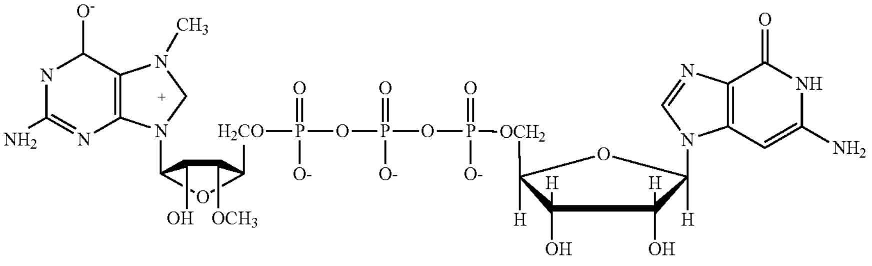

The cap or cap analog can be included during either chemical synthesis or in vitro transcription of the gRNA.

Along similar lines, the 5' end of the gRNA can lack a 5' triphosphate group. For instance, in vitro transcribed gRNAs can be phosphatase-treated (e.g., using calf intestinal alkaline phosphatase) to remove a 5' triphosphate group.

Another common modification involves the addition, at the 3' end of a gRNA, of a plurality (e.g., 1-10, 10-20, or 25-200) of adenine (A) residues referred to as a polyA tract. The polyA tract can be added to a gRNA during chemical synthesis, following in vitro transcription using a polyadenosine polymerase (e.g., *E. coli* Poly(A)Polymerase), or in vivo by means of a polyadenylation sequence, as described in Maeder.

It should be noted that the modifications described herein can be combined in any suitable manner, e.g., a gRNA, whether transcribed in vivo from a DNA vector, or in vitro transcribed gRNA, can include either or both of a 5' cap structure or cap analog and a 3' polyA tract.

Guide RNAs can be modified at a 3' terminal U ribose. For example, the two terminal hydroxyl groups of the U ribose can be oxidized to aldehyde groups and a concomitant opening of the ribose ring to afford a modified nucleoside as shown below:

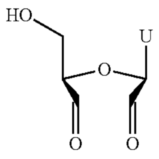

wherein "U" can be an unmodified or modified uridine.

The 3' terminal U ribose can be modified with a 2'3' cyclic phosphate as shown below:

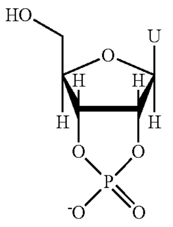

wherein "U" can be an unmodified or modified uridine.

Guide RNAs can contain 3' nucleotides which can be stabilized against degradation, e.g., by incorporating one or more of the modified nucleotides described herein. In certain embodiments, uridines can be replaced with modified uridines, e.g., 5-(2-amino)propyl uridine, and 5-bromo uridine, or with any of the modified uridines described herein; adenosines and guanosines can be replaced with modified adenosines and guanosines, e.g., with modifications at the 8-position, e.g., 8-bromo guanosine, or with any of the modified adenosines or guanosines described herein.

In certain embodiments, sugar-modified ribonucleotides can be incorporated into the gRNA, e.g., wherein the 2' OH-group is replaced by a group selected from H, —OR, —R (wherein R can be, e.g., alkyl, cycloalkyl, aryl, aralkyl, heteroaryl or sugar), halo, —SH, —SR (wherein R can be, e.g., alkyl, cycloalkyl, aryl, aralkyl, heteroaryl or sugar), amino (wherein amino can be, e.g., $NH_2$; alkylamino, dialkylamino, heterocyclyl, arylamino, diarylamino, heteroarylamino, diheteroarylamino, or amino acid); or cyano (—CN). In certain embodiments, the phosphate backbone can be modified as described herein, e.g., with a phosphothioate (PhTx) group. In certain embodiments, one or more of the nucleotides of the gRNA can each independently be a modified or unmodified nucleotide including, but not limited to 2'-sugar modified, such as, 2'-O-methyl, 2'-O-methoxyethyl, or 2'-Fluoro modified including, e.g., 2'-F or 2'-O-methyl, adenosine (A), 2'-F or 2'-O-methyl, cytidine (C), 2'-F or 2'-O-methyl, uridine (U), 2'-F or 2'-O-methyl, thymidine (T), 2'-F or 2'-O-methyl, guanosine (G), 2'-O-methoxyethyl-5-methyluridine (Teo), 2'-O-methoxyethyladenosine (Aeo), 2'-O-methoxyethyl-5-methylcytidine (m5Ceo), and any combinations thereof.

Guide RNAs can also include "locked" nucleic acids (LNA) in which the 2' OH-group can be connected, e.g., by a C1-6 alkylene or C1-6 heteroalkylene bridge, to the 4' carbon of the same ribose sugar. Any suitable moiety can be used to provide such bridges, include without limitation methylene, propylene, ether, or amino bridges; O-amino (wherein amino can be, e.g., $NH_2$; alkylamino, dialkylamino, heterocyclyl, arylamino, diarylamino, heteroarylamino, or diheteroarylamino, ethylenediamine, or polyamino) and aminoalkoxy or $O(CH_2)_n$-amino (wherein amino can be, e.g., $NH_2$; alkylamino, dialkylamino, heterocyclyl, arylamino, diarylamino, heteroarylamino, or diheteroarylamino, ethylenediamine, or polyamino).

In certain embodiments, a gRNA can include a modified nucleotide which is multicyclic (e.g., tricyclo; and "unlocked" forms, such as glycol nucleic acid (GNA) (e.g., R-GNA or S-GNA, where ribose is replaced by glycol units attached to phosphodiester bonds), or threose nucleic acid (TNA, where ribose is replaced with α-L-threofuranosyl-(3'→2')).

Generally, gRNAs include the sugar group ribose, which is a 5-membered ring having an oxygen. Exemplary modified gRNAs can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). Although the majority of sugar analog alterations are localized to the 2' position, other sites are amenable to modification, including the 4' position. In certain embodiments, a gRNA comprises a 4'-S, 4'-Se or a 4'-C-aminomethyl-2'-O-Me modification.

In certain embodiments, deaza nucleotides, e.g., 7-deaza-adenosine, can be incorporated into the gRNA. In certain embodiments, O- and N-alkylated nucleotides, e.g., N6-methyl adenosine, can be incorporated into the gRNA. In certain embodiments, one or more or all of the nucleotides in a gRNA are deoxynucleotides.

Dead gRNA Molecules

Dead guide RNA (dgRNA) molecules according to the present disclosure include dead guide RNA molecules that comprise reduced, low, or undetectable cleavage activity. The targeting domain sequences of dead guide RNAs are shorter in length by 1, 2, 3, 4, 5, 6, 7, 8, 9, or 10 nucleotides compared to the targeting domain sequence of active guide RNAs. In certain embodiments, dead guide RNA molecules may comprise a targeting domain comprising 15 nucleotides or fewer in length, 14 nucleotides or fewer in length, 13 nucleotides or fewer in length, 12 nucleotides or fewer in length, or 11 nucleotides or fewer in length. In some embodiments, dead guide RNAs are configured such that they do not provide an RNA guided-nuclease cleavage event. Dead guide RNAs may be generated by removing the 5' end of a gRNA targeting domain sequence, which results in a truncated targeting domain sequence. For example, if a gRNA sequence, configured to provide a cleavage event (i.e., 17 nucleotides or more in length), has a targeting domain sequence that is 20 nucleotides in length, a dead guide RNA may be created by removing 5 nucleotides from the 5' end of the gRNA sequence. For example, dgRNAs used herein may comprise a targeting domain set forth in Table 2 or Table 10 that has been truncated from the 5' end of the gRNA sequence and comprises 15 nucleotides or fewer in length. In certain embodiments, the dgRNA may be configured to bind (or associate with) a nucleic acid sequence within or proximal to a target region (e.g., the CCAAT box target region, 13 nt target region, proximal HBG1/2 promoter target sequence, and/or the GATA1 binding motif in BCL11Ae) to be edited. For example, any of the dgRNAs set forth in Table 10 may be employed to bind a nucleic acid sequence proximal to the 13 nt target region or CCAAT box target region. In certain embodiments, proximal to may denote the region within 10, 25, 50, 100, or 200 nucleotides of a target region (e.g., the CCAAT box target region, 13 nt target region, proximal HBG1/2 promoter target sequence, and/or the GATA1 binding motif in BCL11Ae). In certain embodiments, the dead guide RNA is not configured to recruit an exogenous trans-acting factor to a target region. In certain embodiments, the dgRNA is configured such that it does not provide a DNA cleavage event when complexed with an RNA-guided nuclease. Skilled artisans will appreciate that dead guide RNA molecules may be designed to comprise targeting domains complementary to regions proximal to or within a target region in a target nucleic acid. In certain embodiments, dead guide RNAs comprise targeting domain sequences that are complementary to the transcription strand or non-transcription strand of double stranded DNA. The dgRNAs herein may include modifications at the 5' and 3' end of the dgRNA as described for guide RNAs in the section "gRNA modifications" herein. For example, in certain embodiments, dead guide RNAs may include an anti-reverse cap analog (ARCA) at the 5' end of the RNA. In certain embodiments, dgRNAs may include a polyA tail at the 3' end.

In certain embodiments, the use of a dead guide RNA with the genome editing systems and methods disclosed herein may increase the total editing level of an active guide RNA. In certain embodiments, the use of a dead guide RNA with the genome editing systems disclosed herein and methods thereof may increase the frequency of deletions. In certain embodiments, the deletions may extend from the cut site of the active guide RNA toward the dead guide RNA binding site. In this way the dead guide RNA can change the directionality of an active guide RNA and orient editing toward a desired target region.

RNA-Guided Nucleases

RNA-guided nucleases according to the present disclosure include, but are not limited to, naturally-occurring Class 2 CRISPR nucleases such as Cas9, and Cpf1, as well as other nucleases derived or obtained therefrom. In functional terms, RNA-guided nucleases are defined as those nucleases that: (a) interact with (e.g., complex with) a gRNA; and (b) together with the gRNA, associate with, and optionally cleave or modify, a target region of a DNA that includes (i) a sequence complementary to the targeting domain of the gRNA and, optionally, (ii) an additional sequence referred to as a "protospacer adjacent motif," or "PAM," which is described in greater detail below. As the following examples will illustrate, RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g., Cas9 vs. Cpf1), species (e.g., *S. pyogenes* vs. *S. aureus*) or variation (e.g., full-length vs. truncated or split; naturally-occurring PAM specificity vs. engineered PAM specificity, etc.) of RNA-guided nuclease.

The PAM sequence takes its name from its sequential relationship to the "protospacer" sequence that is complementary to gRNA targeting domains (or "spacers"). Together with protospacer sequences, PAM sequences define target regions or sequences for specific RNA-guided nuclease/gRNA combinations.

Various RNA-guided nucleases may require different sequential relationships between PAMs and protospacers. In general, Cas9s recognize PAM sequences that are 3' of the protospacer as visualized relative to the top or complementary strand.

Cpf1, on the other hand, generally recognizes PAM sequences that are 5' of the protospacer.

In addition to recognizing specific sequential orientations of PAMs and protospacers, RNA-guided nucleases can also recognize specific PAM sequences. *S. aureus* Cas9, for instance, recognizes a PAM sequence of NNGRRT (SEQ ID NO: 986) or NNGRRV (SEQ ID NO: 987), wherein the N residues are immediately 3' of the region recognized by the gRNA targeting domain. *S. pyogenes* Cas9 recognizes NGG PAM sequences. And *F. novicida* Cpf1 recognizes a TTN PAM sequence. PAM sequences have been identified for a variety of RNA-guided nucleases, and a strategy for identifying novel PAM sequences has been described by Shmakov 2015. It should also be noted that engineered RNA-guided nucleases can have PAM specificities that differ from the PAM specificities of reference molecules (for instance, in the case of an engineered RNA-guided nuclease, the reference molecule may be the naturally occurring variant from which the RNA-guided nuclease is derived, or the naturally occurring variant having the greatest amino acid sequence homology to the engineered RNA-guided nuclease). Examples of PAMs that may be used according to the embodiments herein include, without limitation, the sequences set forth in SEQ ID NOs:199-205. In certain embodiments, a PAM sequence in a target nucleic acid may be configured such that the PAM is facing outward (e.g., PAM-out). In certain embodiments, a PAM facing outward may be a PAM sequence that is located outside of the target region, with each protospacer (or genomic region with homology to the guide) falling within the region encompassed by the two respective PAMs.

In addition to their PAM specificity, RNA-guided nucleases can be characterized by their DNA cleavage activity: naturally-occurring RNA-guided nucleases typically form DSBs in target nucleic acids, but engineered variants have been produced that generate only SSBs (discussed above; see also Ran 2013, incorporated by reference herein), or that do not cut at all.

Cas9

Crystal structures have been determined for *S. pyogenes* Cas9 (Jinek 2014), and for *S. aureus* Cas9 in complex with a unimolecular guide RNA and a target DNA (Nishimasu 2014; Anders 2014; and Nishimasu 2015).

A naturally occurring Cas9 protein comprises two lobes: a recognition (REC) lobe and a nuclease (NUC) lobe; each of which comprise particular structural and/or functional domains. The REC lobe comprises an arginine-rich bridge helix (BH) domain, and at least one REC domain (e.g., a REG1 domain and, optionally, a REC2 domain). The REC lobe does not share structural similarity with other known proteins, indicating that it is a unique functional domain. While not wishing to be bound by any theory, mutational analyses suggest specific functional roles for the BH and REC domains: the BH domain appears to play a role in gRNA:DNA recognition, while the REC domain is thought to interact with the repeat:anti-repeat duplex of the gRNA and to mediate the formation of the Cas9/gRNA complex.

The NUC lobe comprises a RuvC domain, an HNH domain, and a PAM-interacting (PI) domain. The RuvC domain shares structural similarity to retroviral integrase superfamily members and cleaves the non-complementary (i.e., bottom) strand of the target nucleic acid. It may be formed from two or more split RuvC motifs (such as RuvC I, RuvCII, and RuvCIII in *S. pyogenes* and *S. aureus*). The HNH domain, meanwhile, is structurally similar to HNN endonuclease motifs, and cleaves the complementary (i.e., top) strand of the target nucleic acid. The PI domain, as its name suggests, contributes to PAM specificity. Examples of polypeptide sequences encoding Cas9 RuvC-like and Cas9 HNH-like domains that may be used according to the embodiments herein are set forth in SEQ ID NOs:15-23, 52-123 (RuvC-like domains) and SEQ ID NOs:24-28, 124-198 (HNH-like domains).

While certain functions of Cas9 are linked to (but not necessarily fully determined by) the specific domains set forth above, these and other functions may be mediated or influenced by other Cas9 domains, or by multiple domains on either lobe. For instance, in *S. pyogenes* Cas9, as described in Nishimasu 2014, the repeat:antirepeat duplex of the gRNA falls into a groove between the REC and NUC lobes, and nucleotides in the duplex interact with amino acids in the BH, PI, and REC domains. Some nucleotides in the first stem loop structure also interact with amino acids in multiple domains (PI, BH and REC1), as do some nucleotides in the second and third stem loops (RuvC and PI domains). Examples of polypeptide sequences encoding Cas9 molecules that may be used according to the embodiments herein are set forth in SEQ ID NOs:1-2, 4-6, 12, 14.

Cpf1

The crystal structure of Acidaminococcus sp. Cpf1 in complex with crRNA and a double-stranded (ds) DNA target including a TTTN PAM sequence has been solved (Yamano 2016, incorporated by reference herein). Cpf1, like Cas9, has two lobes: a REC (recognition) lobe, and a NUC (nuclease) lobe. The REC lobe includes REC1 and REC2 domains, which lack similarity to any known protein structures. The NUC lobe, meanwhile, includes three RuvC domains (RuvC-I, -II and -III) and a BH domain. However, in contrast to Cas9, the Cpf1 REC lobe lacks an HNH domain, and includes other domains that also lack similarity to known protein structures: a structurally unique PI domain, three Wedge (WED) domains (WED-I, -II and -III), and a nuclease (Nuc) domain.

While Cas9 and Cpf1 share similarities in structure and function, it should be appreciated that certain Cpf1 activities are mediated by structural domains that are not analogous to any Cas9 domains. For instance, cleavage of the complementary strand of the target DNA appears to be mediated by the Nuc domain, which differs sequentially and spatially from the HNH domain of Cas9. Additionally, the non-targeting portion of Cpf1 gRNA (the handle) adopts a pseudoknot structure, rather than a stem loop structure formed by the repeat:antirepeat duplex in Cas9 gRNAs.

Modifications of RNA-Guided Nucleases

The RNA-guided nucleases described above have activities and properties that can be useful in a variety of applications, but the skilled artisan will appreciate that RNA-guided nucleases can also be modified in certain instances, to alter cleavage activity, PAM specificity, or other structural or functional features.

Turning first to modifications that alter cleavage activity, mutations that reduce or eliminate the activity of domains within the NUC lobe have been described above. Exemplary mutations that may be made in the RuvC domains, in the Cas9 HNH domain, or in the Cpf1 Nuc domain are described in Ran 2013 and Yamano 2016, as well as in Cotta-Ramusino. In general, mutations that reduce or eliminate activity in one of the two nuclease domains result in RNA-guided nucleases with nickase activity, but it should be noted that the type of nickase activity varies depending on which domain is inactivated. As one example, inactivation of a RuvC domain of a Cas9 will result in a nickase that cleaves the complementary or top strand.

On the other hand, inactivation of a Cas9 HNH domain results in a nickase that cleaves the bottom or non-complementary strand.

Modifications of PAM specificity relative to naturally occurring Cas9 reference molecules has been described for both *S. pyogenes* (Kleinstiver 2015a) and *S. aureus* (Kleinstiver 2015b). Modifications that improve the targeting fidelity of Cas9 have also been described (Kleinstiver 2016). Each of these references is incorporated by reference herein.

RNA-guided nucleases have been split into two or more parts (see, e.g., Zetsche 2015a; Fine 2015; both incorporated by reference).

RNA-guided nucleases can be, in certain embodiments, size-optimized or truncated, for instance via one or more deletions that reduce the size of the nuclease while still retaining gRNA association, target and PAM recognition, and cleavage activities. In certain embodiments, RNA guided nucleases are bound, covalently or non-covalently, to another polypeptide, nucleotide, or other structure, optionally by means of a linker. Exemplary bound nucleases and linkers are described by Guilinger 2014, which is incorporated by reference herein.

RNA-guided nucleases also optionally include a tag, such as, but not limited to, a nuclear localization signal to facilitate movement of RNA-guided nuclease protein into the nucleus. In certain embodiments, the RNA-guided nuclease can incorporate C- and/or N-terminal nuclear localization signals. Nuclear localization sequences are known in the art and are described in Maeder and elsewhere.

The foregoing list of modifications is intended to be exemplary in nature, and the skilled artisan will appreciate, in view of the instant disclosure, that other modifications may be possible or desirable in certain applications. For brevity, therefore, exemplary systems, methods and compositions of the present disclosure are presented with reference to particular RNA-guided nucleases, but it should be understood that the RNA-guided nucleases used may be modified in ways that do not alter their operating principles. Such modifications are within the scope of the present disclosure.

RNA-Guided Helicases

RNA-guided helicases according to the present disclosure include, but are not limited to, naturally-occurring RNA-guided helicases that are capable of unwinding nucleic acid. As discussed supra, catalytically active RNA-guided nucleases cleave or modify a target region of DNA. It has also been shown that certain RNA-guided nucleases, such as Cas9, also have helicase activity that enables them to unwind nucleic acid. In certain embodiments, the RNA-guided helicases according to the present disclosure may be any of the RNA-nucleases described herein and supra in the section entitled "RNA-guided nucleases." In certain embodiments, the RNA-guided nuclease is not configured to recruit an exogenous trans-acting factor to a target region. In certain embodiments, an RNA-guided helicase may be an RNA-guided nuclease configured to lack nuclease activity. For example, in certain embodiments, an RNA-guided helicase may be a catalytically inactive RNA-guided nuclease that lacks nuclease activity, but still retains its helicase activity. In certain embodiments, an RNA-guided nuclease may be mutated to abolish its nuclease activity (e.g., dead Cas9), creating a catalytically inactive RNA-guided nuclease that is unable to cleave nucleic acid, but which can still unwind DNA. In certain embodiments, an RNA-guided helicase may be complexed with any of the dead guide RNAs as described herein. For example, a catalytically active RNA-guided helicase (e.g., Cas9 or Cpf1) may form an RNP complex with a dead guide RNA, resulting in a catalytically inactive dead RNP (dRNP). In certain embodiments, a catalytically inactive RNA-guided helicase (e.g., dead Cas9) and a dead guide RNA may form a dRNP. These dRNPs, although incapable of providing a cleavage event, still retain their helicase activity that is important for unwinding nucleic acid.

Nucleic Acids Encoding RNA-Guided Nucleases

Nucleic acids encoding RNA-guided nucleases, e.g., Cas9, Cpf1 or functional fragments thereof, are provided herein. Examples of nucleic acid sequences encoding Cas9 molecules that may be used according to the embodiments herein are set forth in SEQ ID NOs:3, 7-11, 13. Exemplary nucleic acids encoding RNA-guided nucleases have been described previously (see, e.g., Cong 2013; Wang 2013; Mali 2013; Jinek 2012).

In some cases, a nucleic acid encoding an RNA-guided nuclease can be a synthetic nucleic acid sequence. For example, the synthetic nucleic acid molecule can be chemically modified. In certain embodiments, an mRNA encoding an RNA-guided nuclease will have one or more (e.g., all) of the following properties: it can be capped; polyadenylated; and substituted with 5-methylcytidine and/or pseudouridine.

Synthetic nucleic acid sequences can also be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein. Examples of codon optimized Cas9 coding sequences are presented in Cotta-Ramusino.

In addition, or alternatively, a nucleic acid encoding an RNA-guided nuclease may comprise a nuclear localization sequence (NLS). Nuclear localization sequences are known in the art.

Functional Analysis of Candidate Molecules

Candidate RNA-guided nucleases, gRNAs, and complexes thereof, can be evaluated by standard methods known in the art (see, e.g., Cotta-Ramusino). The stability of RNP complexes may be evaluated by differential scanning fluorimetry, as described below.

Differential Scanning Fluorimetry (DSF)

The thermostability of ribonucleoprotein (RNP) complexes comprising gRNAs and RNA-guided nucleases can be measured via DSF. The DSF technique measures the thermostability of a protein, which can increase under favorable conditions such as the addition of a binding RNA molecule, e.g., a gRNA.

A DSF assay can be performed according to any suitable protocol, and can be employed in any suitable setting, including without limitation (a) testing different conditions (e.g., different stoichiometric ratios of gRNA:RNA-guided nuclease protein, different buffer solutions, etc.) to identify optimal conditions for RNP formation; and (b) testing modifications (e.g., chemical modifications, alterations of sequence, etc.) of an RNA-guided nuclease and/or a gRNA to identify those modifications that improve RNP formation or stability. One readout of a DSF assay is a shift in melting temperature of the RNP complex; a relatively high shift suggests that the RNP complex is more stable (and may thus have greater activity or more favorable kinetics of formation, kinetics of degradation, or another functional characteristic) relative to a reference RNP complex characterized by a lower shift. When the DSF assay is deployed as a screening tool, a threshold melting temperature shift may be specified, so that the output is one or more RNPs having a melting temperature shift at or above the threshold. For instance, the threshold can be 5-10° C. (e.g., 5°, 6°, 7°, 8°, 90, 10°) or more, and the output may be one or more RNPs characterized by a melting temperature shift greater than or equal to the threshold.

Two non-limiting examples of DSF assay conditions are set forth below:

To determine the best solution to form RNP complexes, a fixed concentration (e.g., 2 μM) of Cas9 in water+10× SYPRO Orange® (Life Technologies cat #S-6650) is dispensed into a 384 well plate. An equimolar amount of gRNA diluted in solutions with varied pH and salt is then added. After incubating at room temperature for 10' and brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

The second assay consists of mixing various concentrations of gRNA with fixed concentration (e.g., 2 μM) Cas9 in optimal buffer from assay 1 above and incubating (e.g., at RT for 10') in a 384 well plate. An equal volume of optimal buffer+10× SYPRO Orange® (Life Technologies cat #S-6650) is added and the plate sealed with Microseal® B adhesive (MSB-1001). Following brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

Genome Editing Strategies

The genome editing systems described above are used, in various embodiments of the present disclosure, to generate edits in (i.e., to alter) targeted regions of DNA within or obtained from a cell. Various strategies are described herein to generate particular edits, and these strategies are generally described in terms of the desired repair outcome, the number and positioning of individual edits (e.g., SSBs or DSBs), and the target sites of such edits.

Genome editing strategies that involve the formation of SSBs or DSBs are characterized by repair outcomes including: (a) deletion of all or part of a targeted region; (b) insertion into or replacement of all or part of a targeted region; or (c) interruption of all or part of a targeted region. This grouping is not intended to be limiting, or to be binding to any particular theory or model, and is offered solely for economy of presentation. Skilled artisans will appreciate that the listed outcomes are not mutually exclusive and that some repairs may result in other outcomes. The description of a particular editing strategy or method should not be understood to require a particular repair outcome unless otherwise specified.

Replacement of a targeted region generally involves the replacement of all or part of the existing sequence within the targeted region with a homologous sequence, for instance through gene correction or gene conversion, two repair outcomes that are mediated by HDR pathways. HDR is promoted by the use of a donor template, which can be single-stranded or double stranded, as described in greater detail below. Single or double stranded templates can be exogenous, in which case they will promote gene correction, or they can be endogenous (e.g., a homologous sequence within the cellular genome), to promote gene conversion. Exogenous templates can have asymmetric overhangs (i.e., the portion of the template that is complementary to the site of the DSB may be offset in a 3' or 5' direction, rather than being centered within the donor template), for instance as described by Richardson 2016 (incorporated by reference herein). In instances where the template is single stranded, it can correspond to either the complementary (top) or non-complementary (bottom) strand of the targeted region.

Gene conversion and gene correction are facilitated, in some cases, by the formation of one or more nicks in or around the targeted region, as described in Ran and Cotta-Ramusino. In some cases, a dual-nickase strategy is used to form two offset SSBs that, in turn, form a single DSB having an overhang (e.g., a 5' overhang).

Interruption and/or deletion of all or part of a targeted sequence can be achieved by a variety of repair outcomes. As one example, a sequence can be deleted by simultaneously generating two or more DSBs that flank a targeted region, which is then excised when the DSBs are repaired, as is described in Maeder for the LCA10 mutation. As another example, a sequence can be interrupted by a deletion generated by formation of a double strand break with single-stranded overhangs, followed by exonucleolytic processing of the overhangs prior to repair.

One specific subset of target sequence interruptions is mediated by the formation of an indel within the targeted sequence, where the repair outcome is typically mediated by NHEJ pathways (including Alt-NHEJ). NHEJ is referred to as an "error prone" repair pathway because of its association with indel mutations. In some cases, however, a DSB is repaired by NHEJ without alteration of the sequence around it (a so-called "perfect" or "scarless" repair); this generally requires the two ends of the DSB to be perfectly ligated. Indels, meanwhile, are thought to arise from enzymatic processing of free DNA ends before they are ligated that adds and/or removes nucleotides from either or both strands of either or both free ends.

Because the enzymatic processing of free DSB ends may be stochastic in nature, indel mutations tend to be variable, occurring along a distribution, and can be influenced by a variety of factors, including the specific target site, the cell type used, the genome editing strategy used, etc. Even so, it is possible to draw limited generalizations about indel formation: deletions formed by repair of a single DSB are most commonly in the 1-50 bp range, but can reach greater than 100-200 bp. Insertions formed by repair of a single DSB tend to be shorter and often include short duplications of the sequence immediately surrounding the break site. However, it is possible to obtain large insertions, and in these cases, the inserted sequence has often been traced to other regions of the genome or to plasmid DNA present in the cells.

Indel mutations—and genome editing systems configured to produce indels—are useful for interrupting target sequences, for example, when the generation of a specific final sequence is not required and/or where a frameshift mutation would be tolerated. They can also be useful in settings where particular sequences are preferred, insofar as the certain sequences desired tend to occur preferentially from the repair of an SSB or DSB at a given site. Indel mutations are also a useful tool for evaluating or screening the activity of particular genome editing systems and their components. In these and other settings, indels can be characterized by (a) their relative and absolute frequencies in the genomes of cells contacted with genome editing systems and (b) the distribution of numerical differences relative to the unedited sequence, e.g., ±1, ±2, ±3, etc. As one example, in a lead-finding setting, multiple gRNAs can be screened to identify those gRNAs that most efficiently drive cutting at a target site based on an indel readout under controlled conditions. Guides that produce indels at or above a threshold frequency, or that produce a particular distribution of indels, can be selected for further study and development. Indel frequency and distribution can also be useful as a readout for evaluating different genome editing system implementations or formulations and delivery methods, for instance by keeping the gRNA constant and varying certain other reaction conditions or delivery methods.

Multiplex Strategies

Genome editing systems according to this disclosure may also be employed for multiplex gene editing to generate two or more DSBs, either in the same locus or in different loci. Any of the RNA-guided nucleases and gRNAs disclosed herein may be used in genome editing systems for multiplex gene editing. Strategies for editing that involve the formation of multiple DSBs, or SSBs, are described in, for instance, Cotta-Ramusino.

As disclosed herein, multiple gRNAs may be used in genome editing systems to introduce alterations (e.g., deletions, insertions) into the 13 nt target region of HBG1 and/or HBG2. In certain embodiments, one or more gRNAs comprising a targeting domain set forth in SEQ ID NOs:251-901, 940-942 may be used to introduce alterations in the 13 nt target region of HBG1 and/or HBG2. In other embodiments, multiple gRNAs may be used in genome editing systems to introduce alterations into the GATA1 binding motif in BCL11Ae. In certain embodiments, one or more gRNAs comprising a targeting domain set forth in SEQ ID NOs:952-955 may be used to introduce alterations in the GATA1 binding motif in BCL11Ae. Multiple gRNAs may also be used in genome editing systems to introduce alterations into the GATA1 binding motif in BCL11Ae and the 13 nt target region of HBG1 and/or HBG2. In certain embodiments, one or more gRNAs comprising a targeting domain set forth in SEQ ID NOs:952-955 may be used to introduce alterations in the GATA1 binding motif in BCL11Ae and one or more gRNAs comprising a targeting domain set forth in SEQ ID NOs:251-901, 940-942 may be used to introduce alterations in the 13 nt target region of HBG1 and/or HBG2.

Donor Template Design

Donor template design is described in detail in the literature, for instance in Cotta-Ramusino. DNA oligomer donor templates (oligodeoxynucleotides or ODNs), which can be single stranded (ssODNs) or double-stranded (dsODNs), can be used to facilitate HDR-based repair of DSBs or to boost overall editing rate, and are particularly useful for introducing alterations into a target DNA sequence, inserting a new sequence into the target sequence, or replacing the target sequence altogether.

Whether single-stranded or double stranded, donor templates generally include regions that are homologous to regions of DNA within or near (e.g., flanking or adjoining) a target sequence to be cleaved. These homologous regions are referred to here as “homology arms,” and are illustrated schematically below:

[5' homology arm]-[replacement sequence]-[3' homology arm].

The homology arms can have any suitable length (including 0 nucleotides if only one homology arm is used), and 3' and 5' homology arms can have the same length, or can differ in length. The selection of appropriate homology arm lengths can be influenced by a variety of factors, such as the desire to avoid homologies or microhomologies with certain sequences such as Alu repeats or other very common elements. For example, a 5' homology arm can be shortened to avoid a sequence repeat element. In other embodiments, a 3' homology arm can be shortened to avoid a sequence repeat element. In some embodiments, both the 5' and the 3' homology arms can be shortened to avoid including certain sequence repeat elements. In addition, some homology arm designs can improve the efficiency of editing or increase the frequency of a desired repair outcome. For example, Richardson 2016, which is incorporated by reference herein, found that the relative asymmetry of 3' and 5' homology arms of single stranded donor templates influenced repair rates and/or outcomes.

Replacement sequences in donor templates have been described elsewhere, including in Cotta-Ramusino et al. A replacement sequence can be any suitable length (including zero nucleotides, where the desired repair outcome is a deletion), and typically includes one, two, three or more sequence modifications relative to the naturally-occurring sequence within a cell in which editing is desired. One common sequence modification involves the alteration of the naturally-occurring sequence to repair a mutation that is related to a disease or condition of which treatment is desired. Another common sequence modification involves the alteration of one or more sequences that are complementary to, or then, the PAM sequence of the RNA-guided nuclease or the targeting domain of the gRNA(s) being used to generate an SSB or DSB, to reduce or eliminate repeated cleavage of the target site after the replacement sequence has been incorporated into the target site.

Where a linear ssODN is used, it can be configured to (i) anneal to the nicked strand of the target nucleic acid, (ii) anneal to the intact strand of the target nucleic acid, (iii) anneal to the plus strand of the target nucleic acid, and/or (iv) anneal to the minus strand of the target nucleic acid. An ssODN may have any suitable length, e.g., about, at least, or no more than 150-200 nucleotides (e.g., 150, 160, 170, 180, 190, or 200 nucleotides).

It should be noted that a template nucleic acid can also be a nucleic acid vector, such as a viral genome or circular double stranded DNA, e.g., a plasmid. Nucleic acid vectors comprising donor templates can include other coding or non-coding elements. For example, a template nucleic acid can be delivered as part of a viral genome (e.g., in an AAV or lentiviral genome) that includes certain genomic backbone elements (e.g., inverted terminal repeats, in the case of an AAV genome) and optionally includes additional sequences coding for a gRNA and/or an RNA-guided nuclease. In certain embodiments, the donor template can be adjacent to, or flanked by, target sites recognized by one or more gRNAs, to facilitate the formation of free DSBs on one or both ends of the donor template that can participate in repair of corresponding SSBs or DSBs formed in cellular DNA using the same gRNAs. Exemplary nucleic acid vectors suitable for use as donor templates are described in Cotta-Ramusino, which is incorporated by reference.

Whatever format is used, a template nucleic acid can be designed to avoid undesirable sequences. In certain embodiments, one or both homology arms can be shortened to avoid overlap with certain sequence repeat elements, e.g., Alu repeats, LINE elements, etc.

In certain embodiments, silent, non-pathogenic SNPs may be included in the ssODN donor template to allow for identification of a gene editing event.

In certain embodiments, a donor template may be a non-specific template that is non-homologous to regions of DNA within or near a target sequence to be cleaved. In certain embodiments, donor templates for use in targeting the GATA1 binding motif in BCL11Ae may include, without limitation, non-target specific templates that are nonhomologous to regions of DNA within or near the GATA1 binding motif in BCL11Ae. In certain embodiments, donor templates for use in targeting the 13 nt target region may include, without limitation, non-target specific templates that are nonhomologous to regions of DNA within or near the 13 nt target region.

Target Cells

Genome editing systems according to this disclosure can be used to manipulate or alter a cell, e.g., to edit or alter a target nucleic acid. The manipulating can occur, in various embodiments, in vivo or ex vivo.

A variety of cell types can be manipulated or altered according to the embodiments of this disclosure, and in some cases, such as in vivo applications, a plurality of cell types are altered or manipulated, for example by delivering genome editing systems according to this disclosure to a plurality of cell types. In other cases, however, it may be desirable to limit manipulation or alteration to a particular cell type or types. In some embodiments, the cell is an animal or plant cell. In some embodiments, the cell is a mammalian, primate, or human cell. In some embodiments, the cell is a human cell, e.g., a cell form described herein. For instance, it can be desirable in some instances to edit a cell with limited differentiation potential or a terminally differentiated cell, such as a photoreceptor cell in the case of Maeder, in which modification of a genotype is expected to result in a change in cell phenotype. In other cases, however, it may be desirable to edit a less differentiated, multipotent or pluripotent, stem or progenitor cell. By way of example, the cell may be an embryonic stem cell, induced pluripotent stem cell (iPSC), hematopoietic stem/progenitor cell (HSPC), or other stem or progenitor cell type that differentiates into a cell type of relevance to a given application or indication.

As a corollary, the cell being altered or manipulated is, variously, a dividing cell or a non-dividing cell, depending on the cell type(s) being targeted and/or the desired editing outcome.

When cells are manipulated or altered ex vivo, the cells can be used (e.g., administered to a subject) immediately, or they can be maintained or stored for later use. Those of skill in the art will appreciate that cells can be maintained in culture or stored (e.g., frozen in liquid nitrogen) using any suitable method known in the art.

Implementation of Genome Editing Systems: Delivery, Formulations, and Routes of Administration As discussed above, the genome editing systems of this disclosure can be implemented in any suitable manner, meaning that the components of such systems, including without limitation the RNA-guided nuclease, gRNA, and optional donor template nucleic acid, can be delivered, formulated, or administered in any suitable form or combination of forms that results in the transduction, expression or introduction of a genome editing system and/or causes a desired repair outcome in a cell, tissue or subject. Tables 3 and 4 set forth several, non-limiting examples of genome editing system implementations. Those of skill in the art will appreciate, however, that these listings are not comprehensive, and that other implementations are possible. With reference to Table 3 in particular, the table lists several exemplary implementations of a genome editing system comprising a single gRNA and an optional donor template. However, genome editing systems according to this disclosure can incorporate multiple gRNAs, multiple RNA-guided nucleases, and other components such as proteins, and a variety of implementations will be evident to the skilled artisan based on the principles illustrated in the table. In the table, [N/A] indicates that the genome editing system does not include the indicated component.

TABLE 3

| Genome editing components | | | |
|---|---|---|---|
| RNA-guided Nuclease | gRNA | Donor Template | Comments |
| Protein | RNA | [N/A] | An RNA-guided nuclease protein complexed with a gRNA molecule (an RNP complex) |
| Protein | RNA | DNA | An RNP complex as described above plus a single-stranded or double stranded donor template. |
| Protein | DNA | [N/A] | An RNA-guided nuclease protein plus gRNA transcribed from DNA. |
| Protein | DNA | DNA | An RNA-guided nuclease protein plus gRNA-encoding DNA and a separate DNA donor template. |
| Protein | DNA | | An RNA-guided nuclease protein and a single DNA encoding both a gRNA and a donor template. |
| DNA | | | A DNA or DNA vector encoding an RNA-guided nuclease, a gRNA and a donor template. |
| DNA | DNA | [N/A] | Two separate DNAs, or two separate DNA vectors, encoding the RNA-guided nuclease and the gRNA, respectively. |
| DNA | DNA | DNA | Three separate DNAs, or three separate DNA vectors, encoding the RNA-guided nuclease, the gRNA and the donor template, respectively. |
| DNA | | [N/A] | A DNA or DNA vector encoding an RNA-guided nuclease and a gRNA |
| DNA | | DNA | A first DNA or DNA vector encoding an RNA-guided nuclease and a gRNA, and a second DNA or DNA vector encoding a donor template. |
| DNA | DNA | | A first DNA or DNA vector encoding an RNA-guided nuclease and second DNA or DNA vector encoding a gRNA and a donor template. |
| DNA | DNA | | A first DNA or DNA vector encoding an RNA-guided nuclease and a donor template, and a second DNA or DNA vector encoding a gRNA |
| DNA | RNA | | A DNA or DNA vector encoding an RNA-guided nuclease and a donor template, and a gRNA |
| RNA | | [N/A] | An RNA or RNA vector encoding an RNA-guided nuclease and comprising a gRNA |

TABLE 3-continued

| Genome editing components | | | |
|---|---|---|---|
| RNA-guided Nuclease | gRNA | Donor Template | Comments |
| RNA | | DNA | An RNA or RNA vector encoding an RNA-guided nuclease and comprising a gRNA, and a DNA or DNA vector encoding a donor template. |

Table 4 summarizes various delivery methods for the components of genome editing systems, as described herein. Again, the listing is intended to be exemplary rather than limiting.

TABLE 4

| Delivery Vector/Mode | | Delivery into Non-Dividing Cells | Duration of Expression | Genome Integration | Type of Molecule Delivered |
|---|---|---|---|---|---|
| Physical (e.g., electroporation, particle gun, Calcium Phosphate transfection, cell compression or squeezing) | | YES | Transient | NO | Nucleic Acids and Proteins |
| Viral | Retrovirus | NO | Stable | YES | RNA |
| | Lentivirus | YES | Stable | YES/NO with modifications | RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |
| | Biological liposomes: Erythrocyte Ghosts and Exosomes | YES | Transient | NO | Nucleic Acids |

Nucleic Acid-Based Delivery of Genome Editing Systems

Nucleic acids encoding the various elements of a genome editing system according to the present disclosure can be administered to subjects or delivered into cells by art-known methods or as described herein. For example, RNA-guided nuclease-encoding and/or gRNA-encoding DNA, as well as donor template nucleic acids can be delivered by, e.g., vectors (e.g., viral or non-viral vectors), non-vector based methods (e.g., using naked DNA or DNA complexes), or a combination thereof.

Nucleic acids encoding genome editing systems or components thereof can be delivered directly to cells as naked DNA or RNA, for instance by means of transfection or electroporation, or can be conjugated to molecules (e.g., N-acetylgalactosamine) promoting uptake by the target cells (e.g., erythrocytes, HSCs). Nucleic acid vectors, such as the vectors summarized in Table 4, can also be used.

Nucleic acid vectors can comprise one or more sequences encoding genome editing system components, such as an RNA-guided nuclease, a gRNA and/or a donor template. A vector can also comprise a sequence encoding a signal peptide (e.g., for nuclear localization, nucleolar localization, or mitochondrial localization), associated with (e.g., inserted into or fused to) a sequence coding for a protein. As one example, a nucleic acid vectors can include a Cas9 coding sequence that includes one or more nuclear localization sequences (e.g., a nuclear localization sequence from SV40).

The nucleic acid vector can also include any suitable number of regulatory/control elements, e.g., promoters, enhancers, introns, polyadenylation signals, Kozak consensus sequences, or internal ribosome entry sites (IRES). These elements are well known in the art, and are described in Cotta-Ramusino.

Nucleic acid vectors according to this disclosure include recombinant viral vectors. Exemplary viral vectors are set forth in Table 4, and additional suitable viral vectors and their use and production are described in Cotta-Ramusino. Other viral vectors known in the art can also be used. In addition, viral particles can be used to deliver genome editing system components in nucleic acid and/or peptide form. For example, "empty" viral particles can be assembled to contain any suitable cargo. Viral vectors and viral particles can also be engineered to incorporate targeting ligands to alter target tissue specificity.

In addition to viral vectors, non-viral vectors can be used to deliver nucleic acids encoding genome editing systems according to the present disclosure. One important category of non-viral nucleic acid vectors are nanoparticles, which can be organic or inorganic. Nanoparticles are well known in the art, and are summarized in Cotta-Ramusino. Any suitable nanoparticle design can be used to deliver genome editing system components or nucleic acids encoding such components. For instance, organic (e.g., lipid and/or polymer) nanoparticles can be suitable for use as delivery vehicles in certain embodiments of this disclosure. Exemplary lipids for use in nanoparticle formulations, and/or gene transfer are shown in Table 5, and Table 6 lists exemplary polymers for use in gene transfer and/or nanoparticle formulations.

TABLE 5

| Lipids used for gene transfer | | |
|---|---|---|
| Lipid | Abbreviation | Feature |
| 1,2-Dioleoyl-sn-glycero-3-phosphatidylcholine | DOPC | Helper |
| 1,2-Dioleoyl-sn-glycero-3-phosphatidylethanolamine | DOPE | Helper |
| Cholesterol | | Helper |
| N-[1-(2,3-Dioleyloxy)propyl]N,N,N-trimethylammonium chloride | DOTMA | Cationic |
| 1,2-Dioleoyloxy-3-trimethyl ammonium-propane | DOTAP | Cationic |

TABLE 5-continued

Lipids used for gene transfer

| Lipid | Abbreviation | Feature |
|---|---|---|
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethylpyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-(N' ,N'-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxyethyl)]-dimethylammonium chloride | CLIP-1 | Cationic |
| rac-[2(2,3-Dihexadecyloxypropyl-oxymethyloxy)ethyl]bromide | CLIP-6 | Cationic |
| Ethyldimyristoylphosphatidylcholine | EDMPC | Cationic |
| 1,2-Distearyloxy-N,N-dimethyl-3-aminopropane | DSDMA | Cationic |
| 1,2-Dimyristoyl-trimethylammonium propane | DMTAP | Cationic |
| O,O'-Dimyristyl-N-lysyl aspartate | DMKE | Cationic |
| 1,2-Distearoyl-sn-glycero-3-ethylphosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamidine | diC14-amidine | Cationic |
| Octadecenolyoxy[ethyl-2-heptadecenyl-3 hydroxyethyl] imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propylamino)-N-ditetradecylcarbamoylme-ethyl-acetamide | RPR209120 | Cationic |
| 1,2-dilinoleyloxy-3-dimethylaminopropane | DLinDMA | Cationic |
| 2,2-dilinoleyl-4-dimethylaminoethyl-[1,3]- dioxolane | DLin-KC2-DMA | Cationic |
| dilinoleyl- methyl-4-dimethylaminobutyrate | DLin-MC3-DMA | Cationic |

TABLE 6

Polymers used for gene transfer

| Polymer | Abbreviation |
|---|---|
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine) biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amido ethylenimine) | SS-PAEI |

TABLE 6-continued

Polymers used for gene transfer

| Polymer | Abbreviation |
|---|---|
| Triethylenetetramine | TETA |
| Poly(β-aminoester) | |
| Poly(4-hydroxy-L-proline ester) | PHP |
| Poly(allylamine) | |
| Poly(α-[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly (2-(dimethylamino)ethyl methacrylate) | pDMAEMA |
| Poly(2-aminoethyl propylene phosphate) | PPE-EA |
| Chitosan | |
| Galactosylated chitosan | |
| N-Dodacylated chitosan | |
| Histone | |
| Collagen | |
| Dextran-spermine | D-SPM |

Non-viral vectors optionally include targeting modifications to improve uptake and/or selectively target certain cell types. These targeting modifications can include e.g., cell specific antigens, monoclonal antibodies, single chain antibodies, aptamers, polymers, sugars (e.g., N-acetylgalactosamine (GalNAc)), and cell penetrating peptides. Such vectors also optionally use fusogenic and endosome-destabilizing peptides/polymers, undergo acid-triggered conformational changes (e.g., to accelerate endosomal escape of the cargo), and/or incorporate a stimuli-cleavable polymer, e.g., for release in a cellular compartment. For example, disulfide-based cationic polymers that are cleaved in the reducing cellular environment can be used.

In certain embodiments, one or more nucleic acid molecules (e.g., DNA molecules) other than the components of a genome editing system, e.g., the RNA-guided nuclease component and/or the gRNA component described herein, are delivered. In certain embodiments, the nucleic acid molecule is delivered at the same time as one or more of the components of the Genome editing system. In certain embodiments, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Genome editing system are delivered. In certain embodiments, the nucleic acid molecule is delivered by a different means than one or more of the components of the genome editing system, e.g., the RNA-guided nuclease component and/or the gRNA component, are delivered. The nucleic acid molecule can be delivered by any of the delivery methods described herein. For example, the nucleic acid molecule can be delivered by a viral vector, e.g., an integration-deficient lentivirus, and the RNA-guided nuclease molecule component and/or the gRNA component can be delivered by electroporation, e.g., such that the toxicity caused by nucleic acids (e.g., DNAs) can be reduced. In certain embodiments, the nucleic acid molecule encodes a therapeutic protein, e.g., a protein described herein. In certain embodiments, the nucleic acid molecule encodes an RNA molecule, e.g., an RNA molecule described herein.

Delivery of RNPs and/or RNA Encoding Genome Editing System Components

RNPs (complexes of gRNAs and RNA-guided nucleases) and/or RNAs encoding RNA-guided nucleases and/or gRNAs, can be delivered into cells or administered to subjects by art-known methods, some of which are described in Cotta-Ramusino. In vitro, RNA-guided nuclease-encoding and/or gRNA-encoding RNA can be delivered, e.g., by microinjection, electroporation, transient cell compression or squeezing (see, e.g., Lee 2012). Lipid-mediated transfection, peptide-mediated delivery, GalNAc- or other conjugate-mediated delivery, and combinations thereof, can also be used for delivery in vitro and in vivo. A protective, interactive, non-condensing (PINC) system may be used for delivery.

In vitro delivery via electroporation comprises mixing the cells with the RNA encoding RNA-guided nucleases and/or gRNAs, with or without donor template nucleic acid molecules, in a cartridge, chamber or cuvette and applying one or more electrical impulses of defined duration and amplitude. Systems and protocols for electroporation are known in the art, and any suitable electroporation tool and/or protocol can be used in connection with the various embodiments of this disclosure.

Route of Administration

Genome editing systems, or cells altered or manipulated using such systems, can be administered to subjects by any suitable mode or route, whether local or systemic. Systemic modes of administration include oral and parenteral routes. Parenteral routes include, by way of example, intravenous, intramarrow, intraarterial, intramuscular, intradermal, subcutaneous, intranasal, and intraperitoneal routes. Components administered systemically can be modified or formulated to target, e.g., HSCs, hematopoietic stem/progenitor cells, or erythroid progenitors or precursor cells.

Local modes of administration include, by way of example, intramarrow injection into the trabecular bone or interfemoral injection into the marrow space, and infusion into the portal vein. In certain embodiments, significantly smaller amounts of the components (compared with systemic approaches) can exert an effect when administered locally (for example, directly into the bone marrow) compared to when administered systemically (for example, intravenously). Local modes of administration can reduce or eliminate the incidence of potentially toxic side effects that may occur when therapeutically effective amounts of a component are administered systemically.

Administration can be provided as a periodic bolus (for example, intravenously) or as continuous infusion from an internal reservoir or from an external reservoir (for example, from an intravenous bag or implantable pump). Components can be administered locally, for example, by continuous release from a sustained release drug delivery device.

In addition, components can be formulated to permit release over a prolonged period of time. A release system can include a matrix of a biodegradable material or a material which releases the incorporated components by diffusion. The components can be homogeneously or heterogeneously distributed within the release system. A variety of release systems can be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used. Typically the microspheres are composed of a polymer of lactic acid and glycolic acid, which are structured to form hollow spheres. The spheres can be approximately 15-30 microns in diameter and can be loaded with components described herein. In some embodiments, genome editing systems, system components and/or nucleic acids encoding system components, are delivered with a block copolymer such as a poloxamer or a poloxamine.

Multi-Modal or Differential Delivery of Components

Skilled artisans will appreciate, in view of the instant disclosure, that different components of genome editing systems disclosed herein can be delivered together or separately and simultaneously or nonsimultaneously. Separate and/or asynchronous delivery of genome editing system components can be particularly desirable to provide temporal or spatial control over the function of genome editing systems and to limit certain effects caused by their activity.

Different or differential modes as used herein refer to modes of delivery that confer different pharmacodynamic or pharmacokinetic properties on the subject component molecule, e.g., a RNA-guided nuclease molecule, gRNA, template nucleic acid, or payload. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., AAV or lentivirus, delivery.

By way of example, the components of a genome editing system, e.g., a RNA-guided nuclease and a gRNA, can be delivered by modes that differ in terms of resulting half-life or persistent of the delivered component the body, or in a particular compartment, tissue or organ. In certain embodiments, a gRNA can be delivered by such modes. The RNA-guided nuclease molecule component can be delivered by a mode which results in less persistence or less exposure to the body or a particular compartment or tissue or organ.

More generally, in certain embodiments, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In certain embodiments, the first pharmacodynamic or pharmacokinetic property, e.g., distribution, persistence or exposure, is more limited than the second pharmacodynamic or pharmacokinetic property.

In certain embodiments, the first mode of delivery is selected to optimize, e.g., minimize, a pharmacodynamic or pharmacokinetic property, e.g., distribution, persistence or exposure.

In certain embodiments, the second mode of delivery is selected to optimize, e.g., maximize, a pharmacodynamic or pharmacokinetic property, e.g., distribution, persistence or exposure.

In certain embodiments, the first mode of delivery comprises the use of a relatively persistent element, e.g., a nucleic acid, e.g., a plasmid or viral vector, e.g., an AAV or lentivirus. As such vectors are relatively persistent product transcribed from them would be relatively persistent.

In certain embodiments, the second mode of delivery comprises a relatively transient element, e.g., an RNA or protein.

In certain embodiments, the first component comprises gRNA, and the delivery mode is relatively persistent, e.g., the gRNA is transcribed from a plasmid or viral vector, e.g., an AAV or lentivirus. Transcription of these genes would be of little physiological consequence because the genes do not encode for a protein product, and the gRNAs are incapable of acting in isolation. The second component, a RNA-guided nuclease molecule, is delivered in a transient manner, for example as mRNA or as protein, ensuring that the full RNA-guided nuclease molecule/gRNA complex is only present and active for a short period of time.

Furthermore, the components can be delivered in different molecular form or with different delivery vectors that complement one another to enhance safety and tissue specificity.

Use of differential delivery modes can enhance performance, safety, and/or efficacy, e.g., the likelihood of an eventual off-target modification can be reduced. Delivery of immunogenic components, e.g., Cas9 molecules, by less persistent modes can reduce immunogenicity, as peptides from the bacterially-derived Cas enzyme are displayed on the surface of the cell by WIC molecules. A two-part delivery system can alleviate these drawbacks.

Differential delivery modes can be used to deliver components to different, but overlapping target regions. The formation active complex is minimized outside the overlap of the target regions. Thus, in certain embodiments, a first component, e.g., a gRNA is delivered by a first delivery mode that results in a first spatial, e.g., tissue, distribution. A second component, e.g., a RNA-guided nuclease molecule is delivered by a second delivery mode that results in a second spatial, e.g., tissue, distribution. In certain embodiments, the first mode comprises a first element selected from a liposome, nanoparticle, e.g., polymeric nanoparticle, and a nucleic acid, e.g., viral vector. The second mode comprises a second element selected from the group. In certain embodiments, the first mode of delivery comprises a first targeting element, e.g., a cell specific receptor or an antibody, and the second mode of delivery does not include that element. In certain embodiments, the second mode of delivery comprises a second targeting element, e.g., a second cell specific receptor or second antibody.

When the RNA-guided nuclease molecule is delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA and the RNA-guided nuclease molecule are packaged in separated delivery vehicles with distinct but overlapping tissue tropism, the fully functional complex is only be formed in the tissue that is targeted by both vectors.

EXAMPLES

The principles and embodiments described above are further illustrated by the non-limiting examples that follow:

Example 1: Screening of *S. pyogenes* gRNAs Delivered to K562 Cells as Ribonucleoprotein Complexes for Use in Causing 13 nt Deletions in HBG1 and HBG2 Regulatory Regions gRNAs targeting a 26 nt fragment spanning and including the 13 nucleotides at the 13 nt target region of HBG1 and HBG2 were designed by standard methods. After gRNAs were designed in silico and tiered, a subset of the gRNAs were selected and screened for activity and specificity in human K562 cells. The gRNAs selected for screening are set forth in Table 7. Briefly, gRNAs were in vitro transcribed and then complexed with *S. pyogenes* wildtype (Wt) Cas9 protein to form ribonucleoprotein complexes (RNPs). The gRNAs complexed to *S. pyogenes* Cas9 protein were modified sgRNAs ((e.g., 5' ARCA capped and 3' polyA (20A) tail; Table 7) and target the HBG1 and HBG2 regulatory regions. To allow for direct comparison of the activity of these RNPs in K562 cells and human $CD34^+$ cells, RNPs were first delivered to K562 cells by electroporation (Amaxa Nucleofector).

Figure 1:
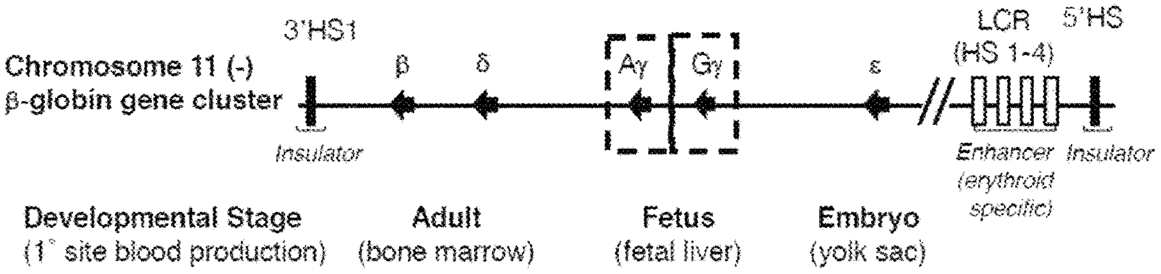
FIG. 1 depicts, in schematic form, HBG1 and HBG2 gene(s) in the context of the γ-globin gene cluster on human chromosome 11.
Figure 2A:
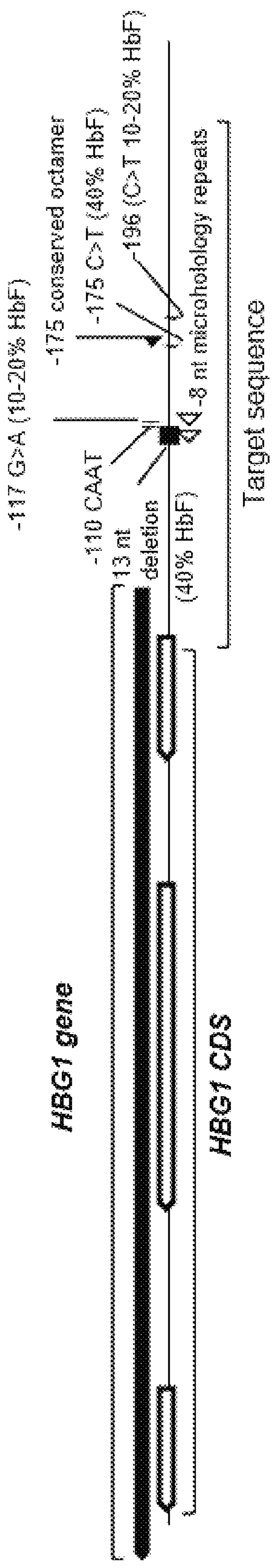
FIGS. 2A-2B depict HBG1 and HBG2 genes, coding sequences (CDS) and small deletions and point mutations in and upstream of the HBG1 and HBG2 proximal promoters that have been identified in patients and associated with elevation of fetal hemoglobin (HbF). Core elements within the proximal promoters (CAAT box, 13 nt sequence) that have been deleted in some patients with hereditary persistence of fetal hemoglobin (HPFH). The 'target sequence' region of each locus, which has been screened for gRNA binding target sites, is also identified.
Figure 2B:
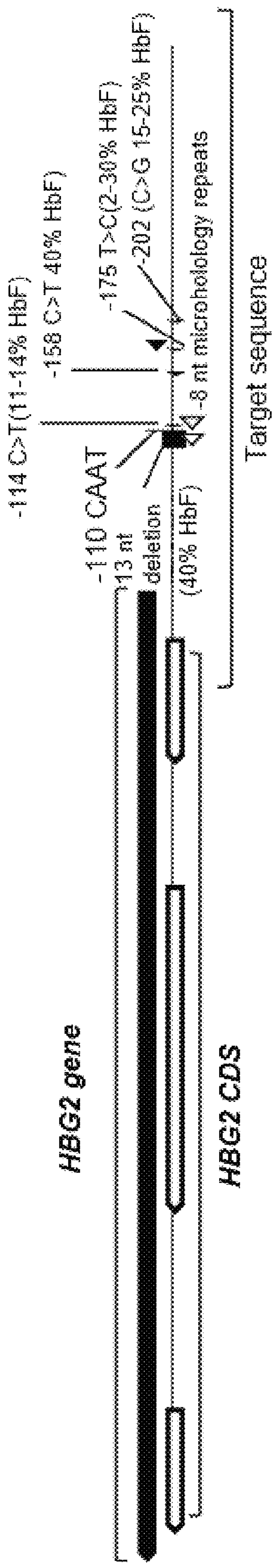
Figure 3A:
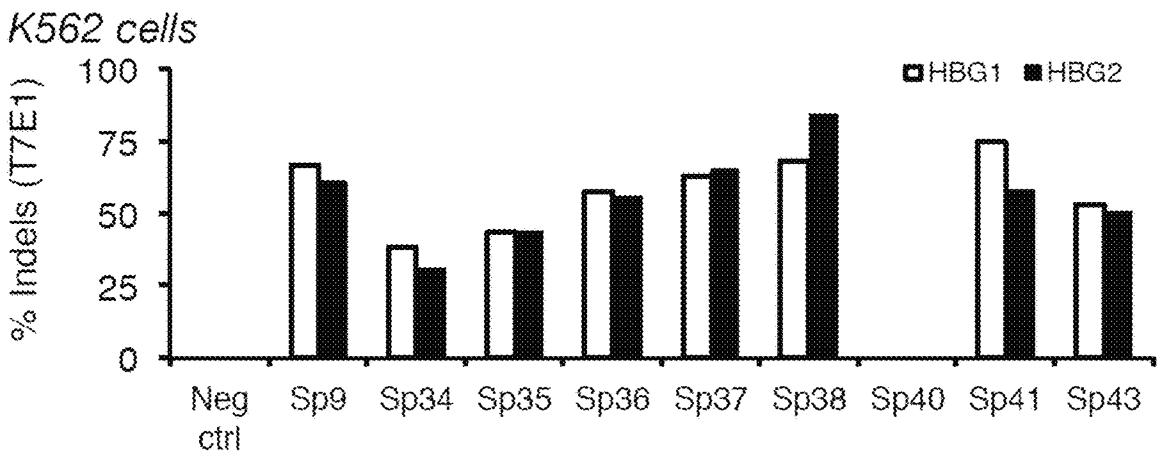
FIGS. 3A-C shows data from gRNA screening for incorporation of the 13 nt deletion in human K562 erythroleukemia cells.

Three days after RNP electroporation, gDNA was extracted from K562 cells and then the HBG1 and HBG2 loci were PCR amplified from the gDNA. Gene editing was evaluated in the PCR products by T7E1 endonuclease assay analysis. Eight out of nine RNPs supported a high percentage of NHEJ. Sp37 RNP, the only gRNA shown to be active in human $CD34^+$ cells (<10% editing in $CD34^+$ cells) was highly active in K562 cells, with >60% indels detected at both HBG1 and HBG2 and eight cut in both the HBG1 and HBG2 targeted regions in the promoter sequences (FIG. 3A).

TABLE 7

| Selected gRNAs for screening in K562 cells or CD34+ cells | | | | | |
|---|---|---|---|---|---|
| gRNA ID | Targeting domain sequence (RNA) | Targeting domain sequence (DNA) | Targeting domain sequence plus PAM (NGG) (RNA) | Targeting domain sequence plus PAM (NGG) (DNA) | Sense |
| Sp9 | GGCUAUUGGUCAAGGCA (SEQ ID NO: 277) | GGCTATTGGTCAAGGCA (SEQ ID NO: 910) | GGCUAUUGGUCAAGGCAAGG (SEQ ID NO: 920) | GGCTATTGGTCAAGGCAAGG (SEQ ID NO: 930) | Antisense |
| Sp36 | CAAGGCUAUUGGUCAAGGCA (SEQ ID NO: 338) | CAAGGCTATTGGTCAAGGCA (SEQ ID NO: 911) | CAAGGCUAUUGGUCAAGGCAAGG (SEQ ID NO: 921) | CAAGGCTATTGGTCAAGGCAAGG (SEQ ID NO: 931) | Antisense |
| Sp40 | UGCCUUGUCAAGGCUAU (SEQ ID NO: 327) | TGCCTTGTCAAGGCTAT (SEQ ID NO: 912) | UGCCUUGUCAAGGCUAUUGG (SEQ ID NO: 922) | TGCCTTGTCAAGGCTATTGG (SEQ ID NO: 932) | Antisense |
| Sp42 | GUUUGCCUUGUCAAGGCUAU (SEQ ID NO: 299) | GTTTGCCTTGTCAAGGCTAT (SEQ ID NO: 913) | GUUUGCCUUGUCAAGGCUAUUGG (SEQ ID NO: 923) | GTTTGCCTTGTCAAGGCTATTGG (SEQ ID NO: 933) | Antisense |
| Sp38 | GACCAAUAGCCUUGACA (SEQ ID NO: 276) | GACCAATAGCCTTGACA (SEQ ID NO: 914) | GACCAAUAGCCUUGACAAGG (SEQ ID NO: 924) | GACCAATAGCCTTGACAAGG (SEQ ID NO: 934) | Sense |
| Sp37 | CUUGACCAAUAGCCUUGACA (SEQ ID NO: 333) | CTTGACCAATAGCCTTGACA (SEQ ID NO: 915) | CUUGACCAAUAGCCUUGACAAGG (SEQ ID NO: 925) | CTTGACCAATAGCCTTGACAAGG (SEQ ID NO: 935) | Sense |
| Sp43 | GUCAAGGCUAUUGGUCA (SEQ ID NO: 278) | GTCAAGGCTATTGGTCA (SEQ ID NO: 916) | GUCAAGGCUAUUGGUCAAGG (SEQ ID NO: 926) | GTCAAGGCTATTGGTCAAGG (SEQ ID NO: 936) | Antisense |
| Sp35 | CUUGUCAAGGCUAUUGGUCA (SEQ ID NO: 339) | CTTGTCAAGGCTATTGGTCA (SEQ ID NO: 917) | CUUGUCAAGGCUAUUGGUCAAGG (SEQ ID NO: 927) | CTTGTCAAGGCTATTGGTCAAGG (SEQ ID NO: 937) | Antisense |
| Sp41 | UCAAGUUUGCCUUGUCA (SEQ ID NO: 310) | TCAAGTTTGCCTTGTCA (SEQ ID NO: 918) | UCAAGUUUGCCUUGUCAAGG (SEQ ID NO: 928) | TCAAGTTTGCCTTGTCAAGG (SEQ ID NO: 938) | Antisense |
| Sp34 | UGGUCAAGUUUGCCUUGUCA (SEQ ID NO: 340) | TGGTCAAGTTTGCCTTGTCA (SEQ ID NO: 919) | UGGUCAAGUUUGCCUUGUCAAGG (SEQ ID NO: 929) | TGGTCAAGTTTGCCTTGTCAAGG (SEQ ID NO: 939) | Antisense |
| Sp85 | AGUAUCCAGUGAGGCCA (SEQ ID NO: 940) | AGTATCCAGTGAGGCCA (SEQ ID NO: 943) | AGUAUCCAGUGAGGCCAGGG (SEQ ID NO: 946) | AGTATCCAGTGAGGCCAGGG (SEQ ID NO: 949) | Antisense |
| SpA | GGCAAGGCUGGCCAACCCAU (SEQ ID NO: 941) | GGCAAGGCTGGCCAACCCAT (SEQ ID NO: 944) | GGCAAGGCUGGCCAACCCAUGGG (SEQ ID NO: 947) | GGCAAGGCTGGCCAACCCATGGG (SEQ ID NO: 950) | Sense |
| SpB | UAUUUGCAUUGAGAUAGUGU (SEQ ID NO: 942) | TATTTGCATTGAGATAGTGT (SEQ ID NO: 945) | UAUUUGCAUUGAGAUAGUGUGGG (SEQ ID NO: 948) | TATTTGCATTGAGATAGTGTGGG (SEQ ID NO: 951) | Sense |

Figure 3B:
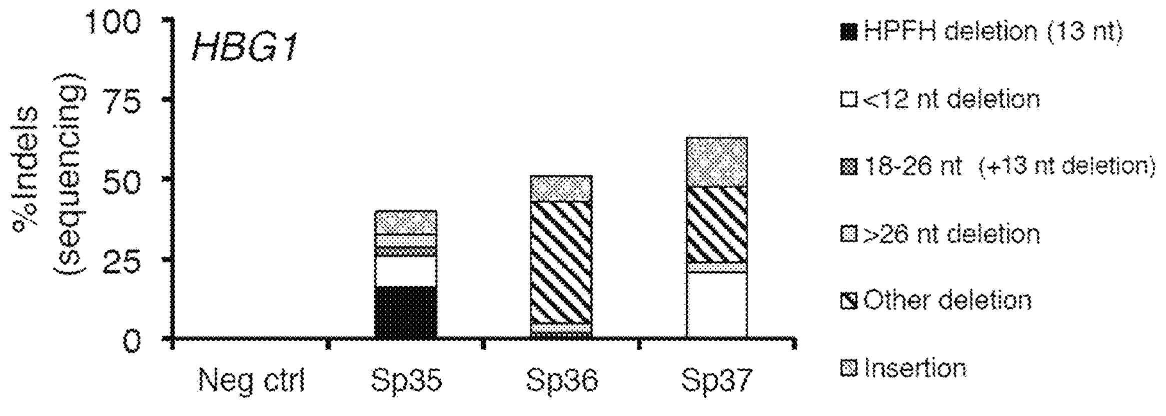
Figure 3C:
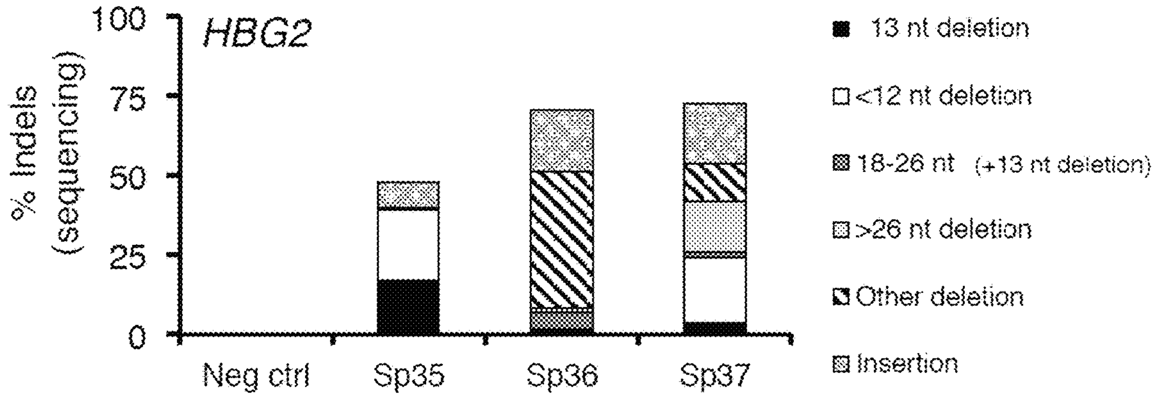

The HBG1 and HBG2 PCR products for the K562 cells that were targeted with the eight active sgRNAs were then analyzed by DNA sequencing analysis and scored for insertions and deletions detected. The deletions were subdivided into precise 13 nt deletions at the target site, 13 nt target site inclusive and proximal small deletions (18-26 nt), 12 nt deletions (i.e., partial deletion) of the 13 nt target site, >26 nt deletions that span a portion of the HPFH target site, and other deletions, e.g., deletions proximal to but outside the HPFH target site. Seven of the eight sgRNAs targeted deletion of the 13 nt (HPFH mutation induction) (FIG. 3B) for HBG1. At least five of the eight sgRNAs also supported targeted deletion of the 13 nt in HBG2 promoter region (FIG. 3C). Note that DNA sequence results for HBG2 in cells treated with HBG Sp34 sgRNA were not available. These data indicate that Cas9 and sgRNA support precise induction of the 13 nt deletions. FIGS. 3B-3C depict examples of the types of deletions observed in target sequences in HBG1.

Figure 4A:
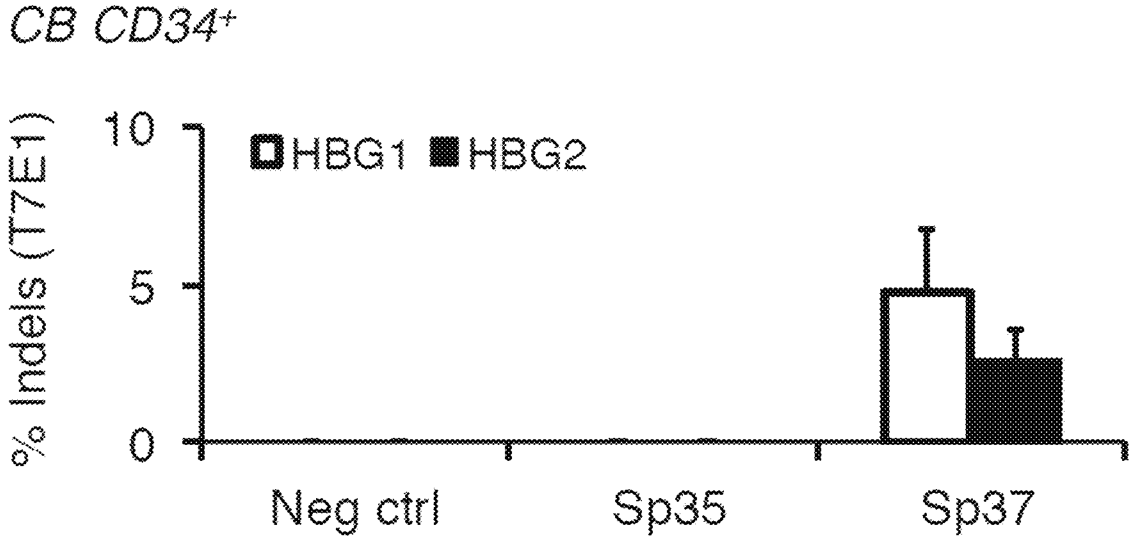
FIGS. 4A-C depicts results of gene editing in human cord blood (CB) and human adult $CD34^+$ cells after electroporation with RNPs complexed to in vitro transcribed *S. pyogenes* gRNAs that target a specific 13 nt sequence for deletion (HBG gRNAs Sp35 and Sp37).

Example 2: Cas9 RNP Containing gRNA Targeting the 13 nt Deletion Mutation Supports Gene Editing in Human Hematopoietic Stem/Progenitor Cells Of the RNPs containing different gRNAs tested in human cord blood (CB) $CD34^+$ cells, only Sp37 resulted in detectable editing at the target site in the HBG1 and HBG2 promoters as determined by T7E1 analysis of indels in HBG1 and HBG2 specific PCR products amplified from gDNA extracted from electroporated CB $CD34^+$ cells from a three cord blood donors (FIG. 4A). The average level of editing detected in cells electroporated with Cas9 protein complexed to Sp37 was 5±2% indels at HBG1 and 3±1% indels detected at HBG2 (3 separate experiments, and CB donors).

Figure 4B:
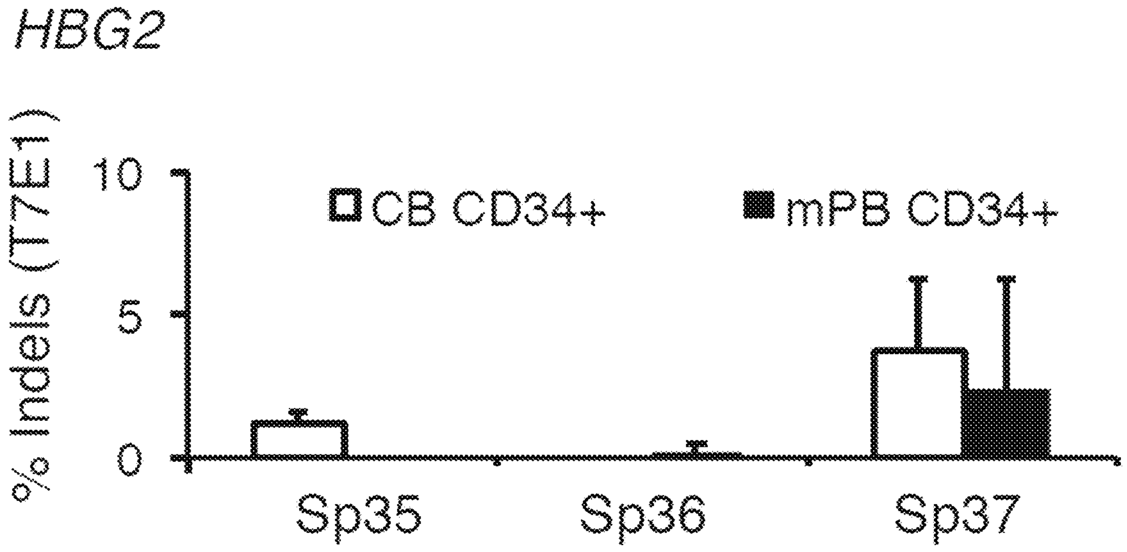

Next, three *S. pyogenes* gRNAs whose target sites are within the HBG promoter (Sp35, Sp36, Sp37) were complexed to wild-type *S. pyogenes* Cas9 protein to form ribonucleoprotein complexes. These HBG targeted RNPS were electroporated into CB $CD34^+$ cells (n=3 donors) and adult mobilized peripheral blood (mPB) $CD34^+$ cell donors (n=3 donors). Then the level of insertions/deletions at the target site was analyzed by T7E1 endonuclease analysis of the HBG2 PCR products amplified from genomic DNA extracted from the samples approximately 3 days after Cas9 RNP delivery. Each of these RNPs supported only low level gene editing in both the CB and adult $CD34^+$ cells across 3 donors and 3 separate experiments (FIG. 4B).

To increase gene editing and the occurrence of the 13 nt deletion at the target site, single strand deoxynucleotide donor repair templates (ssODNs) that encoded 87 nt and 89 nt of homology on each side of the targeted deletion site was generated. The ssODNs, either unmodified at the ends (i.e., ssODN1, SEQ ID NO:906, Table 8) or modified to contain phosphothioates (PhTx) at the 5' and 3' ends (i.e., PhTx ssODN1, SEQ ID NO:909, Table 8). The ssODN was designed to 'encode' the 13 nt deletion with sequence homology arms engineered flanking this absent sequence to create a perfect deletion.

TABLE 8

Single strand deoxynucleotide donor repair templates (ssODN)

| ssODN ID | SEQ ID NO | Sequence |
|---|---|---|
| ssODN1 5' homology arm | 904 | **GGGTGCTTCCTTTTATTCTTCATCCCTAGCCAGCCGCCGGCCCCTGGCCTCACTGGATACTCTAAGACTATTGGTCAAGTTTGCCTT** |
| ssODN1 3' homology arm | 905 | GTCAAGGCAAGGCTGGCCAACCCATGGGTGGAGTTTAGCCAGGGACCGTTTCAGACAGATATTTGCATTGAGATAGTGTGGGGAAGGGG |
| ssODN1 | 906 | **GGGTGCTTCCTTTTATTCTTCATCCCTAGCCAGCCGCCGGCCCCTGGCCTCACTGGATACTCTAAGACTATTGGTCAAGTTTGCCTT**GTCAAGGCAAGGCTGGCCAACCCATGGGTGGAGTTTAGCCAGGGACCGTTTCAGACAGATATTTGCATTGAGATAGTGTGGGGAAGGGG |

TABLE 8-continued

Single strand deoxynucleotide donor repair templates (ssODN)

| ssODN ID | SEQ ID NO | Sequence |
|---|---|---|
| PhTx ssODN1 5' homology arm | 907 | ***GGGTGCTTCCTTTTATTCTTCATCCCTAGCCAGCCGCCGGCCCCTGGCCTCACTGGATACTCTAAGACTATTGGTCAAGTTTGCCTT** |
| PhTx ssODN1 3' homology arm | 908 | GTCAAGGCAAGGCTGGCCAACCCATGGGTGGAGTTTAGCCAGGGACCGTTTCAGACAGATATTTGCATTGAGATAGTGTGGGGAAGGGG* |
| PhTx ssODN1 | 909 | ***GGGTGCTTCCTTTTATTCTTCATCCCTAGCCAGCCGCCGGCCCCTGGCCTCACTGGATACTCTAAGACTATTGGTCAAGTTTGCCTT**GTCAAGGCAAGGCTGGCCAACCCATGGGTGGAGTTTAGCCAGGGACCGTTTCAGACAGATATTTGCATTGAGATAGTGTGGGGAAGGGG* |

Figure 4C:
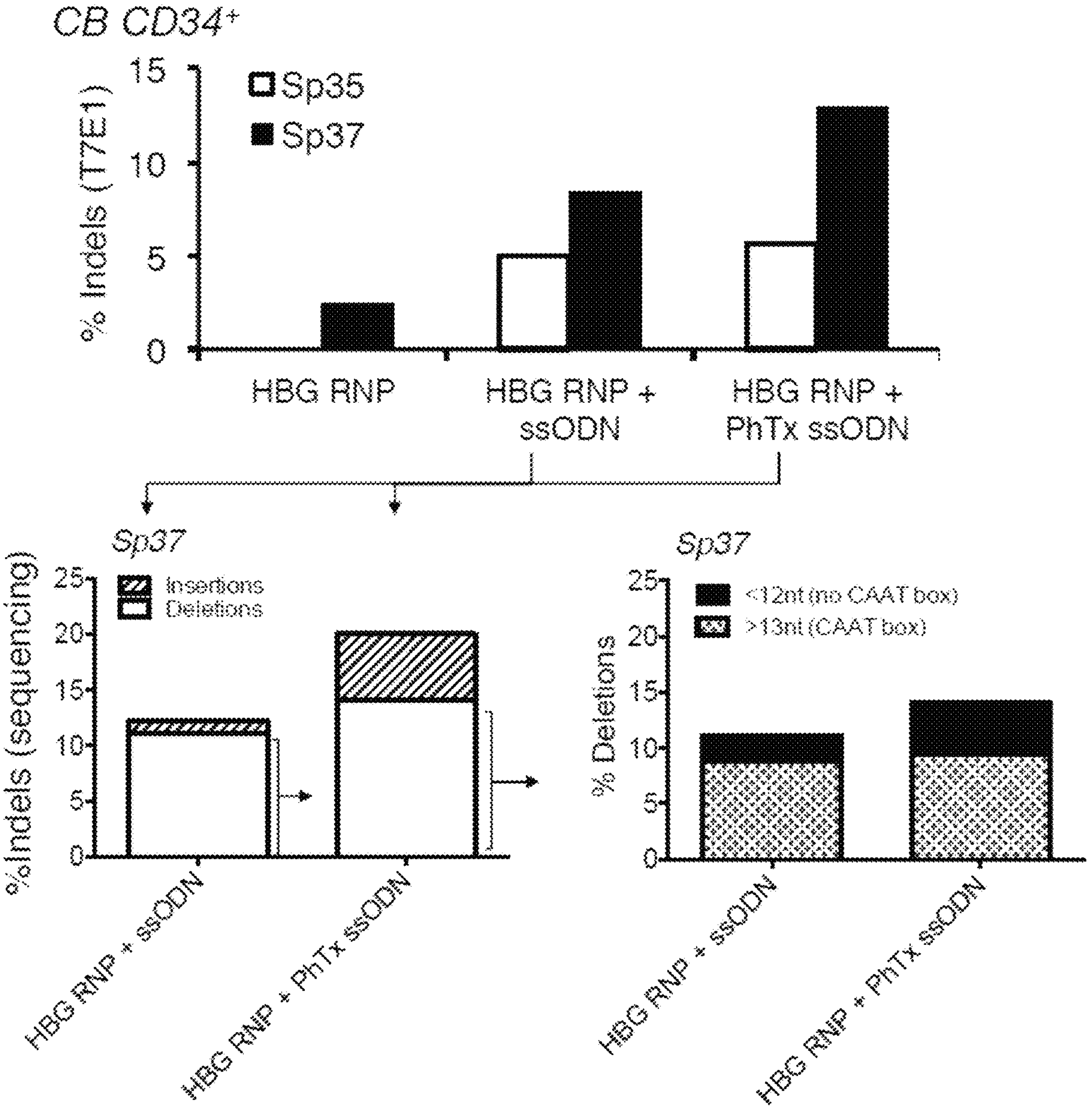

The homology arms flanking the deletion are indicated by bold [5' homology arm] and underline [3' homology arm]).
Note the absence of the 13 bp sequence in ssODN1 and PhTx ssODN1.
*Represents modification by phosphothioate.

ssODN1 and PhTx ssODN1 were co-delivered with RNP targeting HBG containing the Sp37 gRNA (HBG Sp37 RNP) or HBG Sp35 (HBG Sp35 RNP) to CB $CD34^+$ cells. Co-delivery of the ssODN donor encoding the 13 nt deletion with HBG Sp35 RNP or HBG Sp37 RNP led to a 6-fold and 5-fold increase in gene editing of the target site, respectively, as determined by T7E1 analysis of the HBG2 PCR product (FIG. 4C). DNA sequencing analysis (Sanger sequencing) of the HBG2 PCR product indicated that 20% gene editing in cells that were treated with HBG Sp37 RNP and the PhTx modified ssODN1, with 15% deletions and 5% insertions (FIG. 4C, lower left panel). Further analysis of the specific type and size of deletions at the target site revealed that 75% of the total deletions detected contained the 13 nt deletion (which included deletion at c.-110 of the CAAT box in the proximal promoter), the absence of which is associated with elevation of HbF expression (FIG. 4C, lower right panel). The remaining ¼ of deletions were partial deletions that did not span the full 13 nt deletion. These data indicate that co-delivery of a homologous ssODN that is engineered to have a deletion supported precise gene editing (deletion) at HBG in human $CD34^+$ cells.

Figure 5A:
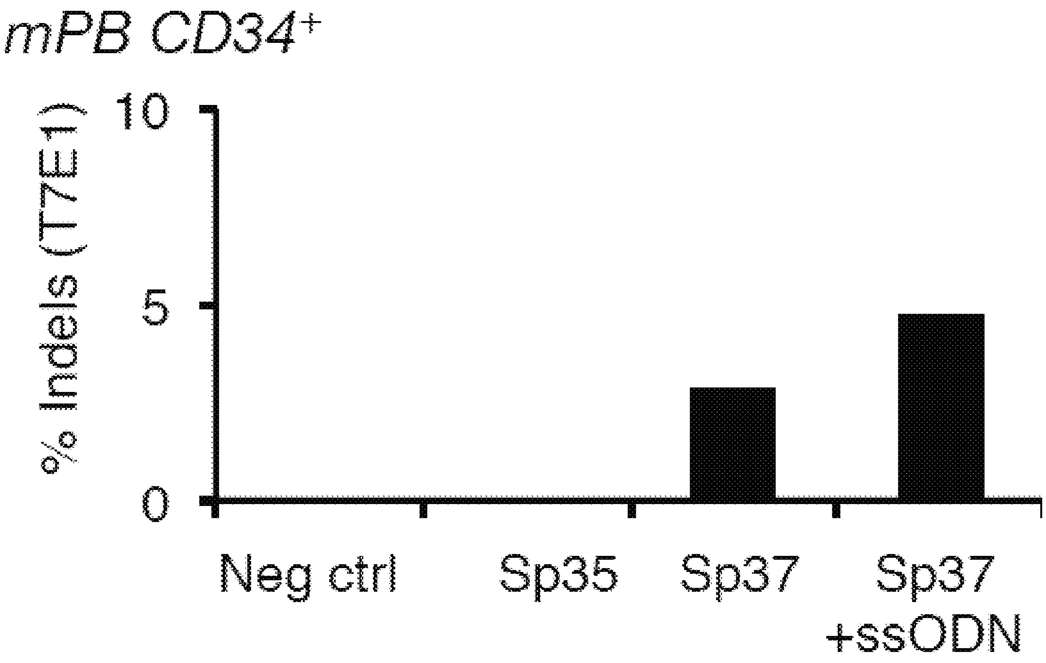
FIGS. 5A-B depicts gene editing of HBG in adult human mobilized peripheral blood (mPB) $CD34^+$ cells and induction of fetal hemoglobin in erythroid progeny of RNP treated cells after electroporation of mPB $CD34^+$ cells with HBG Sp37 RNP+/−ssODN encoding the 13 nt deletion.

Example 3: Cas9 RNP Targeting the 13 nt Deletion Mutation Supports Gene Editing in Human Adult Mobilized Peripheral Blood Hematopoietic Stem/Progenitor Cells with Increased HBG Expression in Erythroblast Progeny To determine whether editing HBG with Cas9 RNP complexed to Sp37 gRNA or Sp35 gRNA (i.e., the gRNAs that target the 13 nt deletion that is associated with HPFH) in the promoter of HBG supports an increase in HBG expression in erythroid progeny of edited $CD34^+$ cells, human adult $CD34^+$ cells from mobilized peripheral blood (mPB) were electroporated with the RNPs. Briefly, mPB $CD34^+$ cells were prestimulated for 2 days with human cytokines and PGE2 in StemSpan SFEM and then electroporated with Cas9 protein precomplexed to Sp35 and Sp37, respectively. T7E1 analysis of HBG PCR product indicated ~3% indels detected for mPB $CD34^+$ cells treated with RNP complexed to Sp37 while no editing was detected for cells that were treated with RNP complexed to Sp35 (FIG. 5A).

Figure 5B:
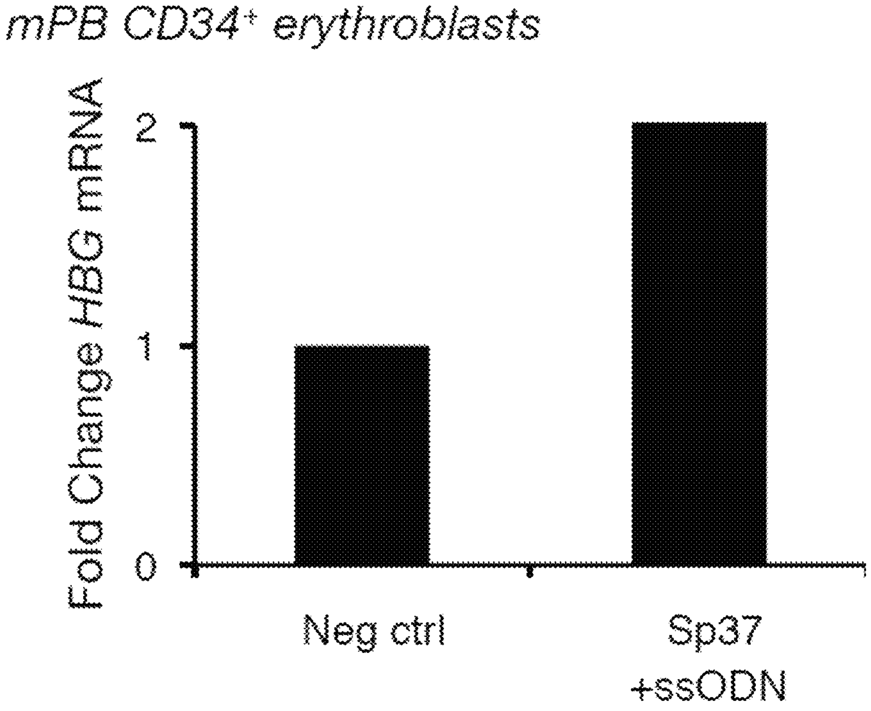
Figure 6A:
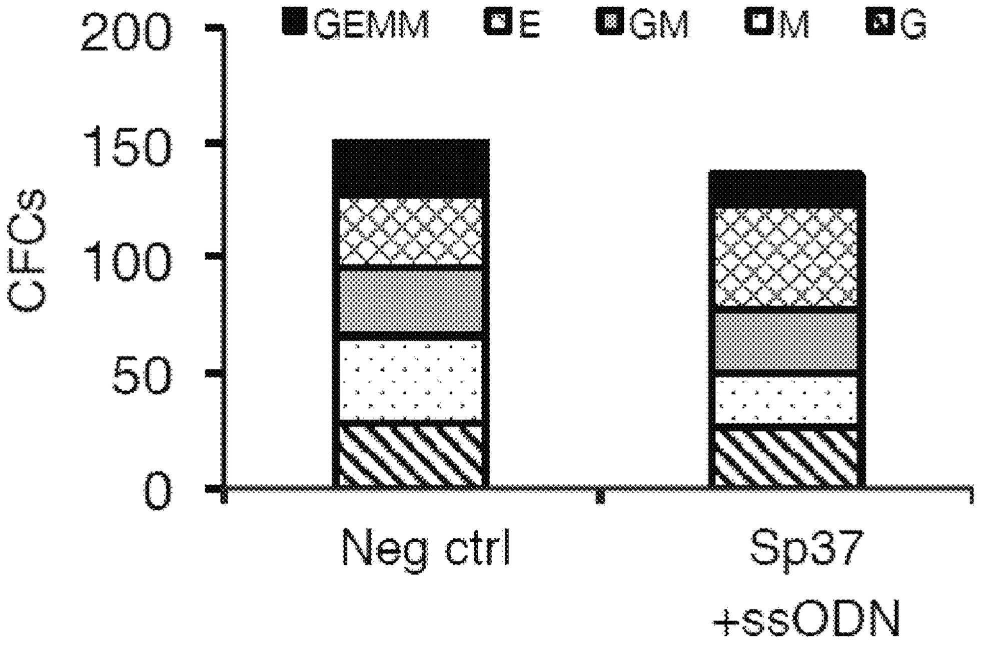
FIGS. 6A-B depicts the ex vivo differentiation potential of RNP treated and untreated mPB CD34+ cells from the same donor.
Figure 6B:
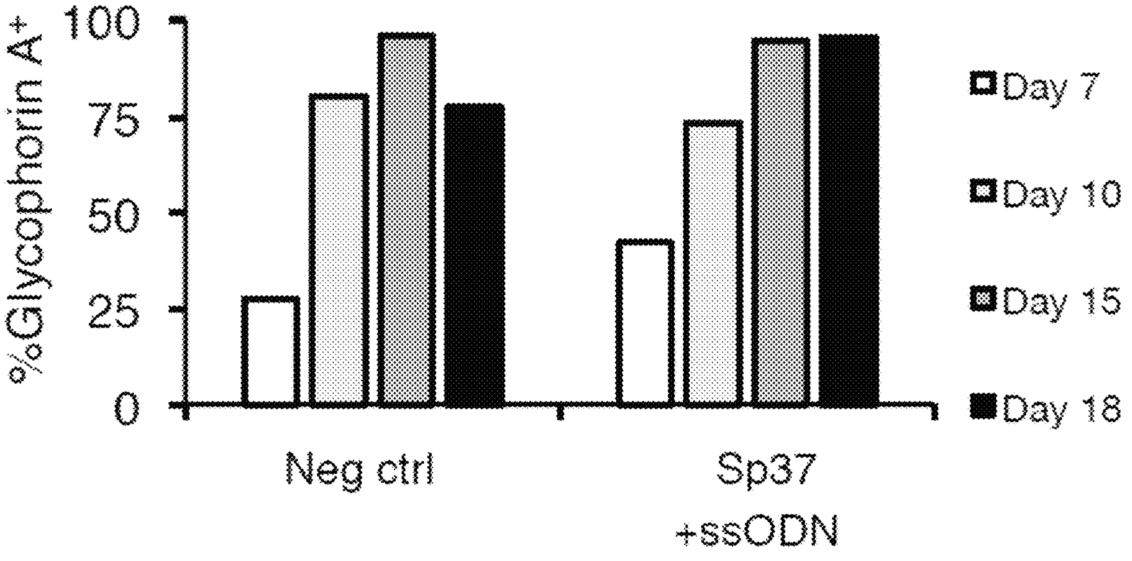

In order to increase gene editing at the target site and to increase the occurrence of the 13 nt deletion at the target site, PhTx ssODN1 (SEQ ID NO:909) was co-delivered with the precomplexed RNP targeting HBG containing the Sp37 gRNA. Co-delivery of the ssODN donor encoding the 13 nt deletion led to a nearly 2-fold increase in gene editing of the target site (FIG. 5A). To determine whether editing HBG increases production of fetal hemoglobin in erythroid progeny of edited adult CD34$^+$ cells, the cells were differentiated into erythroblasts by culture for up to 18 days in the presence of human cytokines (erythropoietin, SCF, IL3), human plasma (Octoplas), and other supplements (hydrocortisone, heparin, transferrin). Over the time course of differentiation, mRNA was collected to evaluate HBG gene expression in the erythroid progeny of RNP treated mPB CD34$^+$ cells and donor matched negative (untreated) controls. By day 7 of differentiation, erythroblast progeny of human CD34$^+$ cells that were treated with HBG Sp37 RNP and 13 nt deletion encoding ssODN (~5% indels detected in gDNA from the bulk cell population by T7E1 analysis) exhibited a 2-fold increase in HBG mRNA production (FIG. 5B). Importantly, CD34$^+$ cells that were electroporated with HBG RNP maintained their ex vivo hematopoietic activity (i.e., no difference in the quantity or diversity of erythroid and myeloid colonies compared to untreated donor matched CD34$^+$ cell negative control), as determined in hematopoietic colony forming cell (CFC) assays (FIG. 6A). Furthermore, the erythroblasts differentiated from RNP treated CD34$^+$ cells maintained the kinetics of differentiation observed for donor matched untreated control cells as determined by flow analysis for acquisition of erythroid phenotype (% Glycophorin A$^+$ cells) (FIG. 6B). These data indicate that targeted disruption of HBG1/HBG2 proximal promoter region supported an increase in HBG expression in erythroid progeny of RNP treated adult hematopoietic stem/progenitor cells without altering differentiation potential.

Figure 7A:
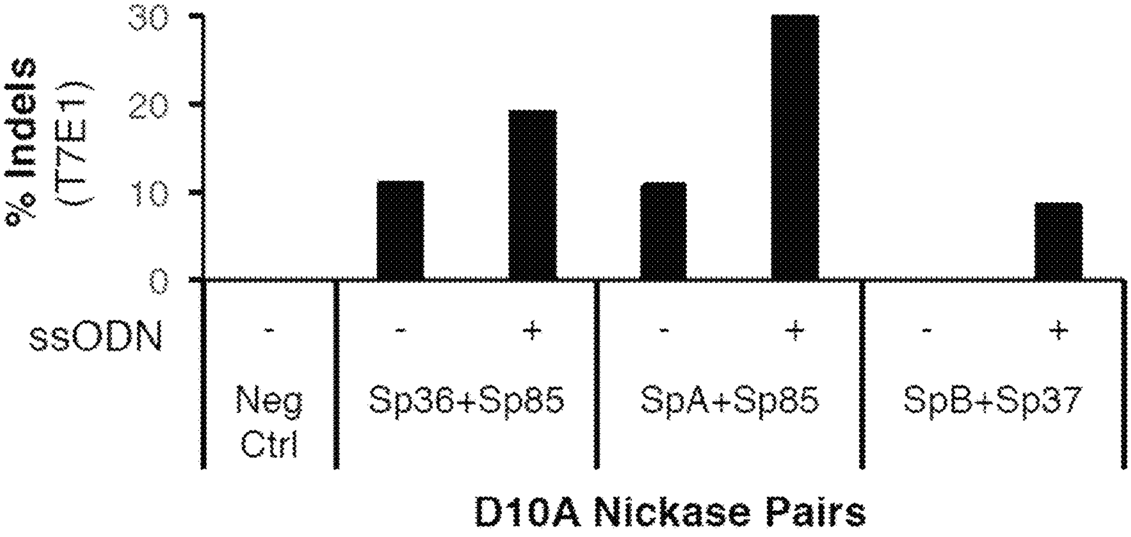
FIG. 7A depicts indels detected by T7E1 analysis of HBG PCR product amplified from gDNA extracted from human mPB $CD34^+$ cells treated with HBG RNPs (D10A paired nickases). For a subset of samples, cells also received ssODN encoding the 13 nt deletion plus silent SNPs to monitor for HDR (ssODN).
Figure 7B:
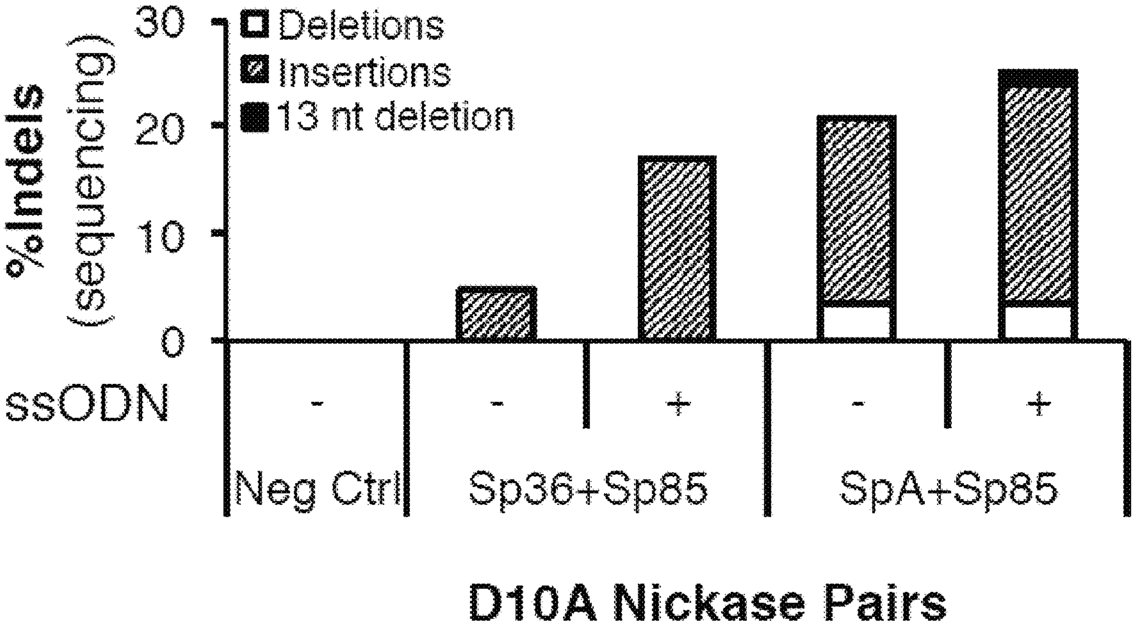
FIG. 7B depicts DNA sequencing analysis for select subset of samples shown in FIG. 7A. The indels were subdivided according to the type of indel (insertion, 13 nt deletion, or other deletion).

Example 4: Cas9 RNP Targeting the HPFH Mutation Supports Gene Editing in Human Adult Mobilized Peripheral Blood Hematopoietic Stem/Progenitor Cells with Increased HBG Expression in Erythroblast Progeny To determine whether co-delivery of paired nickase RNPs targeting HBG would increase targeted disruption of the proximal HBG promoter, mPB CD34$^+$ cells were cultured for 2 days with human cytokines and PGE2 in StemSpan SFEM and then electroporated with *S. pyogenes* D10A Cas9 protein precomplexed to two gRNAs that target sites flanking the site of the 13 nt deletion. The targeting domain sequences for gRNAs used in nickase pairs in this example (including, without limitation, SpA, Sp85 and SpB) are presented in Table 7. D10A nickase pairs were selected such that the PAMs for the targets were oriented outward and the distance between the cut sites were <100 nt. gRNAs were complexed with D10A Cas9 protein to form RNP complexes and then human CD34$^+$ cells and paired nickase were subject to electroporation. To determine whether co-delivery of an ssODN that encoded the 13 nt deletion would increase editing and introduction of the mutation into the cells, in some experiments, ssODN1 was added to the cell RNP mixture prior to electroporation. Approximately 3 days after electroporation, gDNA was extracted from the RNP treated cells and analyzed by T7E1 endonuclease assay and/or Sanger DNA sequencing of HBG2 PCR products amplified from the extracted gDNA. Of the three D10A nickase pairs tested, indels detected by T7E1 endonuclease analysis were increased for one nickase pair (gRNAs SpA+Sp85) samples for which ssODN1 was included (FIG. 7A). DNA sequencing analysis was performed on limited samples shown in FIG. 7A. DNA sequencing analysis showed up to ~27% indels at the target site, with insertions as the dominant indel detected, followed by deletions of the targeted region (area between the cut sites of the paired nickases), and the 13 nt deletion mutation was also detected at a frequency of 2-3% when ssODN1 encoding the deletion was co-delivered (FIG. 7B). Silent, non-pathogenic SNPs were included in the ssODN1 donor template, and were detected in the sequences that contained the 13 nt deletion, indicating that creation of the HFPH mutation occurred through an HDR event.

Figure 8A:
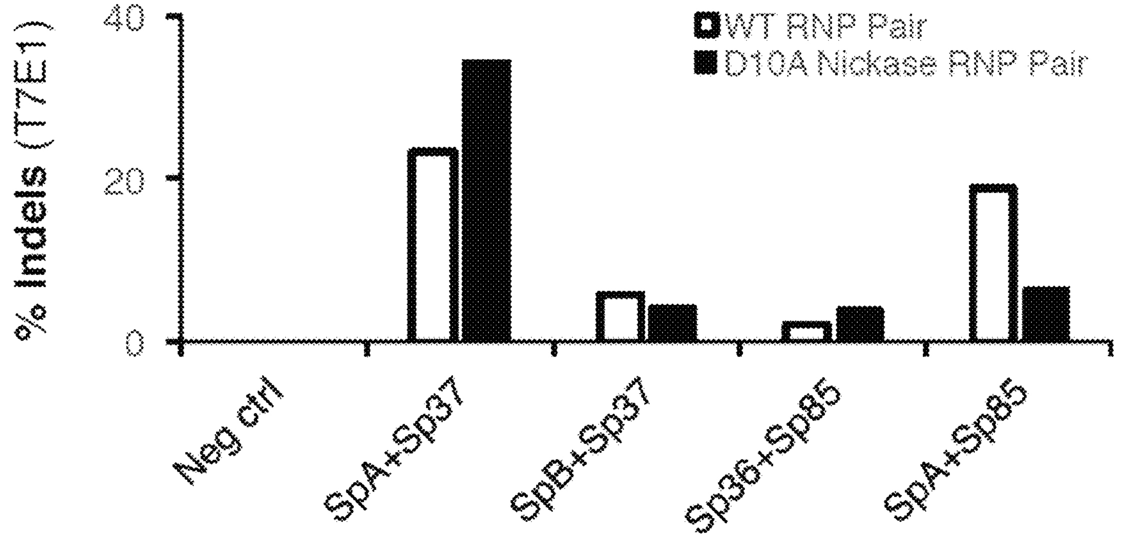
FIG. 8A depicts the indels at the HBG target site after electroporation of mPB $CD34^+$ cells with the indicated pairs of gRNAs complexed in D10A nickase and WT RNP pairs.
Figure 8B:
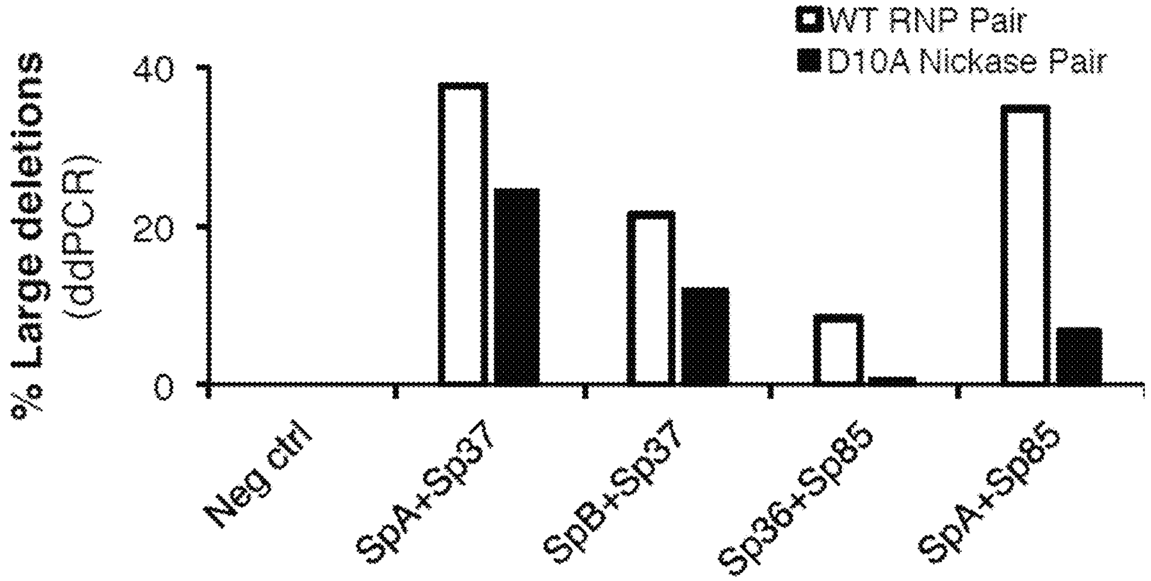
FIG. 8B depicts the large deletion events (e.g., deletion of HBG2) after electroporation of mPB $CD34^+$ cells with the indicated pairs of gRNAs complexed in D10A nickase and WT RNPs.
Figure 8C:
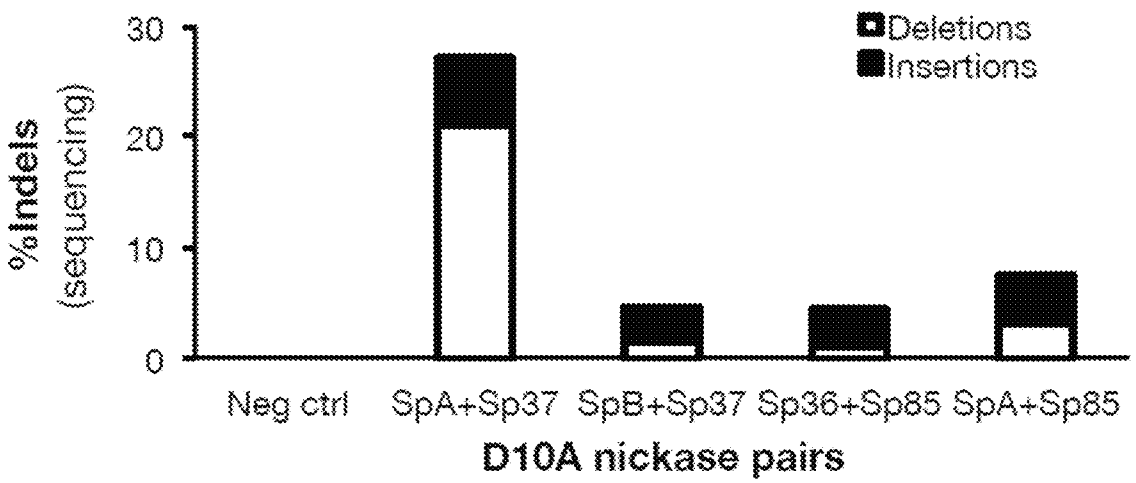
FIG. 8C depicts DNA sequencing analysis and the subtypes of events (insertions, deletions) detected in gDNA from mPB $CD34^+$ cells treated with paired D10A nickase pairs.
Figure 8D:
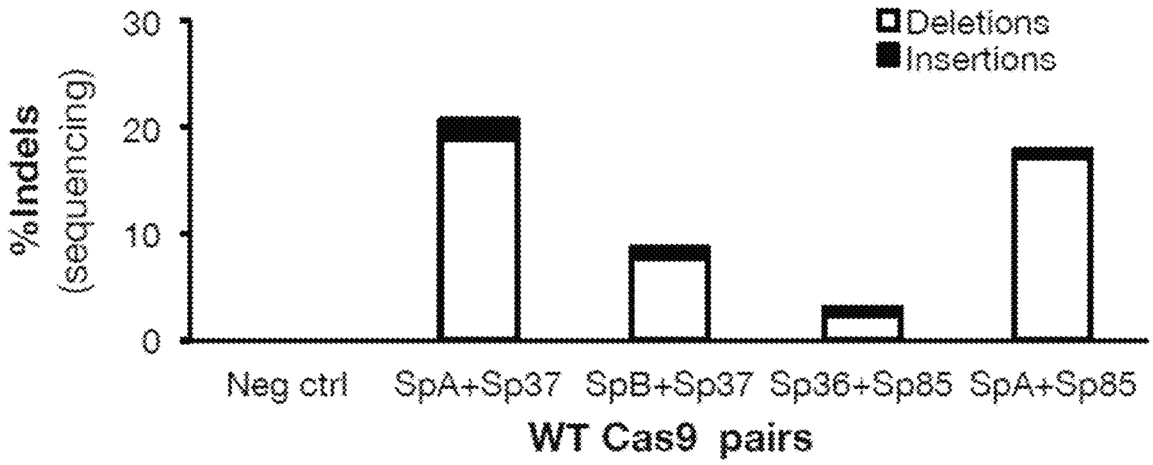
FIG. 8D depicts DNA sequencing analysis and the subtypes of events (insertions, deletions) detected in gDNA from mPB $CD34^+$ cells treated with paired WT RNP pairs.

Example 5: D10A Paired RNPs Electroporated into Adult CD34+ Cells Supports Induction of HbF Protein in Erythroid Progeny To further optimize editing conditions in mPB CD34$^+$ cells at the target site and to evaluate editing in additional human cell donors, human mPB CD34$^+$ cells were electroporated with D10A Cas9 and WT Cas9 paired RNPs targeting HBG. The most efficient guide pair for both D10A Cas9 and WT Cas9 RNPs was Sp37+SpA, which supported >30% indels as determined by T7E1 endonuclease analysis of HBG2 PCR products (FIG. 8A). Given that editing at both HBG1 and HBG2 could result in large deletions of HBG2 and the intergenic region between HBG2 and HBG1, indels were further characterized in order to capture local indels by T7E1 endonuclease assay and sequencing and large deletion by ddPCR analysis. Large deletions were detected in all samples at variable frequencies for both D10A Cas9 and WT Cas9 RNP nickase pairs (FIG. 8B). Illumina sequencing analysis of indels correlated with indels determined by T7E1 analysis (FIG. 8C-8D).

To determine whether CD34$^+$ cells edited with dual nickases at the HBG promoter gave rise to erythroid progeny with elevated HbF expression, donor matched RNP treated and untreated controls were induced toward erythroid differentiation and then evaluated for maintenance of indels during differentiation and for expression of HbF mRNA and protein. The level of editing (as determined by T7E1 endonuclease assay) was evaluated over the first 2 weeks of erythroid differentiation in the progeny of RNP treated cells prior to enucleation. Indels were detected in the erythroid progeny at every time point assayed suggesting that the editing that occurred in the CD34$^+$ cells was maintained during erythroid differentiation and that edited CD34$^+$ cells maintain erythroid differentiation potential.

Figure 9:
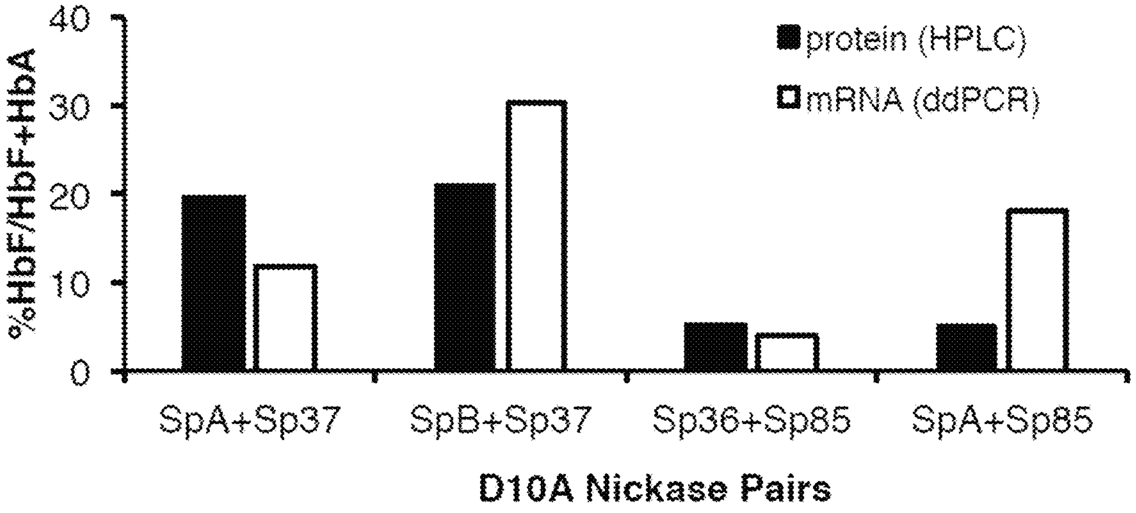
FIG. 9 depicts the summary of HbF protein and mRNA expression in the progeny of mPB $CD34^+$ cells treated with paired RNPs targeting HBG, for the experiments shown in FIGS. 7 and 8. HbF protein (by HPLC analysis) and HbF mRNA expression (ddPCR analysis) were evaluated in erythroid progeny of RNP treated human mPB $CD34^+$ cells (background levels of HbF detected in donor matched untreated controls were subtracted from the levels detected in progeny of RNP treated $CD34^+$ cells).

The levels of HBG mRNA (day 10 of differentiation) and HbF protein (day 20-23 of differentiation) were quantified by ddPCR and HPLC analysis (according to the HPLC method described in Chang 2017 at pp. 143-44, incorporated by reference herein), respectively (FIG. 9). A ~2-fold increase (+40% in in HBG transcripts vs. unedited donor matched control) was observed for HBG:HBA ratio (data not shown) and the ratio of HbF/HbF+HbA (i.e., HBG mRNA/HGB+HBB mRNA) increased to 30% above the level detected in donor matched untreated control samples.

For the D10A Cas9 nickase pairs, upregulation of HbF mRNA and protein was detected in erythroid progeny (FIG. 9). With respect to HbF protein analysis, two pairs supported 20% HbF induction for two D10A nickase pairs. No HbF upregulation was detected in erythroid progeny of WT Cas9 RNP treated $CD34^+$ cells (data not shown).

Figure 10A:
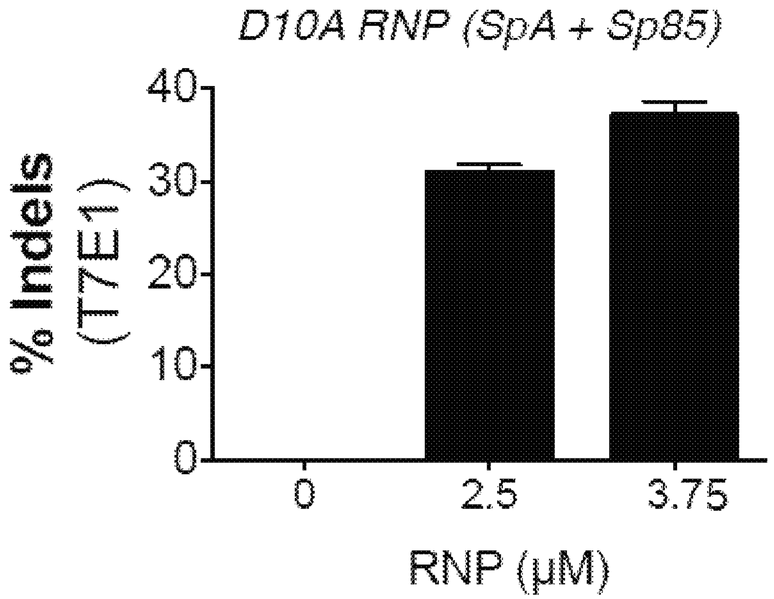
FIGS. 10A-H depicts the indel frequencies and ex vivo and in vivo short-term hematopoietic potential of $CD34^+$ cells after treatment with different concentrations (0, 2.5, 3.75 μM) of paired D10A nickase RNPs (SpA+Sp85). Indels were evaluated by T7E1 analysis (FIG. 10A) and by Illumina sequencing analysis (insertions and deletions, FIG. 10B).
Figure 10B:
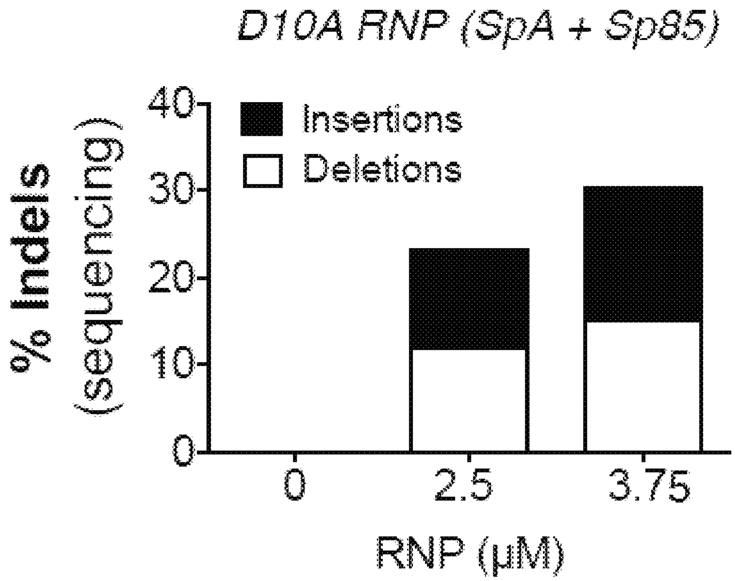
Figure 10C:
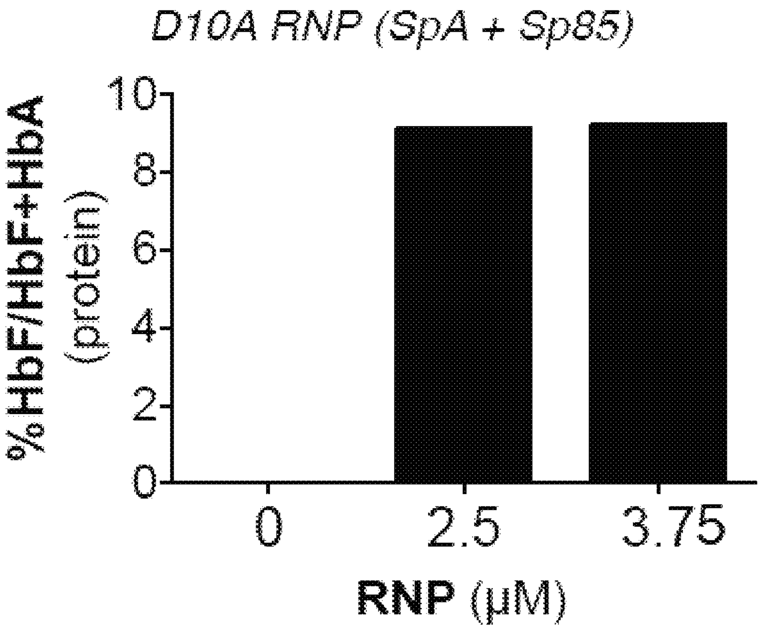
Figure 10D:
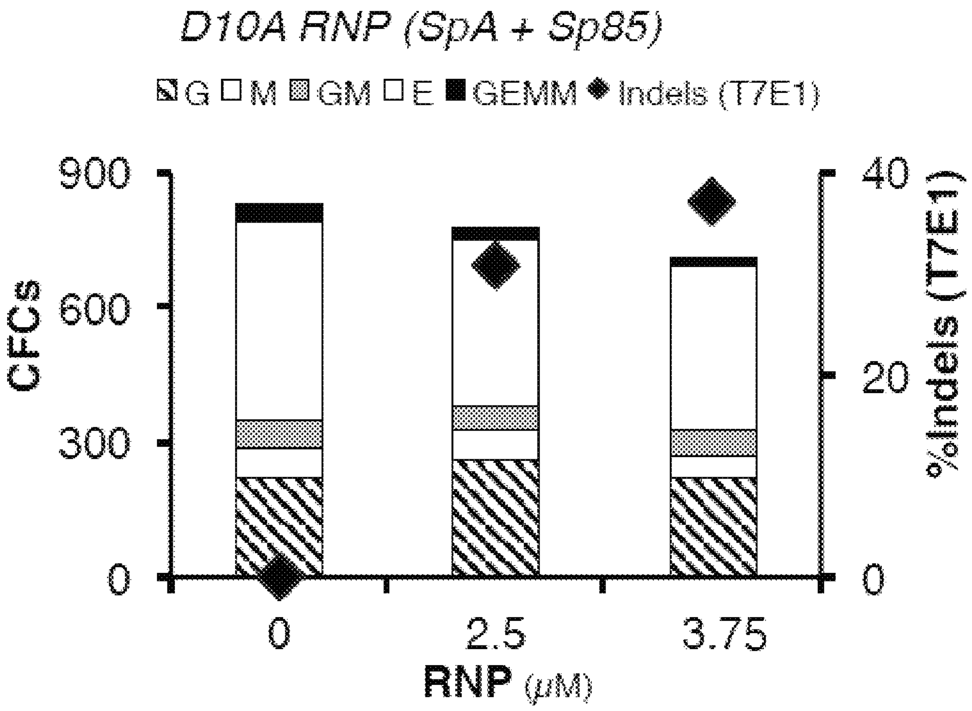
Figure 10E:
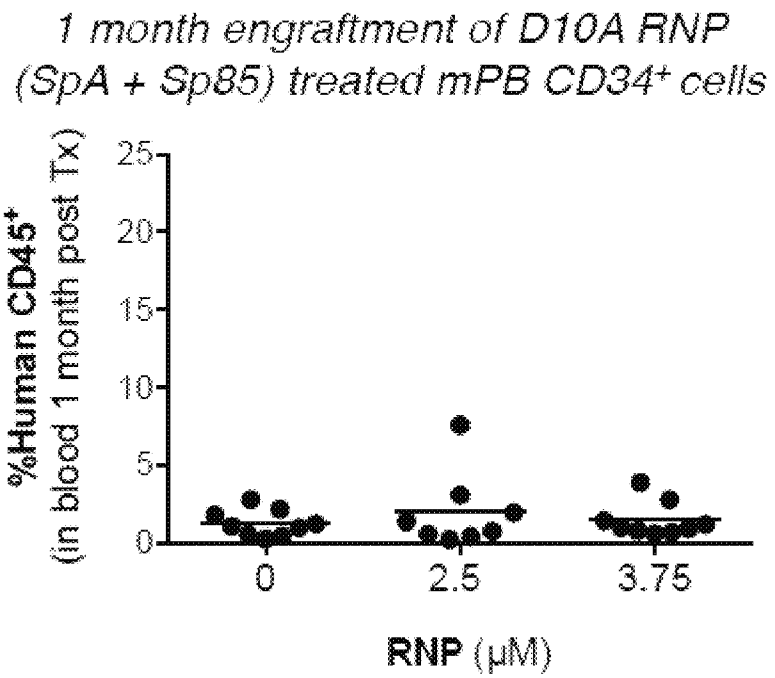
Figure 10F:
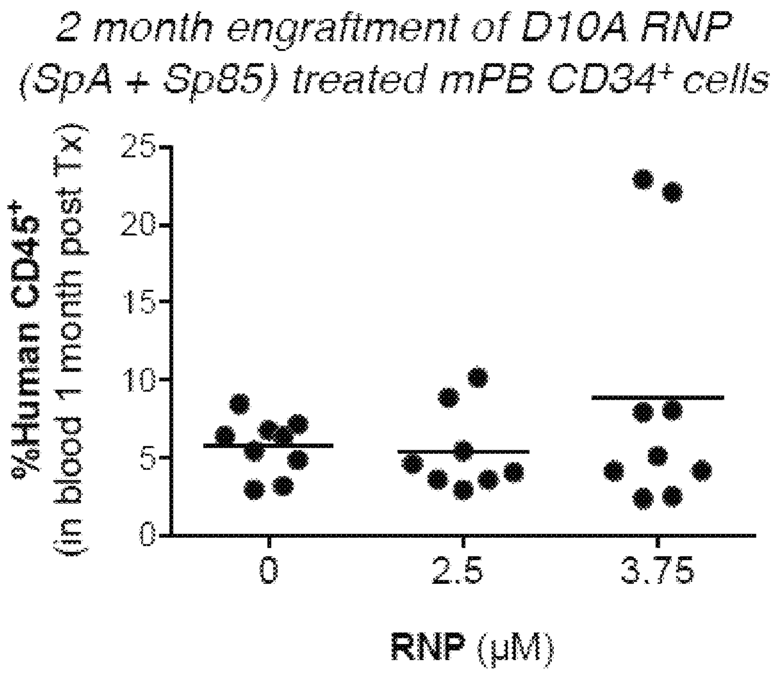
Figure 10G:
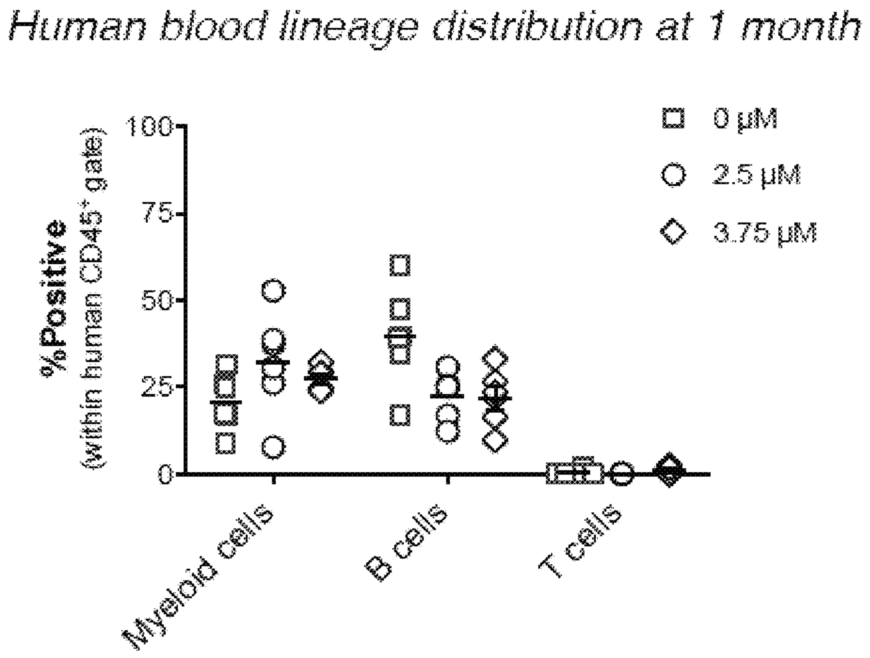
Figure 10H:
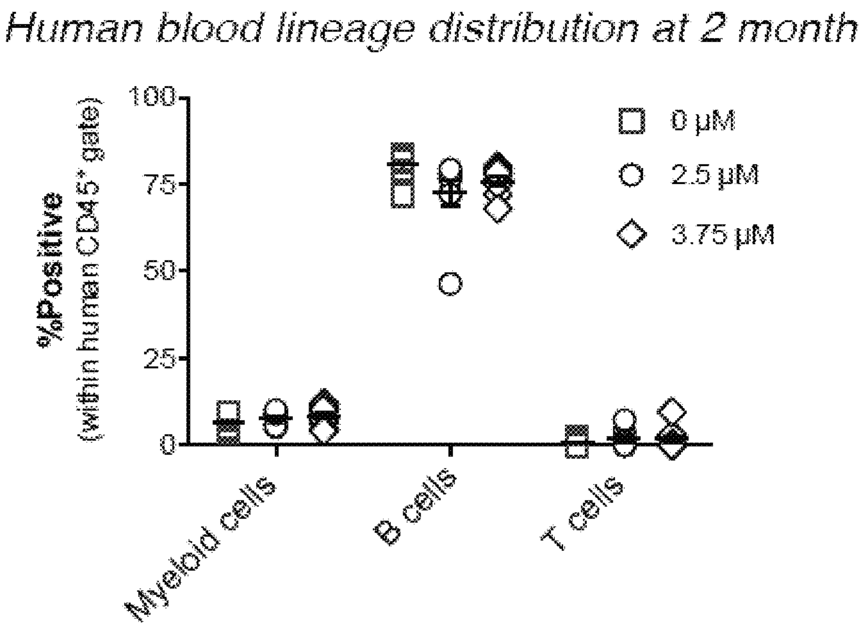

Example 6: Increasing the Dose of RNP Increases Total Editing Efficiency in Human Adult $CD34^+$ Cells at the HBG Locus The concentration of D10A Cas9 RNP for the nickase pair SpA+Sp85 was increased (2.5 μM standard concentration and 3.71 μM) and delivered to mPB $CD34^+$ cells by electroporation. The increased RNP concentration supported an increase in indels at the HBG target site to >30% (FIG. 10A) as determined by T7E1 endonuclease analysis of the HBG PCR product amplified for gDNA extracted 3 days after electroporation of $CD34^+$ cells. Sequencing analysis indicated that increasing the RNP concentration increased insertions (FIG. 10B). Erythroid progeny of RNP treated $CD34^+$ cells also had an increase in HbF protein production (FIG. 10C). Importantly, the hematopoietic colony forming potential was maintained after editing (FIG. 10D). These cells were then transplanted into immunodeficient mice and their engraftment 1 month (FIG. 10E) and 2 months (FIG. 10F) after transplantation was evaluated by sampling the peripheral blood and measuring the percentage of human $CD45^+$ cells. Early engraftment data showed no difference in engraftment between recipient cohorts of donor matched untreated controls (0 μM RNP) and mice transplanted with RNP treated cells. Furthermore, there was no difference in human blood lineage distribution (myeloid, B cell, T cell) within the human $CD45^+$ fraction among cohorts at indicated time points (FIG. 10G-H).

Figure 11A:
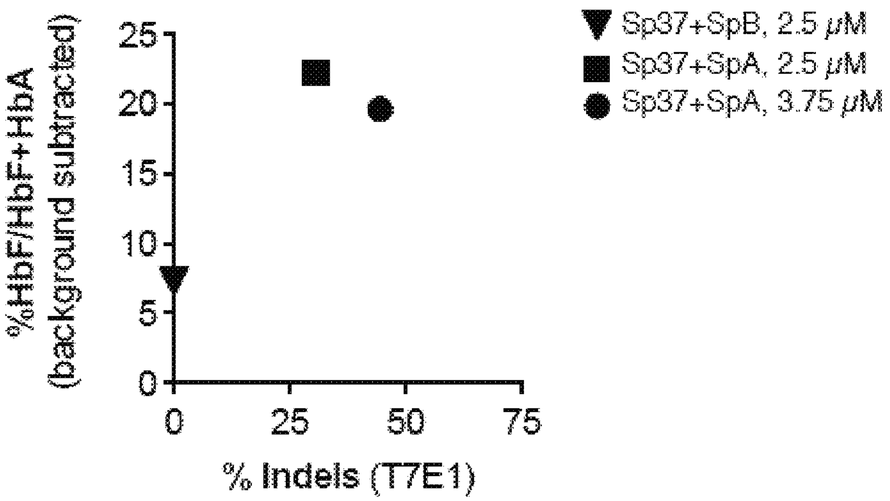
FIG. 11*a* correlates HbF levels as assayed by HPLC and indel frequency as assessed by T7E1 analysis for two D10A nickase RNP pairs (SP37+SPB and SP37+SPA) delivered at the indicated concentrations to mPB $CD34^+$ cells. HbF levels were analyzed in erythroid progeny (day 18) of edited $CD34^+$ cells. HbF protein detected in donor-matched untreated controls were subtracted from edited samples.
Figure 11B:
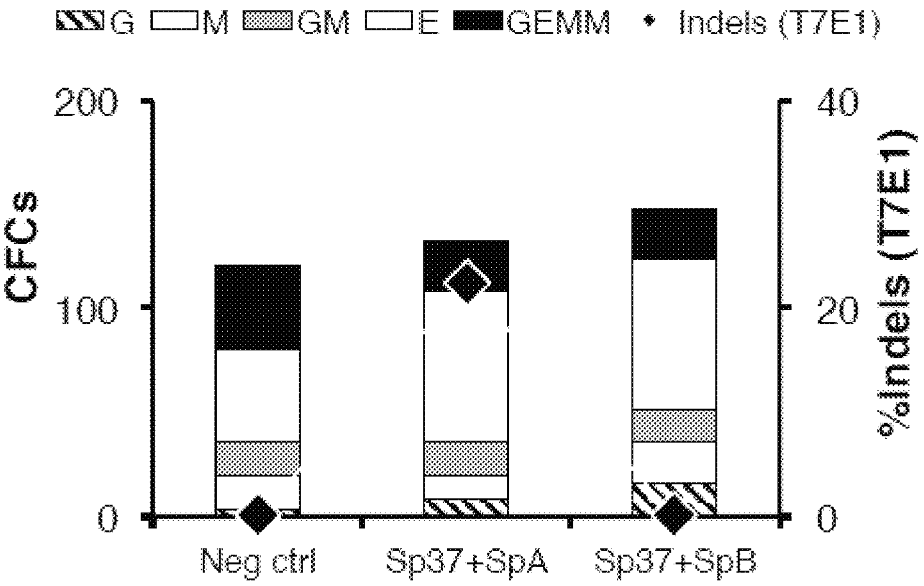
FIG. 11*b* depicts indel rates overlaid on hematopoietic colony forming cell (CFC) activity associated with $CD34^+$ cells treated with the indicated D10A nickase pairs or untreated controls.
Figure 11C:
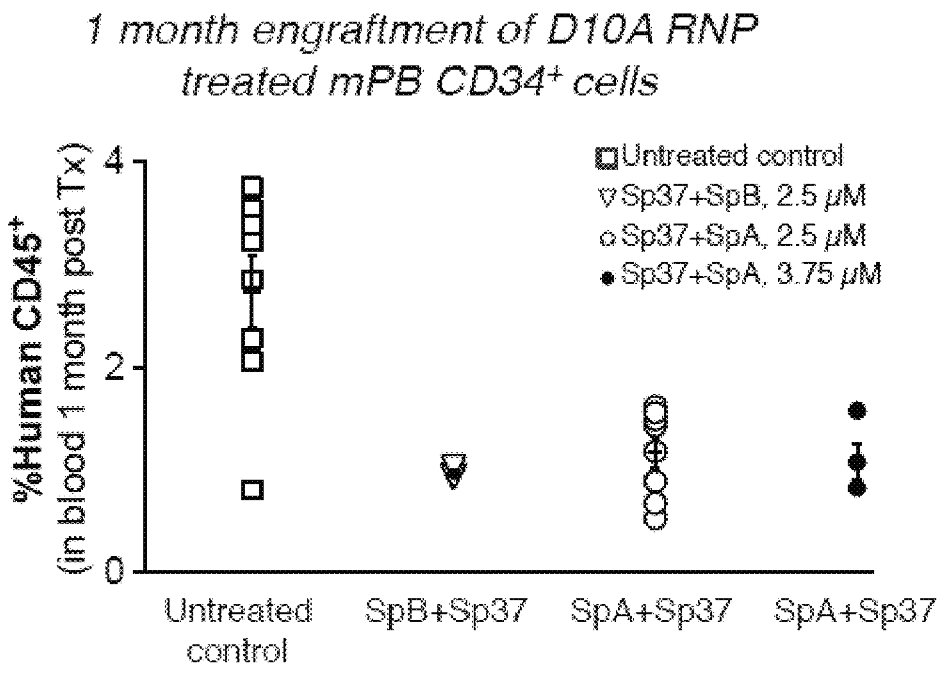
FIG. 11*c* depicts human $CD45^+$ blood cell reconstitution of immunodeficient NSG mice one month after transplantation of mPB $CD34^+$ cells treated with indicated D10 RNP nickase pairs at the concentrations given or donor matched untreated controls.
Figure 11D:
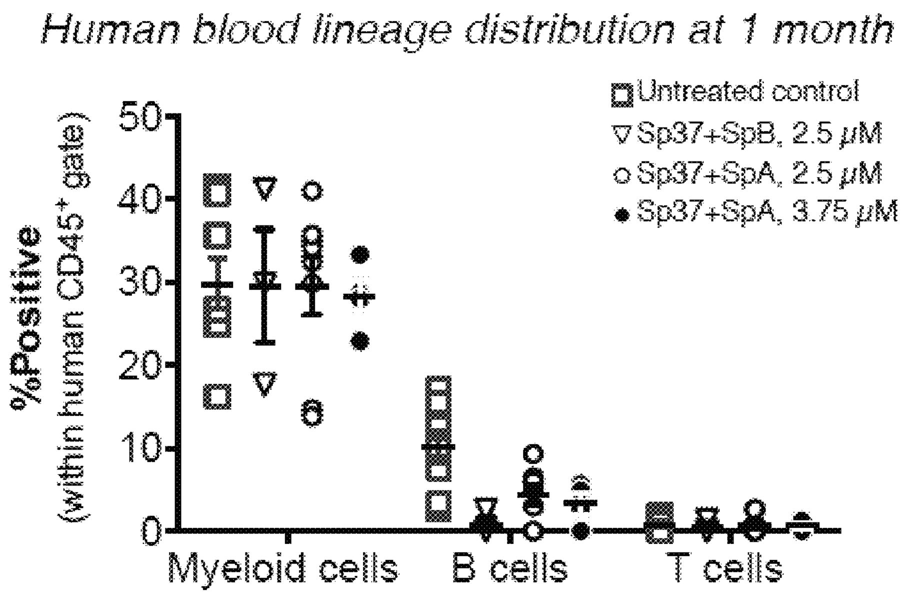
FIG. 11*d* depicts the human blood lineage distribution detected in the human $CD45^+$ fraction in mouse peripheral blood one month post-transplant.

Two additional D10A nickase pairs were also tested in RNP dose response studies in adult mPB $CD34^+$ cells (Sp37+SpA, Sp37+SpB). Here, mPB $CD34^+$ cells were electroporated with D10A paired nickases delivered at 0, 2.5, and 3.75 μM of total RNP. RNP treated cells were differentiated into erythroid progeny and the HbF protein levels (% HbF/HbF+HbA) were analyzed by HPLC analysis. The indel frequency detected in $CD34^+$ cells was plotted with the HbF levels detected in erythroid progeny in order to correlate editing and HbF induction (FIG. 11A). RNP treated and untreated control mPB $CD34^+$ cells were also differentiated into colonies to evaluate ex vivo hematopoietic activity. Colony forming cell (CFC) activity was maintained for the progeny of RNP treated and donor matched untreated control $CD34^+$ cells (FIG. 11B). There was no difference in the percentage of human $CD45^+$ cells in the mouse peripheral blood 1 month after transplantation and no difference in blood lineage distribution (FIG. 11C-D) for cells exposed to different D10A RNP pairs at different doses compared to untreated donor matched control $CD34^+$ cells.

Figure 12:
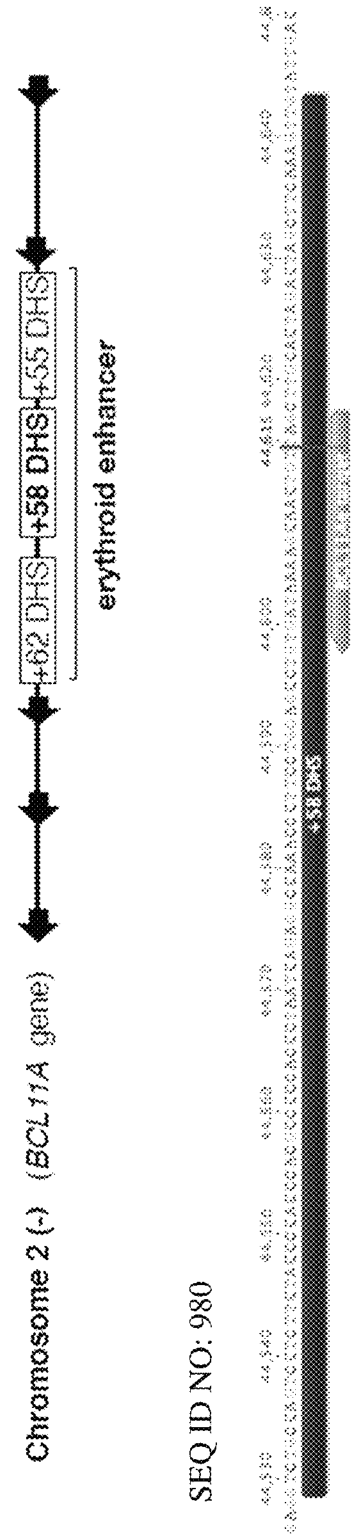
FIG. 12 depicts a target site for derepression of HbF, the GATA1 motif of the +58 DNase I hypersensitive site (DHS)

Example 7: Co-Delivery of RNP Targeting the Erythroid Specific Enhancer of BCL11A and a Non-Specific (N) Single Strand Deoxynucleotide Sequence or Paired RNPs Increases Gene Editing in Human $CD34^+$ Cells and Supports Induction of Fetal Hemoglobin Expression in Erythroid Progeny Fetal hemoglobin expression can be induced through targeted disruption of the erythroid cell specific expression of a transcriptional repressor, BCL11A (Canvers 2015). One potential strategy to increase HbF expression through a gene editing strategy is to multiplex gene editing for introduction of 13 nt deletion associated in the HBG proximal promoter and also for targeted disruption of the GATA1 binding motif in the erythroid specific enhancer of BCL11A that is in the +58 DHS region of intron 2 of the BCL11A gene (FIG. 12). In order to accomplish this multiplex strategy to increase HbF expression through multiplex gene editing, the effect of disruption of BCL11A erythroid enhancer (BCL11Ae) must first be determined as a single editing event.

In this experiment, CB $CD34^+$ cells were electroporated with *S. pyogenes* WT Cas9 complexed to in vitro transcribed sgRNA targeting the GATA1 motif in the +58 DHS region of intron 2 of BCL11A gene (gRNA SpK, Table 9) (FIG. 13A). To determine whether co-delivery of a non-target specific ssODN would increase editing of the target sequence, BCL11Ae RNP was co-delivered with ssODN (which is nonhomologous to the BCL11Ae target sequence, also called a non-specific ssODN) in CB $CD34^+$ cells. T7E1 analysis of BCL11A erythroid enhancer PCR product from gDNA extracted from CB $CD34^+$ cells treated with BCL11Ae RNP indicated that ~5% indels was achieved (FIG. 13A). Co-delivery of BCL11Ae RNP with a non-target specific ssODN increase in indels by 5-fold to 20% as detected by T7E1 endonuclease analysis. Illumina sequencing analysis indicated that >90% of edits had disruption of the GATA1 motif in the +DHS 58 region enhancer in intron 2 of the BCL11A gene (data not shown). To increase editing, human CB $CD34^+$ cells were electroporated with WT Cas9 RNP (single gRNAs complexed to WT Cas9) or with WT Cas9 paired RNPs (paired gRNAs complexed to WT Cas9), so that the cut sites in each pair flank the target site for excision of the GATA1 motif (gRNAs SpC, SpK, SpM, SpN) (Table 9). Two of the single gRNAs and two pairs had >50% indels as determined by T7E1 endonuclease analysis (FIG. 13B).

TABLE 9

Select gRNA sequences targeting BCL11A erythroid enhancer for screening in $CD34^+$ cells

| gRNA ID | Targeting domain sequence (RNA) | Targeting domain sequence (DNA) | Targeting domain sequence plus PAM (NGG) (RNA) | Targeting domain sequence plus PAM (NGG) (DNA) | Sense |
|---|---|---|---|---|---|
| SpK | CUAACAGUUG CUUUUAUCAC (SEQ ID NO: 952) | CTAACAGTTG CTTTTATCAC (SEQ ID NO: 956) | CUAACAGUUGC UUUUAUCACAG G (SEQ ID NO: 960) | CTAACAGTTGCT TTTATCACAGG (SEQ ID NO: 964) | Antisense |
| SpM | GGGCGUGGGU GGGGUAGAAG (SEQ ID NO: 953) | GGGCGTGGGT GGGGTAGAAG (SEQ ID NO: 957) | GGGCGUGGGUG GGGUAGAAGAG G (SEQ ID NO: 961) | GGGCGTGGGTGG GGTAGAAGAGG (SEQ ID NO: 965) | Antisense |

TABLE 9-continued

Select gRNA sequences targeting BCL11A erythroid enhancer for screening in $CD34^+$ cells

| gRNA ID | Targeting domain sequence (RNA) | Targeting domain sequence (DNA) | Targeting domain sequence plus PAM (NGG) (RNA) | Targeting domain sequence plus PAM (NGG) (DNA) | Sense |
|---|---|---|---|---|---|
| SpN | CUCUUAGACA UAACACACCA (SEQ ID NO: 954) | CTCTTAGACA TAACACACCA (SEQ ID NO: 958) | CUCUUAGACAU AACACACCAGG G (SEQ ID NO: 962) | CTCTTAGACATA ACACACCAGGG (SEQ ID NO: 966) | Antisense |
| SpC | AUCAGAGGCC AAACCCUUCC (SEQ ID NO: 955) | ATCAGAGGCC AAACCCTTCC (SEQ ID NO: 959) | AUCAGAGGCCA AACCCUUCCUGG (SEQ ID NO: 963) | ATCAGAGGCCAA ACCCTTCCTGG (SEQ ID NO: 967) | Sense |

Next, human adult bone marrow $CD34^+$ cells were electroporated with the BCL11Ae RNP. DNA sequencing analysis of the BCL11A PCR product amplified from gDNA extracted from marrow $CD34^+$ cells indicated 15% gene editing comprised of insertions and deletions (FIG. 14A). Importantly, all deletions resulted in deletion of the GATA1 motif and all insertions disrupted GATA1 motif through addition of a small number of bp in the motif. $CD34^+$ cells were plated into colony forming assays and the mixed hematopoietic colonies (GEMMs), which correspond to $CD34^+$ cell clones, were picked. gDNA was isolated and analyzed by Illumina sequencing to quantify monoallelic and biallelic disruption of the target site. Most GEMMs differentiated from the $CD34^+$ cell clones had monoallelic disruption and biallelic disruption was also detected, with the overall indel rate ~⅔ higher compared to what was detected in the bulk CD34+ cell population (FIG. 14B). This was likely a reflection of the percentage of common myeloid progenitors (CMPs) that give rise to GEMMs that make up a larger fraction of the heterogeneous $CD34^+$ cells versus the other lineages present, but not captured/differentiated in the short-term CFC assays. The RNP treated marrow $CD34^+$ cells also maintained similar kinetics of erythroid maturation (enucleation, FIG. 14C) and differentiation (phenotype acquisition, FIG. 14D) compared to donor matched untreated control cells. Erythroid progeny of edited marrow $CD34^+$ cells exhibited ~5-fold increase in HbF induction as determined by flow cytometry analysis (FIG. 14E).

Gene editing and induction of fetal hemoglobin was also evaluated in human adult mPB $CD34^+$ cells. Co-delivery of BCL11Ae RNP and a non-specific ssODN supported ~20% indels at the target site (FIG. 15A). To evaluate early induction of fetal hemoglobin in erythroid progeny of edited cells, mPB $CD34^+$ cells were differentiated into erythroblasts and induction of fetal hemoglobin transcription (HBG mRNA) was evaluated by qRT-PCR analysis. The erythroid progeny of BCL11Ae RNP treated $CD34^+$ cells exhibited a 2-fold induction of HBG mRNA compared to untreated controls, suggesting induction of fetal hemoglobin expression (FIG. 15B). The RNP treated marrow $CD34^+$ cells also maintained similar kinetics of differentiation (phenotype acquisition, FIG. 15C) compared to donor matched untreated control cells.

Example 8: Co-Delivery of *S. pyogenes* Cas9 Protein Complexed to a Truncated (15-Mer) "Dead" gRNA Increases Editing of the HBG Promoter Region in Adult Mobilized Peripheral Blood (mPB) $CD34^+$ Cells Delivery of a single wild-type (WT) ribonucleoprotein (RNP) (e.g., WT Cas9 protein complexed to Sp37 guide RNA (gRNA), see Table 10) targeting the HBG promoter supports ~1.5% indels editing in human $CD34^+$ cells (see International Patent Application No. PCT/US17/22377 by Gori et al., filed Mar. 14, 2017, which is incorporated by reference herein). It was hypothesized that co-delivery of a dead RNP (dRNP), comprised of a catalytically active WT Cas9 protein and a truncated dead gRNA (dgRNA) that binds proximal to the target site in the HBG promoter (-110 nt) would increase the accessibility of a WT RNP (e.g., catalytically active WT Cas9 complexed to a full-length gRNA (e.g., Sp37 gRNA, see Table 10)) to the target site. Therefore, dead guide RNAs (dgRNAs) were designed that target the regions proximal to the -110 target site in the HBG promoter and have a truncated targeting domain (see FIG. 16 and Table 10).

To increase editing at the target site in mobilized peripheral blood (mPB) $CD34^+$ cells, WT Cas9 protein was complexed to a truncated gRNA (i.e., dead (d)RNA15-mer version of wild-type SpA, which was truncated (t) at the 5' end of the gRNA sequence (tSpA dgRNA, see Table 10); tSpA dRNP). RNP comprised of dgRNA complexed to WT Cas9 is able to bind to sequence but does not cut genomic DNA homologous to the gRNA sequence. To determine the optimal ratio of dead RNP:WT RNP for the assay, tSpA dRNP:Sp37 WT RNP mixed at different ratios were Nucleofected™ into mPB $CD34^+$ cells, keeping the total RNP concentration constant at 3.75 μM.

TABLE 10

List of selected guide RNAs and dead guide RNAs

| Guide RNA (gRNA)* or Dead guide (dgRNA) ID | Targeting domain sequence (RNA) | Targeting domain sequence (DNA) | Sense |
|---|---|---|---|
| Sp35 gRNA | CUUGUCAAGGCUAUU GGUCA (SEQ ID NO: 339) | CTTGTCAAGGCTATT GGTCA (SEQ ID NO: 917) | Anti-sense |
| Sp37 gRNA | CUUGACCAAUAGCCU UGACA (SEQ ID NO: 333) | CTTGACCAATAGCCT TGACA (SEQ ID NO: 915) | Sense |
| SpA gRNA | GGCAAGGCUGGCCAA CCCAU (SEQ ID NO: 340) | GGCAAGGCTGGCCAA CCCAT (SEQ ID NO: 919) | Sense |
| tSpA dgRNA | GGCUGGCCAACCCAU (SEQ ID NO: 970) | GGCTGGCCAACCCAT (SEQ ID NO:971) | Sense |

TABLE 10-continued

List of selected guide RNAs and dead guide RNAs

| Guide RNA (gRNA)* or Dead guide (dgRNA) ID | Targeting domain sequence (RNA) | Targeting domain sequence (DNA) | Sense |
|---|---|---|---|
| Sp180 dgRNA | GCCGGCGGCUGGCUA (SEQ ID NO: 972) | GCCGGCGGCTGGCTA (SEQ ID NO:973) | |
| Sp181 dgRNA | AGUGAGGCCAGGGGC (SEQ ID NO: 974) | AGTGAGGCCAGGGGC (SEQ ID NO:975) | |
| Sp182 dgRNA | UUAGAGUAUCCAGUG (SEQ ID NO: 976) | TTAGAGTATCCAGTG (SEQ ID NO:977) | |

*None of the guide RNAs or dead guide RNAs in Table 10 and used in the experiments of Example 8 are modified to recruit an exogenous trans-acting factor.

tSpA dRNP co-delivered with Sp37 WT RNP at a ratio of 1:4 (dRNP:Total RNP ratio 1:5; 0.75 μM dRNP:3.75 μM Total RNP) supported a ~4.3-fold increase in indels (as determined by T7E1 endonuclease analysis of HBG2 PCR product amplified from gDNA extracted from CD34$^+$ cells) compared to CD34$^+$ cells treated with 3.75 μM live Sp37 WT RNP alone (FIG. 17). These data show that dRNP paired with WT RNP can increase editing at a target in adult CD34$^+$ cells.

To determine whether co-delivery of dead RNP would increase editing of HBG target site, Sp181 dRNP (comprising Sp181 dgRNA (Table 10)) and tSpA dRNP (comprising tSpA dgRNA (Table 10) targeting the same strand of Sp35) were co-delivered with Sp35 by Maxcyte electroporation into mPB CD34$^+$ cells.

Electroporation of Sp35 WT RNP (3.75 μM) alone does not support detectable indels (by T7E1 endonuclease analysis) (FIG. 18). However, co-delivery of Sp35 WT RNP (3 μM) with either dRNP (Sp181 dRNP and tSpA dRNP) (Sp181 dgRNA (Table 10) or tSpA dgRNA (Table 10), at 0.75 μM) increased indels from 0% to 10% compared to CD34$^+$ cells electroporated with Sp35 WT RNP alone (by T7E1 endonuclease analysis) (FIG. 18). Importantly, the level of indels detected in the mPB CD34$^+$ cells was maintained in the day 7 erythroid progeny of edited cells (FIG. 18, white bars).

Additional dead/WT pairs of RNPs were tested to determine the effect of co-delivery of dead/WT RNPs on editing the target site in the HBG promoter (-110 nt) and resulting expression of HbF. Dead/WT pairs of RNPs (as shown in Table 11) were co-delivered by electroporation into mPB CD34$^+$ cells. dRNP was codelivered with WT RNP (i.e., Sp35 gRNA+tSpA dgRNA, Sp35 gRNA+Sp181 dgRNA, and Sp37 gRNA+tSpA dgRNA) at a ratio of 1:4 (dRNP:Total RNP ratio 1:5; 0.75 μM dRNP:3.75 μM Total RNP).

TABLE 11

Percentage Editing and HbF Production by Co-Delivery of RNPs

| gRNA Pairs | RNPs | Strategy | % Editing (T7E1) | % HbF |
|---|---|---|---|---|
| Sp37 gRNA + SpA gRNA | Sp37 D10A RNP + SpA D10A RNP | D10A* | 22.44 | 11.2 |
| Sp85 gRNA + SpA gRNA | Sp85 D10A RNP + SpA D10A RNP | D10A | 10.5 | 5 |
| Sp36 gRNA + Sp85 gRNA | Sp36 D10A RNP + Sp85 D10A RNP | D10A | 5 | 5.3 |
| Sp35 gRNA + tSpA dgRNA | Sp35 WT RNP + tSpA dRNP | WT Live/Dead | 10 | 9.6 |
| Sp35 gRNA + Sp181 dgRNA | Sp35 WT RNP + Sp181 dRNP | WT Live/Dead | 8.27 | 12.71 |
| Sp37 gRNA + tSpA dgRNA | Sp37 WT RNP + tSpA dRNP | WT Live/Dead | 33.66 | 13.48 |

*=D10A is a Cas9 nickase that makes a single strand nick.

tSpA dRNP co-delivered with Sp35 WT RNP, Sp181 dRNP co-delivered with Sp35 WT RNP, and tSpA dRNP co-delivered with Sp37 WT RNP supported editing of the HBG promoter (as determined by T7E1 endonuclease analysis of HBG2 PCR product amplified from gDNA extracted from CD34$^+$ cells) and resulted in induction of HbF protein (as determined by HPLC analysis of hemoglobin expression in erythroid progeny according to the HPLC method described in Chang 2017 at pp. 143-44 and/or UPLC analysis, incorporated by reference herein) (Table 3). These data show that dRNP paired with WT RNP can support editing at a target region in adult CD34$^+$ cells, resulting in HbF protein expression in erythroid progeny of the edited adult CD34$^+$ cells.

Example 9: Tracking Edited HSC Contribution to Hematopoiesis Based on Tracking Edited Alleles in their Progeny In Vivo DNA lesions created by paired Cas9 WT and nickases (such as the D10A and N863A mutants) can lead to a variety of repair outcomes, including a wide spectrum of insertions and deletions in the region proximal to the nicks (Bothmer 2017). However, in contrast to wild-type Cas9, the repair outcomes induced by paired nickases are more diverse and have a more uniform distribution of frequencies of specific indels (Bothmer 2017).

The diverse repair outcomes obtained after repair of double strand breaks made by WT CRISPR nucleases or after paired nicking can then be used to estimate the diversity of edited HSCs that are contributing to blood production. This is important because for life-long hematopoiesis from an edited cell pool, multiple edited HSCs must retain their ability to produce blood and self-renew for a human life span. For a specific target site, editing using a CRISPR with a gRNA that has specificity for one target site in the genome suggests that only one site will be modified, presenting the challenge of distinguishing edited alleles among the many HSCs, and thus hard to determine whether multiple HSCs are contributing to hematopoiesis. However, this presents a unique advantage to tracking the edited cells based on subtle differences in DNA repair outcomes that can occur within each allele and in each cell. The unique alleles are distinguished from each other based on indel characteristics including the type and size of the edit (insertion, deletion, insertion/deletion, and number of nucleotides deleted or inserted) and on their relative distance to the cut site and within the amplicon. For example, each deletion or insertion observed when sequencing the cell population can be characterized by its position in the genome, its length, and in the case of insertions, its sequence. The combination of these features can be used as an indel barcode to track the persistence of HSCs and their differentiation into mature blood cells as a measure of diversity after editing (FIG. 19). Importantly, unlike in other CRISPR indel barcoding approaches or in contrast to gene therapy approaches, the indel barcode is a potentially functional edit at the target locus, requiring no further modification of the genome for purposes of tracking. Although it is possible for different cells to be independently edited in a way that creates the same edit, tracking by indel barcodes can establish a lower bound on the diversity of a population. Because each allele in a diploid cell can receive a different indel, that possibility must also be accounted for in diversity estimates.

It is hypothesized that if multiple unique indels in hematopoietic stem cells (HSCs) and progeny are detected then edited HSC diversity is maintained after editing. A method of tracking unique edited alleles to determine whether HSC diversity is maintained is disclosed herein. First, an RNA-guided nuclease and guide RNA complexed to form a ribonucleoprotein (RNP) complex for editing is electroporated into cells and several CD34+ cells repair the DNA slightly differently to create unique alleles. Over time after transplantation into an animal, edited HSCs repopulate the blood system and can be collected and sorted based on the different tissues and lineages to evaluate specific unique indels in the long-term engrafted HSCs and in differentiated progeny.

An HBB locus was used as a model to illustrate this method and determine whether HSC diversity is maintained. CD34+ cells were electroporated with D10A nickase RNPs targeting the HBB locus as described using the methods for electroporation provided in Example 1. Before transplantation, genomic DNA was harvested from an aliquot of the bulk pre-infusion $CD34^+$ cell product, sequenced, and reads aligned to a reference sequence encompassing the target site at the HBB locus. The remainder (majority bulk) of the $CD34^+$ cells were transplanted into mice. Four months after transplantation, human cells were purified from the hematopoietic organs of the mice (peripheral blood [PB], spleen, and bone marrow [BM]) and the human cell lineages (myeloid, erythroid, lymphoid, $CD34^+$ or HSCs) were further purified. The genomic DNA was isolated from all of these human cells derived from the engrafted edited HSCs and sequenced (sequencing reads were aligned to the reference locus). The percentage of each unique edited allele over the total sum of all edited alleles detected was plotted to determine their relative contribution (FIG. 20). The black bars represent a group of all unique alleles occurring at low frequencies of total edited alleles. White and grey bars correspond to the top five most abundant unique alleles ranked (FIG. 20). In the bulk $CD34^+$ cell preinfusion product, the top five most abundant clones together make up less than 10% of total edited alleles, consistent with the diversity and heterogeneity of cell types within the bulk $CD34^+$ cell population. There are many unique alleles at less than 1% each grouped into the black bar. An analysis of the top five most abundant alleles in mouse 1 (that is, in vivo after transplantation of and long-term engraftment of edited HSCs derived from the heterogeneous preinfusion product) indicates that there are shared unique HSC alleles across tissues and in different lineages (FIG. 21). An analysis of the top 5 most abundant clones in mouse 2 indicates that, for the most part, different unique alleles are present in vivo compared to mouse 1, but there are also shared alleles across tissues and lineages (FIG. 21). These data show that multiple edited HSCs are making blood in vivo and that a repertoire of unique edits are detected across multiple tissues. This demonstrates that there is diversity among the alleles and that no one edited allele is dominant over others. This method provides a means to survey for any unintended effects of alleles at the target site providing a readout on safety of editing.

Example 10: Co-Delivery of Active RNP with Inactive RNP Increases Total Editing at the Distal CCAAT Box Target Site To determine whether co-delivery of inactive RNP (i.e., dead RNP ("dRNP"), dead guide RNA ("dgRNA") complexed with active Cas9) would increase editing of wild-type active RNP (i.e., active gRNA complexed with active Cas9) at the distal CCAAT box target site of the HBG promotor, 8 μM Sp37 RNP (comprising Sp37 gRNA (SEQ ID NO:333, Table 10) complexed with *S. pyogenes* wildtype Cas9) was delivered alone or co-delivered with 8 μM tSpA dRNP (comprising tSpA dgRNA (SEQ ID NO: 970, Table 10) complexed with *S. pyogenes* wildtype Cas9) by electroporation into mPB CD34+ cells. In this experiment, Sp37 gRNA and tSpA dgRNA were generated via in vitro transcription (IVT). FIG. 22 shows the distal CCAAT box target site at the HBG promoter and the relative locations of homologous sequences to Sp37 gRNA, which binds the CCAAT box target site, and tSpA dgRNA, which binds proximal to the CCAAT box target site. Co-delivery of inactive tSpA dRNP increased total editing of active Sp37 RNP by more than two times the level of editing shown with delivery of active Sp37 RNP alone (FIG. 23). Although the addition of tSpA dRNP resulted in an increase in editing, the increase in editing did not correspond to an increase in HbF protein expression ex vivo (FIG. 23).

To determine whether gRNAs that have been chemically synthesized influence editing compared with gRNA generated via IVT, 8 μM Sp37 RNP (comprising chemically synthesized Sp37 gRNA (SEQ ID NO:333, Table 10) complexed with *S. pyogenes* wildtype Cas9) was delivered or co-delivered with 8 μM tSpA dRNP (comprising chemically synthesized tSpA dgRNA (SEQ ID NO:970, Table 10) complexed with *S. pyogenes* wildtype Cas9) by electroporation into mPB CD34+ cells. Co-delivery of inactive tSpA dRNP comprising chemically synthesized dgRNA with Sp37 RNP comprising chemically synthesized gRNA increased total editing by active Sp37 RNP (as determined by NGS (Illumina sequencing analysis) of HBG1 PCR product amplified from gDNA extracted from CD34+ cells) (FIG. 24). A 6-fold increase in editing with RNP comprising synthetic gRNA was seen versus RNP comprising gRNA generated via IVT (compare FIG. 23 with FIG. 24). Similar to the RNP comprising IVT gRNA, RNP comprising chemically synthesized gRNA increased editing, but did not result in an increase in HbF protein expression (as determined by UPLC tetramer analysis of hemoglobin expression in erythroid progeny of the edited HSPCs). These data indicate that pairing with a dgRNA can increase the total editing level of active gRNA.

Example 11: Co-Delivery of Active RNP with an Inactive RNP Binding Proximally Alters the Indel Profile Different concentrations of inactive dRNP and active RNP were tested to evaluate the effect of co-delivering a proximally binding dRNP with an active RNP on the indel profile. Briefly, active Sp37 RNP (comprising IVT Sp37 gRNA (SEQ ID NO:333, Table 10) complexed with *S. pyogenes* wildtype Cas9) at decreasing concentrations (6.4 μM, 4.0 μM, 1.6 μM, 0 μM) was co-delivered with increasing concentrations (1.6 μM, 4.0 μM, 6.4 μM, 8.0 μM) of inactive tSpA dRNP (comprising IVT tSpA dgRNA (SEQ ID NO:970, Table 10) complexed with *S. pyogenes* wildtype Cas9) by electroporation into mPB CD34+ cells. T7E1 endonuclease analysis indicated that the editing activity of Sp37 RNP at HBG2 can be increased by co-delivering an inactive RNP (FIG. 25). NGS sequencing analysis was performed to quantify the type and frequency of indels generated when delivering Sp37 RNP only or Sp37 RNP paired with tSpA dRNP (FIGS. 26A-D). Co-delivering tSpA dRNP increased the frequency of deletions extending from the active gRNA cut site toward the dgRNA binding site. Increasing the relative dose of tSpA RNP accentuated that effect (FIGS. 26A-D). These data confirm that as the dgRNA concentration increases, the directionality of the deletions generated by the active gRNA changes in favor of deletions extending toward the dgRNA binding site.

The most common deletions (contributing to >1% of all indels) generated with tSpA dRNP co-delivered with Sp37 RNP extended from the Sp37 target site to the tSpA target site, but they did not extend past the tSpA target site (FIG. 27B). This indicates that the maximum length of indels extending from the wildtype cut site to the inactive binding site does not frequently extend beyond the inactive binding site.

Next, the deletions were analyzed to determine whether they are likely to have been generated by microhomology-mediated end joining (MMEJ). While NHEJ repair occurs during all phases of the cell cycle, it is uncertain whether MMEJ repair can occur at high frequency in the G0/G1 phase (Truong 2013), where most of the long-term repopulating hematopoietic stem cells reside. MMEJ repair of DSBs rely on the annealing of DNA ends by base pairing of short microhomology sequences. The sequences of the deletions were systematically analyzed and compared with the sequence flanking the deletion to identify deletions associated with micro-homologies, which may have been generated via the MMEJ repair pathway (as determined by deletions whose sequence starts or ends with 2 nt or more of homology with the sequence flanking the other extremity of the deletion (FIG. 31). Sequencing analysis demonstrated that the most common deletions generated using Sp37 RNP alone were associated with micro-homologies, and were thus likely generated by micro-homology mediated end-joining (MMEJ) repair. In particular, the largest deletions frequently observed (>5 nt long and contributing to >=1% of all indels) using Sp37 RNP alone were all associated with microhomologies whereas co-delivery of tSpA dRNP with Sp37 RNP increased the frequency of large deletions extending toward the inactive dgRNA binding site without relying on micro-homology domains for repair (FIGS. 27A-B).

These data show that pairing with a dgRNA can change the editing outcome (directionality and use of micro-homologies for repair) of an active gRNA. Thus, dgRNA can be used to "orientate" deletions toward a desired target site to increase the frequency of target site disrupting indels. In addition, whereas deletions of length >5 nt are only frequently generated by CRISPRCas9 in the presence microhomology domains (van Overbeek 2016), the dgRNA can be used to increase the frequency of large deletions, independently of the presence of microhomology domains, or in cells lacking the machinery to use the MMEJ repair pathway.

Example 12: Distal CCAAT Box Disrupting Indels Promote HbF Expression

DNA lesions created by single or paired Cas9 RNP (using WT or nickase Cas9 protein, such as the D10A and N863A mutants) can lead to a variety of repair outcomes, including a wide spectrum of insertions and deletions. The phenotypic outcome in edited cells may vary according to the type of generated indels. Characterizing a target domain whose disruption is required to achieve a desired phenotypic outcome can allow the design of dedicated editing approaches aiming at maximizing the frequency of cells in a population of cells having the desired genotype and thus the desired phenotype. In particular, targeting the HBG distal CCAAT box is likely to disrupt the binding of regulatory proteins repressing the expression of the HBG genes. The length and position of indels may affect their capacity to de-repress HBG expression, for example, based on their capacity to prevent the binding of repressive factors or whether they disrupt nearby essential regulatory elements.

To identify indels resulting in productive HbF induction at the proximity of the distal CCAAT box, HSPCs were electroporated by single or paired Cas9 RNP targeting the distal CCAAT box, differentiated into erythroid cells and sorted based on HbF expression into a low HbF expressing fraction and a high HbF expressing fraction. The frequency of each indel was quantified in both fraction, allowing to identify indels enriched in the high-HbF fraction (FIG. 28A).

Briefly, 8 different sets of single or paired Cas9 RNP:

(1) 3 μM Sp37 RNP (comprising IVT Sp37 gRNA (SEQ ID NO:333, Table 10) complexed with *S. pyogenes* D10A Cas9) and 3 μM SpA dRNP (comprising IVT SpA gRNA (SEQ ID NO:340, Table 10) complexed with *S. pyogenes* D10A Cas9);

(2) 4 μM Sp37 RNP (comprising IVT Sp37 gRNA (SEQ ID NO:333, Table 10) complexed with *S. pyogenes* D10A Cas9) and 4 μM tSpA dRNP (comprising IVT SpA gRNA (SEQ ID NO:340, Table 10) complexed with *S. pyogenes* WT Cas9);

(3) 8 μM Sp37 RNP (comprising IVT Sp37 gRNA (SEQ ID NO:333, Table 10) complexed with *S. pyogenes* WT Cas9);

(4) 6.4 μM Sp35 RNP (comprising IVT Sp35 gRNA (SEQ ID NO:339, Table 10) complexed with *S. pyogenes* WT Cas9) and 1.6 μM tSpD RNP (comprising IVT tSpD (targeting domain sequence set forth in SEQ ID NO:978 (RNA) and SEQ ID NO:979 (DNA)) complexed with *S. pyogenes* wildtype Cas9);

(5) 8 μM Sp35 RNP (comprising chemically synthesized Sp35 gRNA (SEQ ID NO:339, Table 10) complexed with *S. pyogenes* WT Cas9);

(6) 8 μM Sp35 RNP (comprising chemically synthesized Sp35 gRNA (SEQ ID NO:339, Table 10) complexed with *S. pyogenes* WT Cas9);

(7) 8 μM Sp35 RNP (comprising chemically synthesized Sp35 gRNA (SEQ ID NO:339, Table 10) complexed with *S. pyogenes* WT Cas9) and 2 μM tSpA dRNP (comprising chemically synthesized tSpA dgRNA (SEQ ID NO:970, Table 10) complexed with *S. pyogenes* WT Cas9); and (8) 8 μM Sp37 RNP (comprising chemically synthesized Sp37 gRNA (SEQ ID NO:333, Table 10) complexed with *S. pyogenes* WT Cas9) and 2 μM tSpA dRNP (comprising IVT tSpA dgRNA (SEQ ID NO:970, Table 10) complexed with *S. pyogenes* WT Cas9) were delivered by electroporation into mPB CD34+ cells and sequenced. Erythroid cells derived from RNP treated HSPCs were sorted based on HbF expression into a low HbF expressing fraction and a high HbF expressing fraction (as determined by the level of staining using an anti-gamma chain antibody) by fluorescence-activated cell sorting. The frequency of each indel was quantified in both fraction by amplification of the HBG PCR amplicon from the extracted gDNA and NGS analysis.

It was observed that most of the indels enriched in the high HbF fraction (i.e., associated with HbF expression) were indels disrupting the distal CCAAT box (FIG. 28B, see "dCCAAT")). Deletions that only disrupted the proximal CCAAT or the KLF binding area (FIG. 28B, see "pCCAAT" and "KLF" respectively) had a detrimental effect or no effect on HbF induction. Deletions that disrupted the distal CCAAT box and that co-disrupted the proximal CCAAT box or the KLF1 binding area appeared to diminish HbF production when compared to deletions only disrupting the distal CCAAT box (FIG. 28B, compare "dCCAAT & pCCAAT" and "dCCAAT & KLF" with "dCCAAT"). While the distal CCAAT box disruption appeared to be necessary for HbF induction, the effect of the deletion length both 5' and 3' of the distal CCAAT box was analyzed. It was determined that deletions of the distal CCAAT box extending up to 22 nt upstream (starting 3' of pos. HBG-88) and up to 15 nt downstream (ending 5' of pos. HBG-131) of the dCCAAT box (positions flanked by the proximal CCAAT box ("pCCAAT") and KLF1 binding area ("KLF") were able to support HbF induction (FIG. 28C and FIG. 28D). In addition, it was determined that deletions of >3 nt of the dCCAAT were more frequently associated with high HbF expression (FIG. 28E). A list of example indels that were shown to induce HbF expression (i.e., productive indels) is found in Table 12.

TABLE 12

Exemplary deletions that induce HbF expression*

| Position Relative to HBG Transcription Start Site | Genomic Location 1 (HBG1) | Genomic Location 2 (HBG2) |
|---|---|---|
| c.−114 to −102 | Hg38 Chr11:5249959 to Hg38 Chr11:5249971 | Hg38 Chr11:5254883 to Hg38 Chr11:5254895 |
| −119:−104 | Hg38 Chr11:5249961 to Hg38 Chr11:5249976 | Hg38 Chr11:5254885 to Hg38 Chr11:5254900 |
| −121:−104 | Hg38 Chr11:5249961 to Hg38 Chr11:5249978 | Hg38 Chr11:5254885 to Hg38 Chr11:5254902 |
| −104:−78 | Hg38 Chr11:5249935 to Hg38 Chr11:5249961 | Hg38 Chr11:5254859 to Hg38 Chr11:5254885 |
| −108:−82 | Hg38 Chr11:5249939 to Hg38 Chr11:5249965 | Hg38 Chr11:5254863 to Hg38 Chr11:5254889 |
| −115:−112 | Hg38 Chr11:5249942 to Hg38 Chr11:5249945 | Hg38 Chr11:5254893 to Hg38 Chr11:5254896 |
| −113:−107 | Hg38 Chr11:5249964 to Hg38 Chr11:5249970 | Hg38 Chr11:5254888 to Hg38 Chr11:5254894 |
| −114:−107 | Hg38 Chr11:5249964 to Hg38 Chr11:5249971 | Hg38 Chr11:5254888 to Hg38 Chr11:5254895 |
| −123:−113 | Hg38 Chr11:5249970 to Hg38 Chr11:5249980 | Hg38 Chr11:5254894 to Hg38 Chr11:5254904 |
| −119:−104 | Hg38 Chr11: 5249961 to Hg38 Chr11: 5249976 | Hg38 Chr11:5254885 to Hg38 Chr11:5254900 |
| −119:−102 | Hg38 Chr11: 5249959 to Hg38 Chr11: 5249976 | Hg38 Chr11:5254883 to Hg38 Chr11:5254900 |
| −127:−103 | Hg38 Chr11: 5249960 to Hg38 Chr11: 5249984 | Hg38 Chr11:5254884 to Hg38 Chr11:5254908 |

*>2 [log2] enrichment in high-HbF fraction not inclusive

Example 13: Co-Delivery of Active RNP with an Inactive RNP can be Used to Change the Type of Indels Disrupting the Distal CCAAT-Box Sequencing analysis resulting from the electroporation of the Sp37 RNP alone showed that 35% of the generated indels disrupted the distal CCAAT box (FIGS. 29A-B and 30A-B). Briefly, 8 µM Sp37 RNP (comprising chemically synthesized Sp37 gRNA (SEQ ID NO:333, Table 10) complexed with *S. pyogenes* wildtype Cas9) was delivered alone or co-delivered with 8 µM tSpA dRNP (comprising chemically synthesized tSpA dgRNA (SEQ ID NO:970, Table 10) complexed with *S. pyogenes* wildtype Cas9) by electroporation into mPB CD34+ cells. Small deletions close to the Sp37 cut site did not disrupt the distal CCAAT box (see FIG. 22 identifying the Sp37 cut site) and FIGS. 29A-B). Most of the distal CCAAT box disruptions generated by Sp37 RNP alone were formed by 27 nt long deletions, which are associated with microhomology domains and thus likely to occur via micro-homology mediated end joining (FIG. 29A and FIG. 31). Codelivery of tSpA dRNP with Sp37 RNP did not increase the frequency of CCAAT box disrupting indels (compare FIGS. 29B and 30B). However, the addition of the tSpA dRNP increased the frequency of distal CCAAT box deletions extending from the active Sp37 gRNA cut site toward the tSpA dgRNA binding site, including HbF-inducing distal CCAAT box deletions (compare FIG. 29A with FIG. 30A and FIG. 28F).

Example 14: Pairing with an Inactive Dead Guide RNA Changes the Editing Outcome in Hematopoietic Stem Cells To determine whether co-delivery of dead RNP increases editing of the distal CCAAT-box target site in long term repopulating hematopoietic stem cells in vivo, mPB CD34+ cells electroporated with dRNP and active RNP were infused into nonirradiated NOD,B6. SCID Il2rγ−/− Kit(W41/W41) ("NBSGW") mice. Briefly, 8 µM Sp37 RNP (comprising in vitro transcribed Sp37 gRNA (SEQ ID NO:333, Table 10) complexed with *S. pyogenes* wildtype Cas9) was delivered alone or co-delivered with 8 µM tSpA dRNP (comprising in vitro transcribed tSpA dgRNA (SEQ ID NO:970, Table 10) complexed with *S. pyogenes* wildtype Cas9) by Maxcyte HBGM34-2 electroporation into mPB CD34+ cells. Cells were then infused into NBSGW mice (n=5) and the percentage of editing in bone marrow engrafted human cells was evaluated after 16 weeks in vivo. Co-delivery with dRNP resulted in increased total editing by Sp37 RNP compared with Sp37 RNP alone (FIG. 32A). In particular, co-delivery with dRNP resulted in increased distal CCAAT box disrupting deletions (FIG. 32B).

Deletions associated with micro-homology domains were observed in cells pre-infusion, but were not frequently observed in vivo 16 weeks after transplantation (FIGS. 32A-C). These data indicate that indels associated with micro-homologies occur at lower frequencies in HSCs and therefore do not frequently persist long term after transplantation of edited mPB CD34+ cells. MMEJ repair is likely favored in the fraction of CD34 cells consisting of actively cycling progenitors. Those progenitors that do not self-renew and thus have a short life span in vivo. The drop in the frequency of micro-homology associated indels observed between pre-infusion and after 16 weeks post infusion may be explained by the progressive disappearance in vivo of those short lived progenitors.

Surprisingly, the co-delivery of tSpA dRNP with Sp37 RNP increased the frequency of distal CCAAT box deletions not associated with micro-homologies pre-infusion (FIG. 32C). While most distal CCAAT box deletions generated by Sp37 RNP alone are associated with micro-homologies and were not frequently observed in vivo 16 weeks after transplantation, distal CCAAT box deletions generated by co-delivery of the inactive tSpA dRNP and not associated with micro-homologies were better maintained in vivo 16 weeks after transplantation (FIGS. 32A-C).

These results demonstrate that co-delivery of inactive dRNP can increase the frequency of indels in cells where the MMEJ repair pathway is reduced, such as quiescent hematopoietic stem cells. In addition, whereas deletions >5 nt are only frequently generated by CRISPRCas9 single RNP in the presence of micro-homologies, using a dRNP promoted the frequency of >5 nt deletions independently of micro-homologies. Finally, using a dRNP that promotes deletions disrupting the target HBG distal CCAAT box can be used to increase the frequency of predicted productive (HbF inducing), distal CCAAT box deletions in hematopoietic stem cells.

SEQUENCES

Genome editing system components according to the present disclosure (including without limitation, RNA-guided nucleases, guide RNAs, donor template nucleic acids, nucleic acids encoding nucleases or guide RNAs, and portions or fragments of any of the foregoing), are exemplified by the nucleotide and amino acid sequences presented in the Sequence Listing. The sequences presented in the Sequence Listing are not intended to be limiting, but rather illustrative of certain principles of genome editing systems and their component parts, which, in combination with the instant disclosure, will inform those of skill in the art about additional implementations and modifications that are within the scope of this disclosure. A list of the sequences presented is provided in the following Table 13.

TABLE 13

Sequences presented in the Sequence Listing:

| SEQ ID NOS: | Description |
|---|---|
| 1-2, 4-6, 12, 14 | Cas9 polypeptides |
| 3, 7-11, 13 | Cas9 coding sequences |
| 15-23, 52-123 | Cas9 RuvC-like domains |
| 24-28, 124-198 | Cas9 HNH-like domains |
| 29-31, 38-51 | Full-length modular and unimolecular gRNAs |
| 32-37 | gRNA proximal and tail domains |
| 199-205 | PAM sequences |
| 251-901, 940-942, 952-955 | gRNA targeting domains (RNA)-see Tables 2, 7, 9, 10 |
| 910-919, 943-945, 956-959 | gRNA targeting domains (DNA)-see Tables 7, 9, 10 |
| 920-929, 946-948, 960-963 | gRNA targeting domains plus PAM (NGG) (RNA)-see Tables 7, 9 |
| 930-939, 949-951, 964-967 | gRNA targeting domains plus PAM (NGG) (DNA)-see Tables 7, 9 |
| 970, 972, 974, 976 | dgRNA targeting domains (RNA)-see Table 10 |
| 971, 973, 975, 977 | dgRNA targeting domains (DNA)-see Table 10 |
| 902, 903 | Human HBG1, 2 promoter sequences including HPFH deletion site |
| 904-909 | Oligonucleotide donor sequences and homology arms-see Table 8 |
| 968-969 | BCL11Ae sequences |

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments described herein. Such equivalents are intended to be encompassed by the following claims.

REFERENCES

Aliyu et al. Am J Hematol 83:63-70 (2008)
Angastiniotis & Modell Ann N Y Acad Sci 850:251-269 (1998)
Anders et al. Nature 513(7519):569-573 (2014)
Bae et al. Bioinformatics 30(10):1473-1475 (2014)
Bothmer et al. Nat Commun 8:13905 (2017)
Bouva Hematologica 91(1):129-132 (2006)
Briner et al. Mol Cell 56(2):333-339 (2014)
Brousseau Am J Hematol 85(1):77-78 (2010)
Canvers et al. Nature 527(12):192-197 (2015)
Chang et al. Mol Ther Methods Clin Dev 4:137-148 (2017)
Chen et al. Nat Commun 8:14958 (2017)
Cong et al. Science 399(6121):819-823 (2013)
Cornish-Bowden Nucleic Acids Res 13(9):3021-3030 (1985)
Davis & Maizels Proc Natl Acad Sci USA 111(10):E924-E932 (2014)
Fine et al. Sci Rep 5:10777 (2015)
Frit et al. DNA Repair (Amst.) 17:81-97 (2014)
Fu et al. Nat Biotechnol 32(3):279-284 (2014)
Guilinger et al. Nat Biotechnol 32(6):577-582 (2014)
Heigwer et al. Nat Methods 11(2):122-123 (2014)
Hinz et al. J Biol Chem 291(48):24851-24856 (2016)
Hsu et al. Nat Biotechnol 31(9):827-832 (2013)
Iyama & Wilson DNA Repair (Amst.) 12(8):620-636 (2013)
Jiang et al. Nat Biotechnol 31(3):233-239 (2013)
Jinek et al. Science 337(6096):816-821 (2012)
Jinek et al. Science 343(6176):1247997 (2014)
Kleinstiver et al. Nature 523(7561):481-485 (2015a)
Kleinstiver et al. Nat Biotechnol 33(12):1293-1298 (2015b)
Kleinstiver et al. Nature 529(7587):490-495 (2016)
Komor et al. Nature 533(7603):420-424 (2016)
Lee et al. Nano Lett 12(12):6322-6327 (2012)
Lewis "Medical-Surgical Nursing: Assessment and Management of Clinical Problems" (2014)
Makarova et al. Nat Rev Microbiol 9(6):467-477 (2011)
Mali et al. Science 339(6121):823-826 (2013)
Martyn et al. Biochim. Biophys Acta 1860 (5):525-536 (2017)
Nishimasu et al. Cell 156(5):935-949 (2014)
Nishimasu et al. Cell 162(5):1113-1126 (2015)
Ran et al. Cell 154(6):1380-1389 (2013)
Ran et al. Nature 520(7546):186-191 (2015)
Richardson et al. Nat Biotechnol 34(3):339-344 (2016)
Shmakov et al. Mol Cell 60:385-397 (2015)
Thein Hum Mol Genet 18(R2):R216-223 (2009)
Truong et al. PNAS 110(19):7720-5 (2013)
Tsai et al. Nat Biotechnol 34(5):483 (2016)
van Overbeek et al 63(4):633-646 (2016)
Wang et al. Cell 153(4):910-918 (2013)
Xiao et al. Bioinformatics 30(8):1180-1182 (2014)
Yamano et al. Cell 165(4):949-962 (2016)
Zetsche et al. Nat Biotechnol 33(2):139-142 (2015a)
Zetsche et al. Cell 163(3):759-771 (2015b)

The invention claimed is:

1. A genome editing system comprising:

a first guide RNA (gRNA) comprising a first targeting domain that differs by no more than 3 nucleotides from SEQ ID NO: 953 or SEQ ID NO:955;

a second gRNA comprising a second targeting domain sequence that differs by no more than 3 nucleotides from SEQ ID NO: 952 or SEQ ID NO:954; and an RNA-guided nuclease, wherein (i) the RNA-guided nuclease and the first gRNA and (ii) the RNA-guided nuclease and the second gRNA are configured to associate within a target region in a target nucleic acid and generate a double stranded break (DSB) in the target nucleic acid whereby to create an indel in the target nucleic acid.

2. The genome editing system of claim 1, wherein the target nucleic acid is a BCL11A gene.

3. The genome editing system of claim 2, wherein the first targeting domain sequence is complementary to a first sequence in a +58 DNase I hypersensitive site (DHS) region of intron 2 of the BCL11A gene.

4. The genome editing system of claim 3, wherein the indel alters the +58 DHS region of intron 2 of the BCL11A gene.

5. The genome editing system of claim 2, wherein the second targeting domain sequence of SEQ ID NO:952 is complementary to a second sequence in a +58 DNase I hypersensitive site (DHS) region of intron 2 of the BCL11A gene.

6. The genome editing system of claim 1, wherein the first and second gRNAs are chemically synthesized.

7. A method of altering a cell, comprising: contacting the cell with a first guide RNA (gRNA) comprising a first targeting domain sequence that differs by no more than 3 nucleotides from SEQ ID NO: 953 or SEQ ID NO:955;

a second gRNA comprising a second targeting domain sequence that differs by no more than 3 nucleotides from SEQ ID NO: 952 or SEQ ID NO:954; and an RNA-guided nuclease;

wherein (i) the RNA-guided nuclease and the first gRNA and (ii) the RNA-guided nuclease and the second gRNA associate within a target region and generate a double stranded break (DSB) in a target nucleic acid whereby to create an indel in the target nucleic acid.

8. The method of claim 7, wherein the target nucleic acid is a BCL11A gene.

9. The method of claim 8, wherein the first targeting domain sequence is complementary to a first sequence in a +58 DNase I hypersensitive site (DHS) region of intron 2 of the BCL11A gene.

10. The method of claim 9, wherein the indel alters the +58 DHS region of intron 2 of the BCL11A gene.

11. The method of claim 8, wherein the second targeting domain sequence of SEQ ID NO:952 is complementary to a second sequence in a +58 DNase I hypersensitive site (DHS) region of intron 2 of the BCL11A gene.

12. The method of claim 7, wherein the first and second gRNAs are chemically synthesized.

13. A method of treating a β-hemoglobinopathy in a subject in need thereof, comprising administering to the subject a population of modified hematopoietic cells, wherein one or more cells of the population have been altered via a method comprising: contacting a cell with a first guide RNA (gRNA) comprising a first targeting domain that differs by no more than 3 nucleotides from SEQ ID NO: 953 or SEQ ID NO:955;

a second gRNA comprising a second targeting domain that differs by no more than 3 nucleotides from SEQ ID NO: 952 or SEQ ID NO:954; and an RNA-guided nuclease;

wherein (i) the RNA-guided nuclease and the first gRNA and (ii) the RNA-guided nuclease and the second gRNA associate within a target region and generate a double stranded break (DSB) in a target nucleic acid whereby to create an indel in the target nucleic acid.

14. The method of claim 13, wherein the target nucleic acid is a BCL11A gene.

15. The method of claim 14, wherein the first targeting domain sequence is complementary to a first sequence in a +58 DNase I hypersensitive site (DHS) region of intron 2 of the BCL11A gene.

16. The method of claim 15, wherein the indel alters the +58 DHS region of intron 2 of the BCL11A gene.

17. The method of claim 14, wherein the second targeting domain sequence of SEQ ID NO:952 is complementary to a second sequence in a +58 DNase I hypersensitive site (DHS) region of intron 2 of the BCL11A gene.

18. The method of claim 13, wherein the first and second gRNAs are chemically synthesized.

* * * * *